(12) United States Patent
Partridge et al.

(10) Patent No.: US 9,682,928 B2
(45) Date of Patent: Jun. 20, 2017

(54) BUMETANIDE ANALOGS, COMPOSITIONS AND METHODS OF USE

(71) Applicant: NeuroPro Therapeutics, Inc., Bahama, NC (US)

(72) Inventors: John J. Partridge, Chapel Hill, NC (US); Daryl W. Hochman, Bahama, NC (US)

(73) Assignee: NeuroPro Therapeutics, Inc., Bahama, NC (US)

( * ) Notice: Subject to any disclaimer, the term of this patent is extended or adjusted under 35 U.S.C. 154(b) by 0 days.

(21) Appl. No.: 14/472,181

(22) Filed: Aug. 28, 2014

(65) Prior Publication Data

US 2015/0080350 A1    Mar. 19, 2015

Related U.S. Application Data

(63) Continuation of application No. 13/138,282, filed as application No. PCT/US2010/000170 on Jan. 22, 2010, now abandoned.

(60) Provisional application No. 61/257,238, filed on Nov. 2, 2009, provisional application No. 61/146,336, filed on Jan. 22, 2009.

(51) Int. Cl.
| | | |
|---|---|---|
| *C07D 295/084* | (2006.01) | |
| *C07C 311/39* | (2006.01) | |
| *A61K 31/4355* | (2006.01) | |
| *C07D 211/44* | (2006.01) | |
| *C07D 231/04* | (2006.01) | |
| *C07D 233/02* | (2006.01) | |
| *C07D 237/02* | (2006.01) | |
| *C07D 239/04* | (2006.01) | |
| *C07D 241/04* | (2006.01) | |
| *C07D 261/02* | (2006.01) | |
| *C07D 263/04* | (2006.01) | |
| *C07D 265/30* | (2006.01) | |
| *C07D 275/02* | (2006.01) | |
| *C07D 277/04* | (2006.01) | |
| *C07D 279/12* | (2006.01) | |
| *C07D 307/52* | (2006.01) | |

(52) U.S. Cl.
CPC ........ *C07C 311/39* (2013.01); *A61K 31/4355* (2013.01); *C07D 211/44* (2013.01); *C07D 231/04* (2013.01); *C07D 233/02* (2013.01); *C07D 237/02* (2013.01); *C07D 239/04* (2013.01); *C07D 241/04* (2013.01); *C07D 261/02* (2013.01); *C07D 263/04* (2013.01); *C07D 265/30* (2013.01); *C07D 275/02* (2013.01); *C07D 277/04* (2013.01); *C07D 279/12* (2013.01); *C07D 295/084* (2013.01); *C07D 307/52* (2013.01)

(58) Field of Classification Search
CPC . C07C 311/39; A61K 31/4355; C07D 211/44; C07D 231/04; C07D 233/02; C07D 237/02; C07D 239/04; C07D 241/04; C07D 261/02; C07D 263/04; C07D 265/30; C07D 275/02; C07D 277/04; C07D 279/12; C07D 295/084; C07D 307/52

See application file for complete search history.

(56) References Cited

U.S. PATENT DOCUMENTS

| | | |
|---|---|---|
| 6,495,601 B1 | 12/2002 | Hochman |
| 2002/0082252 A1 | 6/2002 | Hochman |
| 2005/0267103 A1 | 12/2005 | Hochman |
| 2006/0035914 A1 | 2/2006 | Hochman |
| 2006/0089350 A1 | 4/2006 | Hochman et al. |
| 2007/0149526 A1 | 6/2007 | Hochman et al. |
| 2009/0258844 A1 | 10/2009 | Hochman et al. |
| 2012/0004225 A1 | 1/2012 | Wanaski et al. |
| 2012/0234721 A1 | 9/2012 | Hochman et al. |

*Primary Examiner* — Rebecca Anderson
(74) *Attorney, Agent, or Firm* — Brinks Gilson & Lione

(57) ABSTRACT

The present invention provides bumetanide analogs and compositions comprising such analogs. The present invention also provides pharmaceutical compositions containing these bumetanide analogs and methods for their use. These analogs are particularly useful for the treatment and/or prophylaxis of conditions that involve the $Na^+K^+Cl^-$ co-transporter or $GABA_A$ receptor including but not limited to addictive disorders, Alzheimer's Disease, anxiety disorders, ascites, autism, bipolar disorder, cancer, depression, endothelial corneal dystrophy, edema, epilepsy, glaucoma. Huntington's Disease, insomnia, ischemia, migraine, migraine with aura, neuropathic pain, nociceptive neuralgia, nociceptive pain, ocular diseases, pain, Parkinson's disease, personality disorders, postherpetic neuralgia, psychosis, schizophrenia, seizure disorders, tinnitus, and withdrawal syndromes.

1 Claim, 52 Drawing Sheets

FIGURE 8

Direct Syntheses of a Thioamide Analog

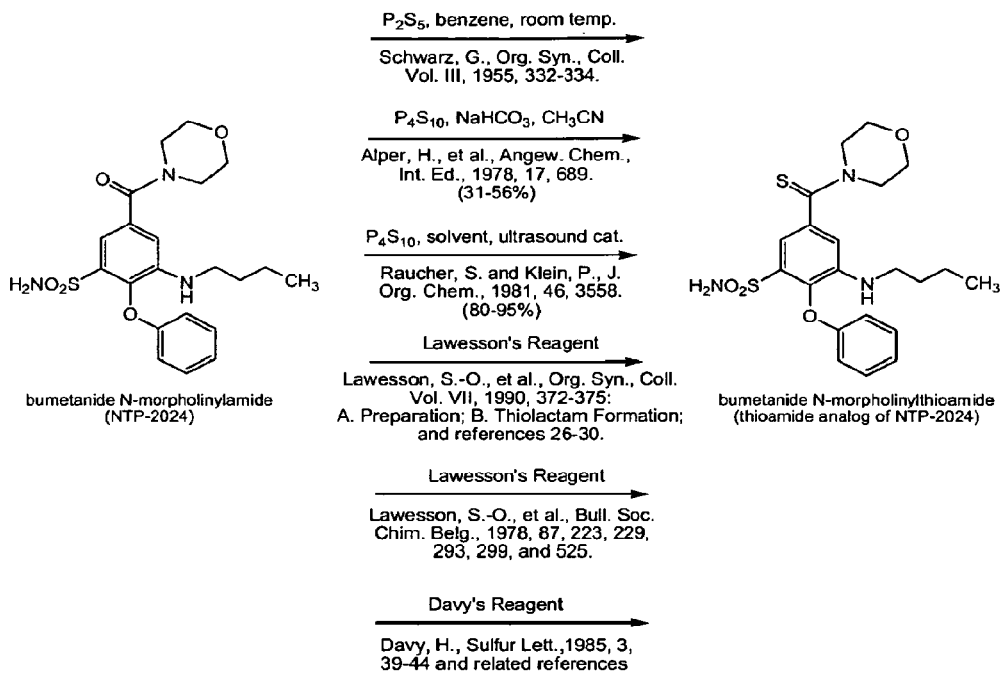

bumetanide N-morpholinylamide
(NTP-2024)

Reagents/conditions (top to bottom):

$P_2S_5$, benzene, room temp.
Schwarz, G., Org. Syn., Coll. Vol. III, 1955, 332-334.

$P_4S_{10}$, $NaHCO_3$, $CH_3CN$
Alper, H., et al., Angew. Chem., Int. Ed., 1978, 17, 689. (31-56%)

$P_4S_{10}$, solvent, ultrasound cat.
Raucher, S. and Klein, P., J. Org. Chem., 1981, 46, 3558. (80-95%)

Lawesson's Reagent
Lawesson, S.-O., et al., Org. Syn., Coll. Vol. VII, 1990, 372-375: A. Preparation; B. Thiolactam Formation; and references 26-30.

Lawesson's Reagent
Lawesson, S.-O., et al., Bull. Soc. Chim. Belg., 1978, 87, 223, 229, 293, 299, and 525.

Davy's Reagent
Davy, H., Sulfur Lett.,1985, 3, 39-44 and related references bumetanide N-morpholinylthioamide
(thioamide analog of NTP-2024)

Thioamide and Thiolactam Review - "Synthesis of Thioamides and Thiolactams", Schaumann, E. in Comprehensive Organic Synthesis, Trost, B. M. Editor-in-Chief, Volume 6, Chapter 2.4, Pergamon Press, Oxford, 1991, pp.419-434.

Lawesson's Reagent Additional References - Lawesson, S.-O., et al., Org. Syn., Coll. Vol.VII, 1990, 372-375 and references therein; Fieser's Reagents for Org. Syn., Vol. 8, 1980, 327; ibid, Vol. 9, 1981, 49-50; ibid, Vol. 10, 1982, 39; ibid, Vol. 11, 1984, 54-55; ibid, Vol. 12, 1986, 59; ibid, Vol. 13, 1988, 38-39; ibid, Vol. 15, 1990, 37, 329; and ibid, Vol. 16, 1992, 37-38.

Davy's Reagent References - Davy, H., JCS, Chem. Commun., 1982, 457; Davy, H., Sulfur Lett., 1985, 3, 39-44; Davy, H., Chem. & Ind., 1985, 824; Davy, H., J. Chem. Res. (S), 1985, 272; Davy, H., J. Chem. Res. (M), 1985, 2701-2712.

Thioester and Thiolactone Review - "Synthesis of Thioesters and Thiolactones", Voss, J. in Comprehensive Organic Synthesis, Trost, B. M. Editor-in-Chief, Volume 6, Chapter 2.5, Pergamon Press, Oxford, 1991, pp.435-460.

Selenoesters and Selenoamide Review - "Synthesis of Selenoesters of All Oxidation States", Ogawa, A. and Sonoda, N. in Comprehensive Organic Synthesis, Trost, B. M. Editor-in-Chief, Volume 6, Chapter 2.6, Pergamon Press, Oxford, 1991, pp.461-484.

FIGURE 9

Direct Syntheses of a Selenoamide Analog

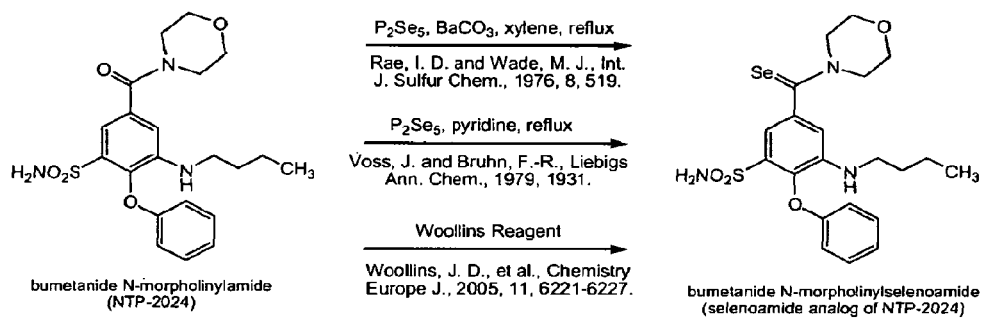

bumetanide N-morpholinylamide (NTP-2024)

$P_2Se_5$, $BaCO_3$, xylene, reflux
Rae, I. D. and Wade, M. J., Int. J. Sulfur Chem., 1976, 8, 519.

$P_2Se_5$, pyridine, reflux
Voss, J. and Bruhn, F.-R., Liebigs Ann. Chem., 1979, 1931.

Woollins Reagent
Woollins, J. D., et al., Chemistry Europe J., 2005, 11, 6221-6227.

bumetanide N-morpholinylselenoamide (selenoamide analog of NTP-2024)

Selenoesters and Selenoamide Review - "Synthesis of Selenoesters of All Oxidation States", Ogawa, A. and Sonoda, N. in Comprehensive Organic Synthesis, Trost, B. M. Editor-in-Chief, Volume 6, Chapter 2.6, Pergamon Press, Oxford, 1991, pp.461-484 (especially pp. 478-481).

Woollins Reagent References - $(PhPSe_2)_2$ References - Woollins, J. D., et al., Chem. Eur. J., 2005, 11, 6221-6227 and Woollins references therein.

Thioamide and Thiolactam Review - "Synthesis of Thioamides and Thiolactams", Schaumann, E. in Comprehensive Organic Synthesis, Trost, B. M. Editor-in-Chief, Volume 6, Chapter 2.4, Pergamon Press, Oxford, 1991, pp.419-434; Alper, H., et al., Angew. Chem. Int. Ed., 1978, 17, 689-690.

Thioester and Thiolactone Review - "Synthesis of Thioesters and Thiolactones", Voss, J. in Comprehensive Organic Synthesis, Trost, B. M. Editor-in-Chief, Volume 6, Chapter 2.5, Pergamon Press, Oxford, 1991, pp.435-460.

Lawesson's Reagent Additional References - Lawesson, S.-O., et al., Org. Syn., Coll. Vol.VII, 1990, 372-375 and references therein; Fieser's Reagents for Org. Syn., Vol. 8, 1980, 327; ibid, Vol. 9, 1981, 49-50; ibid, Vol. 10, 1982, 39; ibid, Vol. 11, 1984, 54-55; ibid, Vol. 12, 1986, 59; ibid, Vol. 13, 1988, 38-39; ibid, Vol. 15, 1990, 37, 329; and ibid, Vol. 16, 1992, 37-38. See selenium analog reagents.

Davy's Reagent References - Davy, H., JCS, Chem. Commun., 1982, 457; Davy, H., Sulfur Lett., 1985, 3, 39-44; Davy, H., Chem. & Ind., 1985, 824; Davy, H., J. Chem. Res. (S), 1985, 272; Davy, H., J. Chem. Res. (M), 1985, 2701-2712. See selenium analog reagents.

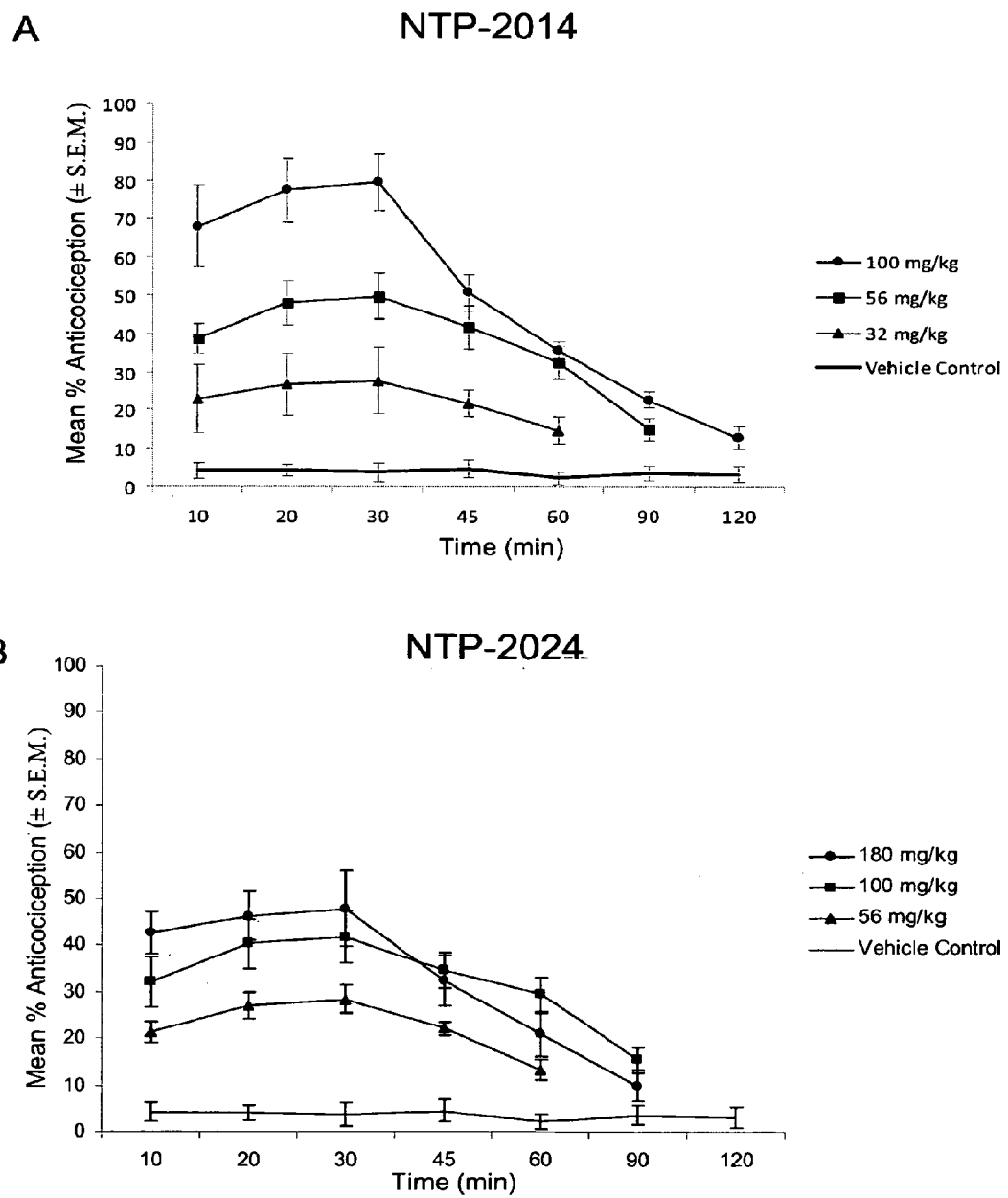
Figure 44A-B

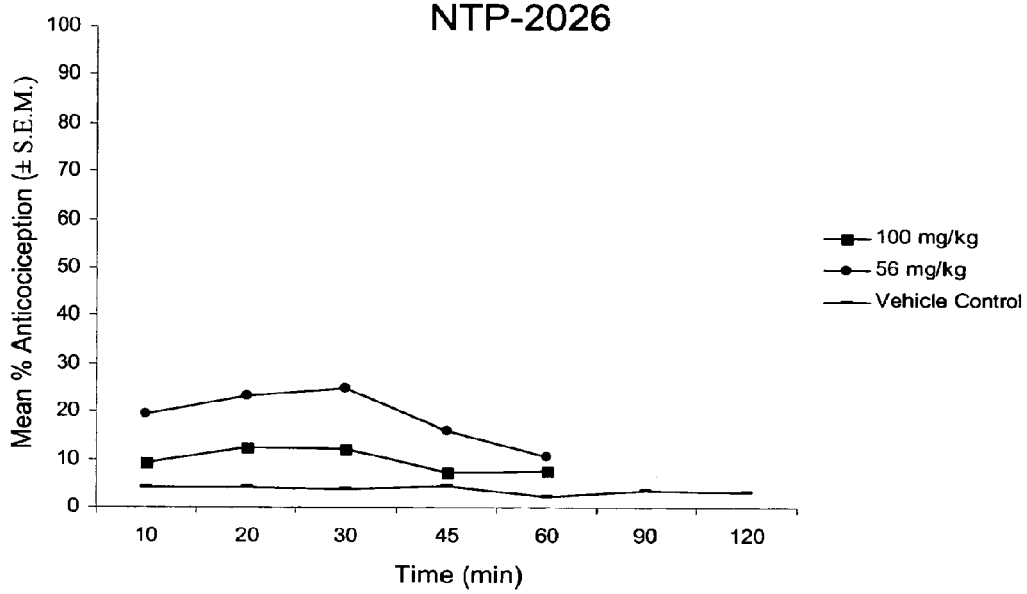
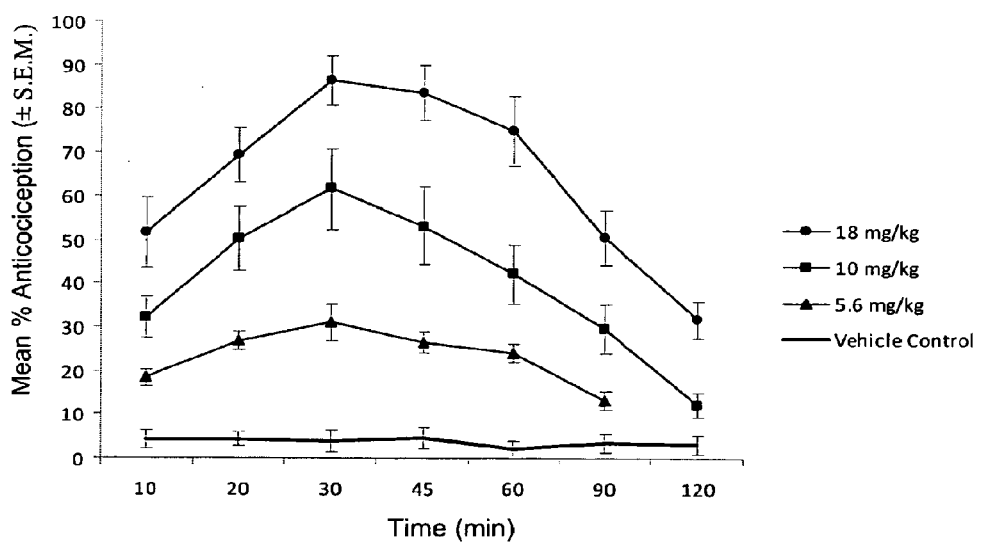
Figure 44C-D

A
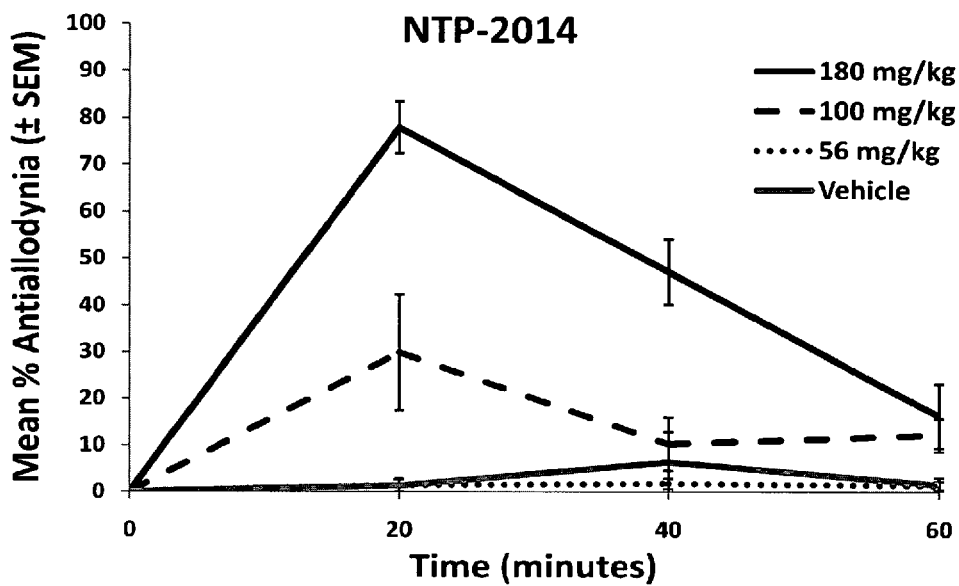
B
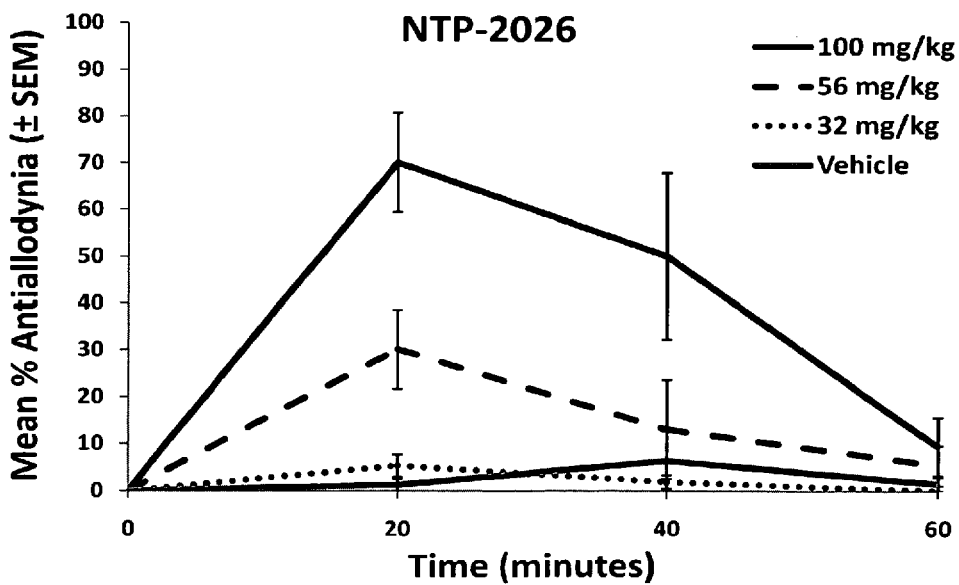
FIGURE 46A-B

BUMETANIDE ANALOGS, COMPOSITIONS AND METHODS OF USE

CROSS-REFERENCE TO RELATED APPLICATIONS

This Application is a continuation of U.S. application Ser. No. 13/138,282 filed Jan. 21, 2011, which is a U.S. National Phase Application of International Patent Application No. PCT/US2010/000170 filed Jan. 22, 2010, which claims priority to U.S. Provisional Patent Application Nos. 61/146,336 filed Jan. 22, 2009, and 61/257,238, filed Nov. 2, 2009. The disclosures of the related and priority patent applications are hereby incorporated by reference in their entireties.

FIELD OF THE INVENTION

The present invention relates to bumetanide, furosemide, piretanide, azosemide, and torsemide analogs, including derivatives, positional isomers, and prodrugs thereof, compositions comprising the same and methods of making and using the same. The present invention also relates to pharmaceutical compositions containing derivatives (including prodrugs) of these compounds and methods for using derivatives of these compounds. Such derivatives (including prodrugs) of bumetanide, furosemide, piretanide, azosemide, and torsemide are particularly useful for the treatment and/or prophylaxis of diseases, disorders, and conditions that involve the $Na^+K^+Cl^-$ co-transporters (NKCC1 or NKCC2 or combinations thereof) including but not limited to addictive disorders, anxiety disorders, ascites, bipolar disorder, cancer, depression, edema, endothelial corneal dystrophy, epilepsy, glaucoma, ischemia, migraine, neuropathic pain, nociceptive neuralgia, ocular diseases, pain, postherpetic neuralgia, and schizophrenia. Compounds described herein are also particularly useful for the treatment and/or prophylaxis of diseases, disorders, and conditions that involve the $GABA_A$ receptor including but not limited to Alzheimer's Disease, addictive disorders, anxiety disorders, autism, bipolar disorder, depression, epilepsy, Huntington's Disease, insomnia, migraine, migraine with aura, neuropathic pain, nociceptive pain, pain, Parkinson's disease, personality disorders, psychosis, schizophrenia, seizure disorders, tinnitus, and withdrawal syndromes.

BACKGROUND OF THE INVENTION $Na^+K^+Cl^-$ Co-Transporters

In absorptive and secretory epithelia, transcellular ion transport depends on specific plasma membrane proteins for mediating ion entry into and exit from cells. In basolateral membrane of almost all epithelia (with exception of choroidal plexus), sodium exit and potassium entrance occur through $Na^+K^+$-ATPase, generating electrochemical gradients that constitute a driving force for $Na^+$ influx and $K^+$ efflux. Transport of these ions following their gradients can be accomplished by specific ion channels, allowing membrane passage of ions alone or by transporters in which $Na^+$ or $K^+$ transport is accompanied by other ions or solutes by means of several different solute transporters. These membrane proteins are known as secondary transporters because ion or molecule translocation is not dependent on ATP hydrolysis but rather on gradients generated by primary transporters. A secondary transport mechanism that is very active in transcellular ion transport in epithelial cells is one in which cations ($Na^+$ or $K^+$) are coupled with chloride, with a stoichiometry of 1:1; therefore, ion translocation produces no change in transmembrane potential. For this reason, these transporters are known as electroneutral cation-$Cl^-$ coupled cotransporters. In addition to being heavily implicated in ion absorptive and secretory mechanisms, electroneutral cation-$Cl^-$ coupled cotransporters play a key role in maintenance and regulation of cell volume in both epithelial and nonepithelial cells. Because $Na^+$ influx and $K^+$ efflux by electroneutral cotransporters are rapidly corrected by $Na^+K^+$-ATPase, the net effect of its activity is $Cl^-$ movement inside or outside cells. This is known to be accompanied by changes in cell volume. Finally, a variety of new physiological roles for electroneutral cotransporters are emerging (e.g., regulation of intraneuronal $Cl^-$ concentration and thus modulation of neurotransmission.) Gamba (2005) "Molecular Physiology and Pathophysiology of Electroneutral Cation-Chloride Cotransporters." Physiol. Rev. 85: 423-493.

Four groups of electroneutral cotransporter systems (also known as "symporters") have been functionally identified based on cation(s) coupled with chloride, stoichiometry of transport process, and sensitivity to inhibitors. These systems include: (1) the benzothiadiazine (or thiazide)-sensitive $Na^+Cl^-$ cotransporter, (2) the sulfamoylbenzoic (or bumetanide) sensitive $Na^+K^+2Cl^-$ cotransporters; (3) the sulfamoylbenzoic (or bumetanide) sensitive $Na^+Cl^-$ cotransporters; and (4) the dihydroindenyloxyalkanoic acid (DIOA)-sensitive $K^+Cl^-$ cotransporter. There is some overlap in sensitivity to inhibitors in the last two groups because $Na^+K^+2Cl^-$ and $K^+Cl^-$ cotransporters can be inhibited by high concentration of DIOA or loop diuretics, respectively; however, affinity for inhibitor and the cation coupled with chloride clearly differentiate between both groups of transporters. Physiological evidence for these transport mechanisms became available at the beginning of the 1980s, and a remarkable amount of information was generated in the following years by characterizing these transport systems in many different cells and experimental conditions. Gamba (2005) "Molecular Physiology and Pathophysiology of Electroneutral Cation-Chloride Cotransporters." Physiol. Rev. 85: 423-493.

One isoform of the $Na^+K^+Cl^-$ cotransporter (NKCC) NKCC1 is widely distributed throughout the body. NKCC1 transports sodium, potassium, and chloride into the cell. NKCC1 is also found throughout the nervous system where it is expressed on astrocytes, oligodendrocytes, and Schwann cells. Lenart, et al. (2004) *The Journal of Neuroscience* 24(43): 9585-9597. Another isoform, NKCC2 is found primarily in the kidney, where it serves to extract sodium, potassium, and chloride from the urine. Haas (1994) "The Na—K—Cl cotransporters." Am J Physiol Cell Physiol 267: C869-C885. Bumetanide, furosemide, piretanide, azosemide, and torsemide are loop diuretics that have a potent diuretic effect. Loop diuretics are antagonists of the $Na^+K^+Cl^-$ cotransporter (e.g., NKCC2) in the thick ascending limb of the loop of Henle and act to inhibit sodium and chloride reabsorption by competing for the $Cl^-$ binding site. See also Russell (January 2000) "Sodium-Potassium-Chloride Cotransport." *Physioglocal Reviews* 80(1): 211-275.

The regulation of $Cl^-$ transport into and out of cells plays a critical role in the maintenance of intracellular volume and the excitability of GABA responsive neurons regulated by at least two ion cotransporters: $Cl^-$ influx is mediated by the NKCC1 which mediates the $Cl^-$ influx and KCC1 or KCC2 which mediates the $Cl^-$ efflux. Kahle, et al. (2004) *Proc. Natl. Acad. Sci. USA* 102(46): 16783-16788. The maintenance of intra- and extracellular electrolyte homeostasis is required for a wide range of essential physiologic processes, including general functions (e.g., maintenance of proper cell volume), specialized cell functions (e.g., control of neuronal excitability), and global functions (e.g., regulation of blood pressure.) This homeostasis is achieved via the regulated movement of $Na^+$, $K^+$, and $Cl^-$ across cell membranes by ion channels, cotransporters, exchangers, and pumps that execute transmembrane electrolyte flux. Kahle, et al. (2004) *Proc. Natl. Acad. Sci. USA* 102(46): 16783-16788.

The predominant mechanism by which intracellular volume is maintained in cells in response to changes in extracellular tonicity is the raising or lowering of intracellular $Cl^-$ concentration ($[Cl^-]_i$), thereby minimizing transmembrane water flux. $[Cl^-]_i$ is modulated by altering the balance between $Cl^-$ entry and exit. The major mediator of $Cl^-$ entry is NKCC1 and $Cl^-$ exit is largely mediated by KCC1. These cotransporters are both regulated by extracellular tonicity: hypertonicity activates NKCC1 and inhibits KCC1, whereas hypotonicity has the opposite effect. Kahle, et al. (2004) *Proc. Natl. Acad. Sci. USA* 102(46): 16783-16788.

An analogous system plays a key role in the control of neuronal excitability. In the adult brain, GABA is the major inhibitory neurotransmitter. If $[Cl^-]_i$ is below its equilibrium potential, $Cl^-$ enters the cell, resulting in hyperpolarization and inhibition. If $[Cl^-]_i$ is above its equilibrium potential, GABA induces $Cl^-$ efflux, depolarization, and neuronal excitation. The importance of $[Cl^-]_i$ regulation has been recognized with the discovery that GABA neurotransmission is not uniformly inhibitory; it is predominantly excitatory in the neonatal period. Similarly, neurons of the suprachiasmatic nucleus show circadian variation in their response to GABA, demonstrating the ability to dynamically regulate $[Cl^-]_i$. Finally, GABA neurotransmission in the peripheral nervous system is predominantly excitatory. Variation in $[Cl^-]_i$ in these neurons is determined by mechanisms highly similar to those governing cell volume. $Cl^-$ influx largely occurs via NKCC1, whereas $Cl^-$ efflux is mediated via the neuronal-specific K—Cl cotransporter KCC2. Kahle, et al. (2004) *Proc. Natl. Acad. Sci. USA* 102(46): 16783-16788.

The mediators of transcellular $Cl^-$ cotransport (Na—Cl cotransporter, NKCC1, NKCC2, KCC1, and KCC2) are all related members of the SLC12A family of cation/$Cl^-$ cotransporters; each takes advantage of inward $Na^+$ or outward $K^+$ gradients to move $Cl^-$ into or out of cells, respectively. The importance of this family of transporters is underscored by their use as pharmacologic targets (thiazide diuretics act at NCC, and loop diuretics act at NKCC2), and that their mutation results in diverse diseases. Disruption of NKCC1 in mouse leads to hearing loss, altered pain perception, neuronal excitability, and altered blood pressure. Kahle, et al. (2004) *Proc. Natl. Acad. Sci. USA* 102(46): 16783-16788.

Major advances have been made in the past decade in molecular identification and characterization of solute carriers. As of 2005, the Human Genome Organization (HUGO) Nomenclature Committee Database recognizes 43 solute carries (SLC) families, which include a total of 298 transporter genes encoding for uniporters (passive transporters), cotransporters (coupled transporters), antiporters (exchangers), vesicular transporters, and mitochondrial transporters. This amount of solute carrier genes represents ~1% of the total pool of genes that have been calculated to compose human genome. Gamba (2005) "Molecular Physiology and Pathophysiology of Electroneutral Cation-Chloride Cotransporters." *Physiol. Rev.* 85: 423-493.

GABA Receptors

Gamma-aminobutyric acid (GABA) is the major inhibitory neurotransmitter in the central nervous system (CNS) where approximately 30% of all synapses use GABA as a transmitter. There are three classes of GABA receptors: $GABA_A$ (ligand-gated ion channel), $GABA_B$ (G protein-coupled receptor), and $GABA_C$ (ligand-gated ion channel). Chloride flux into the cell results from the activation of $GABA_A$ receptors by the binding of GABA molecules, hyperpolarizing the resting membrane potential and decreasing the chances of the post-synaptic neuron propagating an action potential. $GABA_A$ receptors are pentameric and approximately 19 GABA receptor subunits have been cloned from mammals ($6\alpha$, $3\beta$, $3\gamma$, $1\delta$, $1\epsilon$, $1\theta$, $1\pi$, and $3\rho$ subunits). The heterogeneity of GABA subunits is further increased by alternate splicing (e.g., $\gamma2$ short and $\gamma2$ long are the two major splice variants of the $\gamma2$). In general, a functional $GABA_A$ receptor requires $2\alpha$ subunits, $2\beta$ subunits and a third "regulatory" subunit (usually $\gamma$ or $\delta$). WO 2009/100040. The specific subunit combination determines the pharmacological and ligand binding properties of the $GABA_A$ receptor. The most abundant subunit combination found in the CNS is $\alpha_1\beta_2\gamma_2$. This subtype represents approximately 40% of $GABA_A$ receptors in the brain and it is expressed throughout the CNS and is located on post-synaptic cells. WO 2007/002359.

The $GABA_A$ receptors are the targets of a wide range of therapeutic and clinically relevant compounds including benzodiazepines, barbiturates, neurosteroids, ethanol, certain intravenous anesthetics, and subtype specific modulators (e.g., Zolpidem.) These compounds serve as anxiolytics, sedative/hypnotics, anti-epileptic drugs (AED), and memory enhancers. Many of these therapeutics show efficacy but cause side effects due to unwanted effects at $\alpha_1$ and/or $\alpha_2$ $GABA_A$ variants or due to low therapeutic index. For example, benzodiazepines such as diazepam (VALIUM) are excellent anxiolytics but cause unwanted sedative effects when used clinically. WO 2007/002359.

At a cellular level, $GABA_A$ receptors are expressed both at both post-synaptic and extra-synaptic sites (parasynaptic) where they respond to large changes in GABA concentration caused by release of the neurotransmitter into the synaptic space, and extra-synaptically where the receptors respond to lower concentrations of GABA that "leak" from synaptic junctions. The post-synaptic receptors respond to acute changes in neuronal firing whereas the extrasynaptic receptors are responsible for maintaining overall tone of neuronal networks. WO 2009/100040. Tonic inhibition is generated by the persistent activation of extrasynapatic (perisynaptic) $GABA_A$ receptors and regulates the excitability of individual neurons and neural networks. Jia, et al. et al. (2008) *The Journal of Pharmacology and Experimental Therapeutics* 326(2): 475482.

Presynaptic $GABA_A$ receptors situated at extrasynaptic sites may comprise $\alpha_4\beta\delta$ and $\alpha_6\beta\delta$ isoforms. The extrasynaptic $\alpha_4\beta\delta$ and $\alpha_6\beta\delta$ $GABA_A$ receptor isoforms show marked sensitivity to GABA, alcohol, and anesthetics, suggesting that receptors may present a critical site for regulating synaptic function in the developing brain in both physiological and pathological situations. Xiao, et al. et al. (2007) "Presynaptic $GABA_A$ receptors facilitate GABAergic transmission to dopaminergic neurons in the ventral tegmental area of young rats." *J Physiol.* 580(Pt.3):731-43. For example, temporal lobe epilepsy (TLE), Parkinson's disease (PD) and Huntington's disease (HD) are neurodegenerative disorders that involve disruptions in GABA signaling. GABA is the major inhibitory neurotransmitter in the central nervous system (CNS). TLE seizures reflect excess excitation, which may result from local inhibitory circuit dysfunction. PD devastates the input to striatal GABAergic neurones and HD destroys striatal GABAergic neurones. Controlling GABA delivery to specific brain areas should benefit each of these diseases. Directing GABA synthesis, degradation, transport or receptors can control GABA signaling. New drugs targeting GABA synthesis, release, and binding may be used for improved therapeutics treatments for epilepsy and both Parkinson's and Huntington's disease. Kleppner and Tobin (2001) "GABA signaling: therapeutic targets for epilepsy, Parkinson's disease and Huntington's disease." Expert Opin Ther Targets. 5(2):219-39. See also Shumate, et al. et al. (1998) Epilepsy Research (32): 114-128; Fritschy (2008) Frontiers in Molecular Neuroscience 1(5): 1-5; Roberts, et al. et al. (2006) The Journal of Biological Chemistry 281(40): 29431-29435; and Roberts, et al. et al. PNAS 102(33): 11894-11899.

Addictive Disorders

Addictive and/or compulsive disorders, such as eating disorders (including obesity), addiction/physical dependence to stimulants, narcotics (e.g., cocaine, heroin) sedatives/hypnotics, and opioids including alcoholism and smoking are major public health problem that impact society on multiple levels. It has been estimated that substance abuse alone costs the United States more than $484 billion per year.

The alcohol-sensitive $\alpha_4\beta\delta$ $GABA_A$ receptor has also been postulated to be involved in alcohol addiction (alcoholism). For example, reduced expression of $GABA_A$ receptors comprising an $\alpha_4$ subunit in the nucleus accumbens (NAc) decreased the free consumption and preference for alcohol in rats. Further, the nucleus accumbens contributes to the rewarding and reinforcing effects of drugs including alcohol suggesting that the $GABA_A$ receptor, specifically the $\alpha_4\beta\delta$ isoform, in the NAc is an important mediator of alcohol self-administration. Rewal, et al. et al. (Jan. 14, 2009) The Journal of Neuroscience 29(2): 543-549.

Although most $GABA_A$ receptor subunit combinations can be activated by high (anesthetic) alcohol concentrations, so far only very specific $GABA_A$ receptor subunit combinations (containing the $\delta$ as well as the $\beta_3$ subunit) exhibit dose-dependencies that mirror blood alcohol levels associated with mild to moderate intoxication in humans. $GABA_A$ receptors containing the $\delta$ subunit are located either outside or in the perimeter of synapses, but not in the sub-synaptic membrane. WO 2007/002359.

Current strategies for the treatment of additive disorders include psychological counseling and support, use of therapeutic agents, or a combination of both. A variety of agents known to affect the central nervous system have been used in various contexts to treat a number of indications related directly or indirectly to addictive behaviors but a great need remains for improved addictive disorder therapeutics. $GABA_A$ specific agents that have action at the nucleus accumbens might be effective therapies for addictive behaviors.

Alzheimer's Disease

Alzheimer's disease (AD) is an age-related, non-reversible brain disorder that develops over a period of years. Initially, people experience memory loss and confusion, which may be mistaken for the kinds of memory changes that are sometimes associated with normal aging. However, the symptoms of AD gradually lead to behavior and personality changes, a decline in cognitive abilities such as decision-making and language skills, and problems recognizing family and friends. AD ultimately leads to a severe loss of mental function. AD is the most common cause of dementia among people age 65 and older. NINDS Alzheimer's Disease Information Page (Sep. 23, 2009).

The three major hallmarks in the brain that are associated with the disease processes of AD include amyloid plaques and neurofibrillary tangles. Amyloid plaques comprise fragments of β-amyloid peptide mixed with a collection of additional proteins, and remnants of neurons. Neurofibrillary tangles (NFTs) are found inside neurons and comprise tau protein. As neurons die throughout the brain, the affected regions begin to atrophy. By the final stage of AD, damage is widespread and brain tissue has shrunk significantly. NINDS Alzheimer's Disease Information Page (Sep. 23, 2009).

Currently there are no medicines that can slow the progression of AD. However, four FDA-approved medications are used to treat AD symptoms. Unfortunately these medications will not stop or reverse AD, and they appear to help individuals for only a few months to a few years. Donepezil (ARICEPT), rivastigmine (EXELON), and galantamine (REMINYL) are prescribed to treat mild to moderate AD symptoms. Donepezil was recently approved to treat severe AD as well. The newest AD medication is memantine (NAMENDA), which is prescribed to treat moderate to severe AD symptoms. NINDS Alzheimer's Disease Information Page (Sep. 23, 2009). Treatment of a transgenic mouse model of Alzheimer's Disease with picrotoxin, a $GABA_A$ antagonist showed improved cognitive functions in the mice. Yoshiike, et al. et al. (Aug. 21, 2008) "$GABA_A$ receptor-mediated acceleration of aging-associated memory decline in APP/PSI mice and its pharmacological treatment by picrotoxin." PLoS One. 3(8):e3029. Additionally, the expression of NKCC1 has been found to be elevated in Alzheimer's Disease patients. Johanson, et al. (2004) *Cerebrospinal Fluid Research* 1:3. Therefore novel therapies based on the regulation of $GABA_A$ receptor activity may relieve the symptoms of AD.

Anxiety Disorders

Anxiety disorders are classified into several subtypes: anxiety, acute anxiety, panic disorder, social anxiety disorder, obsessive compulsive disorder (OCD), post-traumatic stress disorder (PTSD), generalized anxiety disorder, and specific phobia. American Psychiatric Association. Diagnostic and Statistical Manual of Mental Disorders, 4$^{th}$ edition (1994).

As a group, the anxiety disorders have the highest prevalence in the U.S. of all psychiatric disorders. Kessler, et al. et al. (1994) "Lifetime and 12-month prevalence of DSM-III-R psychiatric disorders in the United States: Results from the National Comorbidity Survey." Arch Gen Psychiatry 51:8-19. Anxiety disorders afflict 15.7 million people in the United States each year, and 30 million people in the United States at some point in their lives. Lepine (2002) "The Epidemiology of Anxiety Disorders: Prevalence and Societal Costs." J. Clin. Psychiatry. 63: Suppl 14:4-8.

Several animal models have been developed which are recognized in the art as being predictive of anxiolytic activity. These include the fear-potentiated startle model, described by Davis in Psychopharmacology 62:1; 1979, Behav. Neurosci. 100:814; 1986 and TiPS, January 1992 Vol. 13, 35-41, the elevated plus model described by Lister in Psychopharmacol. 92:180-185; 1987, and the well-known punished—responding (conflict) model, described, for example, in "Psychopharmacology of Anxiolytics and Antidepressants", edited by S. E. File, pp. 131-153, Raven Press, New York, 1991.

Anxiety disorders are generally treated with drugs and psychotherapy. The most commonly prescribed drugs for all anxiety types are the benzodiazepines, other psychoactive drugs such as selective serotonin reuptake inhibitors (SSRI)

are also used. However, while these drugs show efficacy, both benzodiazepines and SSRIs are also show adverse effects during treatment. Denys and de Geus (August 2005) "Predictors of Pharmacotherapy Response in Anxiety Disorders." Curr Psychiatry Rep. 7(4): 252-7. For example, numerous side effects are associated with long-term use of SSRIs, such as sexual dysfunction and weight gain. Hirschfeld (2003) "Long-term Side Effects of SSRIs: Sexual Dysfunction and Weight Gain." J. Clin. Psychiatry. 64: Suppl 18: 20-4. Further, existing drugs targeting postsynaptic type $GABA_A$ receptors produce undesirable results because they indiscriminately target most of the $GABA_A$ receptors in the brain. WO 2007/136838. In view of nonresponders and deleterious side effects, a great need exists for improved anxiety therapeutics.

Ascites

Ascites is excess fluid in the space between the tissues lining the abdomen and abdominal organs (the peritoneal cavity) typically caused by liver disease. Disorders that may be associated with ascites include: cirrhosis, hepatitis, portal vein thrombosis, constrictive pericarditis, congestive heart failure, liver cancer, ovarian cancer, protein-losing enteropathy, nephrotic syndrome, and pancreatitis. Some agents are available for the treatment of ascites, for example, furosemide but a great need remains for improved ascites therapeutics. See Shiozaki, et al. (2006) *J. Physiol. Sci.* 56(6): 401-406.

Autism

Autism spectrum disorder (ASD) is a range of complex neurodevelopment disorders, characterized by social impairments, communication difficulties, and restricted, repetitive, and stereotyped patterns of behavior. Autistic disorder, sometimes called autism or classical ASD, is the most severe form of ASD, while other conditions along the spectrum include a milder form known as Asperger syndrome, the rare condition called Rett syndrome, and childhood disintegrative disorder and pervasive developmental disorder not otherwise specified (usually referred to as PDD-NOS). Although ASD varies significantly in character and severity, it occurs in all ethnic and socioeconomic groups and affects every age group. Experts estimate that three to six people out of every 1,000 may develop ASD. Males are four times more likely to have ASD than females. NINDS Autism Fact Sheet (September 2009). Furthermore, various GABA A subunit types, such as $\alpha_3$ variant sequences and $\alpha_4$ isoforms have been linked to autism. WO 2009/100040. There is no cure for ASD, thus there exists a great need for therapeutics to treat autism.

Multiple lines of evidence, including genetic and imaging studies, suggest that the anterior cingulate cortex and gamma-amino-butyric acid (GABA) system may be affected in autism. Compared to controls, the autistic patients show a significant decrease in the mean density of $GABA_A$ receptors in the supragranular (46.8%) and infragranular (20.2%) layers of the anterior cingulate cortex (ACC) and in the density of benzodiazepine binding sites in the supragranular (28.9%) and infragranular (16.4%) lamina. In addition, a trend for a decrease in the density of benzodiazepine sites was found in the infragranular layers (17.19%) in the autism group. These findings suggest that in the autistic group this downregulation of both benzodiazepine sites and $GABA_A$ receptors in the ACC may be the result of increased GABA innervation and/or release disturbing the delicate excitation/inhibition balance of principal neurons as well as their output to key limbic cortical targets. These disturbances may underlie the core alterations in socio-emotional behaviors in autism. Oblak, et al. et al. (August 2009) "Decreased $GABA_A$ receptors and benzodiazepine binding sites in the anterior cingulate cortex in autism." Autism Res. 2009 August; 2(4):205-19. Therefore, therapeutics that target the $GABA_A$ receptor may be useful in treating autism.

Bipolar Disorder

Bipolar disorder, also known as manic-depressive illness, is a brain disorder that causes unusual shifts in a person's mood, energy, and ability to function. They can result in damaged relationships, poor job or school performance, and even suicide. About 5.7 million American adults or about 2.6 percent of the population age 18 and older have bipolar disorder in any given year. Bipolar disorder typically develops in late adolescence or early adulthood. However, some people have their first symptoms during childhood, and some develop them late in life. It is often not recognized as an illness, and people may suffer for years before it is properly diagnosed and treated. National Institute of Mental Health "Bipolar Disorder" (2008) Complete Publication.

Bipolar disorder causes dramatic mood swings—from overly "high" and/or irritable to sad and hopeless, and then back again, often with periods of normal mood in between. Severe changes in energy and behavior go along with these changes in mood. The periods of highs and lows are called episodes of mania and depression. National Institute of Mental Health "Bipolar Disorder" (2008) Complete Publication.

Signs and symptoms of mania (or a manic episode) include: increased energy, activity, and restlessness; excessively "high," overly good, euphoric mood; extreme irritability; racing thoughts and talking very fast, jumping from one idea to another, distractibility, difficulty concentrating; little sleep needed; unrealistic beliefs in one's abilities and powers; poor judgment; spending sprees; a lasting period of behavior that is different from usual; increased sexual drive; drug abuse, particularly cocaine, alcohol, and sleeping medications; provocative, intrusive, or aggressive behavior; and/or denial that anything is wrong. A manic episode is diagnosed if elevated mood occurs with three or more of the other symptoms most of the day, nearly every day, for 1 week or longer. National Institute of Mental Health "Bipolar Disorder" (2008) Complete Publication.

Signs and symptoms of depression (or a depressive episode) include: lasting sad, anxious, or empty mood; feelings of hopelessness or pessimism; feelings of guilt, worthlessness, or helplessness; loss of interest or pleasure in activities once enjoyed, including sex; decreased energy, a feeling of fatigue or of being "slowed down"; difficulty concentrating, remembering, making decisions; restlessness or irritability; sleeping too much, or cannot sleep; change in appetite and/or unintended weight loss or gain; chronic pain or other persistent bodily-symptoms that are not caused by physical illness or injury; and/or thoughts of death or suicide, or suicide attempts. A depressive episode is diagnosed if five or more of these symptoms last most of the day, nearly every day, for a period of 2 weeks or longer; National Institute of Mental Health "Bipolar Disorder" (2008) Complete Publication.

A mild to moderate level of mania is called hypomania. Hypomania may feel good to the person who experiences it and may even be associated with good functioning and enhanced productivity. Thus even when family and friends learn to recognize the mood swings as possible bipolar disorder, the person may deny that anything is wrong. Without proper treatment, however, hypomania can become severe mania in some people or can switch into depression.

In some people, however, symptoms of mania and depression may occur together in what is called a mixed bipolar state. Symptoms of a mixed state often include agitation, trouble sleeping, significant change in appetite, psychosis, and suicidal thinking. A person may have a very sad, hopeless mood while at the same time feeling extremely energized.

The classic form of the illness, which involves recurrent episodes of mania and depression, is called bipolar I disorder. Some people, however, never develop severe mania but instead experience milder episodes of hypomania that alternate with depression; this form of the illness is called bipolar II disorder. When four or more episodes of illness occur within a 12-month period, a person is said to have rapid-cycling bipolar disorder. Some people experience multiple episodes within a single week, or even within a single day. Rapid cycling tends to develop later in the course of illness and is more common among women than among men.

Medications known as "mood stabilizers" usually are prescribed to help control bipolar disorder (e.g. lithium or valproic acid-DEPAKOTE/VALPROATE). In addition to medication, psychosocial treatments—including certain forms of psychotherapy, are often used to treat bipolar disorders. Depending on the medication, side effects include weight gain, nausea, tremor, reduced sexual drive or performance, anxiety, hair loss, movement problems, or dry mouth. Lithium treatment can cause low thyroid levels, resulting in the need for thyroid supplementation. Additionally, Valproate® may lead to adverse hormone changes in teenage girls and polycystic ovary syndrome in women who began taking the medication before age 20. Further, women suffering bipolar disorder who wish to conceive, or who become pregnant, face special challenges due to the possible harmful effects of existing mood stabilizing medications on the developing fetus and the nursing infant. National Institute of Mental Health "Bipolar Disorder" (2008) Complete Publication. Improved bipolar disorder therapeutics may be developed that act to increase GABA activity.

Postmortem and genetic studies have linked neuropsychiatric disorders including schizophrenia and bipolar disorder with GABAergic neurotransmission and various specific $GABA_A$ receptor subunits. Further, $GABA_A$ receptor-associated proteins involved in $GABA_A$ receptor trafficking, targeting, clustering, and anchoring that often carry out these functions in a subtype-specific manner. Charych, et al. (2009) "$GABA_A$ receptors and their associated proteins: implications in the etiology and treatment of schizophrenia and related disorders. Neuropharmacology. 57(5-6): 481-95. Therefore, $GABA_A$ receptor specific therapeutics that improve inhibition may be beneficial because bipolar disease is a state of alterations of abnormal inhibition/excitation without adequate inhibition.

Cognition, Learning, and Memory

The cognitive abilities of mammals are thought to be dependent on cortical processing. It has generally been accepted that the most relevant parameters for describing and understanding cortical function are the spatio-temporal patterns of activity. In particular, long-term potentiation and long-term depression have been implicated in memory and learning and may play a role in cognition. Oscillatory and synchronized activities in the brains of mammals have been correlated with distinct behavioral states.

Synchronization of spontaneous neuronal firing activity is thought to be an important feature of a number of normal and pathophysiological processes in the central nervous system. Examples include synchronized oscillations of population activity such as gamma rhythms in the neocortex, which are thought to be involved in cognition (Singer and Gray (1995) Annu. Rev. Neurosci. 18: 855-86), and theta rhythm in hippocampus, which is thought to play roles in spatial memory and in the induction of synaptic plasticity (Heurta and Lisman (1995) Neuron. 15: 1053-63; Heurta and Lisman (1996) J. Neurophysiol. 75: 877-84; O'Keefe (1993) Curr. Opin. Neurobiol. 3: 917-24). To date, most research on the processes underlying the generation and maintenance of spontaneous synchronized activity has focused on synaptic mechanisms. However, there is evidence that nonsynaptic mechanisms may also play important roles in the modulation of synchronization in normal and pathological activities in the central nervous system.

Depression

Depression is a common but serious illness, the most common are major depressive disorder and dysthymic disorder. Major depressive disorder, also called major depression, is characterized by a combination of symptoms that interfere with a person's ability to work, sleep, study, eat, and enjoy once-pleasurable activities. Major depression is disabling and prevents a person from functioning normally. An episode of major depression may occur only once in a person's lifetime, but more often, it recurs throughout a person's life. National Institute of Mental Health "Depression" (2008) Complete Publication.

The forms of depression include:

Dysthymic disorder, also called dysthymia, is characterized by long-term (two years or longer) but less severe symptoms that may not disable a person but can prevent one from functioning normally or feeling well. People with dysthymia may also experience one or more episodes of major depression during their lifetimes.

Psychotic depression, which occurs when a severe depressive illness is accompanied by some form of psychosis, such as a break with reality, hallucinations, and delusions. Postpartum-depression, which is diagnosed if a new mother develops a major depressive episode within one month after delivery. It is estimated that 10 to 15 percent of women experience postpartum depression after giving birth.

Seasonal affective disorder (SAD), which is characterized by the onset of a depressive illness during the winter months, when there is less natural sunlight. The depression generally lifts during spring and summer. SAD may be effectively treated with light therapy, but nearly half of those with SAD do not respond to light therapy alone. Antidepressant medication and psychotherapy can reduce SAD symptoms, either alone or in combination with light therapy. National Institute of Mental Health "Depression" (2008) Complete Publication.

Depression can be treated with a number of methods. The most common treatments are medication and psychotherapy. Antidepressants work to normalize neurotransmitters, notably serotonin, norepinephrine, and dopamine. The newest and among the most popular types of antidepressant medications are called selective serotonin reuptake inhibitors (SSRIs). SSRIs include fluoxetine (Prozac®), citalopram (Celexa®), sertraline (Zoloft®), and several others. Serotonin and norepinephrine reuptake inhibitors (SNRIs) are similar to SSRIs and include venlafaxine (Effexor®) and duloxetine (Cymbalta®). SSRIs and SNRIs are more popular than the older classes of antidepressants, such as tricyclics-named for their chemical structure- and monoamine oxidase inhibitors (MAOIs) because they tend to have fewer side effects. However, medications affect everyone differently-no one-size-fits-all approach to medication exists. National Institute of Mental Health "Depression" (2008) Complete Publication.

For all classes of antidepressants, patients can experience side effects. Antidepressants may cause mild and often temporary side effects in some people, but they are usually not long-term. The most common side effects associated with SSRIs and SNRIs include: headache, nausea, insomnia, nervousness, agitation, and sexual problems. National Institute of Mental Health "Depression" (2008) Complete Publication. Tricyclic antidepressants also can cause side effects including: dry mouth, constipation, bladder problems, sexual problems, blurred vision, and daytime drowsiness. Additionally, patients taking MAOIs must adhere to significant food and medicinal restrictions to avoid potentially serious interactions. They must avoid certain foods that contain high levels of the chemical tyramine, which is found in many cheeses, wines and pickles, and some medications including decongestants. MAOIs interact with tyramine in such a way that may cause a sharp increase in blood pressure, which could lead to a stroke. National Institute of Mental Health "Depression" (2008) Complete Publication.

GABA is involved in both clinical depression and in animal models of depression. Kram, et al. (October 2000) "Effects of learned helplessness on brain GABA receptors." Neuroscience Research 38(2): 193-198. Therefore improved depression therapeutics based on the GABAergic system may provide better medication.

Epilepsy

Epilepsy is characterized by abnormal discharges of cerebral neurons and is typically manifested as various types of seizures. Epileptiform activity is identified with spontaneously occurring synchronized discharges of neuronal populations that can be measured using electrophysiological techniques. Epilepsy is one of the most common neurological disorders, affecting about 1% of the population. There are various forms of epilepsy, including idiopathic, symptomatic, and cryptogenic. Genetic predisposition is thought to be the predominant etiologic factor in idiopathic epilepsy. Symptomatic epilepsy usually develops as a result of a structural abnormality in the brain.

Status epilepticus is a particularly severe form of seizure, which is manifested as multiple seizures that persist for a significant length of time, or serial seizures without any recovery of consciousness between seizures. The overall mortality rate among adults with status epilepticus is approximately 20 percent. Patients who have a first episode are at substantial risk for future episodes and for the development of chronic epilepsy. The frequency of status epilepticus in the United States is approximately 150,000 cases per year, with approximately 55,000 deaths being associated with status epilepticus annually. Sirven and Waterhouse (2003) "Management of Status Epilepticus" American Family Physician 68: 469-476. Acute processes that are associated with status epilepticus include intractable epilepsy, metabolic disturbances (e.g., electrolyte abnormalities, renal failure, and sepsis), central nervous system infection (meningitis or encephalitis), stroke, degenerative diseases, head trauma, drug toxicity, and hypoxia. The fundamental pathophysiology of status epilepticus involves a failure of mechanisms that normally abort an isolated seizure. This failure can arise from abnormally persistent, excessive excitation or ineffective recruitment of inhibition. Studies have shown that excessive activation of excitatory amino acid receptors can cause prolonged seizures and suggest that excitatory amino acids may play a causative role. Status epilepticus can also be caused by penicillin and related compounds that antagonize the effects of γ-aminobutyric acid (GABA), the primary inhibitory neurotransmitter in the brain.

One early diagnostic procedure for epilepsy involved the oral administration of large quantities of water together with injections of vasopressin to prevent the accompanying diuresis. This procedure was found to induce seizures in epileptic patients, but rarely in non-epileptic individuals. Garland, et al. (1943) Lancet 2: 566. Status epilepticus can be blocked in kainic acid-treated rats by intravenous injection of mannitol. Baran, et al. (1987) Neuroscience 21: 679. This effect is similar to that achieved by intravenous injection of urea in human patients. Carter (1962) Epilepsia 3: 198. The treatment in each of these cases increases the osmolarity of the blood and extracellular fluid, resulting in water efflux from the cells and an increase in extracellular space in the brain. Acetazolamide (ACZ), a diuretic with a different mechanism of action (inhibition of carbonic anhydrase), has been studied experimentally as an anticonvulsant (White, et al. (1986) Advance Neurol. 44: 695; Guillaume, at al. (1991) Epilepsia 32: 10) and used clinically on a limited basis (Tanimukai, et al. (1965) Biochem. Pharm. 14: 961; Forsythe, et al. (1981) Develop. Med. Child Neurol. 23: 761). Although its mechanism of anticonvulsant action has not been determined, ACZ does have a clear effect on the cerebral extracellular space.

Traditional anti-epileptic drugs exert their principal effect through one of three mechanisms: (a) inhibition of repetitive, high-frequency neuronal firing by blocking voltage-dependent sodium channels; (b) potentiation of γ-aminobutyric acid (gamma-aminobutyric acid, GABA)-mediated postsynaptic inhibition; and (c) blockade of T-type calcium channels.

Many current anti-epileptic drug therapies exert their pharmacological effects on all brain cells, regardless of their involvement in seizure activity. Common side effects are over-sedation, dizziness, loss of memory and liver damage. Furthermore, 20-30% of epilepsy patients are refractory to current therapy. Therefore there is a great need for improved epilepsy therapeutics to reduce both morbidity and mortality.

Glaucoma

Glaucoma is a group of diseases that can damage the eye's optic nerve and result in vision loss and blindness. Glaucoma occurs when the normal fluid pressure inside the eyes slowly rises. Open-angle glaucoma is the most common form. Other types of glaucoma include: (1) low-tension or normal-tension glaucoma; (2) angle-closure glaucoma; (3) congenital glaucoma; (4) secondary glaucomas; and (5) pigmentary glaucoma including neovascular glaucoma. Everyone is at risk for glaucoma but some populations are at higher risk than others including African Americans over age 40, everyone over age 60, and people with a family history of glaucoma. National Eye Institute Glaucoma Fact Sheet (2008).

Glaucoma is usually detected through a comprehensive eye exam that includes: (a) visual acuity test; (b) visual field test; (c) dilated eye exam; (d) tonometry; and (e) pachymetry. Current glaucoma treatments include medicines, laser trabeculoplasty, conventional surgery, or a combination of any of these, however there is a great need for improved glaucoma therapeutics. National Eye Institute Glaucoma Fact Sheet (2008).

Huntington's Disease

Huntington's disease (HD) results from neuronal degeneration leading to uncontrolled movements, loss of intellectual faculties, and emotional disturbance. HD is an autosomal dominant disease caused by a CAG expansion in the Htt gene that leads to a poly-glutamine expansion in the disease protein huntingtin. GABAergic interneurons are particularly sensitive to the accumulation of mutant huntingtin and die early in the development of HD. Some early symptoms of HD are mood swings, depression, irritability or trouble driving, learning new things, remembering a fact, or making a decision. As the disease progresses, concentration on intellectual tasks becomes increasingly difficult, and the patient may have difficulty feeding himself or herself and swallowing. The rate of disease progression and the age of onset vary from person to person. A genetic test, coupled with a complete medical history and neurological and laboratory tests, helps physicians diagnose HD. Presymptomic testing is available for individuals who are at risk for carrying the HD gene. In 1 to 3 percent of individuals with HD, no family history of HD can be found. NINDS Publication "Huntington's Disease: Hope Through Research" (2009).

Physicians prescribe a number of medications to help control emotional and movement problems associated with HD. In August 2008 the U.S. Food and Drug Administration approved tetrabenazine to treat Huntington's chorea (the involuntary writhing movements), making it the first drug approved for use in the United States to treat the disease. However, drugs used to treat the symptoms of HD have side effects such as fatigue, restlessness, or hyperexcitability. NINDS Publication "Huntington's Disease: Hope Through Research" (2009).

Huntington's disease (HD) is a neurodegenerative disorder that involves disruptions in GABA signaling. GABA is the major inhibitory neurotransmitter in the central nervous system (CNS). HD destroys striatal GABAergic neurons. Directing GABA synthesis, degradation, transport, or receptors can control GABA signaling and so drugs that target these aspects of GABA metabolism may be used for improved therapeutic treatments, for Huntington's disease. Kleppner and Tobin (2001) "GABA signaling: therapeutic targets for epilepsy, Parkinson's disease and Huntington's disease." Expert Opin Ther Targets. 5(2):219-39.

Insomnia

Insomnia is a symptom of any of several sleep disorders, characterized by persistent difficulty falling asleep or staying asleep despite the opportunity. NHLBI Diseases and Conditions Index [Insomnia](October 2009).

Although there are several different degrees of insomnia, three types of insomnia have been clearly identified: transient, acute, and chronic. Transient insomnia lasts from days to weeks. It can be caused by another disorder, by changes in the sleep environment, by the timing of sleep, severe depression, or by stress. Its consequences—sleepiness and impaired psychomotor performance—are similar to those of sleep deprivation. Acute insomnia is the inability to consistently sleep well for a period of between three weeks to six months. Chronic insomnia lasts for years at a time. It can be caused by another disorder, or it can be a primary disorder. Its effects can vary according to its causes. They might include sleepiness, muscular fatigue, hallucinations, and/or mental fatigue; but people with chronic insomnia often show increased alertness. NHLBI Diseases and Conditions Index [Insomnia] (October 2009).

Current insomnia drug therapies that target the $GABA_A$ receptor, hypnotics (e.g., benzodiazepines) may have undesirable side effects, therefore a great need exists for improved insomnia therapeutics with reduced side effects.

Ischemia

Ischemia is a restriction in blood supply, generally due to factors in the blood vessels, with resultant damage or dysfunction of tissue due to inadequate oxygenation and lack of nutrients of the tissue. Insufficient blood supply causes tissue to become hypoxic, or, if no oxygen is supplied at all, anoxic. In contrast with hypoxia, a more general term denoting a shortage of oxygen (usually a result of lack of oxygen in the air being breathed), ischemia is an absolute or relative shortage of the blood supply to an organ. This can cause necrosis (e.g., cell death). In aerobic tissues such as heart and brain, at body temperature necrosis due to ischemia usually takes about 3-4 hours before becoming irreversible. Later, more damage occurs due to the accumulation of metabolic wastes due to lack of adequate blood supply to the tissue. Complete cessation of oxygenation of such organs for more than 20 minutes typically results in irreversible damage.

Inhibition of NKCC1 activity with bumetanide and furosemide significantly reduces the infarct volume and cerebral edema following cerebral focal ischemia suggesting that NKCC1 antagonists may be useful in treating ischemia. Chen and Sun (2005) "The role of Na—K—Cl co-transporter in cerebral ischemia." Neurol. Res. 27(3): 280-286. The typical treatment of ischemia involves "clot-buster" drugs (e.g., Alteplase®) usually given for stroke and heart attack within this time period. However, restoration of blood flow after a period of ischemia can actually be more damaging than the ischemia because reintroduction of oxygen causes a greater production of damaging free radicals, resulting in reperfusion injury. Necrosis is greatly accelerated in reperfusion injury and therefore a great need exists for improved ischemia therapeutics.

Migraine

Migraine headaches afflict 10-20% of the U.S. population, with an estimated loss of 64 million workdays annually. Migraine headache is characterized by pulsating head pain that is episodic, unilateral or bilateral, lasting from 4 to 72 hours and often associated with nausea, vomiting, and hypersensitivity to light and/or sound. When accompanied by premonitory symptoms, such as visual, sensory, speech or motor symptoms, the headache is referred to as "migraine with aura," formerly known as classic migraine. When not accompanied by such symptoms, the headache is referred to as "migraine without aura," formerly known as common migraine. Both types evidence a strong genetic component, and both are three times more common in women than men. The precise etiology of migraine has yet to be determined. It has been theorized that persons prone to migraine have a reduced threshold for neuronal excitability, possibly due to reduced activity of the inhibitory neurotransmitter γ-aminobutyric acid (GABA). GABA normally inhibits the activity of the neurotransmitters serotonin (5-HT) and glutamate, both of which appear to be involved in migraine attacks. The excitatory neurotransmitter glutamate is implicated in an electrical phenomenon called cortical spreading depression, which can initiate a migraine attack, while serotonin is implicated in vascular changes that occur as the migraine progresses.

It has been suggested that cortical spreading depression (CSD) underlies migraines including migraines with visual aura. It is also believed that CSD underlies migraine as part of the trigeminal pain circuit. CSD is characterized by a short burst of intense depolarization in the occipital cortex, followed by a wave of neuronal silence and diminished evoked potentials that advance anteriorly across the surface of the cerebral cortex. Enhanced excitability of the occipital-cortex neurons has been proposed as the basis for CSD. The visual cortex may have a lower threshold for excitability and therefore is most prone to CSD. It has been suggested that mitochondrial disorders, magnesium deficiency, and abnormality of presynaptic calcium channels may be responsible for neuronal hyperexcitability. Welch (1997) "Pathogenesis of Migraine." Seminars in Neurobiol. 17: 4. During a spreading depression event, profound ionic perturbations occur, which include interstitial acidification, extracellular potassium accumulation, and redistribution of sodium and chloride ions to intracellular compartments. In addition, prolonged glial swelling occurs as a homeostatic response to altered ionic extracellular fluid composition, and interstitial neurotransmitter and fatty acid accumulation. Studies have shown that furosemide inhibits regenerative cortical spreading depression in anaesthetized cats. Read, et al. (1997) Cephalagia 17: 826.

Drug therapy is tailored to the severity and frequency of migraine headaches. For occasional attacks, acute treatment may be indicated, but for attacks occurring two or more times per month, or when attacks greatly impact the patient's daily life, prophylactic therapy may be indicated. The side effects of acute and prophylactic treatment agents including serotonin acting agents, beta-blockers, tricyclic antidepressants, anticonvulsants, and botulinum toxin type A injections can limit their use.

GABA modulates nociceptive input to the trigeminocervical complex mainly through $GABA_A$ receptors. Therefore $GABA_A$ receptors may provide a target for the development of new therapeutic agents for both acute and prophylactic treatment of headaches including migraines. Storer, et al. (2001) "GABA receptors modulate trigeminovascular nociceptive neurotransmission in the trigeminocervical complex." *Br J Pharmacol.* 134(4): 896-904.

Nociceptive Pain

Nociceptive pain occurs in response to the activation of a specific subset of peripheral sensory neurons, the nociceptors. It is generally acute (with the exception of arthritic pain), self-limiting and serves a protective biological function by acting as a warning of on-going tissue damage. It is typically well localized and often has an aching or throbbing quality. Examples of include post-operative pain, sprains, bone fractures, burns, bumps, bruises, inflammation (from an infection or arthritic disorder), obstructions, and myofascial pain. Nociceptors are the nerves that sense and respond to parts of the body that suffer from damage. They signal tissue irritation, impending injury, or actual injury. When activated, they transmit pain signals (via the peripheral nerves as well as the spinal cord) to the brain. The pain is typically well localized, constant, and often with an aching or throbbing quality. Visceral pain is the subtype of nociceptive pain that involves the internal organs. It tends to be episodic and poorly localized.

Nociceptive pain is usually treated with opioids and/or non-steroidal anti-inflammatory drugs (NSAIDS) but due to low efficacy, unacceptable and even severe side effects, and addiction potential, their use can be limited. $GABA_A$ receptors are a target for therapeutics to treat nociceptive pain. Hara, et al. (2004) "The Interaction Between Gamma-Aminobutyric Acid Agonists and Diltiazem in Visceral Antinociception in Rats" Anesth Analg 98:1380-1384 reports that the combination of GABA agonists and L-type calcium channel blockers may be used to reduce visceral pain. However, $GABA_A$ agonists are known to have side effects, including sedation, dizziness, euphoria, nausea, and blurred vision. Therefore a great need exists for nociceptive pain therapeutics.

Neuropathic Pain

Neuropathic pain and nociceptive pain differ in their etiology, pathophysiology, diagnosis, and treatment. Neuropathic pain is a common type of chronic, non-malignant pain, which is the result of an injury or malfunction in the peripheral or central nervous system and serves no protective biological function. It is estimated to affect more than 1.6 million people in the U.S. population. Neuropathic pain has many different etiologies, and may occur, for example, due to trauma, diabetes, infection with herpes zoster (shingles), HIV/AIDS (peripheral neuropathies), late-stage cancer, amputation (including mastectomy), carpal tunnel syndrome, chronic alcohol use, exposure to radiation, and as an unintended side-effect of neurotoxic treatment agents, such as certain anti-HIV and chemotherapeutic drugs.

In contrast to nociceptive pain, neuropathic pain is frequently described as "burning," "electric," "tingling," or "shooting" in nature. It is often characterized by chronic allodynia (pain resulting from a stimulus that does not ordinarily elicit a painful response, such as light touch) and hyperalgesia (increased sensitivity to a normally painful stimulus), and may persist for months or years beyond the apparent healing of any damaged tissues.

Taxol-induced peripheral neuropathy model (TIPN) is an art-accepted animal model of neuropathic pain. Cavaletti, et al. (May 1995) "Experimental peripheral neuropathy induced in adult rats by repeated intraperitoneal administration of taxol." Exp Neurol. 133(1): 64-72. Injection of Taxol® intraperitoneally to female Wistar rats induced a peripheral neuropathy that resembles neuropathy in humans. Id. at pages 64; 69. An additional animal model of neuropathic pain comprises the single or five intraperitoneal administration of Taxol® (32 mg/kg) to male Sprague-Dawley rats. Authier, et al. (Dec. 29, 2000) "Description of a short-term Taxol-induced nociceptive neuropathy in rats." Brain Res. 887(2): 239-49.

In a spinal cord injury (SCI) model of neuropathic pain, bumetanide, a NKCC1 antagonist, showed an analgesic effect suggesting that normal or elevated NKCC1 activity plays a role in the development and maintenance of SCI-induced neuropathic pain. Cramer, et al. (2008) "The role of cation-dependent chloride transporters in neuropathic pain following spinal cord injury." *Molecular Pain* 4:36.

Neuropathic pain is difficult to treat. Analgesic drugs that are effective against nociceptive pain (e.g., opioid narcotics and non-steroidal anti-inflammatory drugs) are rarely effective against neuropathic pain. Similarly, drugs that have activity in neuropathic pain are not usually effective against nociceptive pain. The standard drugs that have been used to treat neuropathic pain appear to often act selectively to relieve certain symptoms but not others in a given patient (e.g., relief of allodynia, but not hyperalgesia). Bennett (1998) Hosp. Pract. (Off Ed). 33: 95-98. Treatment agents typically employed in the management of neuropathic pain include tricylic antidepressants (e.g., amitriptyline, imipramine, desimipramine, and clomipramine), systemic local anesthetics, and anti-epileptic drugs (AED) (e.g., phenytoin, carbamazepine, valproic acid, clonazepam, gabapentin, and pregabalin (LYRICA®)). See Lowther (September/October 2005) "Pharmacotherapy Update from the Department of Pharmacy" Vol. VIII, No. 5. Common side effects include over-sedation, dizziness, loss of memory and liver damage. Further, although traditionally not considered useful for the treatment of neuropathic pain, recent studies from genetically modified mice indicate that agents targeting only a subset of benzodiazepine ($GABA_A$) receptors may provide pronounced antihyperalgesic activity against inflammatory and neuropathic pain. Zeilhofer, et al. (2009) "Subtype-selective $GABA_A$ receptor mimetics—novel antihyperalgesic agents?" J Mol Med 87:465-469. Therefore a great need exists for improved neuropathic pain therapeutics.

Neurotoxicity

A variety of chemical and biological agents, as well as some infectious agents, have neurotoxic effects. A common example is the pathophysiological effect of acute ethanol ingestion. Episodic ethanol intoxications and withdrawals, characteristic of binge alcoholism, result in brain damage. Animal models designed to mimic the effects of alcohol in the human have demonstrated that a single dose of ethanol given for 5-10 successive days results in neurodegeneration in the entorhinal cortex, dentate gyrus and olfactory bulbs, accompanied by cerebrocortical edema and electrolyte ($Na^+$ and $K^+$) accumulation. As with other neurodegenerative conditions, research has focused primarily on synaptically based excitotoxic events involving excessive glutamatergic activity, increased intracellular calcium and decreased γ-aminobutyric acid. A great need exists for improved neurotoxicity therapeutics.

Postherpetic Neuralgia

Postherpetic neuralgia (e.g., shingles, herpes zoster) is a painful condition affecting the nerve fibers and skin. Postherpetic neuralgia is a complication of shingles, a second outbreak of the varicella-zoster virus, which initially causes chickenpox. During an initial infection of chickenpox, some of the virus remains in the body, lying dormant inside nerve cells. Years later, the virus may reactivate, causing shingles. Once reactivated, the virus travels along nerve fibers causing pain. When the virus reaches the skin, it produces a rash and blisters. A case of shingles (herpes zoster) usually heals within a month. Some patients continue to feel pain long after the rash and blisters heal—a type of pain called postherpetic neuralgia. A variety of treatments for postherpetic neuralgia exist, although some do not experience complete relief from pain.

Postherpetic neuralgia results when nerve fibers are damaged during an outbreak of shingles. These damaged nerves suffer causing chronic, often excruciating pain that may persist for months—or even years—in the area where shingles first occurred. This complication of shingles occurs much more frequently in older adults. About 50 percent of adults older than 60 experience postherpetic neuralgia after shingles, whereas only 10 percent of all people with shingles do. The symptoms of postherpetic neuralgia are generally limited to the area of the skin where the shingles outbreak first occurred including sharp and jabbing, burning, or deep and aching pain; extreme sensitivity to touch and temperature change; itching and numbness; and headaches. In rare cases, patients might also experience muscle weakness or paralysis—if the nerves involved also control muscle movement. A great need exists for improved postherpetic neuralgia therapeutics.

Ocular Diseases (e.g., Vision Disorders, Ophthalmic Diseases)

It is estimated that the lifetime costs for all people with vision impairment who were born in 2000 will total $2.5 billion (2003 dollars). See generally, Centers for Disease Control and Prevention, Economic Costs Associated with Mental Retardation, Cerebral Palsy, Hearing Loss, & Vision Impairment, United States, 2003, MMWR 2004; 53:57-9. These costs include both direct and indirect costs. Direct medical costs, such as doctor visits, prescription drugs, and inpatient hospital stays, make up 6% of these costs. Direct nonmedical expenses, such as home modifications and special education, make up 16% of the costs. Indirect costs, which include the value of lost wages when a person dies early, cannot work, or is, limited in the amount or type of work he or she can do, make up 77% of the costs. These estimates do not include other expenses, such as hospital outpatient visits, emergency department visits, and family out-of-pocket expenses. The actual economic costs of vision impairment are, therefore, even higher than what is generally reported. U.S. Pat. No. 7,251,528.

Both NKCC and KCC2 are expressed in the outer and inner plexiform layers and colocalized in many-putative amacrine cells and in cells of the ganglion cell layer. However, the somata of putative horizontal cells displayed only NKCC immunoreactivity and many bipolar cells were only immunopositive for KCC2. In the outer retina, application of bumetanide, a specific inhibitor of NKCC activity, (1) increased the steady-state extracellular concentration of $K^+$ ($[K^+]_o$) and enhanced the light-induced decrease in the $[K^+]_o$, (2) increased the sPIII photoreceptor-dependent component of the ERG, and (3) reduced the extracellular space volume. In contrast, in the outer retina, application of furosemide, a specific inhibitor of KCC activity, decreased sPIII and the light-induced reduction in $[K^+]_o$, but had little effect on steady-state $[K^+]_o$. In the inner retina, bumetanide increased the sustained component of the light-induced increase in $[K^+]_o$. These findings thus indicate that NKCC and KCC2 control the $[K^+]_o$ and extracellular space volume in the retina in addition to regulating GABA- and glycine-mediated synaptic transmission. In addition, the anatomical and electrophysiological results together suggest that all of the major neuronal types in the retina are influenced by chloride cotransporter activity. Dmitriev, et al. (July-August 2007) "Multiple functions of cation-chloride cotransporters in the fish retina." Vis Neurosci 24(4): 635-45.

The bumetanide-sensitive $Na^+K^+2Cl^-$ cotransporter (NKCC) also clearly contributes to the $Cl^-$ uptake into the pigmented epithelium (PE), This work reinforces the general consensus that active secretion of $Cl^-$ is the major driving force of aqueous humor formation in mammalian eye and further substantiates the existence of species differences in the mechanism that accomplishes transepithelial $Cl^-$ transport. Kong, et al. (December 2006) "Chloride secretion by porcine ciliary epithelium: New insight into species similarities and differences in aqueous humor formation." Invest Ophthalmol Vis Sci. 47(12): 5428-36.

Additionally, cation-chloride cotransporters are involved in retinal function by mediating neural computation in the retina. The directional responses of DS ganglion cells are mediated in part by the directional release of gamma-aminobutyric acid from starburst dendrites and that the asymmetric distribution of two cotransporters ($K^+Cl^-$ cotransporter and $Na^+K^+Cl^-$ cotransporter) along starburst-cell dendrites mediates direction selectivity. Gavrikov, et al. (Dec. 23, 2003) "Cation-chloride cotransporters mediate neural computation in the retina." *Proc Natl Acad Sci USA* 100(26): 16047-52;

Further, the function of retina depends on cation chloride transporters regulating GABA. In particular, different cation chloride cotransporters in retinal neurons allow for opposite responses to GABA. Thus, in the retina, the opposite effects of GABA on different cell types and on different cellular regions are probably primarily determined by the differential targeting of these two chloride transporters. See e.g., Barbour, et al. (May 1991) "Electrogenic uptake of glutamate and aspartate into glial cells isolated from the salamander (*Ambystoma*) retina." J Physiol. 436: 169-193; Keller, et al. (January 1988) "Regulation of intracellular pH in cultured bovine retinal pigment epithelial cells." Pflugers Arch. 411 (1): 47-52; and Vardi, et al. (Oct. 15, 2000) "Evidence that different cation chloride cotransporters in retinal neurons allow opposite responses to GABA." Journal of Neuroscience 20(20): 7657-63. See also, Basu, et al. (November 1998) "Proton-driven dipeptide uptake in primary cultured rabbit conjunctival epithelial cells." Invest Ophthalmol Vis Sci. 39(12): 2365-73; Cia, et al. (March 2005) Voltage-gated channels and calcium homeostasis in mammalian rod photoreceptors. J Neurophysiol. 93(3): 1468-75; Do, et al. (June 2006) "Swelling-activated $Cl^-$ channels support $Cl^-$ secretion by bovine ciliary epithelium." Invest Ophthalmol Vis Sci. 47(6): 2576-82; Hunt, et al. (November 2005) "Aberrant retinal projections in congenitally deaf mice: how are phenotypic characteristics specified in development and evolution?" Anat Rec A Discov Mol Cell Evol Biol. 287(1): 1051-66; MacLeish and Nurse (July 2007) "Ion channel compartments in photoreceptors: evidence from salamander rods with intact- and ablated terminals." J Neurophysiol. 98(1): 86-95; Mito, et al. (March 1993) "Calcium-dependent regulation of cation transport in cultured human nonpigmented ciliary epithelial cells." Am J Physiol. 264(3 Pt 1): C519-26; Moody (1984) "Effects of intracellular $H^+$ on the electrical properties of excitable cells." Annu Rev Neurosci 7: 257-78; Mroz and Lechene (November 1993) "Extracellular N-methyl-D-glucamine leads to loss of hair-cell sodium, potassium, and chloride." Hear Res. 70(2): 146-50; Schnetkamp (May 8, 1980) "Ion selectivity of the cation transport system of isolated intact cattle rod outer segments: evidence for a direct communication between the rod plasma membrane and the rod disk membranes. *Biochim Biophys Acta*. 598(1): 66-90; and Uhl and Desel (August 1989) "Optical probes of intradiskal processes in rod photoreceptors. II: Light-scattering study of ATP-dependent light reactions." *J Photochem Photobiol B*. 3(4): 549-64.

Accordingly, a number of vision-threatening disorders of the eye presently do not have any effective therapies. One major problem in treatment of such diseases is the inability to deliver therapeutic agents into the eye and maintain them there at therapeutically effective concentrations. Therefore a great need exists for therapeutics to treat ocular diseases.

Parkinson's Disease

Parkinson's disease (PD) belongs to a group of conditions called motor system disorders, which result from the loss of dopamine-producing brain cells. The four primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. PD usually affects people over the age of 50. Early symptoms of PD are subtle and occur gradually. Other symptoms may include depression and other emotional changes; difficulty in swallowing, chewing, and speaking; urinary problems or constipation; skin problems; and sleep disruptions. NINDS Parkinson's Disease Information Page (Sep. 23, 2009).

At present, there is no cure for PD, but a variety of medications provide dramatic relief from the symptoms. Usually, patients are given levodopa combined with carbidopa. Carbidopa delays the conversion of levodopa into dopamine until it reaches the brain. Nerve cells can use levodopa to make dopamine and replenish the brain's dwindling supply. Although levodopa-helps at least three-quarters of parkinsonian cases, not all symptoms respond equally to the drug. Bradykinesia and rigidity respond best, while tremor may be only marginally reduced. Problems with balance and other symptoms may not be alleviated at all. Anticholinergics may help control tremor and rigidity. Other drugs, such as bromocriptine, pramipexole, and ropinirole, mimic the role of dopamine in the brain, causing the neurons to react asthey would to dopamine. An antiviral drug; amantadine, also appears to reduce symptoms. In May 2006, the FDA approved rasagiline (AZILECT®) to be used along with levodopa for patients with advanced PD or as a single-drug treatment for early PD. NINDS Parkinson's Disease Information Page (Sep. 23, 2009).

Parkinson's disease (PD) is a neurodegenerative disorder that involves disruptions in GABA signaling. GABA is the major inhibitory neurotransmitter in the central nervous system (CNS). PD destroys the input to striatal GABAergic neurons. Targeting GABA synthesis, degradation, transport, or receptors with new therapeutics may control GABA signaling, and therefore may be used for improved therapeutic treatments for Parkinson's disease. Kleppner and Tobin (2001) "GABA signaling: therapeutic targets for epilepsy, Parkinson's disease and Huntington's disease." Expert Opin. Ther. Targets. 5(2):219-39.

Schizophrenia

Schizophrenia is a chronic, severe, and disabling brain disorder that affects about 1.1 percent of the U.S. population age 18 and older in a given year. People with schizophrenia sometimes hear voices others do not hear, believe that others are broadcasting their thoughts to the world, or become convinced that others are plotting to harm them. These experiences can make them fearful and withdrawn and cause difficulties when they try to have relationships with others. National Institute of Mental Health "Schizophrenia" website (2008).

Symptoms usually develop in men in their late teens or early twenties and women in the twenties and thirties, but in rare cases, can appear in childhood. They can include hallucinations, delusions, disordered thinking, movement disorders, flat affect, social withdrawal, and cognitive deficits. No cause of schizophrenia has been determined nor is there any curative therapy; however, antipsychotics are used in the treatment of symptoms. National Institute of Mental Health "Schizophrenia" website (2008).

Further, schizophrenia is associated with both decreased numbers and abnormalities in the distribution of GABAergic neurons in the cortex, particularly in the cortical laminae. Kaplan & Sadock's Comprehensive Textbook of Psychiatry ($7^{th}$ Ed) (2008). In the postmortem studies of schizophrenics, antipsychotic naive schizophrenics, and non schizophrenic controls, show a significant decrease in the number of GABA containing inter neurons, and a lessened amount of GABA production within these inter neurons in both of the schizophrenic groups. Nestler (1997) "Schizophrenia. An emerging pathophysiology. Nature 385(6617): 578-9. Therefore therapeutic agents that target the GABA system may be useful in treating schizophrenia.

Tinnitus

Tinnitus is the perception of sound within the human ear in the absence of corresponding external sound. Tinnitus is not a disease but a symptom resulting from a range of underlying causes that can include ear infections, foreign objects or wax in the ear, nose allergies that prevent (or induce) fluid drain and cause wax build-up, and injury from loud noises. Tinnitus can also be caused by hearing impairment and as a side-effect of some medications. Some cases of tinnitus are medically unexplained.

Tinnitus can be perceived in one or both ears or in the head. It is usually described as a ringing noise, but in some patients it takes the form of a high pitched whining, buzzing, hissing, screaming, humming, singing or whistling sound, or as ticking, clicking, roaring, "crickets" or "tree frogs" or "locusts," tunes, songs, or beeping. It has also been described as a "whooshing" sound, as of wind or waves. Tinnitus can be intermittent or it can be continuous in which case it can be the cause of great distress. In some individuals, the intensity of tinnitus can be changed by shoulder, head, tongue, jaw, or eye movements. To date, no satisfactory therapeutics exists for tinnitus.

Partial deafferentation produces a loss of tonic inhibition in the auditory system that may lead to inappropriate neuroplastic changes eventually expressed as the pathophysiology of tinnitus. The pathological down-regulation of GABA provides a potential mechanism for this loss of inhibition. For example, in an animal model of tinnitus, vigabatrin, a GABA agonist, completely and reversibly eliminated the psychophysical evidence of tinnitus. Brozoski. et al. (2007) Vigabatrin, a GABA Transaminase Inhibitor, Reversibly Eliminates Tinnitus in an Animal Model. J Assoc Res Otolaryngol. 8(1): 105-118. Further, the disruption of the NKCC1 gene in mice causes hearing loss. Kahle, et al. (2004) *Proc. Natl. Acad. Sci. USA* 102(46): 16783-16788. Therefore, therapeutics targeting GABAergic system and/or NKCC1 may be useful in the treatment of tinnitus.

Withdrawal Syndrome

Withdrawal syndrome is generally associated with abnormal physical or psychological features that follow the abrupt discontinuation of a drug (e.g., medications, recreational drugs, and/or alcohol) that has the capability of producing physical dependence. (e.g., alcohol withdrawal syndrome, nicotine withdrawal syndrome, opioid withdrawal syndrome, benzodiazepine withdrawal syndrome, methadone withdrawal syndrome, SSRI discontinuation syndrome, hydrocodone withdrawal syndrome). Common withdrawal symptoms include sweating, tremor, vomiting, anxiety, insomnia, and muscle pain. There are different stages of withdrawal. Generally, a person will start to feel worse and worse, hit a plateau, and then the symptoms begin to dissipate. However, withdrawal from certain drugs (e.g., benzodiazepines, alcohol) can be fatal and therefore the abrupt discontinuation of any type of drug is not recommended.

Further, many additions involve compounds which affect the GABAerigic system including but not limited to alcohol and benzodiazepines. Therefore, when a person ceases use of the compound, the GABAergic system is involved in the symptoms of withdrawal syndrome. Nutt and Lingford-Hughes (2008) "Addiction: the clinical interface." *British Journal of Pharmacology* 154(2): 397-405. Therefore agents that act on the GABAergic system may provide therapeutics to treat withdrawal syndromes.

Accordingly, there is a continuing need for compositions and methods for treatment and/or prophylaxis of diseases, disorders, and conditions that involve the $Na^+K^+Cl^-$ co-transporters (e.g., NKCC1 and NKCC2) including but not limited to addictive disorders, anxiety disorders, ascites, bipolar disorder, cancer, endothelial corneal dystrophy, edema, depression, epilepsy, glaucoma, ischemia, migraine, neuropathic pain, nociceptive neuralgia, ocular diseases, pain, postherpetic neuralgia, and schizophrenia. Additionally; there is a continuing need for compositions and methods for treatment and/or prophylaxis of diseases, disorders, and conditions that involve the $GABA_A$ receptors including but not limited to Alzheimer's Disease, addictive disorders, anxiety disorders, autism, bipolar disorder, depression, epilepsy, Huntington's Disease, insomnia, migraine, neuropathic pain, nociceptive pain, pain, Parkinson's disease, personality disorders, psychosis, schizophrenia, seizure disorders, tinnitus, and withdrawal syndromes.

SUMMARY OF THE INVENTION

The present invention provides compounds according to Formulae I, II, III, IV, V, VI, VII, VIII, IX, X, XI, XII, XIII, XIV, XV, XVI, XVII, XVIII, XIX, XX, XXI, XXII, XXIII, XXIV, XXV, and/or XXVI described herein, which are analogs of bumetanide, furosemide, piretanide, azosemide, and torsemide, including derivatives and prodrugs thereof. The compounds of the present invention antagonize NKCC1 and/or $GABA_A$ receptors. The compounds of the present invention may also be useful in the treatment of conditions that involve NKCC1 and/or $GABA_A$ receptors.

Embodiments of the present invention provide compounds according to formula I, II, III, IV, V and/or VI:

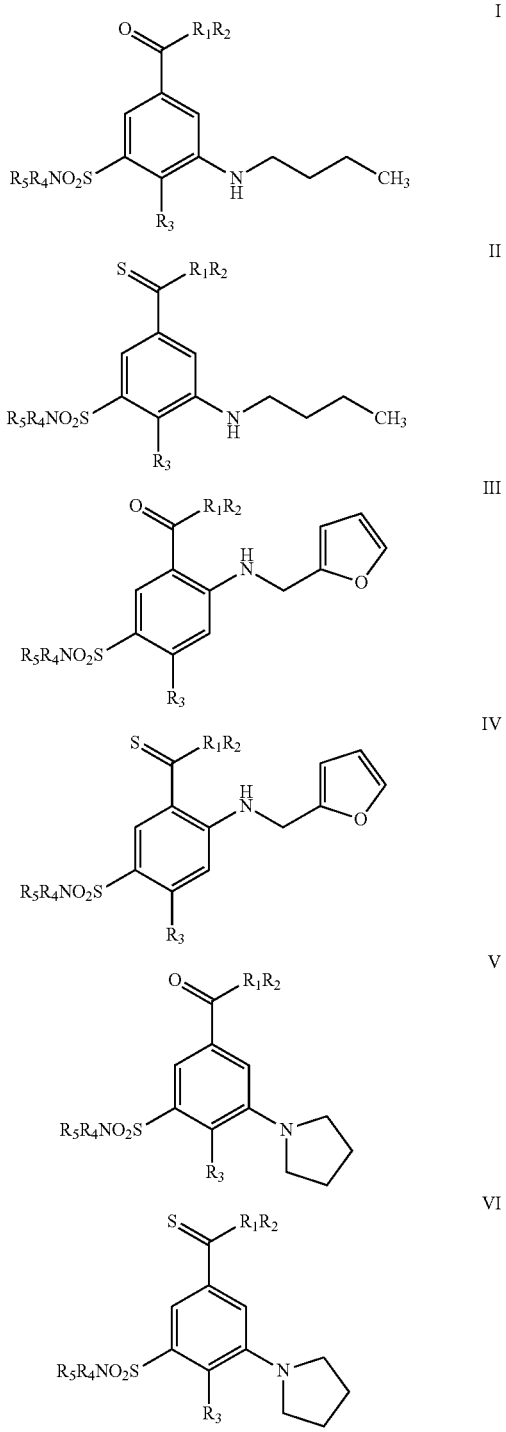

or a pharmaceutically acceptable salt, solvate, tautomer or hydrate thereof, wherein $R_2$ is not present, H, O or S, $R_2$ is not present, H or when $R_1$ is O or S, $R_2$ is selected from the group consisting of hydrogen, alkyl, aralkyl, aryl, alkylaminodialky, alkylcarbonylaminodialkyl, alkyloxycarbonylalkyl, alkylcarbonyloxyalkyl, alkylaldehyde, alkylketoalkyl, alkylamide, alkarylamide, arylamide, an alkylammonium group, alkycarboxylic acid, alkylheteroaryl, alkylhydroxy, a biocompatible polymer such as alkyloxy(polyalkyloxy)alkyhydroxyl, a polyethylene glycol (PEG), polyethylene glycol ester (PEG ester) and a polyethylene glycol ester (PEG ester), methyloxyalkyl, methyloxyalkaryl, methylthioalkyl and methylthioalkaryl, unsubstituted or substituted, and when $R_1$ is not present, $R_2$ selected from the group consisting of hydrogen N,N-dialkylamino, N,N-dialkarylamino, N,N-diarylamino, N-alkyl-N-alkarylamino, N-alkaryl-N-arylamino, N-alkaryl-N-arylamino, unsubstituted or substituted;

$R_3$ is selected from the group consistion of aryl, halo, hydroxyl, alkoxy, and aryloxy, unsubstituted or substituted; and $R_4$ and $R_5$ are each independently selected from the group consisting of hydrogen, alkylaminodialkyl, carbonylalkyl, carbonylalkaryl, carbonylaryl, and salts thereof such as sodium, potassium, calcium, ammonium, trialkylarylammonium and tetraalkylammonium salts, with the following provisos in some embodiments: $R_3$ of formula I is not phenyloxy when $R_1$ is O and $R_2$, $R_4$ and $R_5$ are H, more specifically, in some embodiments, the compound of formula I is not bumetanide; $R_3$ of formula III is not Cl, when $R_1$ is O and $R_2$, $R_4$ and $R_5$ are H, more specifically, in some embodiments, the compound of formula III is not furosemide; $R_2$ of formula III is not methyl when $R_1$ is O, $R_3$ is Cl, and $R_4$ and $R_5$ are H, more specifically, in some embodiments, the compound of formula III is not furosemide methyl ester; $R_3$ of formula V is not phenyloxy when $R_1$ is O and $R_2$, $R_4$ and $R_5$ are H, more specifically, in some embodiments, the compound of formula V is not piretanide.

Embodiments of the present invention provide compounds according to formula VII:

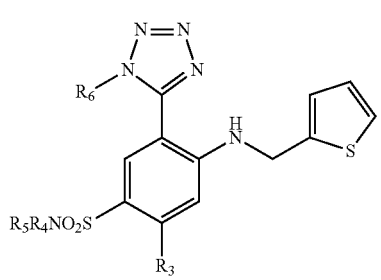

VII or a pharmaceutically acceptable salt, solvate, tautomer or hydrate thereof, wherein $R_3$, $R_4$ and $R_5$ are defined above; and $R_6$ is selected from the group consisting of alkyloxycarbonylalkyl, alkylaminocarbonylalkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl and methylthioalkaryl, unsubstituted or substituted, with the proviso that, in some embodiments, $R_3$ of formula VII is not Cl, when $R_4$, $R_5$ and $R_6$ are H, more specifically, in some embodiments, the compound of formula VII is not azosemide.

Embodiments of the present invention further provide compounds according to formula VIII:

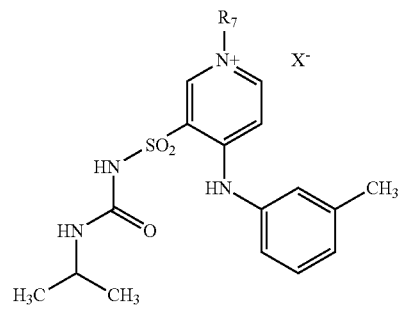

VIII or a pharmaceutically acceptable salt, solvate, tautomer or hydrate thereof, wherein $R_7$ is not present or selected from the group consisting of hydrogen, alkyloxycarbonylalkyl, alkylaminocarbonylalkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl and methylthioalkaryl, unsubstituted or substituted; and $X^-$ is a halide such as bromide, chloride, fluoride, iodide or an anionic moiety such as mesylate or tosylate; alternatively, $X^-$ is not present and the compound forms an "inner" or zwitterionic salt (where $R_7$ is H; See structure VIIa below), with the proviso that, in some embodiments, $R_7$ is always present and $X^-$ is not present and that an acidic proton has been removed from the nitrogen flanked by the carbonyl and sulfonyl moieties. More specifically, in some embodiments, the compound of formula VIII is not torsemide.

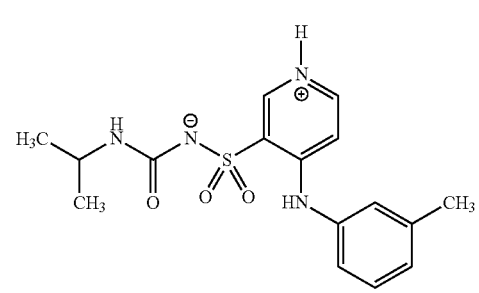

VIIIa

In one aspect, the invention also relates to a compound of the formula IX:

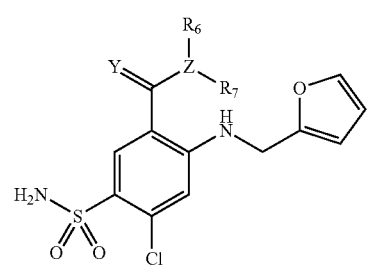

IX or a pharmaceutically acceptable salt thereof, wherein:

Y is oxygen, sulfur, or selenium;

Z is oxygen, sulfur, or nitrogen;

$R_6$ is alkyl, alkylene, alkylcyano, alkylhalo, alkaryl, alkylheterocycloalkyl, or alkylaminodialkyl;

$R_7$ is hydrogen, alkyl, alkaryl, alkylaminodialkyl or alkylheterocycloalkyl; or $R_6$ and $R_7$, together with the atom to which they are attached, form a heterocycloalkyl group; provided that:

if Z is oxygen or sulfur, then $R_7$ is not present;

if Y is oxygen and Z is sulfur, then $R_6$ is not methyl;

if Y is sulfur and Z is sulfur, then $R_6$ is not methyl or alkylaminodialkyl;

if Y is oxygen and Z is oxygen, then $R_6$ is not methyl, ethyl, butyl, methylcyano, unsubstituted benzyl, chloromethyl, 2,2,2-trichloroethyl, ethyl-N-morpholinyl, N,N-dimethyl-2-ethylamino, N,N-dimethyl-3-propylamino or $(CH_3)_2C=CHCH_2CH_2$-(E)-$(CH_3)C=CHCH_2$—;

if Y is oxygen, Z is nitrogen, and $R_7$ is hydrogen, then $R_6$ is not 2-(4-piperazin-1-yl)ethyl, 3-pyridylmethyl, unsubstituted benzyl, or n-butyl;

if Y is oxygen and Z is nitrogen, then $R_6$ and $R_7$ are not both unsubstituted benzyl or ethyl.

In another aspect, the invention relates to a compound of the formula X:

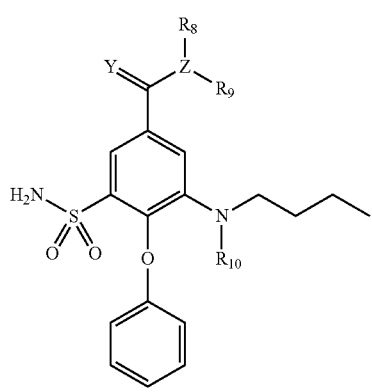

or a pharmaceutically acceptable salt thereof, wherein:

Y is oxygen, sulfur, or selenium;

Z is oxygen, sulfur, or nitrogen;

$R_8$ is hydrogen, alkyl, alkylene, alkylcyano, alkylhalo, alkaryl, alkylheterocycloalkyl, or alkylaminodialkyl;

$R_9$ is hydrogen, alkyl, alkaryl, alkylaminodialkyl or alkylheterocycloalkyl; or $R_8$ and $R_9$, together with the atom to which they are attached, form a heterocycloalkyl group;

$R_{10}$ is hydrogen or alkyl;

provided that:

if Z is oxygen or sulfur, then $R_9$ is not present;

if Z is oxygen and $R_8$ is hydrogen, then $R_{10}$ is not hydrogen or methyl;

if Y is oxygen and Z is oxygen, then $R_8$ is not methyl, unsubstituted benzyl, butyl, or methylcyano;

if Y is oxygen, Z is nitrogen, then $R_9$ is not hydrogen, 2-(4-methylpiperazin-1-yl)ethyl, 3-(4-methylpiperazin-1-yl)propyl, 2-(N-morpholinyl)ethyl, 2-pyridylmethyl, 3-pyridylmethyl, 4-pyridylmethyl, 2-(4-(2-aminoethyl)piperazyn-1-yl)ethyl or a sultamyl group of the formula

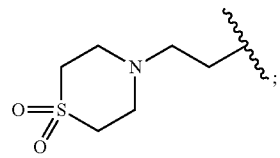 [SMILES: *CCN1CCS(=O)(=O)CC1]

if Y is oxygen and Z is nitrogen, then $R_8$ and $R_9$ are not both ethyl or benzyl; or if Y is oxygen and Z is nitrogen, then $R_8$ and $R_9$, together with the nitrogen atom to which they are attached, do not form a piperazin-1-yl group, a 4-methylpiperazin-1-yl group, or a N-morpholinyl group.

In still another aspect, the invention relates to a compound of the formula XI-XIII:

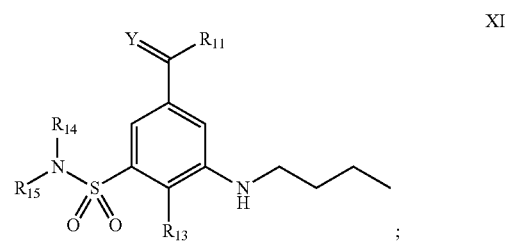

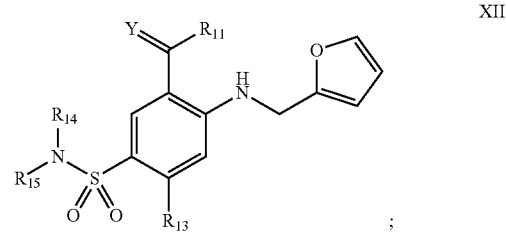

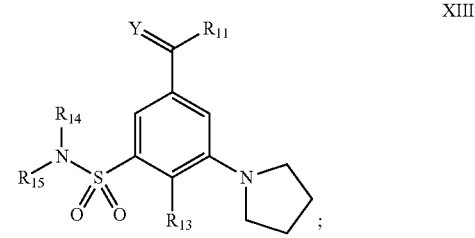

or a pharmaceutically acceptable salt thereof;

wherein:

Y is O, S, or Se;

$R_{11}$ is H, $OR_{12}$, $SR_{12}$, wherein $R_{12}$ is hydrogen, alkyl, aralkyl, aryl, alkylaminodialkyl, alkylcarbonylaminodialkyl, alkyloxycarbonylalkyl, alkylcarbonyloxyalkyl, alkylaldehyde, alkylketoalkyl, alkylamide, alkarylamide, arylamide, an alkylammonium group, alkylcarboxylic acid, alkylheteroaryl, alkylhydroxy, a biocompatible polymer such as alkyloxy(polyalkyloxy)alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl or methylthioalkaryl, unsubstituted or substituted, or $R_{11}$ is N,N-dialkylamino, N,N-dialkarylamino, N,N-diarylamino, N-alkyl-N-alkarylamino, N-alkyl-N-arylamino, or N-alkaryl-N-arylamino, unsubstituted or substituted;

$R_{13}$ is aryl, halo, hydroxy, alkoxy, or aryloxy, unsubstituted or substituted; and $R_{14}$ and $R_{15}$ are each independently hydrogen, alkylaminodialkyl, carbonylalkyl, carbonylalkaryl, or carbonylaryl.

In still another aspect, the invention relates to a compound of the formula XIV:

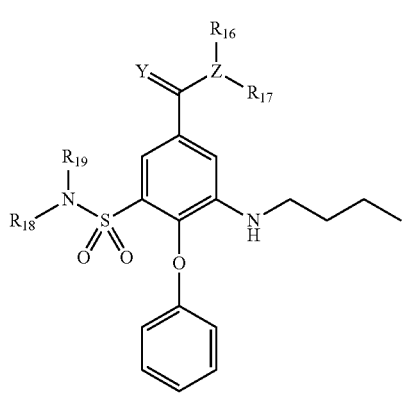

or a pharmaceutically acceptable salt thereof, wherein:

Y is oxygen, sulfur, or selenium;

Z is oxygen, sulfur, or nitrogen;

$R_{16}$ is hydrogen, alkyl, alkylene, alkylcyano, alkylhalo, aryl, alkaryl, alkylheterocycloalkyl, or alkylaminodialkyl;

$R_{17}$ is hydrogen, alkyl, alkaryl, alkylaminodialkyl or alkylheterocycloalkyl; or $R_{16}$ and $R_{17}$, together with the atom to which they are attached, form a heterocycloalkyl group; and $R_{18}$ and $R_{19}$ are each independently hydrogen or alkyl;

provided that if Z is oxygen or sulfur, then $R_{17}$ is not present.

In another aspect, the invention relates to a compound of the formula XV:

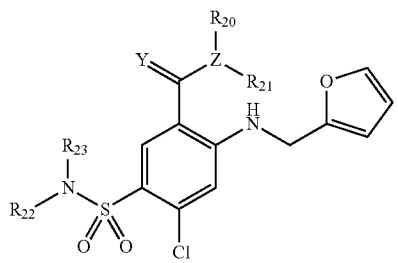

or a pharmaceutically acceptable salt thereof, wherein:

Y is oxygen, sulfur, or selenium;

Z is oxygen, sulfur, or nitrogen;

$R_{20}$ is hydrogen, alkyl, alkylene, alkylcyano, alkylhalo, alkaryl, alkylheterocycloalkyl, or alkylaminodialkyl;

$R_{21}$ is hydrogen, alkyl, alkaryl, alkylaminodialkyl or alkylheterocycloalkyl; or $R_{20}$ and $R_{21}$, together with the atom to which they are attached, form a heterocycloalkyl group; and $R_{22}$ and $R_{23}$ are each independently hydrogen, alkyl, alkenyl, alkoxy, alkaryloxyalkyl, or alkaryl.

The present invention also provides compounds that are derivatives, including prodrugs thereof, of bumetanide. Embodiments of the present invention provide a compound according to Formula XVI:

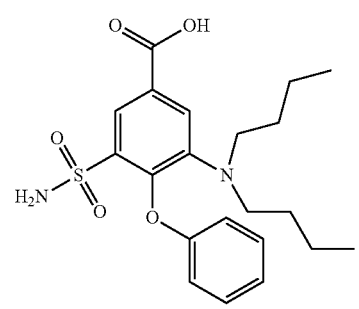 [SMILES: CCCCN(CCCC)c1cc(C(=O)O)cc(S(N)(=O)=O)c1Oc1ccccc1]

(3-Aminosulfonyl-5-N,N-dibutylamino-4-phenoxy-benzoic acid)

A compound of the formula XVII:

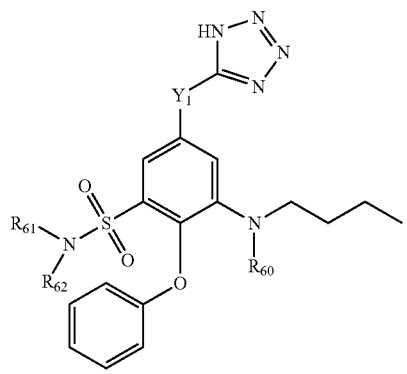

or a pharmaceutically acceptable salt thereof, wherein:

$Y_1$ is —$(CH_2)_x$—, wherein x is either 0, 1, or 2;

$R_{60}$ is hydrogen or alkyl;

$R_{61}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl; and $R_{62}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl, or $R_{61}$ and $R_{62}$, taken together with the nitrogen atom to which they are attached form a 4-8 member cycle which can be substituted or unsubstituted and can have one or more heteroatoms.

A compound of the formula XVIII:

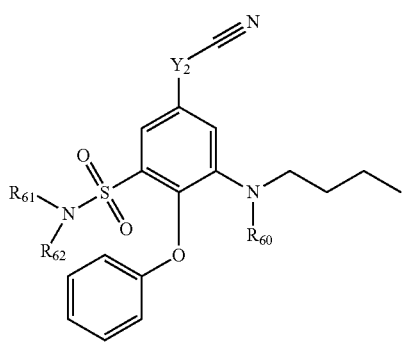

or a pharmaceutically acceptable salt thereof,
wherein:

$Y_2$ is —$(CH_2)_x$—, wherein x is either 0, 1, or 2;

$R_{60}$ is hydrogen or alkyl;

$R_{61}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl; and $R_{62}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl, or $R_{61}$ and $R_{62}$, taken together with the nitrogen atom to which they are attached form a 4-8 member cycle which can be substituted or unsubstituted and can have one or more heteroatoms.

A compound of the formula XIX:

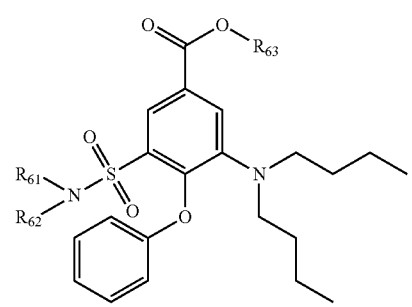

or a pharmaceutically acceptable salt thereof,
wherein:

$R_{61}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl;

$R_{62}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl, or $R_{61}$ and $R_{62}$, taken together with the nitrogen atom to which they are attached form a 4-8 member cycle which can be substituted or unsubstituted and can have one or more heteroatoms; and $R_{63}$ is alkyl, alkylcyano, aryl, heteroaryl, —$CH_2$—C(O)—N($R_{64}$)—$R_{65}$, or —$CH_2$—O—C(O)—$R_{66}$, wherein $R_{64}$, $R_{65}$, and $R_{66}$ are each independently alkyl.

A compound of the formula XX:

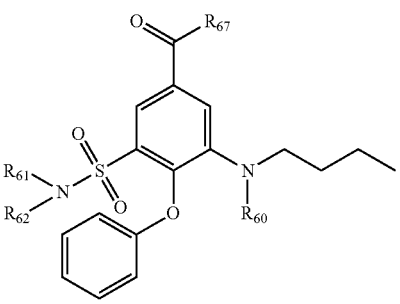

or a pharmaceutically acceptable salt thereof,
wherein:

$R_{60}$ is hydrogen, alkyl, aralkyl, or heteroarylalkyl;

$R_{61}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl;

$R_{62}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl, or $R_{61}$ and $R_{62}$, taken together with the nitrogen atom to which they are attached form a 4-8 member cycle which can be substituted or unsubstituted and can have one or more heteroatoms; and $R_{67}$ is hydrogen, hydroxy, or amino.

A compound of the formula XXI:

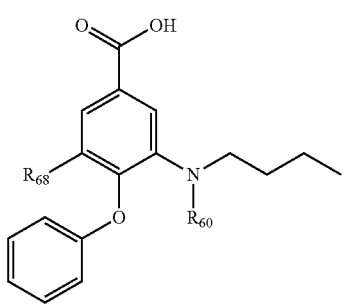

or a pharmaceutically acceptable salt thereof,
wherein:

$R_{60}$ is hydrogen, alkyl, aralkyl, or heteroarylalkyl;

$R_{68}$ is —$SO_2$-alkyl or —N($R_{69}$)—$R_{70}$;

$R_{69}$ is hydrogen, aryl, heteroaryl, cycloalkenyl, cycloalkyl, heterocycloalkyl, alkylcycloalkenyl, alkylcycloalkyl, alkylaryl, alkylheteroaryl or alkylheterocycloalkyl; and $R_{70}$ is hydrogen or $R_{69}$ and $R_{70}$, together with the nitrogen atom to which they are attached, form a heterocycloalkyl.

A compound of the formula XXII:

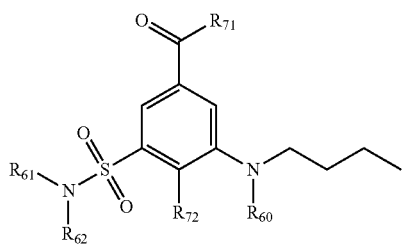

or a pharmaceutically acceptable salt thereof,
wherein:
$R_{60}$ is hydrogen, alkyl, aralkyl, or heteroarylalkyl;
$R_{61}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl;
$R_{62}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl, or $R_{61}$ and $R_{62}$, taken together with the nitrogen atom to which they are attached form a 4-8 member cycle which can be substituted or unsubstituted and can have one or more heteroatoms;
$R_{71}$ is hydroxy or —N($R_{73}$)—$R_{74}$;
$R_{72}$ is halo, aryl, arylamino, heteroarylamino, heterocycloalkyl, heteroaryl, heteroaryloxy, heterocycloalkoxy, or alkythio; and
$R_{73}$ and $R_{74}$ are each independently alkyl.

A compound of the formula XXIII:

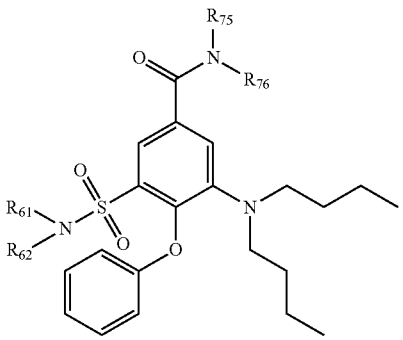

or a pharmaceutically acceptable salt thereof,
wherein:
$R_{60}$ is hydrogen, alkyl, aralkyl, or heteroarylalkyl;
$R_{61}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl;
$R_{62}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl, or $R_{61}$ and $R_{62}$, taken together with the nitrogen atom to which they are attached form a 4-8 member cycle which can be substituted or unsubstituted and can have one or more heteroatoms;
$R_{75}$ is alkyl, aryl, cycloalkenyl, cycloalkyl, heteroaryl, heterocycloalkyl, cycloalkylalkyl, heteroarylalkyl, or dialkylaminoalkyl; and
$R_{76}$ is hydrogen, alkyl, aralkyl, or heteroarylalkyl.

A compound of the formula XXIV:

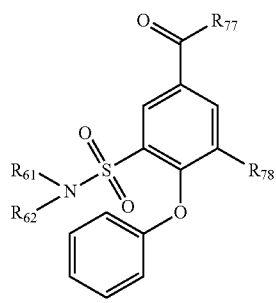

or a pharmaceutically acceptable salt thereof,
wherein:
$R_{61}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl;
$R_{62}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl, or $R_{61}$ and $R_{62}$, taken together with the nitrogen atom to which they are attached form a 4-8 member cycle which can be substituted or unsubstituted and can have one or more heteroatoms;
$R_{77}$ is hydroxy or —N($R_{79}$)—$R_{80}$;
$R_{78}$ is —N($R_{81}$)—$R_{82}$ or heterocycloalkyl;
$R_{79}$ is alkyl, alkaryl, or alkylheteroaryl;
$R_{80}$ and $R_{81}$ are each independently hydrogen, alkyl, alkaryl, or alkylheteroaryl; and
$R_{82}$ is hydrogen, alkyl, aryl or $R_{81}$ and $R_{82}$, together with the nitrogen atom to which they are attached, form a heterocycloalkyl.

A compound of the formula XXV:

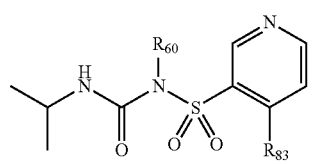

or a pharmaceutically acceptable salt thereof,
wherein:
$R_{60}$ is hydrogen, alkyl, aralkyl, or heteroarylalkyl; and
$R_{83}$ is halo, aryl, heteroaryl, arylamino, heteroarylamino, aryloxy, heteroaryloxy, arylthio, or heteroarylthio.

A compound of the formula XXV:

XXVI or a pharmaceutically acceptable salt thereof, wherein:

Y is oxygen, sulfur, or selenium;

Z is oxygen, sulfur, or nitrogen;

$R_{61}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl;

$R_{62}$ is hydrogen, lower alkyl, lower alkenyl, alkaryl, alkylheteroaryl, aryl, cycloalkenyl, cycloalkyl, dialkylaminoalkyl, heterocycloalkyl, or heteroaryl, or $R_{61}$ and $R_{62}$, taken together with the nitrogen atom to which they are attached form a 4-8 member cycle which can be substituted or unsubstituted and can have one or more heteroatoms;

$R_{72}$ is halo, aryl, arylamino, heteroarylamino, heterocycloalkyl, heteroaryl, heteroaryloxy, heterocycloalkoxy, or alkythio;

$R_{84}$ is alkenyl, alkyl, alkylcyano, alkylhalo, alkaryl, alkylheteroaryl, alkylcycloalkenyl, alkylcycloalkyl, alkylheterocycloalkyl, or alkylaminodialkyl;

$R_{85}$ is hydrogen, alkenyl, alkyl, alkylcyano, alkylhalo, alkaryl, alkylheteroaryl, alkylcycloalkenyl, alkylcycloalkyl, alkylheterocycloalkyl, or alkylaminodialkyl;

$R_{86}$ is —N($R_{87}$)—$R_{88}$, cycloalkenyl, cycloalkyl, or heterocycloalkyl; and $R_{87}$ and $R_{88}$ are each independently hydrogen, alkyl, alkaryl, or alkylheteroaryl, or $R_{87}$ and $R_{88}$, together with the nitrogen atom to which they are attached, form a heterocycloalkyl, provided that if Z is oxygen or sulfur, $R_{85}$ is not present.

Methods of Use

Embodiments of the present invention provide methods of making the compounds including analogs of bumetanide, furosemide, piretanide, azosemide, and torsemide, including derivatives and prodrugs thereof described herein and further provide intermediate compounds formed through the synthetic methods described herein to provide the compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, and/or XXVI.

In still another aspect, the invention relates to a method for treating addictive disorders, Alzheimer's Disease, anxiety disorders, ascites, autism, bipolar disorder, cancer, depression, edema, endothelial corneal dystrophy, epilepsy, glaucoma, Huntington's Disease, insomnia, ischemia, migraine with aura, migraine, neuropathic pain, nociceptive neuralgia, nociceptive pain, ocular diseases, pain, Parkinson's disease, personality disorders, postherpetic neuralgia, psychosis, schizophrenia, seizure disorders, tinnitus, or withdrawal syndromes comprising administering an effective amount of a compound of the formula VII:

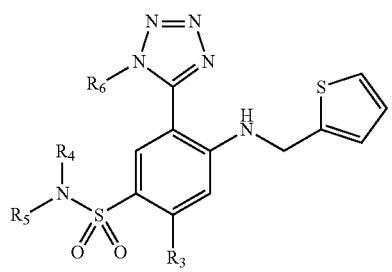

VII or a pharmaceutically acceptable salt thereof, wherein:

$R_3$ is selected from the group consisting of aryl, halo, hydroxy, alkoxy, and aryloxy, unsubstituted or substituted;

$R_4$ and $R_5$ are each independently selected from the group consisting of hydrogen, alkylaminodialkyl, carbonylalkyl, carbonylalkaryl, carbonylaryl and salts thereof; and $R_6$ is selected from the group consisting of alkyloxycarbonylalkyl, alkylaminocarbonylalkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl and methylthioalkaryl, unsubstituted or substituted.

In yet another aspect, the invention relates to a method for treating addictive disorders, Alzheimer's Disease, anxiety disorders, ascites, autism, bipolar disorder, cancer, depression, edema, endothelial corneal dystrophy, epilepsy, glaucoma, Huntington's Disease, insomnia, ischemia, migraine with aura, migraine, neuropathic pain, nociceptive neuralgia, nociceptive pain, ocular diseases, pain, Parkinson's disease, personality disorders, postherpetic neuralgia, psychosis, schizophrenia, seizure disorders, tinnitus, or withdrawal syndromes comprising administering an effective amount of a compound of the formula VIII:

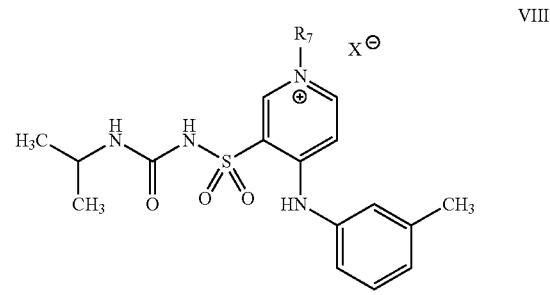

VIII or a pharmaceutically acceptable salt or a zwitterion thereof, wherein:

$R_7$ is selected from the group consisting of hydrogen, alkyloxycarbonylalkyl, alkylaminocarbonylalkyl, alkylaminodialkyl, alkylhydroxy, a biocompatible polymer such as allyloxy(polyalkyloxy)alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl and methylthioalkaryl, unsubstituted or substituted; and $X^-$ is a halide or an anionic moiety; or $X^-$ is not present.

In still another aspect, the invention relates to a method for treating addictive disorders, Alzheimer's Disease, anxiety disorders, ascites, autism, bipolar disorder, cancer, depression, edema, endothelial corneal dystrophy, epilepsy, glaucoma, Huntington's Disease, insomnia, ischemia, migraine with aura, migraine, neuropathic pain, nociceptive neuralgia, nociceptive pain, ocular diseases, pain, Parkinson's disease, personality disorders, postherpetic neuralgia, psychosis, schizophrenia, seizure disorders, tinnitus, or withdrawal syndromes comprising administering an effective amount of a compound of the formula IX:

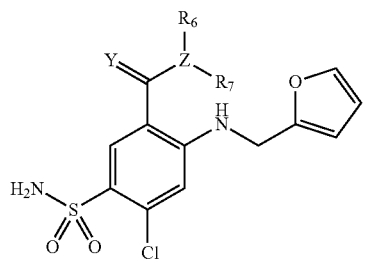

or a pharmaceutically acceptable salt thereof, wherein:

Y is oxygen, sulfur, or selenium;

Z is oxygen, sulfur, or nitrogen;

$R_6$ is hydrogen, alkyl, alkylene, alkylcyano, alkylhalo, alkaryl, alkylheterocycloalkyl or alkylaminodialkyl; and $R_7$ is hydrogen, alkyl, alkaryl, alkylaminodialkyl or alkylheterocycloalkyl; or $R_6$ and $R_7$, together with the atom to which they are attached, form a heterocycloalkyl group; provided that if Z is oxygen or sulfur, then $R_7$ is not present.

In a preferred mode, the compound administered for this method meets the provisos recited above.

In another aspect, the invention relates to a method of inhibiting the $Na^+K^+Cl^-$ cotransporters comprising administering a therapeutically effective amount of a compound of the formula IX:

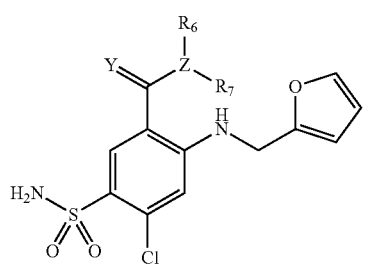

or a pharmaceutically acceptable salt thereof, wherein:

Y is oxygen, sulfur, or selenium;

Z is oxygen, sulfur, or nitrogen;

$R_6$ is hydrogen, alkyl, alkylene, alkylcyano, alkylhalo, alkaryl, alkylheterocycloalkyl or alkylaminodialkyl; and $R_7$ is hydrogen, alkyl, alkaryl, alkylaminodialkyl or alkylheterocycloalkyl; or $R_6$ and $R_7$, together with the atom to which they are attached, form a heterocycloalkyl group; provided that if Z is oxygen or sulfur, then $R_7$ is not present.

In yet another aspect, the invention relates to a method of inhibiting the NKCC 1 (CCC1, BSC2) isoform of the $Na^+K^+Cl^-$ cotransporters comprising administering a therapeutically effective amount of a compound of the formula IX:

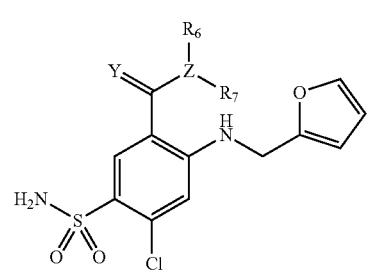

or a pharmaceutically acceptable salt thereof, wherein:

Y is oxygen, sulfur, or selenium;

Z is oxygen, sulfur, or nitrogen;

$R_6$ is hydrogen, alkyl, alkylene, alkylcyano, alkylhalo, alkaryl, alkylheterocycloalkyl or alkylaminodialkyl; and $R_7$ is hydrogen, alkyl, alkaryl, alkylaminodialkyl or alkylheterocycloalkyl; or $R_6$ and $R_7$, together with the atom to which they are attached, form a heterocycloalkyl group; provided that if Z is oxygen or sulfur, then $R_7$ is not present.

In still another aspect, the invention relates to a method of inhibiting the NKCC2 (CCC2, BSC1) isoform of the $Na^+K^+Cl^-$ cotransporters comprising administering an effective amount of a compound of the formula IX:

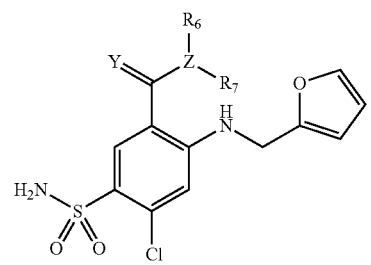

or a pharmaceutically acceptable salt thereof, wherein:

Y is oxygen, sulfur, or selenium;

Z is oxygen, sulfur, or nitrogen;

$R_6$ is hydrogen, alkyl, alkylene, alkylcyano, alkylhalo, alkaryl, alkylheterocycloalkyl or alkylaminodialkyl; and $R_7$ is hydrogen, alkyl, alkaryl, alkylaminodialkyl or alkylheterocycloalkyl; or $R_6$ and $R_7$, together with the atom to which they are attached, form a heterocycloalkyl group; provided that if Z is oxygen or sulfur, then $R_7$ is not present.

In another aspect, the invention relates to a method of inhibiting both the NKCC1 (CCC1, BSC2) isoform and the NKCC2 (CCC2, BSC1) isoform of the $Na^+K^+Cl^-$ cotransporters comprising administering a therapeutically effective amount of a compound of the formula IX:

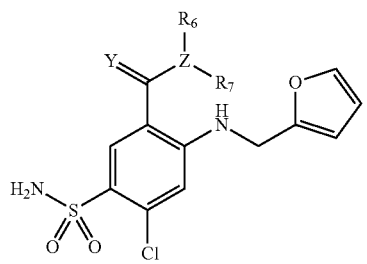

or a pharmaceutically acceptable salt thereof,
wherein:
Y is oxygen, sulfur, or selenium;
Z is oxygen, sulfur, or nitrogen;
R$_6$ is hydrogen, alkyl, alkylene, alkylcyano, alkylhalo, alkaryl, alkylheterocycloalkyl or alkylaminodialkyl; and
R$_7$ is hydrogen, alkyl, alkaryl, alkylaminodialkyl or alkylheterocycloalkyl; or
R$_6$ and R$_7$, together with the atom to which they are attached, form a heterocycloalkyl group; provided that if Z is oxygen or sulfur, then R$_7$ is not present.

In yet another aspect, the invention relates to a method for treating addictive disorders, Alzheimer's Disease, anxiety disorders, ascites, autism, bipolar disorder, cancer, depression, edema, endothelial corneal dystrophy, epilepsy, glaucoma, Huntington's Disease, insomnia, ischemia, migraine with aura, migraine, neuropathic pain, nociceptive neuralgia, nociceptive pain, ocular diseases, pain, Parkinson's disease, personality disorders, postherpetic neuralgia, psychosis, schizophrenia, seizure disorders, tinnitus, or withdrawal syndromes comprising administering an effective amount of a compound of the formula X:

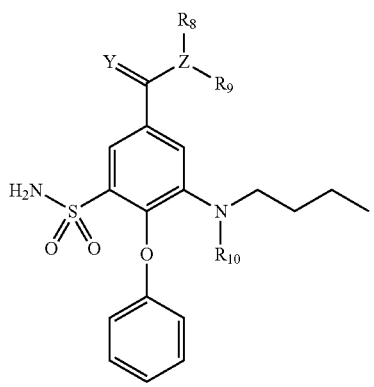

or a pharmaceutically acceptable salt thereof,
wherein:
Y is oxygen, sulfur, or selenium;
Z is oxygen, sulfur, or nitrogen;
R$_8$ is hydrogen, alkyl, alkylene, alkylcyano, alkylhalo, alkaryl, alkylheterocycloalkyl, or alkylaminodialkyl;
R$_9$ is hydrogen, alkyl, alkaryl, dialkylaminoalkyl or alkylheterocycloalkyl; or
R$_8$ and R$_9$, together with the atom to which they are attached, form a heterocycloalkyl group; and
R$_{10}$ is hydrogen or alkyl;
provided that if Z is oxygen or sulfur, then R$_9$ is not present.

In a preferred mode, the compound administered for this method meets the provisos recited above.

In still another aspect, the invention relates to a method of inhibiting the Na$^+$K$^+$Cl$^-$ cotransporters comprising administering a therapeutically effective amount of a compound of the formula X:

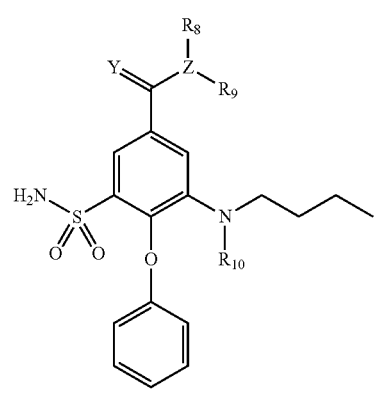

or a pharmaceutically acceptable salt thereof,
wherein:
Y is oxygen, sulfur, or selenium;
Z is oxygen, sulfur, or nitrogen;
R$_8$ is hydrogen, alkyl, alkylene, alkylcyano, alkylhalo, alkaryl, alkylheterocycloalkyl, or alkylaminodialkyl;
R$_9$ is hydrogen, alkyl, alkaryl, dialkylaminoalkyl or alkylheterocycloalkyl; or
R$_8$ and R$_9$, together with the atom to which they are attached, form a heterocycloalkyl group; and
R$_{10}$ is hydrogen or alkyl;
provided that if Z is oxygen or sulfur, then R$_9$ is not present.

In yet another aspect, the invention relates to a method of inhibiting the NKCC 1 (CCC1, BSC2) isoform of the Na$^+$K$^+$Cl$^-$ cotransporters comprising administering a therapeutically effective amount of a compound of the formula X:

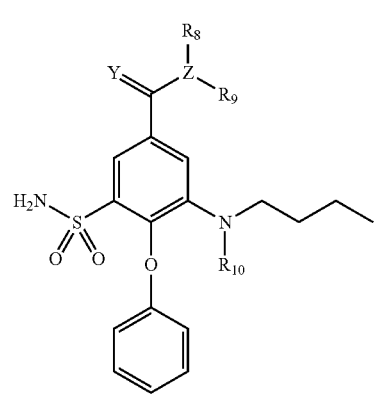

or a pharmaceutically acceptable salt thereof,
wherein:
Y is oxygen, sulfur, or selenium;
Z is oxygen, sulfur, or nitrogen;

R₈ is hydrogen, alkyl, alkylene, alkylcyano, alkylhalo, alkaryl, alkylheterocycloalkyl, or alkylaminodialkyl;

R₉ is hydrogen, alkyl, alkaryl, dialkylaminoalkyl or alkylheterocycloalkyl; or

R₈ and R₉, together with the atom to which they are attached, form a heterocycloalkyl group; and R₁₀ is hydrogen or alkyl;

provided that if Z is oxygen or sulfur, then R₉ is not present.

In another aspect, the invention relates to a method of inhibiting the NKCC2 (CCC2, BSC1) isoform of the Na⁺K⁺Cl⁻ cotransporters comprising administering a therapeutically effective amount of a compound of the formula X:

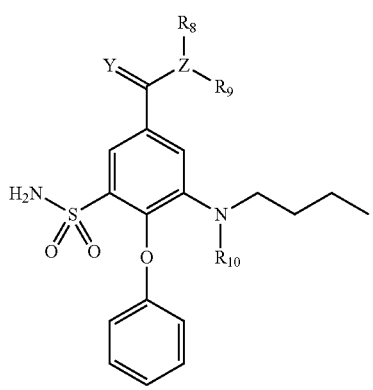

X or a pharmaceutically acceptable salt thereof,
wherein:

Y is oxygen, sulfur, or selenium;

Z is oxygen, sulfur, or nitrogen;

R₈ is hydrogen, alkyl, alkylene, alkylcyano, alkylhalo, alkaryl, alkylheterocycloalkyl, or alkylaminodialkyl;

R₉ is hydrogen, alkyl, alkaryl, dialkylaminoalkyl or alkylheterocycloalkyl; or

R₈ and R₉, together with the atom to which they are attached, form a heterocycloalkyl group; and R₁₀ is hydrogen or alkyl;

provided that if Z is oxygen or sulfur, then R₉ is not present.

In still another aspect, the invention relates to a method of inhibiting both the NKCC1 (CCC1, BSC2) isoform and the NKCC2 (CCC2, BSC1) isoform of the Na⁺K⁺Cl⁻ cotransporters comprising administering a therapeutically effective amount of a compound of the formula X:

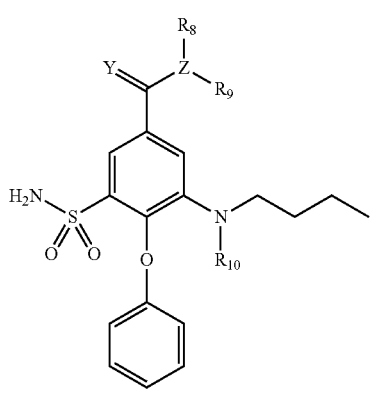

X or a pharmaceutically acceptable salt thereof,
wherein:

Y is oxygen, sulfur, or selenium;

Z is oxygen, sulfur, or nitrogen;

R₈ is hydrogen, alkyl, alkylene, alkylcyano, alkylhalo, alkaryl, alkylheterocycloalkyl, or alkylaminodialkyl;

R₉ is hydrogen, alkyl, alkaryl, dialkylaminoalkyl or alkylheterocycloalkyl; or

R₈ and R₉, together with the atom to which they are attached, form a heterocycloalkyl group; and R₁₀ is hydrogen or alkyl;

provided that if Z is oxygen or sulfur, then R₉ is not present.

In still another aspect, the invention relates to a method for treating addictive disorders, Alzheimer's Disease, anxiety disorders, ascites, autism, bipolar disorder, cancer, depression, edema, endothelial corneal dystrophy, epilepsy, glaucoma, Huntington's Disease, insomnia, ischemia, migraine with aura, migraine, neuropathic pain, nociceptive neuralgia, nociceptive pain, ocular diseases, pain, Parkinson's disease, personality disorders, postherpetic neuralgia, psychosis, schizophrenia, seizure disorders, tinnitus, or withdrawal syndromes comprising administering an effective amount of a compound of the formulae XI-XIII:

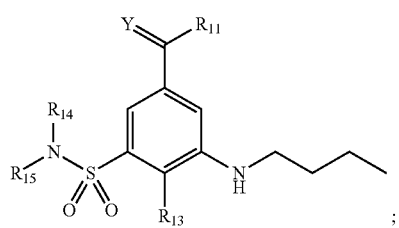

XI

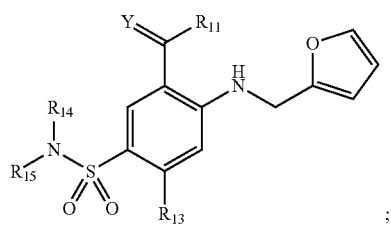

XII

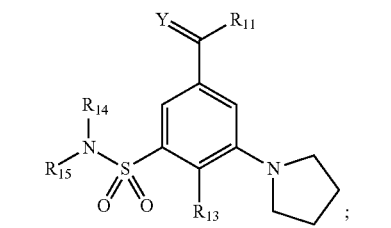

XIII or a pharmaceutically acceptable salt thereof;
wherein:

Y is O, S, or Se;

R₁₁ is H, OR₁₂, SR₁₂, wherein R₁₂ is hydrogen, alkyl, aralkyl, aryl, alkylaminodialkyl, alkylcarbonylaminodialkyl, alkyloxycarbonylalkyl, alkylcarbonyloxyalkyl, alkylaldehyde, alkylketoalkyl, alkylamide, alkarylamide, arylamide, an alkylammonium group, alkylcarboxylic acid, alkylheteroaryl, alkylhydroxy, a biocompatible polymer such as alkyloxy(polyalkyloxy) alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl or methylthioalkaryl, unsubstituted or substituted, or $R_{11}$ is N,N-dialkylamino, N,N-dialkarylamino, N,N-diarylamino, N-alkyl-N-alkarylamino, N-alkyl-N-arylamino, or N-alkaryl-N-arylamino, unsubstituted or substituted;

$R_{13}$ is aryl, halo, hydroxy, alkoxy, or aryloxy, unsubstituted or substituted; and $R_{14}$ and $R_{15}$ are each independently hydrogen, alkylaminodialkyl, carbonylalkyl, carbonylalkaryl, or carbonylaryl.

In still another aspect, the invention relates to a method for treating addictive disorders, Alzheimer's Disease, anxiety disorders, ascites, autism, bipolar disorder, cancer, depression, edema, endothelial corneal dystrophy, epilepsy, glaucoma, Huntington's Disease, insomnia, ischemia, migraine with aura, migraine, neuropathic pain, nociceptive neuralgia, nociceptive pain, ocular diseases, pain, Parkinson's disease, personality disorders, postherpetic neuralgia, psychosis, schizophrenia, seizure disorders, tinnitus, or withdrawal syndromes comprising administering an effective amount of a compound of the formula XIV:

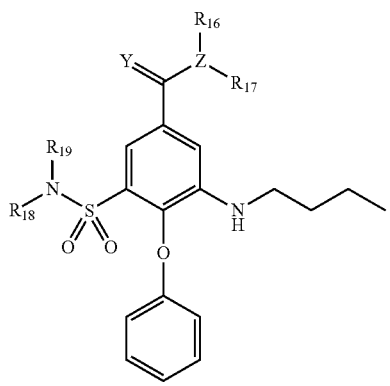

XIV or a pharmaceutically acceptable salt thereof,
wherein:
Y is oxygen, sulfur, or selenium;
Z is oxygen, sulfur, or nitrogen;
$R_{16}$ is hydrogen, alkyl, alkylene, alkylcyano, alkylhalo, aryl, alkaryl, alkylheterocycloalkyl, or alkylaminodialkyl;
$R_{17}$ is hydrogen, alkyl, alkaryl, alkylaminodialkyl or alkylheterocycloalkyl; or
$R_{16}$ and $R_{17}$, together with the atom to which they are attached, form a heterocycloalkyl group; and
$R_{18}$ and $R_{19}$ are each independently hydrogen or alkyl; provided that if Z is oxygen or sulfur, then $R_9$ is not present.

In another aspect, the invention relates to a method for treating addictive disorders, Alzheimer's Disease, anxiety disorders, ascites, autism, bipolar disorder, cancer, depression, edema, endothelial corneal dystrophy, epilepsy, glaucoma, Huntington's Disease, insomnia, ischemia, migraine with aura, migraine, neuropathic pain, nociceptive neuralgia, nociceptive pain, ocular diseases, pain, Parkinson's disease, personality disorders, postherpetic neuralgia, psychosis, schizophrenia, seizure disorders, tinnitus, or withdrawal syndromes comprising administering an effective amount of a compound of the formula XV:

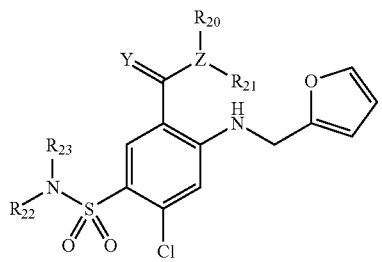

XV or a pharmaceutically acceptable salt thereof,
wherein:
Y is oxygen, sulfur, or selenium;
Z is oxygen, sulfur, or nitrogen;
$R_{20}$ is hydrogen, alkyl, alkylene, alkylcyano, alkylhalo, alkaryl, alkylheterocycloalkyl, or alkylaminodialkyl;
$R_{21}$ is hydrogen, alkyl, alkaryl, alkylaminodialkyl or alkylheterocycloalkyl; or
$R_{20}$ and $R_{21}$, together with the atom to which they are attached, form a heterocycloalkyl group; and
$R_{22}$ and $R_{23}$ are each independently hydrogen, alkyl, alkenyl, alkoxy, alkaryloxyalkyl, or alkaryl.

The present invention also provides compounds that are derivatives, including prodrugs thereof, of bumetanide. Embodiments of the present invention provide a compound according to Formula XVI:

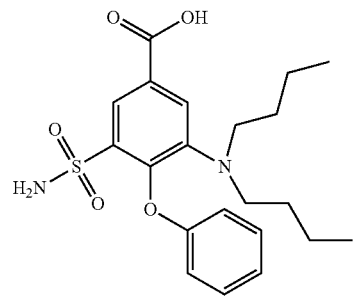

(3-Aminosulfonyl-5-N,N-dibutylamino-4-phenoxybenzoic acid)

The present invention provides methods for treating a condition selected from the group consisting of addictive disorders, Alzheimer's Disease, anxiety disorders, ascites, autism, bipolar disorder, cancer, depression, endothelial corneal dystrophy, edema, epilepsy, glaucoma, Huntington's Disease, insomnia, ischemia, migraine, migraine with aura, neuropathic pain, nociceptive neuralgia, nociceptive pain, ocular diseases, pain, Parkinson's disease, personality disorders, postherpetic neuralgia, psychosis, schizophrenia, seizure disorders, tinnitus, and withdrawal syndromes comprising administering an effective amount of a compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, and/or XXVI. In a preferred embodiment, these compounds are selective antagonists of NKCC1 and/or particular $GABA_A$ receptors.

The present invention also provides methods of using the compounds of formulas I-XXVI for treating disorders involving the $Na^+K^+Cl^-$ co-transporters including but not limited to addictive disorders (e.g., compulsive disorders, eating disorders (e.g., obesity), addiction to narcotics/physical dependence, alcohol addiction, narcotic addiction, cocaine addiction, heroin addiction, opiate addiction, alcoholism, and smoking); anxiety disorders (e.g., anxiety, acute anxiety, panic disorder, social anxiety disorder, obsessive compulsive disorder (OCD), post-traumatic stress disorder (PTSD), generalized anxiety disorder, and specific phobia); ascites (e.g., peritoneal cavity fluid, peritoneal fluid excess, hydroperitoneum, abdominal dropsy, cancer related to ascites, tumors related to ascites); bipolar disorder (e.g., manic-depressive illness, manic phase, depressive phase, mixed bipolar state, bipolar I disorder, bipolar II disorder, rapid-cycling bipolar disorder, bipolar I disorder, bipolar II disorder, rapid-cycling bipolar disorder); cancer (e.g., tumors, cancer related to ascites, tumors related to ascites); depression (e.g., psychotic depression, postpartum depression, seasonal affective disorder (SAD), cortical spreading depression, dysthymia (mild depression)); edema (e.g., central nervous system edema); endothelial corneal dystrophy (e.g., post-chamber ocular diseases); epilepsy (e.g., seizures, epileptic seizures, a seizure cluster, an acute seizure (e.g., status epilepticus), seizure disorder, and other neurological disorders involving seizures (e.g., cerebral palsy, Ohtahara Syndrome)); glaucoma (e.g., increased intraocular pressure, angle-closure glaucoma, neovascular glaucoma, open-angle glaucoma); ischemia (e.g., cardiac ischemia (myocardial ischemia), intestinal ischemia, mesenteric artery ischemia (acute mesenteric ischemia), hepatic ischemia, and cerebral ischemia (brain ischemia)); migraine (e.g., migraine including headache, migraine variant, migraine headache, cervical migraine syndrome, acute confusional migraine, migraine with aura, migraine without aura); neuropathic pain (e.g., diabetic neuropathy, diabetic neuropathy, nerve injury, nerve tract injury, neuropathic pain associated with visceral and/or somatic pain, peripheral neuropathy, chemotherapy-induced neuropathy, chemotherapy-induced peripheral neuropathy, neuralgia, polyneuropathy, mononeuropathy, mononeuritis multiplex, autonomic neuropathy, symmetrical peripheral neuropathy, radiculopathy, large fiber peripheral neuropathy, small fiber peripheral neuropathy, idiopathic neuropathic pain); nociceptive neuralgia; ocular diseases (e.g., diseases of retina-retinal detachment and injury response; diseases of electrical transmission between various retinal elements such as rods, cones, amacrine and horizontal cells, activity of retinal ganglion cells, dysfunction of Müller (glial) cells, abnormal function of the retinal pigment epithelium; dysfunction of formation of the retina in development and the appropriate maintenance of neural connections following maturation and development; regulation of normal electrolyte homeostasis in various chorioretinal and vitreoretinal diseases; abnormal function of Müller cells in diabetic retinopathy; loss of normal electrical activity in degenerative diseases of retina, inherited and those of unknown etiology; inflammatory diseases and conditions of the eye such as chorioretinitis, multiple sclerosis; infectious processes in the eye with abnormal inflammatory and injury responses; uveitis; abnormal function of Müller cells of retina and disease thereof; dysfunction of RPE-retinal pigment epithelium (e.g., diseases of RPE); endothelial (posterior) corneal dystrophies, which result from primary endothelial dysfunction, (e.g., Fuchs endothelial corneal dystrophy (FECD), posterior polymorphous corneal dystrophy (PPCD) and congenital hereditary endothelial dystrophy (CHED)); retinitis pigmentosa; age-related macular degeneration (e.g., dry age-related macular degeneration, exudative age-related macular degeneration, and myopic degeneration); retinopathy (e.g., diabetic retinopathy, proliferative vitreoretinopathy, and toxic retinopathy) and diseases of aqueous humor formation (e.g., glaucoma)); pain (e.g., chronic inflammatory pain, pain associated with arthritis, fibromyalgia, back pain, cancer-associated pain, chemotherapy-induced neuropathy, chemotherapy-induced peripheral neuropathy, HIV-treatment induced neuropathy. HIV-treatment induced neuralgia, pain associated with digestive disease, pain associated with Crohn's disease, pain associated with autoimmune disease, pain associated with endocrine disease, pain associated with diabetic neuropathy, pain associated with shingles or herpes zoster, phantom limb pain, spontaneous pain, chronic post-surgical pain, chronic temporomandibular pain, causalgia, postherpetic neuralgia, AIDS-related pain, complex regional pain syndromes type I and II, trigeminal neuralgia, chronic back pain, pain associated with spinal cord injury and/or recurrent acute pain); postherpetic neuralgia (e.g., shingles, herpes zoster); and schizophrenia. In a preferred embodiment, these compounds are selective antagonists of NKCC1.

The present invention also provides methods of using the compounds of formulas I-XXVI for treating disorders involving a $GABA_A$ receptor including but not limited to Alzheimer's Disease (AD), addictive disorders (e.g., compulsive disorders, eating disorders (e.g., obesity, anorexia nervosa, bulimia), addiction to narcotics/physical dependence, alcohol addiction, narcotic addiction, cocaine addiction, heroin addiction, opiate addiction, alcoholism, and smoking); anxiety disorders (e.g., anxiety, acute anxiety, panic disorder, social anxiety disorder, obsessive compulsive disorder (OCD), post-traumatic stress disorder (PTSD), generalized anxiety disorder, and specific phobia); autism (e.g., Autism spectrum disorder (ASD)); bipolar disorder (e.g., manic-depressive illness, manic phase, depressive phase, mixed bipolar state, bipolar I disorder, bipolar II disorder, rapid-cycling bipolar disorder, bipolar I disorder, bipolar II disorder); depression (e.g., psychotic depression, postpartum depression, seasonal affective disorder (SAD), cortical spreading depression, dysthymia (mild depression)); epilepsy (e.g., seizures, epileptic seizures, a seizure cluster, an acute seizure (e.g., status epilepticus), seizure disorder, and other neurological disorders involving seizures (e.g., cerebral palsy, Ohtahara Syndrome)); Huntington's Disease (HD) (e.g., Huntington's chorea); insomnia, migraine (e.g., migraine including headache, migraine variant, migraine headache, cervical migraine syndrome, acute confusional migraine, migraine with aura, migraine without aura, chronic migraine, transformed migraine); neuropathic pain (e.g., diabetic neuropathy, cluster headache, nerve injury, nerve tract injury, neuropathic pain associated with visceral and/or somatic pain, peripheral neuropathy, chemotherapy-induced neuropathy, chemotherapy-induced peripheral neuropathy, HIV-treatment induced neuropathy, HIV-treatment induced neuralgia, neuralgia, polyneuropathy, mononeuropathy, mononeuritis multiplex, autonomic neuropathy, symmetrical peripheral neuropathy, radiculopathy, large fiber peripheral neuropathy, small fiber peripheral neuropathy, idiopathic neuropathic pain); nociceptive pain; pain (e.g., acute pain, chronic inflammatory pain, pain associated with arthritis, fibromyalgia, back pain, cancer-associated pain, chemotherapy-induced neuropathy, chemotherapy-induced peripheral neuropathy, pain associated with digestive disease, pain associated with Crohn's disease, pain associated with autoimmune disease, pain associated with endocrine disease, pain associated with diabetic neuropathy, pain associated with shingles or herpes zoster, phantom limb pain, spontaneous pain, chronic post-surgical pain, chronic temporomandibular pain, causalgia, postherpetic neuralgia, AIDS-related pain, complex regional pain syndromes type I and II, trigeminal neuralgia, chronic back pain, pain associated with spinal cord injury, incisional post operative, trauma associated, burns, recurrent acute pain, head pain, headache, nonmigrainous, specific non-migraine head pains, tic dolureaux, postherpetic neuralgia, ice pick headache); Parkinson's disease, personality disorders, psychosis, seizure disorders, personality disorders, schizophrenia, tinnitus, and withdrawal syndromes (e.g., alcohol withdrawal syndrome, nicotine withdrawal syndrome, opioid withdrawal syndrome, benzodiazepine withdrawal syndrome, methadone withdrawal syndrome, SSRI discontinuation syndrome, hydrocodone withdrawal syndrome, cocaine withdrawal syndrome, heroin withdrawal syndrome). In a preferred embodiment, these compounds are selective antagonists of $GABA_A$ receptors. In a preferred embodiment, these compounds are selective antagonists of $GABA_A$ receptors comprising an $\alpha_6$ subunit. In a more preferred embodiment, these compounds are selective antagonists of $GABA_A$ receptors comprising an $\alpha_5$ subunit. In a still more preferred embodiment, these compounds are selective antagonists of $GABA_A$ receptors comprising an $\alpha_4$ subunit.

The present invention further provides methods for treating a patient diagnosed with risk factors for a condition selected from the group consisting of addictive disorders, Alzheimer's Disease, anxiety disorders, ascites, autism, bipolar disorder, cancer, depression, endothelial corneal dystrophy, edema, epilepsy, glaucoma, Huntington's Disease, insomnia, ischemia, migraine, migraine with aura, neuropathic pain, nociceptive neuralgia, nociceptive pain, ocular diseases, pain, Parkinson's disease, personality disorders, postherpetic neuralgia, psychosis, schizophrenia, seizure disorders, tinnitus, and withdrawal syndromes comprising administering an effective amount of a compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, and/or XXVI. In a preferred embodiment, these compounds are selective antagonists of NKCC1 and/or $GABA_A$ receptors.

The present invention still further provides methods of using the compounds of formulas I-XXVI for treating a patient diagnosed with risk factors for disorders involving the $Na^+K^+Cl^-$ co-transporters including but not limited to addictive disorders (e.g., compulsive disorders, eating disorders (e.g., obesity), addiction to narcotics/physical dependence, alcohol addiction, narcotic addiction, cocaine addiction, heroin addiction, opiate addiction, alcoholism, and smoking); anxiety disorders (e.g., anxiety, acute anxiety, panic disorder, social anxiety disorder, obsessive compulsive disorder (OCD), post-traumatic stress disorder (PTSD), generalized anxiety disorder, and specific phobia); ascites (e.g., peritoneal cavity fluid, peritoneal fluid excess, hydroperitoneum, abdominal dropsy, cancer related to ascites, tumors related to ascites); bipolar disorder (e.g., manic-depressive illness, manic phase, depressive phase, mixed bipolar state, bipolar I disorder, bipolar II disorder, rapid-cycling bipolar disorder, bipolar I disorder, bipolar II disorder, rapid-cycling bipolar disorder); cancer (e.g., tumors, cancer related to ascites, tumors related to ascites); depression (e.g., psychotic depression, postpartum depression, seasonal affective disorder (SAD), cortical spreading depression, dysthymia (mild depression)); edema (e.g., central nervous system edema); endothelial corneal dystrophy (e.g., post-chamber ocular diseases); epilepsy (e.g., seizures, epileptic seizures, a seizure cluster, an acute seizure (e.g., status epilepticus), seizure disorder, and other neurological disorders involving seizures (e.g., cerebral palsy, Ohtahara Syndrome)); glaucoma (e.g., increased intraocular pressure, angle-closure glaucoma, neovascular glaucoma, open-angle glaucoma); ischemia (e.g., cardiac ischemia (myocardial ischemia), intestinal ischemia, mesenteric artery ischemia (acute mesenteric ischemia), hepatic ischemia, and cerebral ischemia (brain ischemia)); migraine (e.g., migraine including headache, migraine variant, migraine headache, cervical migraine syndrome, acute confusional migraine, migraine with aura, migraine without aura); neuropathic pain (e.g., diabetic neuropathy, diabetic neuropathy, nerve injury, nerve tract injury, neuropathic pain associated with visceral and/or somatic pain, peripheral neuropathy, chemotherapy-induced neuropathy, chemotherapy-induced peripheral neuropathy, HIV-treatment induced neuropathy, HIV-treatment induced neuralgia, neuralgia, polyneuropathy, mononeuropathy, mononeuritis multiplex, autonomic neuropathy, symmetrical peripheral neuropathy, radiculopathy, large fiber peripheral neuropathy, small fiber peripheral neuropathy, idiopathic neuropathic pain); nociceptive neuralgia; ocular diseases (e.g., diseases of retina-retinal detachment and injury response; diseases of electrical transmission between various retinal elements such as rods, cones, amacrine and horizontal cells, activity of retinal ganglion cells, dysfunction of Müller (glial) cells, abnormal function of the retinal pigment epithelium; dysfunction of formation of the retina in development and the appropriate maintenance of neural connections following maturation and development; regulation of normal electrolyte homeostasis in various chorioretinal and vitreoretinal diseases; abnormal function of Müller cells in diabetic retinopathy; loss of normal electrical activity in degenerative diseases of retina, inherited and those of unknown etiology; inflammatory diseases and conditions of the eye such as chorioretinitis, multiple sclerosis; infectious processes in the eye with abnormal inflammatory and injury responses; uveitis; abnormal function of Müller cells of retina and disease thereof; dysfunction of RPE-retinal pigment epithelium (e.g., diseases of RPE); endothelial (posterior) corneal dystrophies, which result from primary endothelial dysfunction, (e.g., Fuchs endothelialcorneal dystrophy (FECD), posterior polymorphous corneal dystrophy (PPCD) and congenital, hereditary endothelial dystrophy (CHED)); retinitis pigmentosa; age-related macular degeneration (e.g., dry age-related macular degeneration, exudative age-related macular degeneration, and myopic degeneration); retinopathy (e.g., diabetic retinopathy, proliferative vitreoretinopathy, and toxic retinopathy) and diseases of aqueous humor formation (e.g., glaucoma)); pain (e.g., chronic inflammatory pain, pain associated with arthritis, fibromyalgia, back pain, cancer-associated pain, chemotherapy-induced neuropathy, chemotherapy-induced peripheral neuropathy, pain associated with digestive disease, pain associated with Crohn's disease, pain associated with autoimmune disease, pain associated with endocrine disease, pain associated with diabetic neuropathy, pain associated with shingles or herpes zoster, phantom limb pain, spontaneous pain, chronic post-surgical pain, chronic temporomandibular pain, causalgia, postherpetic neuralgia, AIDS-related pain, complex regional pain syndromes type I and II, trigeminal neuralgia, chronic back pain, pain associated with spinal cord injury and/or recurrent acute pain); postherpetic neuralgia (e.g., shingles, herpes zoster); and schizophrenia. In a preferred embodiment, these compounds are selective antagonists of NKCC1.

The present invention still further provides methods of using the compounds of formulas I-XXVI for treating a patient diagnosed with risk factors for disorders involving a $GABA_A$ receptor including but not limited to Alzheimer's Disease (AD), addictive disorders (e.g., compulsive disorders, eating disorders (e.g., obesity, anorexia nervosa, bulimia), addiction to narcotics/physical dependence, alcohol addiction, narcotic addiction, cocaine addiction, heroin addiction, opiate addiction, alcoholism, and smoking); anxiety disorders (e.g., anxiety, acute anxiety, panic disorder, social anxiety disorder, obsessive compulsive disorder (OCD), post-traumatic stress disorder (PTSD), generalized anxiety disorder, and specific phobia); autism (e.g., Autism spectrum disorder (ASD)); bipolar disorder (e.g., manic-depressive illness, manic phase, depressive phase, mixed bipolar state, bipolar I disorder, bipolar II disorder, rapid-cycling bipolar disorder, bipolar I disorder, bipolar II disorder); depression (e.g., psychotic depression, postpartum depression, seasonal affective disorder (SAD), cortical spreading depression, dysthymia (mild depression)); epilepsy (e.g., seizures, epileptic seizures, a seizure cluster, an acute seizure (e.g., status epilepticus), seizure disorder, and other neurological disorders involving seizures (e.g., cerebral palsy, Ohtahara Syndrome)); Huntington's Disease (HD) (e.g., Huntington's chorea); insomnia, migraine (e.g., migraine including headache, migraine variant, migraine headache, cervical migraine syndrome, acute confusional migraine, migraine with aura, migraine without aura, chronic migraine, transformed migraine); neuropathic pain (e.g., diabetic neuropathy, cluster headache, nerve injury, nerve tract injury, neuropathic pain associated with visceral and/or somatic pain, peripheral neuropathy, chemotherapy-induced neuropathy, chemotherapy-induced peripheral neuropathy. HIV-treatment induced neuropathy, HIV-treatment induced neuralgia, neuralgia, polyneuropathy, mononeuropathy, mononeuritis multiplex, autonomic neuropathy, symmetrical peripheral neuropathy, radiculopathy, large fiber peripheral neuropathy, small fiber peripheral neuropathy, idiopathic neuropathic pain); nociceptive pain; pain (e.g., acute pain, chronic inflammatory pain, pain associated with arthritis, fibromyalgia, back pain, cancer-associated pain, chemotherapy-induced neuropathy, chemotherapy-induced peripheral neuropathy, pain associated with digestive disease, pain associated with Crohn's disease, pain associated with autoimmune disease, pain associated with endocrine disease, pain associated with diabetic neuropathy, pain associated with shingles or herpes zoster, phantom limb pain, spontaneous pain, chronic post-surgical pain, chronic temporomandibular pain, causalgia, postherpetic neuralgia, AIDS-related pain, complex regional pain syndromes type I and II, trigeminal neuralgia, chronic back pain, pain associated with spinal cord injury, incisional post operative, trauma associated, burns, recurrent acute pain, head pain, headache, nonmigrainous, specific non-migraine head pains, tic dolureaux, postherpetic neuralgia, ice pick headache); Parkinson's disease, personality disorders, psychosis, seizure disorders, personality disorders, schizophrenia, tinnitus, and withdrawal syndromes (e.g., alcohol withdrawal syndrome, nicotine withdrawal syndrome, opioid withdrawal syndrome, benzodiazepine withdrawal syndrome, methadone withdrawal syndrome, SSRI discontinuation syndrome, hydrocodone withdrawal syndrome, cocaine withdrawal syndrome, heroin withdrawal syndrome). In a preferred embodiment, these compounds are selective antagonists of $GABA_A$ receptors. In a preferred embodiment, these compounds are selective antagonists of $GABA_A$ receptors comprising an $\alpha_6$ subunit. In a more preferred embodiment, these compounds are selective antagonists of $GABA_A$ receptors comprising an $\alpha_5$ subunit. In a still more preferred embodiment, these compounds are selective antagonists of $GABA_A$ receptors comprising an $\alpha_4$ subunit.

Embodiments of the present invention provide a pharmaceutical composition comprising a compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, and/or XXVI, a pharmaceutically acceptable salt, solvate, tautomer, hydrate, or combination thereof and a pharmaceutically acceptable carrier, excipient, or diluent.

Embodiments of the present invention provide methods of making the compounds including compounds described herein and further provide intermediate compounds formed through the synthetic methods described herein to provide the compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, and/or XXVI.

Embodiments of the present invention provide kits including the compounds including compounds described herein. These kits may be used in the treatment methods disclosed herein. In another embodiment, the kits may include instructions, directions, labels, warnings, or information pamphlets.

Embodiments of the present invention further provide methods of treating a disease, condition, or disorder, especially the disorders described herein.

Embodiments of the present invention provide uses of the compounds including compounds described herein for the preparation of a medicament for carrying out the aforementioned utilities.

In addition, compounds of the present invention may be used for the regulation of psychiatric disorders and neurological disorders and to modulate neuronal synchronization as well as improve CNS function. In some embodiments, the compound of the prodrug is provided in an amount effective for regulating a CNS disorder, and/or a disorder involving the $Na^+K^+Cl^-$ co-transporters and/or a disorder involving the $GABA_A$ receptor. In particular embodiments, the CNS disorder is Alzheimer's Disease, addictive disorders, anxiety disorders, autism, bipolar disorder, depression, epilepsy, Huntington's Disease, insomnia, migraine, migraine with aura, neuropathic pain, nociceptive pain, pain, Parkinson's disease, personality disorders, psychosis, schizophrenia, seizure disorders, tinnitus, or withdrawal syndromes.

In a further embodiment, the compounds described herein may be used in methods of neuroprotection (e.g., reducing damage following stroke, head trauma, reducing damage from neurodegenerative diseases like Alzheimer's disease Huntington's Disease, and Parkinson's disease) and to reduce neurotoxicity (e.g., damage from ethanol).

In another embodiment, the compounds described herein may be used in methods to improve cognition, learning, or memory. Alternatively, the compounds described herein may be used as cognition, learning, or memory aids.

In one embodiment, the compounds described herein modulate or improve the function of the retina in ocular diseases with inappropriate retinal activity. In another embodiment, the compounds described herein regulate the intracellular pH of retinal pigment epithelial cells. In another embodiment, the compounds described herein regulate, change, or modulate the chloride concentration to regulate glial cell function of retina.

In a preferred embodiment, the compounds described herein show improved CNS pharmacologic properties and increased transit across the blood-brain barrier (BBB).

In a preferred embodiment, the compounds described herein show differential activity with stronger effect on the central nervous system and less diuretic effects. For example, the compounds described herein may be used in long-term (maintenance) therapy without significant diuretic effect. Also, the analogs of bumetanide, furosemide, piretanide, azosemide, and torsemide described herein may be used in combination therapy with diuretics because of their lack of diuretic effect. Additionally, the compounds described herein do not interfere with diuretics or cause severe side effects when administered in conjunction with or concurrently with a diuretic.

In a preferred embodiment, the compounds described herein are targeted to be more specific for the treatment of one or more of the described conditions and diseases. Further, these compounds show less instance of effects on systems other than the targeted systems. Also the compounds described herein have fewer or no side effects when used in combination with other drugs (e.g., fewer undesirable medication interactions). Additionally, the compounds described herein, especially the analogs and prodrugs may be dosed at high levels (>100 mg) with no adverse effects (e.g., the compounds are well-tolerated at high dosages).

In a preferred embodiment, the compounds described herein act to modulate the anion levels in a central nervous system (CNS) cell (e.g., glia and neurons). In a more preferred embodiment, the compounds described herein act to modulate the intracellular chloride levels in a CNS cell. In yet-another embodiment, analogs (including prodrugs) of bumetanide, furosemide, piretanide, azosemide, and torsemide described herein decrease the intracellular chloride level in a CNS cell.

In another embodiment, the compounds described herein decrease the intracellular chloride level (concentration) in a CNS cell wherein said CNS cell is a spinal cord neural cell, a glial cell (e.g., an oligodendrocyte, a Schwann cell, an astrocyte, a microglial cell) or a neuron (e.g., medium spiny GABA-ergic neuron or a large cholinergic neuron).

In another embodiment, the compounds described herein may be administered in combination with a second agent.

In a preferred embodiment, the compounds described herein may be administered prophylactically to prevent, lessen the severity of, or delay the onset of symptoms of the conditions described herein. In another embodiment, the compounds described herein may be administered prophylactically to prevent, lessen the severity of, or delay the reoccurrence of the conditions described herein.

In a preferred embodiment, the compounds described herein are targeted to be more specific for the treatment of one or more of the described conditions and diseases. Further, these compounds show less instance of effects on systems other than the targeted systems. Also the compounds described herein have fewer or no side effects when used in combination with other drugs (e.g., fewer undesirable medication interactions). Additionally, the compounds described herein, especially the analogs and prodrugs may be dosed at high levels (e.g., >100 mg/kg) with no or minimal adverse effects (e.g., the compounds are well-tolerated at high dosages).

Selective Activity

Embodiments of the present invention provide compounds (including analogs and prodrugs) capable of passage across the blood-brain barrier comprising a compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, and/or XXVI, or a pharmaceutically acceptable salt, solvate, tautomer or hydrate thereof. In some embodiments, compounds of the present invention may have increased lipophilicity and/or reduced diuretic effects compared to the diuretic or diuretic-like compounds from which they are derived. The lipiphilicity can be measured by determining the hydrophile-lipophile balance (HLB) or the partition coefficient (e.g., the distribution of a compound between water and octanol). In further embodiments, the compounds of the present invention may result in fewer undesirable side effects when employed in the regulatory, (i.e., preventive, management), and/or treatment, methods described herein.

In some embodiments, the level of diuresis that occurs following administration of an effective amount of a compound provided below as Formula I-XXVI, is less than about 99%, 90%, 80%, 70%, 60%, 50%, 40%, 30%, 20% or 10% of that which occurs following administration of an effective amount of the parent molecule from which the compound is derived. For example, the compound may be less diuretic than the parent molecule when administered at the same mg/kg dose. Alternatively, the compound may be more potent than the parent molecule from which it is derived, so that a smaller dose of the compound may be required for effective relief of symptoms, and thus, may elicit less of a diuretic effect. Similarly, the compound may have a longer duration of effect in treating disorders than the parent molecule. Accordingly, compounds of the present invention may be administered less frequently than the parent molecule, and thus may lead to a lower total diuretic effect within any given period of time.

In a preferred embodiment, the compounds described herein show selective activity with stronger effect on the central nervous system and limited, minimal, or no diuretic effects. The preferred analogs of bumetanide, furosemide, piretanide, azosemide, or torsemide will produce less than one-fifth, more preferably less than one-seventh, of the diuretic effect produced by the parent compound. For example, the compounds described herein (including prodrugs thereof) may typically be used in long-term therapy (e.g., maintenance therapy) without significant diuretic effect. Also, the analogs of bumetanide, furosemide, piretanide, azosemide, and torsemide described herein may be used in combination therapy with diuretics because they produce minimal diuretic effect. Additionally, the compounds described herein (including prodrugs thereof) do not interfere with diuretics or cause severe side effects when administered in conjunction with or concurrently with a diuretic.

The compounds of the present invention of Formulae I, II, III, IV, V, VI, VII, VIII, IX, X, XI, XII, XI, XIV, XV, XVI, XVII, XV, XIX, XX, XXI, XXII, XXIII, XXIV, XXV, and/or XXVI described herein may be used for the regulation, including prevention, management and treatment, of a range of conditions including, but not limited to disorders that involve at least one of the $Na^+K^+Cl^-$ cotransporters. Embodiments of the present invention encompass compounds (including prodrugs thereof) described herein which modulate, regulate, inhibit, stimulate, activate, and/or bind to electroneutral cation-chloride cotransporter co-transporters including but not limited to $Na^+Cl^-$ cotransporters (e.g., thiazide-sensitive $Na^+Cl^-$ cotransporters); apical bumetanide-sensitive $Na^+K^+Cl^-$ cotransporters (e.g., NKCC2); basolateral bumetanide-sensitive $Na^+K^+Cl^-$ cotransporters (e.g., NKCC1); and $K^+Cl^-$ cotransporters (e.g., KCC1, KCC2, KCC3, KCC4). In a preferred embodiment, the electroneutral cation-chloride cotransporter is a bumetanide-sensitive $Na^+K^+Cl^-$ cotransporter (e.g., NKCC1, NKCC2).

In some embodiments, compounds of the present invention may have increased lipophilicity and/or reduced diuretic effects compared to the diuretic or diuretic-like compounds from which they are derived. The lipiphilicity can be measured by determining the hydrophile-lipophile balance (HLB) or the partition coefficient (e.g., the distribution of a compound between water and octanol). In further embodiments, the compounds of the present invention may result in fewer undesirable side effects when employed in the regulatory (i.e., preventive, management) and/or treatment methods described herein.

In one embodiment, the invention comprises a method of inhibiting apical bumetanide-sensitive $Na^+K^+Cl^{31}$ cotransporters (e.g., NKCC2) comprising administering a composition comprising an effective amount of a compound of the Formulae I-XXVI or a pharmaceutically acceptable salt thereof. In another embodiment, the invention comprises a method of inhibiting basolateral bumetanide-sensitive $Na^+K^+Cl^-$ cotransporters (e.g., NKCC1) comprising administering a composition comprising an effective amount of a compound of the Formulae I-XXVI or a pharmaceutically acceptable salt thereof. In another embodiment, the invention comprises a method of inhibiting basolateral bumetanide-sensitive $Na^+K^+Cl^-$ cotransporters (e.g., NKCC1) and apical bumetanide-sensitive $Na^+K^+Cl^-$ cotransporters (e.g., NKCC2) comprising administering a composition comprising an effective amount of a compound of the Formulae I-XXVI or a pharmaceutically acceptable salt thereof.

In a preferred embodiments, the invention comprises a method of inhibiting basolateral bumetanide-sensitive $Na^+K^+Cl^-$ cotransporters (e.g., NKCC1) comprising administering a composition comprising a compound described herein, wherein the inhibition of apical bumetanide-sensitive $Na^+K^+Cl^-$ cotransporters (e.g., NKCC2) is no more than 50%, more preferably nor more than 25%, or even more preferably no more than 15% of the effect on basolateral bumetanide-sensitive $Na^+K^+Cl^-$ cotransporters (e.g., NKCC1). In yet another embodiment, the invention comprises a method of inhibiting apical bumetanide-sensitive $Na^+K^+Cl^-$ cotransporters (e.g., NKCC2) comprising administering a composition comprising a compound described herein, wherein the inhibition of basolateral bumetanide-sensitive $Na^+K^+Cl^-$ cotransporters (e.g., NKCC1) is no more than 50%, more preferably nor more than 25%, or even more preferably no more than 15% of the effect on apical bumetanide-sensitive $Na^+K^+Cl^-$ cotransporters (e.g., NKCC2). Some preferred bumetanide, furosemide, piretanide, azosemide, and torsemide analogs and derivatives, described herein, may not act on the $GABA_A$ receptor or show only minimal activity toward $GABA_A$ receptors.

The compounds of the present invention of Formulae I, II, III, IV, V, VI, VII, VIII, IX, X, XI, XII, XIII, XIV, XV, XVI, XVII, XVI, XIX, XX, XXI, XXII, XXIII, XXIV, and/or XXV described herein may be used for the regulation, including prevention, management and treatment, of a range of conditions including, but not limited to disorders that involve at least one of the $GABA_A$ receptor.

In another embodiment, compounds described herein may show selective effect on a subset of $GABA_A$ receptors in the CNS and less of the side-effects usually associated with agents that act on $GABA_A$ receptors. For example, compounds described herein exhibit less sedation and less suppression of respiration, cognition, or motor function. In another embodiment, compounds described herein may show a selective effect on $GABA_A$ receptors comprising an $\alpha_5$ subunit or an $\alpha_6$ subunit. In another embodiment, compounds described herein show a selective effect on $GABA_A$ receptors comprising an $\alpha_4$ subunit.

In one embodiment, the invention comprises a method for antagonizing parasynaptic $GABA_A$ receptors comprising administering a composition comprising an effective amount of a compound of the Formulae I-XXVI or a pharmaceutically acceptable salt thereof. In another embodiment, the invention comprises a method for antagonizing parasynaptic $GABA_A$ receptors comprising an $\alpha_4$ subunit comprising administering a composition comprising an effective amount of a compound of the Formulae I-XXVI or a pharmaceutically acceptable salt thereof. In yet another embodiment, the invention comprises a method for antagonizing parasynaptic $GABA_A$ receptors comprising an as subunit comprising administering a composition comprising an effective amount of a compound of the Formulae I-XXVI or a pharmaceutically acceptable salt thereof. In a further embodiment, the invention comprises a method for antagonizing parasynaptic $GABA_A$ receptors comprising an as subunit comprising administering a composition comprising an effective amount of a compound of the Formulae I-XXVI or a pharmaceutically acceptable salt thereof.

In another embodiment, the invention comprises a method for antagonizing parasynaptic $GABA_A$ receptors comprising an $\alpha_4$ subunit comprising administering a composition comprising a compound described herein, wherein the antagonism of $GABA_A$ receptors with an $\alpha_1$ subunit is no more than 50%, more preferably nor more than 25%, or even more preferably no more than 15% of the effect on a $GABA_A$ receptor with an $\alpha_4$ receptor. In yet another embodiment, the invention comprises a method for antagonizing parasynaptic $GABA_A$ receptors comprising an $\alpha_5$ subunit comprising administering a composition comprising a compound described herein, wherein the antagonism of a $GABA_A$ receptor with an $\alpha_1$ subunit is no more than 50%, more preferably nor more than 25%, or even more preferably no more than 15% of the effect on a $GABA_A$ receptor with an $\alpha_5$ receptor. In a further embodiment, the invention comprises a method for antagonizing parasynaptic $GABA_A$ receptors comprising an $\alpha_6$ subunit comprising administering a composition comprising a compound described herein, wherein the antagonism of a $GABA_A$ receptor with an a, subunit is no more than 50%, more preferably nor more than 25%, or even more preferably no more than 15% of the effect on a $GABA_A$ receptor with an $\alpha_6$ receptor.

The compounds described herein may preferentially bind $GABA_A$ receptors. In one embodiment, the compounds described herein may preferentially bind $GABA_A$ receptors comprising an $\alpha_4$ subunit. In another embodiment, the compounds described herein may preferentially bind $GABA_A$ receptors comprising an $\alpha_5$ subunit. In a further embodiment, the compounds described herein may preferentially bind $GABA_A$ receptors comprising an $\alpha_6$ subunit. In another embodiment, the compounds described herein may preferentially bind $GABA_A$ receptors comprising an $\alpha_3$ subunit. In a further embodiment, the compounds described herein may preferentially bind $GABA_A$ receptors comprising an $\alpha_2$ subunit.

The compounds described herein may have antagonistic effects on $GABA_A$ receptors located parasynaptically. In one embodiment, the compounds described herein may have antagonistic effects on $GABA_A$ receptors comprising an $\alpha_4$ subunit located parasynaptically. In another embodiment, the compounds described herein may have an antagonistic effect on $GABA_A$ receptors comprising an as subunit located parasynaptically. In a further embodiment, the compounds described herein may have an antagonistic effect on $GABA_A$ receptors comprising an $\alpha_6$ subunit located parasynaptically.

Preferential binding of the compounds of this invention may be reflected in the effective concentration ($EC_{50}$), i.e., the concentration of the compound in vitro at which the antagonist effect is half the maximal antagonism demonstrated by the respective compound on the particular receptor. In particular, more preferred compounds of this invention will be those whose $EC_{50}$ for $GABA_A$ receptors with $\alpha_6$ subunits are no more than 50%, more preferably nor more than 25%, or even more preferably no more than 15% of the $EC_{50}$ of the same compound for $GABA_A$ receptors having $\alpha_1$ subunits. Even more preferred are compounds whose $EC_{50}$ for $\alpha_4$-containing $GABA_A$ receptors is no more than 50%, more preferably nor more than 25%, or even more preferably no more than 15% of the $EC_{50}$ for $\alpha_1$-containing $GABA_A$ receptors. Preferential binding for other receptors can be characterized similarly.

The compounds described herein are effective in humans and animals to decrease seizures, decrease pain responses, and decrease migraine in humans and animal models. For example, compounds described herein may preferentially bind to $GABA_A$ receptor subtypes and have an antagonistic effect on $GABA_A$ receptors that is different from classic benzodiazepine and barbiturate mechanisms. Unlike many bumetanide, furosemide, piretanide, azosemide, and torsemide analogs and derivatives, compounds described herein may not act on the $Na^+K^+2Cl^-$ cotransporter (NKCC1 or NKCC2). Unlike bumetanide, furosemide, piretanide, azosemide, and torsemide, compounds described herein (e.g., NTP-2014) do not elicit diuresis in animal models. For example, compounds described (e.g., NTP-2014) herein do not increase urine output, sodium excretion, or potassium excretion.

Embodiments of the present invention further provide methods of treating a disease, condition, or disorder described herein. In an embodiment, the present invention provides methods for the use of the compounds described herein for the manufacture of a composition for the treatment of a disease, condition, or disorder described herein. In another embodiment, the present invention provides for compositions for use in treating a disease, condition, or disorder described herein comprising a compound described herein.

The foregoing and other objects and aspects of the present invention are explained in greater detail in reference to the drawing and description set forth herein.

BRIEF DESCRIPTION OF THE DRAWINGS

FIG. 8 is a scheme showing alternative methods for obtaining bumetanide N-morpholinothioamide. See Schwarz, G., Org. Syn., Coll. Vol. III, 1955, 332-334; Alper, H., et al., Angew. Chem., Int. Ed., 1978, 17, 689. (31-56%); Raucher, S. and Klein, P., J. Org. Chem., 1981, 46, 3558. (80-95%); Lawesson, S.-O., et al., Org. Syn., Coll. Vol. VII, 1990, 372-375: A. Preparation; B. Thiolactam Formation; as well as and references 26-30 therein; Davy, H., Sulfur Lett., 1985, 3, 39-44 and related references; "Synthesis of Thioamides and Thiolactams", Schaumann, E. in Comprehensive Organic Synthesis, Trost, B. M. Editor-in-Chief, Volume 6, Chapter 2.4, Pergamon Press, Oxford, 1991, pp. 419-434; Lawesson, S.-O., et al., Org. Syn., Coll. Vol. VII, 1990, 372-375 and references therein; Fieser's Reagents for Org. Syn., Vol. 8, 1980, 327; ibid, Vol. 9, 1981, 49-50; ibid, Vol. 10, 1982, 39; ibid, Vol. 11, 1984, 54-55; ibid, Vol. 12, 1986, 59; ibid, Vol. 13, 1988, 38-39; ibid, Vol. 15, 1990, 37, 329; and ibid, Vol. 16, 1992, 37-38; Davy, H., JCS, Chem. Commun., 1982, 457; Davy, H., Sulfur Lett., 1985, 3, 39-44; Davy, H., Chem. & Ind., 1985, 824; Davy, H., J. Chem. Res. (S), 1985, 272; Davy, H., J. Chem. Res. (M), 1985, 2701-2712; "Synthesis of Thioesters and Thiolactones", Voss, J. in Comprehensive Organic Synthesis, Trost, B. M. Editor-in-Chief, Volume 6, Chapter 2.5, Pergamon Press, Oxford, 1991, pp. 435-460; "Synthesis of Selenoesters of All Oxidation States", Ogawa, A. and Sonoda, N. in Comprehensive Organic Synthesis, Trost, B. M. Editor-in-Chief, Volume 6, Chapter 2.6, Pergamon Press, Oxford, 1991, pp. 461-484.

FIG. 9 is a scheme showing alternative methods for obtaining bumetanide N-morpholinoselenoamide. See Rae, I. D. and Wade, M. J., Int. J. Sulfur Chem., 1976, 8, 519; Voss, J. and Bruhn, F.-R., Liebigs Ann. Chem., 1979, 1931; Woollins, J. D., et al., Chemistry Europe J., 2005, 11, 6221-6227; "Synthesis of Selenoesters of All Oxidation States", Ogawa, A. and Sonoda, N. in Comprehensive Organic Synthesis, Trost, B. M. Editor-in-Chief, Volume 6, Chapter 2.6, Pergamon Press, Oxford, 1991, pp. 461-484; Woollins, J. D., et al., Chem. Eur. J., 2005, 11, 6221-6227 and Woollins references therein; "Synthesis of Thioamides and Thiolactams", Schaumann, E. in Comprehensive Organic Synthesis, Trost, B. M. Editor-in-Chief, Volume 6, Chapter 2.4, Pergamon Press, Oxford, 1991, pp. 419-434; Lawesson, S.-O., et al., Org. Syn., Coll. Vol. VII, 1990, 372-375 and references therein; Fieser's Reagents for Org. Syn., Vol. 8, 1980, 327; ibid, Vol. 9, 1981, 49-50; ibid, Vol. 10, 1982, 39; ibid, Vol. 11, 1984, 54-55; ibid, Vol. 12, 1986, 59; ibid, Vol. 13, 1988, 38-39; ibid, Vol. 15, 1990, 37, 329; and ibid, Vol. 16, 1992, 37-38; Davy, H., JCS, Chem. Commun., 1982, 457; Davy, H., Sulfur Lett., 1985, 3, 39-44; Davy, H., Chem. & Ind., 1985, 824; Davy, H., J. Chem. Res. (S), 1985, 272; Davy, H., J. Chem. Res. (M), 1985, 2701-2712.

FIG. 15A shows the after-discharge activity elicited by 4 seconds of electrical stimulation to the primate sensory cortex. FIG. 15B shows a typical spike amplitude of all the spikes comprising the burst. The area of envelope combines a measurement of duration and spike amplitude. This is of particular relevance because sometimes the duration can be dramatically reduced by a treatment, leaving spikes essentially the same size (hence the spike height measurement fails in this case). Occasionally, the spike amplitude is greatly diminished by a treatment, but low-amplitude rumbling lasting many seconds can be elicited by electrical stimulation (hence the duration measurement fails in this case). Thus the area of the envelope captures both types of changes simultaneously, and can be thought of as the average spike amplitude multiplied by the duration (but over very short duration steps to approximate the area-integral). See Haglund and Hochman (Feb. 23, 2005) *J. Neurophysiol.* 94: 907-918.

FIG. 41C illustrates that the $EC_{50}$=20.2 μM for NTP-2014 in $\alpha_4$ or in $\alpha_6$ containing $GABA_A$ receptor isoforms.

FIG. 44A-D illustrates that NTP-2014 showed effective analgesic effects in a mouse model of nociceptive pain (e.g., tail flick test).

FIG. 46A-C illustrates that NTP-2014 showed effective analgesic effects in a mouse, Chung model of neuropathic pain.

DETAILED DESCRIPTION

Figure 1:
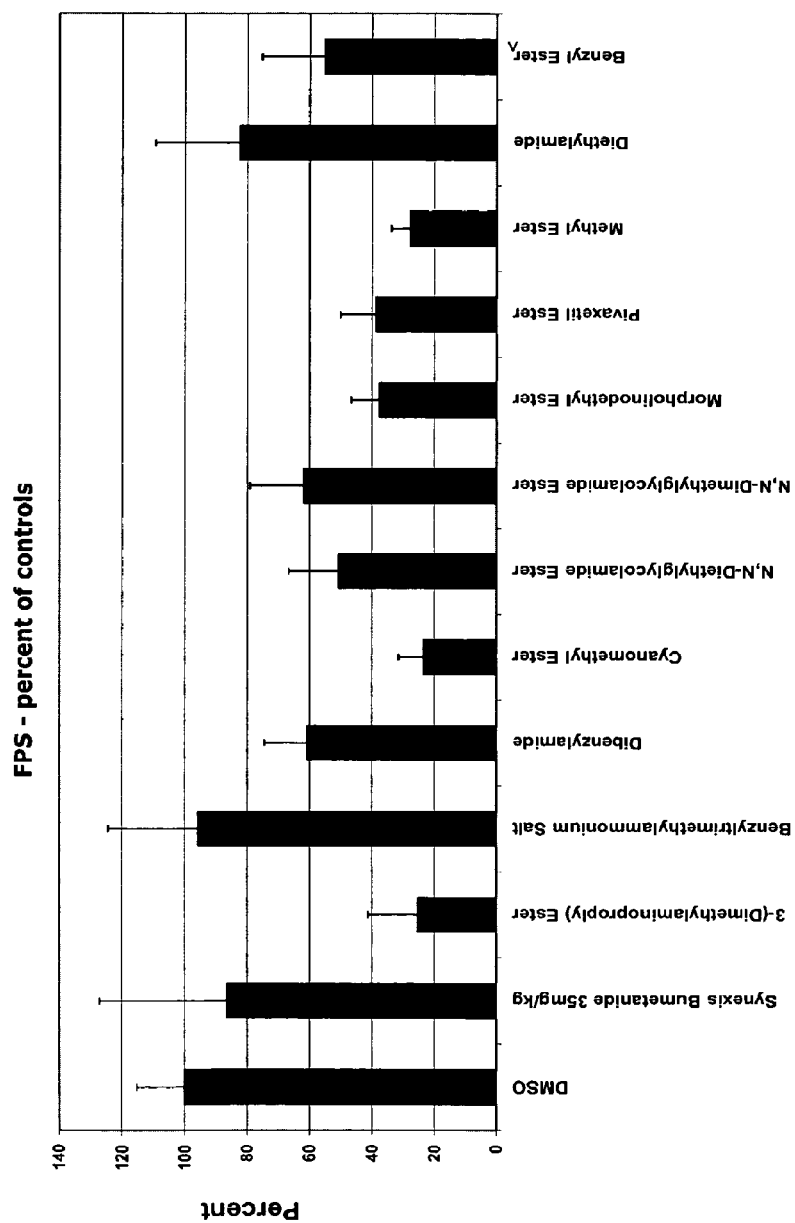
FIG. 1 presents a graph depicting the results of bumetanide analogs on the difference in startle amplitude in comparison to control as a measure of the ability of the bumetanide analogs to alleviate anxiety. See EXAMPLE 137

The foregoing and other aspects of the present invention will now be described in more detail with respect to embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Definitions

The terminology used in the description of the invention herein is for the purpose of describing particular embodiments only and is not intended to be limiting of the invention. As used in the description of the embodiments of the invention and the appended claims, the singular forms "a," "an" and "the" are intended to include the plural forms as well, unless the context clearly indicates otherwise. Also, as used herein, "and/or" refers to and encompasses any and all possible combinations of one or more of the associated listed items. Furthermore, "about," as used herein when referring to a measurable value such as an amount of a compound, dose, time, temperature is meant to encompass variations of 20%, 10%, 5%, 1%, 0.5%, or even 0.1% of the specified amount. Unless otherwise defined, all terms, including technical and scientific terms used in the description, have the same meaning as commonly understood by one of ordinary skill in the art to which this invention belongs.

All publications, patent applications, patents, and other references mentioned herein are incorporated by reference in their entirety.

"Administration" as used herein, refers broadly to any means by which a composition is given to a patient. A preferred route of administration is oral, and unless otherwise indicated, any reference herein to "administration" includes "oral administration."

"Alkenyl" as used herein, refers broadly to a straight or branched chain hydrocarbon radical having one or more double bonds and containing from 2 to 20 carbon atoms. Examples of alkenyl groups include propenyl, butenyl, pentenyl, and the like. "Cycloalkenyl" or "cyclic alkenyl" as used herein refers to carbocycles containing no heteroatoms, and includes mono-, bi-, and tricyclic saturated carbocycles, as well as fused rings systems. Examples of cycloalkenyl groups include cyclopropenyl, cyclopentenyl, cyclohexenyl, cyclopentadienyl, cyclohexadienyl, and the like. Such alkenyl and cycloalkenyl groups may be optionally substituted as described herein.

"Alkyl" as used herein refers broadly to a straight or branched chain saturated hydrocarbon radical. "Alkyl" also refers broadly to cyclic (i.e., cycloalkyl) alkyl groups. Examples of alkyl groups include, but are not limited to, straight chained alkyl groups including methyl, ethyl, n-propyl, n-butyl, n-pentyl, n-hexyl, n-heptyl, n-octyl, and branched alkyl groups including isopropyl, tert-butyl, isoamyl, neopentyl, iso-amyl, and the like. "Cycloalkyl" or "cyclic alkyl" as used herein refers to carbocycles containing no heteroatoms, and includes mono-, bi- and tricyclic saturated carbocycles, as well as fused ring systems. Examples of cycloalkyl include cyclopropyl, cyclobutyl, cyclopentyl, cyclohexyl, cycloheptyl, and the like. The cycloalkyl can be substituted or unsubstituted, and cyclic alkyl groups including cyclopropyl, cyclopentyl, cyclohexyl, cycloheptyl, and the like. Such alkyl groups may be optionally substituted as described herein.

"Alkylcyano" refers broadly to a straight or branched chain, saturated or partially unsaturated hydrocarbon radical bonded to a cyano (i.e., C≡N) group.

"Alkylhalo" refers broadly to a straight or branched chain, saturated or partially unsaturated hydrocarbon radical bonded to a halogen (e.g., fluoro, chloro, bromo, and iodo).

"Alkaryl" as used herein refers broadly to a straight or branched chain, saturated hydrocarbon radical bonded to an aryl group. Examples of alkaryl groups include, but are not limited to, benzyl, 4-chlorobenzyl, methylbenzyl, dimethylbenzyl, ethylphenyl, propyl-(4-nitrophenyl), and the like. Such alkaryl groups may be optionally substituted described herein.

"Alkylene" as used herein refers broadly to a straight or branched chain having two terminal monovalent radical centers derived by the removal of one hydrogen atom from each of the two terminal carbon atoms of straight-chain parent alkane.

"Aryl" or "Ar" as used herein refers broadly to an aromatic group or to an optionally substituted aromatic group fused to one or more optionally substituted aromatic groups, optionally substituted with suitable substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl, 2-naphthyl, 1-naphthyl, and the like.

"Alkoxy" as used herein alone or as part of another group, refers broadly to an alkyl group, as defined herein, appended to the parent molecular moiety through an oxy group. In some embodiments, the alkyl group can be interrupted by one or more heteroatoms (e.g., O, S, or N). Examples of alkoxy include, but are not limited to, methoxy, ethoxy, propoxy, 2-propoxy, butoxy, tert-butoxy, pentyloxy, hexyloxy, ethyloxyethyl, and the like.

"Alkaryloxy" or "oxyalkaryl" as used herein refers broadly to the group —O-alkyl-aryl wherein Ar is aryl. Examples include, but are not limited to, benzyloxy, oxybenzyl, 2-naphthyloxy, and oxy-2-naphthyl.

"Alkaryloxyalkyl" or "alkyloxyalkaryl" as used herein refers broadly to the group -alkyl-O-alkyl-aryl wherein Ar is aryl. Examples include, but are not limited to benzyloxyethyl.

"Analogs," as used herein, refer broadly to the modification or substitution of one or more chemical moieties on a parent compound and may include derivatives, positional isomers, and prodrugs of the parent compound.

"Aryloxy" as used herein refers broadly to the group —ArO wherein Ar is aryl or heteroaryl. Examples include, but are not limited to, phenoxy, benzyloxy, and 2-naphthyloxy.

"Amino" as used herein refers broadly to —NH$_2$ in which one or both of the hydrogen atoms may optionally be replaced by alkyl or aryl or one of each, optionally substituted.

"Alkylthio" or "thioalkyl," as used herein alone or as part of another group, refers broadly to an alkyl group, as defined herein, appended to the parent molecular moiety through a sulfur moiety. Representative examples of alkylthio include, but are not limited to, methylthio, thiomethyl, ethylthio, thioethyl, n-propylthio, thio-n-propyl, isopropylthio, thioisopropyl, n-butylthio, thio-n-butyl, and the like.

"Arylthio" or "thioaryl," as used herein refers broadly to the group —ArS wherein Ar is aryl. Examples include, but are not limited to, phenylthio, thiophenyl, 2-naphthylthio, and thio-2-naphthyl.

"Alkarylthio" or "thioalkaryl" as used herein refers broadly to the group —S-alkyl-aryl wherein Ar is aryl.

Examples include, but are not limited to, benzylthio, thiobenzyl, 2-naphthylthio, and thio-2-naphthyl.

"Alkylheterocycloalkyl" as used herein refers to as used herein refers broadly to a straight or branched chain, saturated hydrocarbon radical bonded to a heterocycloalkyl group.

"Biocompatible polymer" as used herein refers broadly to a polymer moiety that is substantially non-toxic and does not tend to produce substantial immune responses, clotting or other undesirable effects. Accordingly to some embodiments of the present invention, polyalkylene glycol is a biocompatible polymer where, as used herein, polyalkylene glycol refers to straight or branched polyalkylene glycol polymers such as polyethylene glycol, polypropylene glycol, and polybutylene glycol, and further includes the monoalkylether of the polyalkylene glycol. In some embodiments of the present invention, the polyalkylene glycol polymer is a lower alkyl polyalkylene glycol moiety such as a polyethylene glycol moiety (PEG), a polypropylene glycol moiety, or a polybutylene glycol moiety. PEG has the formula —HO(CH$_2$CH$_2$O)$_n$H, where n can range from about 1 to about 4000 or more. In some embodiments, n is 1 to 100, and in other embodiments, n is 5 to 30. The PEG moiety can be linear or branched. In further embodiments, PEG can be attached to groups such as hydroxyl, alkyl, aryl, acyl, or ester. In some embodiments, PEG can be an alkoxy PEG, such as methoxy-PEG (or mPEG), where one terminus is a relatively inert alkoxy group, while the other terminus is a hydroxyl group.

"Bioavailability", as used herein, refers broadly to the availability of a drug to an animal following administration and may be used interchangeably with "systemic exposure" (e.g., the bioavailability of a drug is expressed as the systemic exposure of a cell to drugs).

"Carboxy" as used herein refers broadly to the group —CO$_2$H.

"Cycloalkyl" as used herein refers to carbocycles containing no heteroatoms, and includes mono-, bi- and tricyclic saturated carbocycles, as well as fused ring systems. Examples of cycloalkyl include cyclopropyl, cyclobutyl, cyclopentyl, cyclohexyl, and the like. The cycloalkyl can be substituted or unsubstituted.

"Effective amount" or "effective," as used herein, refers broadly to a dose that causes a relief of symptoms of a disease or disorder as noted through clinical testing and evaluation, patient observation, and/or the like. "Effective amount" or "effective" further can further designate a dose that causes a detectable change in biological or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. As is generally understood in the art, the dosage will vary depending on the administration routes, symptoms, and body weight of the patient but also depending upon the compound being administered.

"Halo" as used herein refers broadly to bromo, chloro, fluoro, or iodo. Alternatively, the term "halide" as used herein refers broadly to bromide, chloride, fluoride, or iodide.

"Hydroxy" as used herein refers broadly to the group —OH.

"Heteroaryl" as used herein refers to an aromatic five- or six-membered ring where at least one atom consists of a heteroatom (e.g., O, S, or N), and the remaining atoms are carbon. The five-membered rings have two double bounds, and the six-membered rings have three double bonds. The heteroaryl group can be monocyclic or bicyclic (fused or non-fused). Examples of monocyclic heteroaryl groups include furanyl, thiophene-yl, pyrrolyl, oxazolyl, thiazolyl, imidazolyl, pyrazolyl, isoxazolyl, isothiazolyl, oxadiazolyl, thiazolyl, thiadiazolyl, pyridinyl, pyridazinyl, pyrimidinyl, pyrazinyl, triazinyl, and the like. Examples of bicyclic heteroaryl groups include indolizinyl, indolyl, isoindolyl, benzofuranyl, benzothiophene-yl, indazolyl, benzimidazolyl, benzthiazolyl, purinyl, quinolinyl, isoquinolinyl, cinnolinyl, phthalazinyl, quinazolinyl, quinoxalinyl, napthyridinyl, pteridinyl, and the like. The heteroaryl group can be substituted or unsubstituted.

"Heterocycloalkyl" as used herein refers to a cycloalkyl group where at least one of the carbon atoms in the ring is replaced by a heteroatom (e.g., O, S, or N). The heterocycloalkyl group can be monocyclic or bicyclic (fused or non-fused). Examples of monocyclic heterocycloalkyl groups include azetidinyl, pyrrolidinyl, piperidinyl, homopiperidinyl, piperazinyl, morpholinyl, thiomorpholinyl, 1-oxothiomorpholinyl, 1,1-dioxothiomorpholinyl, tetrahydrooxazolyl, tetrahydroisoxazolyl, tetrahydroimidazolyl, tetrahydropyrazolyl, tetrahydrothiazolidinyl, tetrahydroisothiazolidinyl, tetrahydropyrimidinyl, tetrahydropyridazinyl, 4-piperadonyl, and the like. Examples of bicyclic non-fused heterocycloalkyl groups include quinuclidinyl, adamantyl, 2-azobicyclo[3.2.1]octyl, and the like.

Examples of fused heterocycloalkyl groups include any of the aforementioned monocyclic heterocycloalkyl groups fused with another cycloalkyl or heterocycloalkyl group. The heterocycloalkyl group can be substituted or unsubstituted.

"Hydrate" as used herein refers broadly to the compound when the solvent is water.

"Increased" or "increase" as used herein, refers broadly to a quantified change in a measurable quality that is larger than the margin of error inherent in the measurement technique, preferably an increase by about 2-fold or greater relative to a control measurement, more preferably an increase by about 5-fold or greater, and most preferably an increase by about 10-fold or greater. In particular, the term "increase," as used herein, refers broadly to make greater, as in number, size, strength, or quality; add to; and/or augment. "Increase," as used herein, also encompasses expand, extend, prolong, augment, enlarge, grow, develop, and/or swell. "Increase," as used herein, additionally encompasses where a given parameter (e.g., level, amount, size, scope, duration, weight) is greater, as in number, size, strength, or quality, than it once was. Furthermore, the "increase" in any number, size, strength, or quality of a given parameter may be determined as between to two or more time points, especially if before or after a treatment, event, or administration of an agent or composition. Further, "increase" refers broadly to significant or detectable, functionally, analytically, and/or clinically, changes in the number, size, strength, or quality of a given parameter in question.

"Mammal" as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, chimpanzees, chinchillas, cattle, dogs, goats, gorillas, hamsters, horses, humans, lemurs, llamas, mice, non-human primates, pigs, rats, sheep, shrews, and tapirs. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C., hereby incorporated by reference in its entirety.

"N-oxide" or "amine N-oxide" as used herein refers broadly to a chemical structure having an N—O bond where the nitrogen is positively charged and the oxygen is negatively charged.

"N-substituted sulfonamide" as used herein refers broadly to a chemical structure having the —$SO_2$—NH(R) group. In this context, the R-group includes, but is not limited to lower alkyl (e.g., $C_1$-$C_5$ alkyl), lower alkenyl (e.g., $C_2$-$C_6$ alkenyl), alkaryl, aryl, cycloalkenyl, cycloalkyl, dialkylaminoalkyl, heterocycloalkyl, and heteroaryl.

"N,N-disubstituted sulfonamide" as used herein refers broadly to a chemical structure having the —$SO_2$—NRR' group. In this context, the R and R' are the same or different and are independently lower alkyl, lower alkenyl, alkaryl, aryl, cycloalkenyl, cycloalkyl, dialkylaminoalkyl, heterocycloalkyl, heteroaryl or taken together with the nitrogen atom to which they are attached form a 4-8 member cycle which can be substituted or unsubstituted and can have one or more heteroatoms (e.g., N, O, or S).

"Parasynaptic" as used herein, refers broadly to receptors (e.g., $GABA_A$ receptors) located outside or in the perimeter of the synapse (e.g., synaptic cleft). Also, "parasynaptic" refers broadly to any receptors located perisynaptically, extrasynaptically, and presynaptically.

"Patient" as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. Animals may be mammals, reptiles, birds, amphibians, or invertebrates.

"Pharmaceutically acceptable salt" as used herein, refers broadly to a salt form of a compound permitting its use or formulation as a pharmaceutical and which retains the biological effectiveness of the free acid and base of the specified compound and that is not biologically or otherwise undesirable.

"Prophylactically effective amount" as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Protective," as used herein, refers broadly to reducing the incidence or severity of the disease in a patient. Protective, as used herein, refers broadly to inhibiting the disease, arresting the development of the disease or its clinical symptoms, and/or causing regression of the disease or its clinical symptoms. Prevention also preferably includes preventing or reducing incidence or severity of disease in a patient.

"Protective effect amount," as used herein, refers broadly to the amount of a compound that, when administered to a patient reduces the severity of the incidence of signs and/or symptoms, slows the development of the incidence of signs and/or symptoms, prevents the development of the incidence of signs and/or symptoms. The "protective effective amount" may vary depending on the disease and its severity and the age, weight, medical history, predisposition to conditions, preexisting conditions, of the patient to be treated.

"Quaternary ammonium" as used herein refers broadly to a chemical structure having four bonds to the nitrogen with a positive charge on the nitrogen in the "onium" state, i.e., "$R_4N^+$" or "quaternary nitrogen," wherein R is an organic substituent such as alkyl or aryl. The term "quaternary ammonium salt" as used herein refers broadly to the association of the quaternary ammonium cation with an anion.

"Signs" of disease, as used herein, refers broadly to any abnormality indicative of disease, discoverable on examination of the patient; an objective indication of disease, in contrast to a symptom, which is a subjective indication of disease.

"Symptoms" of disease as used herein, refers broadly to any morbid phenomenon or departure from the normal in structure, function, or sensation, experienced by the patient and indicative of disease.

"Subjects" as used herein, refers broadly to anyone suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g., rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

The present invention can also be carried out on animal subjects, particularly mammalian subjects such as mice, rats, dogs, cats, cattle, goats, sheep, and horses for veterinary purposes, and for drug screening and drug development purposes. The present invention can also be carried out on avians including chickens, ducks, turkeys, geese, quail, pheasant, ratites (e.g., ostrich) and domesticated birds (e.g., parrots and canaries), and birds in ovo. "Subjects" is used interchangeably with "patients."

"Solvate" as used herein refers broadly is intended to refer to a pharmaceutically acceptable solvate form of a specified compound that retains the biological effectiveness of such compound, for example, resulting from a physical association of the compound with one or more solvent molecules. Examples of solvates, without limitation, include compounds of the invention in combination with water, 1-propanol, 2-propanol, ethanol, methanol, DMSO, ethyl acetate, acetic acid, or ethanolamine.

"Substituted" as used herein refers broadly to replacement of one or more of the hydrogen atoms of the group replaced by substituents known to those skilled in the art and resulting in a stable compound as described below. Examples of suitable replacement groups include, but are not limited to, alkyl, acyl, alkenyl, alkynyl cycloalkyl, aryl, alkaryl, hydroxy, thio, alkoxy, aryloxy, acyl, amino, amido, carboxy, carboxyalkyl, thiocarboxyalkyl, carboxyaryl, thiocarboxyaryl, halo, oxo, mercapto, sulfinyl, sulfonyl, sulfonamido, amidino, carbamoyl, cycloalkyl, heterocycloalkyl, dialkylaminoalkyl, carboxylic acid, carboxamido, haloalkyl, dihaloalkyl, trihaloalkyl, trihaloalkoxy, alkylthio, aralkyl, alkylsulfonyl, arylthio, amino, alkylamino, dialkylamino, guanidino, ureido, nitro and the like. Substitutions are permissible when such combinations result in compounds stable for the intended purpose. For example, substitutions are permissible when the resultant compound is sufficiently robust to survive isolation to a useful degree of purity from a reaction mixture, and formulation into a therapeutic or diagnostic agent or reagent.

"Therapy" or "therapeutic" as used herein refers broadly to treating a disease, arresting or reducing the development of the disease or its clinical symptoms, and/or relieving the disease, causing regression of the disease or its clinical symptoms. Therapy encompasses prophylaxis, prevention, treatment, cure, regimen, remedy, minimization, reduction, alleviation, and/or providing relief from a disease, signs, and/or symptoms of a disease. Therapy encompasses an alleviation of signs and/or symptoms in patients with ongoing disease signs and/or symptoms (e.g., pain, inflammation.) Therapy also encompasses "prophylaxis" and "prevention." Prophylaxis includes preventing disease occurring subsequent to treatment of a disease in a patient or reducing the incidence or severity of the disease in a patient. The term "reduced," for purpose of therapy, refers broadly to the clinical significant reduction in signs and/or symptoms. Therapy includes treating relapses or recurrent signs and/or symptoms (e.g., of pain.) Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease.

Therapy can be for patients with risk factors, at risk patients in a susceptible population, patients with a history of disease, patients with symptoms, patients with signs, patients with signs but no symptoms, and patients with symptoms but no signs. Therapy can also be for patients without risk factors, not at risk, patients not in a susceptible population, patients no history of disease, patients with no symptoms, patients without signs. Therapy can alleviate, allay, abate, assuage, curtail, decrease, ease, lessen, lighten, make better, make healthy, mitigate, mollify, pacify, relieve, rehabilitate, remedy, repair, and/or soothe a disease, disease signs, and/or disease symptoms.

"Treating" or "treatment," as used herein, refers broadly to a course of therapy where signs and/or symptoms are present in the patient. The term "reduced," for purpose of therapy, refers broadly to clinically significant reduction in signs and/or symptoms. Treatment includes treating chronic disease ("maintenance") and acute disease. Treatment can be for patients with risk factors, at risk patients in a susceptible population, patients with a history of disease, and/or patients with symptoms, patients with signs. Treatment can alleviate, allay, abate, assuage, curtail, decrease, ease, lessen, lighten, make better, make healthy, mitigate, mollify, pacify, relieve, rehabilitate, remedy, repair, and/or soothe a disease, disease signs, and/or disease symptoms. By the terms "treating" or "treatment" of a disorder involving the $Na^+K^+Cl^-$ co-transporters, it is intended that the severity of the disorder or the symptoms of the disorder are reduced, or the disorder is partially or entirely eliminated, as compared to that which would occur in the absence of treatment. Treatment does not require the achievement of a complete cure of the disorder. By the terms "preventing" or "prevention" of the disorder involving the $Na^+K^+Cl^-$ co-transporters, it is intended that the inventive methods eliminate or reduce the incidence or onset of the disorder, as compared to that which would occur in the absence of treatment. Alternatively stated, the present methods slow, delay, control, or decrease the likelihood or probability of the disorder in the subject, as compared to that which would occur in the absence of treatment. Further, the terms "treating" or "treatment" of a disorder involving the $GABA_A$ receptor, are intended that the severity of the disorder or the symptoms of the disorder are reduced, or the disorder is partially or entirely eliminated, as compared to that which would occur in the absence of treatment. Treatment does not require the achievement of a complete cure of the disorder.

"Therapeutically effective amount" as used herein, refers broadly to the amount of a compound that, when administered to a patient for treating a disease, is sufficient to effect such treatment for the disease. Therapeutically effective amount can be an amount effective for prophylaxis, and/or an amount effective for prevention. Therapeutically effective amount can be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "therapeutically effective amount" can vary depending on the disease and its severity and the age, weight, medical history, predisposition to conditions, preexisting conditions, of the patient to be treated. The term "effective amount" is taken to be synonymous with "therapeutically effective amount" for purposes of this invention.

1. Compounds

According to some embodiments, the present invention provides novel compounds. Thus, any of the R groups as defined herein can be excluded or modified in order to exclude a known compound and/or provide a novel compound. Compounds of the present invention can include compounds according to formula I, II, III, IV, V, VI, VII, VIII, IX, X, XI, XII, XII, XIV, XV, and/or XVI:

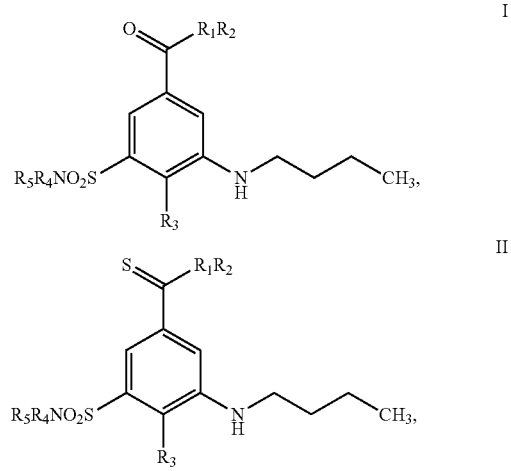

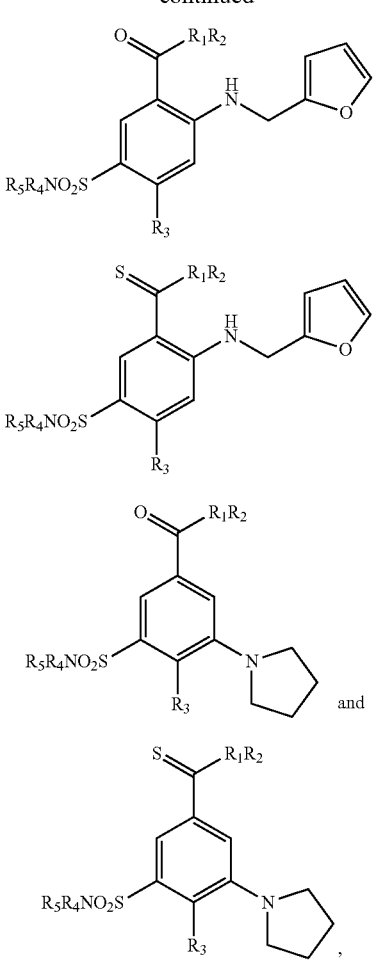

or a pharmaceutically acceptable salt, solvate, tautomer or hydrate thereof, wherein $R_1$ is not present, H, O or S;

$R_2$ is not present, H or when $R_1$ is O or S, $R_2$ is selected from the group consisting of hydrogen, alkyl, aralkyl, aryl, alkylaminodialkyl, alkylcarbonylaminodialkyl, alkyloxycarbonylalkyl, alkylcarbonyloxyalkyl, alkylaldehyde, alkylketoalkyl, alkylamide, alkarylamide, arylamide, an alkylammonium group, alkylcarboxylic acid, alkylheteroaryl, alkylhydroxy, a biocompatible polymer such as alkyloxy(polyalkyloxy)alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl and methylthioalkaryl, unsubstituted or substituted, and when $R_1$ is not present, $R_2$ is selected from the group consisting of hydrogen, N,N-dialkylamino, N,N-dialkarylamino, N,N-diarylamino, N-alkyl-N-alkarylamino, N-alkyl-N-arylamino, N-alkaryl-N-arylamino, unsubstituted or substituted;

$R_3$ is selected from the group consisting of aryl, halo, hydroxy, alkoxy, and aryloxy, unsubstituted or substituted; and $R_4$ and $R_5$ are each independently selected from the group consisting of hydrogen, alkylaminodialkyl, carbonylalkyl, carbonylalkaryl, carbonylaryl, and salts thereof such as sodium, potassium, calcium, ammonium, trialkylarylammonium and tetraalkylammonium salts, with the following provisos in some embodiments: $R_3$ of formula I is not phenyloxy when $R_1$ is O and $R_2$, $R_4$ and $R_5$ are H, more specifically, in some embodiments, the compound of formula I is not bumetanide; $R_3$ of formula III is not Cl, when $R_1$ is O and $R_2$, $R_4$ and $R_5$ are H, more specifically, in some embodiments, the compound of formula III is not furosemide; $R_2$ of formula III is not methyl when $R_1$ is O, $R_3$ is Cl, and $R_4$ and $R_5$ are H, more specifically, in some embodiments, the compound of formula III is not furosemide methyl ester, $R_3$ of formula V is not phenyloxy when $R_1$ is O and $R_2$, $R_4$ and $R_5$ are H, more specifically, in some embodiments, the compound of formula V is not piretanide.

In some embodiments of the present invention, the compound of formula I can be bumetanide, bumetanide aldehyde, bumetanide methyl ester, bumetanide cyanomethyl ester, bumetanide ethyl ester, bumetanide isoamyl ester, bumetanide octyl ester, bumetanide benzyl ester, bumetanide dibenzylamide, bumetanide diethylamide, bumetanide morpholinoethyl ester, bumetanide 3-(dimethylaminopropyl) ester, bumetanide N,N-diethylglycolamido ester, bumetanide N,N-dimethylglycolamido ester, bumetanide pivaxetil ester, bumetanide propaxetil ester, bumetanide methoxy(polyethyleneoxy)$_{n-1}$-ethyl ester, bumetanide benzyltrimethylammonium salt and bumetanide cetyltrimethylammonium salt. In particular embodiments, the compound is not bumetanide.

In other embodiments of the present invention, the compound of formula I can be bumetanide [—(C═O)—SH] thioacid, bumetanide S-methyl thioester, bumetanide S-cyanomethyl thioester, bumetanide S-ethyl thioester, bumetanide S-isoamyl thioester, bumetanide S-octyl thioester, bumetanide S-benzyl thioester, bumetanide S-(morpholinoethyl)thioester, bumetanide S-[3-(dimethylaminopropyl)] thioester, bumetanide S—(N,N-diethylglycolamido)thioester, bumetanide S—(N,N-dimethylglycolamido)thioester, bumetanide S-pivaxetil thioester, bumetanide S-propaxetil thioester, bumetanide S-[methoxy(polyethyleneoxy), -ethyl] thioester, bumetanide [—(C═O)—S—] benzyltrimethylammonium thioacid salt and bumetanide [—(C═O)—S—] cetyltrimethylammonium thioacid salt.

In some embodiments of the present invention, the compound of formula II can be metastable bumetanide [—(C═S)—OH] thioacid, bumetanide O-methyl thioester, bumetanide O-cyanomethyl thioester, bumetanide O-ethyl thioester, bumetanide O-isoamyl thioester, bumetanide O-octyl thioester, bumetanide O-benzyl thioester, bumetanide O-(morpholinoethyl)thioester, bumetanide O-[3-(dimethylaminopropyl)] thioester, bumetanide O—(N,N-diethylglycolamido)thioester, bumetanide, O—(N,N-dimethylglycolamido)thioester, bumetanide O-pivaxetil thioester, bumetanide O-propaxetil thioester, bumetanide O-[methoxy(polyethyleneoxy)$_{n-1}$-ethyl] thioester, bumetanide [—(C═S)—O—] benzyltrimethyl ammonium thioacid salt and bumetanide [(C—S)—O—] cetyltrimethylammonium thioacid salt.

In some embodiments of the present invention, the compound of formula H can be bumetanide thioaldehyde, bumetanide [—(C═S)—SH] dithioacid, bumetanide methyl dithioester, bumetanide cyanomethyl dithioester, bumetanide ethyl dithioester, bumetanide isoamyl dithioester, bumetanide octyl dithioester, bumetanide benzyl dithioester, bumetanide dibenzylthioamide, bumetanide diethylthioamide, bumetanide morpholinoethyl dithioester, bumetanide 3-(dimethylaminopropyl)dithioester, bumetanide N,N-diethylglycolamido dithioester, bumetanide N,N-dimethylglycolamido dithioester, bumetanide pivaxetil dithioester, bumetanide propaxetil dithioester, bumetanide methoxy(polyethylencoxy)$_{n-1}$-ethyl dithioester, bumetanide benzyltrimethylammonium dithioacid salt and bumetanide cetyltrimethylammonium dithioacid salt.

In other embodiments of the present invention, the compound of formula III can be furosemide, furosemide aldehyde, furosemide methyl ester, furosemide cyanomethyl ester, furosemide ethyl ester, furosemide isoamyl ester, furosemide octyl ester, furosemide benzyl ester, furosemide dibenzylamide, furosemide diethylamide, furosemide morpholinoethyl ester, furosemide 3-(dimethylaminopropyl) ester, furosemide N,N-diethylglycolamido ester, furosemide N,N-dimethylglycolamido ester, furosemide pivaxetil ester, furosemide propaxetil ester, furosemide methoxy(polyethyleneoxy)$_{n-1}$-ethyl ester, furosemide benzyltrimethylammonium acid salt and furosemide cetyltrimethylammonium acid salt. In particular embodiments, the compound is not furosemide.

In further embodiments of the present invention, the compound of formula III can be furosemide [—(C=O)—SH] thioacid, furosemide S-methyl thioester, furosemide S-cyanomethyl thioester, furosemide S-ethyl thioester, furosemide S-isoamyl thioester, furosemide S-octyl thioester, furosemide S-benzyl thioester, furosemide S-(morpholinoethyl)thioester, furosemide S-[3-(dimethylaminopropyl)] thioester, furosemide S—(N,N-diethylglycolamido)thioester, furosemide S—(N,N-dimethylglycolamido)thioester, furosemide S-pivaxetil thioester, furosemide S-propaxetil thioester, furosemide S-[methoxy(polyethyleneoxy)$_{n-1}$-ethyl] thioester, furosemide [—(C=O)—S"] benzyltrimethylammonium thioacid salt and furosemide [—(C=O)—S"] cetyltrimethylammonium thioacid salt.

In other embodiments of the present invention, the compound of formula IV can be metastable furosemide [—(C=S)—OH] thioacid, furosemide O-methyl thioester, furosemide O-cyanomethyl thioester, furosemide O-ethyl thioester, furosemide O-isoamyl thioester, furosemide O-octyl thioester, furosemide O-benzyl thioester, furosemide O-(morpholinoethyl)thioester, furosemide O-[3-(dimethylaminopropyl)] thioester, furosemide O—(N,N-diethylglycolamido)thioester, furosemide O—(N,N-dimethylglycolamido)thioester, furosemide O-pivaxetil thioester, furosemide O-propaxetil thioester, furosemide O-[methoxy(polyethyleneoxy)$_{n-1}$-ethyl] thioester, furosemide [—(C=S)—O—] benzyltrimethylammonium thioacid salt and furosemide [—(C=S)—O—] cetyltrimethylammonium thioacid salt.

In further embodiments of the present invention, the compound of formula IV can be furosemide thioaldehyde, furosemide [—(C=S)—SH] dithioacid, furosemide methyl dithioester, furosemide cyanomethyl dithioester, furosemide ethyl dithioester, furosemide isoamyl dithioester, furosemide octyl dithioester, furosemide benzyl dithioester, furosemide dibenzylamide, furosemide diethylamide, furosemide dibenzylthioamide, furosemide diethylthioamide, furosemide morpholinoethyl dithioester, furosemide 3-(dimethylaminopropyl)dithioester, furosemide N,N-diethylglycolamido dithioester, furosemide N,N-dimethylglycolamido dithioester, furosemide pivaxetil dithioester, furosemide propaxetil dithioester, furosemide methoxy(polyethyleneoxy)$_{n-1}$-ethyl dithioester, furosemide benzyltrimethylammonium dithioacid salt and furosemide cetyltrimethylammonium dithioacid salt.

In still further embodiments of the present invention, the compound of formula V can be piretanide, piretanide aldehyde, piretanide methyl ester, piretanide cyanomethyl ester, piretanide ethyl ester, piretanide isoamyl ester, piretanide octyl ester, piretanide benzyl ester, piretanide dibenzylamide, piretanide diethylamide, piretanide morpholinoethyl ester, piretanide 3-(dimethylaminopropyl) ester, piretanide N,N-diethylglycolamide ester, piretanide dimethylglycolamide ester, piretanide pivaxetil ester, piretanide propaxetil ester, piretanide methoxy(polyethyleneoxy)$_{n-1}$-ethyl ester, piretanide benzyltrimethylammonium salt and piretanide cetyltrimethylammonium salt. In particular embodiments, the compound is not piretanide. Piretanide monoalkyl (substituted and unsubstituted) amides and thioamides and pharmaceutically acceptable salts thereof are also contemplated. Non-limiting examples of such piretanide monoalkyl amides include piretanide monobenzylamide, piretanide monoethylamide, piretanide monobenzylthioamide, piretanide monoethylthioamide, and pharmaceutically acceptable salts thereof.

In some embodiments of the present invention, the compound of formula V can be piretanide [—(C=O)—SH] thioacid, piretanide S-methyl thioester, piretanide S-cyanomethyl thioester, piretanide S-ethyl thioester, piretanide S-isoamyl thioester, piretanide S-octyl thioester, piretanide S-benzyl thioester, piretanide S-(morpholinoethyl)thioester, piretanide S-[3-(dimethylaminopropyl)] thioester, piretanide S—(N,N-diethylglycolamido)thioester, piretanide S—(N,N-dimethylglycolamido)thioester, piretanide S-pivaxetil thioester, piretanide S-propaxetil thioester, piretanide S-[methoxy(polyethyleneoxy)$_{n-1}$-ethyl] thioester, piretanide [—(C=O)—S—] benzyltrimethylammonium thioacid salt and piretanide [—(C=O)—S—] cetyltrimethylammonium thioacid salt.

In further embodiments of the present invention, the compound of formula VI can be metastable piretanide [—(C=S)—OH] thioacid, piretanide O-methyl thioester, piretanide O-cyanomethyl thioester, piretanide O-ethyl thioester, piretanide O-isoamyl thioester, piretanide O-octyl thioester, piretanide O-benzyl thioester, piretanide O-(morpholinoethyl)thioester, piretanide O-[3-(dimethylaminopropyl)] thioester, piretanide O—(N,N-diethylglycolamido) thioester, piretanide, O—(N,N-dimethylglycolamido) thioester, piretanide O-pivaxetil thioester, piretanide O-propaxetil thioester, piretanide O-[methoxy(polyethyleneoxy)$_{n-1}$-ethyl] thioester, piretanide [—(C=S)—O—] benzyltrimethylammonium thioacid salt and piretanide [—(C=S)—O—] cetyltrimethylammonium thioacid salt.

In some embodiments of the present invention, the compound of formula VI can be piretanide thioaldehyde, piretanide [—(C=S)—SH] dithioacid, piretanide methyl dithioester, piretanide cyanomethyl dithioester, piretanide ethyl dithioester, piretanide isoamyl dithioester, piretanide octyl dithioester, piretanide benzyl dithioester, piretanide dibenzylthioamide, piretanide diethylthioamide, piretanide morpholinoethyl dithioester, piretanide 3-(dimethylaminopropyl)dithioester, piretanide N,N-diethylglycolamido dithioester, piretanide N,N-dimethylglycolamido dithioester, piretanide pivaxetil dithioester, piretanide propaxetil dithioester, piretanide methoxy(polyethyleneoxy)$_{n-1}$-ethyl dithioester, piretanide benzyltrimethylammonium dithioacid salt and piretanide cetyltrimethylammonium dithioacid salt. Piretanide monoalkyl (substituted and unsubstituted)thioamides and pharmaceutically acceptable salts thereof are also contemplated. Non-limiting examples of such piretanide monoalkyl thioamides include piretanide monobenzylthioamide, piretanide monoethylthioamide, and pharmaceutically acceptable salts thereof.

In other embodiments of the present invention, the compound of formula VII can be tetrazolyl-substituted azosemides (e.g. methoxymethyl tetrazolyl-substituted azosemides, methylthiomethyl tetrazolyl-substituted azosemides and N-mPEG350-tetrazolyl-substituted azosemides), azosemide benzyltrimethylammonium salt, and/or azosemide cetyltrimethylammonium salt.

In some embodiments of the present invention, the compound of formula VIII can be pyridine-substituted torsemide quaternary ammonium salts or the corresponding inner salts (zwitterions). Examples include, but are not limited to, methoxymethyl pyridinium torsemide salts, methylthiomethyl pyridinium torsemide salts, and N-mPEG350-pyridinium torsemide salts.

Embodiments of the present invention further provide intermediate compounds formed through the synthetic methods described herein to provide the compounds of Formula I, II, III, IV, V, VI, VII, VIII, IX, X, XI, XII, XIII, XIV, XVI, XVII, XVIII, XVI, XIX, XX, XXI, XXII, XXIII, XXIV, XXV, and/or XXVI. The intermediate compounds may possess utility as therapeutic agents for the range of indications described herein and/or reagents for further synthesis methods and reactions.

As noted previously, any of the R groups as defined herein can be excluded from the compounds of the present invention, particularly with reference to denoting novel compounds of the present invention.

In some embodiments, the present invention encompasses the following compounds, including esters, amides, N-substituted sulfonamides and N,N-disubstituted sulfonamides thereof:

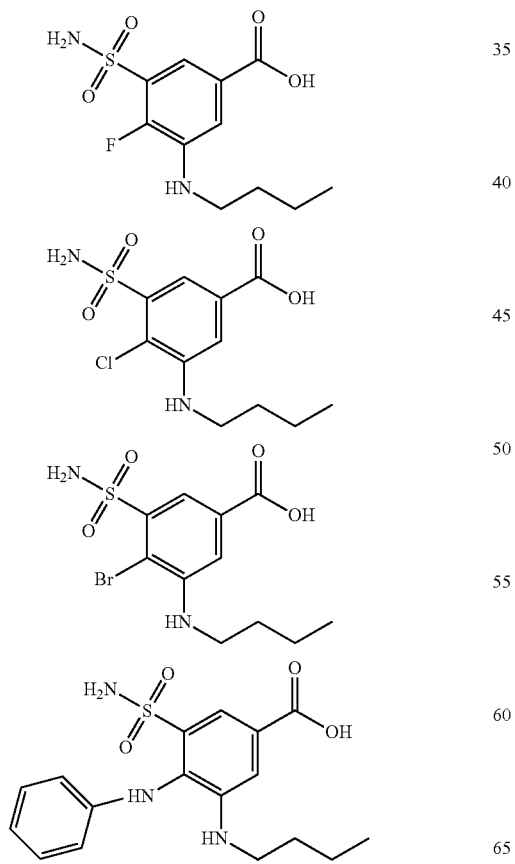

-continued

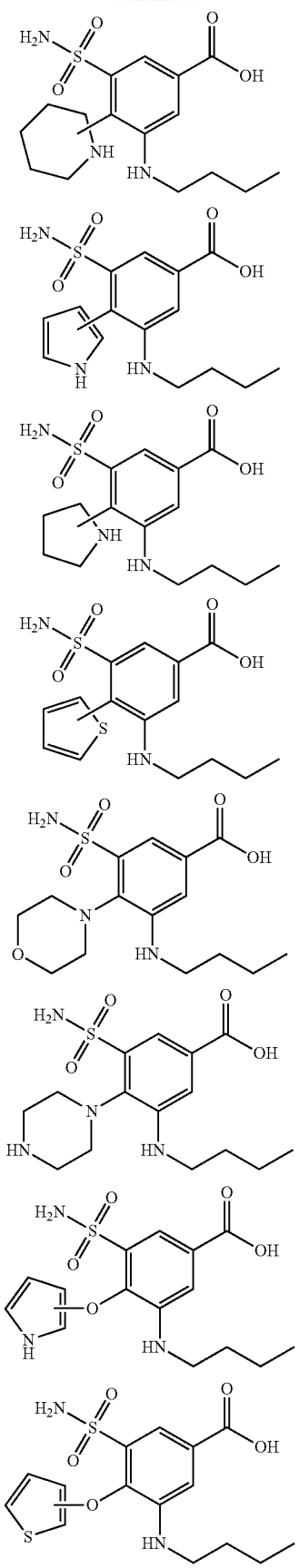

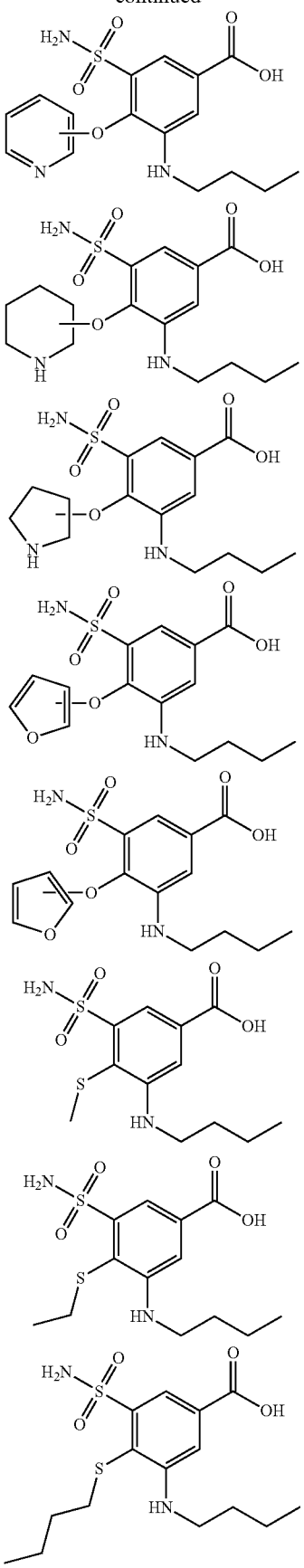
In other embodiments, the present invention encompasses the following compounds, including esters and amides thereof:
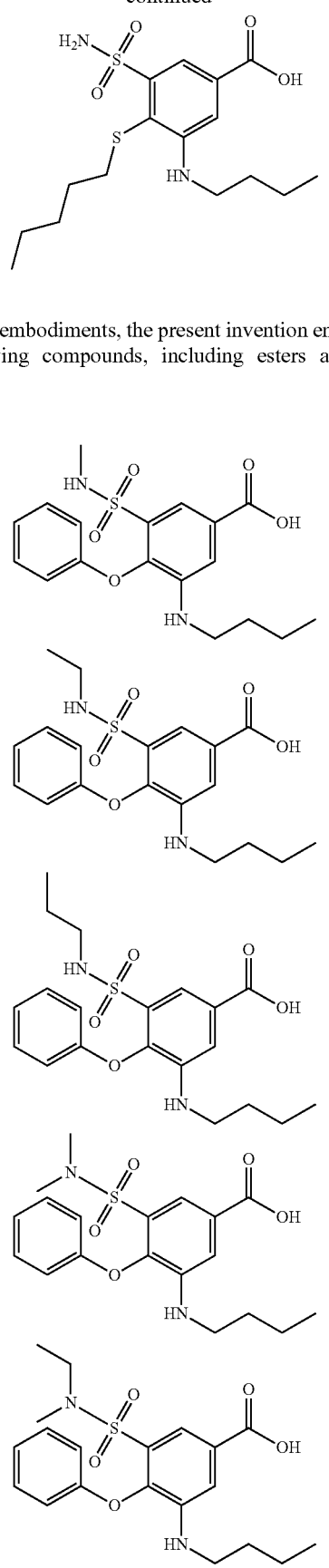

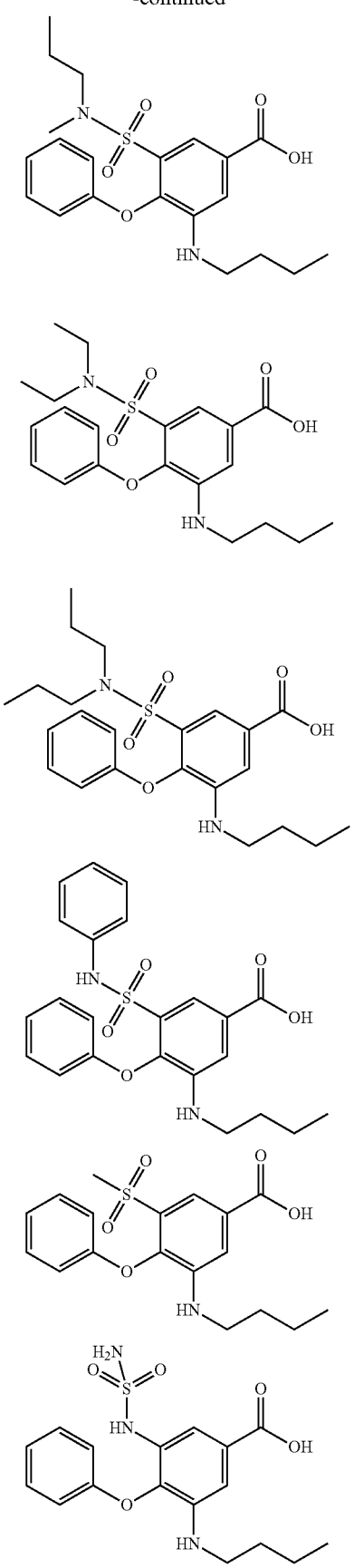
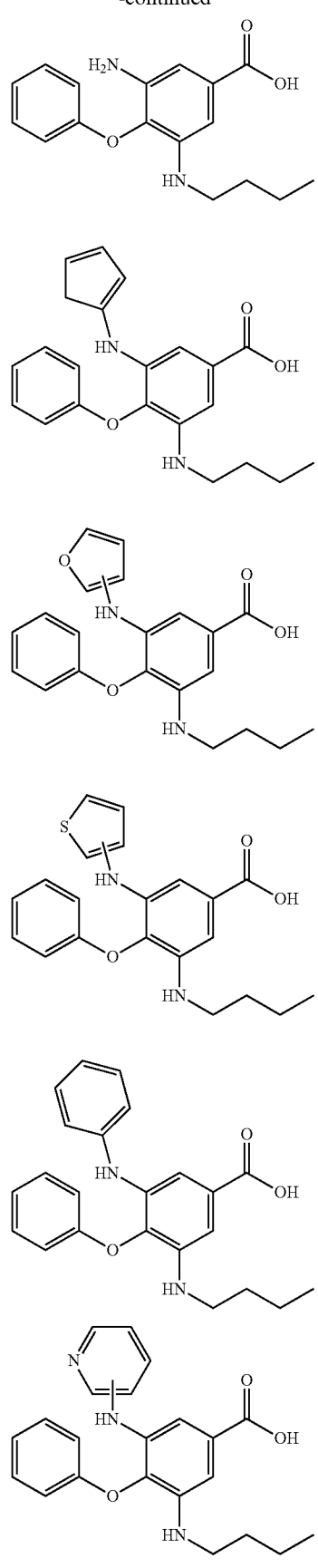

77
-continued
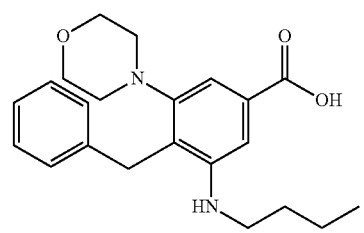
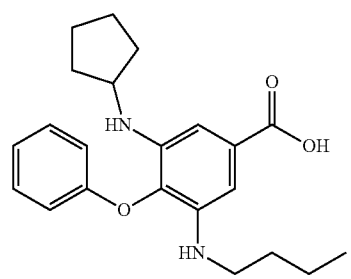
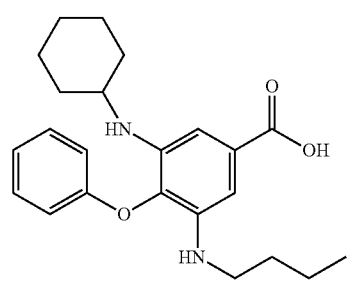
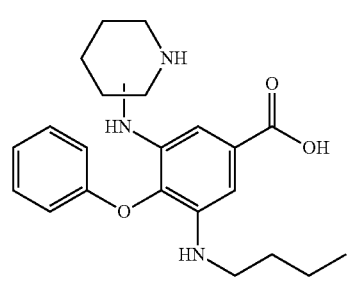
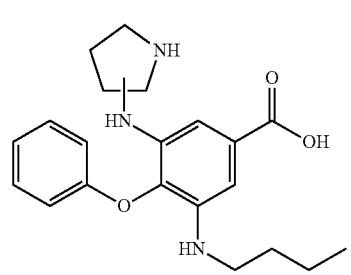
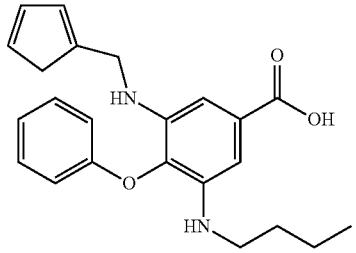
78
-continued
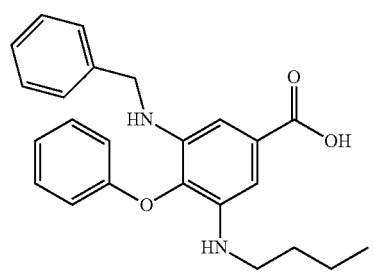
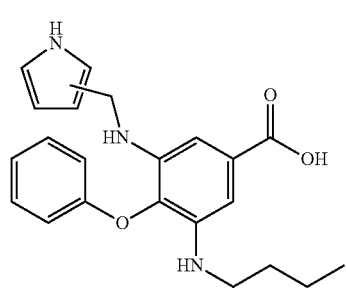
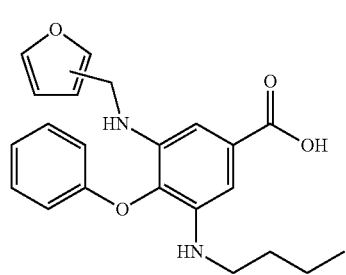
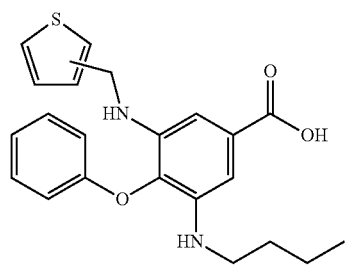
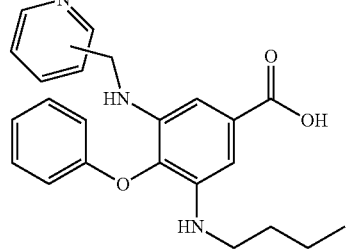
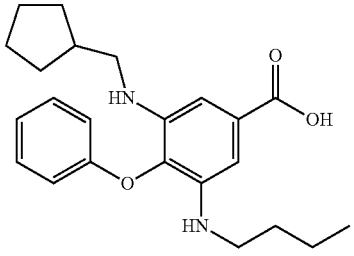

-continued
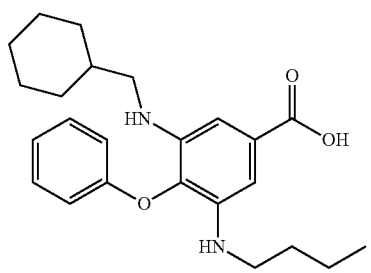
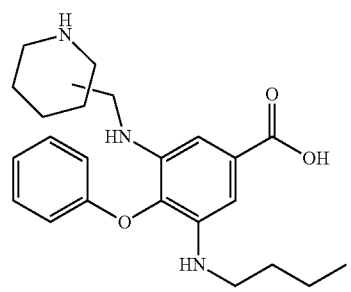
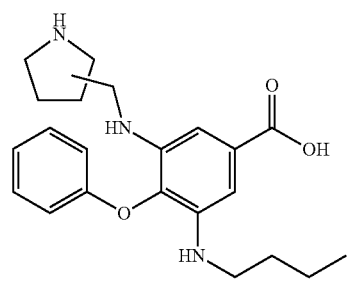
In still other embodiments, the present invention encompasses the following compounds:
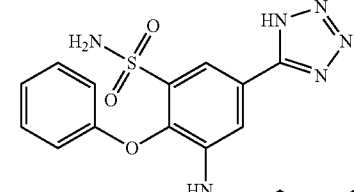
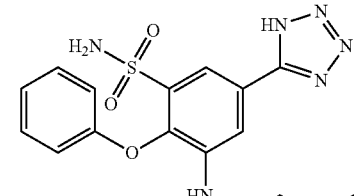
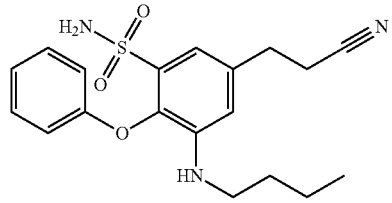
-continued
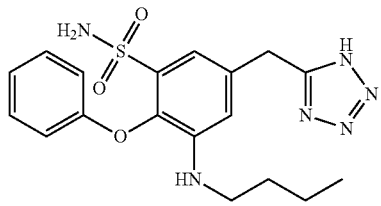
In yet other embodiments, the present invention encompasses the following compounds, including esters, amides, N-substituted sulfonamides and N,N-disubstituted sulfonamides thereof:
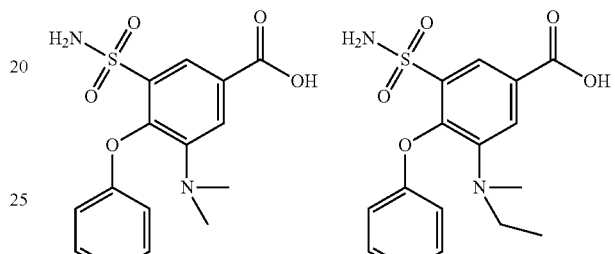
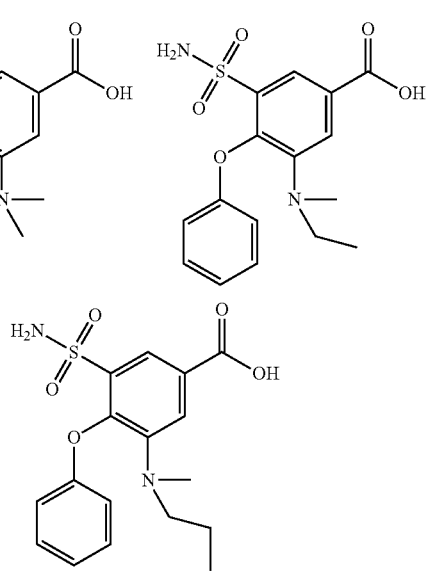
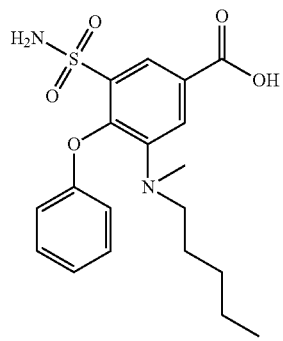
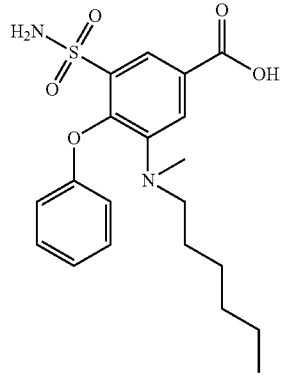

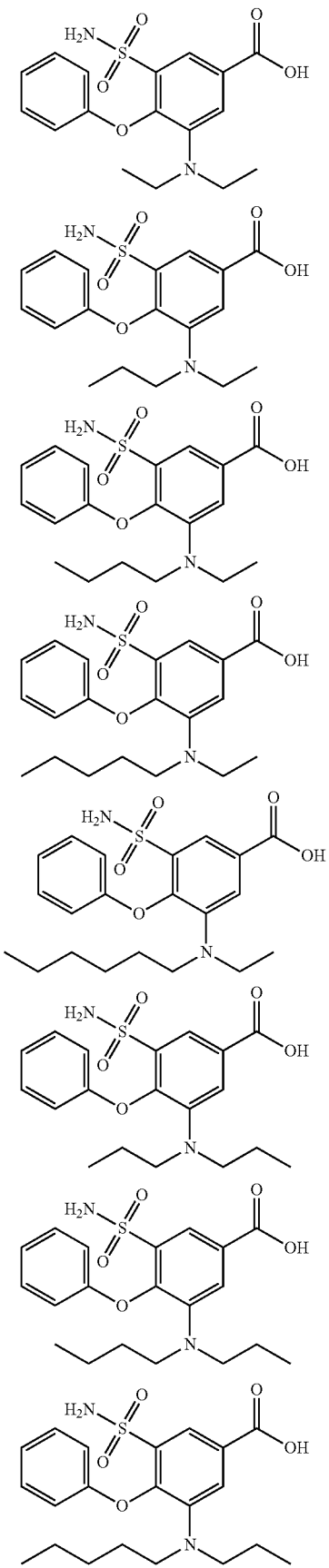
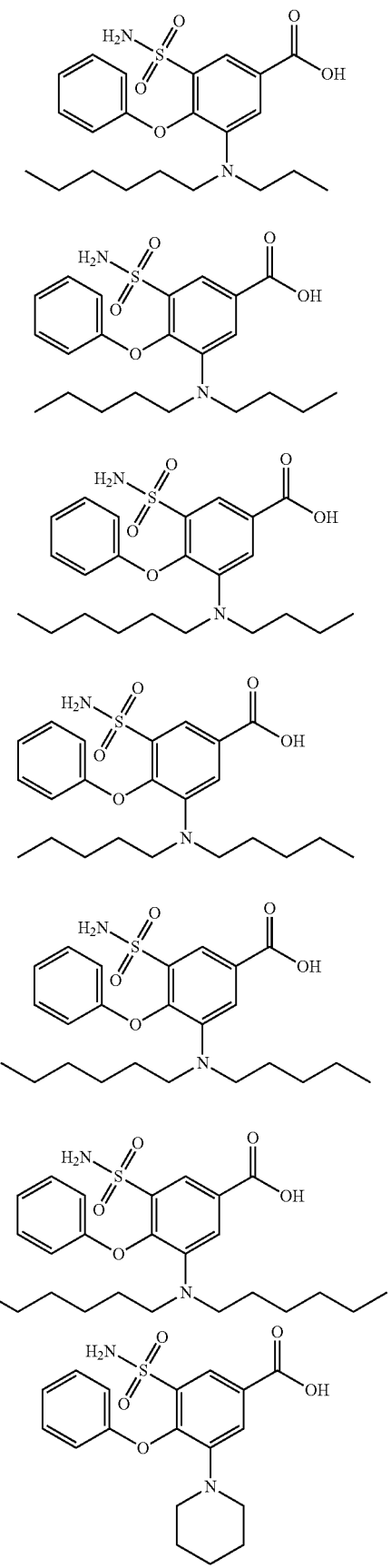

83
-continued
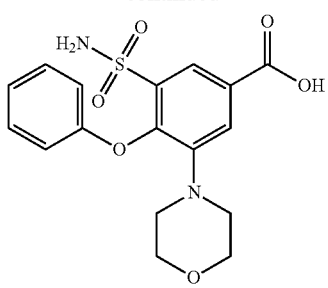
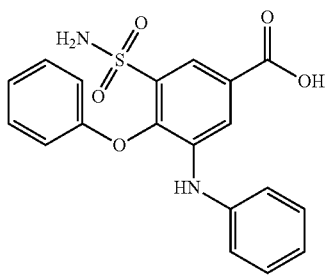
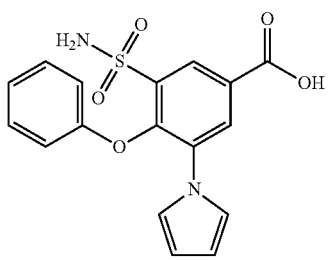
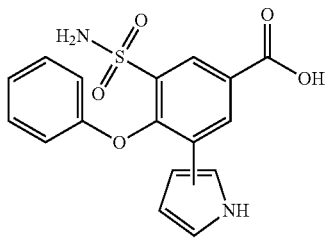
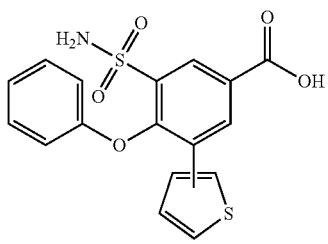
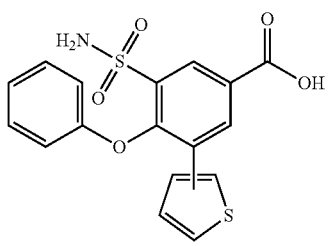
84
-continued
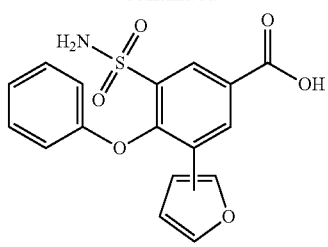
In yet other embodiments, the present invention encompasses the following compounds, including N-substituted sulfonamides and NN-disubstituted sulfonamides thereof:
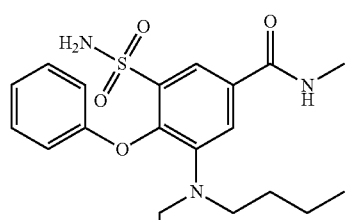
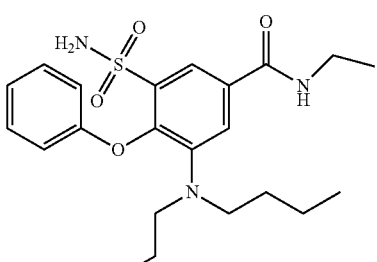
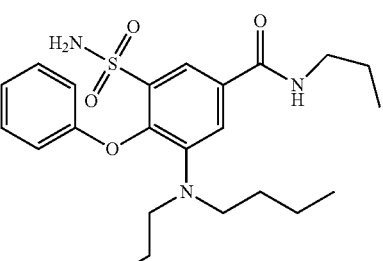
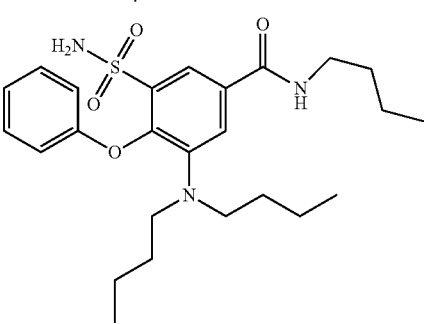

85
-continued
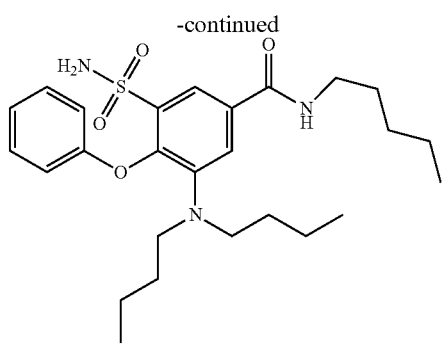
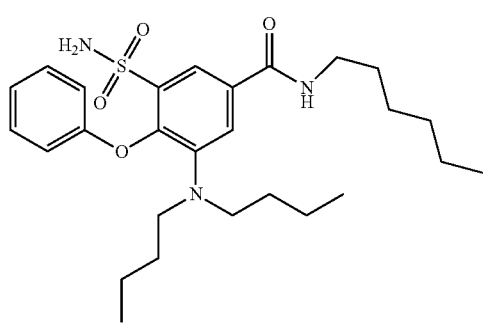
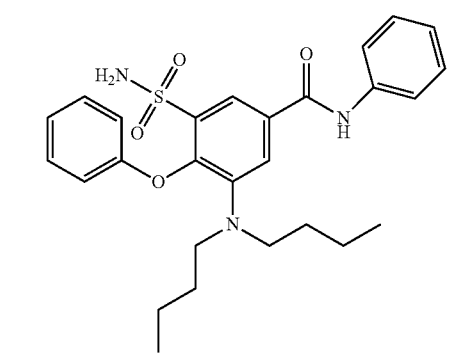
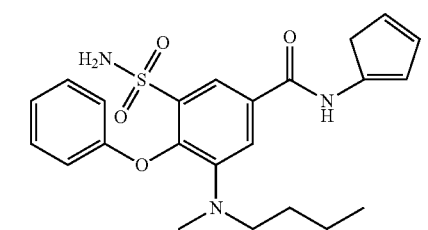
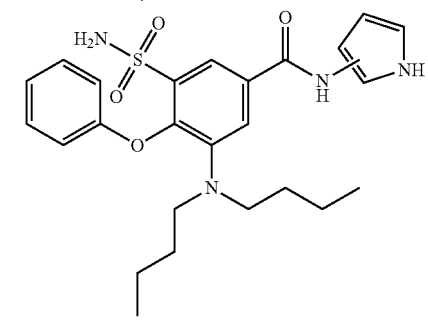
86
-continued
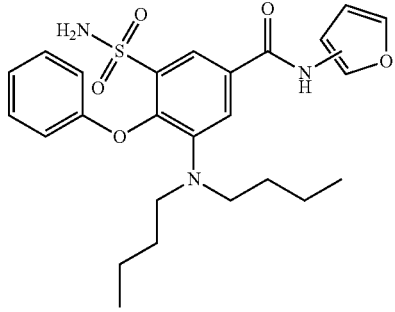
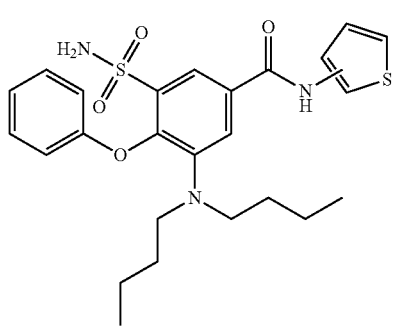
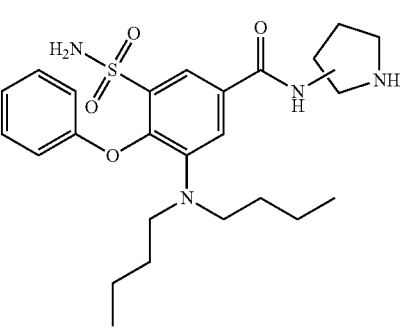
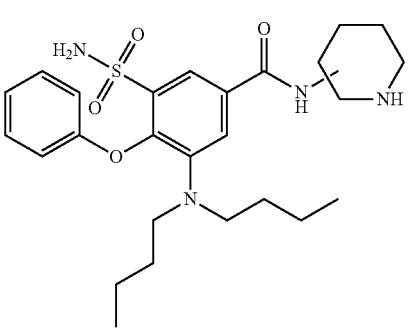
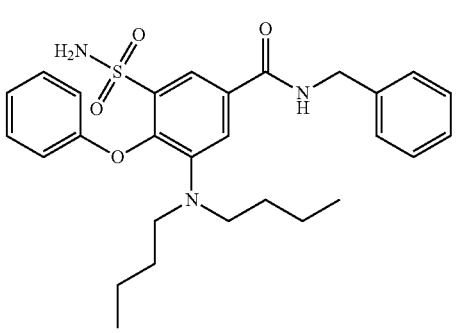

87
-continued
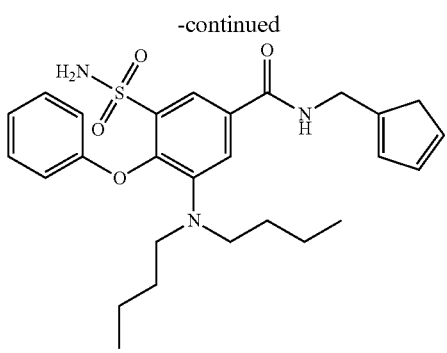
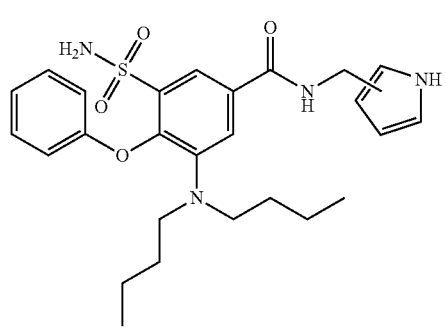
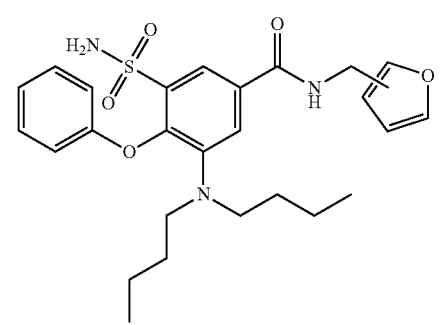
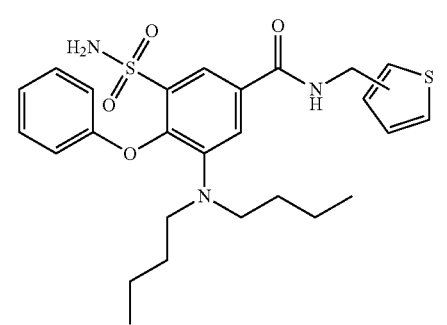
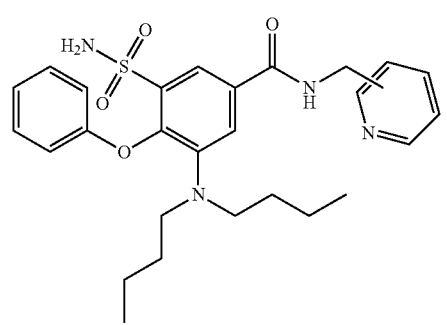
88
-continued
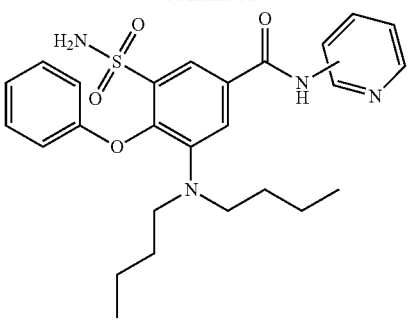
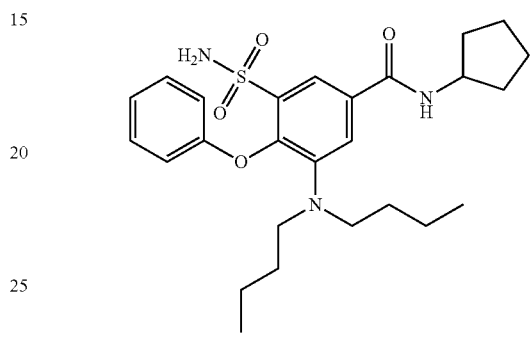
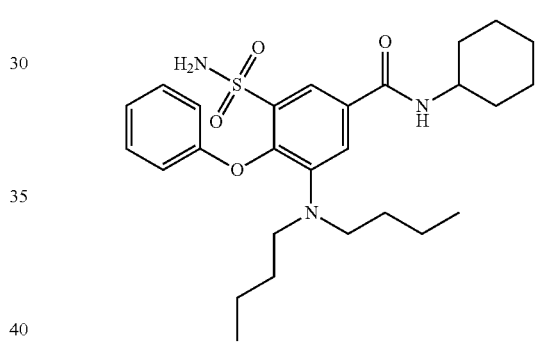
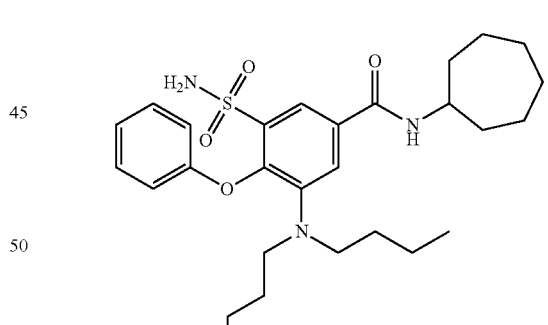
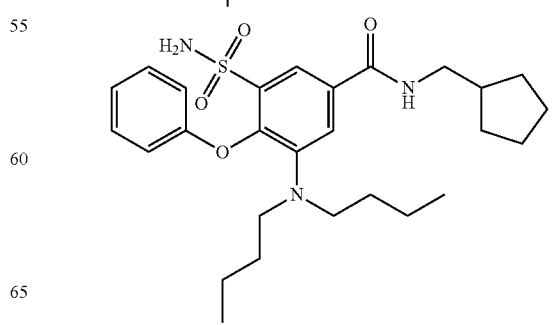

89
-continued
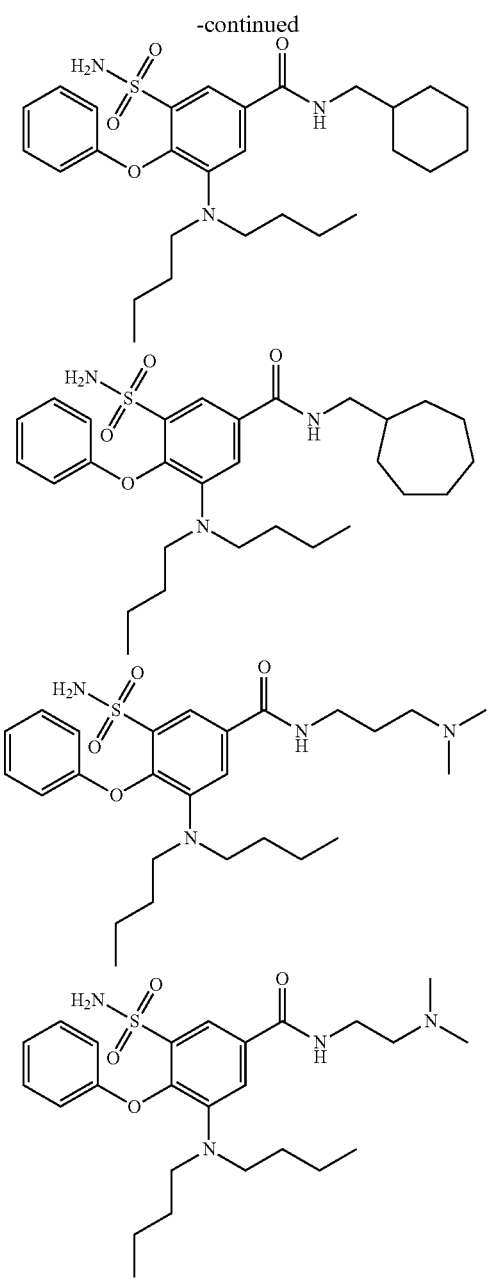
In yet other embodiments, the present invention encompasses the following compounds, N-substituted sulfonamides and N,N-disubstituted sulfonamides thereof:
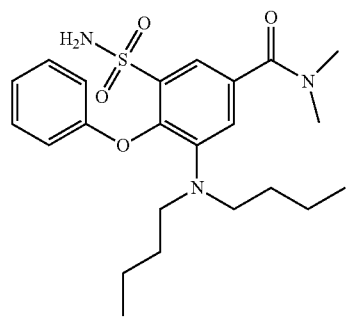
90
-continued
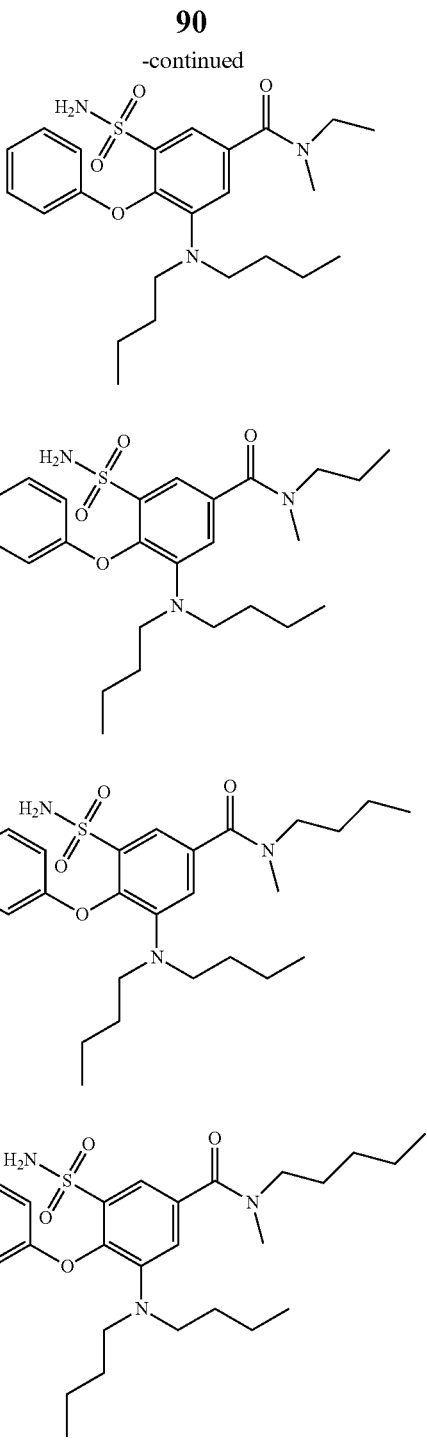
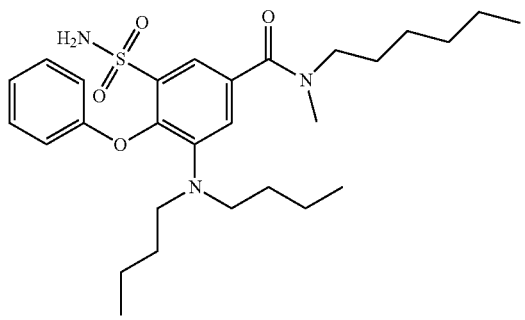

91
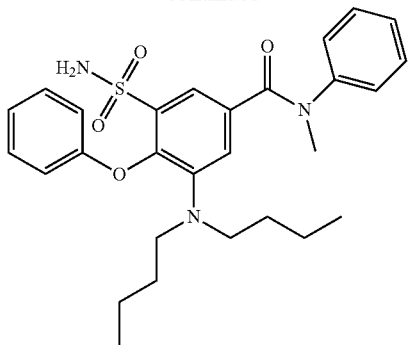
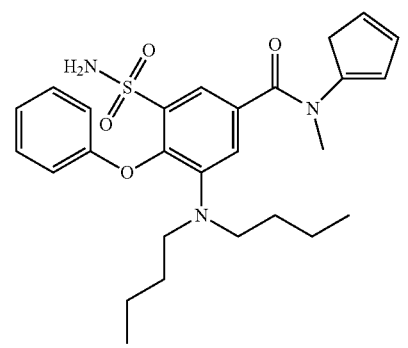
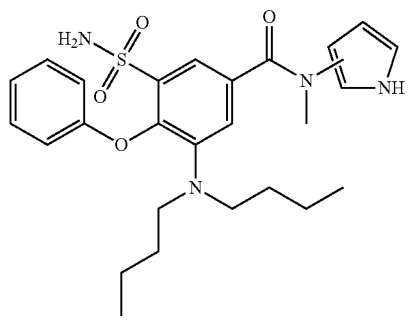
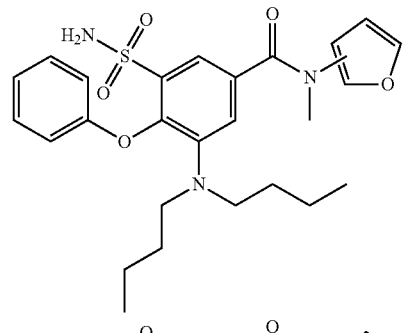
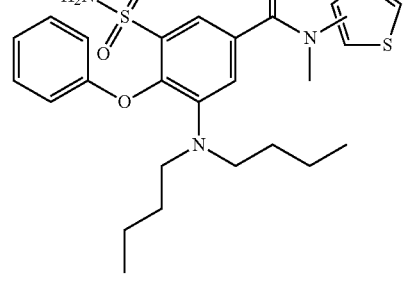
92
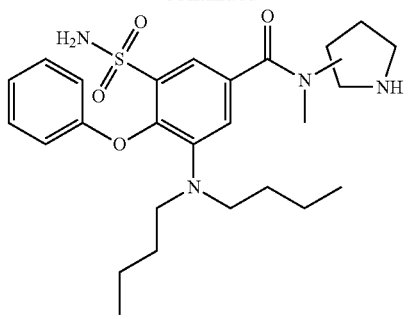
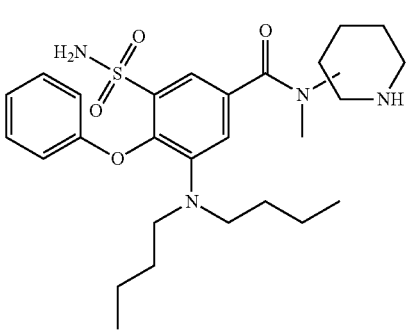
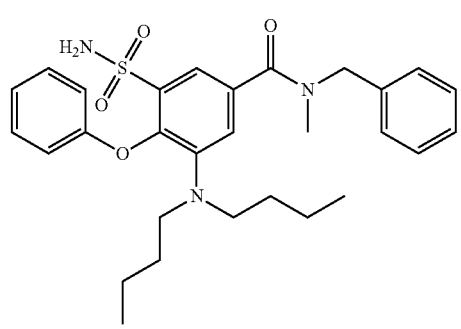
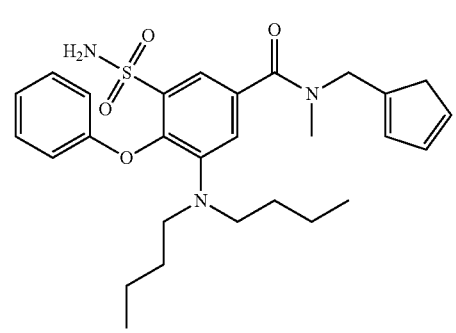
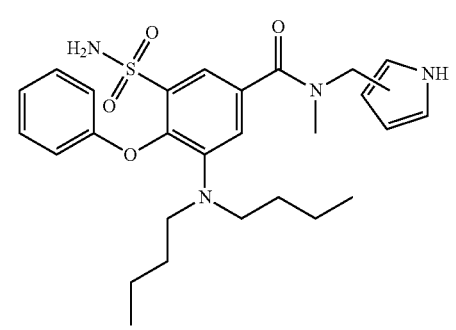

93
-continued
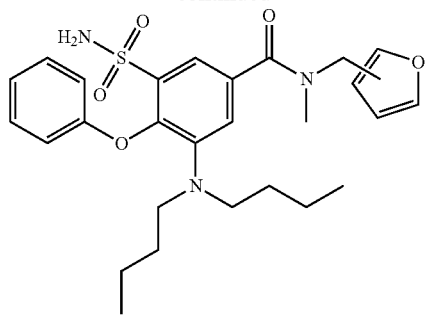
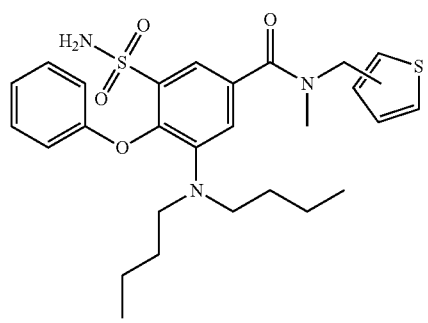
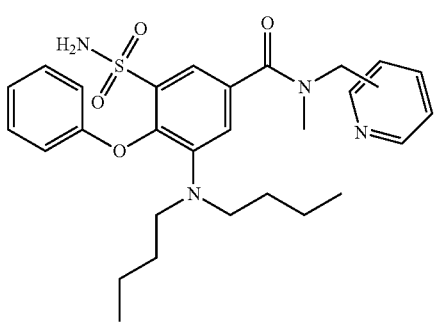
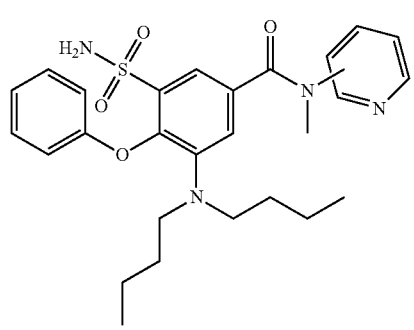
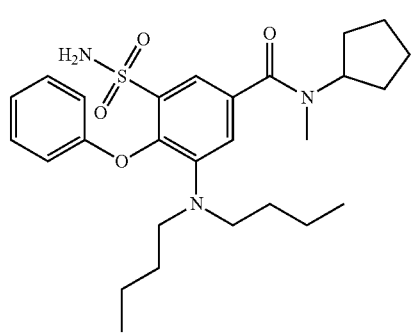
94
-continued
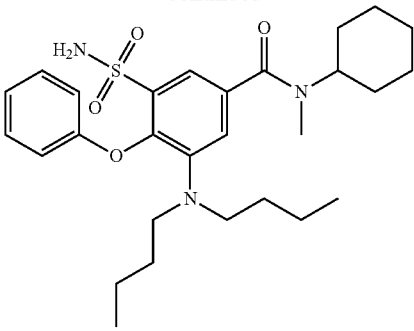
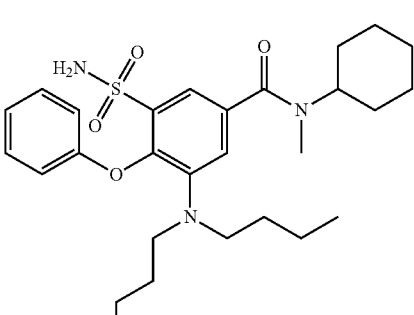
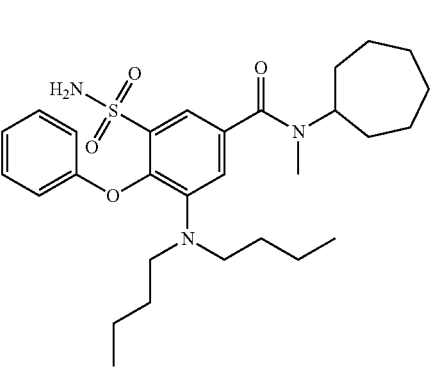
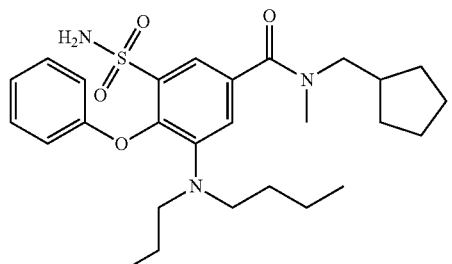
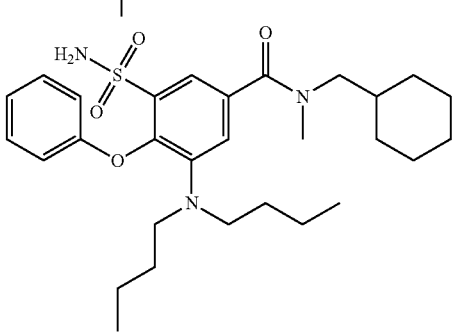

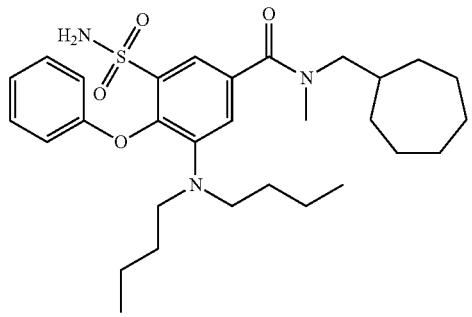
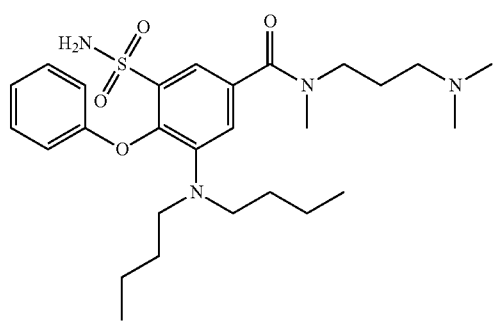
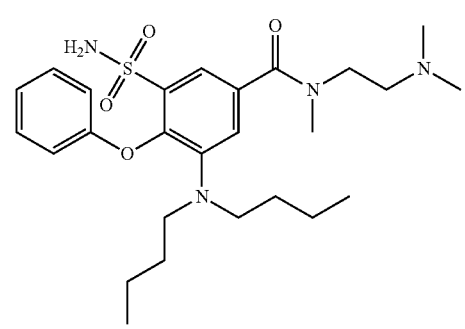
In other embodiments, the present invention encompasses the following compounds, including esters, amides, N-substituted sulfonamides and N,N-disubstituted sulfonamides thereof:
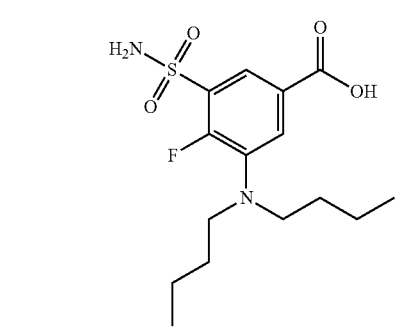
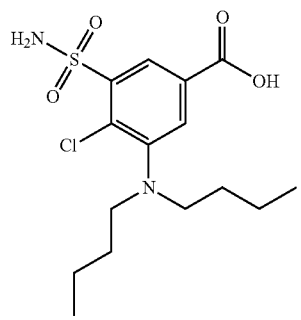
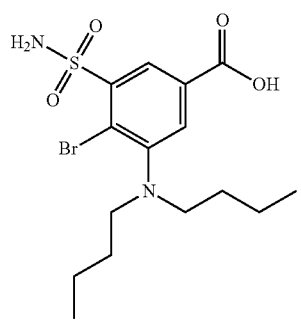
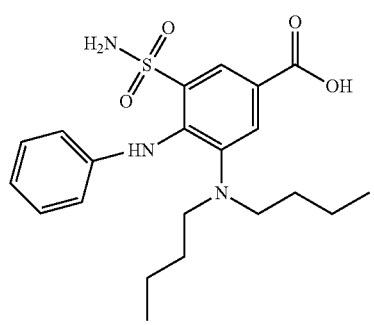
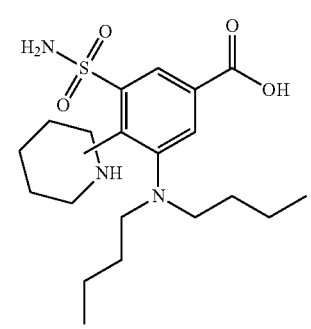
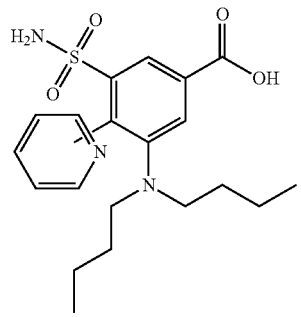

-continued
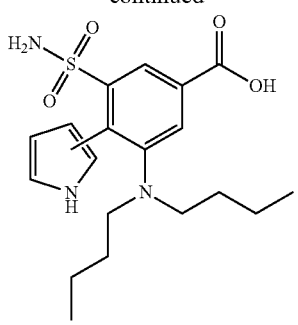
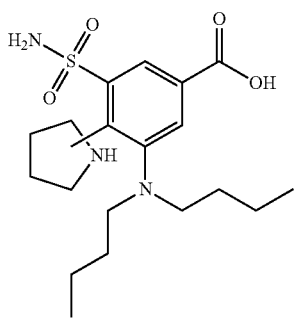
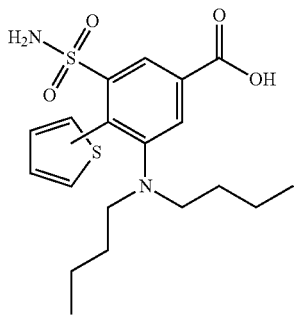
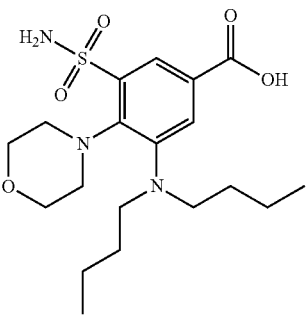
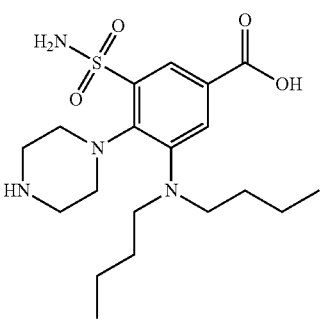
-continued
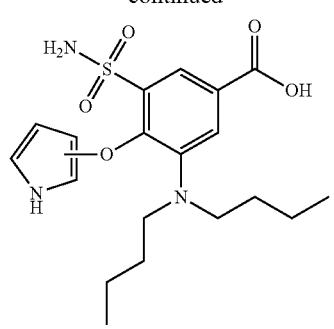
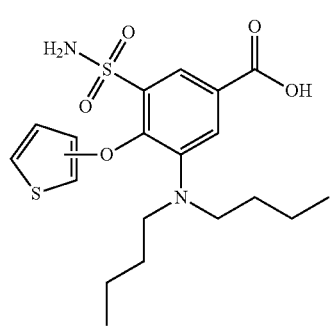
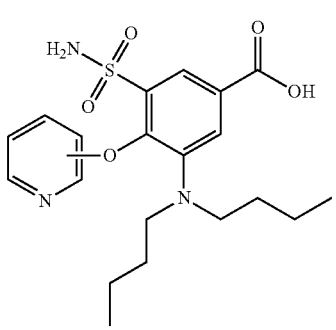
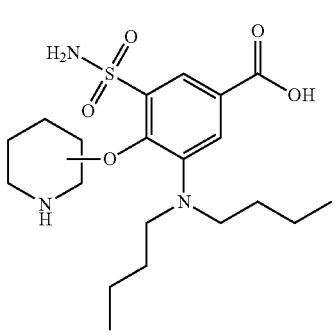
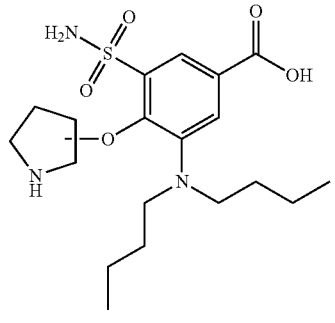

99
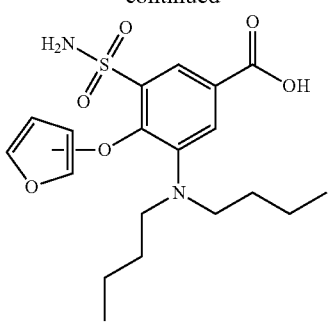
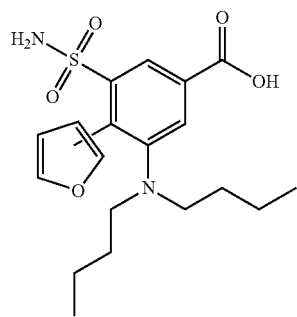
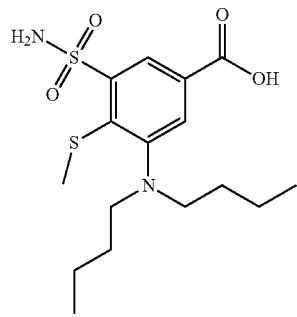
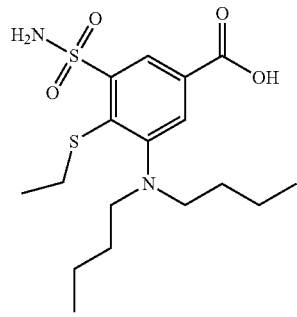
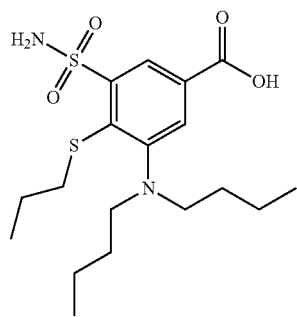
100
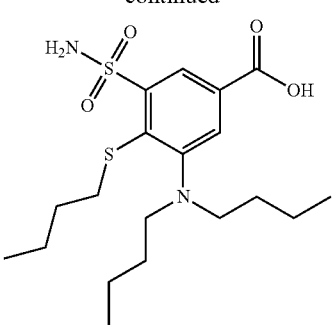
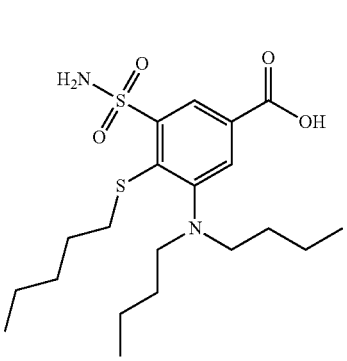
In other embodiments, the present invention encompasses the following compounds, including esters and amides thereof:
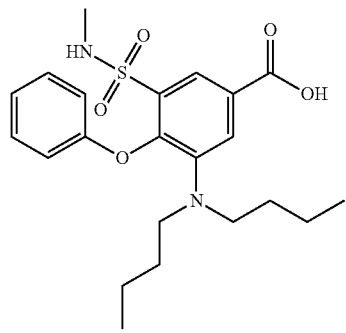
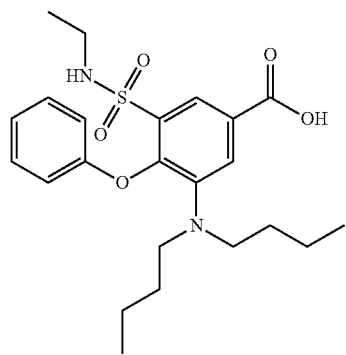

101
-continued
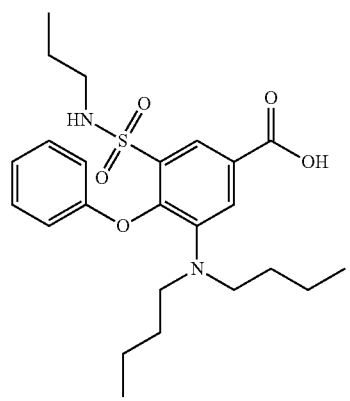
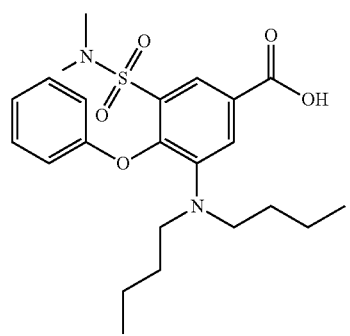
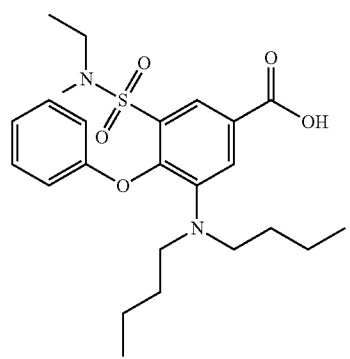
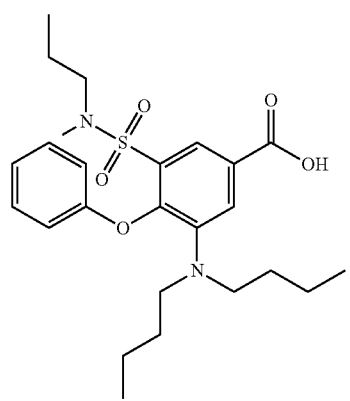
102
-continued
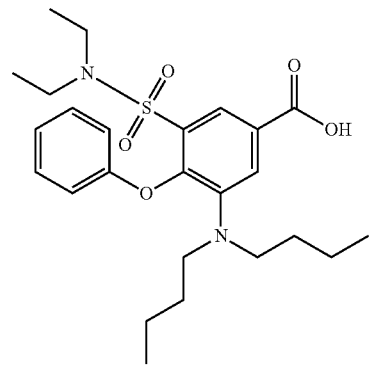
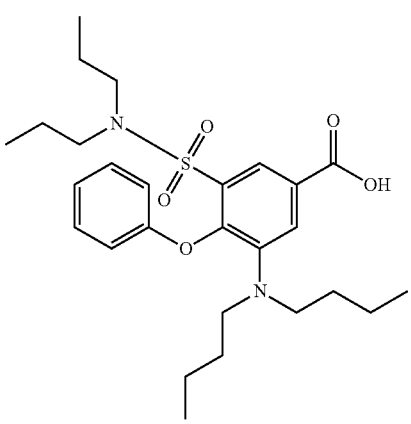
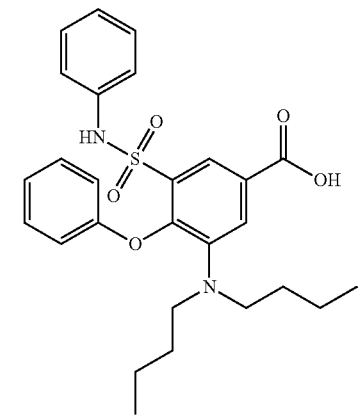
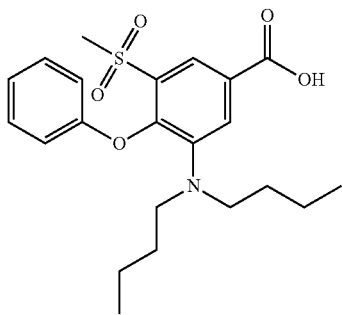

103
-continued
104
-continued
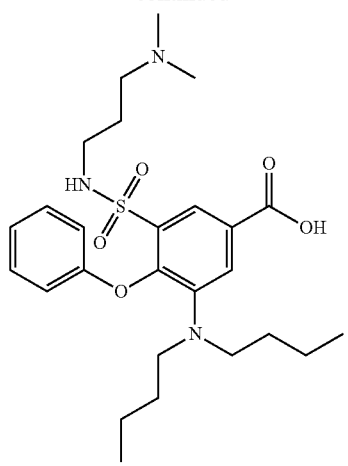
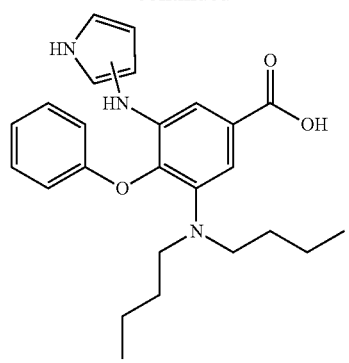
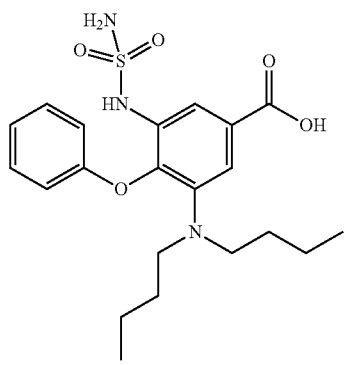
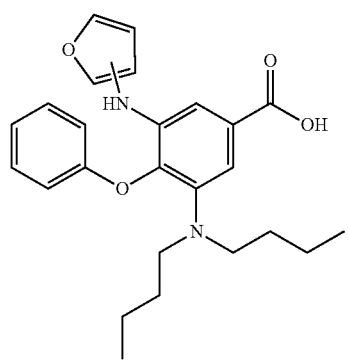
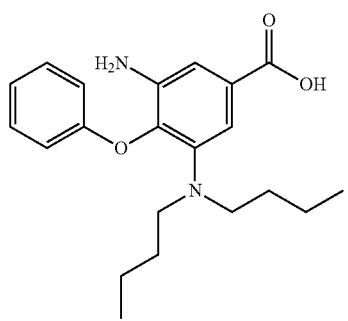
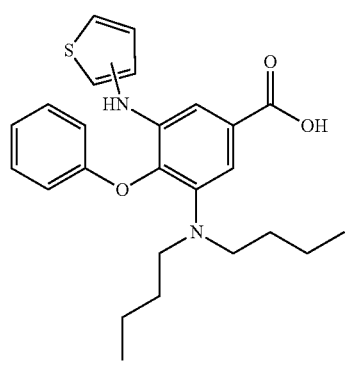
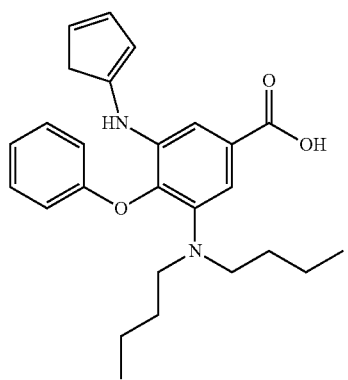
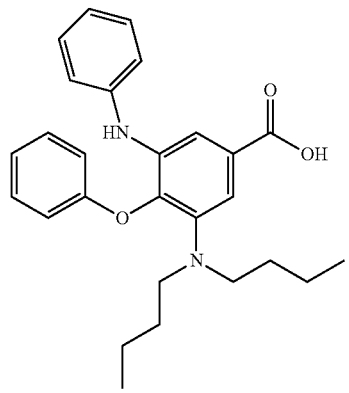

105
-continued
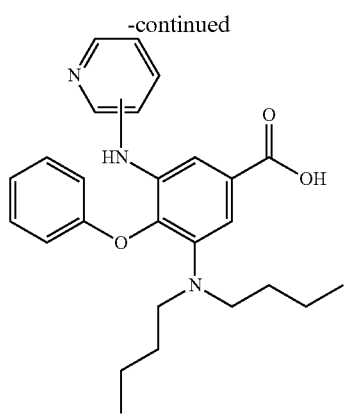
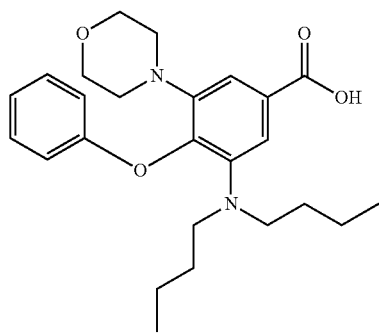
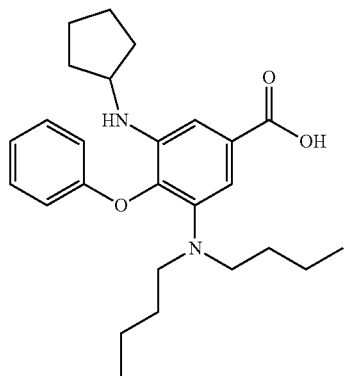
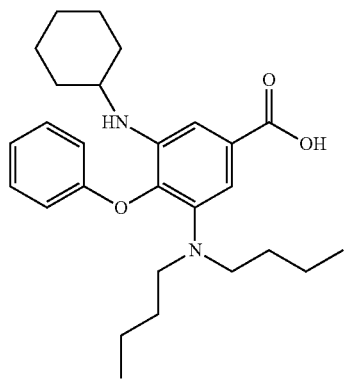
106
-continued
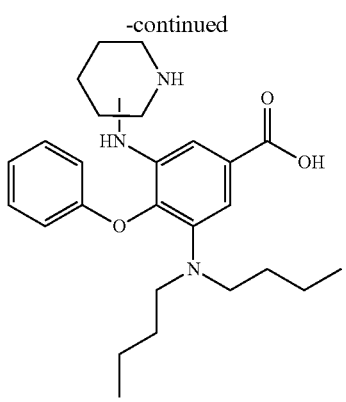
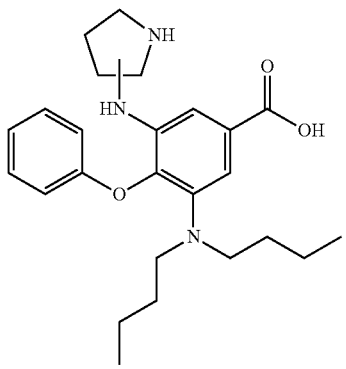
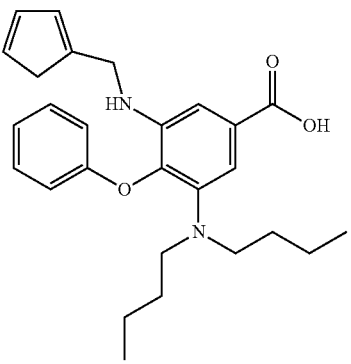
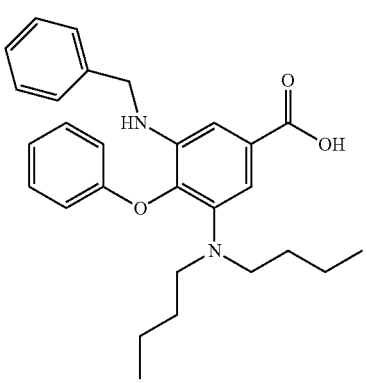

107
-continued
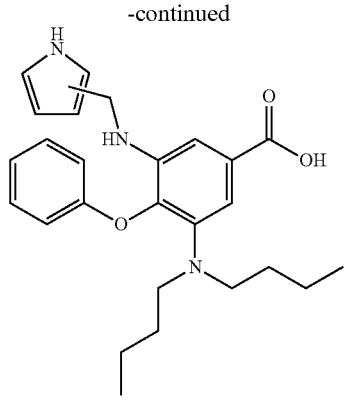
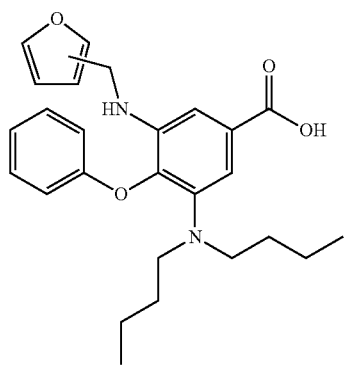
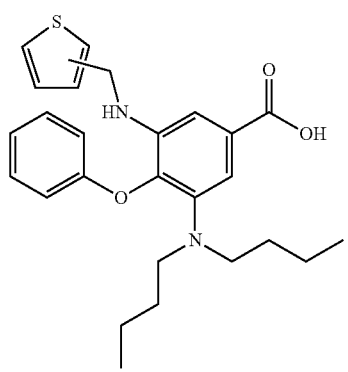
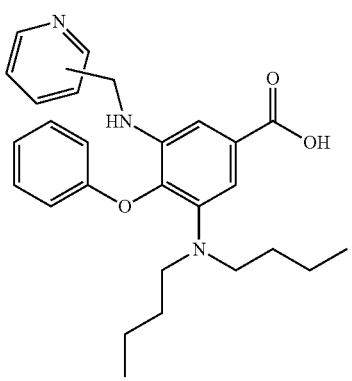
108
-continued
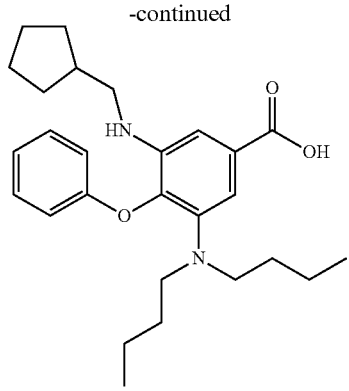
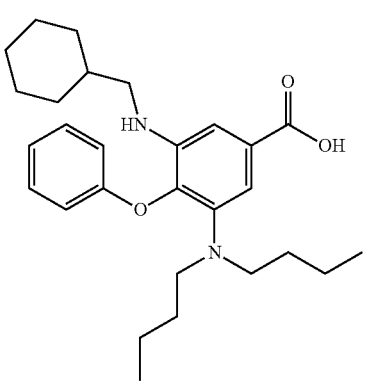
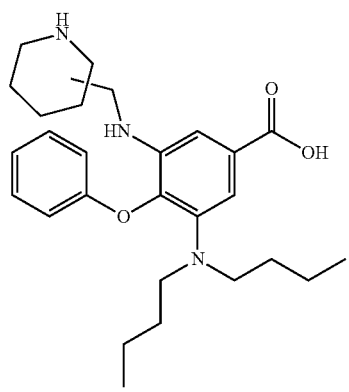
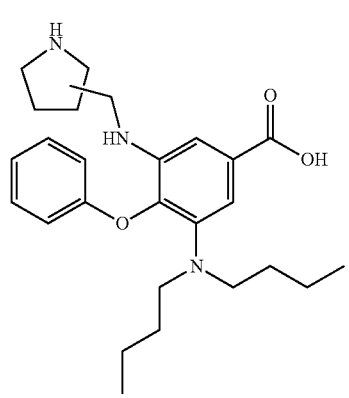
In other embodiments, the present invention encompasses the following compounds, including N-substituted sulfonamides and N,N-disubstituted sulfonamides:

109
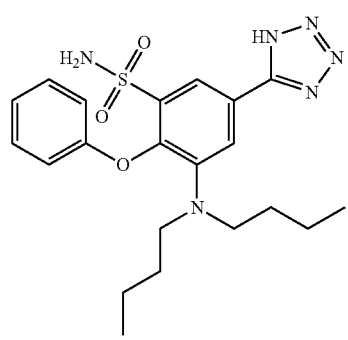
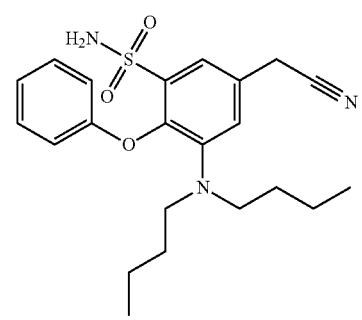
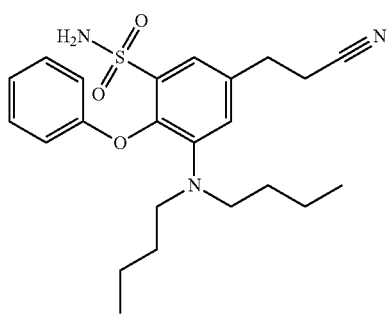
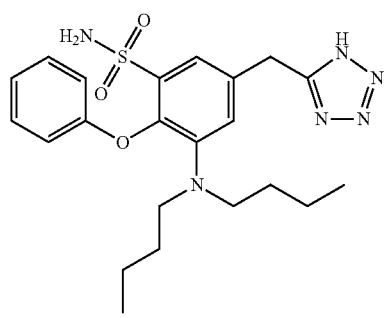
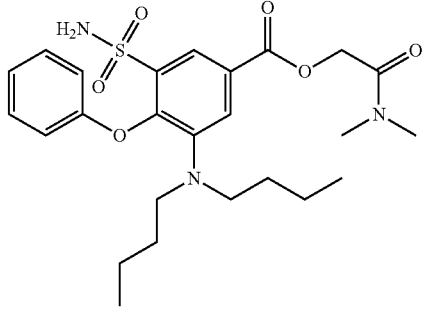
110
-continued
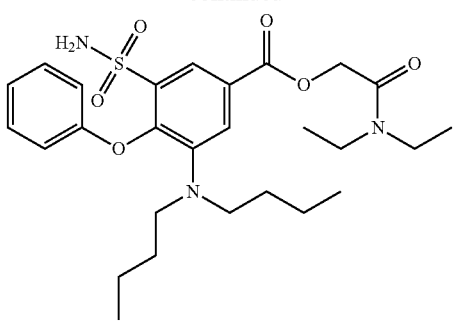
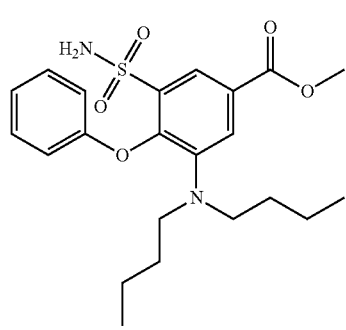
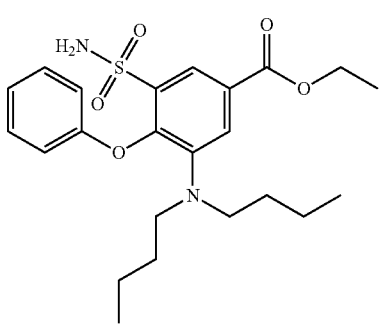
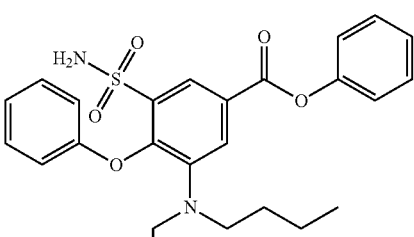
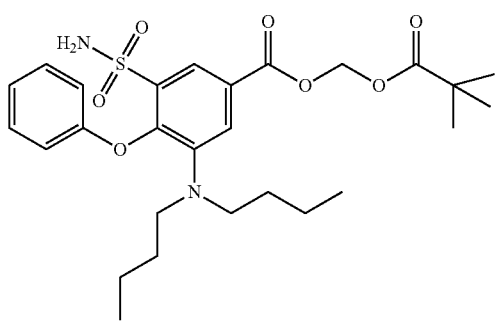

-continued

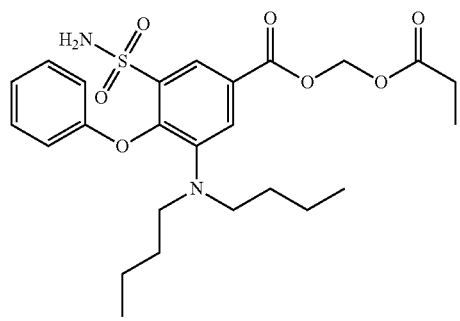

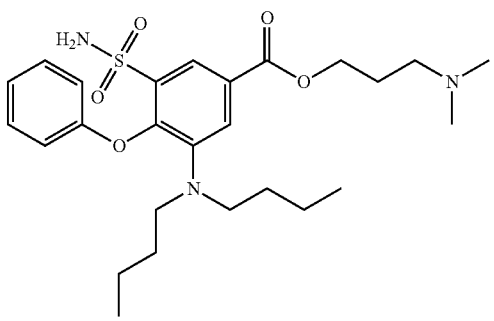

2. Synthetic Methods

Embodiments of the present invention provide methods of modifying diuretic or diuretic-like compounds to increase lipophilicity of the diuretic or diuretic-like compounds. The lipiphilicity can be measured by determining the hydrophile-lipophile balance (HLB) or the partition coefficient (e.g., the distribution of a compound between water and octanol). In some embodiments, the compound is a diuretic or diuretic-like compound, and in particular embodiments, the compound is termed a "loop diuretic." For a discussion of pharmacological properties of diuretics. See generally, Hardman, Limbird, and Gilman, (Eds.) (2001) Goodman & Gilman's The Pharmacological Basis of Therapeutics, McGraw-Hill Medical Publishing Division (10th ed).

Further included as a diuretic or diuretic-like compound are compounds that affect cation-chloride cotransporters. As used herein, a cotransporter is electroneutral, moving equal amounts of oppositely charged ionic species from one side of a membrane to another. As used herein, a cation-chloride cotransporter refers to a cotransporter that moves one or several cations with an equal number of chloride ions. Exemplary cation chloride cotransporters include, but are not limited to, the loop diuretic-sensitive $Na^+$, $K^+$, $2Cl^-$ cotransporter in the brain (NKCC 1), and the thiazide-sensitive $Na^+$, $Cl^-$ cotransporter (NCC). Discussions regarding the molecular classification of cation-chloride cotransporters, their physiology, and pharmacology can be found in Mount, et al. (1998) "The electroneutral cation-chloride cotransporters." J Exp Biol 201: 2091-2102; Russell (January 2000) "Sodium-potassium-chloride cotransport." Physiol Rev. 80(1):211-76.

The NKCC1 brain-specific cotransporter is an isoform of its kidney analog, NKCC2. Furosemide and bumetanide are classic examples of NKCC antagonists.

The thiazide-sensitive cotransporter is antagonized by thiazide diuretics. Exemplary thiazide diuretics include, but are not limited to, chlorothiazide, hydrochlorothiazide, and benzthiazide.

Modification of the diuretic or diuretic-like compound can include reacting the diuretic or diuretic-like compound with a functional group and/or compound selected from the group consisting of an aluminum hydride, alkyl halide, alcohol, aldehyde, alkaryl halide, mono- and dialkylamine, mono- and dialkarylamine, mono- and diarylamine, and quaternary ammonium salt, unsubstituted or substituted, or combinations thereof. Non-limiting examples of compounds that may be used as a starting material are exemplified below.

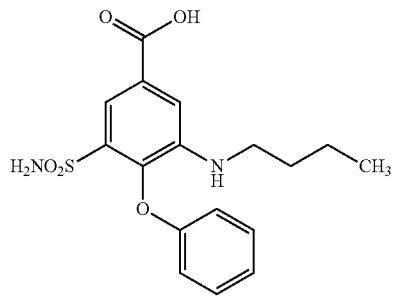

bumetanide
Merck Index, 13th

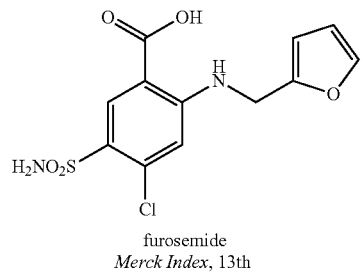

furosemide
Merck Index, 13th

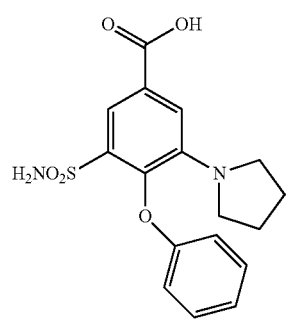

piretanide
Merck Index, 13th
Edition, 2001, 7575.

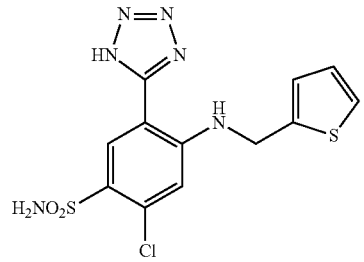

azosemide
Merck Index, 13th
Edition, 2001, 924.

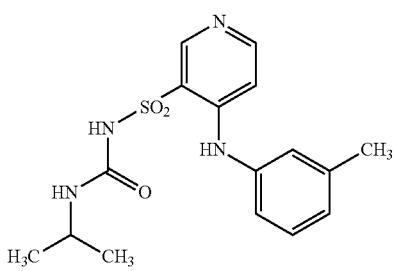

toresemide
*Merck Index*, 13th
Edition, 2001, 9629.

The compounds
of Formula I, II, III, IV, V, VI, VII, VIII, IX, X, XI, XII, XIII, XIV, XV, XVI, XVII, XVIII, XIX, XX, XXI, XXII, XXIII, XXIV, XXV, and/or XXVI can be synthesized using traditional synthesis techniques well known to those skilled in the art. More specific synthesis routes are described below.

A. Bumetanide Analogs, Thiobumetanide Analogs and Dithiobumetanide Analogs

1. Thiobumetanide and Dithiobumetanide

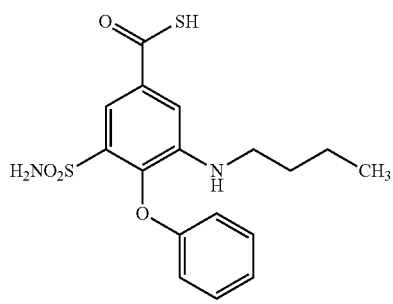

thiobumetanide [—(C=O)—SH]
bumetanide [—(C=O)—SH] thioacid

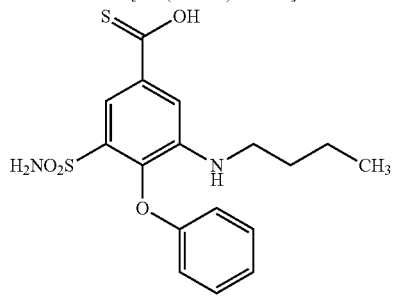

thiobumetanide [—(C=S)—OH]
bumetanide [—(C=S)—OH] thioacid

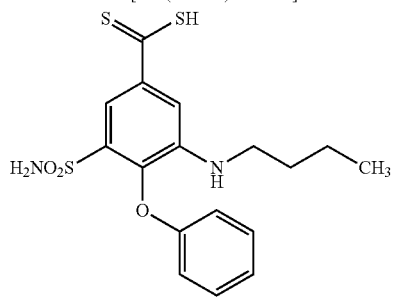

bumetanide dithioacid

The thiobumetanide analogs are synthesized by reacting the carboxylic acid moiety of bumetanide with various reagents. For example, bumetanide may undergo conversion to the corresponding thioacid by treatment with thionyl chloride to form the corresponding bumetanide acid chloride followed by reaction with sodium hydrogen sulfide to give thiobumetanide [—(C=O)—SH], also known as bumetanide [—(C=O)—SH] thioacid by the methodology of Noble, P. and Tarbell, *Org. Synth., Coll. Vol. IV*, John Wiley & Sons, Inc., New York, 1963, 924-927. See Scheme 1. Thiobumetanide may undergo conversion to the corresponding bumetanide thioacid chloride with thionyl chloride, followed by treatment of the thioacid chloride with sodium hydrogen sulfide to give dithiobumetanide [—(C=S)—SH], also known as bumetanide [—(C=S)—SH] dithioacid by similar methodology. Reaction of bumetanide thioacid chloride with secondary amines will give the corresponding bumetanide thioamides. Bumetanide may also undergo reaction with phosphorous pentasulfide to yield bumetanide dithioacid. For reviews of this body of chemistry, See "Thioacyl Halides," "Thiocarboxylic O-Acid Esters" and "Dithiocarboxylic Acid Esters," all by Glass. R. S. in Science of Synthesis, (Charette, A. B., Ed.), Volume 22, Thieme Chemistry, 2005, Chapters 22.1.2, 22.1.3 and 22.1.4 and references therein. See also "Synthesis of Thioamides and Thiolactams", Schaumann, E., in Comprehensive Organic Synthesis, (Trost, B. M. and Fleming, I., Eds.), Pergamon Press, 1991, Volume 6, Chapter 2.4, pp. 450-460 and references therein, each of which are herein incorporated by reference in their entirety.

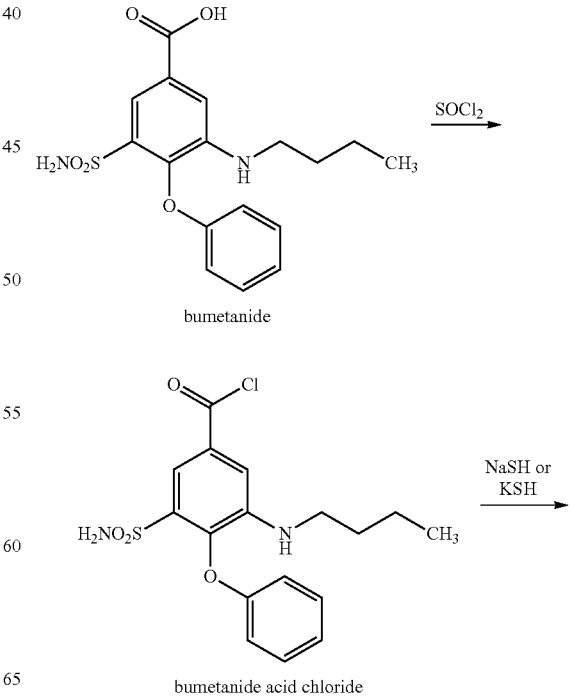

Scheme 1. Synthesis of Thiobumetanide
{Bumetanide [—(C=O)—SH] Thioacid} bumetanide bumetanide acid chloride

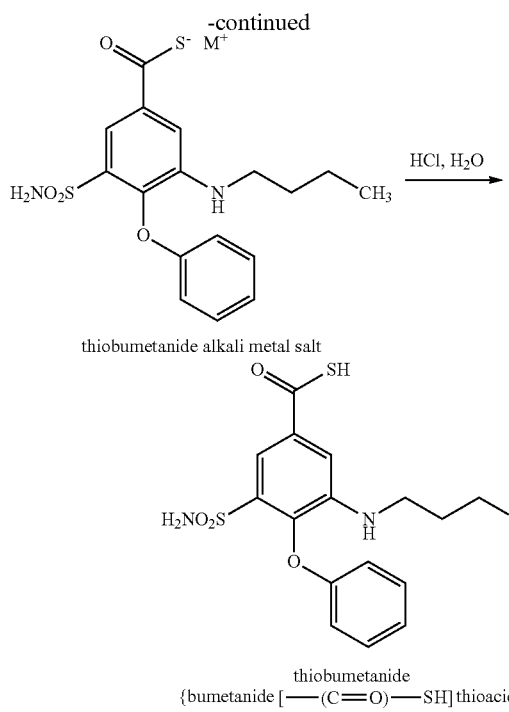

2. Bumetanide and S-Thiobumetanide Analogs

The bumetanide analogs are synthesized by reacting the carboxylic acid moiety of bumetanide with various reagents. For example, bumetanide may undergo esterification via reaction with alcohols, including linear, branched, substituted, or unsubstituted alcohols. Bumetanide or thiobumetanide may also be alkylated via reaction with suitable substituted and unsubstituted alkyl halides and alkaryl halides, including chloroacetonitrile, benzyl chloride, 1-(dimethylamino)propyl chloride, 2-chloro-N,N-diethylacetamide, and the like. PEG-type esters may be formed by alkylation using alkyloxy(polyalkyloxy)alkyl halides such as MeO-PEG350-Cl and the like or alkyloxy(polyalkyloxy)alkyl tosylates such as MeO-PEG1000-OTs and the like. "Axetil"-type esters may also be formed by alkylation by using alkyl halides such as chloromethyl pivalate or chloromethyl propionate. Bumetanide may also undergo amidation by reaction with suitable substituted or unsubstituted alkyl amines or aryl amines, either after conversion to the acid chloride or by using an activator, such as 1-ethyl-3-(3-dimethylaminopropyl)carbodiimide (EDC). Bumetanide or thiobumetanide may also be reacted with a quaternary ammonium hydroxide, such as benzyltrimethylammonium hydroxide or cetyltrimethylammonium hydroxide, to form bumetanide or thiobumetanide quaternary ammonium salts. Schemes 2, 3 and 4 present synthesis schemes of some exemplary compounds according to formula I.

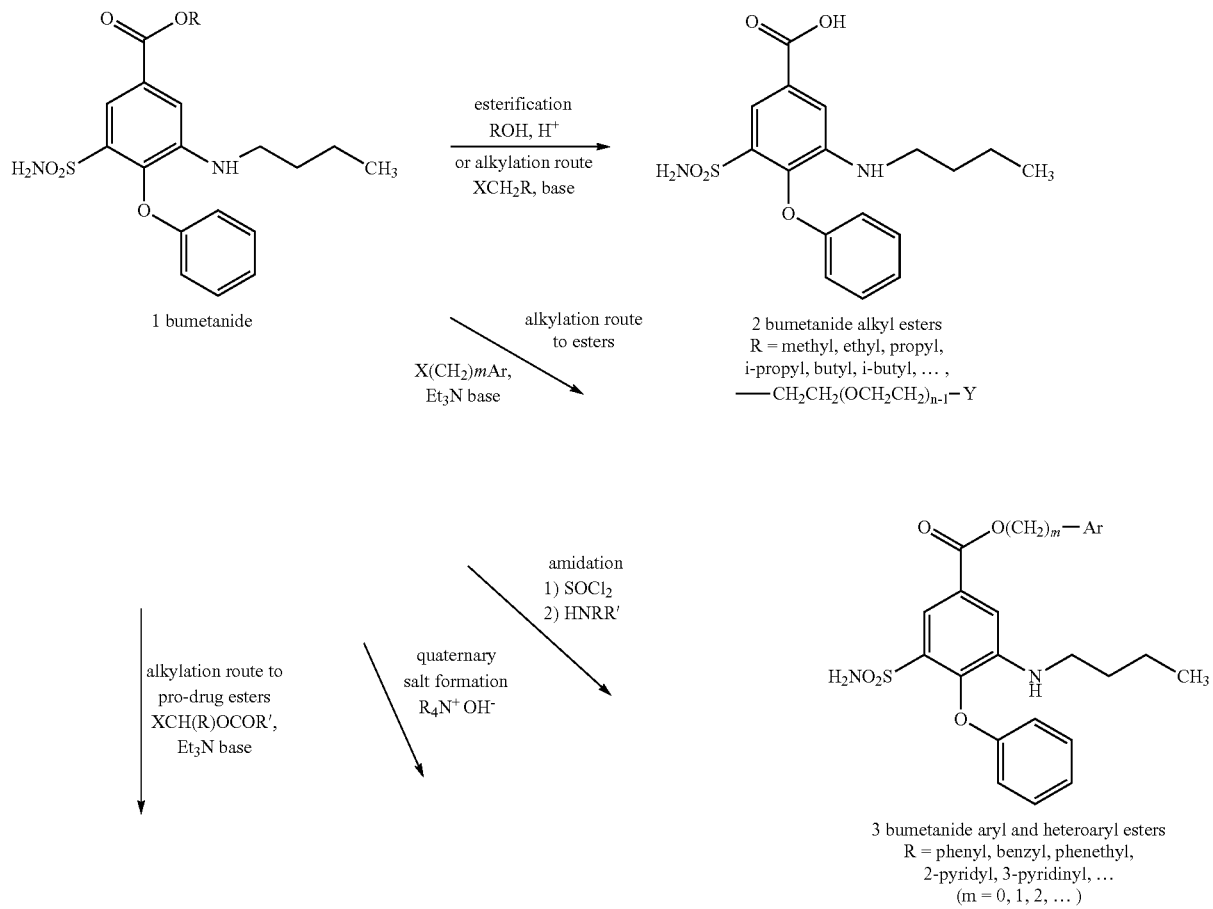

Scheme 2. Synthesis of Exemplary Compounds According to Formula I

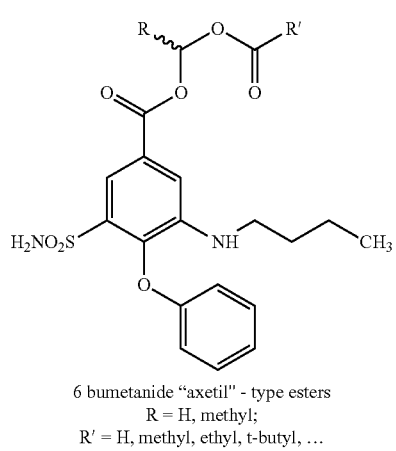

6 bumetanide "axetil" - type esters
R = H, methyl;
R' = H, methyl, ethyl, t-butyl, ...

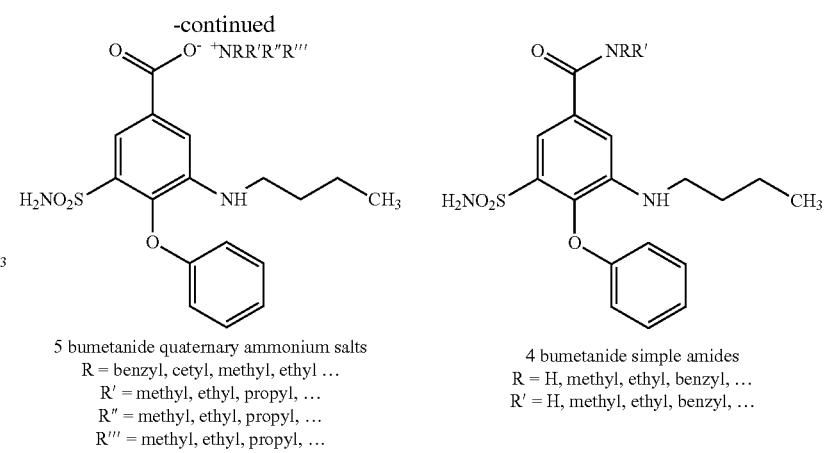

-continued 5 bumetanide quaternary ammonium salts
R = benzyl, cetyl, methyl, ethyl ...
R' = methyl, ethyl, propyl, ...
R" = methyl, ethyl, propyl, ...
R''' = methyl, ethyl, propyl, ...

4 bumetanide simple amides
R = H, methyl, ethyl, benzyl, ...
R' = H, methyl, ethyl, benzyl, ...

Scheme 3. Synthesis of Exemplary Compounds Accoriding to Formula I

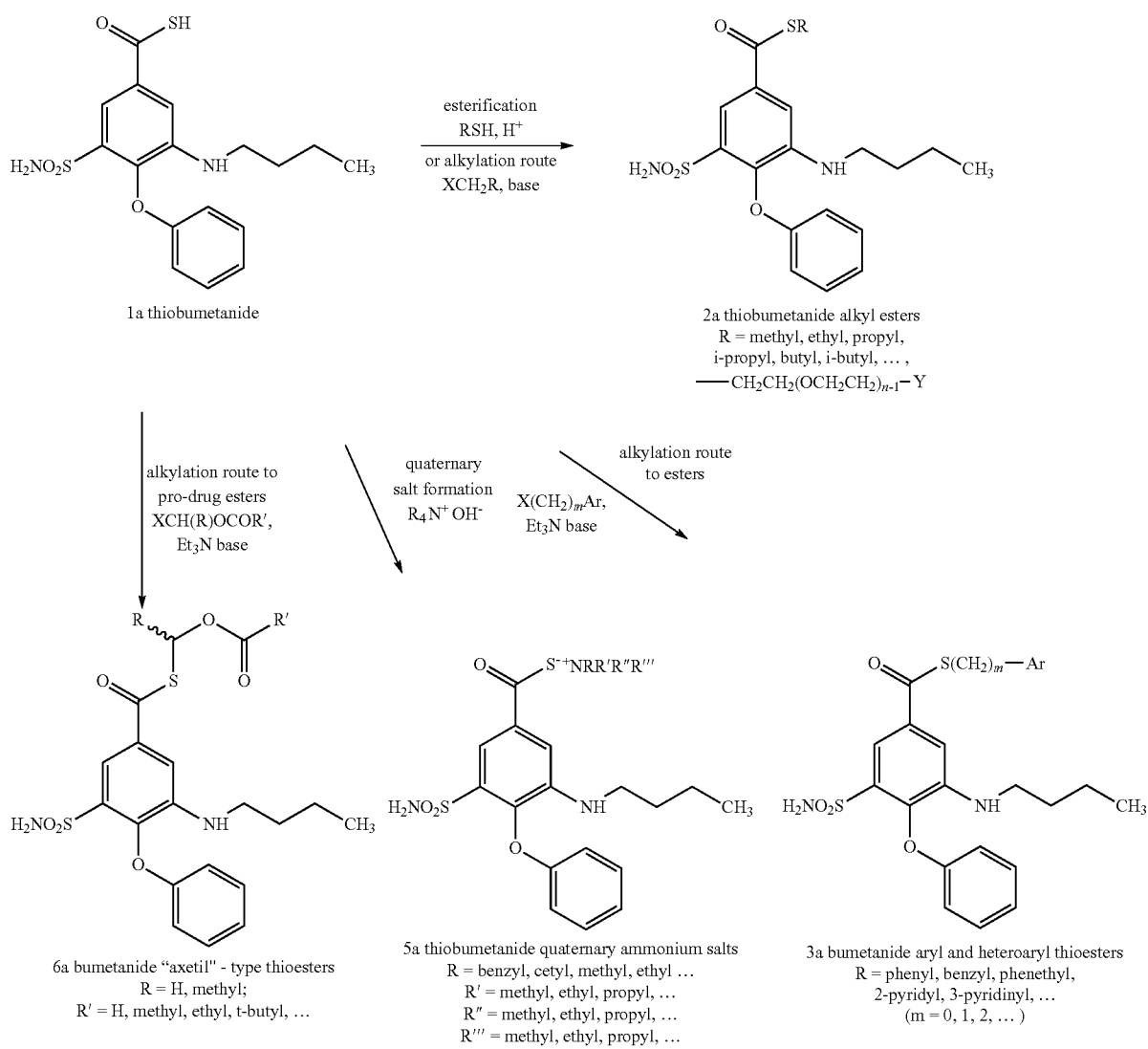

Bumetanide salts, thiobumetanide and S-thiobumetanide esters should readily undergo acid- and base-catalyzed hydrolysis to produce the carboxylic acid containing molecule bumetanide by methods well known in the art (See Yang, W. and Drueckhammer, D. G., *J. Amer. Chem. Soc.*, 2001, 123 (44) 11004-11009 and references therein). (See Scheme 4).

Scheme 4. Hydrolysis of Bumetanide, thiobumetanide, and S-thiobumetanide esters

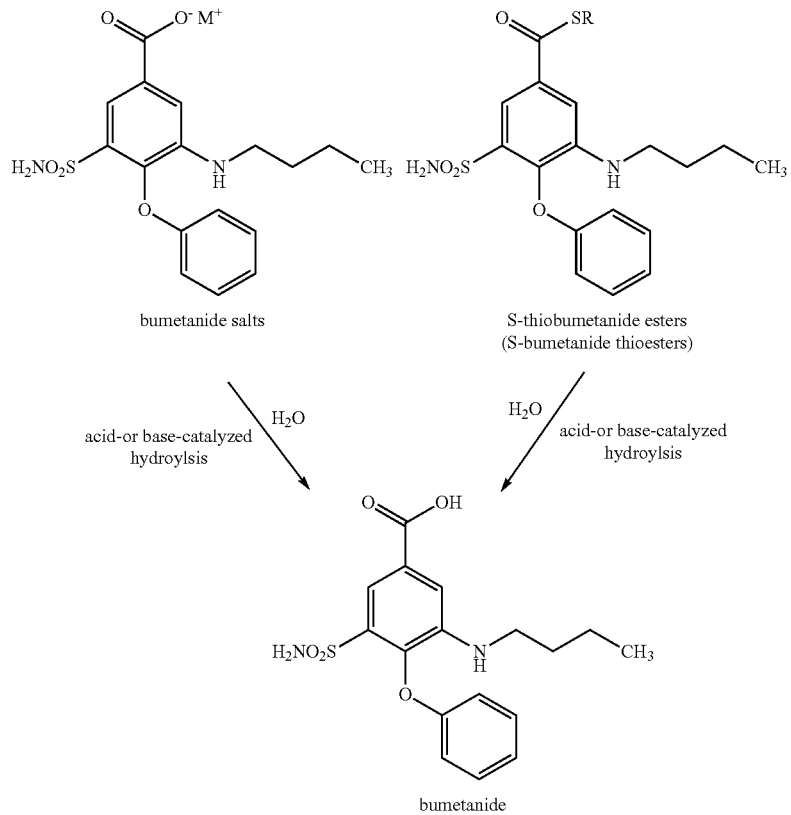

3. O-Substituted Thiobumetanide Analogs and Dithiobumetanide Analogs

Bumetanide may undergo conversion to the corresponding thioacid by treatment with thionyl chloride to form the corresponding acid chloride followed by reaction with sodium hydroxide or sodium hydrogen sulfide to give metastable O-thiobumetanide and dithiobumetanide by the methodology of Noble, P. and Tarbell, D. S., Org. Synth., Coll. Vol. IV, John Wiley & Sons, Inc., New York, 1963, 924-927. (See Schemes 5 and 6).

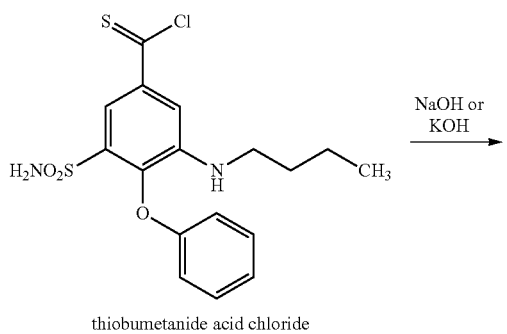

Scheme 5. Synthesis of Metastable Thiobumetanide {Bumetanide [—(C═S)—OH] thioacid}

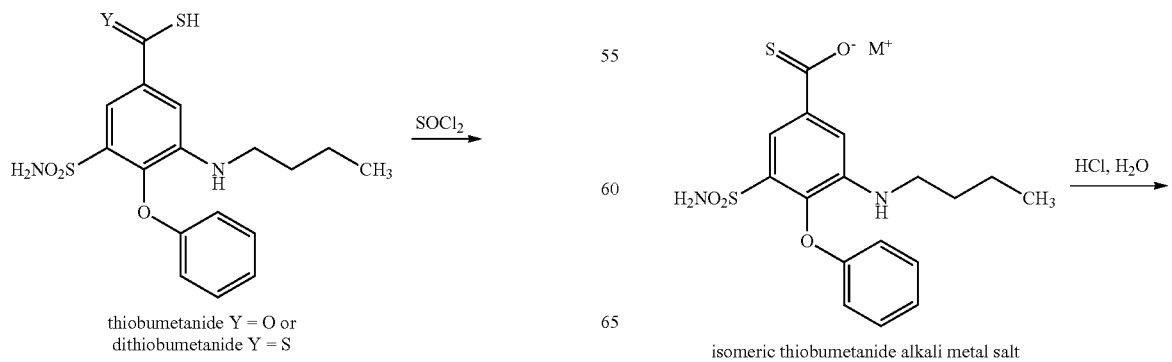

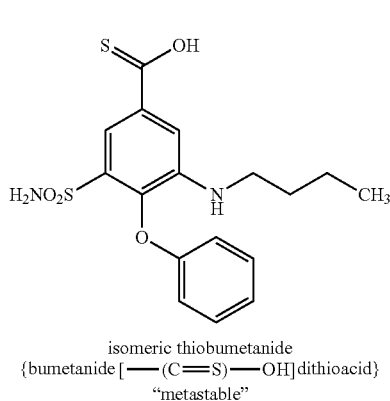

isomeric thiobumetanide
{bumetanide [—(C=S)—OH]dithioacid}
"metastable"

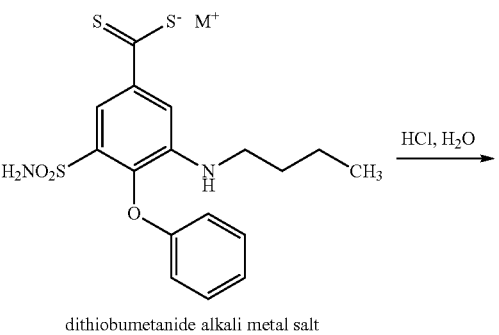

dithiobumetanide alkali metal salt

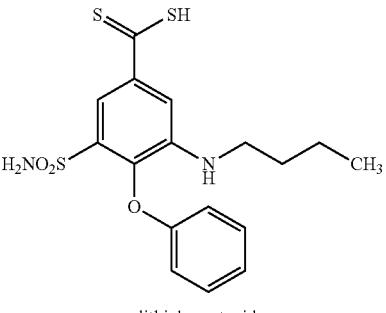

dithiobumetanide
{bumetanide [—(C=S)—SH]dithioacid}

Scheme 6. Synthesis of Dithiobumetanide
{Bumetanide [—(C=S)—SH] Dithioacid}

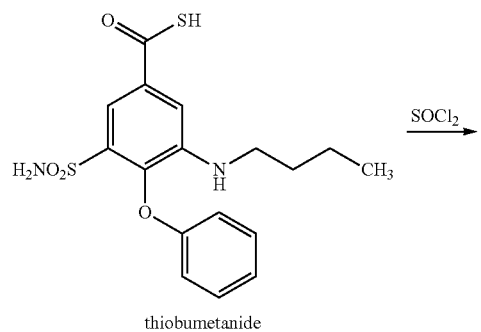

thiobumetanide

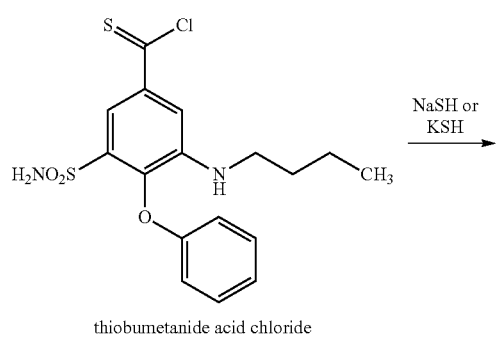

thiobumetanide acid chloride

The thiobumetanide analogs are, in turn, synthesized by reacting the thiocarboxylic acid moiety of S-thiobumetanide with various reagents. For example, S-thiobumetanide may undergo esternficauion via reaction with alcohols and thiols, including linear, branched, substituted, or unsubstituted alcohols and thiols. S-Thiobumetanide may also be alkylated via reaction with suitable substituted and unsubstituted alkyl halides and alkaryl halides, including chloroacetonitrile, benzyl chloride, 1-(dimethylamino)propyl chloride, 2-chloro-N,N-diethylacetamide, and the like. PEG-type esters may be formed by alkylation using alkyloxv(polyalkyloxy)alkyl halides such as MeO-PEG350-Cl and the like or alkvloxy(polyalkyloxy)alkyl tosylates such as MeO-PEG1000-OTs and the like. "Axetil"-type esters may also be formed by alkylation by using alkyl halides such as chloromethyl pivalate or chloromethyl propionate. S-Thiobumetanide may also be reacted with a quaternary ammonium hydroxide, such as benzyltrimethylammonium hydroxide or cetyltrimethylammonium hydroxide, to form thiobumetanide quaternary ammonium salts. See Schemes 7, 8 and 9, which present some exemplary compounds according to formula II.

Scheme 7. Synthesis of Exemplary Compounds According to Formula II
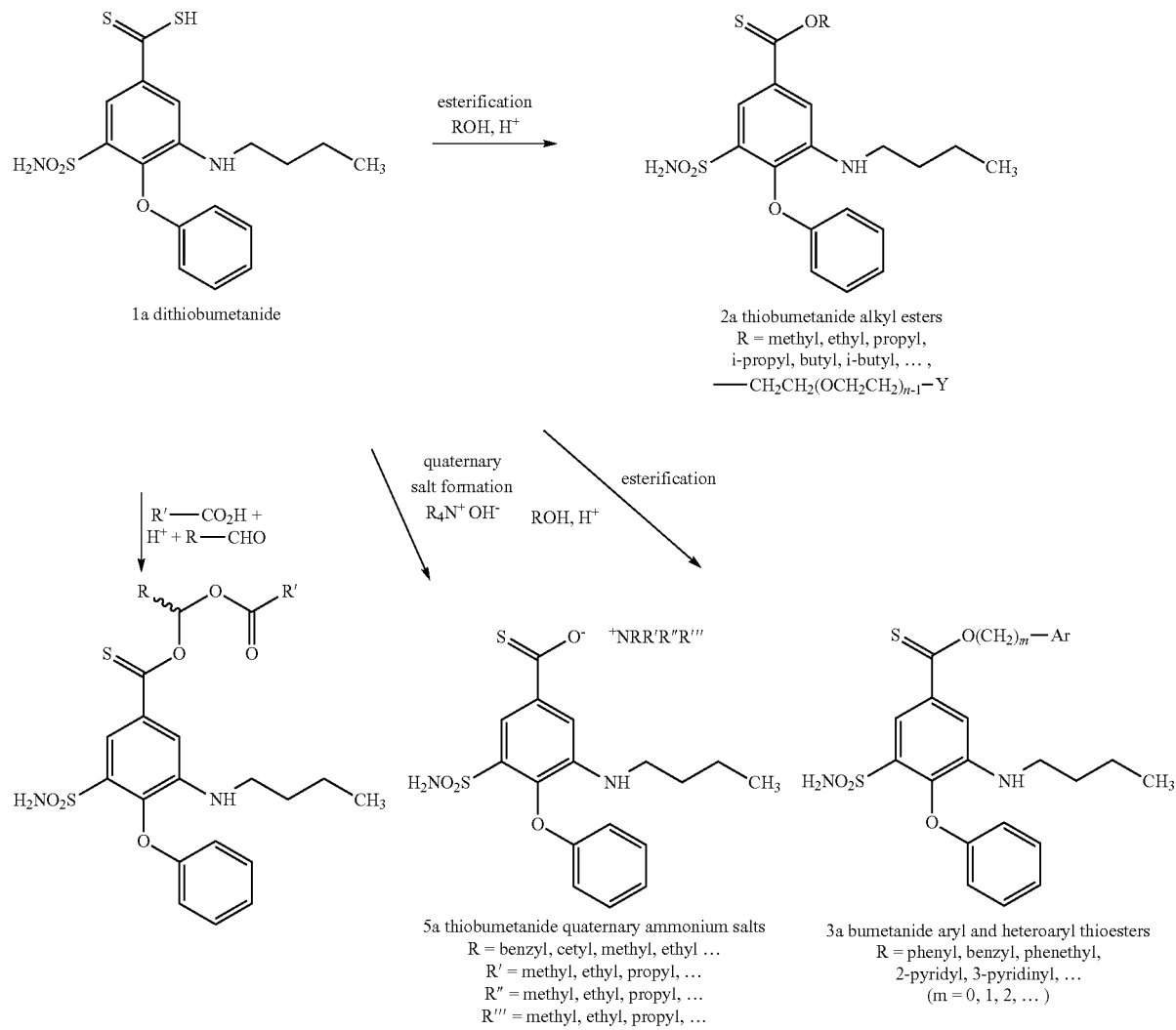
Scheme 8. Synthesis of Exemplary Compounds According to Formula II
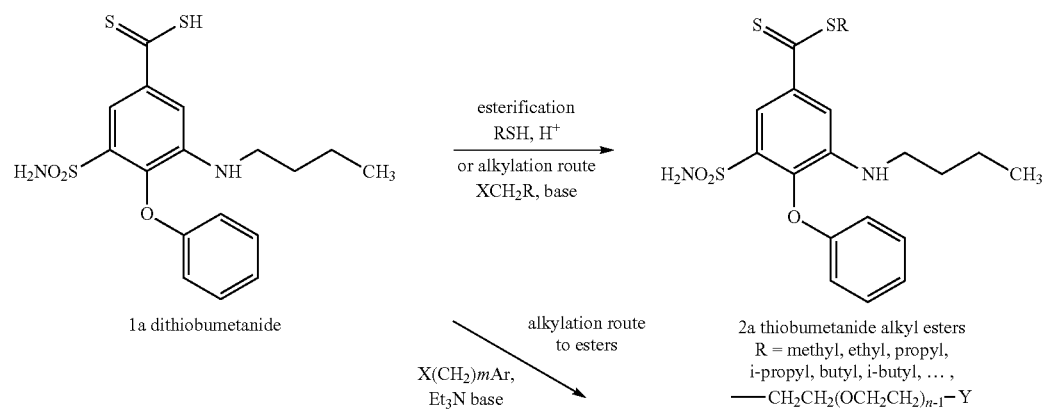

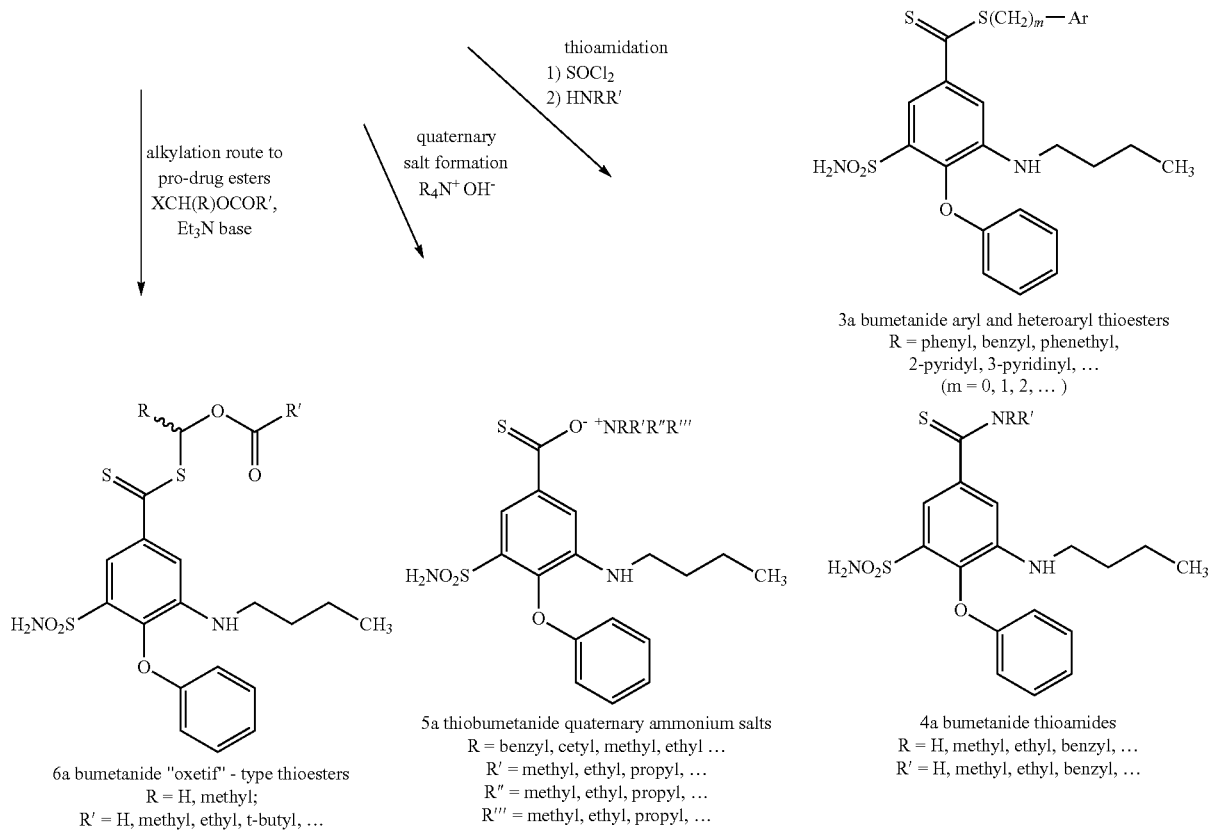

Thiobumetanide, thiobumetanide amides, O-thiobumetanide esters and dithiobumetanide esters should readily undergo acid- and base-catalyzed hydrolysis to produce the carboxylic acid containing molecule bumetanide by methods well known in the art (See Yang, W. and Drueckhammer, D. G., *J. Amer. Chem. Soc.*, 2001, 123 (44), 11004-11009 and references therein). For additional reviews of this body of chemistry, See "Thioacyl Halides", "Thiocarboxylic O-Acid Esters" and "Dithiocarboxylic Acid Esters", all by Glass, R. S. in Science of Synthesis, (Charette, A. B., Ed.), Volume 22, Thieme Chemistry, 2005, Chapters 22.1.2, 22.1.3 and 22.1.4 and references therein. See also "Synthesis of Thioamides and Thiolactams," Schaumann, E., in Comprehensive Organic Synthesis, (Trost, B. M. and Fleming, I., Eds.), Pergamon Press, 1991, Volume 6, Chapter 2.4, pp. 450-460 and references therein. (See Scheme 9).

Scheme 9. Hydrolysis of Thiobumetanide, thiobumetanide amides, O-thiobumetanide Esters and Dithiobumetanide Esters

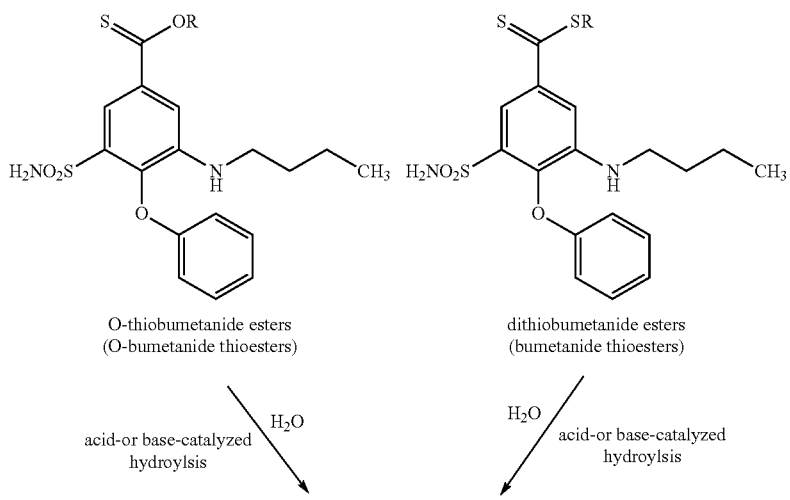

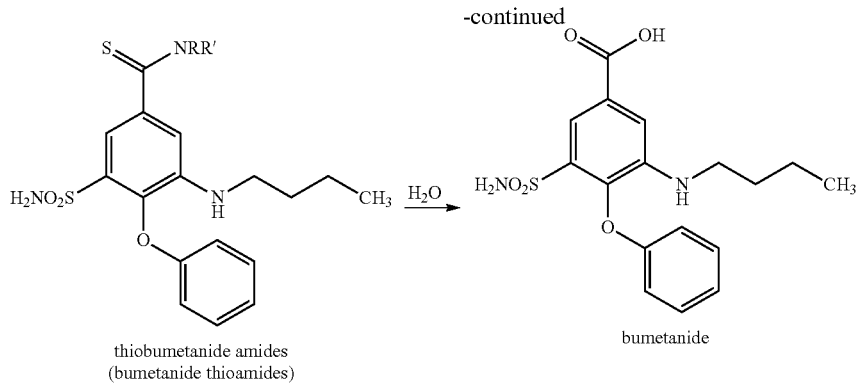

thiobumetanide amides
(bumetanide thioamides)

bumetanide

4. Thio- and Selenobumetanide Analogs Comprising Cyclic Amides

Figure 2:
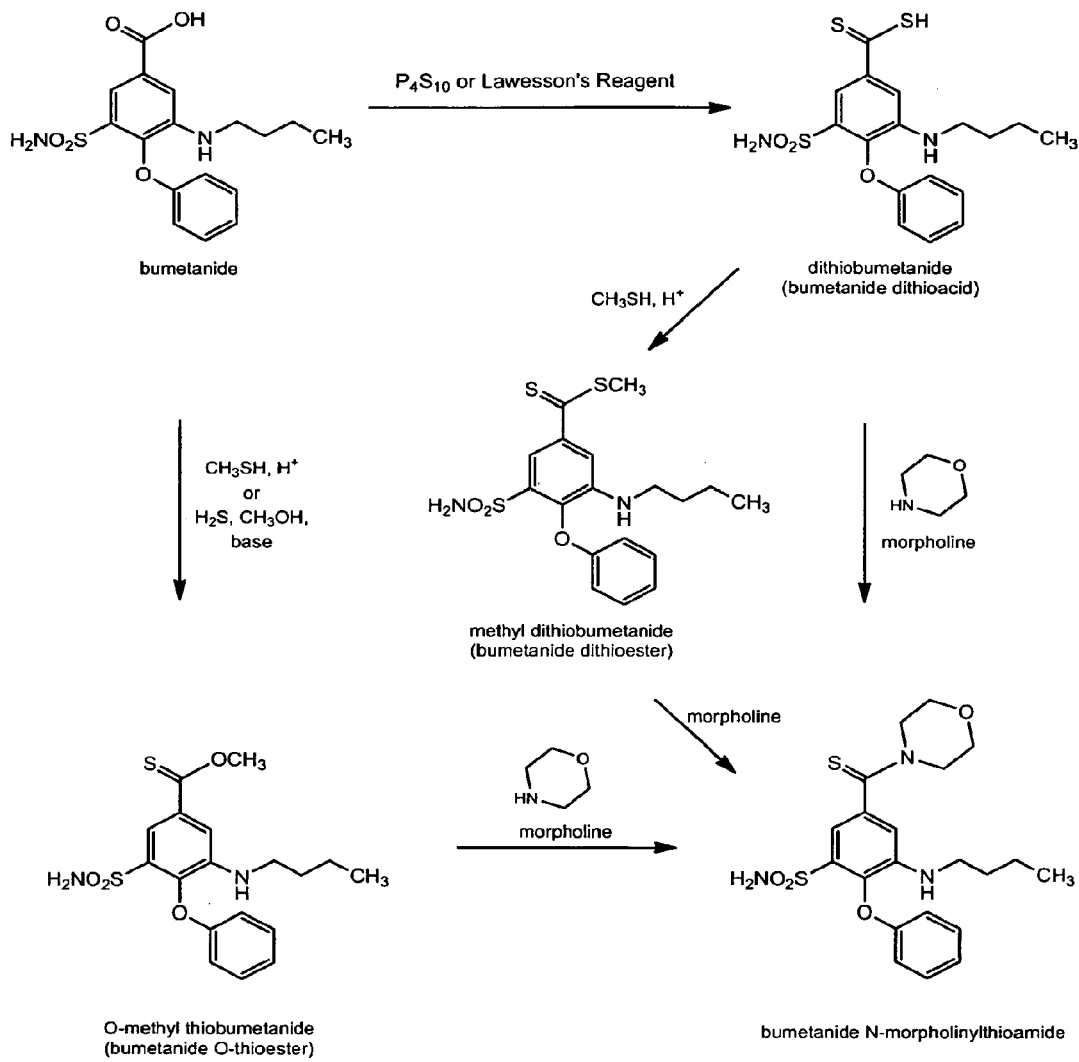
FIG. 2 is a scheme showing different pathways for the synthesis of the thiobumetanide analog comprising a cyclic amide, which is bumetanide N-morpholinothioamide NTP-2024. See Lawesson, S.-O., et al., Org. Syn, Coll. Vol. VII, 1990, 372-375 and references cited therein.
Figure 3:
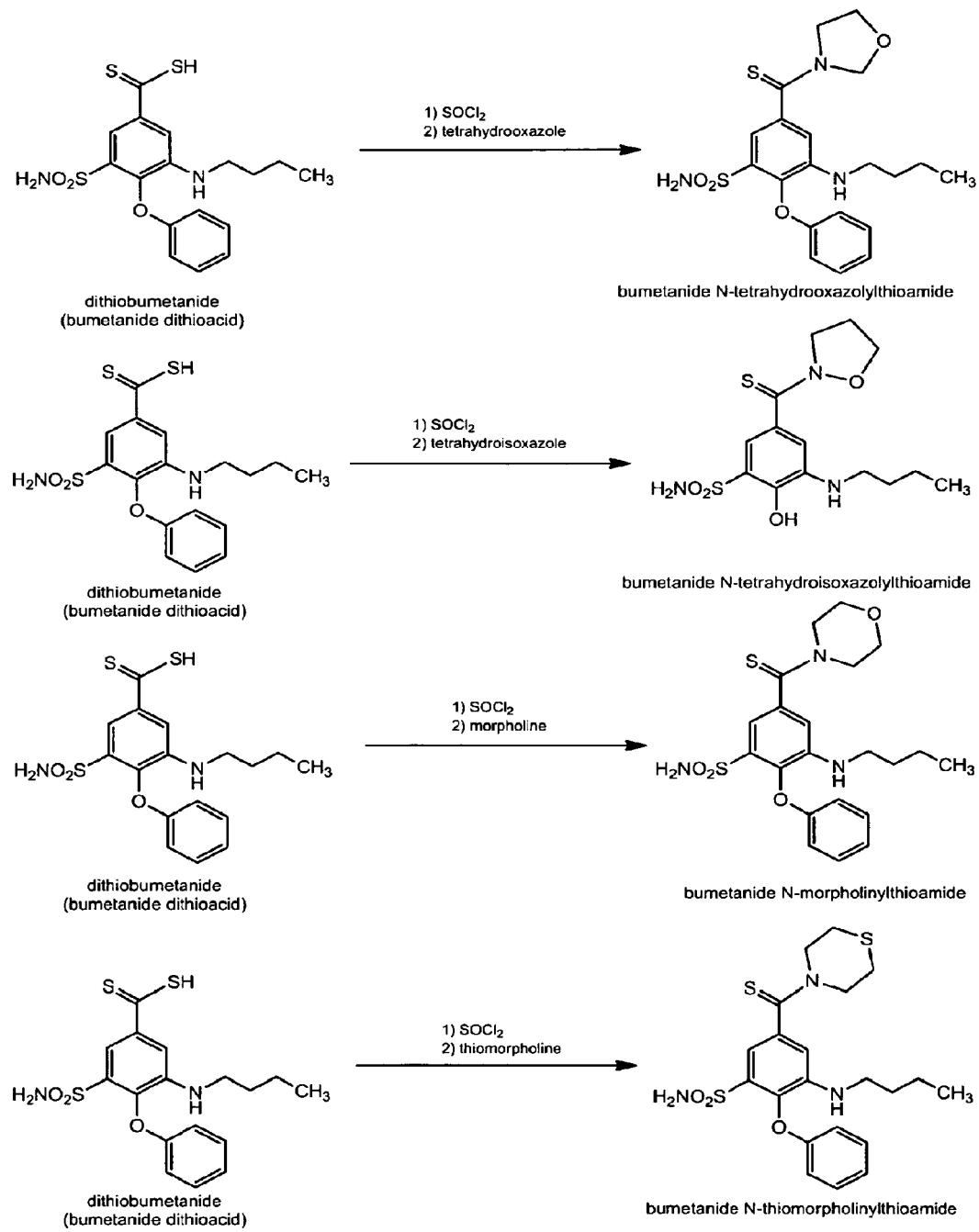
FIGS. 3-7 are schemes showing syntheses for thiobumetanide analogs comprising a cyclic amide. Thioamide formation can occur in two steps via a) conversion of the carboxylic acid into the corresponding acid halide with reagents such as thionyl chloride and b) by direct reaction of the acid halide with a primary or secondary amine. The thioamide formation can also occur in one step via 1-ethyl-3-(3-dimethylaminopropyl)carbodiimide and 1-hydroxybenzotriazole (EDC-HOBt) peptide-type coupling of the carboxylic acid and the amine. For each of the syntheses shown in FIG. 2 the thioamide bond can be formed in one step using an EDC-HOBt "peptide-type" coupling. For the synthesis of dithiobumetanide (i.e., bumetanide dithioacid) and some acyclic thioamides, see U.S. Patent Application Publication No. 2007/0149526A1.
Figure 4:
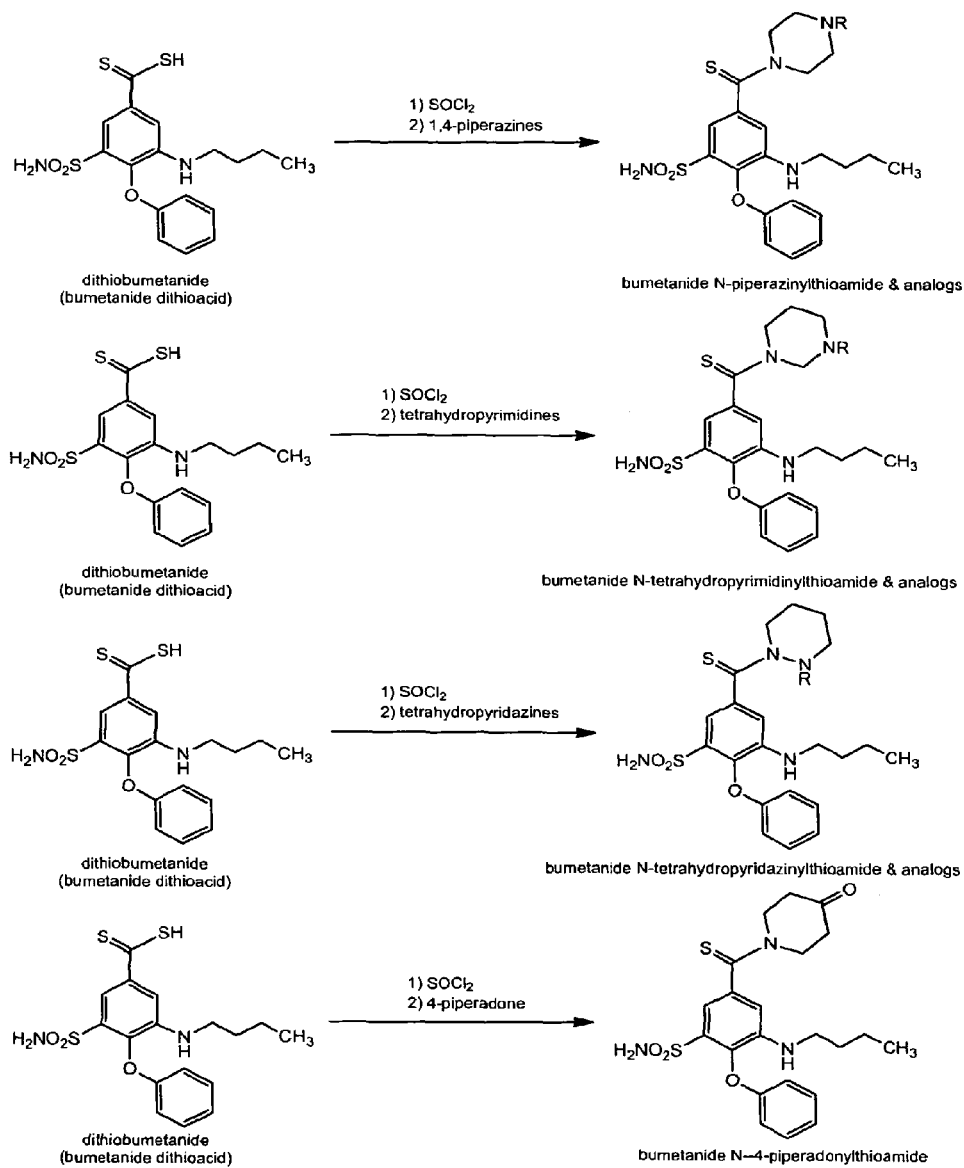
Figure 5:
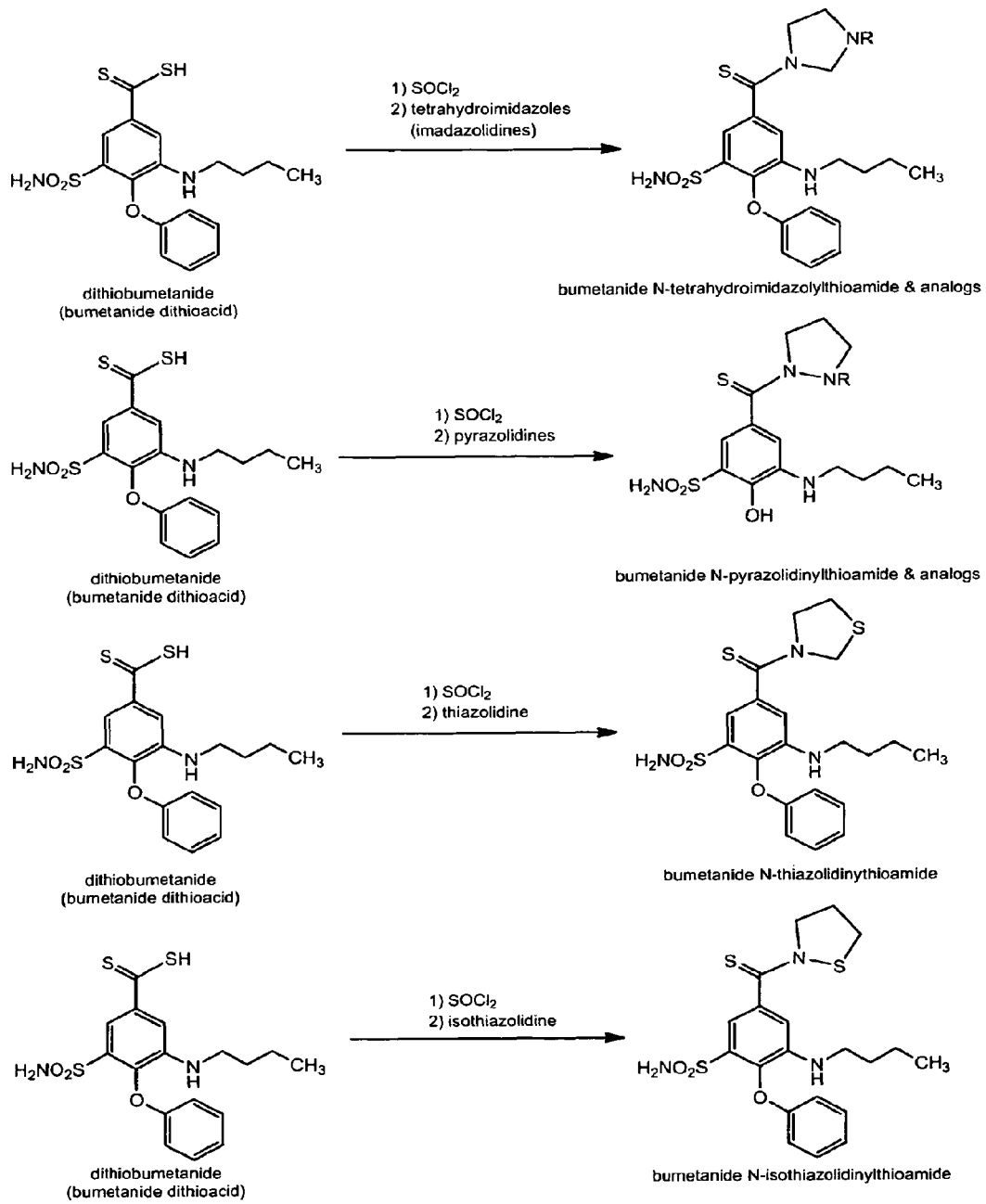
Figure 6:
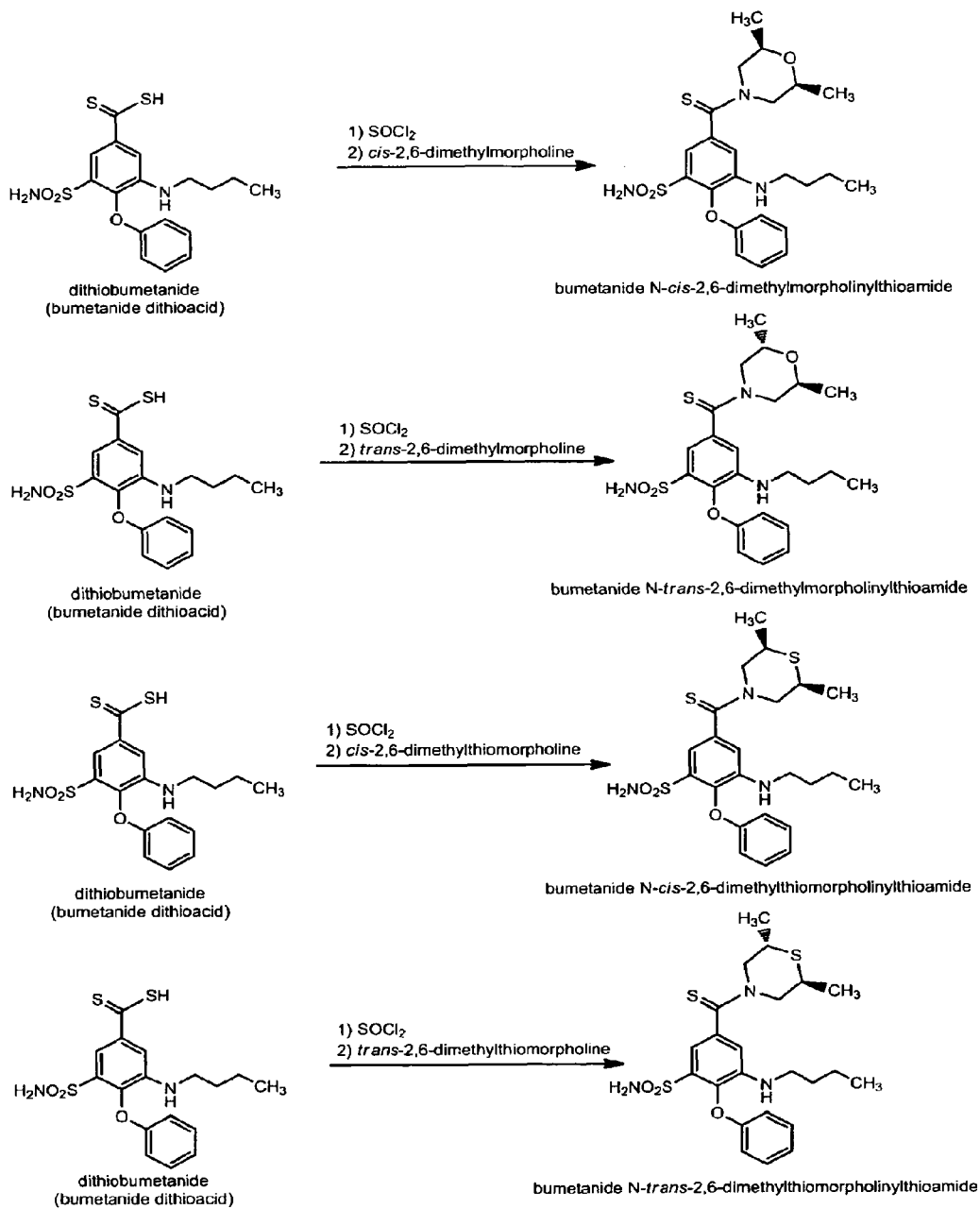
Figure 7:
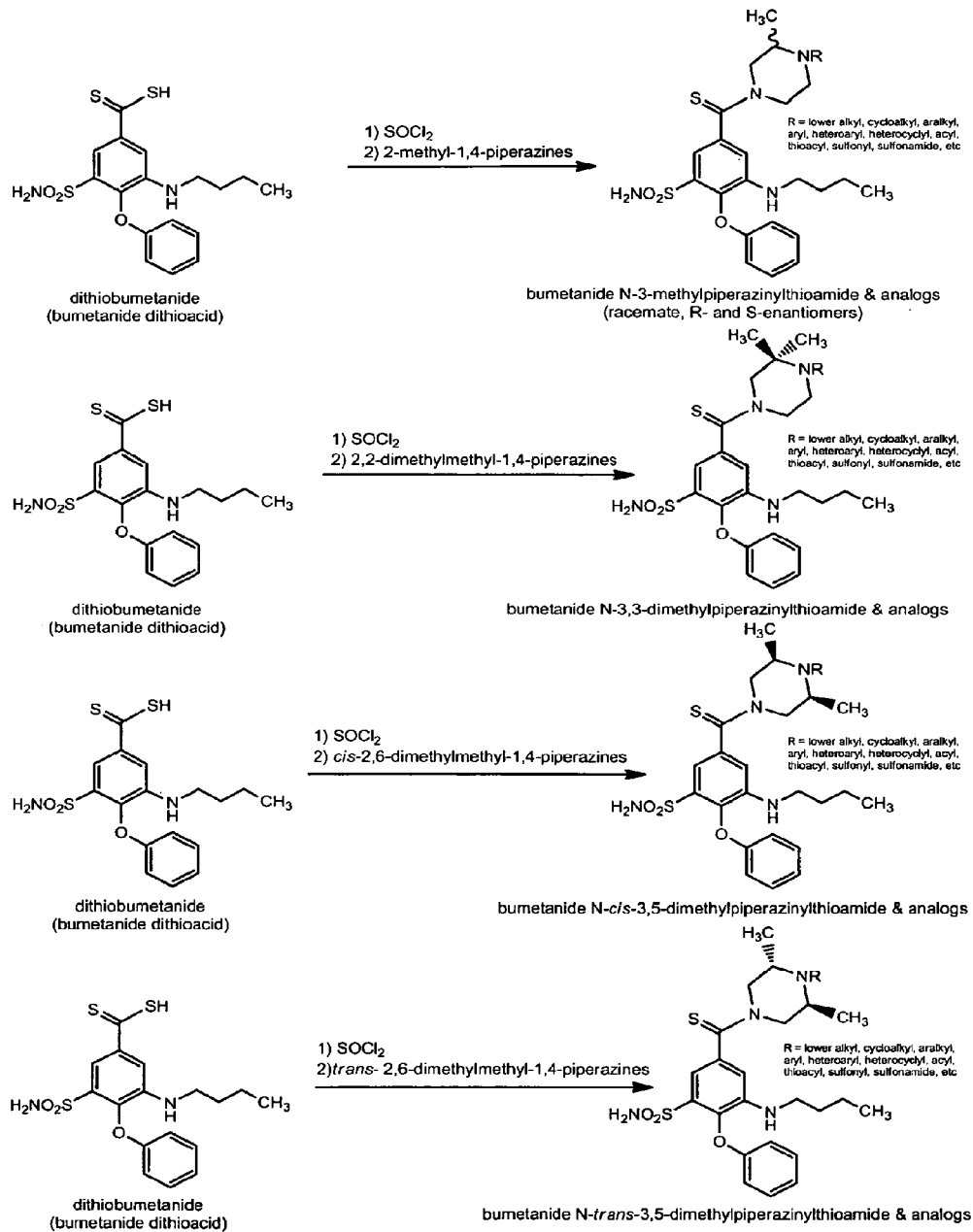

Bumetanide may be converted to a thiobumetanide analog comprising a cyclic amide via a dithiobumetanide intermediate, as shown in FIG. 2. In FIG. 2, the thiobumetanide analog comprising a cyclic amide is bumetanide N-morpholinothioamide. The same dithiobumetanide intermediate may be used to prepare a variety of additional thiobumetanide analogs comprising acyclic amide as shown in FIGS. 3-7. Alternative methods for obtaining bumetanide N-morpholinothioamide are shown in FIG. 8. Similar chemistries may be used to obtain selenobumetanide analogs, in general, and specifically selenobumetanide analogs comprising cyclic amides. For example, instead of $P_2S_5$ as shown in FIG. 8, $P_2Se_5$ or equivalent reagents could be used to generate the correspondingselenobumetanide analog comprising a cyclic amide as shown in FIG. 8A. Rae, I. D. and Wade, M. J., Int. J. Sulfur Chem., 1976, 8, 519; Voss, J. and Bruhn, F.-R., Liebigs Ann. Chem., 1979, 1931; and Woollins, J. D., et al., Chemistry Europe J., 2005, 11, 6221-6227.

B. Furosemide Analogs, Thiofurosemide Analogs, and Dithiofurosemide Analogs

1. Thiofurosemide and Dithiofurosemide

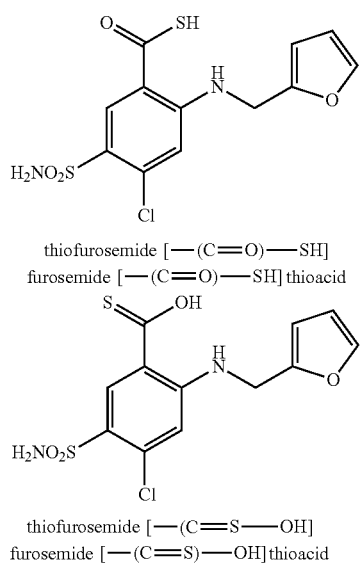

thiofurosemide [—(C═O)—SH]
furosemide [—(C═O)—SH] thioacid thiofurosemide [—(C═S)—OH]
furosemide [—(C═S)—OH] thioacid

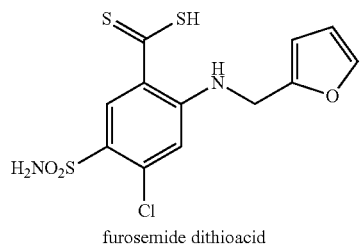

furosemide dithioacid

The thiofurosemide analogs are synthesized by reacting the carboxylic acid moiety of furosemide with various reagents. For example, furosemide may undergo conversion to the corresponding thioacid by treatment with thionyl chloride to form the corresponding furosemide acid chloride followed by reaction with sodium hydrogen sulfide to give thiofurosemide [—(C═O)—SH], also known as furosemide [—(C═O)—SH] thioacid by the methodology of Noble, P. and Tarbell, D. S., Org. Synth., Coll. Vol. IV, John Wiley & Sons, Inc., New York, 1963, 924-927. (See Scheme 10).

Thiofurosemide may undergo conversion to the corresponding furosemide thioacid chloride with thionyl chloride, followed by treatment of the thioacid chloride with sodium hydrogen sulfide to give dithiofurosemide [—(C═S)—SH], also known as furosemide [—(C═S)—SH] dithioacid by similar methodology. (See Scheme 10) Reaction of furosemide thioacid chloride with secondary amines will give the corresponding furosemide thioamides. Furosemide may also undergo reaction with phosphorous pentasulfide to yield furosemide dithioacid. For reviews of this body of chemistry, See "Thioacyl Halides", "Thiocarboxylic O-Acid Esters" and "Dithiocarboxylic Acid Esters", all by Glass, R. S. in Science of Synthesis, (Charette, A. B., Ed.), Volume 22, Thieme Chemistry, 2005, Chapters 22.1.2, 22.1.3 and 22.1.4 and references therein. See also "Synthesis of Thioamides and Thiolactams," Schaumann, E., in Comprehensive Organic Synthesis, (Trost, B. M. and Fleming, I., Eds.), Pergamon Press, 1991, Volume 6, Chapter 2.4, pp. 450-460 and references therein.

129

Scheme 10. Synthesis of Thiofurosemide
{Fursemide[—(C=O)—SH] Thioacid}

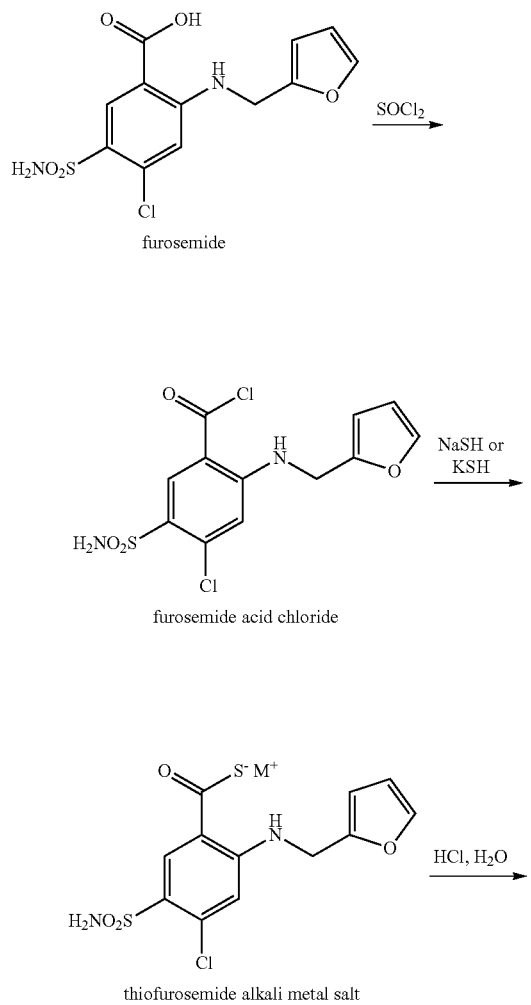

furosemide furosemide acid chloride thiofurosemide alkali metal salt

130

-continued

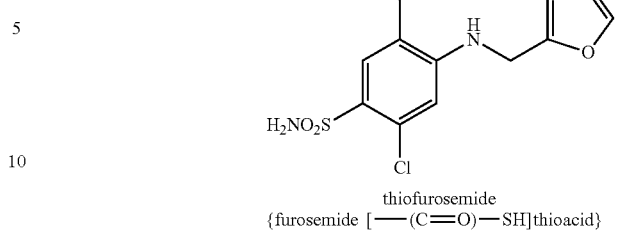

thiofurosemide
{furosemide [—(C=O)—SH]thioacid}

2. Furosemide and S-Furosemide Analogs

The furosemide analogs are synthesized by methods analogous to those used in the synthesis of the bumetanide analogs. Furosemide may undergo esterification via reaction with alcohols, including linear, branched, substituted, or unsubstituted alcohols. Furosemide or thiofurosemide may also be alkylated via reaction with suitable substituted and unsubstituted alkyl halides and alkaryl halides, including for example, chloroacetonitrile, benzyl chloride, 1-(dimethylamino)propyl chloride, 2-chloro-N,N-diethylacetamide, and the like. PEG-type esters may be formed by alkylation using alkyloxy(polyalkyloxy)alkyl halides such as MeO-PEG350-Cl and the like or alkyloxy(polyalkyloxy)alkyl tosylates such as MeO-PEG1000-OTs and the like. "Axetil"-type esters may also be formed by alkylation by using alkyl halides such as chloromethyl pivalate or chloromethyl propionate. Furosemide may also undergo amidation by reaction with suitable substituted or unsubstituted alkyl amines or aryl amines, either after conversion to the acid chloride or by using an activator, such as 1-ethyl-3-(3-dimethylaminopropyl)carbodiimide (EDC). Furosemide or thiofurosemide may also be reacted with a quaternary ammonium hydroxide, such as benzyltrimethylammonium hydroxide or cetyltrimethylammonium hydroxide, to form furosemide or thiofurosemide quaternary ammonium salts. Schemes, 11, 12, and 13 present some exemplary compounds according to formula III.

Scheme 11. Synthesis of Exemplary Compounds According to Formula III

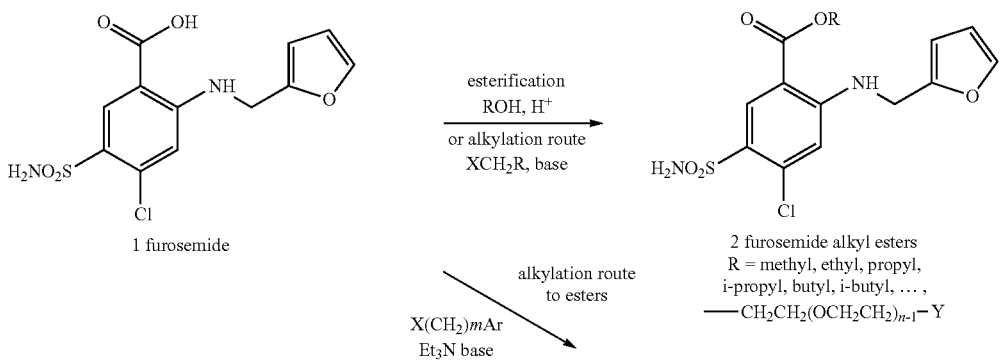

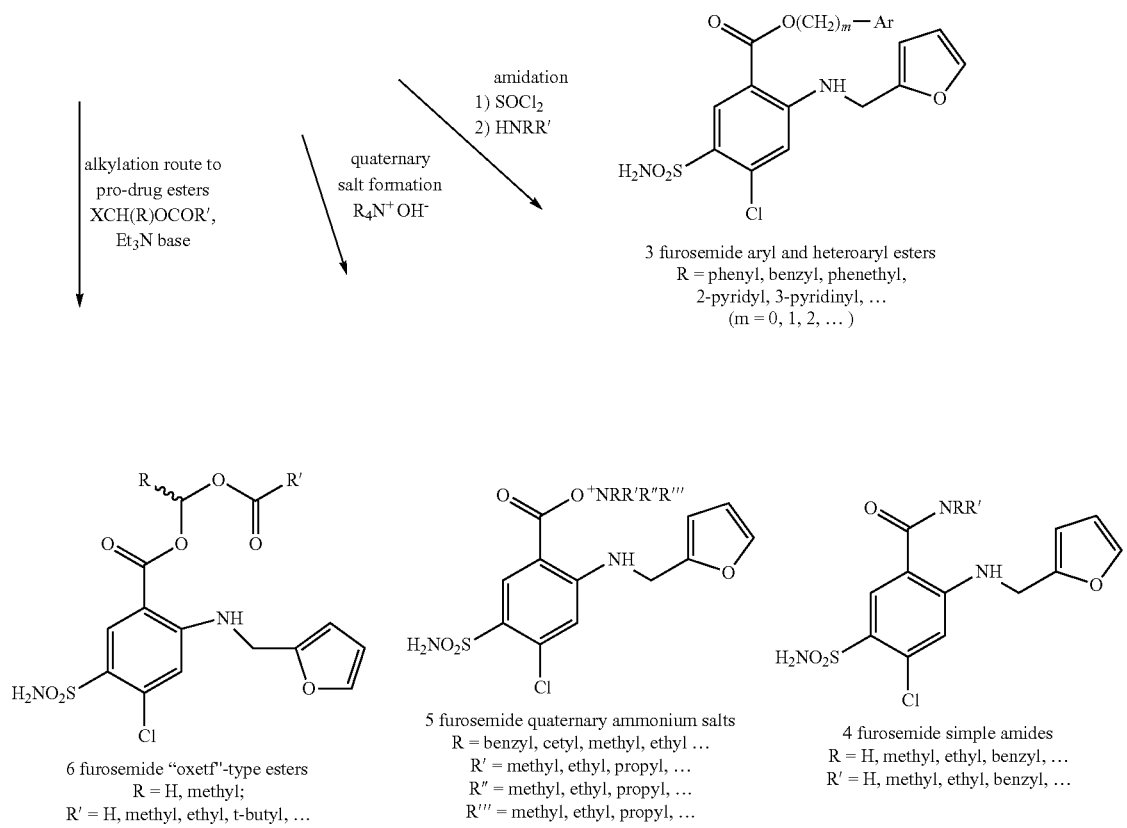
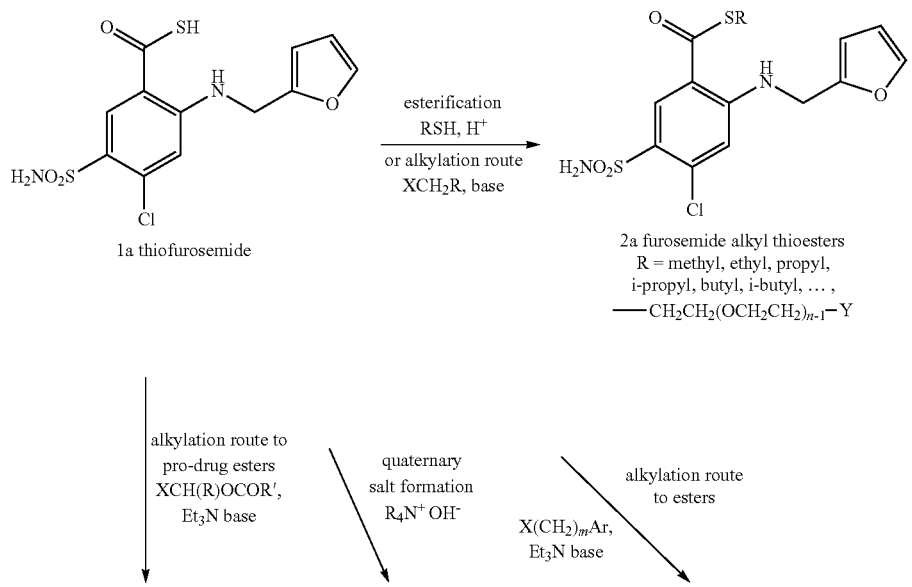
Scheme 12. Synthesis of Exemplary Compounds According to Formula III

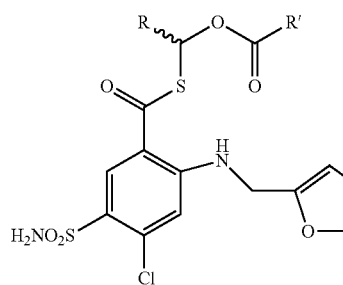

6 furosemide "axetil"-type thioesters
R = H, methyl;
R' = H, methyl, ethyl, t-butyl, ...

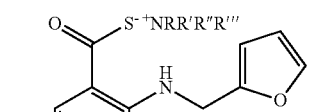

5a thiofurosemide quaternary ammonium salts
R = benzyl, cetyl, methyl, ethyl ...
R' = methyl, ethyl, propyl, ...
R" = methyl, ethyl, propyl, ...
R''' = methyl, ethyl, propyl, ...

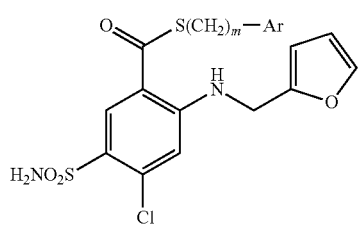

3a furosemide aryl and heteroaryl thioesters
R = phenyl, benzyl, phenethyl,
2-pyridyl, 3-pyridinyl, ...
(m = 0, 1, 2, ... )

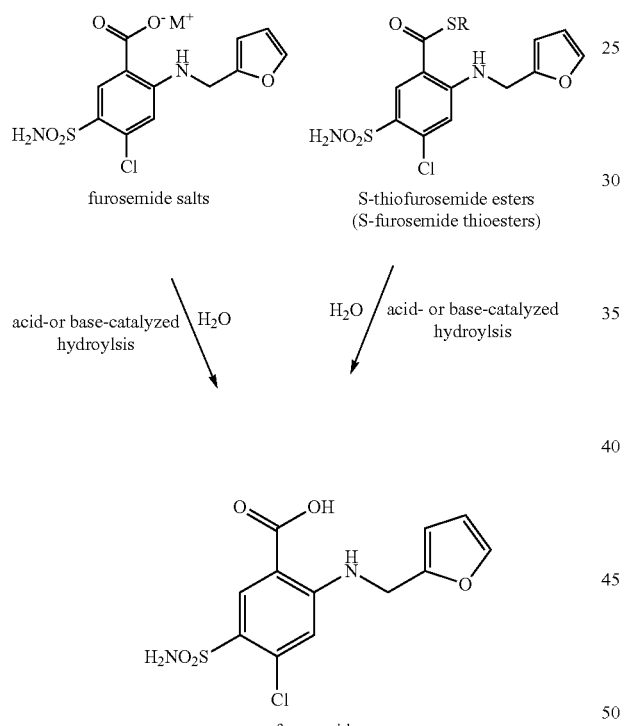

Scheme 13. Hydrolysis of Thiofurosemide salts and S-thiofurosemide Esters

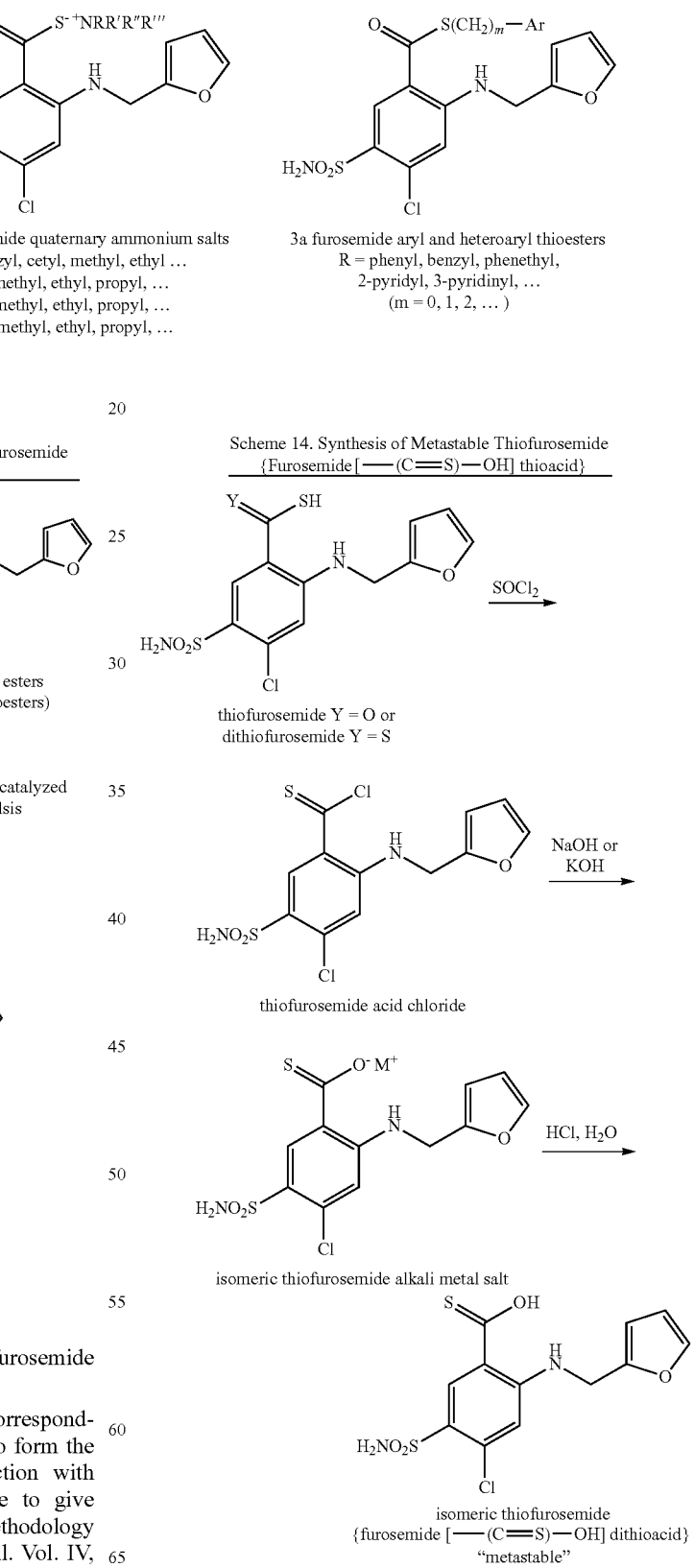

Scheme 14. Synthesis of Metastable Thiofurosemide {Furosemide [—(C=S)—OH] thioacid}

3. O-Substituted Thiofurosemide and Dithiofurosemide Analogs

Furosemide may undergo conversion to the corresponding thioacid by treatment with thionyl chloride to form the corresponding acid chloride followed by reaction with sodium hydroxide or sodium hydrogen sulfide to give O-thiofurosemide and dithiofurosemide by the methodology of Noble, P. and Tarbell, D. S., Org. Synth., Coll. Vol. IV, John Wiley & Sons, Inc., New York, 1963, 924-927. (See Schemes 14 and 15).

Scheme 15. Synthesis of Dithiofurosemide
{Furosemide [——(C═S)——SH] Dithioacid}

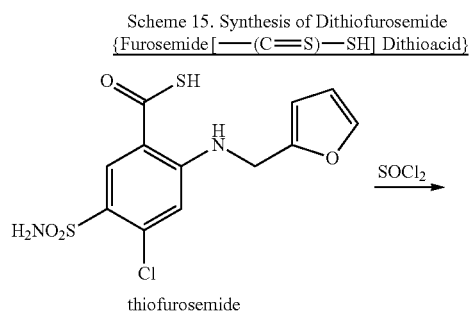

thiofurosemide

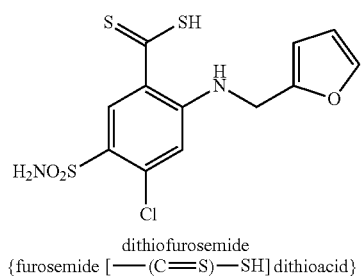

dithiofurosemide
{furosemide [——(C═S)——SH] dithioacid}

The thiofurosemide analogs are, in turn, synthesized by reacting the thiocarboxylic acid moiety of thiofurosemide with various reagents. For example, thiofurosemide may undergo esterification via reaction with alcohols or thiols, including linear, branched, substituted, or unsubstituted alcohols and thiols. S-Thiofurosemide may also be alkylated via reaction with suitable substituted and unsubstituted alkyl halides and alkaryl halides, including chloroacetonitrile, benzyl chloride, 1-(dimethylamino)propyl chloride, 2-chloro-N,N-diethylacetamide, and the like. PEG-type esters may be formed by alkylation using alkyloxy(polyalkyloxy)alkyl halides such as MeO-PEG350-Cl and the like or alkyloxy(polyalkyloxy)alkyl tosylates such as MeO-PEG1000-OTs and the like. "Axetil"-type esters may also be formed by alkylation by using alkyl halides such as chloromethyl pivalate or chloromethyl propionate. Thiofurosemide may also be reacted with a quaternary ammonium hydroxide, such as benzyltrimethylammonium hydroxide or cetyltrimethylammonium hydroxide, to form thiofurosemide quaternary ammonium salts. Schemes 14, 15, 16, 17, and 18 present synthesis schemes of some exemplary compounds according to formula IV.

Scheme 16. Synthesis of Exemplary Compounds According to Formula IV

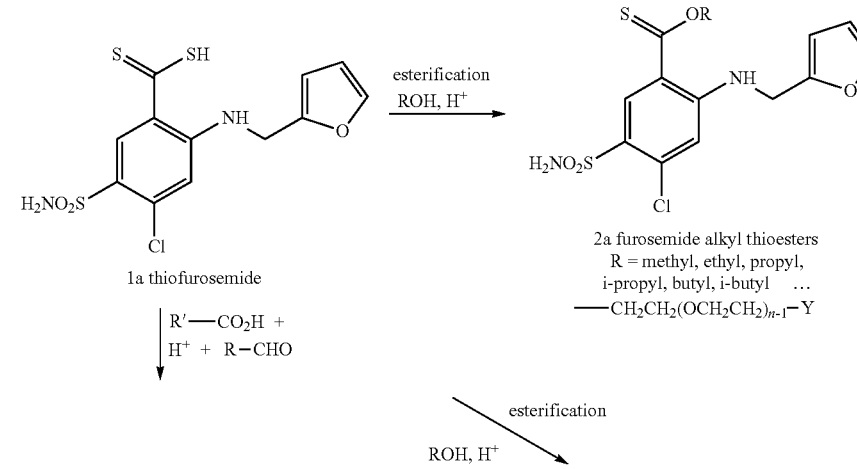

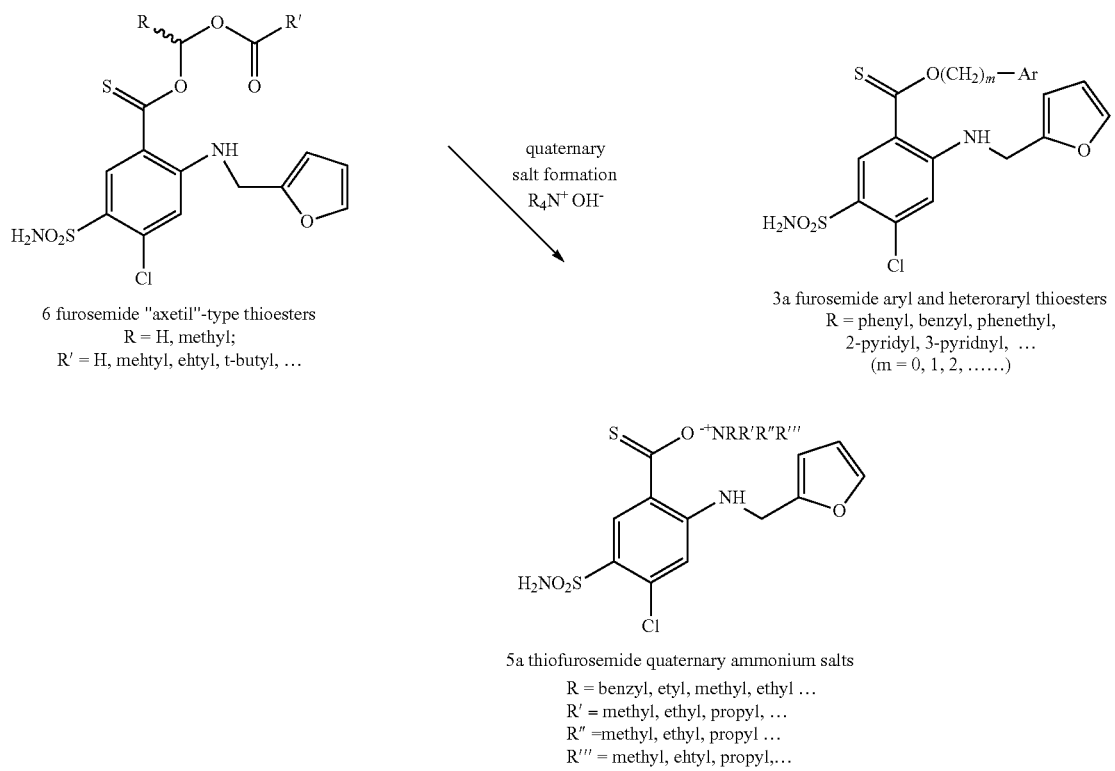

6 furosemide "axetil"-type thioesters
R = H, methyl;
R' = H, mehtyl, ehtyl, t-butyl, ...

3a furosemide aryl and heteroraryl thioesters
R = phenyl, benzyl, phenethyl,
2-pyridyl, 3-pyridnyl, ...
(m = 0, 1, 2, ......)

5a thiofurosemide quaternary ammonium salts
R = benzyl, etyl, methyl, ethyl ...
R' = methyl, ethyl, propyl, ...
R" = methyl, ethyl, propyl ...
R'" = methyl, ehtyl, propyl,...

Scheme 17. Synthesis of Exemplary Compounds According to FOrmula IV

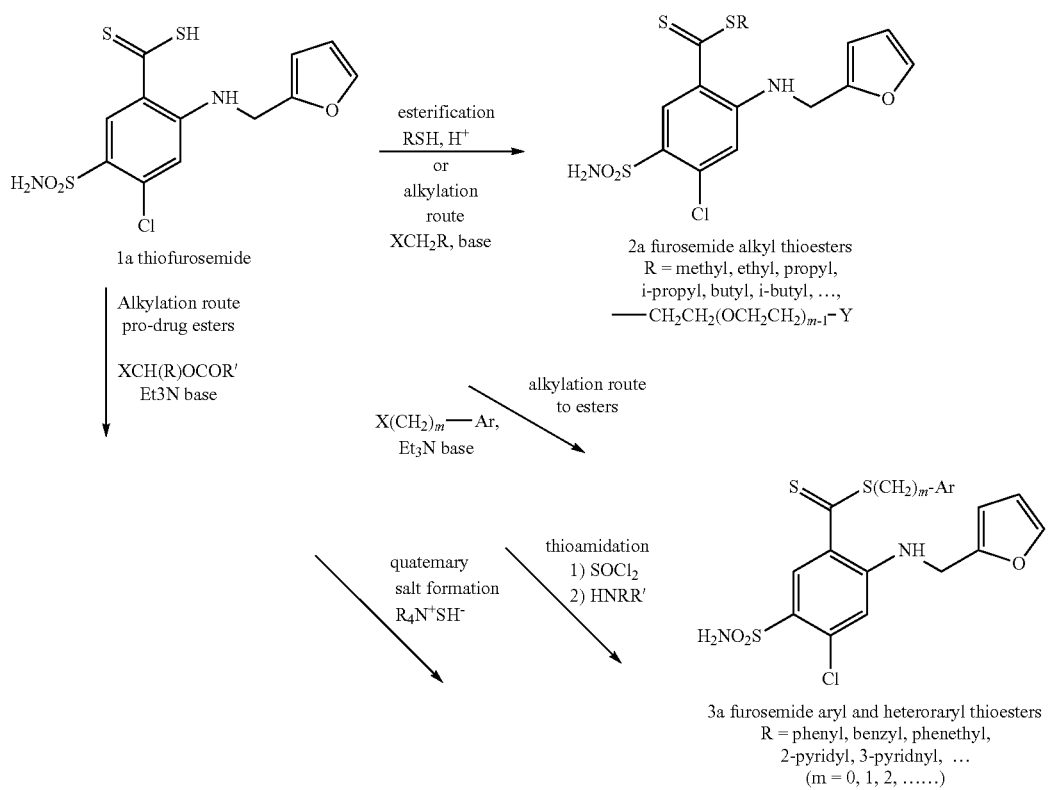

1a thiofurosemide 2a furosemide alkyl thioesters
R = methyl, ethyl, propyl,
i-propyl, butyl, i-butyl, ...,
—CH$_2$CH$_2$(OCH$_2$CH$_2$)$_{m-1}$-Y 3a furosemide aryl and heteroraryl thioesters
R = phenyl, benzyl, phenethyl,
2-pyridyl, 3-pyridnyl, ...
(m = 0, 1, 2, ......)

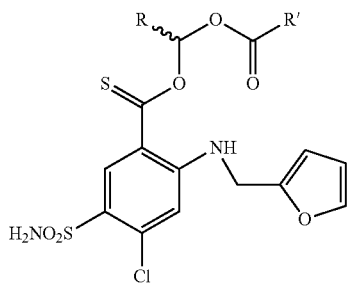

6 furosemide "axetil" -type thioesters
R = H, methyl;
R' = H, mehtyl, ehtyl, t-butyl, ...

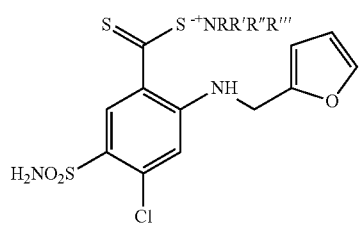

5a thiofurosemide quaternary ammonium salts
R = benzyl, etyl, methyl, ethyl ...
R' = methyl, ethyl, propyl, ...
R" =methyl, ethyl, propyl ...
R''' = methyl, ehtyl, propyl,...

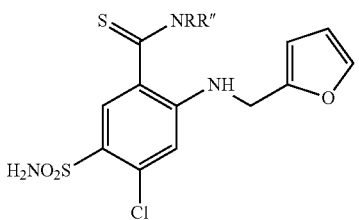

4a furosemide thioamides
R = H, methyl, ethyl, benzyl ...
R' = methyl, ethyl, benzyl, ...

Thiofurosemide, thiofurosemide amides and S-thiofurosemide esters should readily undergo acid- and base-catalyzed hydrolysis to produce the carboxylic acid containing molecule furosemide by methods well known in the art (See Yang, W. and Drueckhammer, D. G., *J. Amer. Chem. Soc.,* 2001, 123 (44), 11004-11009 and references therein). For additional reviews of this body of chemistry, See "Thioacyl Halides", "Thiocarboxylic O-Acid Esters" and "Dithiocarboxylic Acid Esters", all by Glass, R. S. in Science of Synthesis, (Charette, A. B.; Ed.), Volume 22, Thieme Chemistry, 2005, Chapters 22.1.2, 22.1.3 and 22.1.4 and references therein. See also "Synthesis of Thioamides and Thiolactams," Schaumann, E., in Comprehensive Organic Synthesis, (Trost, B. M. and Fleming, I., Eds.), Pergamon Press, 1991, Volume 6, Chapter 2.4, pp. 450-460 and references therein. (See Scheme 18).

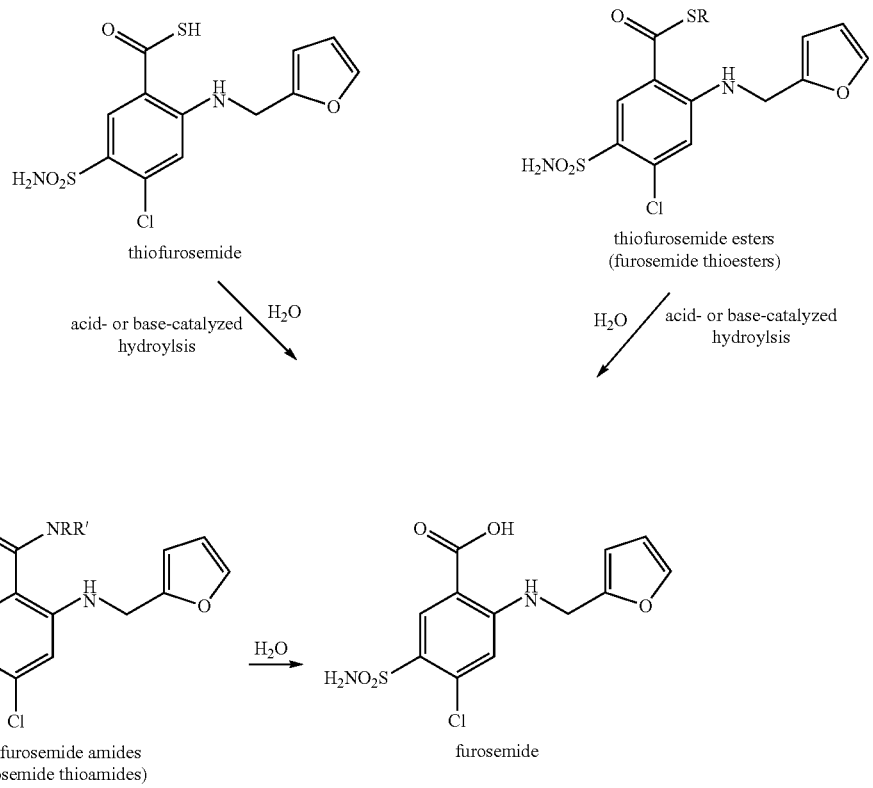

Scheme 18. Hydrolysis of Thiofurosemide, Thiofurosemide Amides, and S-thiofurosemide Esters C. Piretanide Analogs, Thiopiretanide Analogs, and Dithiopiretanide Analogs 1. Thiopiretanide and Dithiopiretanide

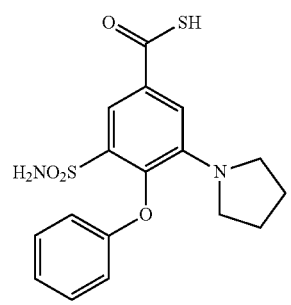

thiopiretanide [—(C=O)—SH]
piretanide [—(C=O)—SH] thioacid

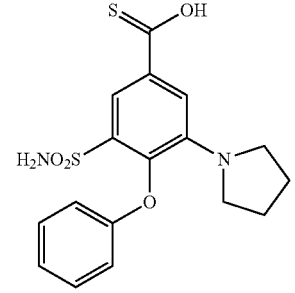

thiopiretanide [—(C=S)—OH]
piretanide [—(C=S)—OH] thioacid

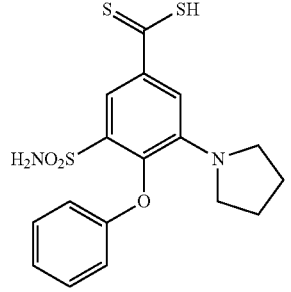

piretanida dithioacid

The piretanide analogs are synthesized by reacting the carboxylic acid moiety of piretanide with various reagents. For example, piretanide may undergo conversion to the corresponding thioacid by treatment with thionyl chloride to form the corresponding piretanide acid chloride followed by reaction with sodium hydrogen sulfide to give thiopiretanide [—(C=O)—SH], also known as piretanide [—(C—O)—SH] thioacid by the methodology of Noble, P. and Tarbell, D. S., Org. Synth., Coll. Vol. IV, John Wiley & Sons, Inc., New York, 1963, 924-927. See Scheme 19. Thiopiretanide may undergo conversion to the corresponding piretanide thioacid chloride with thionyl chloride, followed by treatment of the thioacid chloride with sodium hydrogen sulfide to give dithiopiretanide [—(C=S)—SH], also known as piretanide [—(C=S)—SH] dithioacid by similar methodology. Reaction of piretanide thioacid chloride with secondary amines will give the corresponding piretanide thioamides. Piretanide may also undergo reaction with phosphorous pentasulfide to yield piretanide dithioacid. For reviews of this body of chemistry, See "Thioacyl Halides", "Thiocarboxylic O-Acid Esters" and "Dithiocarboxylic Acid Esters", all by Glass, R. S. in Science of Synthesis, (Charette, A. B., Ed.), Volume 22. Thieme Chemistry, 2005, Chapters 22.1.2, 22.1.3 and 22.1.4 and references therein. See also "Synthesis of Thioamides and Thiolactams," Schaumann, E., in Comprehensive Organic Synthesis, (Trost, B. M. and Fleming, I., Eds.), Pergamon Press, 1991, Volume 6, Chapter 2.4, pp. 450-460 and references therein.

Scheme 19. Synthesis of Thiopiretanide {Piretanide [—C=O)-SH] Thioacid}

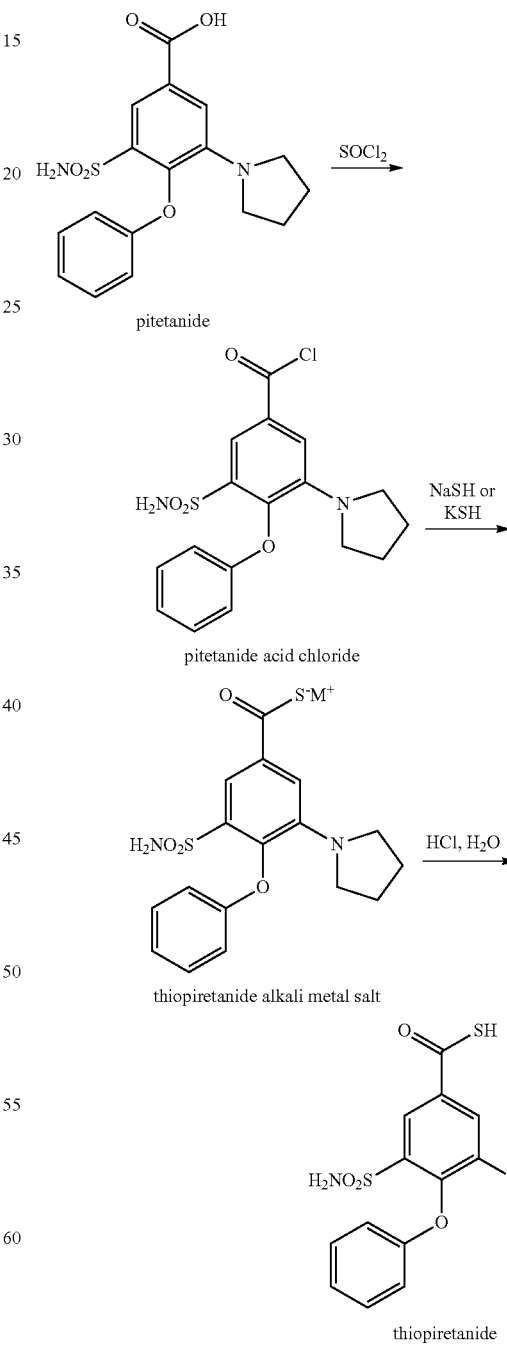

2. Piretanide and S-Thiopiretanide Analogs

Piretanide may undergo esterification via reaction with alcohols, including linear, branched, substituted, or unsubstituted alcohols. Piretanide or thiopiretanide may also be alkylated via reaction with suitable substituted and unsubstituted alkyl halides and alkaryl halides, including chloroacetonitrile, benzyl chloride, 1-(dimethylamino)propyl chloride, 2-chloro-N,N-diethylacetamide, and the like. PEG-type esters may be formed by alkylation using alkyloxy(polyalkyloxy)alkyl halides such as MeO-PEG350-Cl and the like or alkyloxy(polyalkyloxy)alkyl tosylates such as MeO-PEG1000-OTs and the like. "Axetil"-type esters may also be formed by alkylation by using alkyl halides such as chloromethyl pivalate or chloromethyl propionate. Piretanide may also undergo amidation by reaction with suitable substituted or unsubstituted alkyl amines or aryl amines, either after conversion to the acid chloride or by using an activator, such as 1-ethyl-3-(3-dimethylaminopropyl)carbodiimide (EDC). Piretanide or thiopiretanide may also be reacted with a quaternary ammonium hydroxide, such as benzyltrimethylammonium hydroxide or cetyltrimethylammonium hydroxide, to form piretanide or thiopiretanide quaternary ammonium salts. Schemes 19, 20, 21 and 22 present synthesis schemes of some exemplary compounds according to formula V.

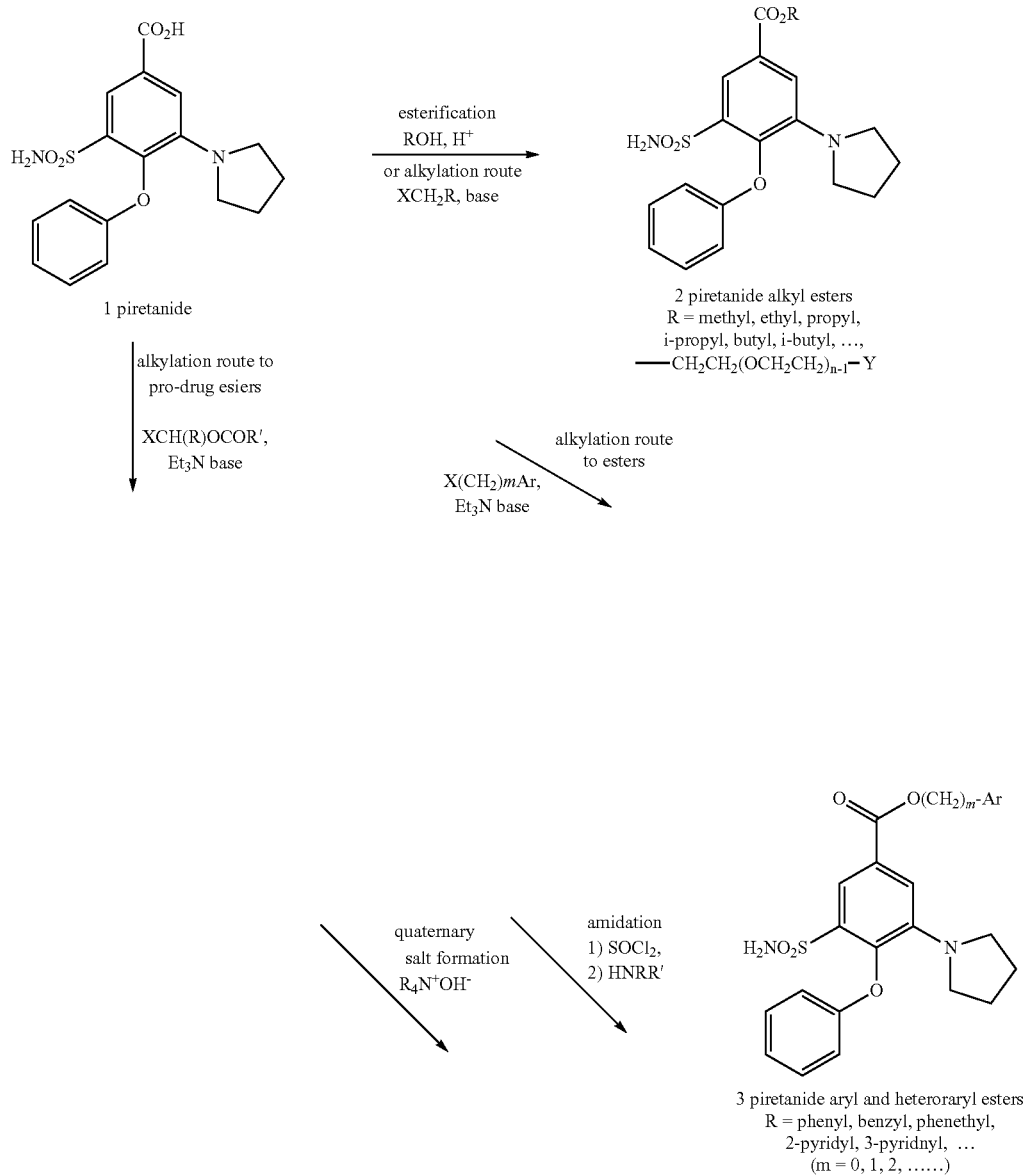

-continued

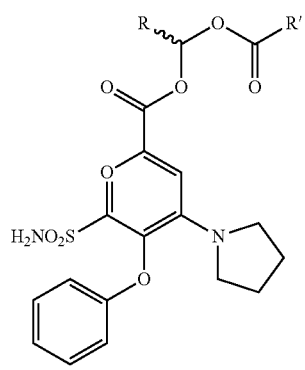

6 piretanide "axetil" -type esters
R = H, methyl:
R' = H, methyl, ethyl, t-butyl, ...

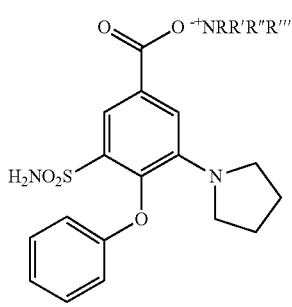

5 piretanide quaternary ammonium salts
R = benzyl, etyl, methyl, ethyl ...
R' = methyl, ethyl, propyl, ...
R" =methyl, ethyl, propyl ...
R''' = methyl, ehtyl, propyl,...

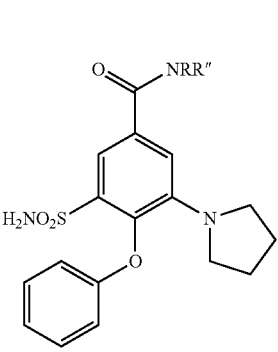

4 piretanide simple amides
R = H, methyl, ethyl, benzyl ...
R' = methyl, ethyl, benzyl, ...

Scheme 21. Synthesis of Exemplary Compounds According to Formula V

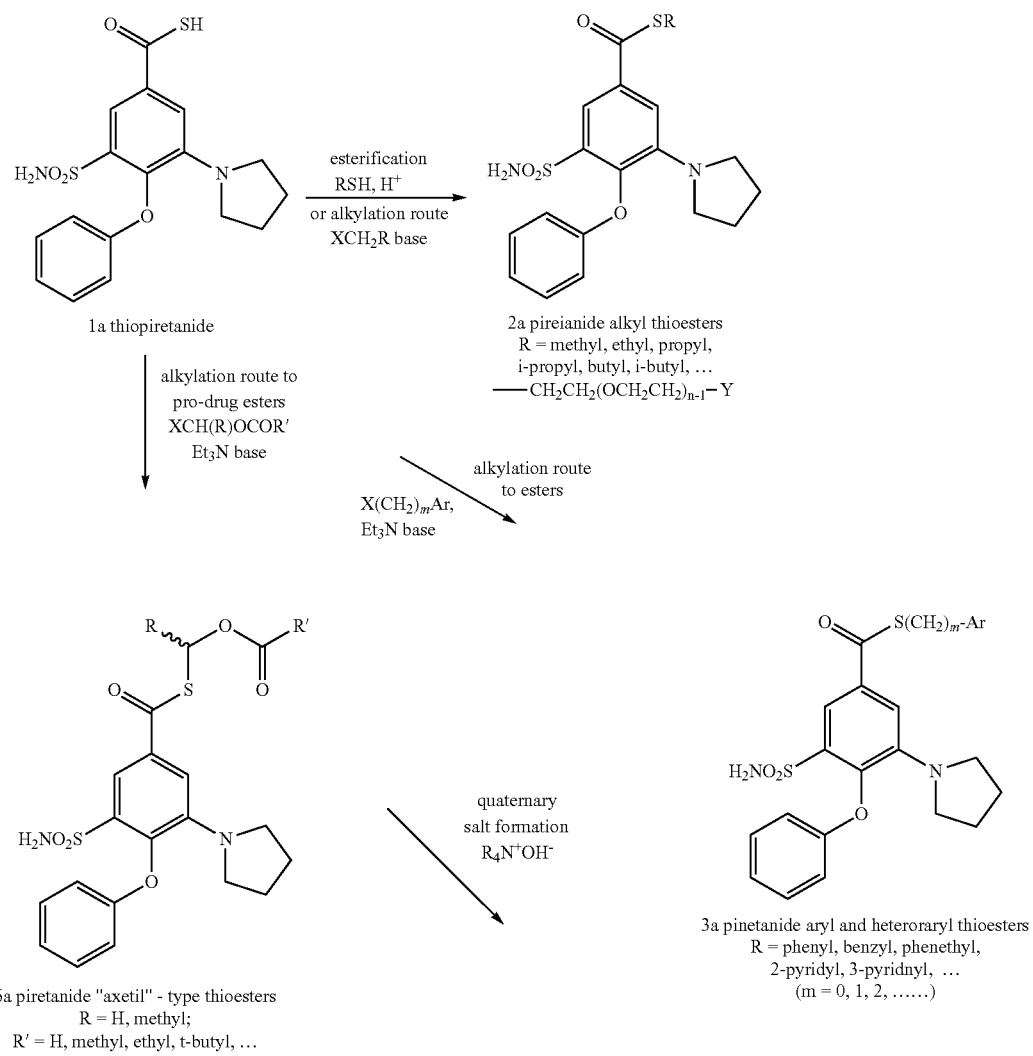

-continued

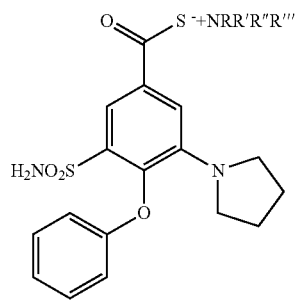

5a thiopiretanide quaternary ammonium salts
R = benzyl, cetyl, methyl, ethyl ...
R' = methyl, ethyl, propyl, ...
R" = methyl, ethyl, propyl, ...
R''' = methyl, ehtyl, propyl,...

Thiopiretanide salts and S-thiopiretanide esters should readily undergo acid- and base-catalyzed hydrolysis to produce the carboxylic acid containing molecule bumetanide by methods well known in the art (See Yang, W., Drueckhammer D. G., *J. Amer. Chem. Soc.,* 2001, 123 (44), 11004-11009 and references therein). (See Scheme 22).

Scheme 22. Hydrolysis of Thiopiretanide salts and S-thiopiretanide Esters

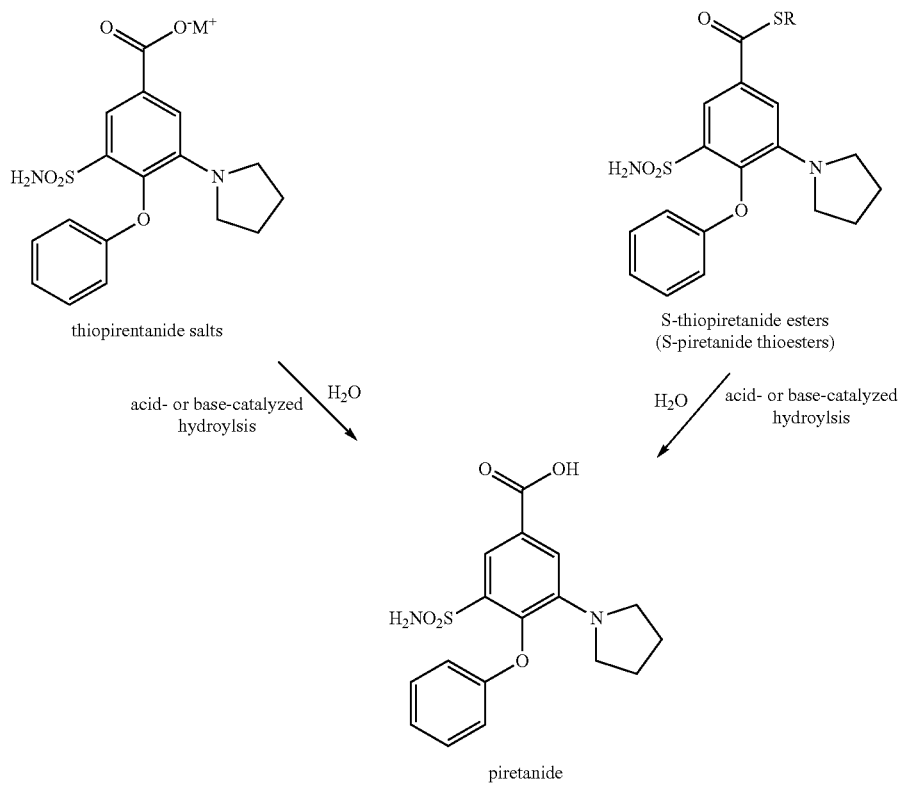

3. O-Substituted Thiopiretanide Analogs Dithiopiretanide Analogs

Piretanide may undergo conversion to the corresponding thioacid by treatment with thionyl chloride to form the corresponding acid chloride followed by reaction with sodium hydroxide or sodium hydrogen sulfide to give metastable O-thiopiretanide and dithiopiretanide by the methodology of Noble, P. and Tarbell, D. S., Org. Synth., Coll. Vol. IV, John Wiley & Sons, Inc., New York, 1963, 924-927. See Schemes 23 and 24.

Scheme 23. Synthesis of Metastable Thiopiretanide {Piretanide [—C(=S)—OH] thioacid}

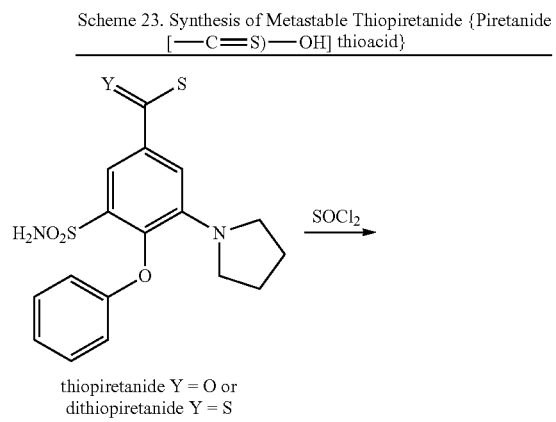

Scheme 24. Synthesis of Dithiopiretanide {Piretanide [—(C=S)—SH] Dithioacid}

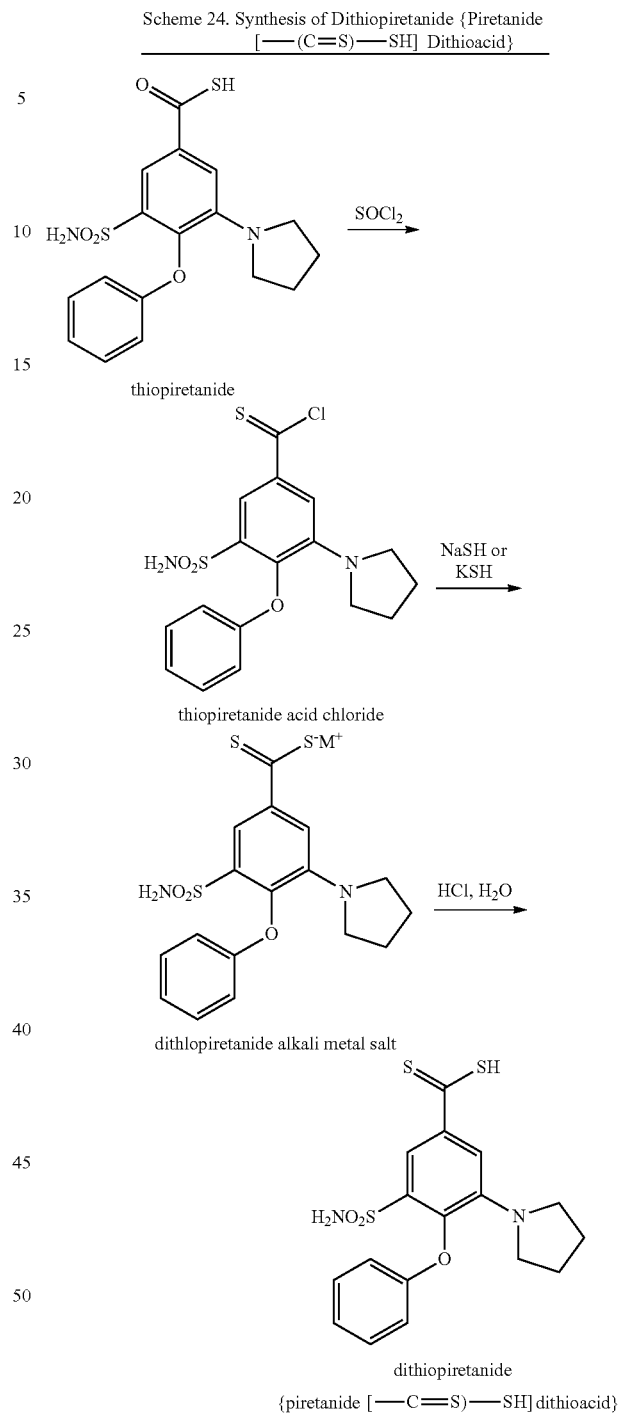

The thiopiretanide analogs are synthesized by methods analogous to those used in the synthesis of the piretanide analogs. Specifically, thiopiretanide may undergo esterification via reaction with thiols, including linear, branched, substituted, or unsubstituted thiols. Thiopiretanide may also be alkylated via reaction with suitable substituted and unsubstituted alkyl halides and alkaryl halides, including chloroacetonitrile, benzyl chloride, 1-(dimethylamino)propyl chloride, 2-chloro-N,N-diethylacetamide, and the like. PEG-type esters may be formed by alkylation using alkyloxy(polyalkyloxy)alkyl halides such as MeO-PEG350-Cl and the like or alkyloxy(polyalkyloxy)alkyl tosylates such as MeO-PEG1000-OTs and the like. "Axetil"-type thioesters may also be formed by alkylation by using alkyl halides such as chloromethyl pivalate or chloromethyl propionate. Thiopiretanide may also be reacted with a quaternary ammonium hydroxide, such as benzyltrimethylammonium hydroxide or cetyltrimethylammonium hydroxide, to form thiopiretanide quaternary ammonium salts. Schemes 23, 24, 25, 26, and 27 present some exemplary compounds according to formula VI.

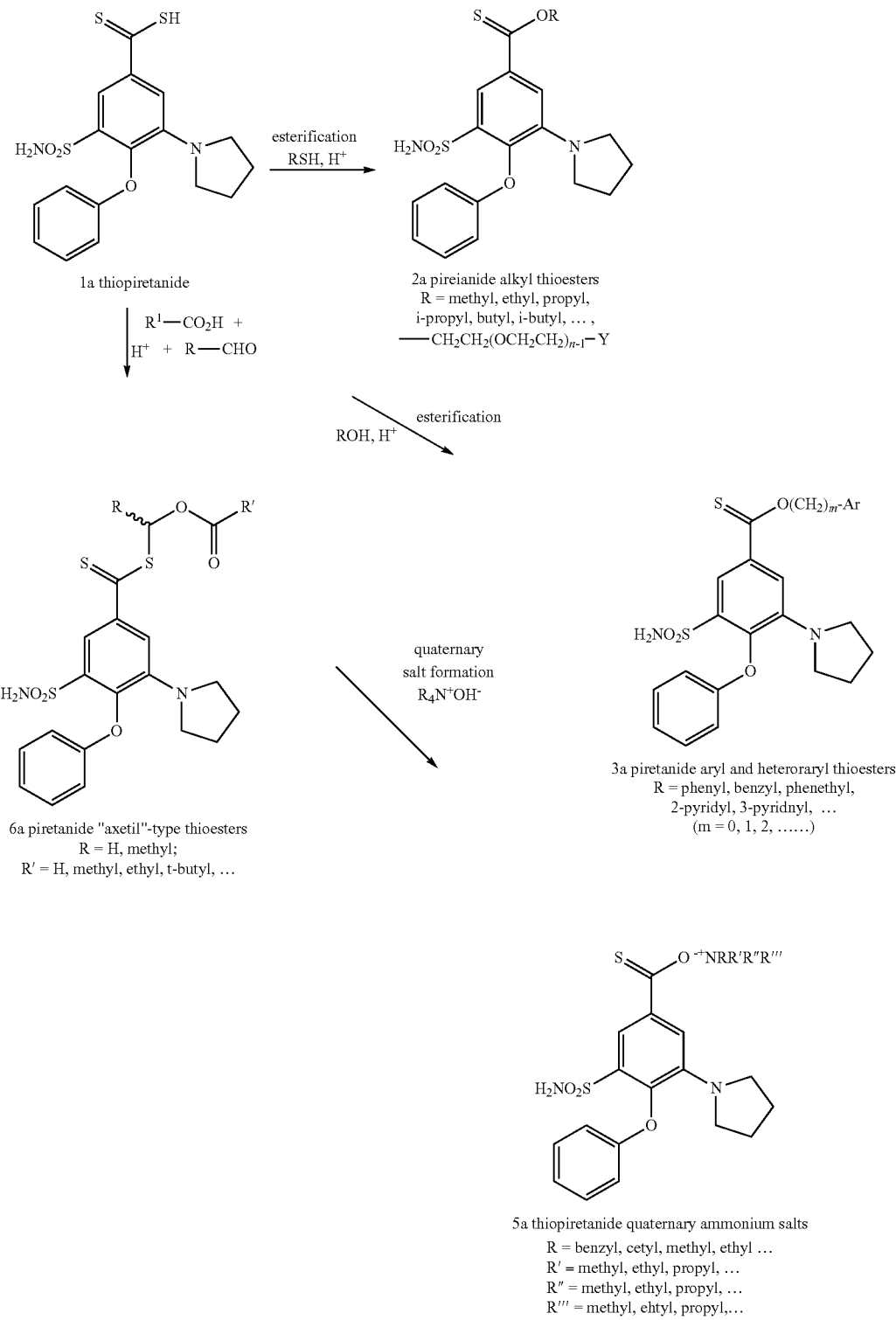

Scheme 25. Synthesis of Exemplary Compounds According to Formula VI

Scheme 26. Synthesis of Exemplary Compounds According to Formula VI

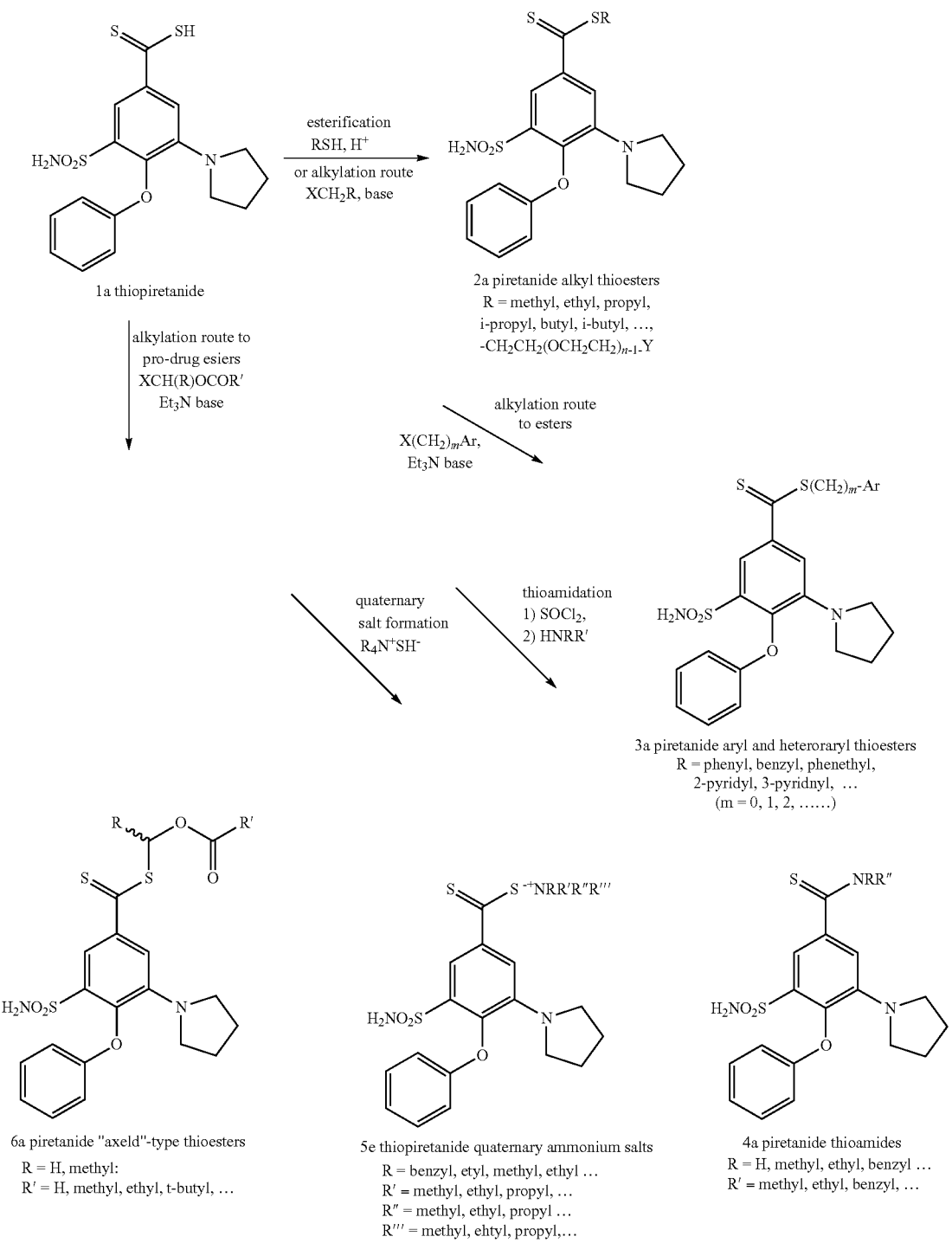

Thiopiretanide, thiopiretanide amides and thiopiretanide esters should readily undergo acid and base-catalyzed hydrolysis to produce the carboxylic acid containing molecule piretanide by methods well known in the art (Sec Yang, W. and Druсckhammer, D. G., *J. Amer. Chem. Soc.,* 2001, 123 (44), 11004-11009 and references therein). For additional reviews of this body of chemistry, See "Thioacyl Halides", "Thiocarboxylic O-Acid Esters" and "Dithiocarboxylic Acid Esters", all by Glass, R. S. in Science of Synthesis, (Charette, A. B., Ed.), Volume 22, Thieme Chemistry, 2005, Chapters 22.1.2, 22.1.3 and 22.1.4 and references therein. See also "Synthesis of Thioamides and Thiolactams," Schaumann, E., in Comprehensive Organic Synthesis, (Trost, B. M. and Fleming, I., Eds.), Pergamon Press, 1991, Volume 6, Chapter 2.4, pp. 450-460 and references therein. (See Scheme 27).

Scheme 27. Hydrolysis of Thiopiretanide, Thiopiretanide Amides, and Thiopiretanide Esters

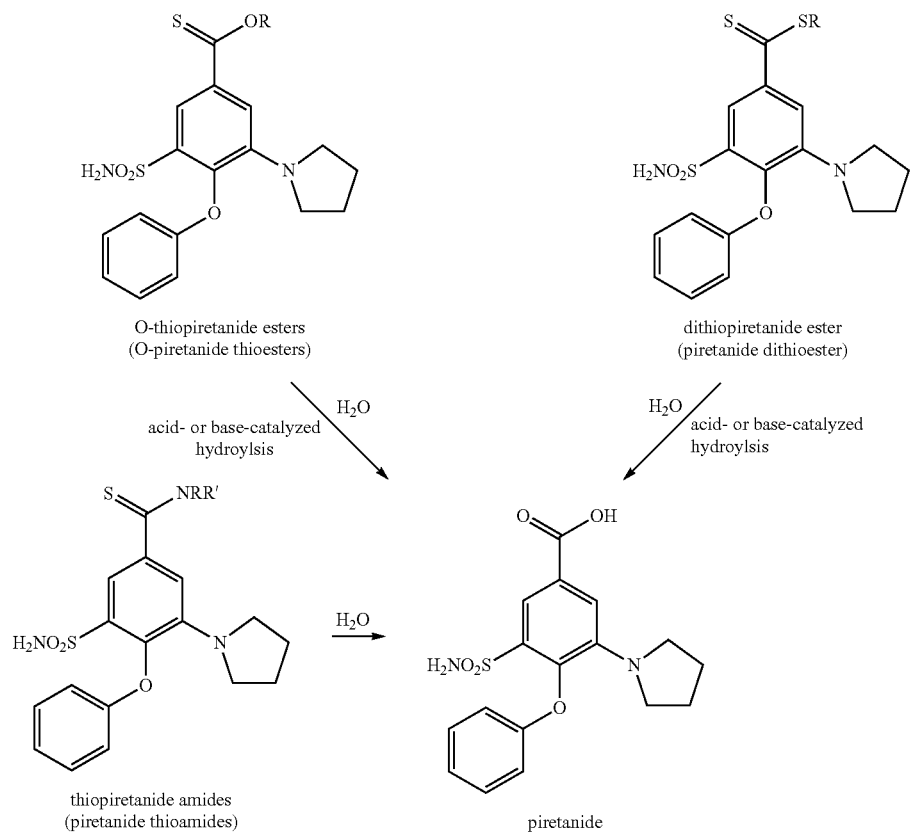

D. Azosemide Analogs

The azosemide analogs are synthesized by the reaction of various reagents with the tetrazolyl moiety of azosemide. Azosemide may undergo hydroxyalkylation with the addition of an aldehyde, whereby a hydroxylalkyl functionality is formed. An alcohol may optionally be reacted along with the aldehyde to obtain an ether. An alkyl thiol may optionally be added with the aldehyde to form a thioether. Azosemide may also be alkylated by the addition of suitable alkyl halides or alkaryl halides, including alkyl or alkaryl halides comprising an ether or thioether linkage, such as methyl chloromethyl ether and benzyl chloromethyl thioether. PEG-type ethers may be formed by alkylation using alkyloxy(polyalkyloxy)alkyl halides such as MeO-PEG350-Cl and the like or alkyloxy(polyalkyloxy)alkyl tosylates such as MeO-PEG1000-OTs and the like. "Axetil"-type analogs may also be formed via addition of alkyl or alkaryl halides, such as chloromethyl pivalate or chloromethyl propionate. Azosemide may also be reacted with a quaternary ammonium salt, such as benzyltrimethylammonium-bromide and base such as sodium hydroxide or cetyltrimethylammonium bromide and base such as sodium hydroxide, in order to form an azosemide quaternary ammonium salt. Scheme 28 below presents a synthesis scheme of some exemplary compounds according to formula VII.

Scheme 28. Synthesis of Exemplary Compounds According to Formula VII

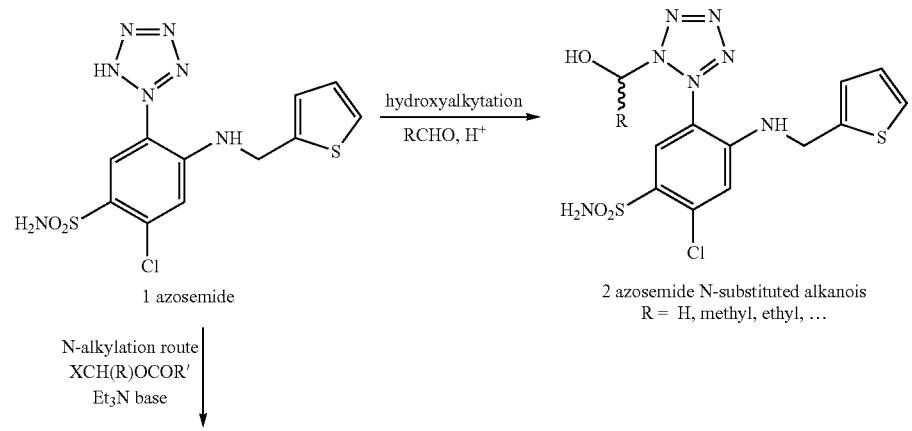

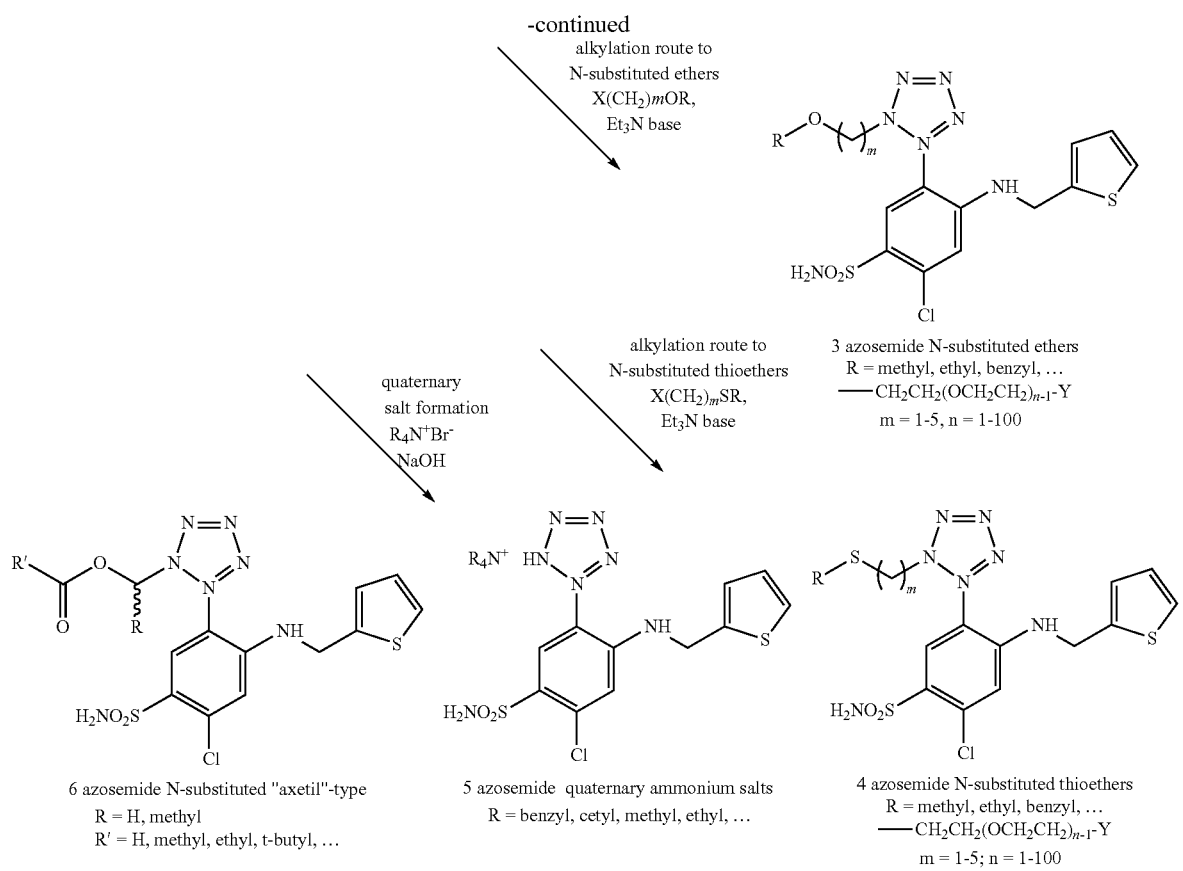

E. Torsemide Analogs

The torsemide (also known as torasemide) analogs are synthesized by the reaction of various reagents with the pyridine moiety of torsemide. Torsemide may undergo alkylation by the addition of suitable alkyl or alkaryl halides, including benzyl chloride, to form N-substituted quaternary ammonium salts. Alkyl halides and alkaryl halides comprising an ether linkage, including methyl chloromethyl ether and benzyl chloromethyl ether, may be used to form N-substituted ether quaternary ammonium salts. Alkyl halides and alkaryl halides comprising a thioether linkage, including methyl chloromethyl thioether and benzyl chloromethyl thioether, may be used to form N-substituted thioether quaternary ammonium salts. PEG-type ether-containing quaternary ammonium salts may be formed by alkylation using alkyloxy(polyalkyloxy)alkyl halides such as MeO-PEG350-Cl and the like or alkyloxy(polyalkyloxy)alkyl tosylates such as MeO-PEG000-OTs and the like. "Axetil"-type quaternary ammonium salts may also be formed via the addition of alkyl halides such as chloromethyl pivalate or chloromethyl propionate. Scheme 29 below presents a synthesis scheme of some exemplary compounds according to formula VIII.

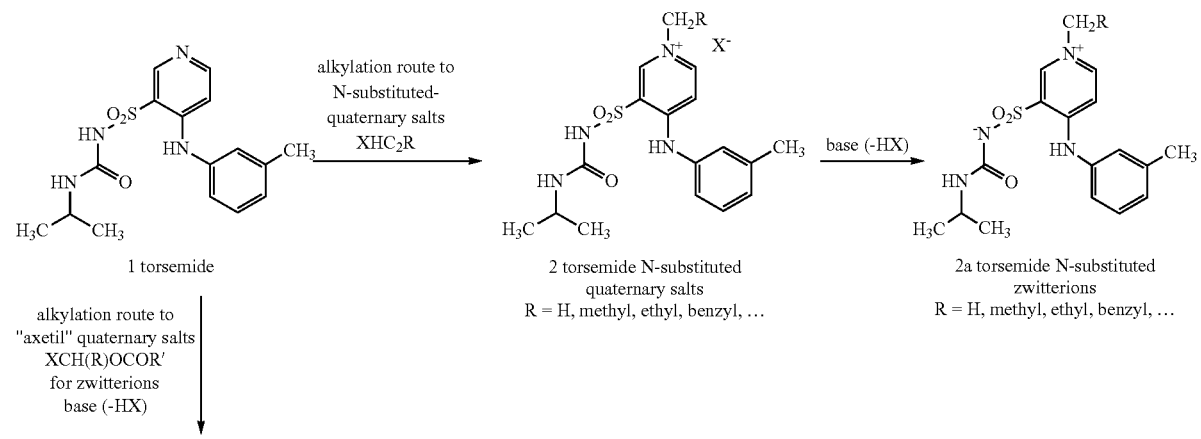

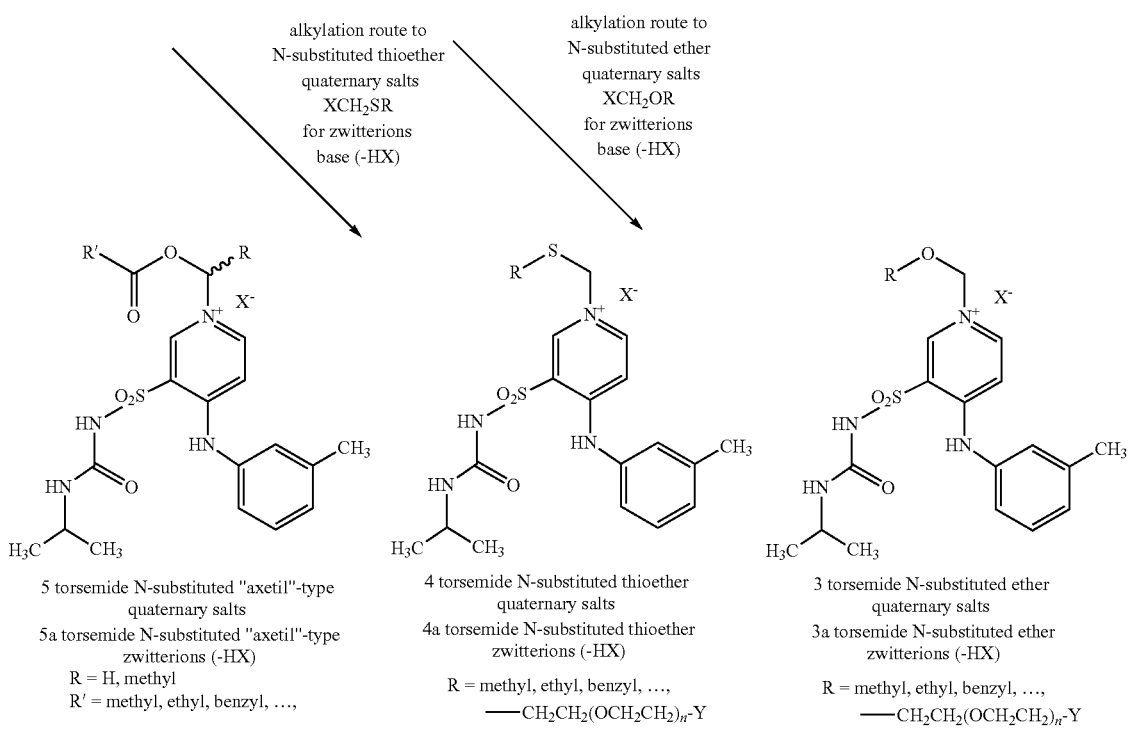

F. Benzaldehyde Analogs of Bumetanide, Piretanide, and Furosemide

The substituted benzoic acids bumetanide, piretanide, and furosemide can be selectively reduced to the corresponding bumetanide aldehyde, piretanide aldehyde and furosemide aldehyde using amine-substituted ammonium hydrides such as bis(4-methylpiperazinyl)aluminum hydride by literature methods. See Muraki, M. and Mukiayama, T., Chem. Letters, 1974, 1447; Muraki, M. and Mukiayama, T., Chem. Letters, 1975, 215; and Hubert, T., D., Eyman, D. P. and Wiemier, D. F., J. Org. Chem., 1984, 2279. (See Scheme 30). It is well known that the more lipophilic benzaldehydes readily air-oxidize into the more hydrophilic benzoic acids and that benzaldehydes are also metabolized into the corresponding benzoic acids in vivo, via the use of NADPH co-factor and with a number of oxidative P450 enzymes.

Scheme 30. Synthesis of Exemplary Benzaldehyde Analogs of Bumetanide, Piretanide, and Furosemide -continued

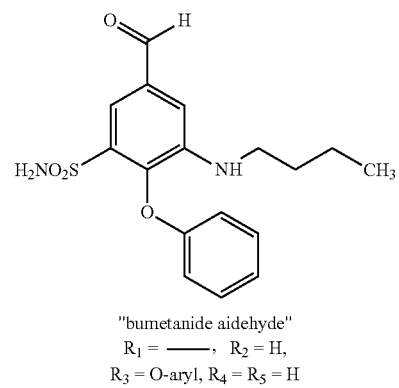

"bumetanide aldehyde"
$R_1 = \text{———}$, $R_2 = H$,
$R_3 = \text{O-aryl}$, $R_4 = R_5 = H$

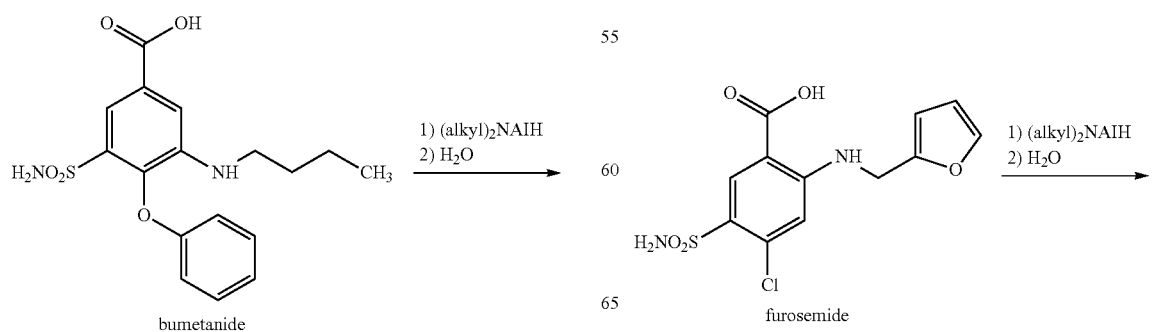

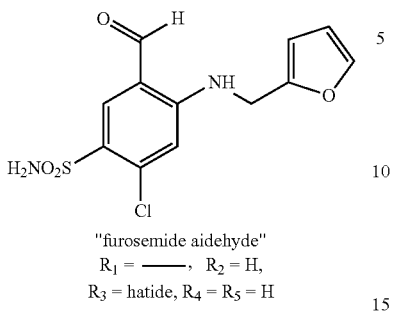

"furosemide aidehyde"
R₁ = ———, R₂ = H,
R₃ = hatide, R₄ = R₅ = H

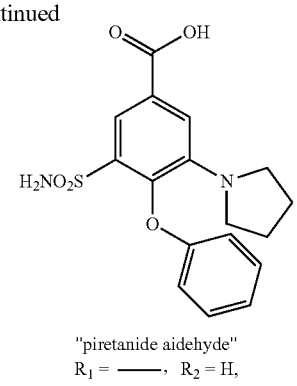

"piretanide aidehyde"
R₁ = ———, R₂ = H,
R₃ = O-aryl, R₄ = R₅ = H

For reduction procedures used to convert benzoic acids to the corresponding benzaldehydes see:
Muraki, M and Muldayama, T., Chem. Letters. 1974, 1447; Ibid, 1975, 215:
Hubert, T., D., Eymna, D.P. and Wiemer. D. F., J. Org. Chem., 1984, 2279.

The lipophilic thiobenzaldehydes can also be prepared from the corresponding benzaldehydes by treating agents including hydrogen sulfide and diphosphorus pentasulfide (See Smith, M. B. and March, J., March's Advanced Organic Chemistry, Fifth Edition, 2001, John Wiley & Sons, Inc., New York, Part 2, Chapter 16, pp. 1185-1186. C. Sulfur Nucleophiles, Section 16-10 The Addition of $H_2S$ and Thiols to Carbonyl Compounds.) (See Scheme 31). In turn these thiobenzaldehydes are readily converted back into the corresponding benzaldehydes under hydrolytic conditions. It is well known that the more lipophilic benzaldehydes readily air-oxidize into the more hydrophilic benzoic acids and that benzaldehydes are also metabolized into the corresponding benzoic acids in vivo, via the use of NADPH co-factor and with a number of oxidative P450 enzymes. A similar mechanism can be applied for the conversions of thiobenzaldehydes to thiobenzoic acids and then benzoic acids.

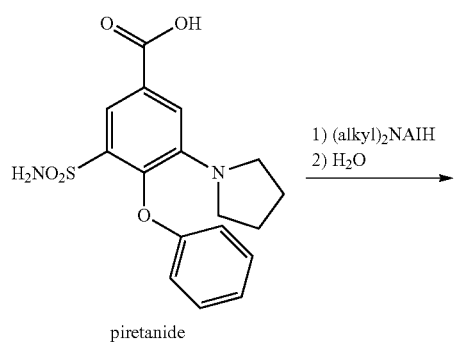

piretanide 1) (alkyl)₂NAIH
2) H₂O

Scheme 31. Synthesisi ofExemplary Thiobenzaldehyde Analogs of Bumetanide, Piretanide, and Furosemide

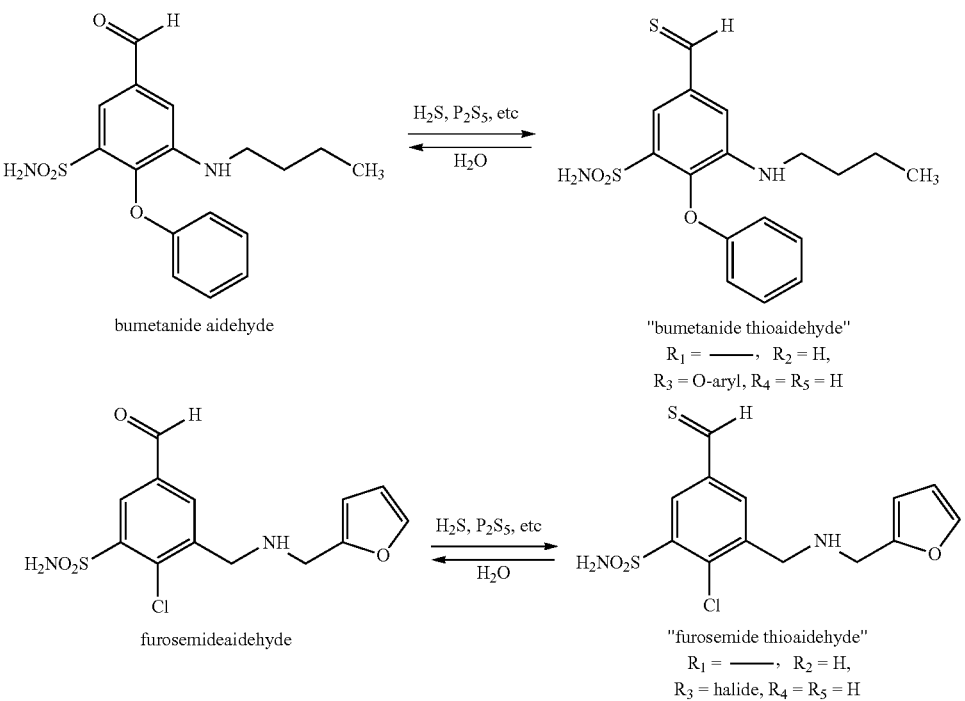

bumetanide aidehyde

"bumetanide thioaidehyde"
R₁ = ———, R₂ = H,
R₃ = O-aryl, R₄ = R₅ = H furosemideaidehyde "furosemide thioaidehyde"
R₁ = ———, R₂ = H,
R₃ = halide, R₄ = R₅ = H

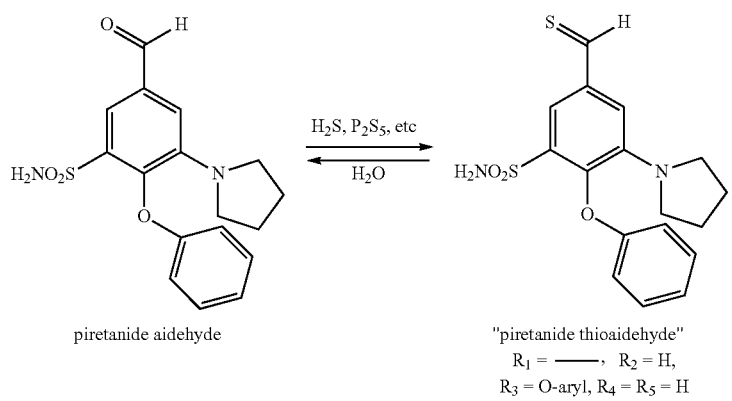

piretanide aldehyde    "piretanide thioaldehyde"
$R_1 = \text{———}$, $R_2 = H$,
$R_3 = O\text{-aryl}$, $R_4 = R_5 = H$ G. PEG-Type Analogs of Bumetanide, Piretanide and Furosemide and Their Thioacid Counterparts Thiobumetanide, Thiopiretanide, Thiofurosemide Dithiobumetanide, Dithiopiretanide and Dithiofurosemide The PEG-type esters of bumetanide, furosemide, and piretanide may be formed by alkylation using alkyloxy(polyalkyloxy)alkyl halides such as MeO-PEG350-Cl and the like or alkyloxy(polyalkyloxy)alkyl tosylates such as MeO-PEG1000-OTs and the like. (See Scheme 32).

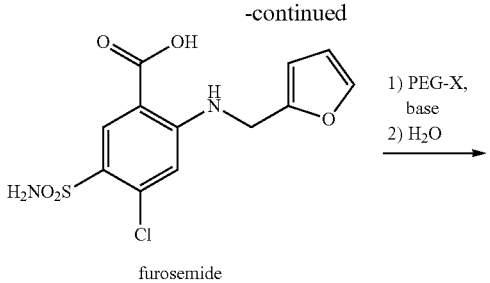

furosemide

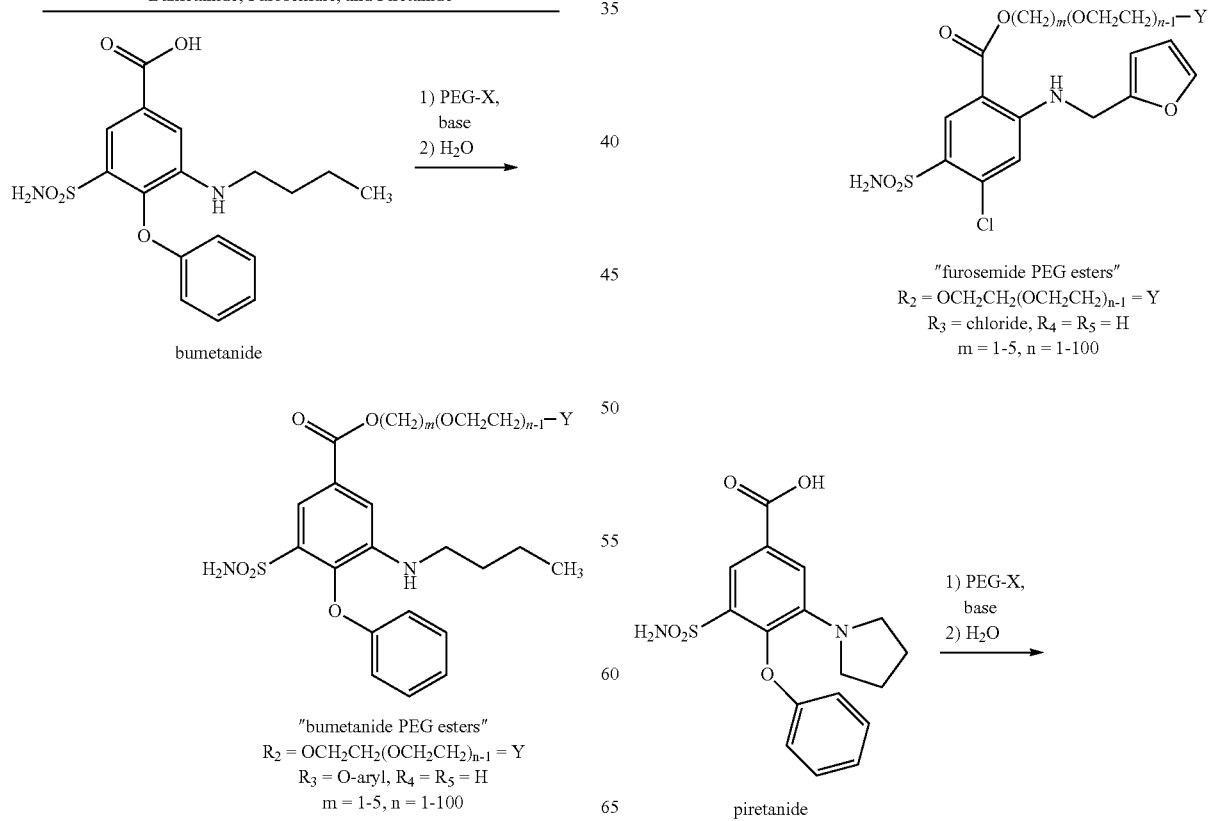

Scheme 32. Synthesis of Ememplary Polyethylene Glycol Esters of Bumetanide, Furosemdie, and Piretanide bumetanide "bumetanide PEG esters"
$R_2 = OCH_2CH_2(OCH_2CH_2)_{n-1} = Y$
$R_3 = O\text{-aryl}$, $R_4 = R_5 = H$
$m = 1\text{-}5$, $n = 1\text{-}100$ "furosemide PEG esters"
$R_2 = OCH_2CH_2(OCH_2CH_2)_{n-1} = Y$
$R_3 = $ chloride, $R_4 = R_5 = H$
$m = 1\text{-}5$, $n = 1\text{-}100$ piretanide -continued

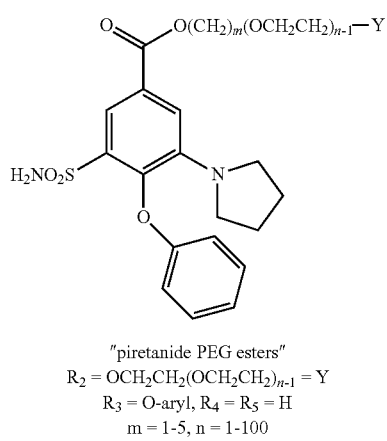

"piretanide PEG esters"
R₂ = OCH₂CH₂(OCH₂CH₂)$_{n-1}$ = Y
R₃ = O-aryl, R₄ = R₅ = H
m = 1-5, n = 1-100

PEG-X is X—(CH₂)$_m$(OCH₂CH₃)$_{n-1}$—Y, where X is halo or other leaving group (mesylate "OMs", tosylate "OTs") and Y is OH or an alcohol protectiong group such as an alkyl group, an aryl group, an aryl group or an ester group, and where m = 1-5 and n = 1-100.

The PEG-type esters of thiobumetanide, thiofurosemide, and thiopiretanide may be formed by alkylation using alkyloxy(polyalkyloxy)alkyl halides such as MeO-PEG350-Cl and the like or alkyloxy(polyalkyloxy)alkyl tosylates such as MeO-PEG1000-OTs and the like. (See Scheme 33)

Scheme 33. Synthesis of Ememplary Polyethylene Glycol Thioesters of Thiobumetanide, Thiofurosemdie, and Thipiretanide

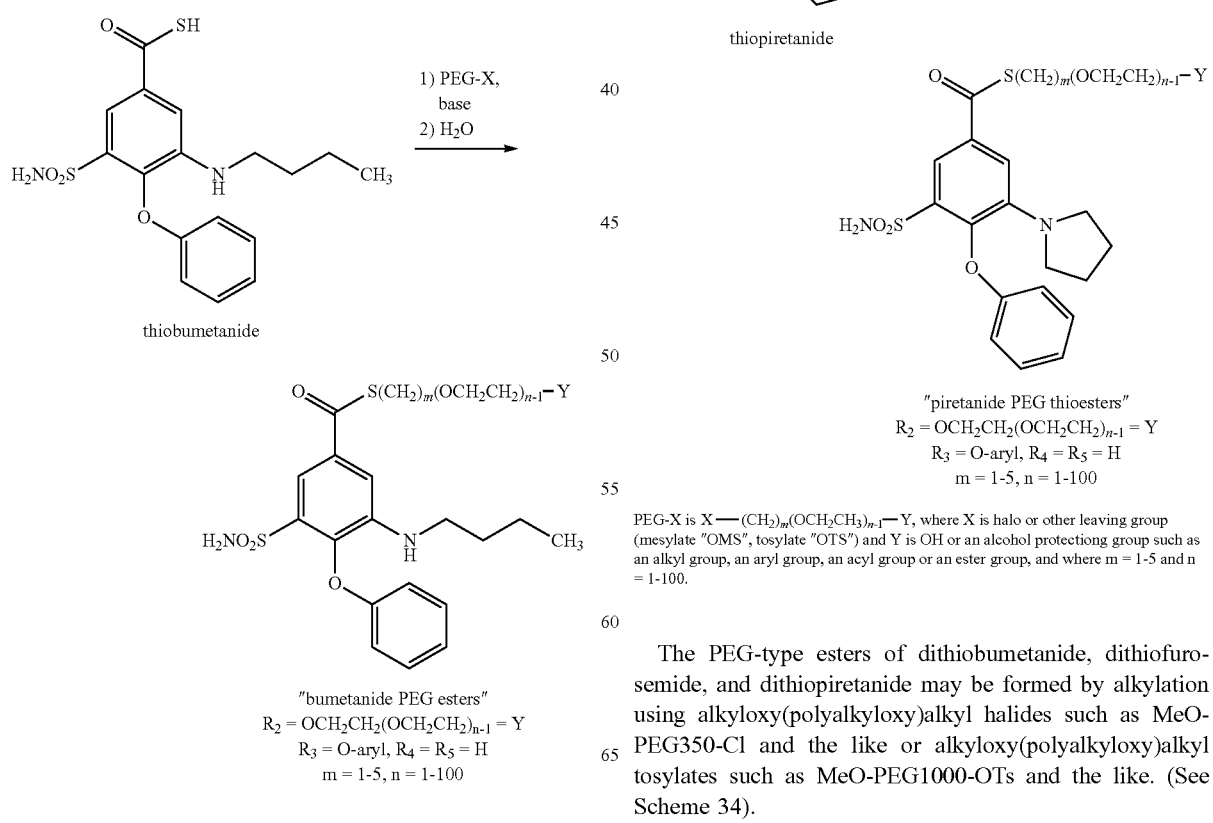

-continued

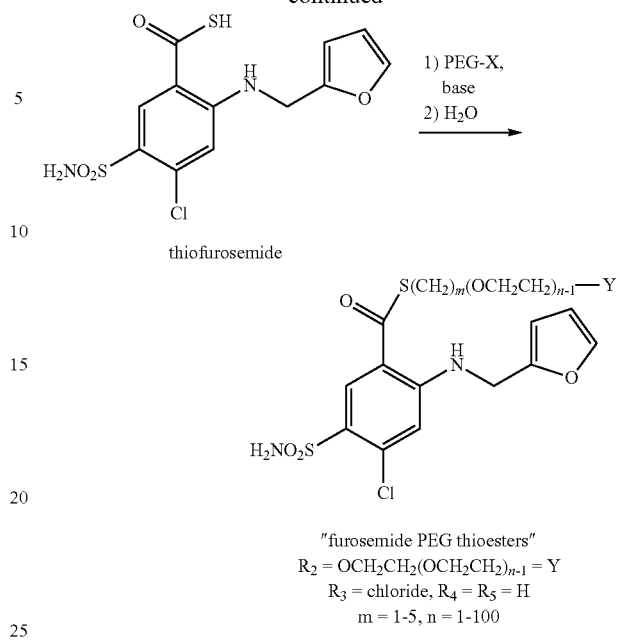

"furosemide PEG thioesters"
R₂ = OCH₂CH₂(OCH₂CH₂)$_{n-1}$ = Y
R₃ = chloride, R₄ = R₅ = H
m = 1-5, n = 1-100

"piretanide PEG thioesters"
R₂ = OCH₂CH₂(OCH₂CH₂)$_{n-1}$ = Y
R₃ = O-aryl, R₄ = R₅ = H
m = 1-5, n = 1-100

PEG-X is X—(CH₂)$_m$(OCH₂CH₃)$_{n-1}$—Y, where X is halo or other leaving group (mesylate "OMS", tosylate "OTS") and Y is OH or an alcohol protectiong group such as an alkyl group, an aryl group, an acyl group or an ester group, and where m = 1-5 and n = 1-100.

The PEG-type esters of dithiobumetanide, dithiofurosemide, and dithiopiretanide may be formed by alkylation using alkyloxy(polyalkyloxy)alkyl halides such as MeO-PEG350-Cl and the like or alkyloxy(polyalkyloxy)alkyl tosylates such as MeO-PEG1000-OTs and the like. (See Scheme 34).

Scheme 33. Synthesis of Ememplary Polyethylene Glycol Dithioesters of Dithiobumetanide, Dithiofurosemdie, and Dithipiretanide

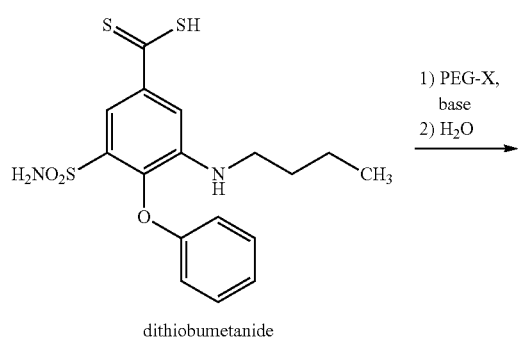

dithiobumetanide

1) PEG-X, base
2) H₂O

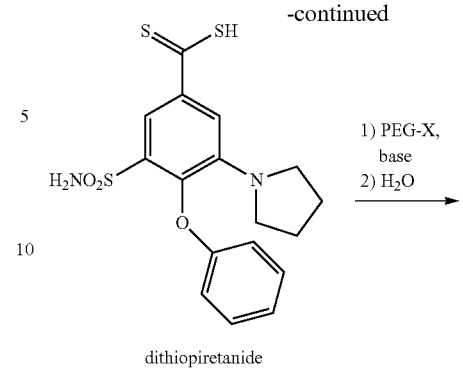

dithiopiretanide

1) PEG-X, base
2) H₂O

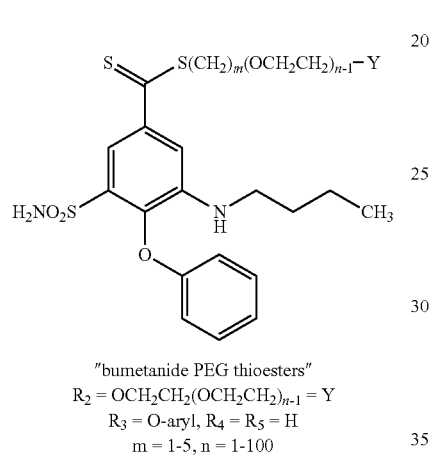

"bumetanide PEG thioesters"
$R_2 = OCH_2CH_2(OCH_2CH_2)_{n-1} = Y$
$R_3$ = O-aryl, $R_4 = R_5$ = H
m = 1-5, n = 1-100

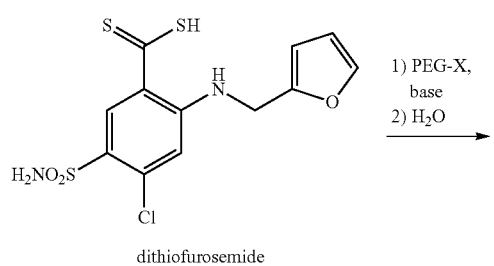

dithiofurosemide

1) PEG-X, base
2) H₂O

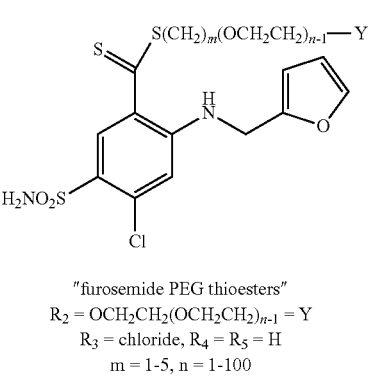

"furosemide PEG thioesters"
$R_2 = OCH_2CH_2(OCH_2CH_2)_{n-1} = Y$
$R_3$ = chloride, $R_4 = R_5$ = H
m = 1-5, n = 1-100

-continued

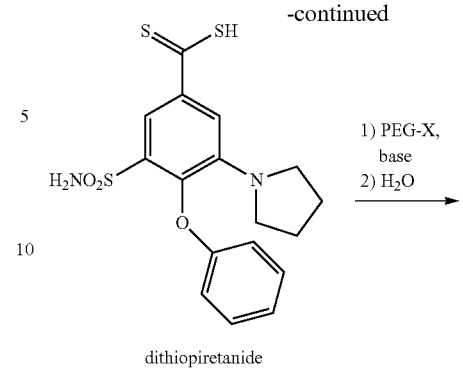

"piretanide PEG thioesters"
$R_2 = OCH_2CH_2(OCH_2CH_2)_{n-1} = Y$
$R_3$ = O-aryl, $R_4 = R_5$ = H
m = 1-5, n = 1-100

PEG-X is X—$(CH_2)_m(OCH_2CH_3)_{n-1}$—Y, where X is halo or other leaving group (mesylate "OMS", tosylate "OTS") and Y is OH or an alcohol protectiong group such as an alkyl group, an aryl group, an acyl group or an ester group, and where m = 1-5 and n = 1-100.

H. PEG-Type Analogs of Azosemide and Torsemide

The PEG-type ethers of azosemide and torsemide may be formed by alkylation using alkyloxy(polyalkyloxy)alkyl halides such as MeO-PEG350-Cl and the like or alkyloxy (polyalkyloxy)alkyl tosylates such as MeO-PEG1000-OTs and the like. (See Scheme 35).

Scheme 35. Synthesis of Exemplary Alkylene Polyethylene Glycol Ethers of Azosemide and Torsemide

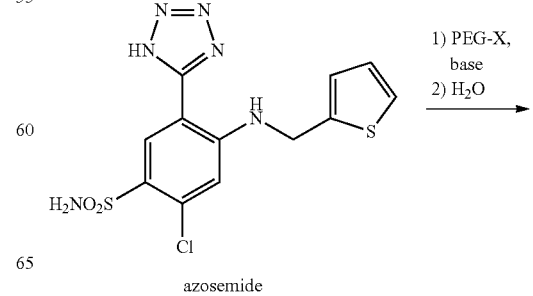

azosemide

1) PEG-X, base
2) H₂O

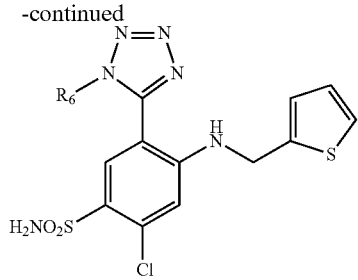

"azosemide PEG ethers"
$R_6 = (CH_2)_mOCH_2CH_2(OCH_2CH_2)_{n-1}-Y$
$R_3$ = chloride, $R_4 = R_5 = H$
m = 1-5, n = 1-100

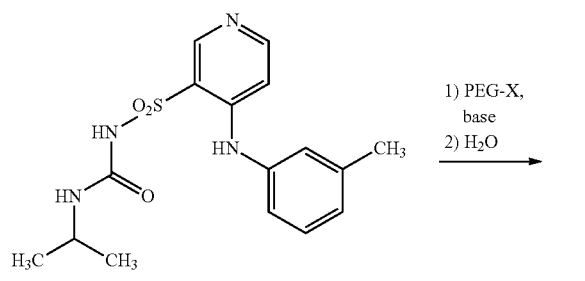

torsemide

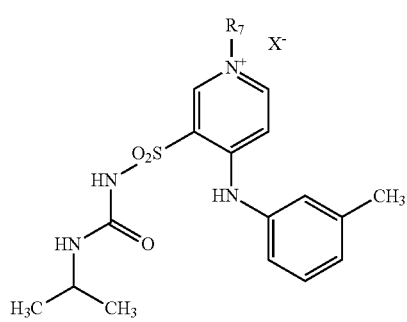

"torsemide PEG ether quaternary ammonium salts"
$R_7 = (CH_2)_mOCH_2CH_2(OCH_2CH_2)_{n-1}-Y$
$X^-$ = halide, mesylate, tosylate
m = 1-5, n = 1-100

PEG-X is $X-(CH_2)_m(OCH_2CH_2)_{n-1}-Y$, where X is halo or other leaving group (mesylate "OMS", tosylate "OTS") and Y is OH or an alcohol protectiong group such as an alkyl group, an aryl group, an acyl group or an ester group, and where m = 1-5 and n = 1-100.

I. Additional Bumetanide Analogs

Additional bumetanide analogs can be synthesized according to the syntheses shown below in Schemes 36-66. In the case of an N-substituted sulfonamide having one $R_{31}$ group, $R_{31}$ is lower alkyl, lower alkenyl, alkaryl, aryl, heterocycloalkyl, or heteroaryl. In the case of a disubstituted sulfonamide having two $R_{31}$ groups, each $R_{31}$ group is the same or different and are independently lower alkyl, lower alkenyl, alkaryl, aryl, heterocycloalkyl, heteroaryl or taken together with the nitrogen atom to which they attached form a 4-8 member cycle which can be substituted or unsubstituted and can have one or more heteroatoms (e.g., N, O or S).

Scheme 36. Synthesis of Exemplary 4-Anilino Analogs of Bumetanide

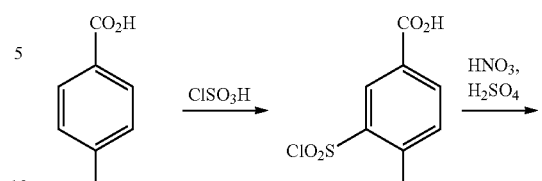

1 p-chlorobenzoic acid, 99% Aldrich 135585-1 KG, 1 kg/$135.00

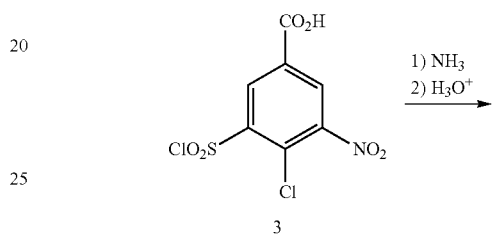

3

4 4-chloro-3-nitro-5-sulfonamido-benzoic acid, Longyou Northen, China, 25 kg drums 5 aniline >99%, Aldrich 132934-2 KG 2.0 kg/$66.50

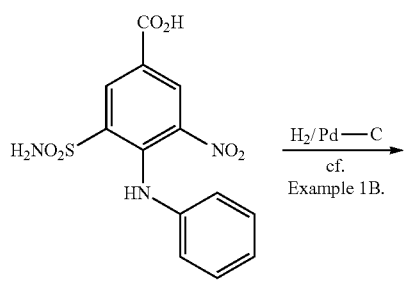

6

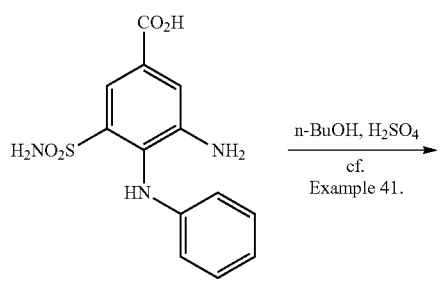

7

-continued

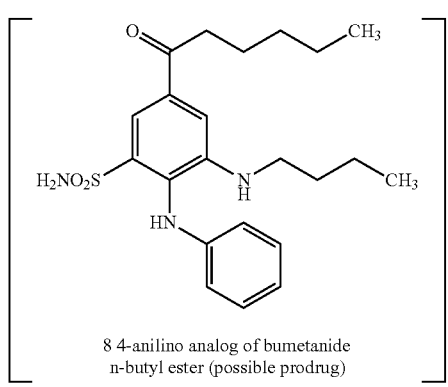

8 4-anilino analog of bumetanide
n-butyl ester (possible prodrug)

1) NaOH
2) $H_3O^+$
cf.
Example
9 & 41.

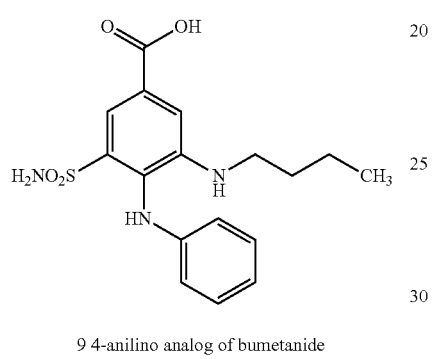

9 4-anilino analog of bumetanide cf. Feit, P. W., Loevene Kemiske Fabr./Leo Pharmaceuticals, U.S. Pat. No. 3,806,534 (Apr. 23, 1974).

Scheme 37. Synthesis of Exemplary 4-Thiophenyl Analogs of Bumetanide

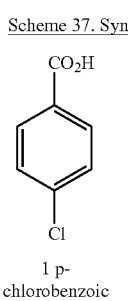

1 p-chlorobenzoic acid,
99% Aldrich
135585-1 KG,
1 kg/$135.00

ClSO$_3$H

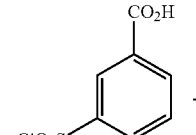

2

HNO$_3$,
H$_2$SO$_4$

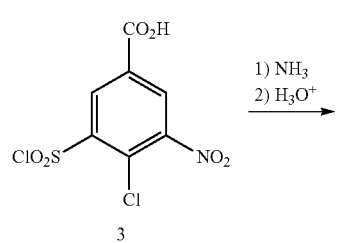

3

1) NH$_3$
2) H$_3$O$^+$

-continued

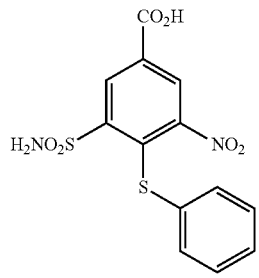

4 4-chloro-3-nitro-5-sulfonamido-benzoic acid, Longyou Northen, China, 25 kg drums

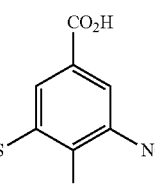

5 thiophenol
>99%, Aldrich
T32808- 1KG
1.0 kg/$93.20

NaHCO$_3$
cf.
Example 1A.

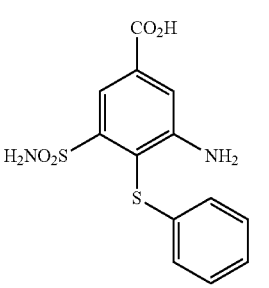

6

H$_2$/Pd—C
cf.
Example 1B.

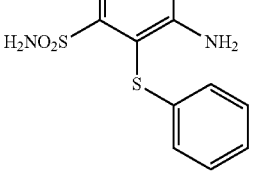

7 n-BuOH, H$_2$SO$_4$
cf.
Example 41.

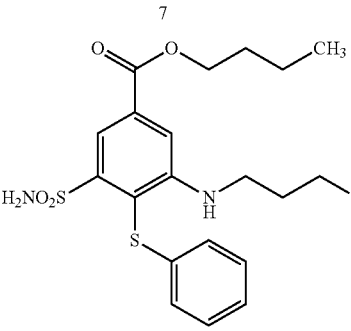

8 4-thiophenyl analog of bumetanide
n-butyl ester (possible prodrug)

1) NaOH
2) H$_3$O$^+$
cf.
Example
41 & 50.

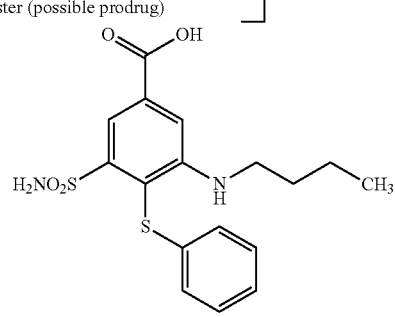

9 4-thiophenyl analog of bumetanide cf. Feit, P. W., Loevene Kemiske Fabr./Leo Pharmaceuticals, U.S. Pat. No. 3,806,534 (Apr. 23, 1974).

Scheme 38. Synthesis of Bumetanide
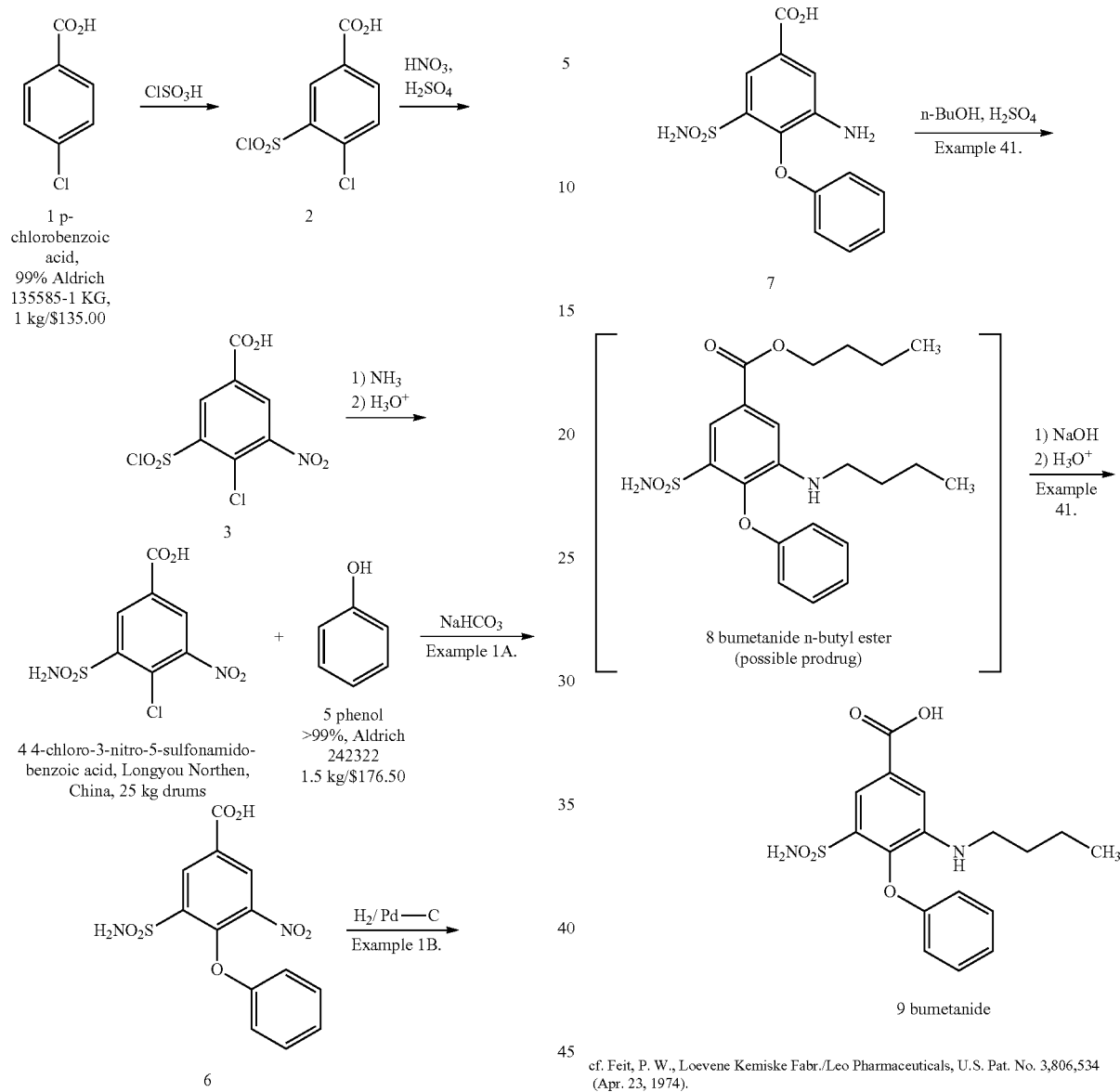
cf. Feit, P. W., Loevene Kemiske Fabr./Leo Pharmaceuticals, U.S. Pat. No. 3,806,534 (Apr. 23, 1974).
Scheme 39. Synthesis of N-substituted Bumetanide
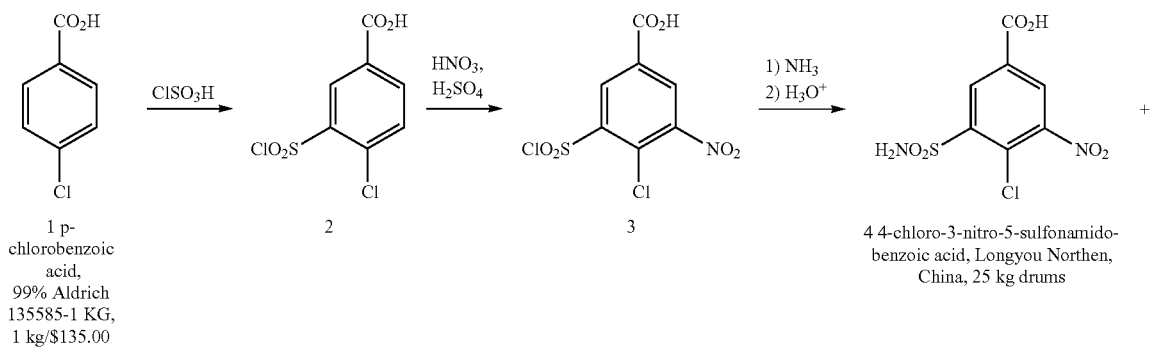

-continued
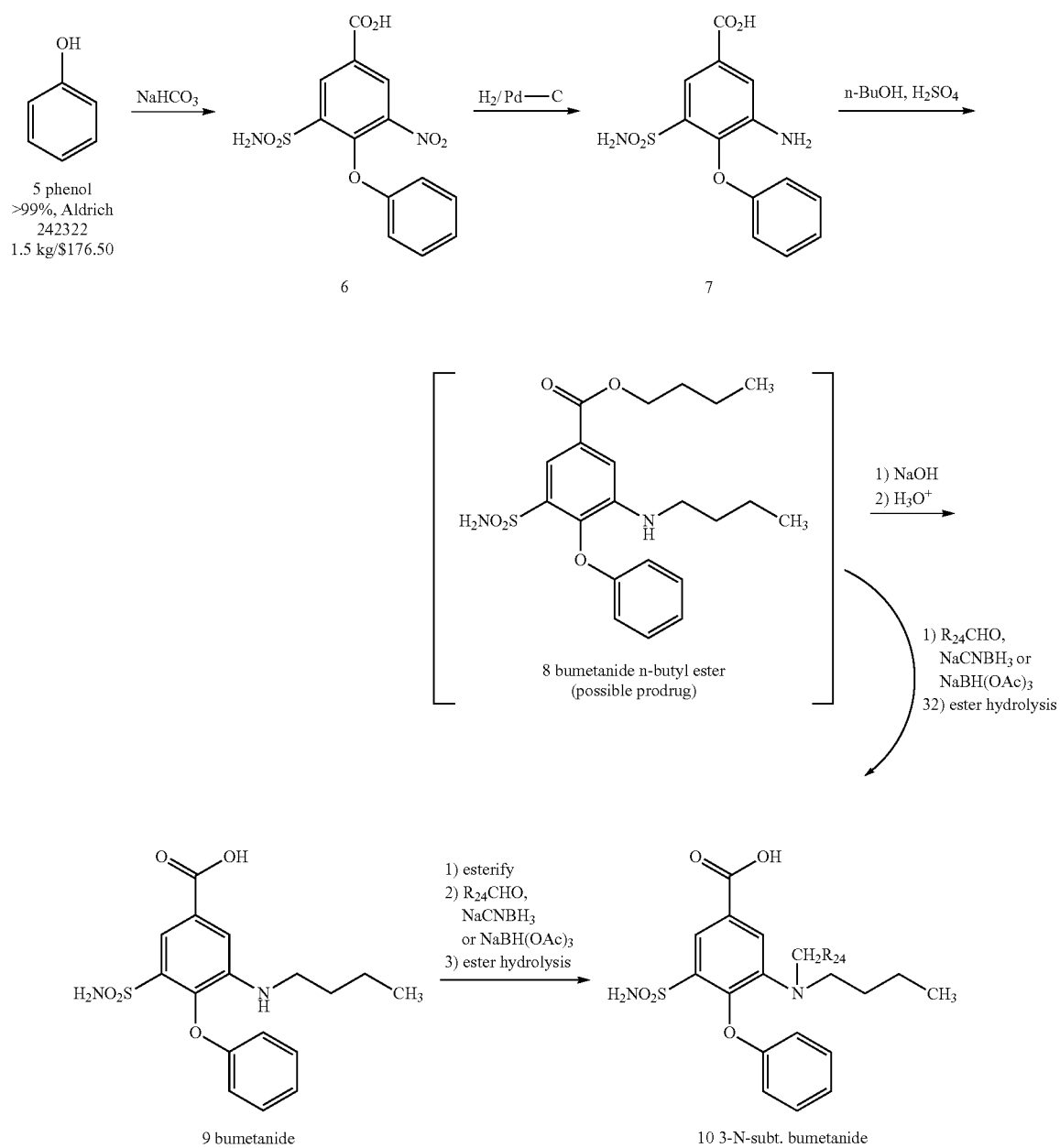
Scheme 40. Synthesis of 4-Anilino-N-substituted Bumetanide
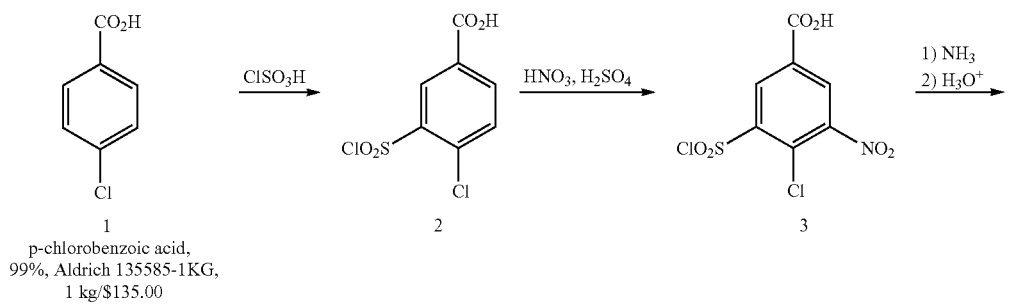

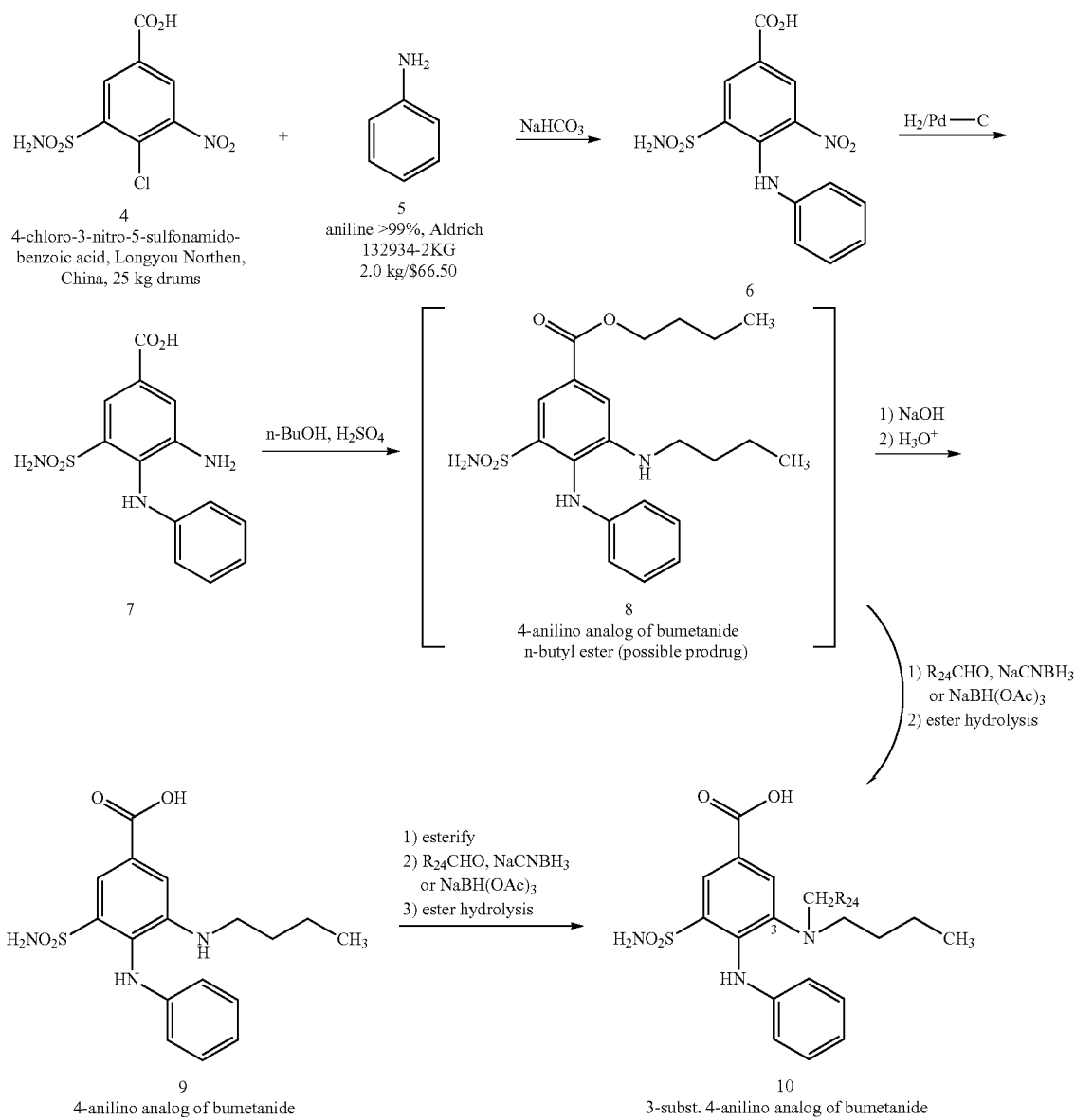
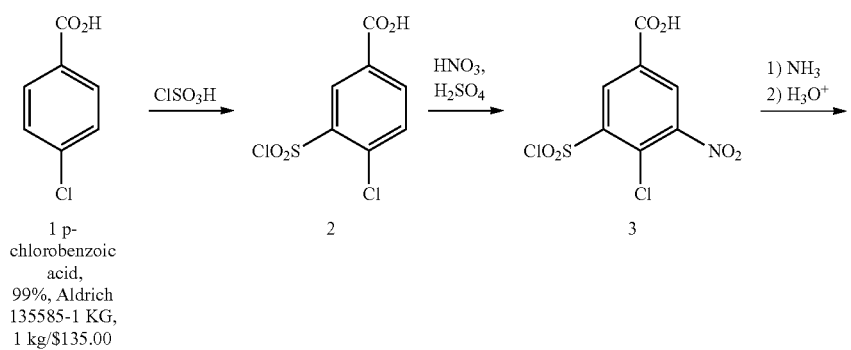
Scheme 41. Synthesis of 4-chloro-N-substituted Bumetanide

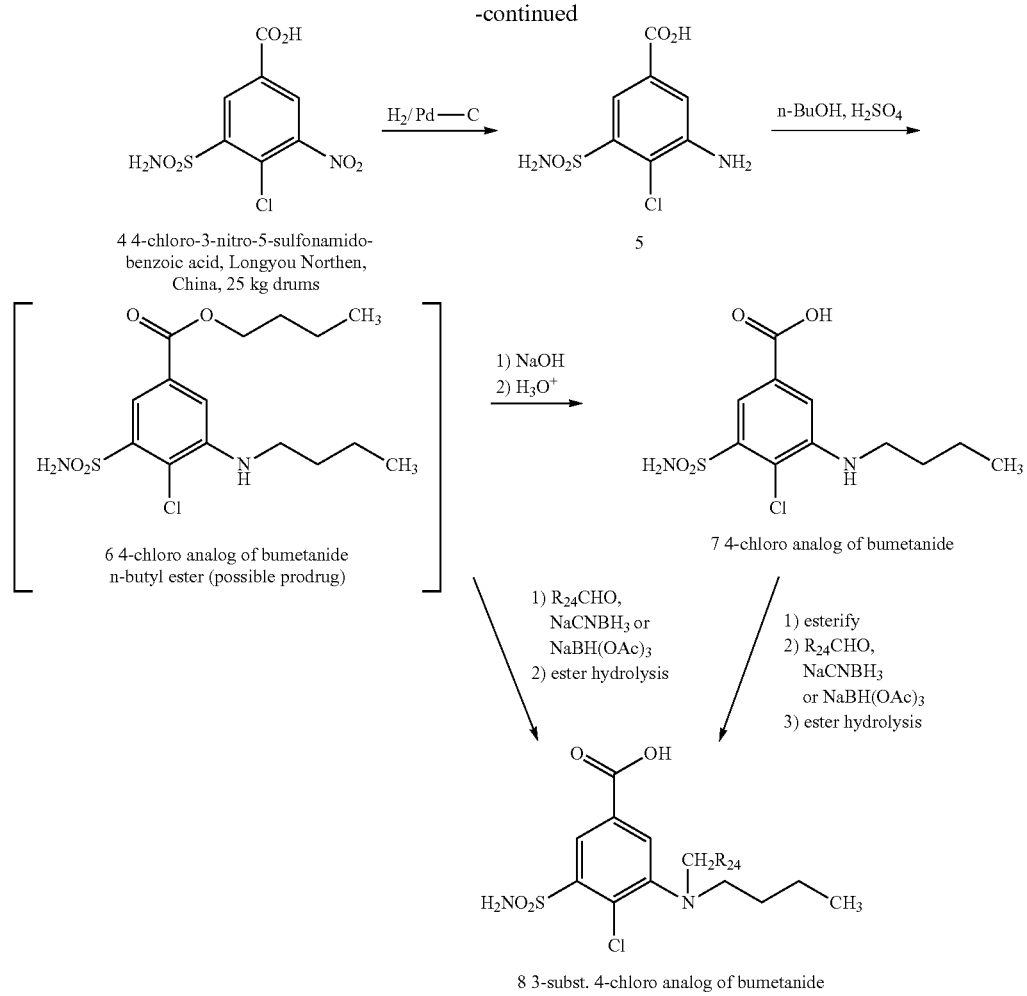
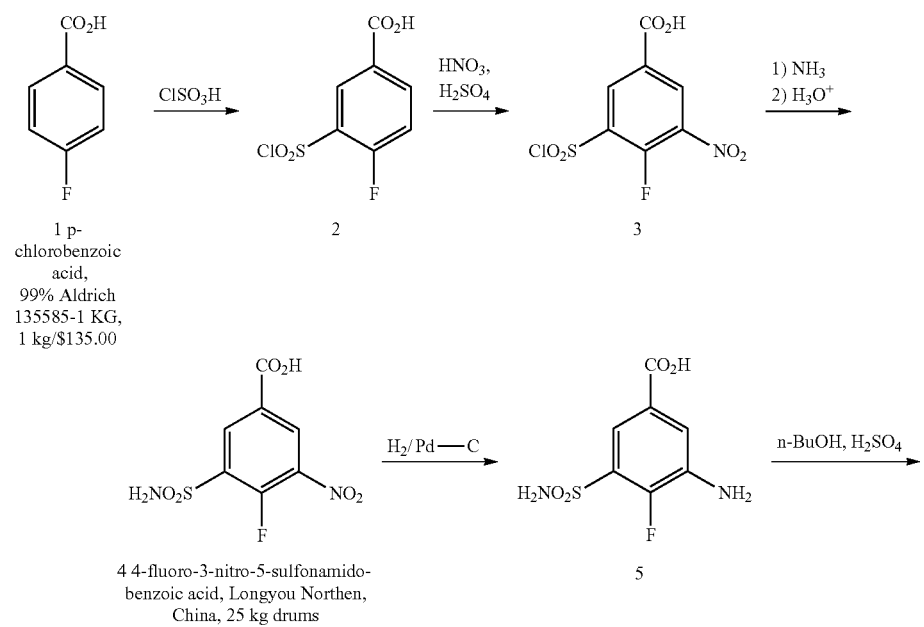
Scheme 41. Synthesis of 4-fluoro-N-substituted Bumetanide

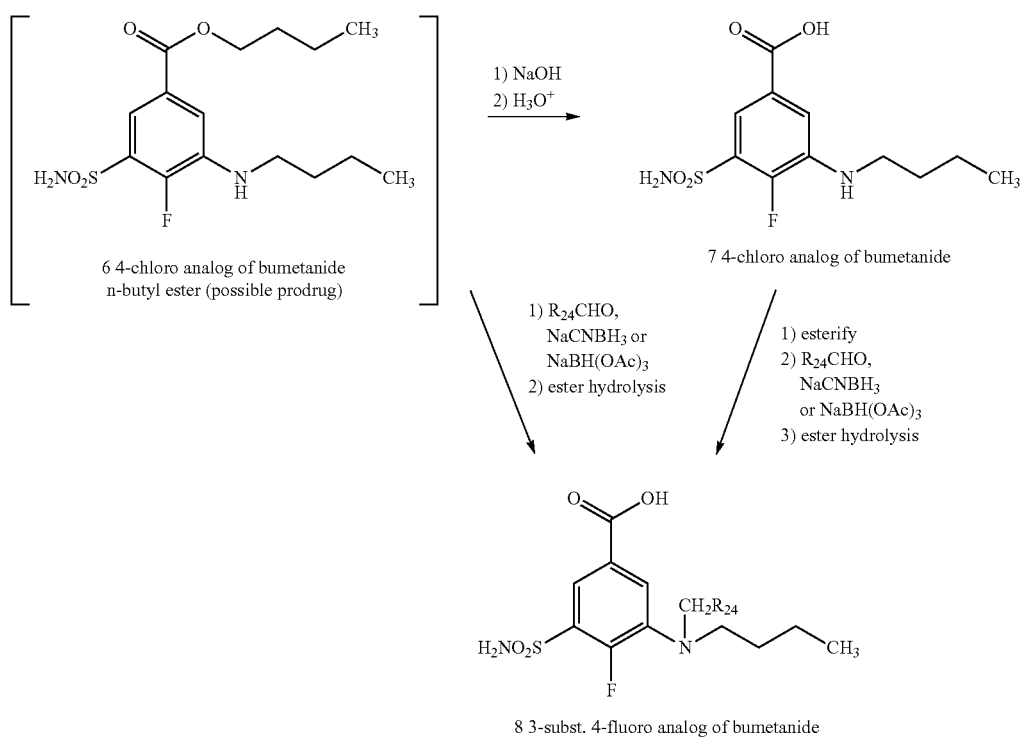
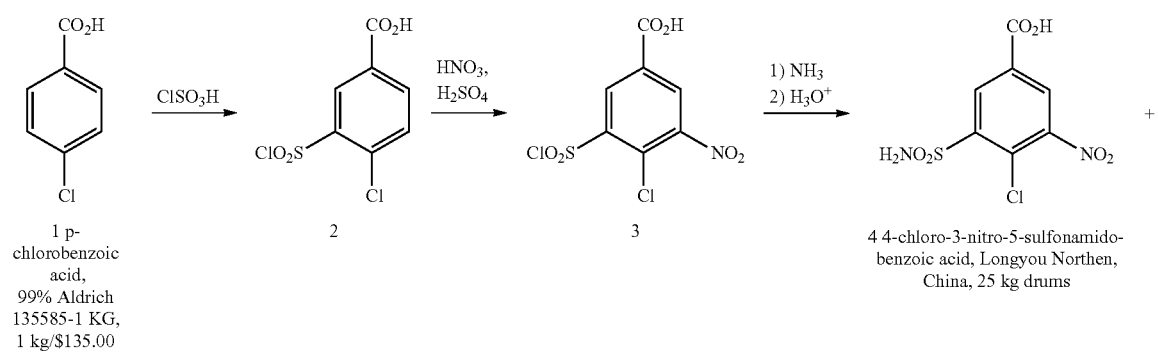
Scheme 43. Synthesis of 3-aryl Bumetanide and 3-aryl-N-substituted Bumetanide
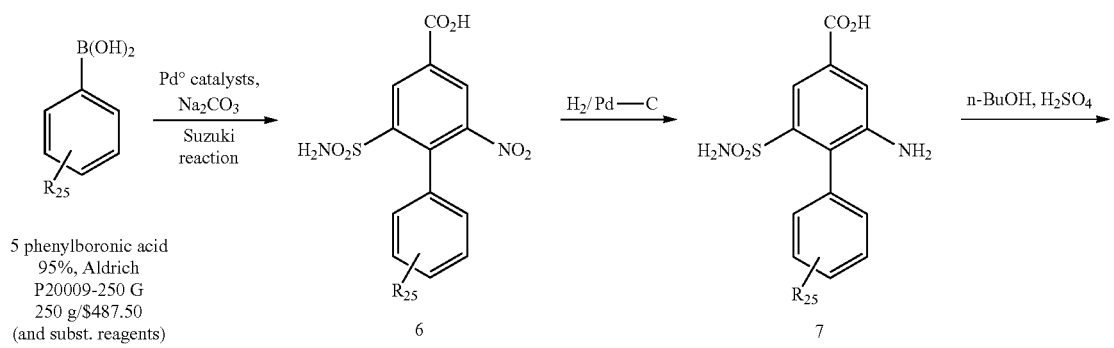

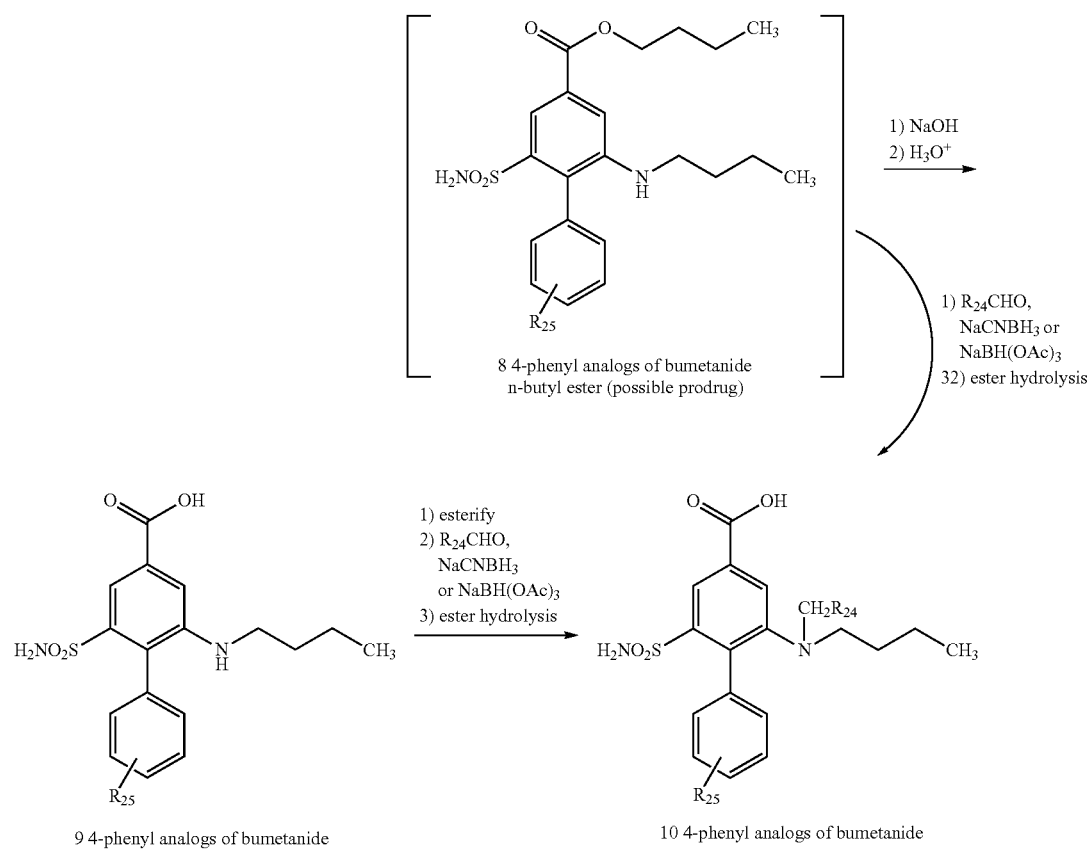
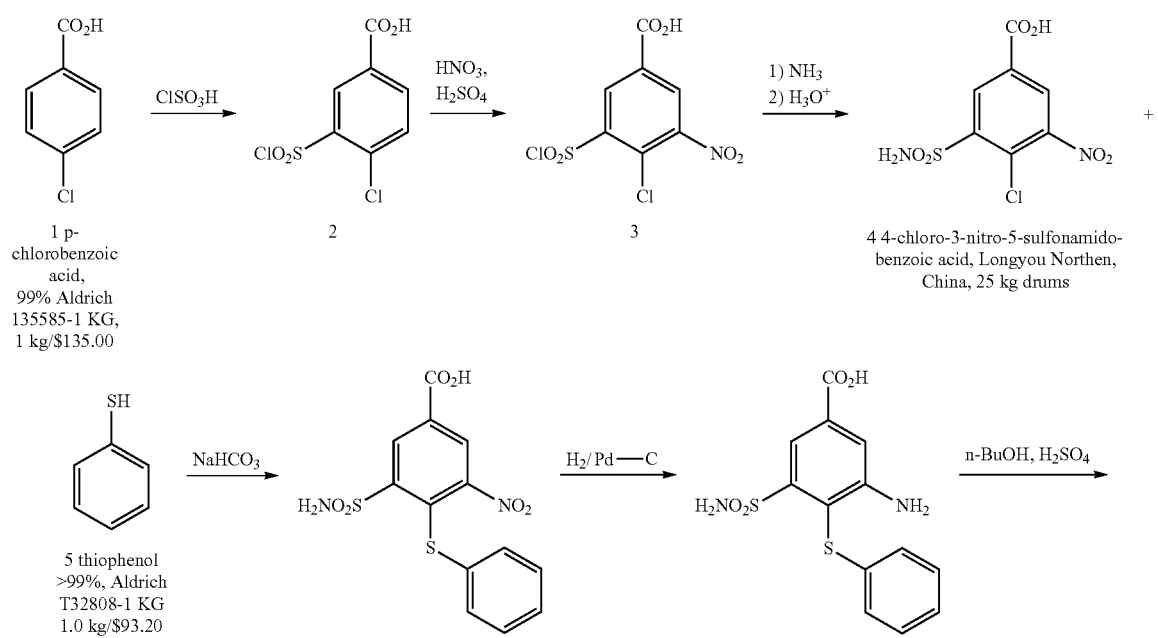
Scheme 44. Synthesis of 3-thioaryl-N-substituted Bumetanide

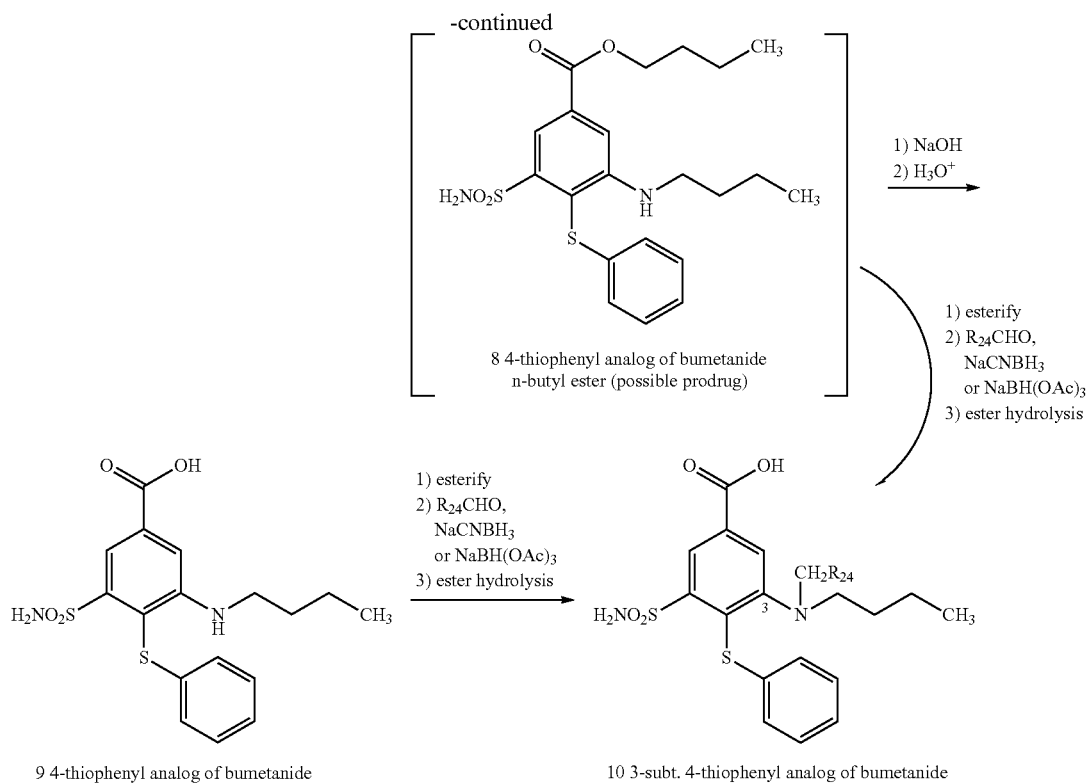
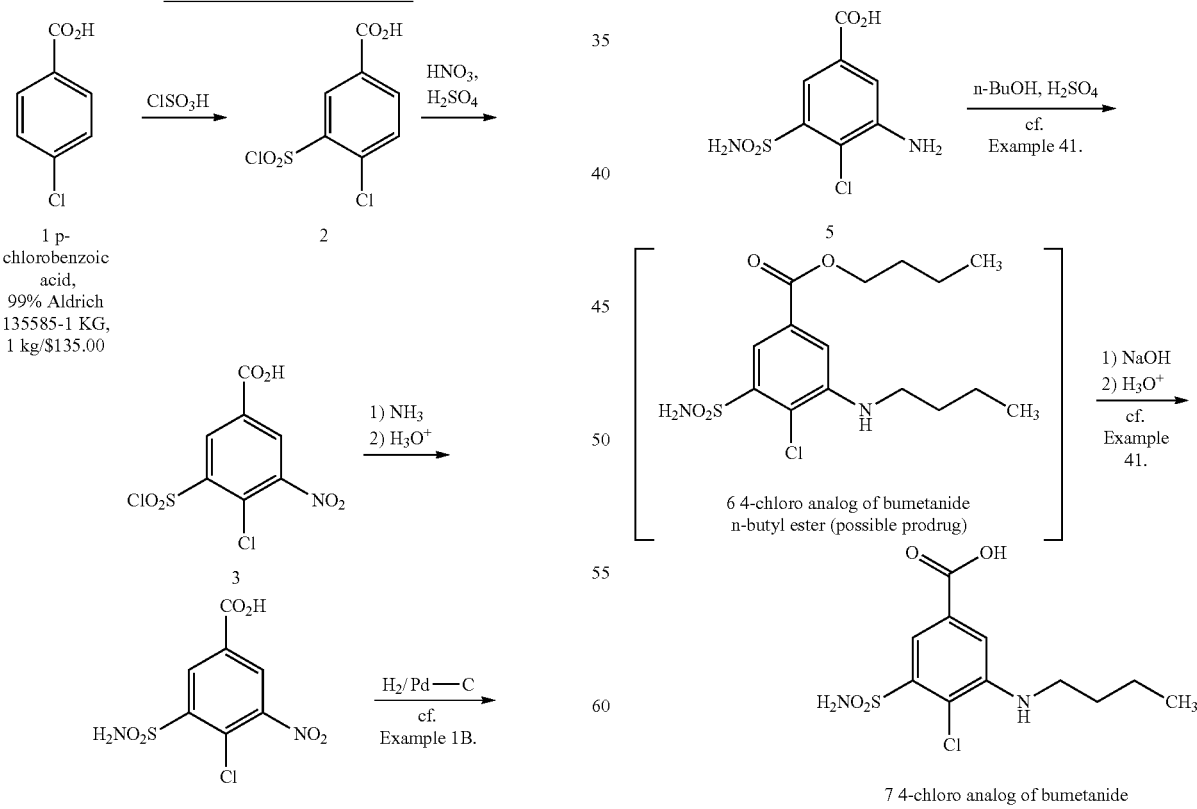
Scheme 45. 4-chloro Bumetanide
cf. Feit, P. W., Loevene Kemiske Fabr./Leo Pharmaceuticals, U.S. Pat. No. 3,806,534 (Apr. 23, 1974).

Scheme 46. 4-fluoro Bumetanide

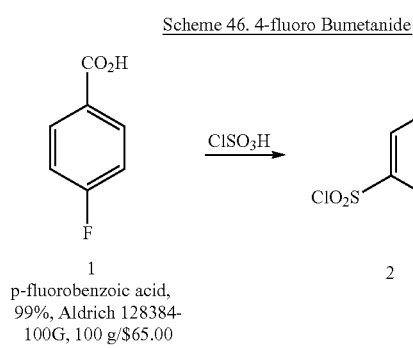

1
p-fluorobenzoic acid,
99%, Aldrich 128384-
100G, 100 g/$65.00

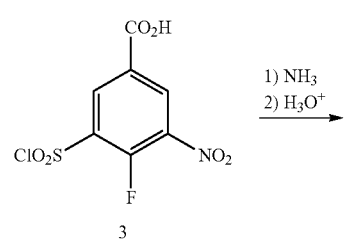

3

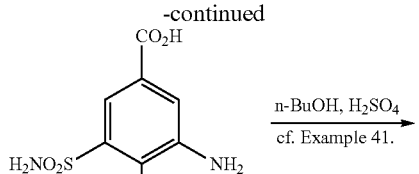

5

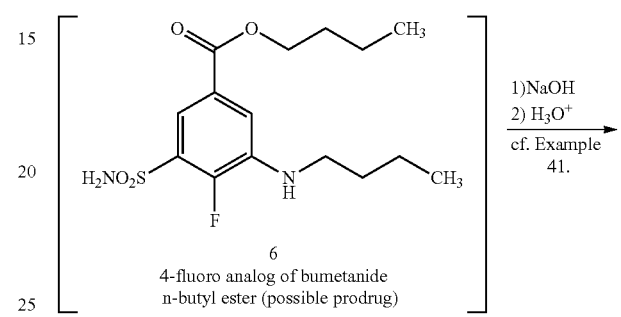

6
4-fluoro analog of bumetanide
n-butyl ester (possible prodrug)

4
4-fluoro-3-nitro-5-sulfonamido-
benzoic acid 7
4-fluoro analog bumetanide cf. Feit, P. W., Loevens Kemiske Fabr./Leo Pharmaceuticals,
U.S. Pat. No. 3,806,534 (Apr. 23, 1974).

Scheme 47 and 48. Bumetanide Esters, Amides, Sulfonamides, Aldehydes, and Nitriles

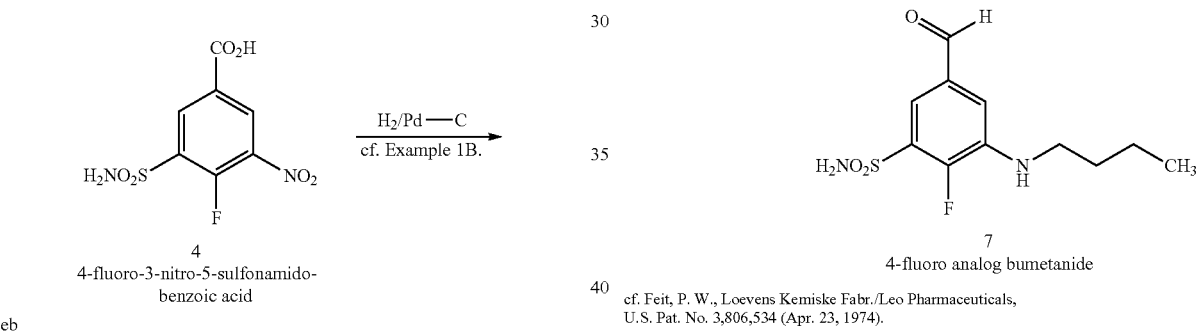

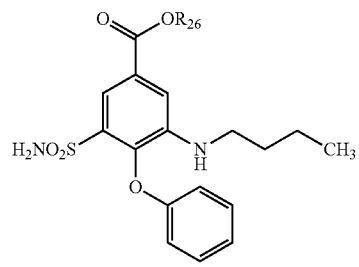

bumetanide esters
$R_{26}$ = lower alkyl, lower alkenyl,
alkaryl, aryl, heterocyclic, heteroaryl

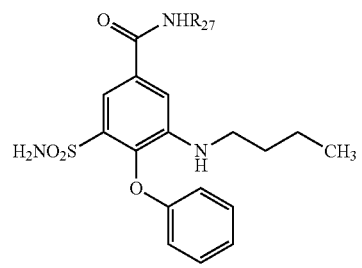

bumetanide
monosubstituted amides
$R_{27}$ = lower alkyl, lower alkenyl,
alkaryl, aryl, heterocyclic, heteroaryl

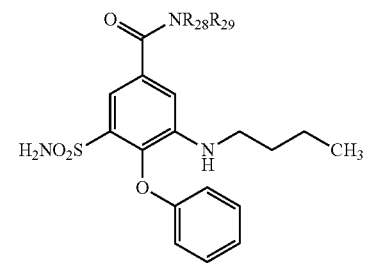

bumetanide
disubstituted amides
$R_{28}$ and $R_{29}$ = lower alkyl, lower alkenyl,
alkaryl, aryl, heterocyclic, heteroaryl and
taken together in 4-8 member cycic versions
(subst/unsubst. with N, O, S)

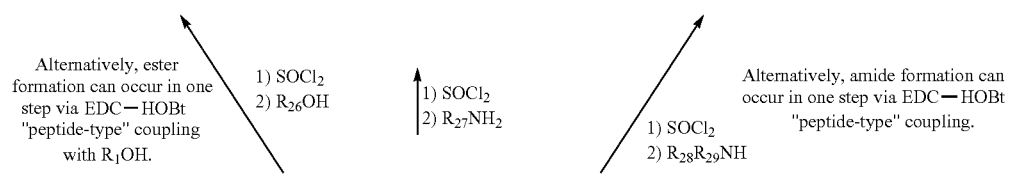

Alternatively, ester formation can occur in one step via EDC—HOBt "peptide-type" coupling with R₁OH.

1) SOCl₂
2) R₂₆OH

1) SOCl₂
2) R₂₇NH₂

1) SOCl₂
2) R₂₈R₂₉NH

Alternatively, amide formation can occur in one step via EDC—HOBt "peptide-type" coupling.

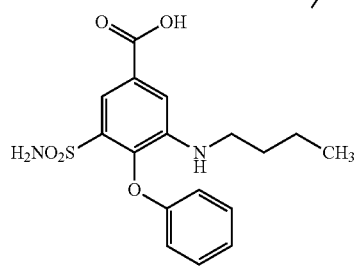
bumetanide 1) base + 2 equiv. R₃₁X; or 2 equiv. diazoalkane
2) acid- or base-cat. ester hydroylsis 1) base + 3 equiv. R₃₁X; or 3 equiv. diazoalkane
2) acid- or base-cat. ester hydroylsis 1) acid chloride reduction → R₃₀ = CHO, or
2) acid chloride + ammonia → R₃₀ = CONH₂ or
3) R₃₀ = CONH₂ amide + POCl₃ → R₃₀ = CN

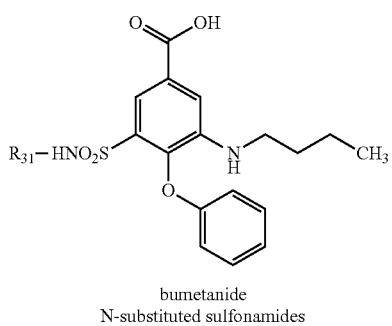

bumetanide
N-substituted sulfonamides

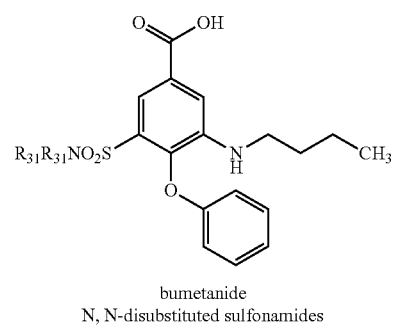

bumetanide
N, N-disubstituted sulfonamides

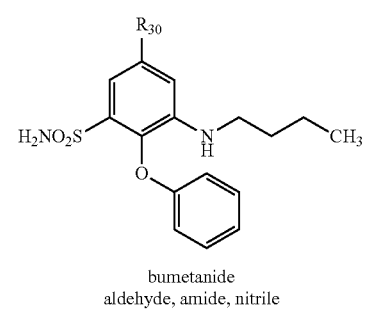

bumetanide
aldehyde, amide, nitrile

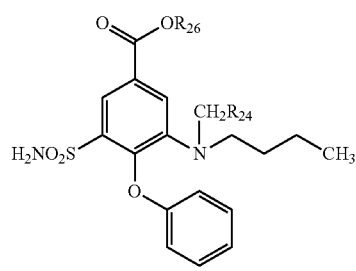

3-N-subst. bumetanide esters
R₂₆ = lower alkyl, lower alkenyl, alkaryl, aryl, heterocyclic, heteroaryl

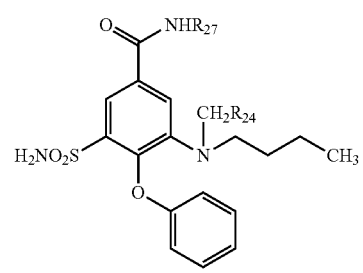

3-N-subst. bumetanide monosubstituted amides
R₂₇ = lower alkyl, lower alkenyl, alkaryl, aryl, heterocyclic, heteroaryl

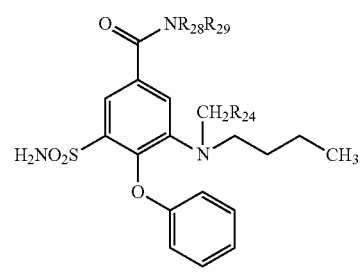

3-N-subst. bumetanide disubstituted amides
R₂₈ and R₂₉ = lower alkyl, lower alkenyl, alkaryl, aryl, heterocyclic, heteroaryl and taken together in 4-8 member cycic versions (subst/unsubst. with N, O, S)

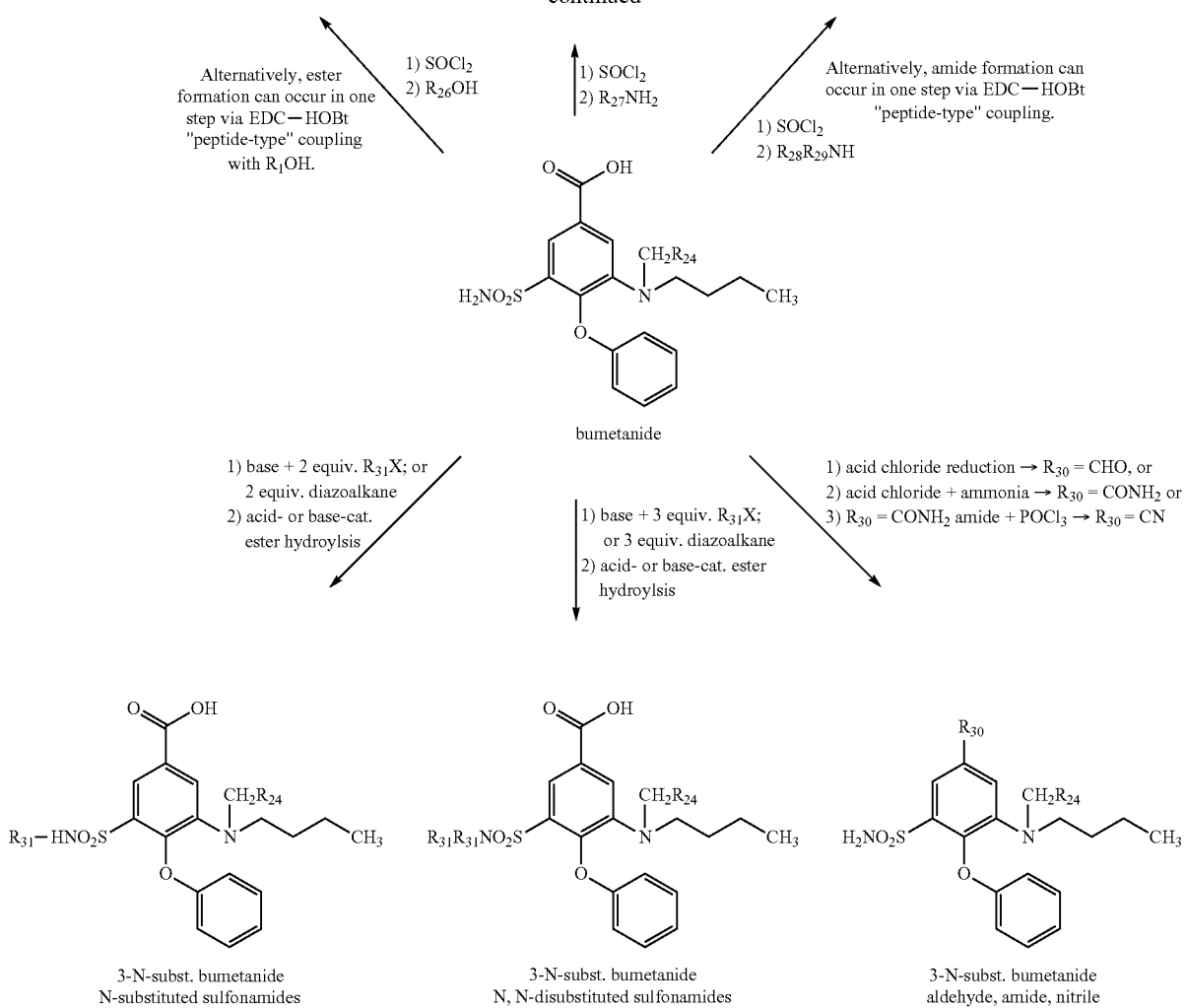
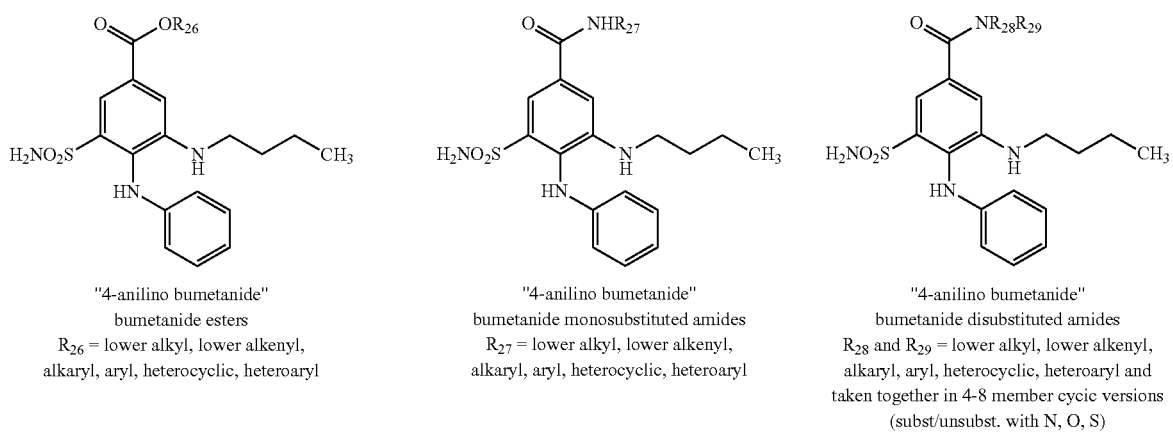
Scheme 49 and 50. 4-anilino Bumetanide Esters, Amides, Sulfonamides, Aldehydes, and Nitriles -continued

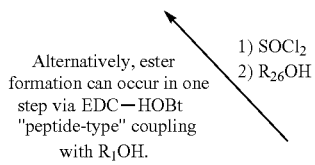
Alternatively, ester formation can occur in one step via EDC—HOBt "peptide-type" coupling with R₁OH.

1) SOCl₂
2) R₂₆OH

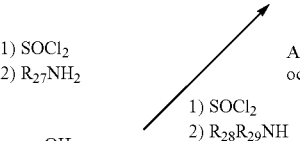
1) SOCl₂
2) R₂₇NH₂

1) SOCl₂
2) R₂₈R₂₉NH

Alternatively, amide formation can occur in one step via EDC—HOBt "peptide-type" coupling.

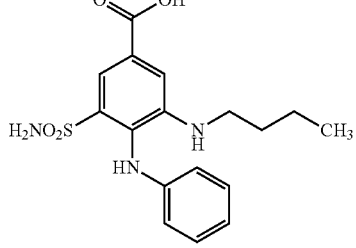
"4-anilino bumetanide"

1) base + 2 equiv. R₃₁X; or 2 equiv. diazoalkane
2) acid- or base-cat. ester hydroylsis 1) base + 3 equiv. R₃₁X; or 3 equiv. diazoalkane
2) acid- or base-cat. ester hydroylsis 1) acid chloride reduction → R₃₀ = CHO, or
2) acid chloride + ammonia → R₃₀ = CONH₂ or
3) R₃₀ = CONH₂ amide + POCl₃ → R₃₀=CN

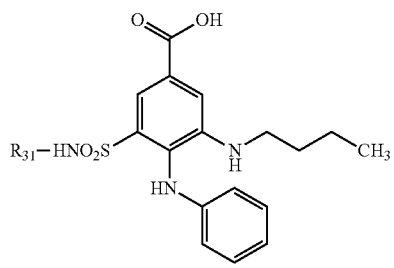

"4-anilino bumetanide"
bumetanide
N-substituted sulfonamides

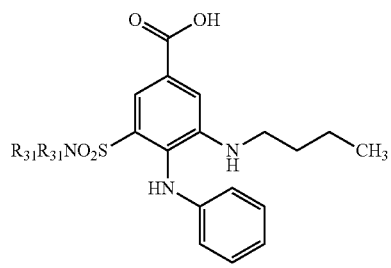

"4-anilino bumetanide"
bumetanide
N,N-disubstituted sulfonamides

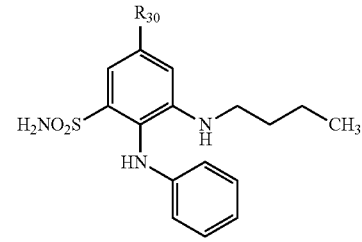

"4-anilino bumetanide"
bumetanide
aldehyde, amide, nitrile

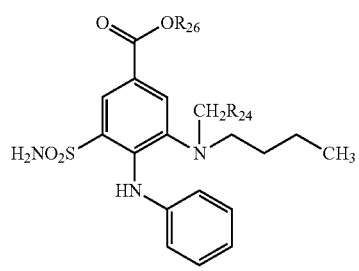

3-N-subst.
"4-anilino bumetanide" bumetanide esters
R₂₆ = lower alkyl, lower alkenyl, alkaryl, aryl, heterocyclic, heteroaryl

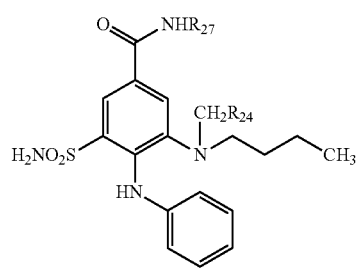

3-N-subst.
"4-anilino bumetanide" bumetanide monosubstituted amides
R₂₇ = lower alkyl, lower alkenyl, alkaryl, aryl, heterocyclic, heteroaryl

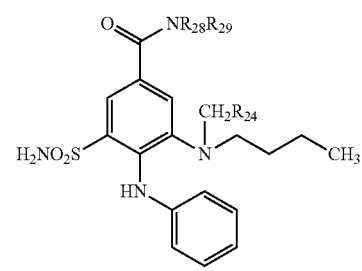

3-N-subst.
"4-anilino bumetanide" bumetanide disubstituted amides
R₂₈ and R₂₉ = lower alkyl, lower alkenyl, alkaryl, aryl, heterocyclic, heteroaryl and taken together in 4-8 member cycic versions (subst/unsubst. with N, O, S)

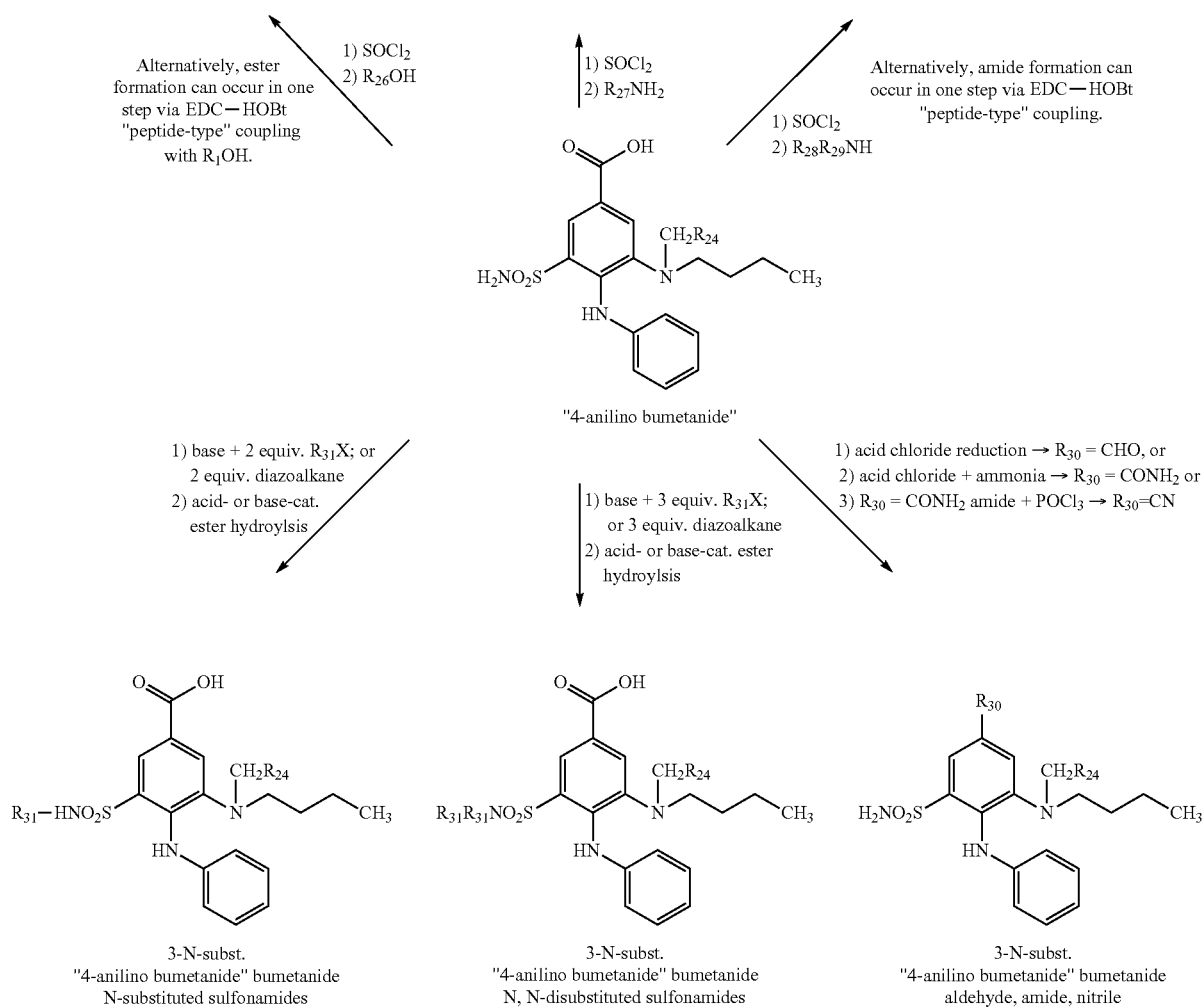
where R$_{24}$ is methyl, ethyl, proply, butyl, pentyl, hexyl, benzyl ...
Scheme 51 and 52. 4-thioaryl Bumetanide Esters, Amides, Sulfonamides, Aldehydes, and Nitriles
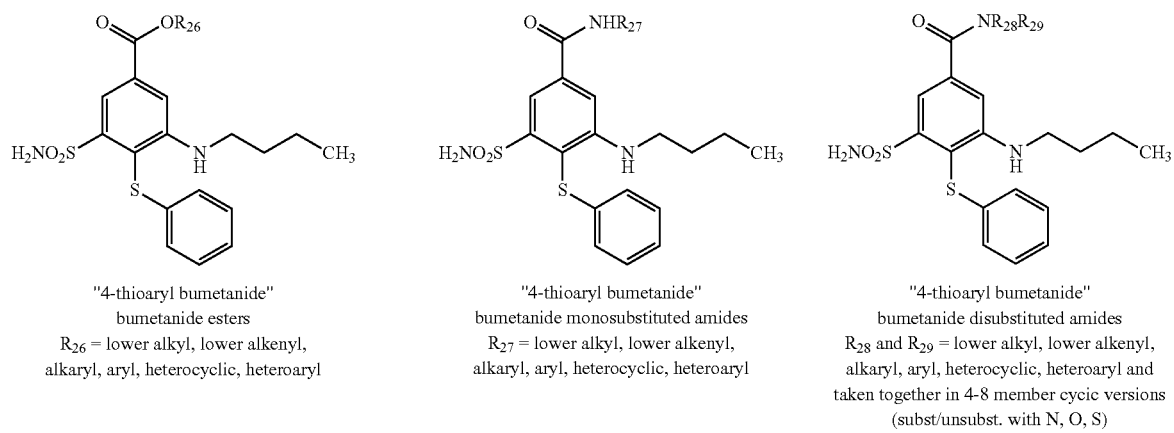

-continued

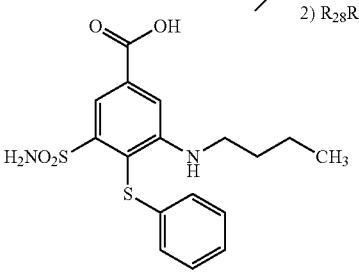

Alternatively, ester formation can occur in one step via EDC—HOBt "peptide-type" coupling with R₁OH.

1) SOCl₂
2) R₂₆OH

1) SOCl₂
2) R₂₇NH₂

1) SOCl₂
2) R₂₈R₂₉NH

Alternatively, amide formation can occur in one step via EDC—HOBt "peptide-type" coupling.

"4-thioaryl bumetanide"

1) base + 2 equiv. R₃₁X; or
2 equiv. diazoalkane
2) acid- or base-cat. ester hydroylsis 1) base + 3 equiv. R₃₁X;
or 3 equiv. diazoalkane
2) acid- or base-cat. ester hydroylsis 1) acid chloride reduction → R₃₀ = CHO, or
2) acid chloride + ammonia → R₃₀ = CONH₂ or
3) R₃₀ = CONH₂ amide + POCl₃ → R₃₀ = CN

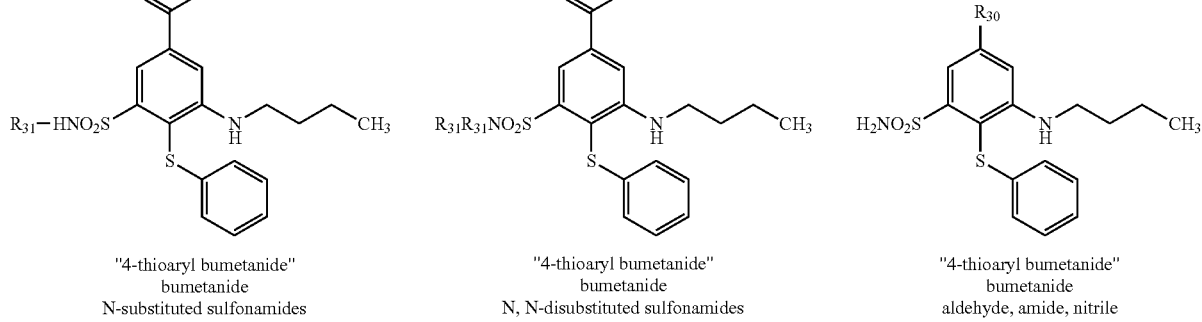

"4-thioaryl bumetanide"
bumetanide
N-subsituted sulfonamides

"4-thioaryl bumetanide"
bumetanide
N, N-disubstituted sulfonamides

"4-thioaryl bumetanide"
bumetanide
aldehyde, amide, nitrile

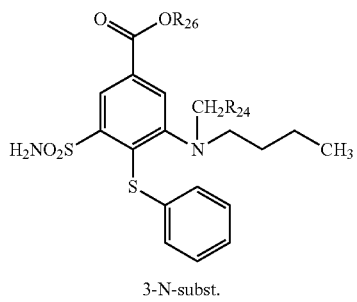

3-N-subst.
"4-thioaryl bumetanide" bumetanide esters
R₂₆ = lower alkyl, lower alkenyl, alkaryl, aryl, heterocyclic, heteroaryl

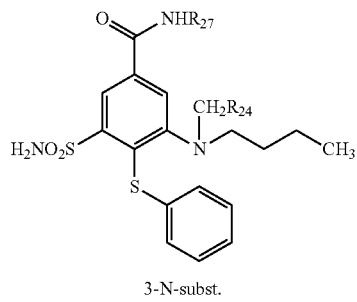

3-N-subst.
"4-thioaryl bumetanide"
bumetanide monosubstituted amides
R₂₇ = lower alkyl, lower alkenyl, alkaryl, aryl, heterocyclic, heteroaryl

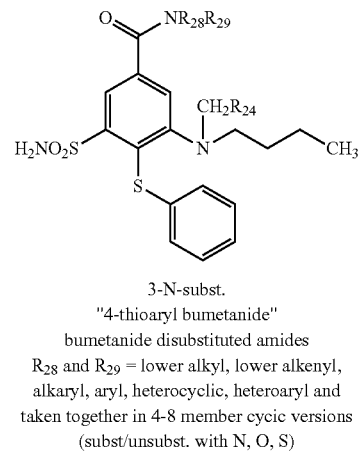

3-N-subst.
"4-thioaryl bumetanide"
bumetanide disubstituted amides
R₂₈ and R₂₉ = lower alkyl, lower alkenyl, alkaryl, aryl, heterocyclic, heteroaryl and taken together in 4-8 member cycic versions (subst/unsubst. with N, O, S)

-continued

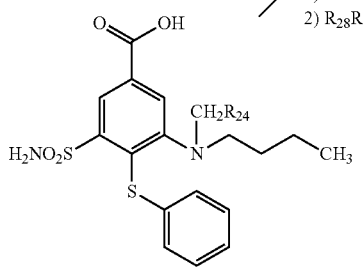

"4-thioaryl bumetanide"

Alternatively, ester formation can occur in one step via EDC—HOBt "peptide-type" coupling with R₁OH.

1) SOCl₂
2) R₂₆OH

1) SOCl₂
2) R₂₇NH₂

1) SOCl₂
2) R₂₈R₂₉NH

Alternatively, amide formation can occur in one step via EDC—HOBt "peptide-type" coupling.

1) base + 2 equiv. R₃₁X; or 2 equiv. diazoalkane
2) acid- or base-cat. ester hydroylsis 1) base + 3 equiv. R₃₁X; or 3 equiv. diazoalkane
2) acid- or base-cat. ester hydroylsis 1) acid chloride reduction → R₃₀ = CHO, or
2) acid chloride + ammonia → R₃₀ = CONH₂ or
3) R₃₀ = CONH₂ amide + POCl₃ → R₃₀=CN

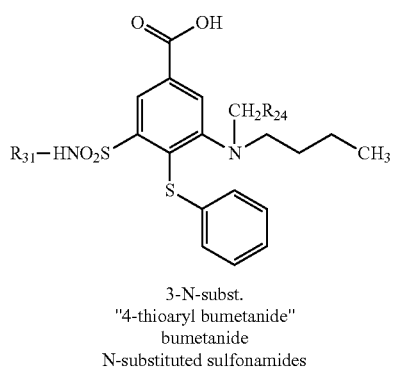

3-N-subst. "4-thioaryl bumetanide" bumetanide N-substituted sulfonamides where R₂₄ is methyl, ethyl, propyl, butyl, pentyl, hexyl, benzyl ...

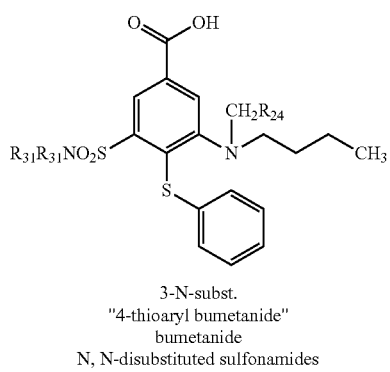

3-N-subst. "4-thioaryl bumetanide" bumetanide N, N-disubstituted sulfonamides

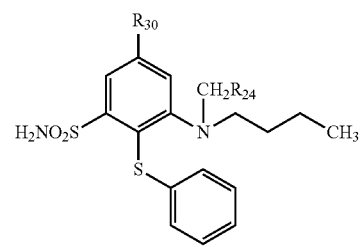

3-N-subst. "4-thioaryl bumetanide" bumetanide aldehyde, amide, nitrile

Scheme 53 and 54. 4-chloro Bumetanide Esters, Amides, Sulfonamides, Aldehydes, and Nitriles

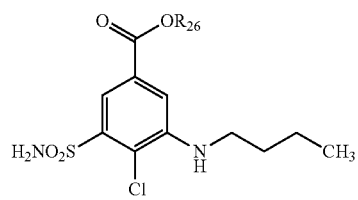

"4-chloro bumetanide" esters
R₂₆ = lower alkyl, lower alkenyl, alkaryl, aryl, heterocyclic, heteroaryl

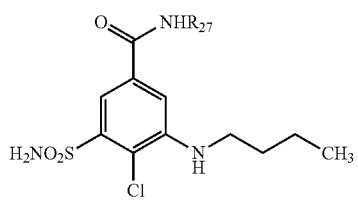

"4-chloro bumetanide" bumetanide monosubstituted amides
R₂₇ = lower alkyl, lower alkenyl, alkaryl, aryl, heterocyclic, heteroaryl

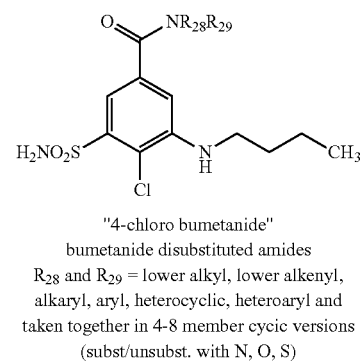

"4-chloro bumetanide" bumetanide disubstituted amides
R₂₈ and R₂₉ = lower alkyl, lower alkenyl, alkaryl, aryl, heterocyclic, heteroaryl and taken together in 4-8 member cycic versions (subst/unsubst. with N, O, S)

-continued

Alternatively, ester formation can occur in one step via EDC—HOBt "peptide-type" coupling with R₁OH.

1) SOCl₂
2) R₂₆OH

1) SOCl₂
2) R₂₇NH₂

1) SOCl₂
2) R₂₈R₂₉NH

Alternatively, amide formation can occur in one step via EDC—HOBt "peptide-type" coupling.

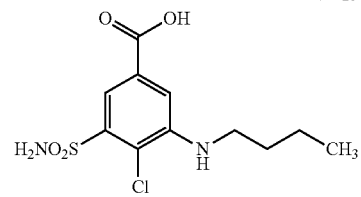

"4-chloro bumetanide"

1) base + 2 equiv. R₃₁X; or 2 equiv. diazoalkane
2) acid- or base-cat. ester hydroylsis 1) base + 3 equiv. R₃₁X; or 3 equiv. diazoalkane
2) acid- or base-cat. ester hydroylsis 1) acid chloride reduction → R₃₀ = CHO, or
2) acid chloride + ammonia → R₃₀ = CONH₂ or
3) R₃₀ = CONH₂ amide + POCl₃ → R₃₀ = CN

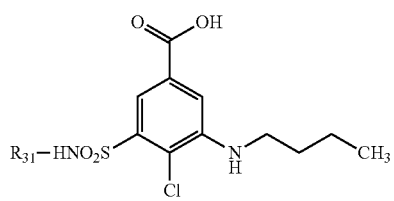

"4-chloro bumetanide" bumetanide
N-substituted sulfonamides

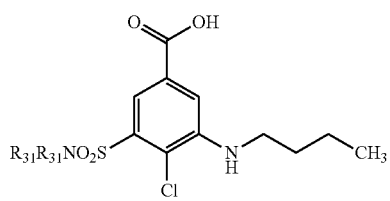

"4-chloro bumetanide" bumetanide
N, N-disubstituted sulfonamides

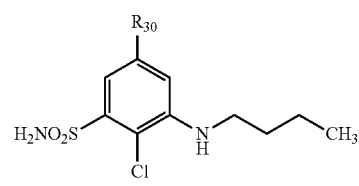

"4-chloro bumetanide" bumetanide
aldehyde, amide, nitrile

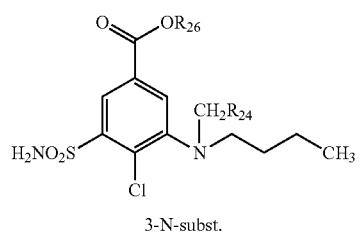

3-N-subst.
"4-chloro bumetanide" esters
R₂₆ = lower alkyl, lower alkenyl, alkaryl, aryl, heterocyclic, heteroaryl

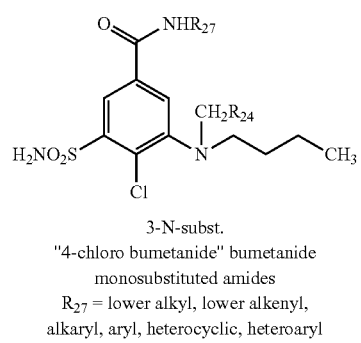

3-N-subst.
"4-chloro bumetanide" bumetanide
monosubstituted amides
R₂₇ = lower alkyl, lower alkenyl, alkaryl, aryl, heterocyclic, heteroaryl

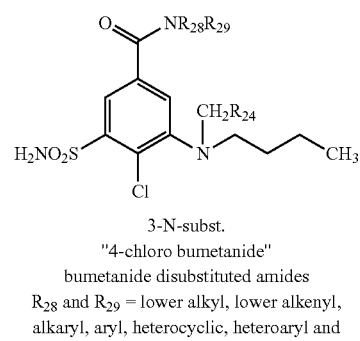

3-N-subst.
"4-chloro bumetanide"
bumetanide disubstituted amides
R₂₈ and R₂₉ = lower alkyl, lower alkenyl, alkaryl, aryl, heterocyclic, heteroaryl and taken together in 4-8 member cycic versions (subst/unsubst. with N, O, S)

203

204

-continued

Alternatively, ester formation can occur in one step via EDC—HOBt "peptide-type" coupling with $R_1OH$.

1) $SOCl_2$
2) $R_{26}OH$

1) $SOCl_2$
2) $R_{27}NH_2$

1) $SOCl_2$
2) $R_{28}R_{29}NH$

Alternatively, amide formation can occur in one step via EDC—HOBt "peptide-type" coupling.

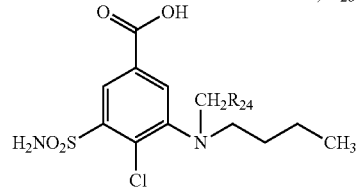

"4-chloro bumetanide"

1) base + 2 equiv. $R_{31}X$; or
2 equiv. diazoalkane
2) acid- or base-cat. ester hydroylsis 1) base + 3 equiv. $R_{31}X$;
or 3 equiv. diazoalkane
2) acid- or base-cat. ester hydroylsis 1) acid chloride reduction → $R_{30}$ = CHO, or
2) acid chloride + ammonia → $R_{30}$ = $CONH_2$ or
3) $R_{30}$ = $CONH_2$ amide + $POCl_3$ → $R_{30}$ = CN

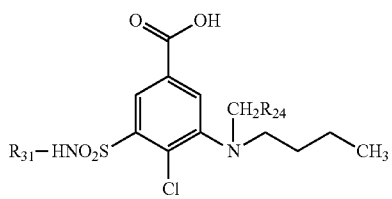

3-N-subst.
"4-chloro bumetanide" bumetanide
N-substituted sulfonamides where $R_{24}$ is methyl, ethyl, proply, butyl, pentyl, hexyl, benzyl ...

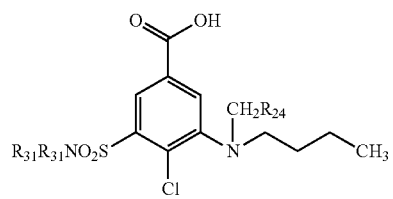

3-N-subst.
"4-chloro bumetanide" bumetanide
N, N-disubstituted sulfonamides

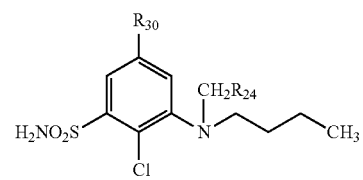

3-N-subst.
"4-chloro bumetanide" bumetanide
aldehyde, amide, nitrile

Scheme 55 and 56. 4-fluoro Bumetanide Esters, Amides, Sulfonamides, Aldehydes, and Nitriles

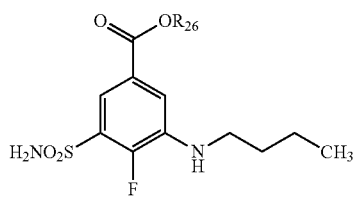

"4-fluoro bumetanide" esters
$R_{26}$ = lower alkyl, lower alkenyl, alkaryl, aryl, heterocyclic, heteroaryl

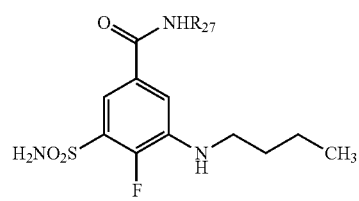

"4-fluoro bumetanide" bumetanide monosubstituted amides
$R_{27}$ = lower alkyl, lower alkenyl, alkaryl, aryl, heterocyclic, heteroaryl

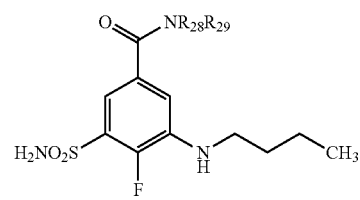

"4-fluoro bumetanide"
bumetanide disubstituted amides
$R_{28}$ and $R_{29}$ = lower alkyl, lower alkenyl, alkaryl, aryl, heterocyclic, heteroaryl and taken together in 4-8 member cycic versions (subst/unsubst. with N, O, S)

-continued

Alternatively, ester formation can occur in one step via EDC—HOBt "peptide-type" coupling with R₁OH.

1) SOCl₂
2) R₂₆OH

1) SOCl₂
2) R₂₇NH₂

1) SOCl₂
2) R₂₈R₂₉NH

Alternatively, amide formation can occur in one step via EDC—HOBt "peptide-type" coupling.

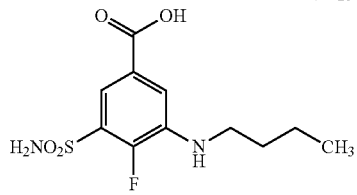

"4-fluoro bumetanide"

1) base + 2 equiv. R₃₁X; or 2 equiv. diazoalkane
2) acid- or base-cat. ester hydroylsis 1) base + 3 equiv. R₃₁X; or 3 equiv. diazoalkane
2) acid- or base-cat. ester hydroylsis 1) acid chloride reduction → R₃₀ = CHO, or
2) acid chloride + ammonia → R₃₀ = CONH₂ or
3) R₃₀ = CONH₂ amide + POCl₃ → R₃₀ = CN

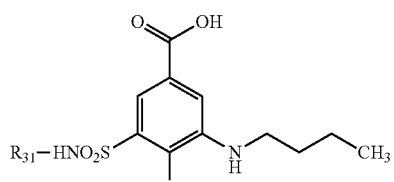

"4-fluoro bumetanide" bumetanide
N-subsubstituted sulfonamides

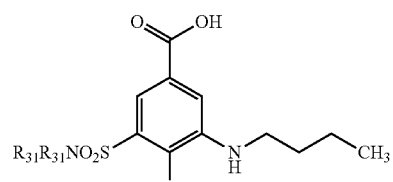

"4-fluoro bumetanide" bumetanide
N, N-disubstituted sulfonamides

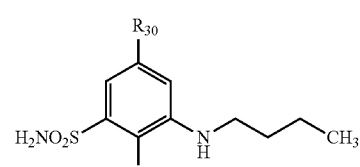

"4-fluoro bumetanide" bumetanide
aldehyde, amide, nitrile

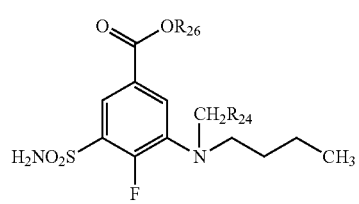

3-N-subst.
"4-fluoro bumetanide" esters
R₂₆ = lower alkyl, lower alkenyl, alkaryl, aryl, heterocyclic, heteroaryl

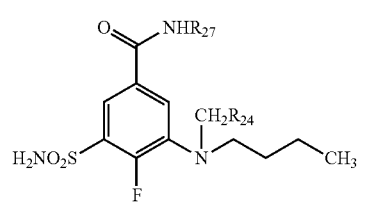

3-N-subst.
"4-fluoro bumetanide" bumetanide
monosubstituted amides
R₂₇ = lower alkyl, lower alkenyl, alkaryl, aryl, heterocyclic, heteroaryl

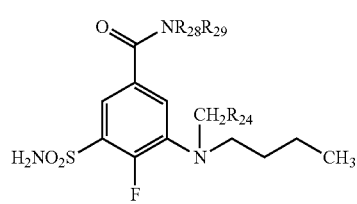

3-N-subst.
"4-fluoro bumetanide"
bumetanide disubstituted amides
R₂₈ and R₂₉ = lower alkyl, lower alkenyl, alkaryl, aryl, heterocyclic, heteroaryl and taken together in 4-8 member cycic versions (subst/unsubst. with N, O, S)

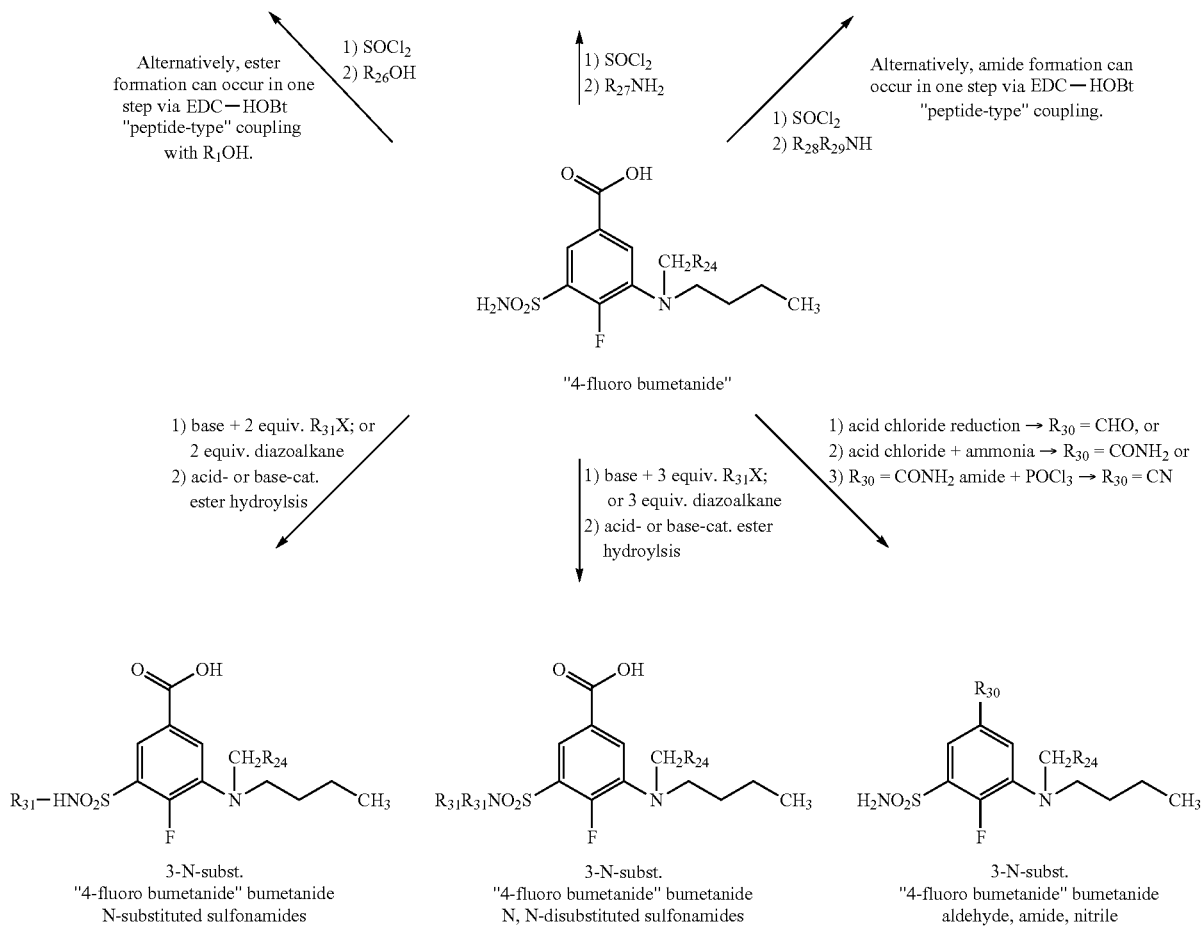
where R$_{24}$ is methyl, ethyl, propyl, butyl, pentyl, hexyl, benzyl ...
Schemes 57 and 58. 4-phenyl Bumetanide Esters, Amides, Sulfonamides, Aldehydes, and Nitriles
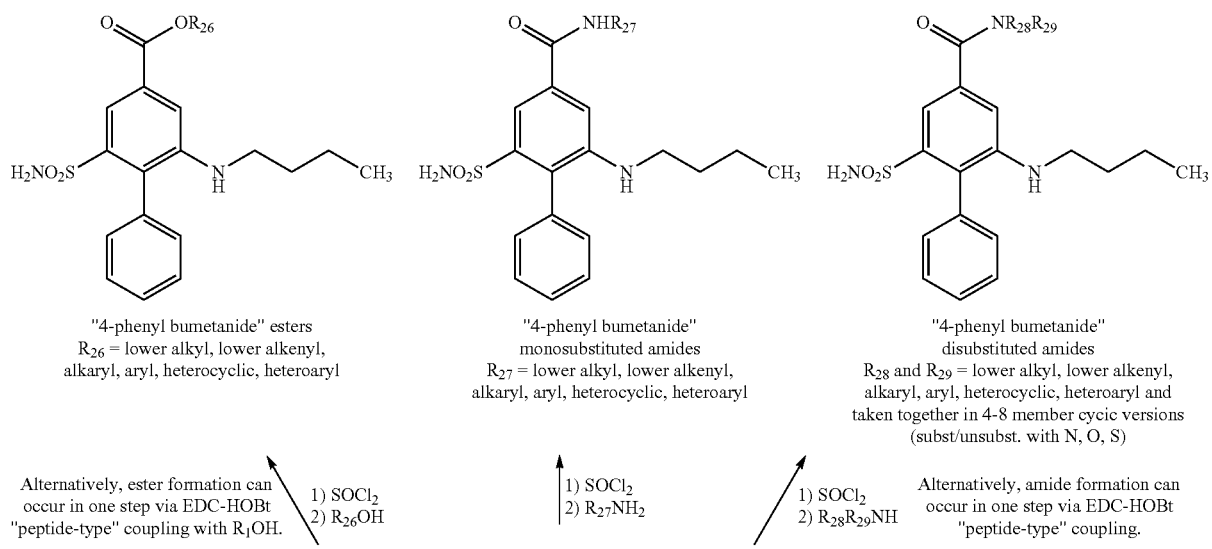

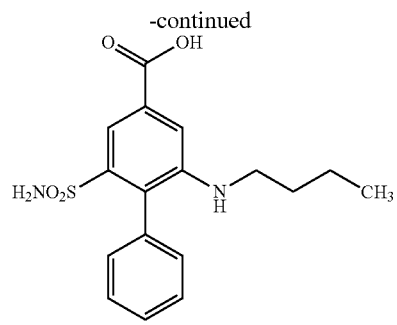

"4-phenyl bumetanide"

1) base + 2 equiv. R₃₁X; or
2 equiv. diazoalkane
2) acid- or base-cat. ester hydroylsis 1) base + 3 equiv. R₃₁X; or
3 equiv. diazoalkane
2) acid- or base-cat. ester hydroylsis 1) acid chloride reduction → $R_{30}$ = CHO, or
2) acid chloride + ammonia → $R_{30}$ = $CONH_2$ or
3) $R_{30}$ = $CONH_2$ amide + $POCl_3$ → $R_{30}$ = CN

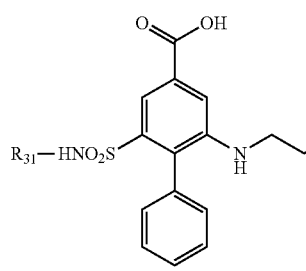

"4-phenyl bumetanide"
N-substituted sulfonamides

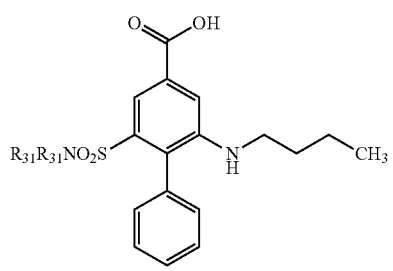

"4-phenyl bumetanide"
N, N-disubstituted sulfonamides

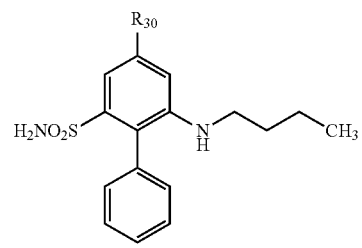

"4-phenyl bumetanide"
aldehyde, amide, nitrile

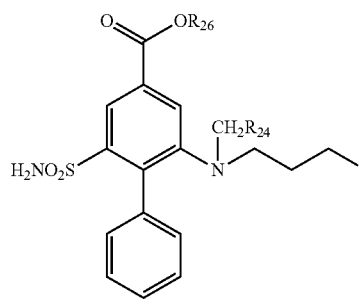

3-N-subst. "4-phenyl bumetanide" esters
$R_{26}$ = lower alkyl, lower alkenyl, alkaryl, aryl, heterocyclic, heteroaryl

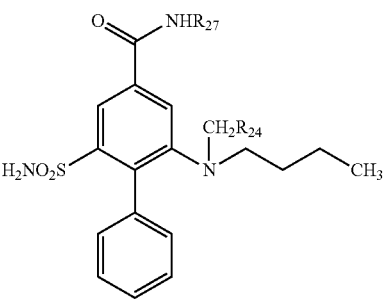

3-N-subst. "4-phenyl bumetanide" monosubstituted amides
$R_{27}$ = lower alkyl, lower alkenyl, alkaryl, aryl, heterocyclic, heteroaryl

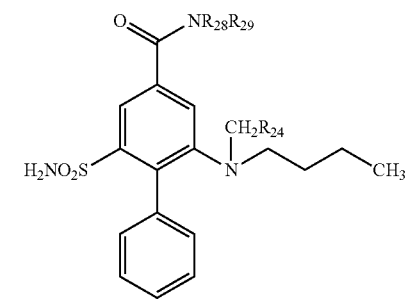

3-N-subst. "4-phenyl bumetanide" disubstituted amides
$R_{28}$ and $R_{29}$ = lower alkyl, lower alkenyl, alkaryl, aryl, heterocyclic, heteroaryl and taken together in 4-8 member cycic versions (subst/unsubst. with N, O, S)

Alternatively, ester formation can occur in one step via EDC-HOBt "peptide-type" coupling with $R_1OH$.

1) $SOCl_2$
2) $R_{26}OH$

1) $SOCl_2$
2) $R_{27}NH_2$

1) $SOCl_2$
2) $R_{28}R_{29}NH$

Alternatively, amide formation can occur in one step via EDC-HOBt "peptide-type" coupling.

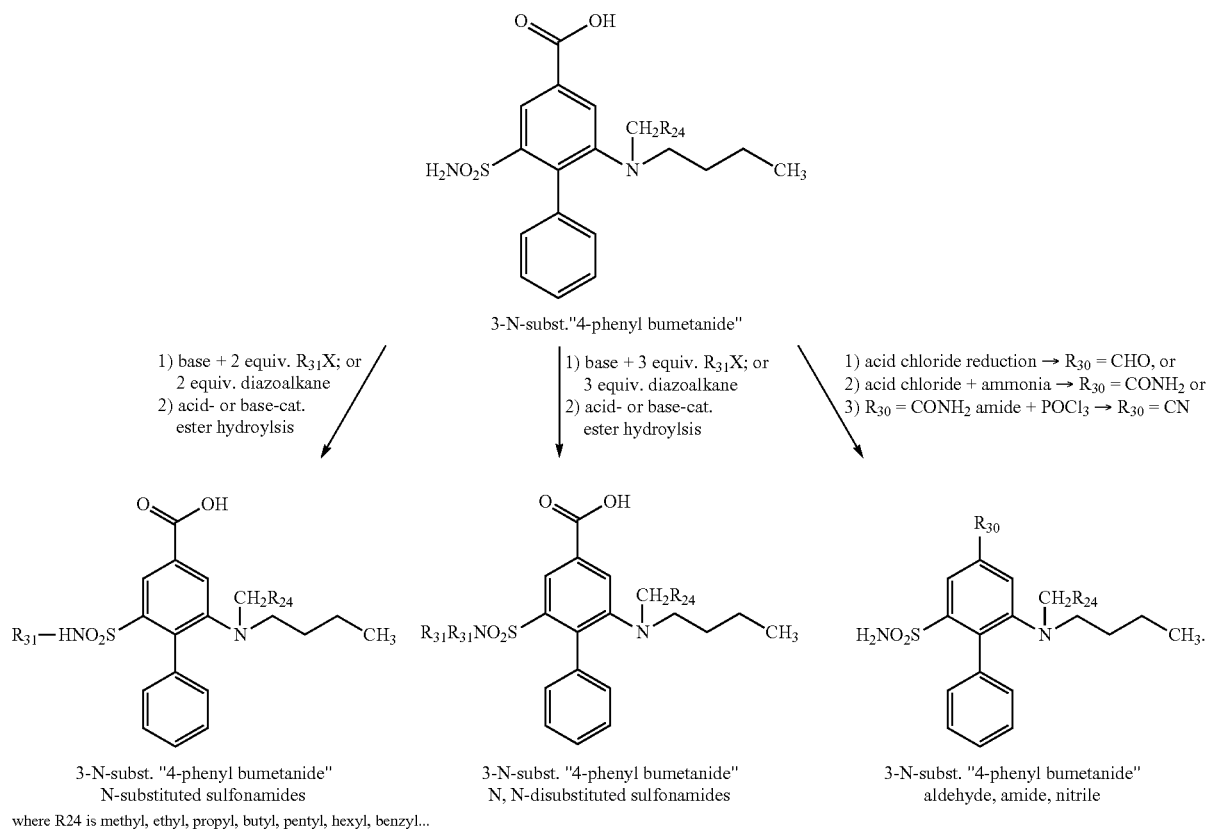
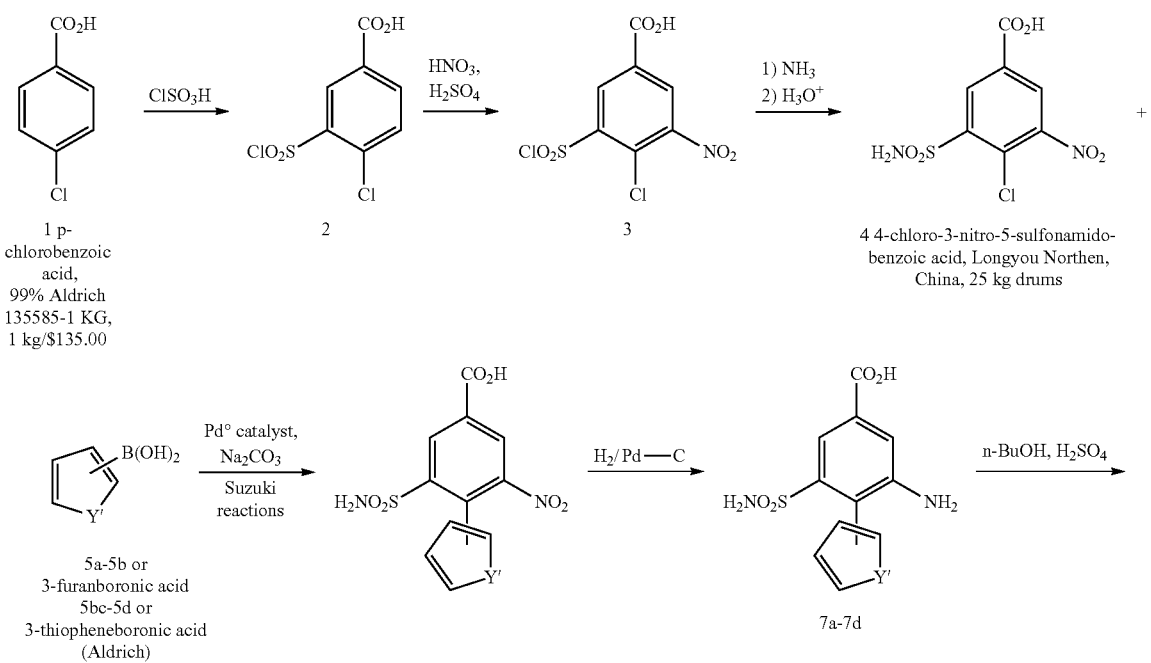
Scheme 59. 4-heterocyclo Bumetanide

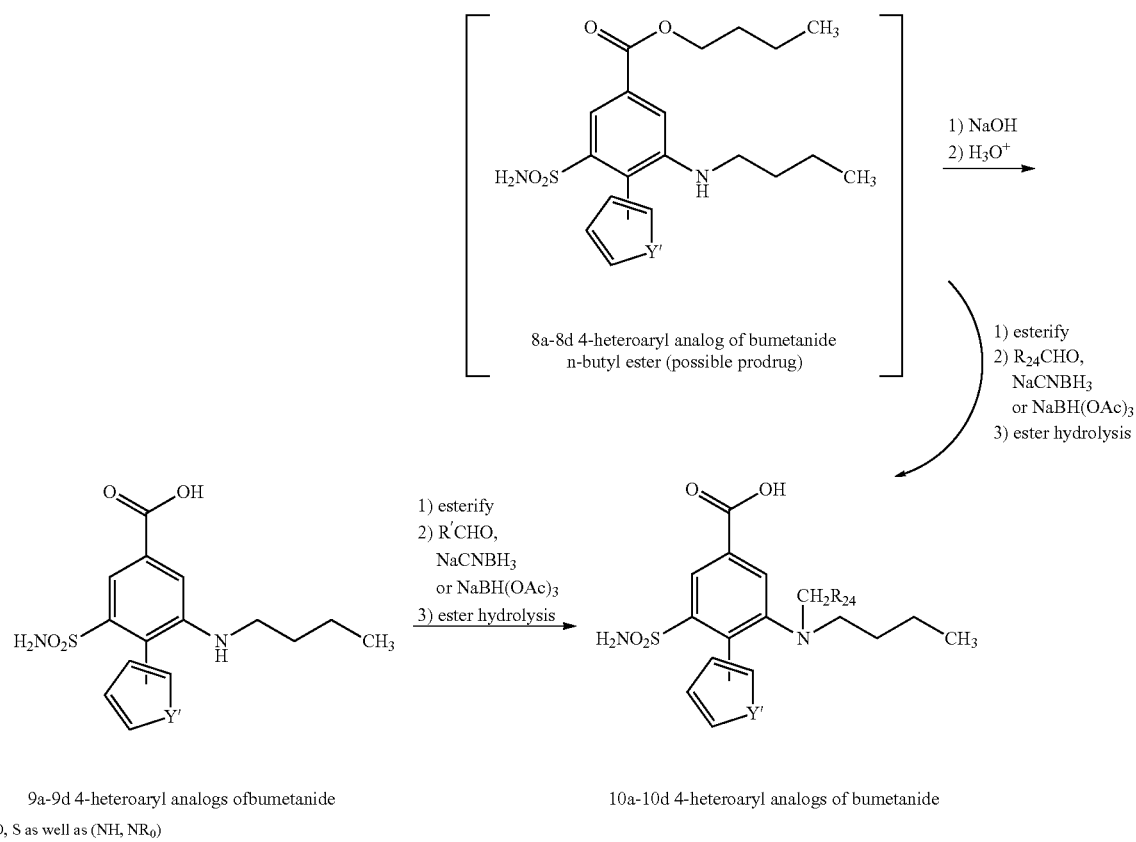
9a-9d 4-heteroaryl analogs of bumetanide
10a-10d 4-heteroaryl analogs of bumetanide
Y' = O, S as well as (NH, NR₀)
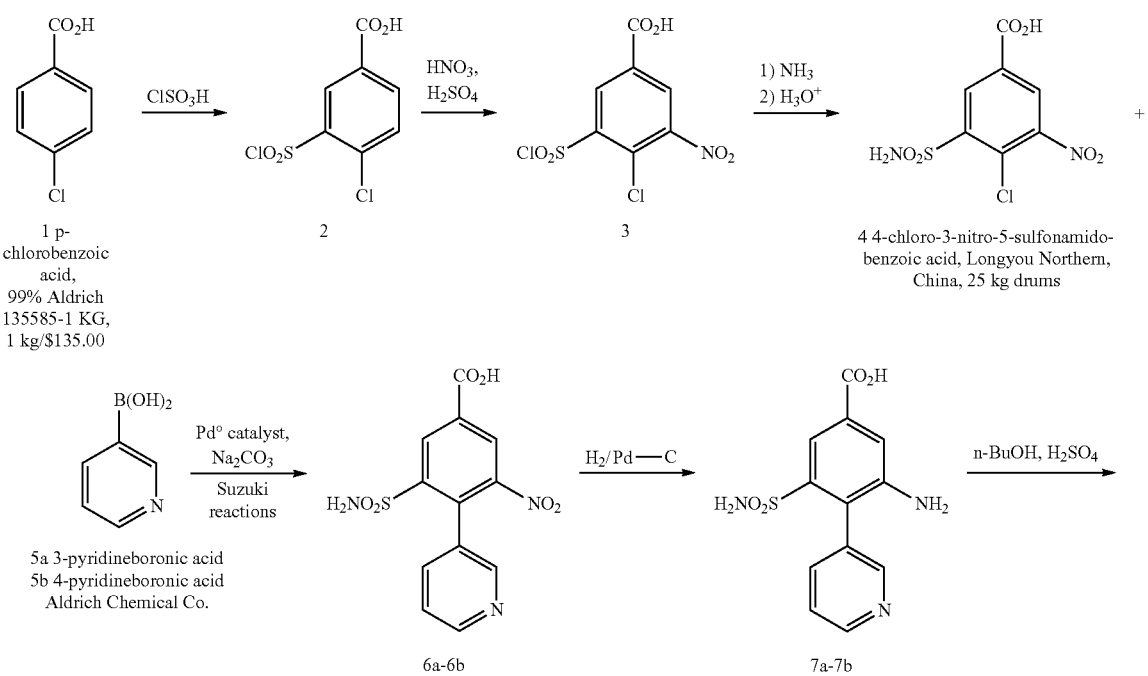
Scheme 60. 4-(3- or 4-pyridyl) Bumetanide
1 p-chlorobenzoic acid, 99% Aldrich 135585-1 KG, 1 kg/$135.00
4 4-chloro-3-nitro-5-sulfonamido-benzoic acid, Longyou Northern, China, 25 kg drums
5a 3-pyridineboronic acid
5b 4-pyridineboronic acid
Aldrich Chemical Co.
6a-6b
7a-7b -continued

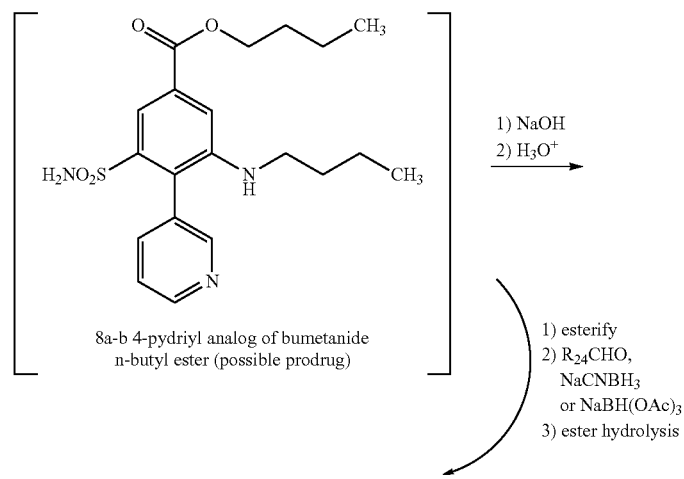

1) NaOH
2) H₃O⁺

8a-b 4-pydriyl analog of bumetanide n-butyl ester (possible prodrug)

1) esterify
2) R₂₄CHO, NaCNBH₃ or NaBH(OAc)₃
3) ester hydrolysis

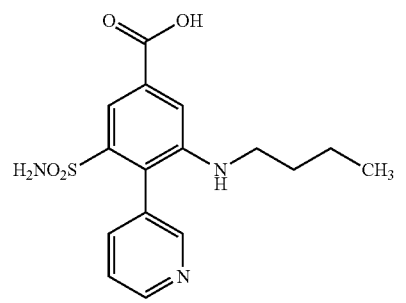

9a-9b 4-(3- or 4-pyridyl) analog of bumetanide 1) esterify
2) R'CHO, NaCNBH₃ or NaBH(OAc)₃
3) ester hydrolysis

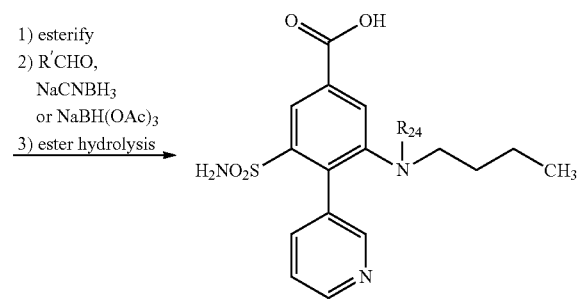

10a-10b 3-subst. 4-(3- or 4-pyridyl) analog of bumetanide

Schemes 61, 62, 63, and 64. 4-Furanyl Bumetanide Esters, Amides, Sulfonamides, Aldehydes, and Nitriles

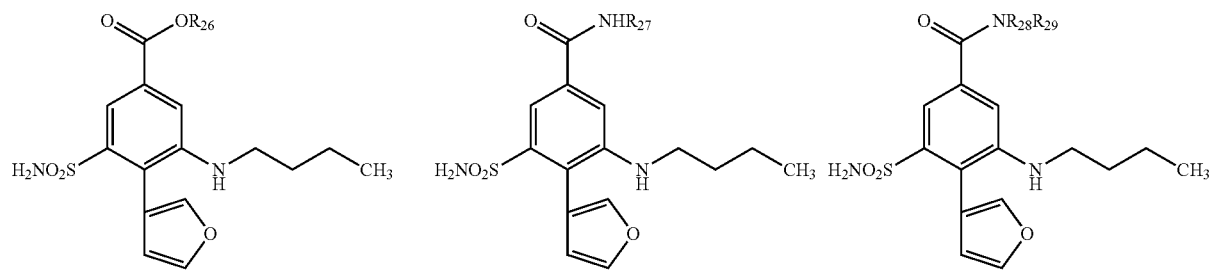

"4-(3-furanyl) bumetanide" esters
R₂₆ = lower alkyl, lower alkenyl, alkaryl, aryl, heterocyclic, heteroaryl "4-(3-furanyl)I bumetanide" monosubstituted amides
R₂₇ = lower alkyl, lower alkenyl, alkaryl, aryl, heterocyclic, heteroaryl "4-(3-furanyl) bumetanide" disubstituted amides
R₂₈ and R₂₉ = lower alkyl, lower alkenyl, alkaryl, aryl, heterocyclic, heteroaryl and taken together in 4-8 member cycic versions (subst/unsubst. with N, O, S)

Alternatively, ester formation can occur in one step via EDC-HOBt "peptide-type" coupling with R₁OH.

1) SOCl₂
2) R₂₆OH

1) SOCl₂
2) R₂₇NH₂

1) SOCl₂
2) R₂₈R₂₉NH

Alternatively, amide formation can occur in one step via EDC-HOBt "peptide-type" coupling.

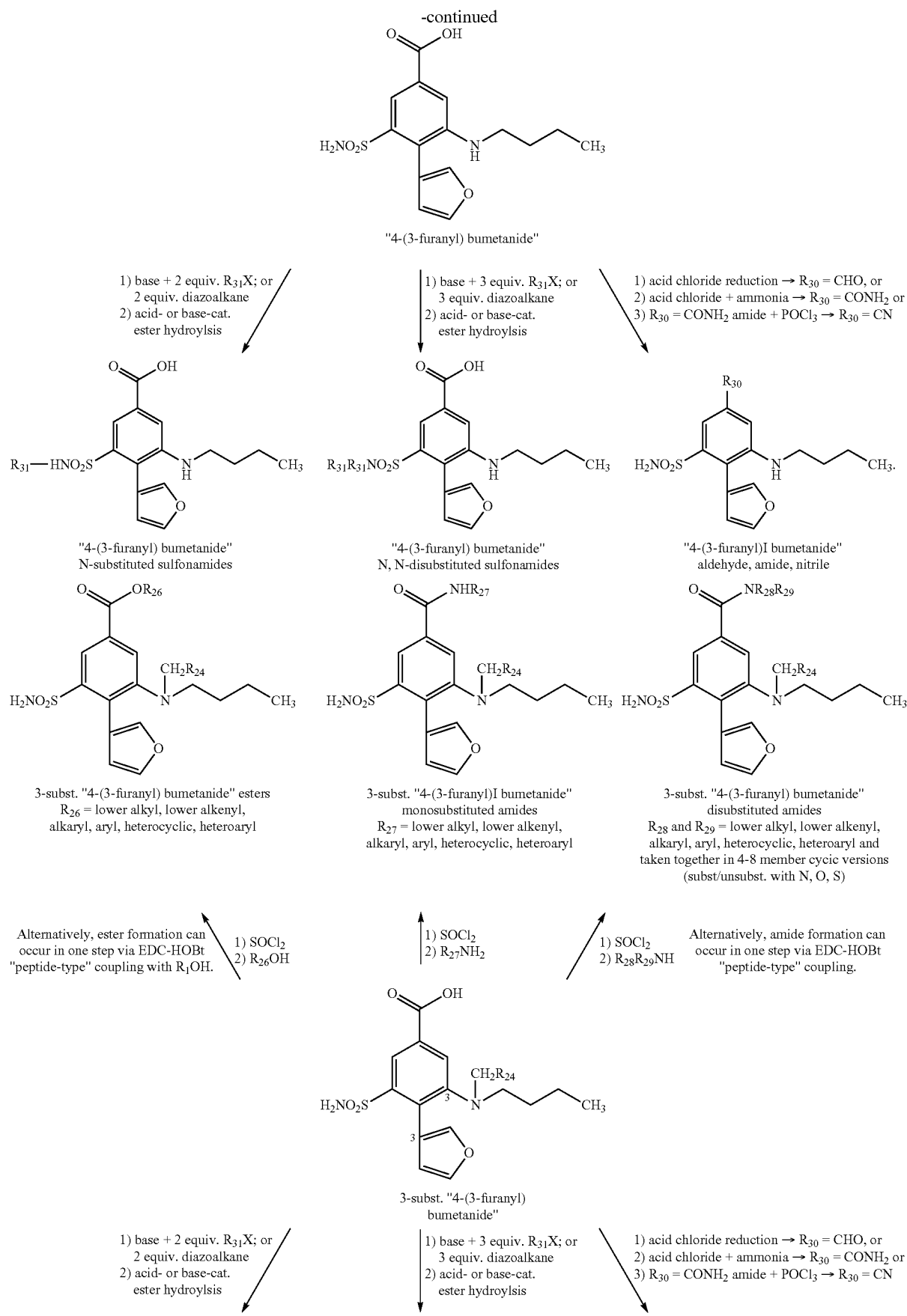

-continued

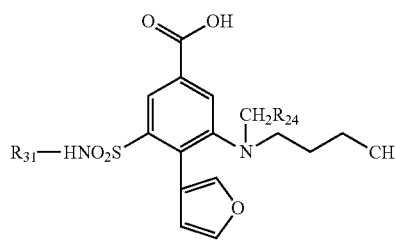

3-subst. "4-(3-furanyl) bumetanide"
N-substituted sulfonamides where R24 is methyl, ethyl, propyl, butyl, pentyl, hexyl, benzyl...

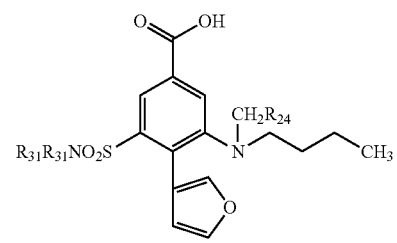

3- subst. "4-(3-furanyl) bumetanide"
N, N-disubstituted sulfonamides

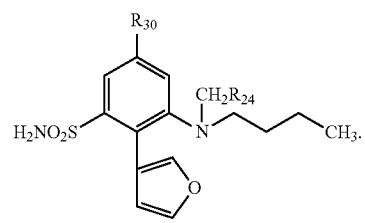

3-subst. "4-(3-furanyl)I bumetanide"
aldehyde, amide, nitrile

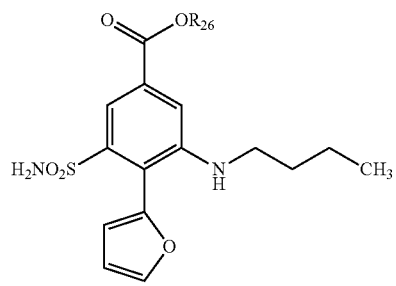

"4-(2-furanyl) bumetanide" esters
$R_{26}$ = lower alkyl, lower alkenyl, alkaryl, aryl, heterocyclic, heteroaryl

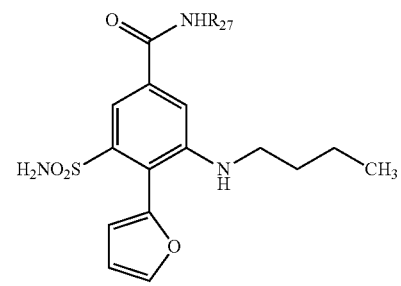

"4-(2-furanyl)I bumetanide"
monosubstituted amides
$R_{27}$ = lower alkyl, lower alkenyl, alkaryl, aryl, heterocyclic, heteroaryl

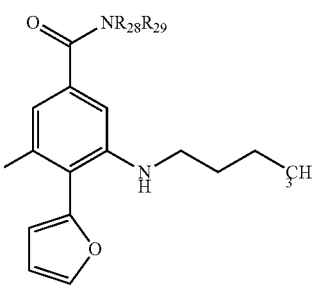

"4-(2-furanyl) bumetanide"
disubstituted amides
$R_{28}$ and $R_{29}$ = lower alkyl, lower alkenyl, alkaryl, aryl, heterocyclic, heteroaryl and taken together in 4-8 member cycic versions (subst/unsubst. with N, O, S)

Alternatively, ester formation can occur in one step via EDC-HOBt "peptide-type" coupling with $R_1OH$.

1) $SOCl_2$
2) $R_{26}OH$

1) $SOCl_2$
2) $R_{27}NH_2$

1) $SOCl_2$
2) $R_{28}R_{29}NH$

Alternatively, amide formation can occur in one step via EDC-HOBt "peptide-type" coupling.

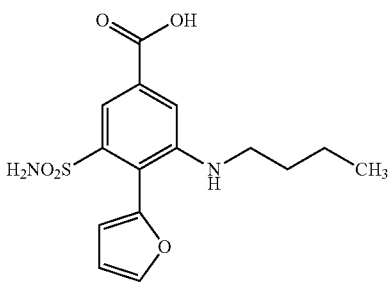

"4-(2-furanyl) bumetanide"

1) base + 2 equiv. $R_{31}X$; or
   2 equiv. diazoalkane
2) acid- or base-cat.
   ester hydroylsis 1) base + 3 equiv. $R_{31}X$; or
   3 equiv. diazoalkane
2) acid- or base-cat.
   ester hydroylsis 1) acid chloride reduction → $R_{30}$ = CHO, or
2) acid chloride + ammonia → $R_{30}$ = $CONH_2$ or
3) $R_{30}$ = $CONH_2$ amide + $POCl_3$ → $R_{30}$ = CN

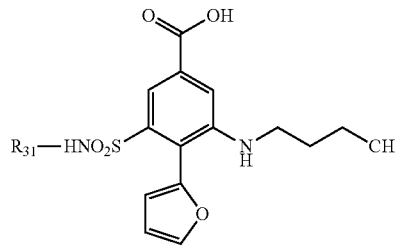

"4-(2-furanyl) bumetanide"
N-substituted sulfonamides

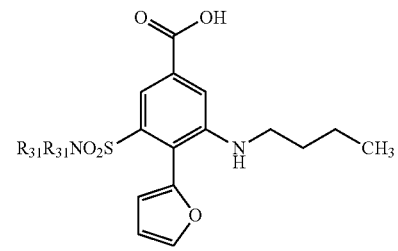

"4-(2-furanyl) bumetanide"
N, N-disubstituted sulfonamides

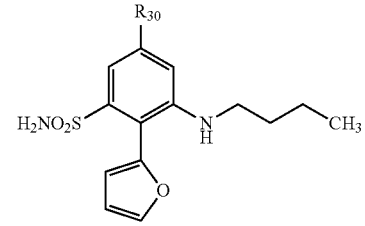

"4-(2-furanyl)I bumetanide"
aldehyde, amide, nitrile

-continued

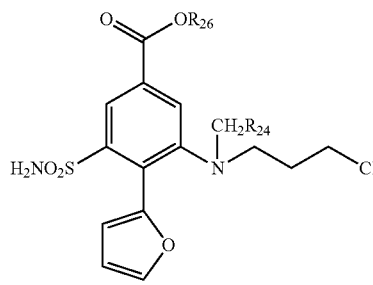

3-subst. "4-(2-furanyl) bumetanide" esters
$R_{26}$ = lower alkyl, lower alkenyl, alkaryl, aryl, heterocyclic, heteroaryl

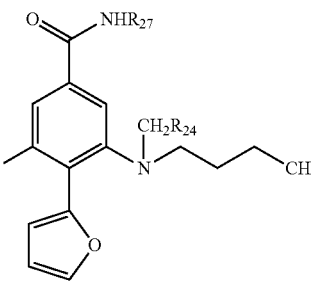

3-subst. "4-(2-furanyl)I bumetanide" monosubstituted amides
$R_{27}$ = lower alkyl, lower alkenyl, alkaryl, aryl, heterocyclic, heteroaryl

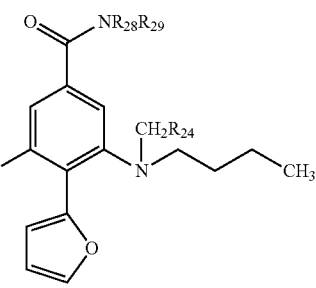

3-subst. "4-(2-furanyl) bumetanide" disubstituted amides
$R_{28}$ and $R_{29}$ = lower alkyl, lower alkenyl, alkaryl, aryl, heterocyclic, heteroaryl and taken together in 4-8 member cyclic versions (subst/unsubst. with N, O, S)

Alternatively, ester formation can occur in one step via EDC-HOBt "peptide-type" coupling with $R_1$OH.

1) $SOCl_2$
2) $R_{26}$OH

1) $SOCl_2$
2) $R_{27}NH_2$

1) $SOCl_2$
2) $R_{28}R_{29}NH$

Alternatively, amide formation can occur in one step via EDC-HOBt "peptide-type" coupling.

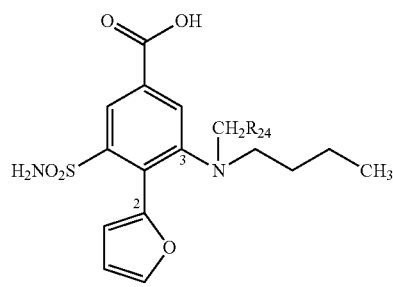

3-subst. "4-(2-furanyl) bumetanide"

1) base + 2 equiv. $R_{31}$X; or 2 equiv. diazoalkane
2) acid- or base-cat. ester hydroylsis 1) base + 3 equiv. $R_{31}$X; or 3 equiv. diazoalkane
2) acid- or base-cat. ester hydroylsis 1) acid chloride reduction → $R_{30}$ = CHO, or
2) acid chloride + ammonia → $R_{30}$ = $CONH_2$ or
3) $R_{30}$ = $CONH_2$ amide + $POCl_3$ → $R_{30}$ = CN

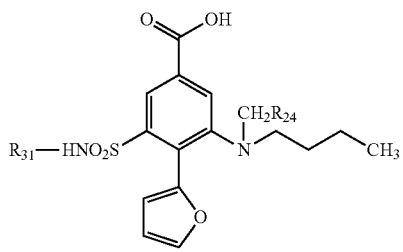

3-subst. "4-(2-furanyl) bumetanide" N-substituted sulfonamides

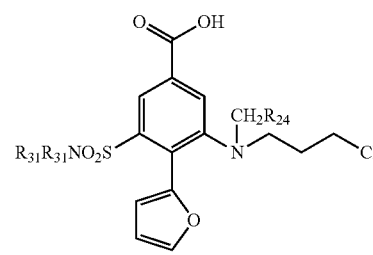

3-subst. "4-(2-furanyl) bumetanide" N, N-disubstituted sulfonamides

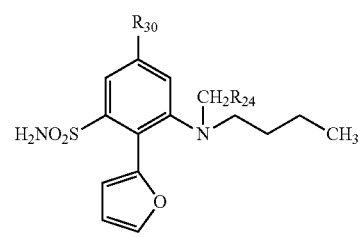

3-subst. "4-(2-furanyl)I bumetanide" aldehyde, amide, nitrile where $R_{24}$ is methyl, ethyl, propyl, butyl, pentyl, hexyl, benzyl...

Schemes 65 and 66. 4-pyridyl Bumetanide Esters, Amides, Sulfonamides, Aldehydes, and Nitriles

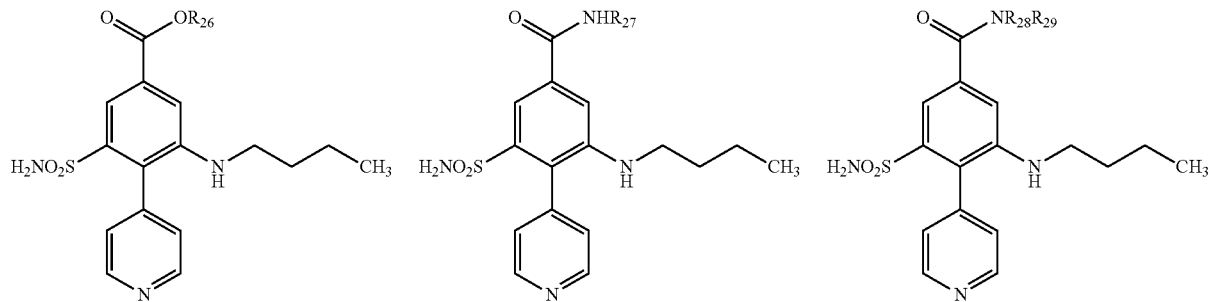

"4-(4-pyridyl) bumetanide" esters
$R_{26}$ = lower alkyl, lower alkenyl, alkaryl, aryl, heterocyclic, heteroaryl "4-(4-pyridyl)I bumetanide" monosubstituted amides
$R_{27}$ = lower alkyl, lower alkenyl, alkaryl, aryl, heterocyclic, heteroaryl "4-(4-pyridyl) bumetanide" disubstituted amides
$R_{28}$ and $R_{29}$ = lower alkyl, lower alkenyl, alkaryl, aryl, heterocyclic, heteroaryl and taken together in 4-8 member cycic versions (subst/unsubst. with N, O, S)

Alternatively, ester formation can occur in one step via EDC-HOBt "peptide-type" coupling with $R_1$OH.
1) SOCl$_2$
2) $R_{26}$OH 1) SOCl$_2$
2) $R_{27}$NH$_2$ 1) SOCl$_2$
2) $R_{28}R_{29}$NH
Alternatively, amide formation can occur in one step via EDC-HOBt "peptide-type" coupling.

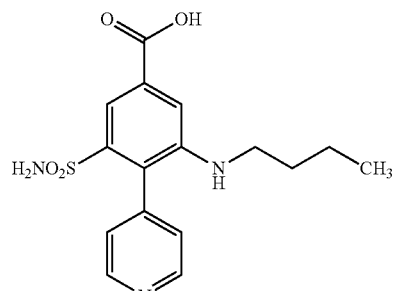

"4-(4-pyridyl) bumetanide"

1) base + 2 equiv. $R_{31}$X; or 2 equiv. diazoalkane
2) acid- or base-cat. ester hydroylsis 1) base + 3 equiv. $R_{31}$X; or 3 equiv. diazoalkane
2) acid- or base-cat. ester hydroylsis 1) acid chloride reduction → $R_{30}$ = CHO, or
2) acid chloride + ammonia → $R_{30}$ = CONH$_2$ or
3) $R_{30}$ = CONH$_2$ amide + POCl$_3$ → $R_{30}$ = CN

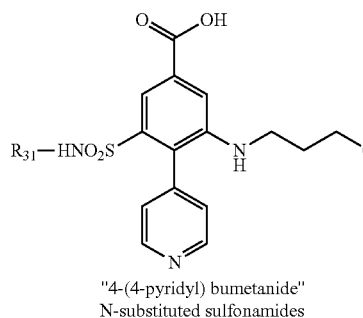

"4-(4-pyridyl) bumetanide"
N-substituted sulfonamides

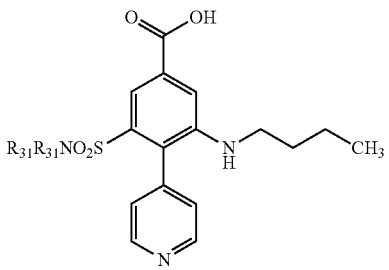

"4-(4-pyridyl) bumetanide"
N,N-disubstituted sulfonamides

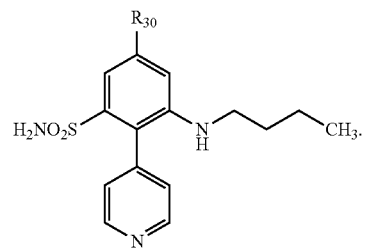

"4-(4-pyridyl)I bumetanide"
aldehyde, amide, nitrile

"4-(3-pyridyl) bumetanide" esters, amides, sulfonamides, aldehydes, and nitriles are made in a similar fashion.

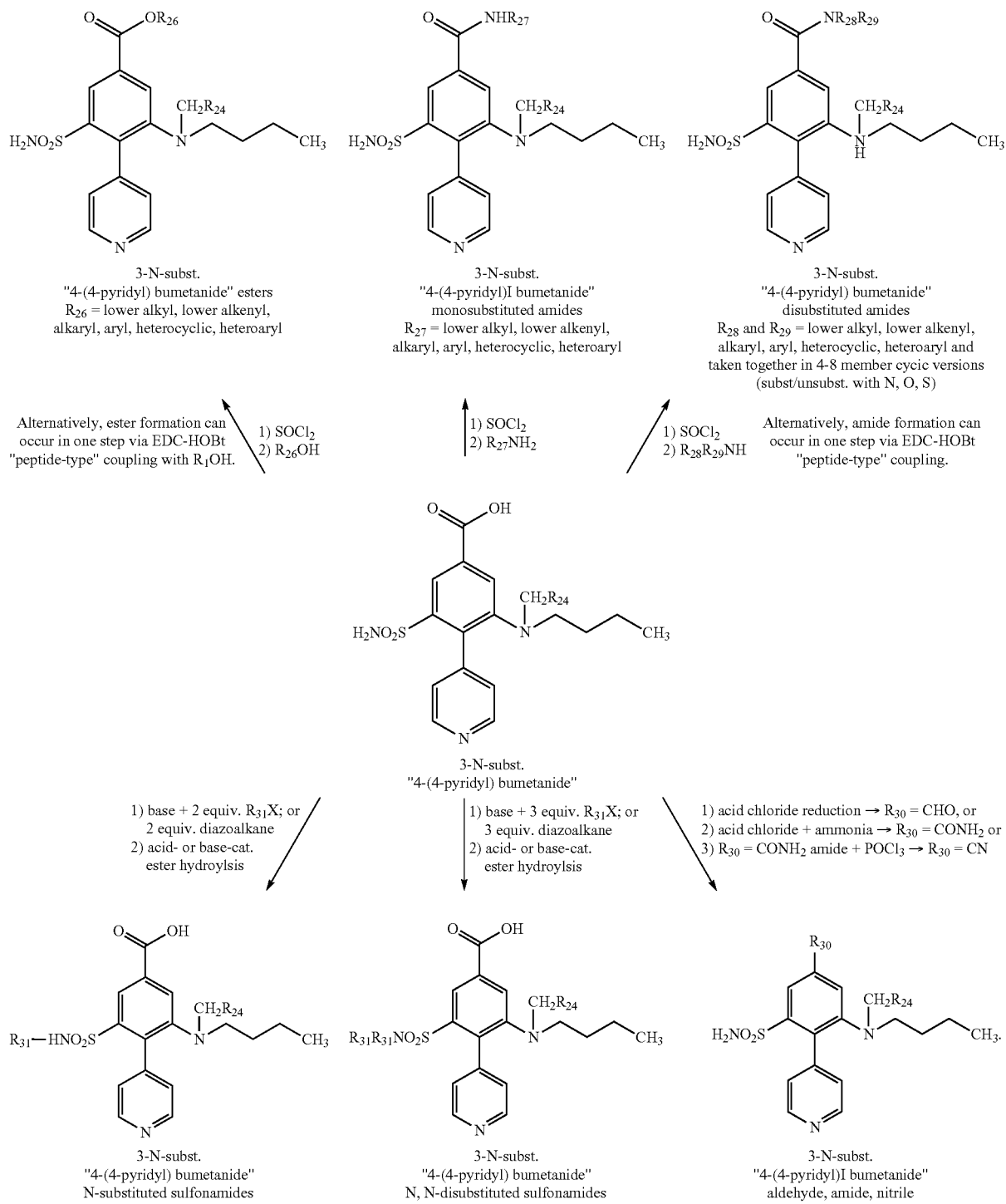

Where $R_{24}$ is methyl, ethyl, propyl, butyl, pentyl, hexyl, benzyl...
3-N-substituted "4-(3-pyridyl) bumetanide" esters, amides, sulfonamides, aldehydes, and nitriles are made in a similar fashion.

J. Additional Furosemnide Analogs

Additional furosemide analogs can be synthesized according to the syntheses shown below in Schemes 67-70. In the case of an N-substituted sulfonamide having one $R_{31}$ group, $R_{31}$ is lower alkyl, lower alkenyl, alkaryl, aryl, heterocycloalkyl, or heteroaryl. In the case of a disubstituted sulfonamide having two $R_{31}$ groups, each $R_{31}$ group is the same or different and are independently lower alkyl, lower alkenyl, alkaryl, aryl, heterocycloalkyl, heteroaryl or taken together with the nitrogen atom to which they attached form a 4-8 member cycle which can be substituted or unsubstituted and can have one or more heteroatoms (e.g., N, O or S).

Scheme 67. Synthesis of Furosemide
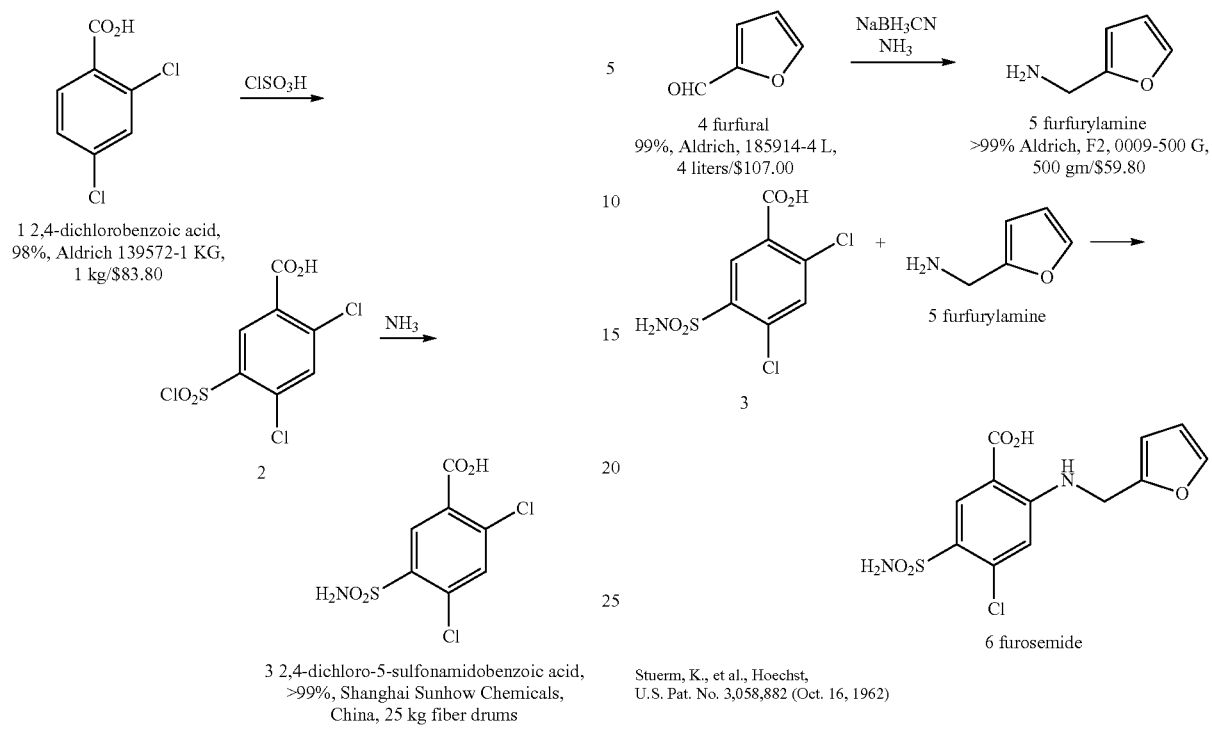
Stuerm, K., et al., Hoechst,
U.S. Pat. No. 3,058,882 (Oct. 16, 1962)
Scheme 68. Synthesis of 4-Substituted Furosemide
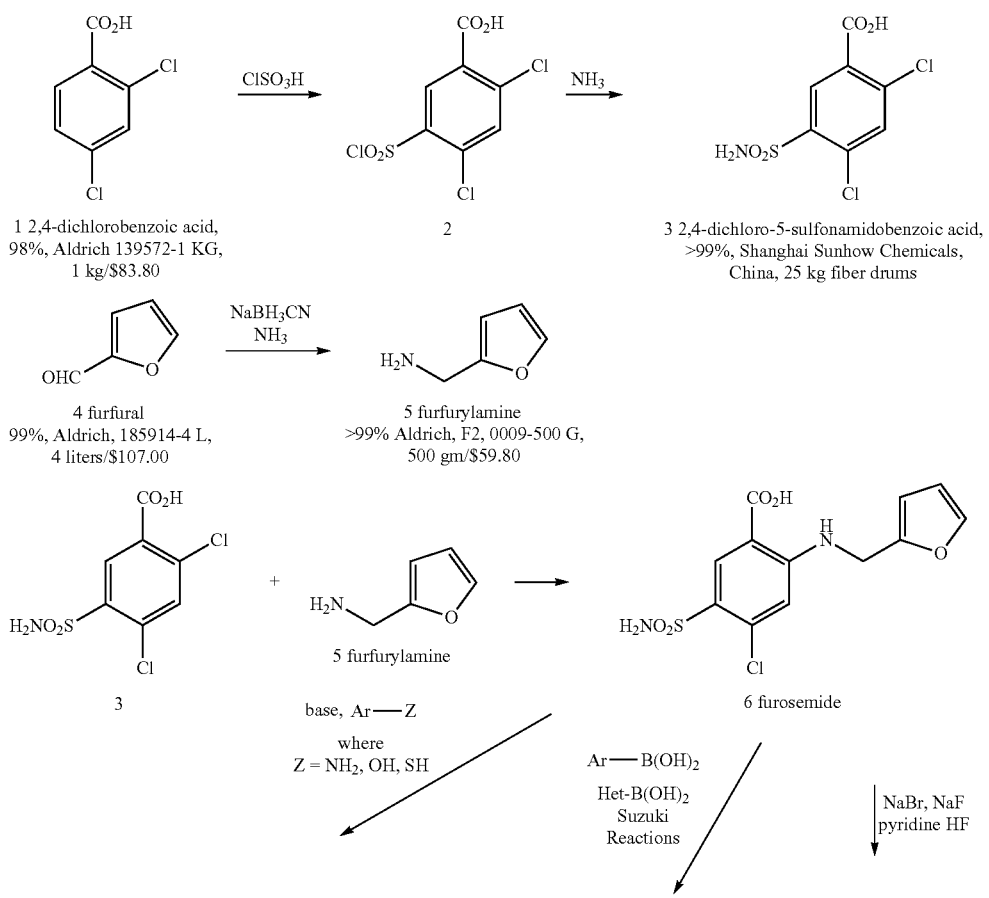

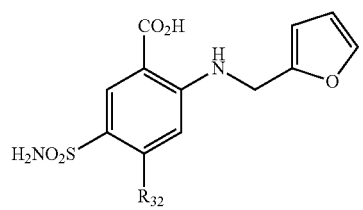

$R_{32}$ = NHAr, OAr, SAr

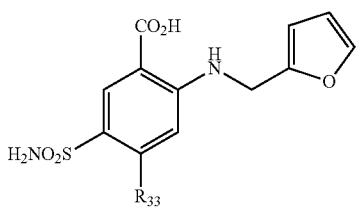

$R_{33}$ = Ar, Het

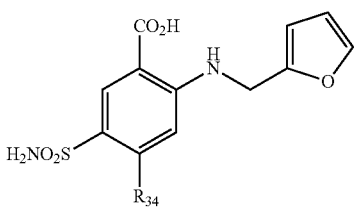

$R_{34}$ = halo, bromo, fluoro

Scheme 69. Furosemide Esters, Amides, Sulfonamides, Aldehydes, and Nitriles

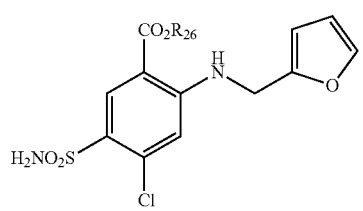

furosemide esters
$R_{26}$ = lower alkyl, lower alkenyl, alkaryl, aryl, heterocyclic, heteroaryl

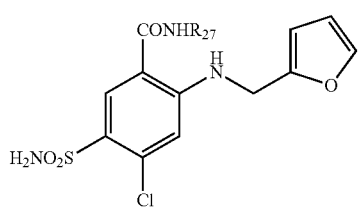

furosemide monosubstituted amides
$R_{27}$ = lower alkyl, lower alkenyl, alkaryl, aryl, heterocyclic, heteroaryl

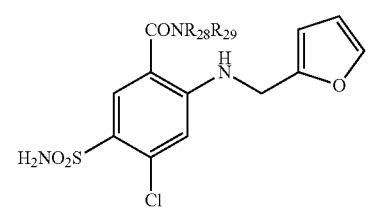

furosemide disubstituted amides
$R_{28}$ and $R_{29}$ = lower alkyl, lower alkenyl, alkaryl, aryl, heterocyclic, heteroaryl and taken together in 4-8 member cyclic versions (subst/unsubst. with N, O, S)

Alternatively, ester formation can occur in one step via EDC-HOBt "peptide-type" coupling with $R_1OH$.

1) $SOCl_2$
2) $R_{26}OH$

1) $SOCl_2$
2) $R_{27}NH_2$

1) $SOCl_2$
2) $R_{28}R_{29}NH$

Alternatively, amide formation can occur in one step via EDC-HOBt "peptide-type" coupling.

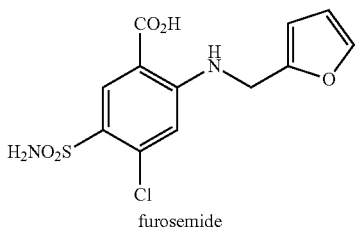

furosemide 1) base + 2 equiv. $R_{31}X$; or
2 equiv. diazoalkane
2) acid- or base-cat. ester hydroylsis 1) base + 2 equiv. $R_{31}X$; or
3 equiv. diazoalkane
2) base + $R_{31}X$
3) acid- or base-cat. ester hydroylsis 1) acid chloride reduction → $R_{30}$ = CHO, or
2) acid chloride + ammonia → $R_{30}$ = $CONH_2$ or
3) $R_{30}$ = $CONH_2$ amide + $POCl_3$ → $R_{30}$ = CN

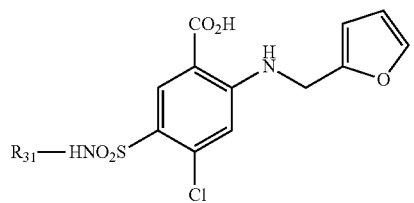

furosemide N-substituted sulfonamides
$R_{31}$ = lower alkyl, lower alkenyl, alkaryl, aryl, heterocyclic, heteroaryl

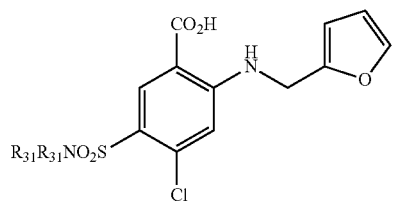

furosemide N,N-disubstituted sulfonamides
$R_{31}$ and $R_{31}$ = lower alkyl, lower alkenyl, alkaryl, aryl, heterocyclic, heteroaryl and taken together in 4-8 member cyclic versions (subst/unsubst. with N, O, and S)

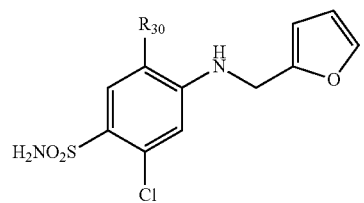

furosemide aldehyde, amide, nitrile

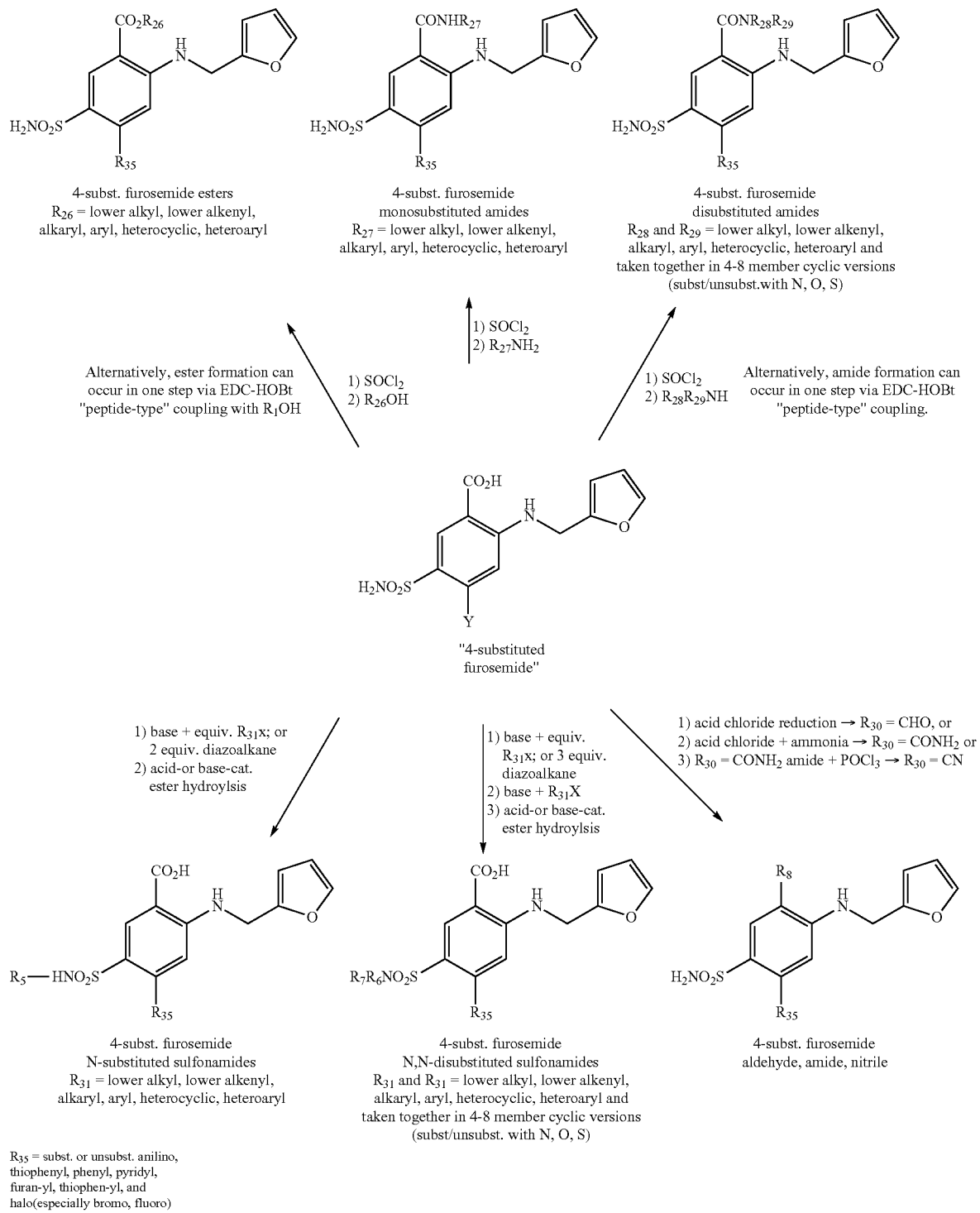

Scheme 70. 4-substituted Furosemide Esters, Amides, Sulfonamides, Aldehydes, and Nitriles

K. Additional Piretanide Analogs

Additional piretanide analogs can be synthesized according to the syntheses shown below in Schemes 71-74. In the case of an N-substituted sulfonamide having one $R_{31}$ group, $R_{31}$ is lower alkyl, lower alkenyl, alkaryl, aryl, heterocycloalkyl, or heteroaryl. In the case of a disubstituted sulfonamide having two $R_{31}$ groups, each $R_{31}$ group is the same or different and are independently lower alkyl, lower alkenyl, alkaryl, aryl, heterocycloalkyl, heteroaryl or taken together with the nitrogen atom to which they attached form a 4-8 member cycle which can be substituted or unsubstituted and can have one or more heteroatoms (e.g., N, O or S).

Scheme 71. Synthesis of Piretanide

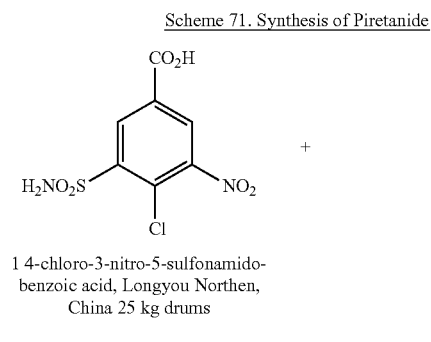

1 4-chloro-3-nitro-5-sulfonamido-
benzoic acid, Longyou Northen,
China 25 kg drums

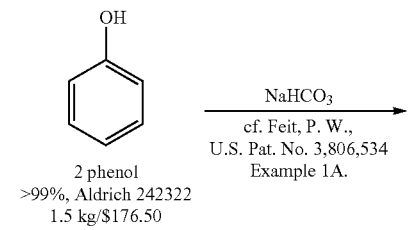

2 phenol
>99%, Aldrich 242322
1.5 kg/$176.50

NaHCO$_3$
cf. Feit, P. W.,
U.S. Pat. No. 3,806,534
Example 1A.

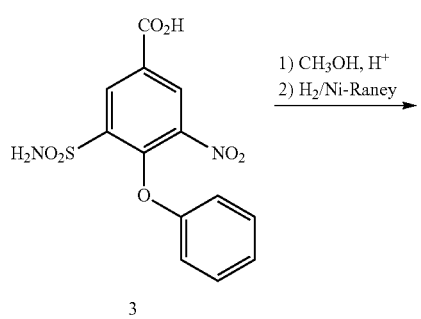

3

1) CH$_3$OH, H$^+$
2) H$_2$/Ni-Raney

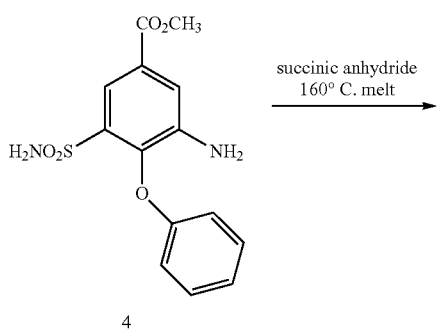

4 succinic anhydride
160° C. melt

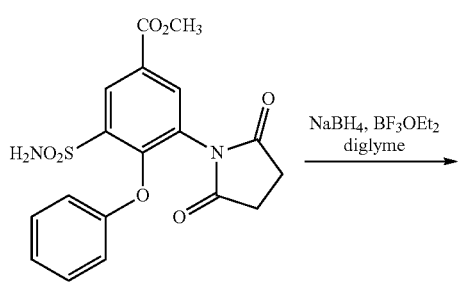

5

NaBH$_4$, BF$_3$OEt$_2$
diglyme

-continued

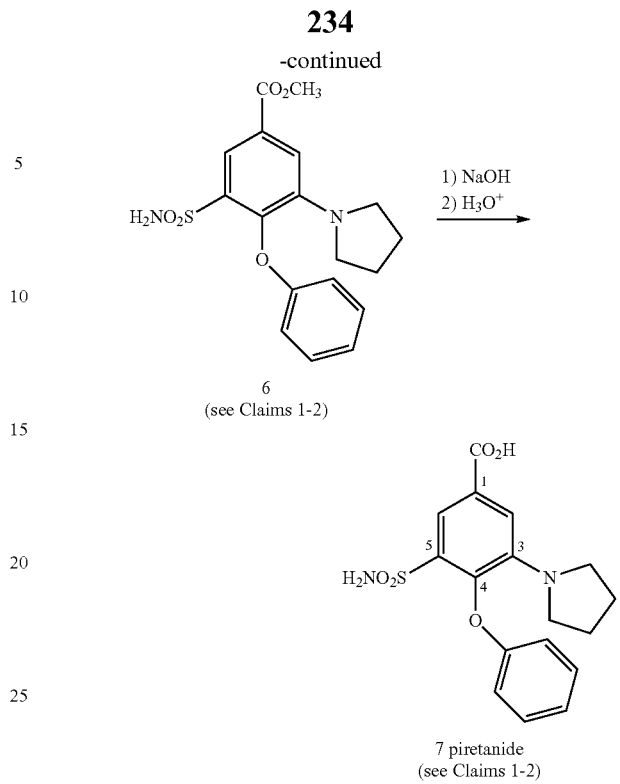

6
(see Claims 1-2)

1) NaOH
2) H$_3$O$^+$ 7 piretanide
(see Claims 1-2)

Bormann, D., Merkel, W., and Muschaweck, R.,
(Hoechst) U.S. Pat. No. 4,010,273 (Mar. 01, 1977).
25 page patent, 62 examples, 8 claims - a variety of
4-substituents are disclosed but not claimed

Scheme 72. Synthesis of 4-substituted Piretanide

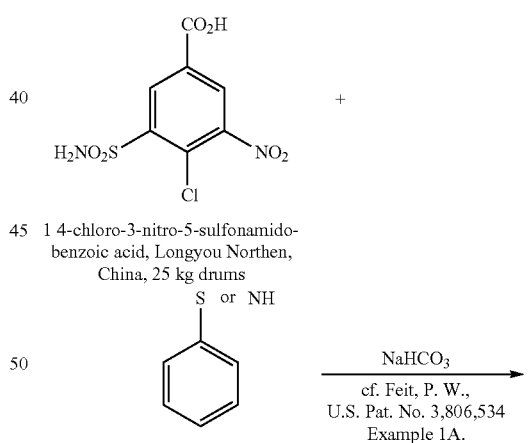

1 4-chloro-3-nitro-5-sulfonamido-
benzoic acid, Longyou Northen,
China, 25 kg drums 2 aniline (Z = NH$_2$) or
2 thiophenol (Z = SH)

NaHCO$_3$
cf. Feit, P. W.,
U.S. Pat. No. 3,806,534
Example 1A.

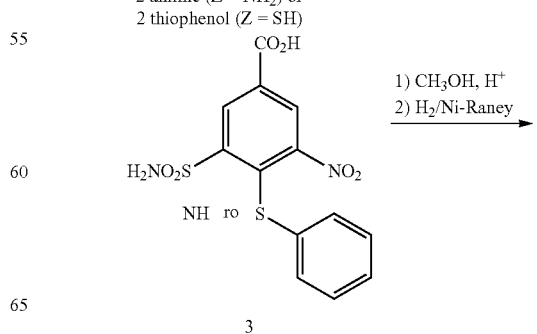

3

1) CH$_3$OH, H$^+$
2) H$_2$/Ni-Raney

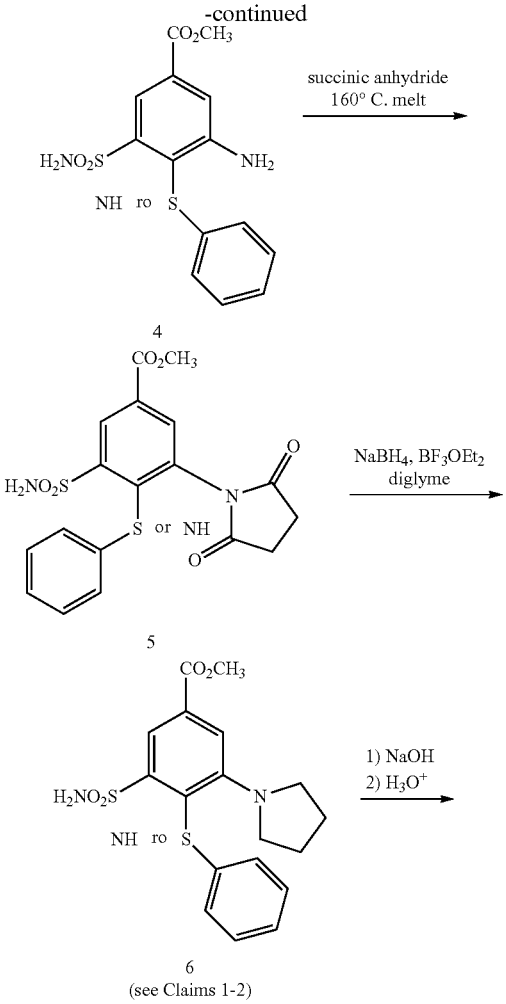
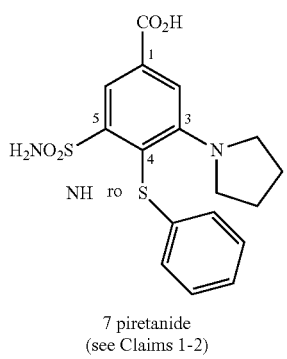

7 piretanide
(see Claims 1-2)

$R_{35}$ = subst. or unsubst. anilino, thiophenyl, phenyl, pyridyl, furan-yl, thiophen-yl, and halo (especially chloro, fluoro)

for the synthesis of other $R_{35}$ = 4-subst. analogs of piretanide, see the equivalent bumetanide schematics Scheme 73. Piretanide Esters, Amides, and Sulfonamides

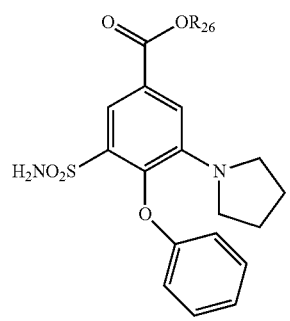

piretanide esters
$R_{26}$ = lower alkyl, lower alkenyl, alkaryl, aryl, heterocyclic, heteroaryl

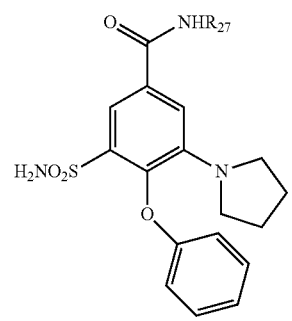

piretanide monosubstituted amides
$R_{27}$ = lower alkyl, lower alkenyl, alkaryl, aryl, heterocyclic, heteroaryl

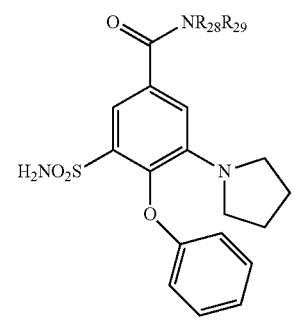

piretanide disubstituted amides
$R_{28}$ and $R_{29}$ = lower alkyl, lower alkenyl, alkaryl, aryl, heterocyclic, heteroaryl and taken together in 4-8 member cyclic versions (subst/unsubst. with N, O, S)

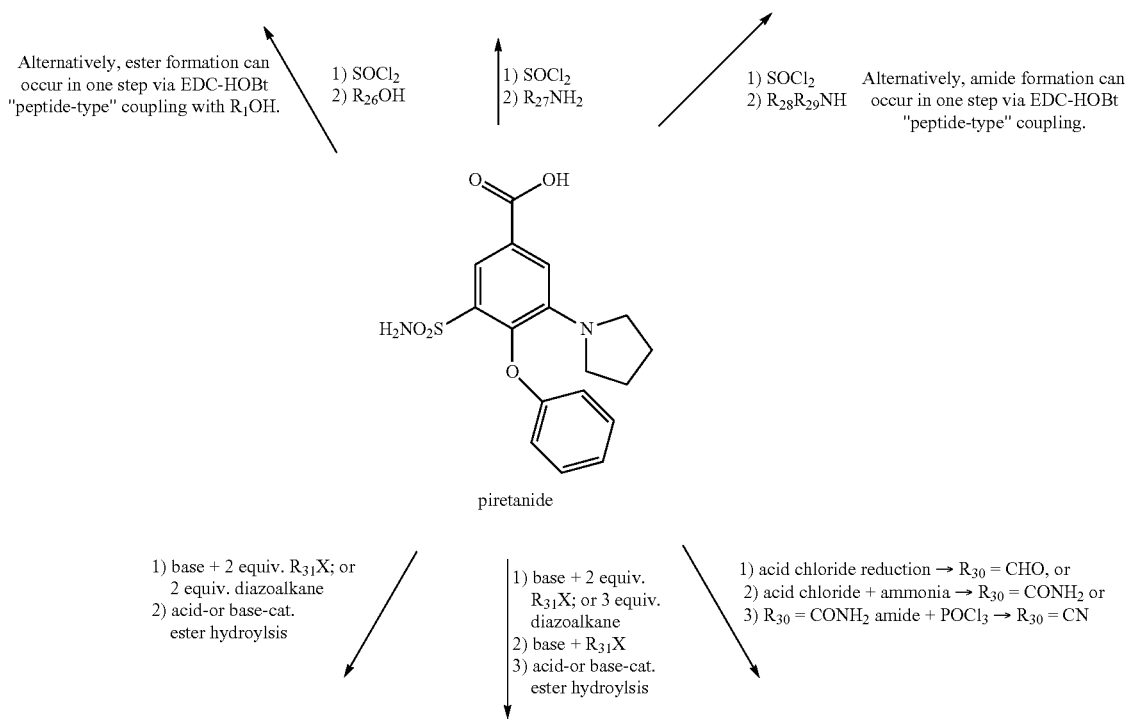
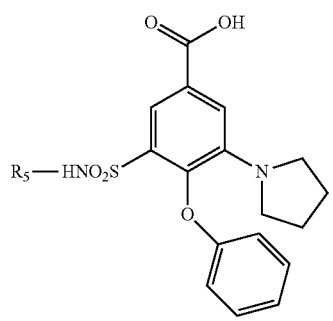
piretanide
N-substituted sulfonamides
R_31 = lower alkyl, lower alkenyl,
alkaryl, aryl, heterocyclic, heteroaryl
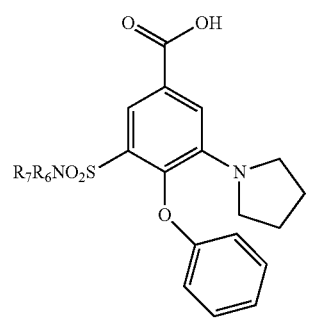
piretanide
N, N-disubstituted sulfonamides
R_31 and R_31 = lower alkyl, lower alkenyl,
alkaryl, aryl, heterocyclic, heteroaryl and taken
together in 4-8 member cyclic versions
(subst/unsubst. with N, O, S)
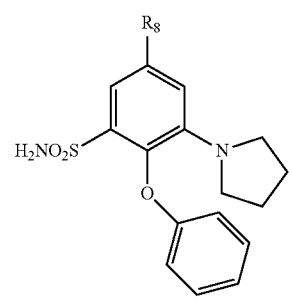
piretanide
aldehyde, amide, nitrile

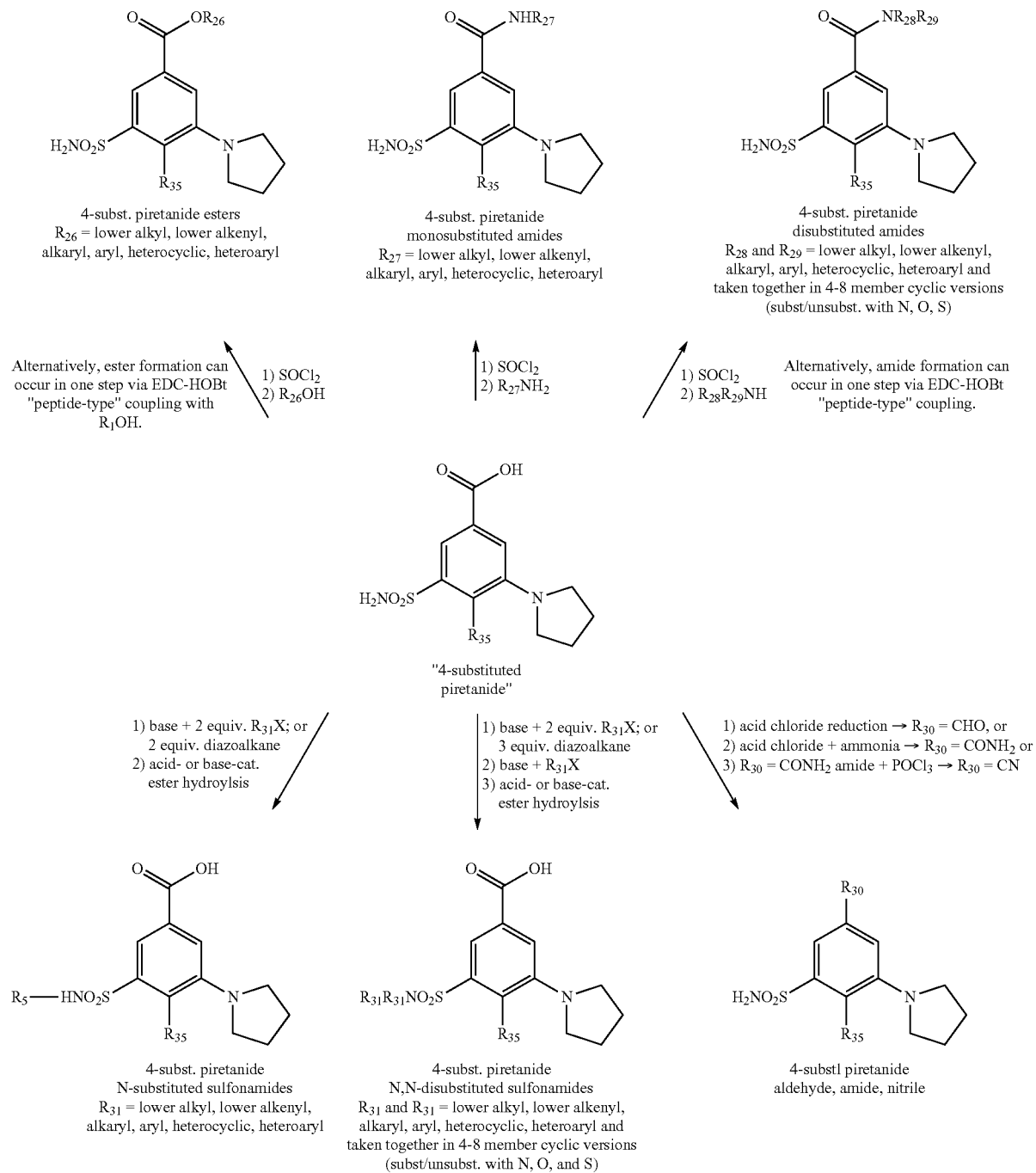

Scheme 74. 4-substituted Piretanide Esters, Amides, and Sulfonamides

L. Additional Azosemide Analogs

Additional azosemide analogs can be synthesized according to the syntheses shown below in Schemes 75-78. In the case of an N-substituted sulfonamide having one $R_{31}$ group, $R_{31}$ is lower alkyl, lower alkenyl, alkaryl, aryl, heterocycloalkyl, or heteroaryl. In the case of a disubstituted sulfonamide having two $R_{31}$ groups, each $R_{31}$ group is the same or different and are independently lower alkyl, lower alkenyl, alkaryl, aryl, heterocycloalkyl, heteroaryl or taken together with the nitrogen atom to which they attached form a 4-8 member cycle which can be substituted or unsubstituted and can have one or more heteroatoms (e.g., N, O or S).

Scheme 75. Synthesis of Azosemide
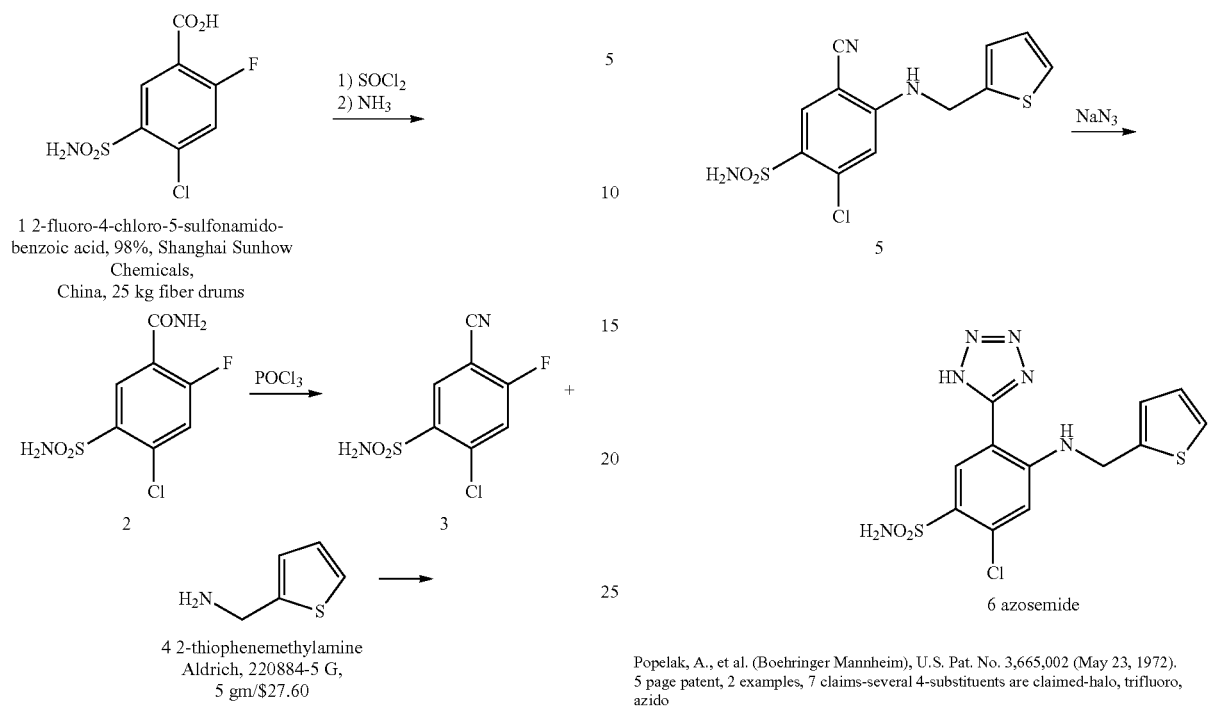
Popelak, A., et al. (Boehringer Mannheim), U.S. Pat. No. 3,665,002 (May 23, 1972).
5 page patent, 2 examples, 7 claims-several 4-substituents are claimed-halo, trifluoro, azido
Scheme 76. Synthesis of 4-substituted Azosemide
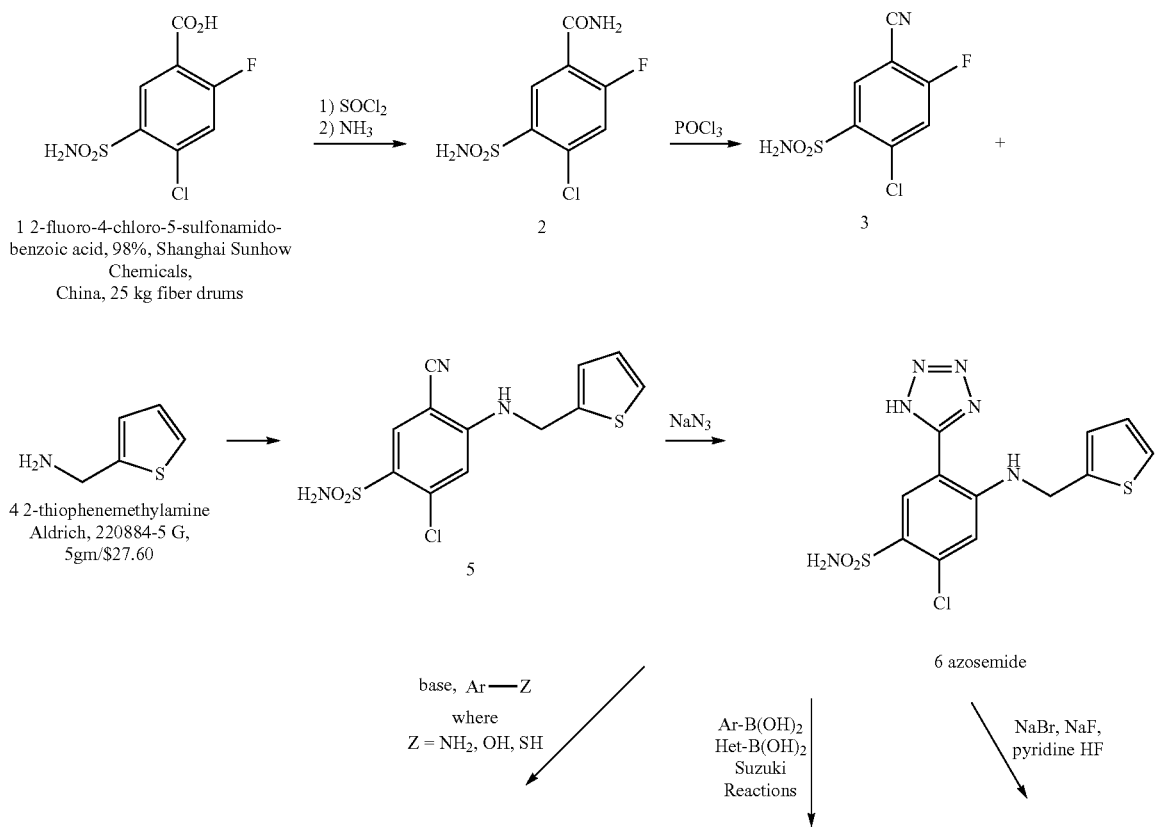

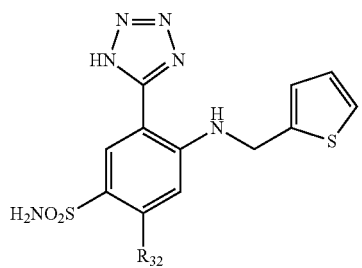

7 4-subst. azosemide
R$_{32}$ = NHAr, OAr, SAr

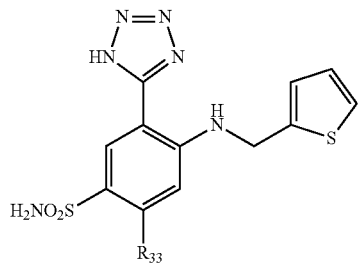

8 4-subst. azosemide
R$_{33}$ = Ar, Het

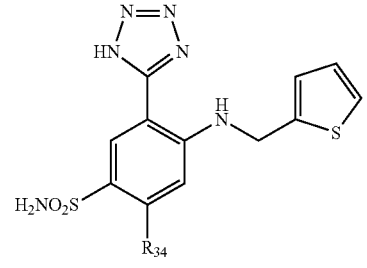

9 4-subst. azosemide
R$_{34}$ = halo (bromo, fluoro)

Scheme 77. Azosemide Esters, Amides, and Sulfonamides

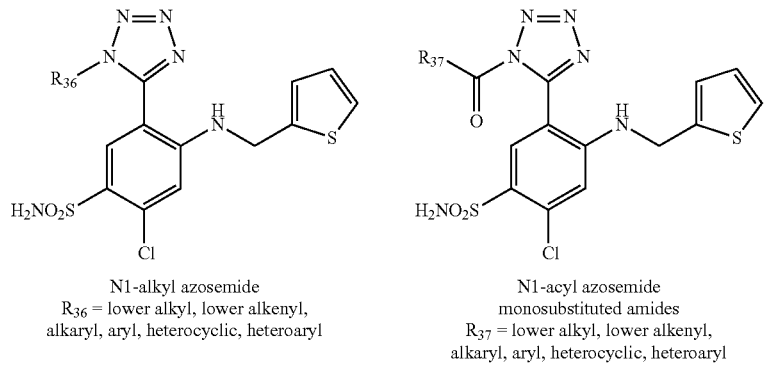

N1-alkyl azosemide
R$_{36}$ = lower alkyl, lower alkenyl,
alkaryl, aryl, heterocyclic, heteroaryl N1-acyl azosemide
monosubstituted amides
R$_{37}$ = lower alkyl, lower alkenyl,
alkaryl, aryl, heterocyclic, heteroaryl base, R$_{36}$X base, R$_{37}$COX

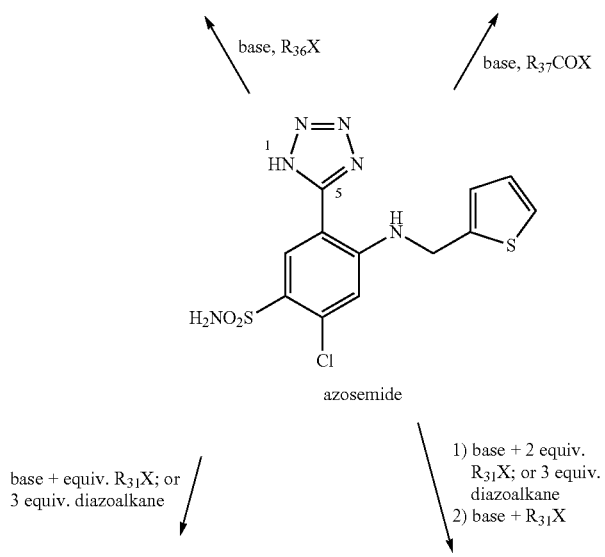

azosemide base + equiv. R$_{31}$X; or
3 equiv. diazoalkane 1) base + 2 equiv.
   R$_{31}$X; or 3 equiv.
   diazoalkane
2) base + R$_{31}$X -continued

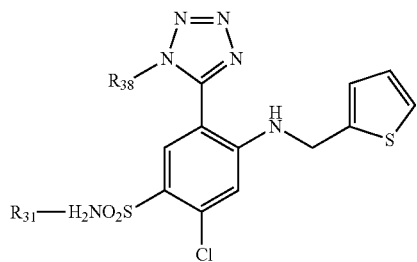

N1-alkyl azosemide
N-substituted sulfonamides
$R_{31}$ = lower alkyl, lower alkenyl,
alkaryl, aryl, heterocyclic, heteroaryl

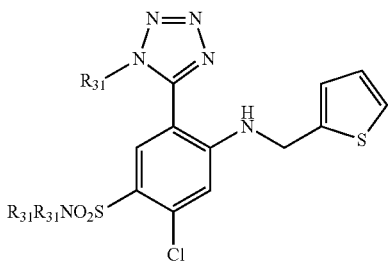

N1-alkyl azosemide
N, N-disubtituted sulfonamides
$R_{31}$ and $R_{31}$ = lower alkyl, lower alkenyl,
alkaryl, aryl, heterocyclic, heteroaryl and
taken together in 4-8 member cyclic versions
(subst/unsubst. with N, O, S)

X = halo, mesylate, tosylate

Scheme 78. 4-substituted Azosemide Esters, Amides, and Sulfonamides

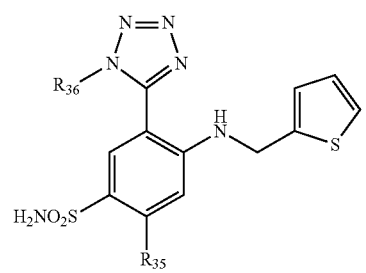

N1-alkyl azosemide
$R_{36}$ = lower alkyl, lower alkenyl,
alkaryl, aryl, heterocyclic, heteroaryl

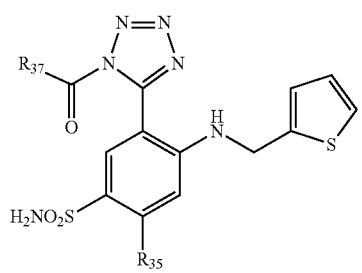

$N_1$-acyl azosemide
monosubstituted amides
$R_{37}$ = lower alkyl, lower alkenyl,
alkaryl, aryl, heterocyclic, heteroaryl ↖ base, $R_{36}$X    ↗ base, $R_{37}$COX X = halo, mesylate, tosylate $R_{35}$ = subst. or unsubst. anilino,
thiophenyl, phenyl, pyridyl,
furan-yl, thiophen-yl, and
halo (especially bromo, fluoro)

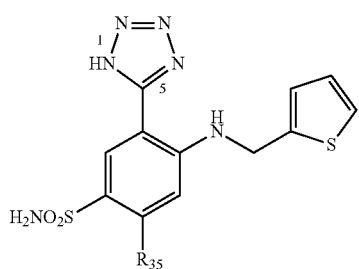

4-subst. azosemide

↙ base + 2 equiv. $R_{31}$X; or
2 equiv. diazoalkane

↘ 1) base + 2 equiv.
$R_{31}$X; or 3 equiv.
diazoalkane
2) base + $R_{31}$X

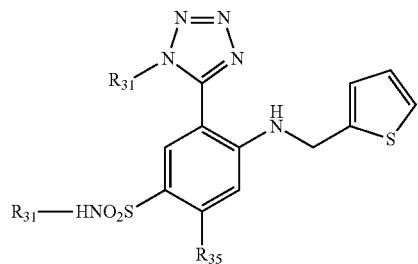

N1-alkyl azosemide
N-substituted sulfonamides
$R_{31}$ = lower alkyl, lower alkenyl,
alkaryl, aryl, heterocyclic, heteroaryl

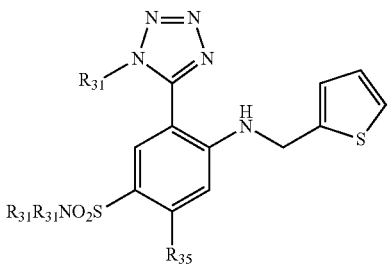

N1-alkyl azosemide
N,N-disubstituted sulfonamides
$R_{31}$ and $R_{31}$ = lower alkyl, lower alkenyl,
alkaryl, aryl, heterocyclic, heteroaryl and
taken together in 4 - 8 member cyclic versions
(subst/unsubst. with N, O, S)

M. Additional Torsemide Analogs

Additional torsemide analogs can be synthesized according to the syntheses shown below in Schemes 79-82.

Scheme 79. Synthesis of Torsemide

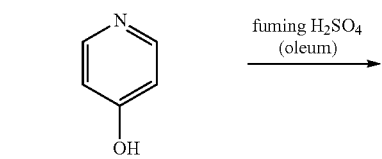

1 4-hydroxypyridine
95%, Aldrich 120618-500 G,
500 g/$348.50

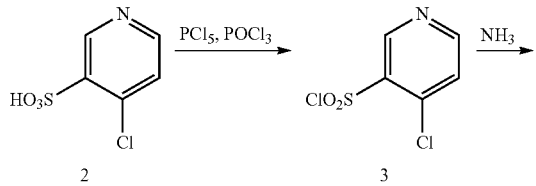

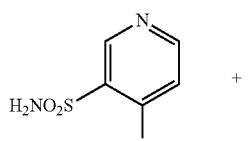

4 4-chloro-pyridine-3-
sulfonamide, Taizhou Hwasun,
China, bulk quotes

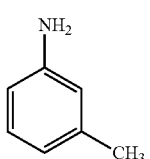

5 m-toluidine
99%, Aldrich 511218-1L
1.0 L/$68.50

-continued

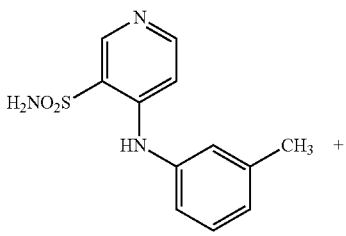

6 4-(3-methylanilino)-3-
sulfonamido-pyridine, Taizhou,
Hwasun,
China, bulk quotes

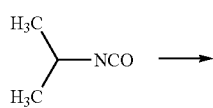

7 isopropyl isocyanate
>98%, Aldrich 141070-25 G
25 g/$78.40

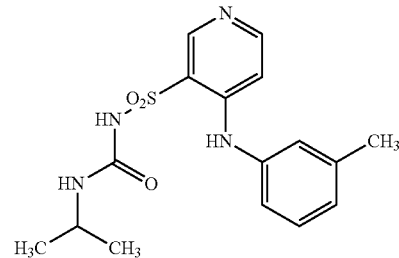

8 torsemide

Delarge, J. E.,, et al. ( A. Christiaens), U.S. Pat. No. 4,018,929 (Apr. 19, 1977);
Kordova, M. (TEVA), U.S. Pat. No. 6,670,478 B2 (Dec. 30, 2003)

Scheme 80. Synthesis of 4-substituted Torsemide
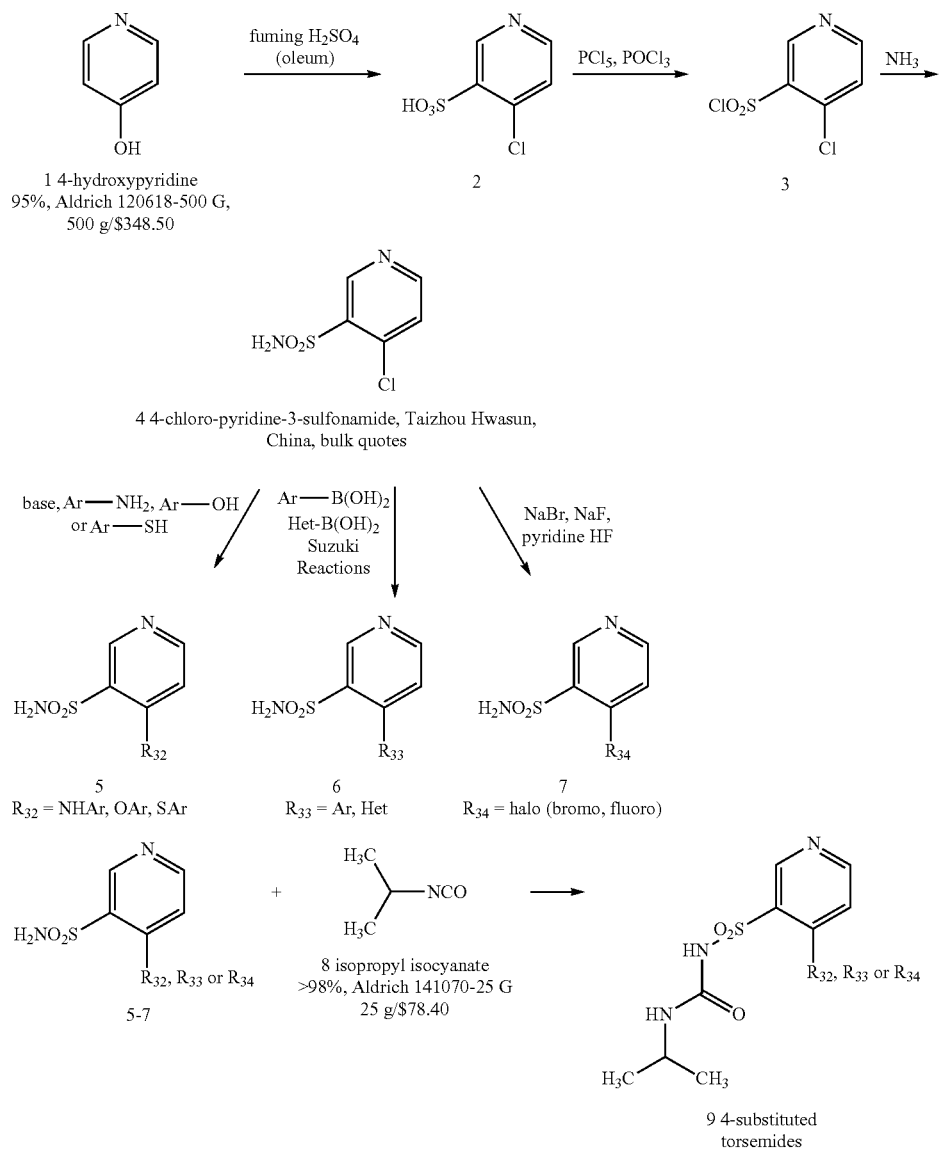
Scheme 81. Torsemide Analogs
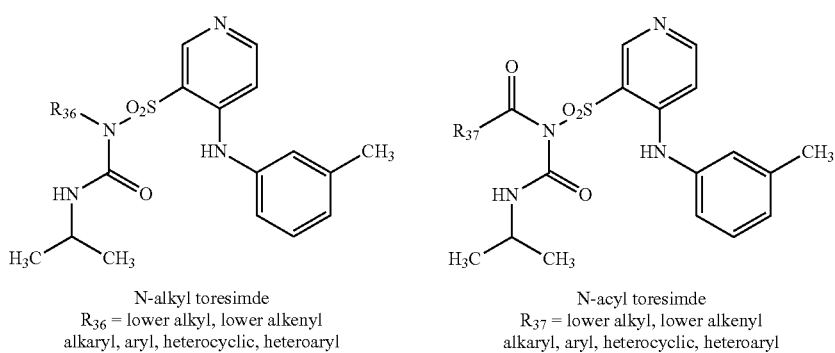

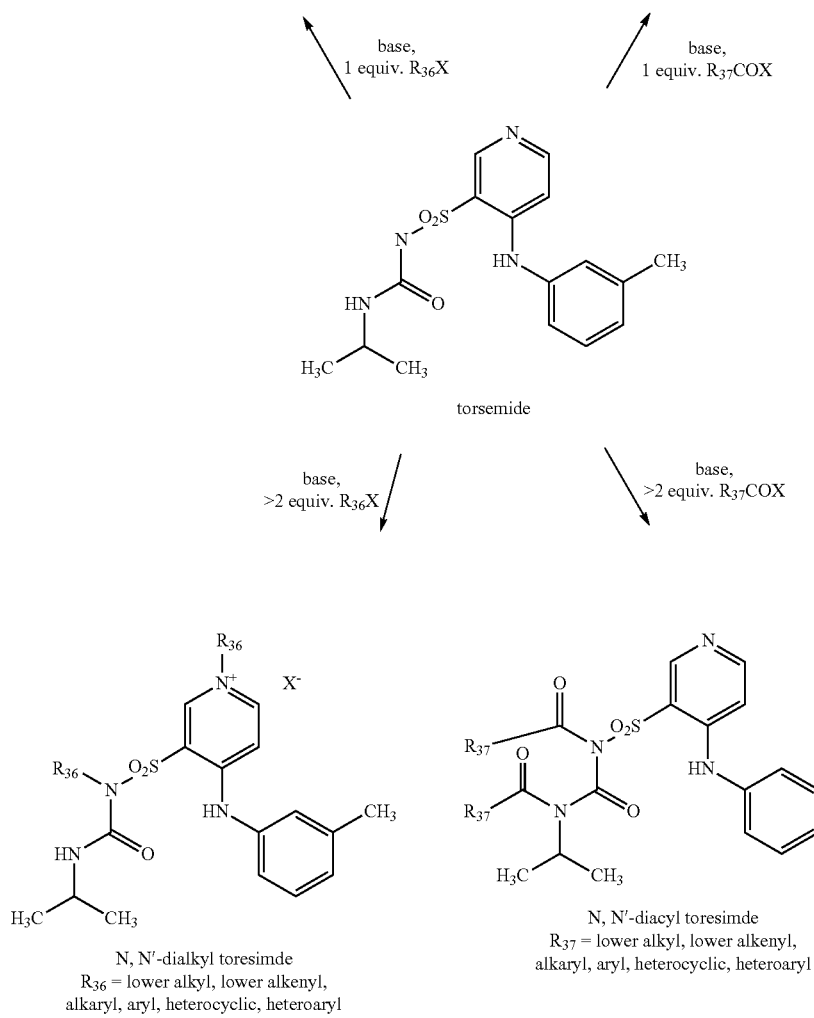
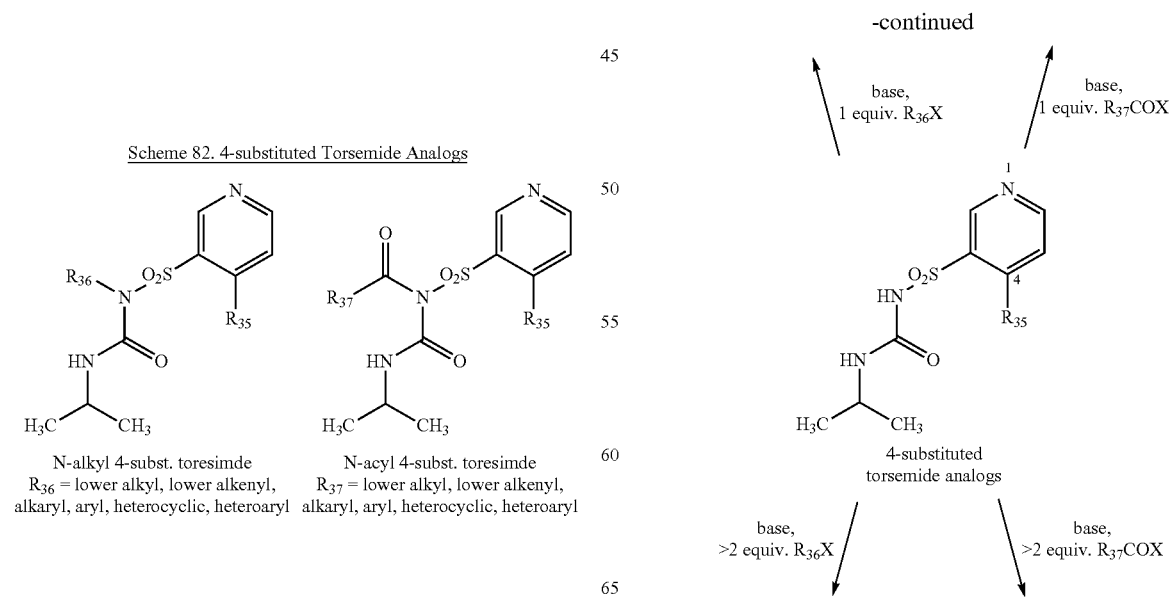
Scheme 82. 4-substituted Torsemide Analogs

N. Additional Bumetanide Analogs

Compounds can also be synthesized that are bumetanide isomers and analogs of those isomers. These so-called "bumetanide-furosemide hybrid" compounds, due to the fact that the bumetanide N-butyl group is attached at the same position where furosemide would have its furanyl methyl amino group, can be synthesized according to the syntheses shown below in Schemes 83-89. In the case of an N-substituted sulfonamide having one $R_{31}$ group, $R_{31}$ is lower alkyl, lower alkenyl, alkaryl, aryl, heterocycloalkyl, or heteroaryl. In the case of a disubstituted-sulfonamide having two $R_{31}$ groups, each $R_{31}$ group is the same or different and are independently lower alkyl, lower alkenyl, alkaryl, aryl, heterocycloalkyl, heteroaryl or taken together with the nitrogen atom to which they attached form a 4-8 member cycle which can be substituted or unsubstituted and can have one or more heteroatoms (e.g., N, O or S).

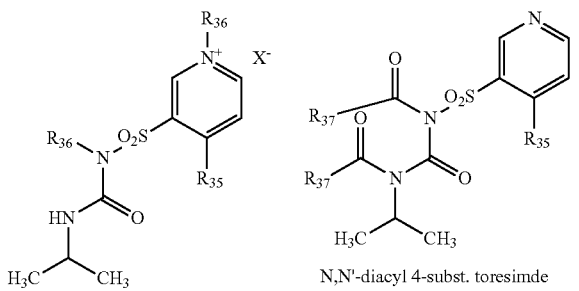

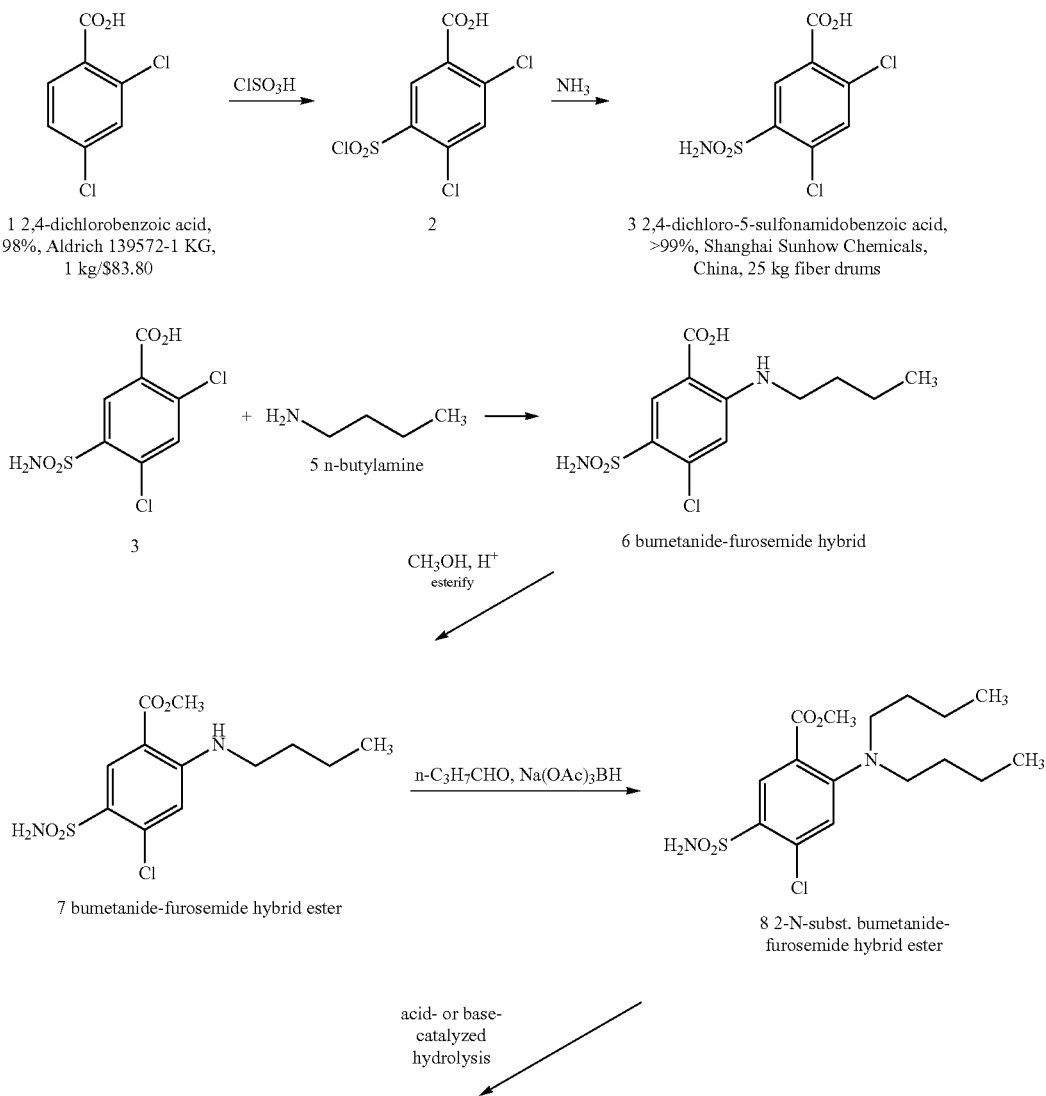

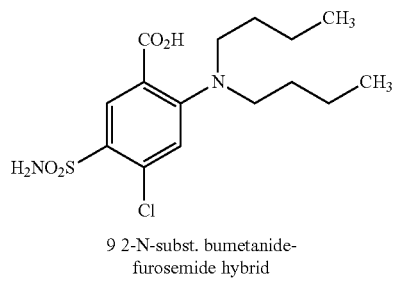
9 2-N-subst. bumetanide-furosemide hybrid
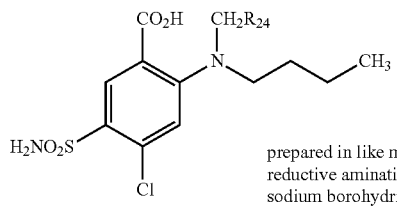
prepared in like manner by esterification, reductive amination with aldehydes + sodium borohydride derivatives and ester hydrolysis
10 2-N-subst. bumetanide-furosemide hybrid
Schemes 84 and 85. Synthesis of N-substituted Bumetanide Analogs
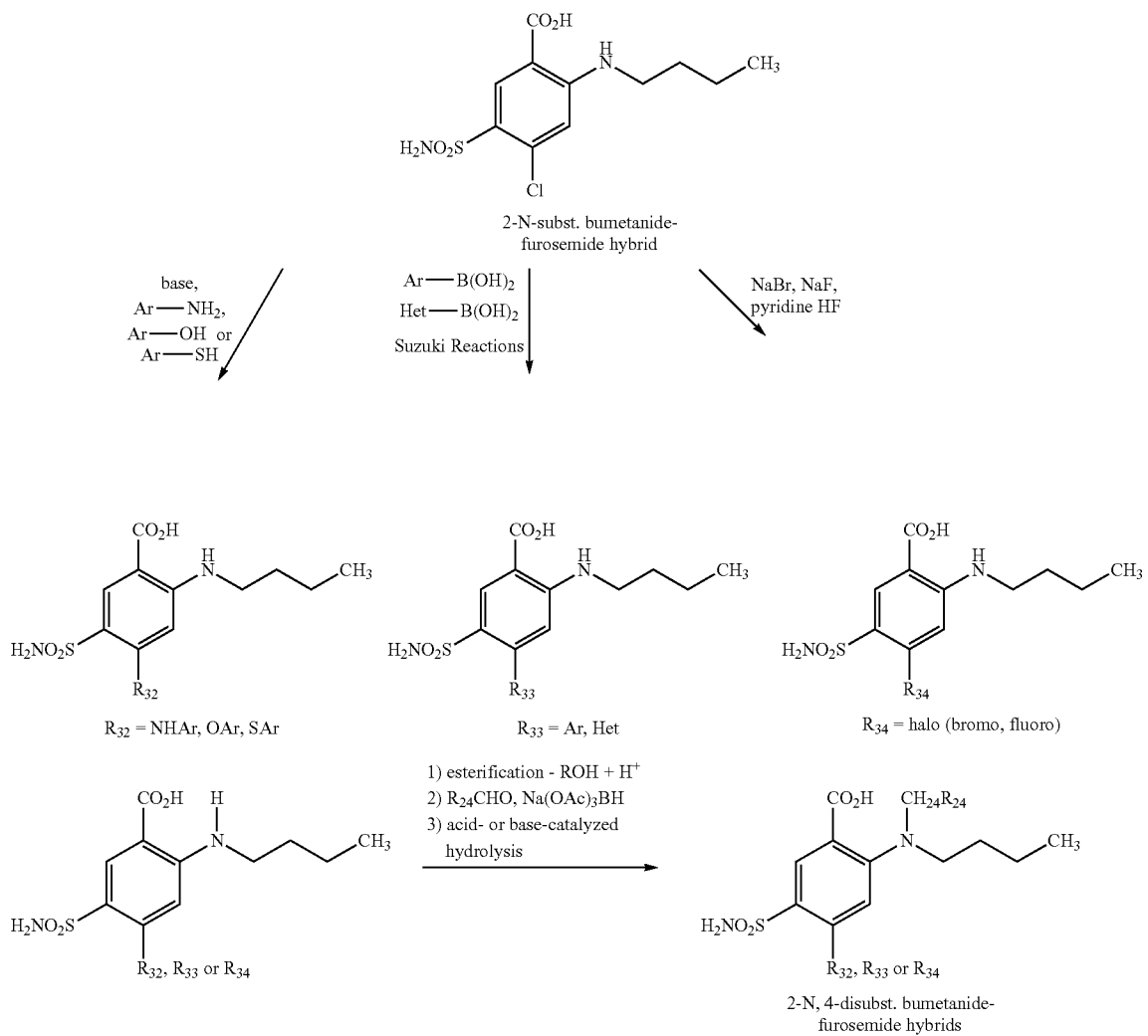

-continued

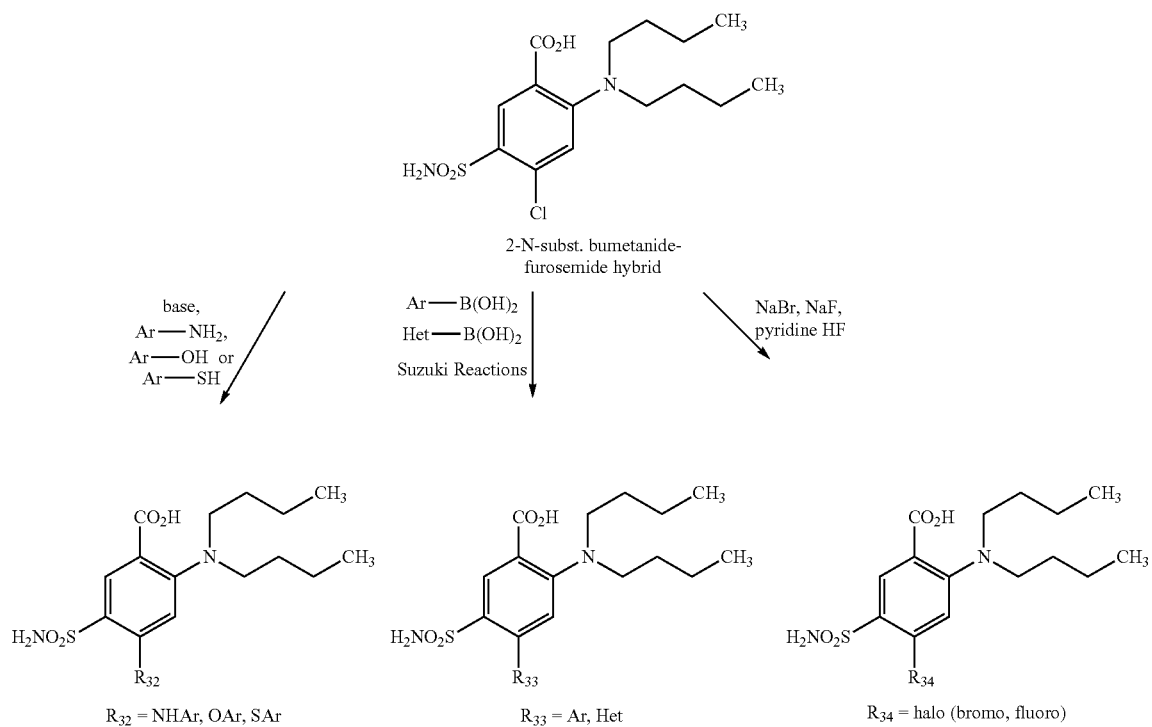

2-N-subst. bumetanide-furosemide hybrid $R_{32}$ = NHAr, OAr, SAr $R_{33}$ = Ar, Het $R_{34}$ = halo (bromo, fluoro)

1) esterification - ROH + H⁺
2) R₂₄CHO, Na(OAc)₃BH
3) acid- or base-catalyzed hydrolysis

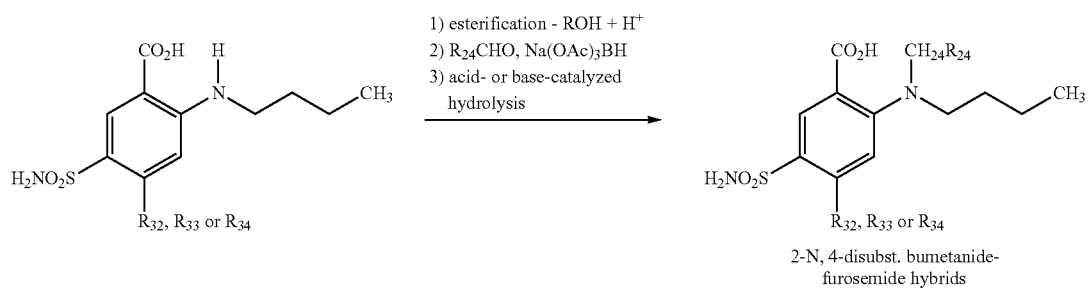

2-N, 4-disubst. bumetanide-furosemide hybrids

Schemes 86 and 87. Bumetanide and N-substituted Bumetanide Analogs

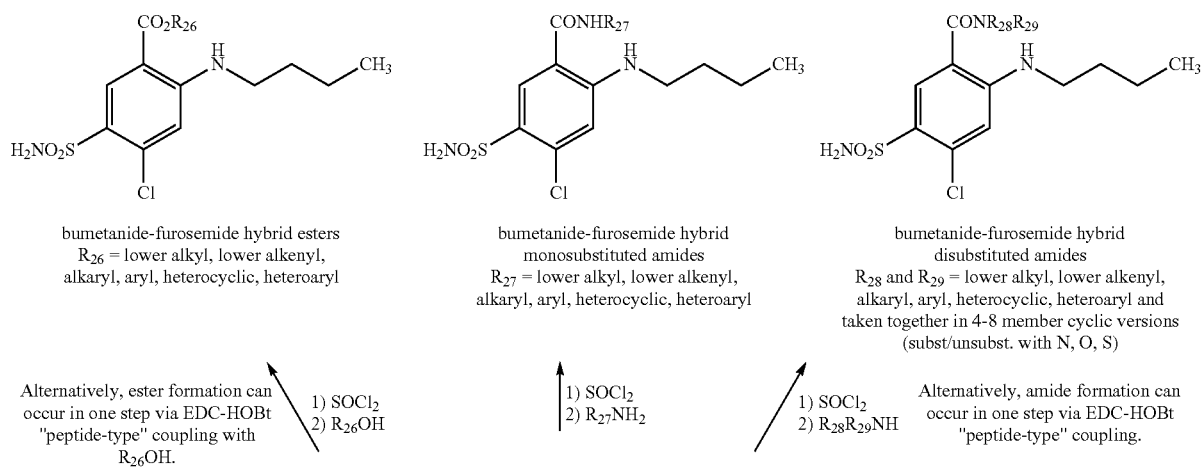

bumetanide-furosemide hybrid esters
$R_{26}$ = lower alkyl, lower alkenyl, alkaryl, aryl, heterocyclic, heteroaryl bumetanide-furosemide hybrid monosubstituted amides
$R_{27}$ = lower alkyl, lower alkenyl, alkaryl, aryl, heterocyclic, heteroaryl bumetanide-furosemide hybrid disubstituted amides
$R_{28}$ and $R_{29}$ = lower alkyl, lower alkenyl, alkaryl, aryl, heterocyclic, heteroaryl and taken together in 4-8 member cyclic versions (subst/unsubst. with N, O, S)

Alternatively, ester formation can occur in one step via EDC-HOBt "peptide-type" coupling with $R_{26}$OH.

1) SOCl₂
2) $R_{26}$OH

1) SOCl₂
2) $R_{27}$NH₂

1) SOCl₂
2) $R_{28}R_{29}$NH

Alternatively, amide formation can occur in one step via EDC-HOBt "peptide-type" coupling.

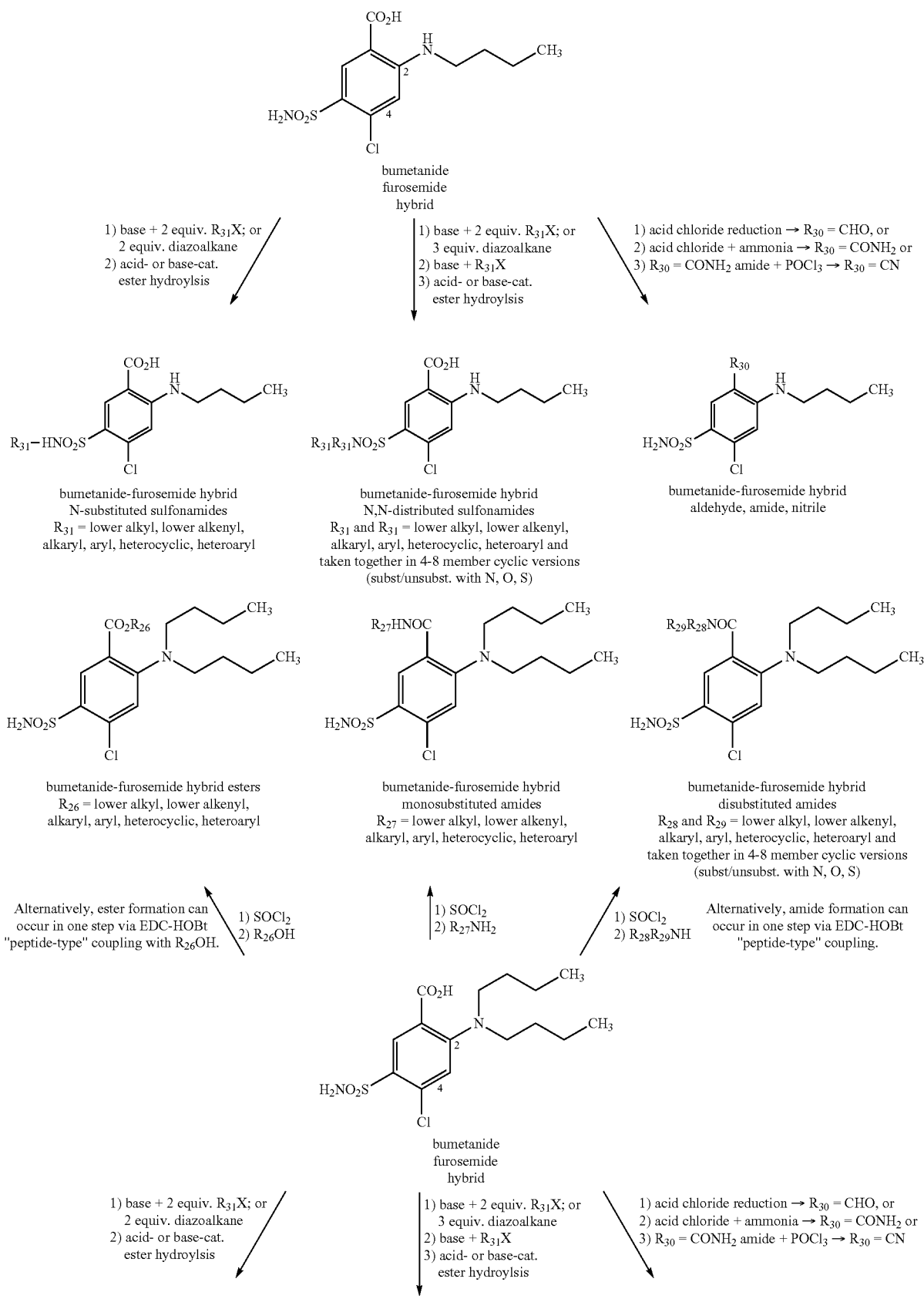

261

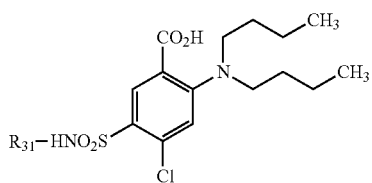

bumetanide-furosemide hybrid
N-substituted sulfonamides
$R_{31}$ = lower alkyl, lower alkenyl,
alkaryl, aryl, heterocyclic, heteroaryl -continued

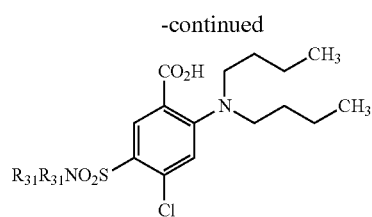

bumetanide-furosemide hybrid
N,N-distributed sulfonamides
$R_{31}$ and $R_{31}$ = lower alkyl, lower alkenyl,
alkaryl, aryl, heterocyclic, heteroaryl and
taken together in 4-8 member cyclic versions
(subst/unsubst. with N, O, S)

262

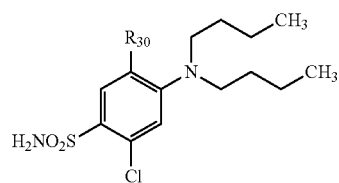

bumetanide-furosemide hybrid
aldehyde, amide, nitrile

Schemes 88 and 89. 4-substituted Bumetanide and 4-substituted N-substituted Bumetanide Analogs

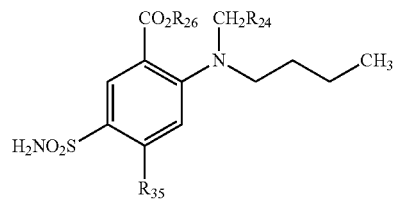

2-N,4-disubstituted
bumetanide-furosemide hybrid esters
$R_{26}$ = lower alkyl, lower alkenyl,
alkaryl, aryl, heterocyclic, heteroaryl

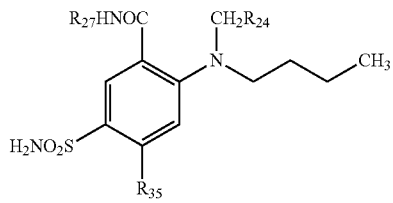

2-N,4-disubstituted
bumetanide-furosemide hybrid
monosubstituted amides
$R_{27}$ = lower alkyl, lower alkenyl,
alkaryl, aryl, heterocyclic, heteroaryl

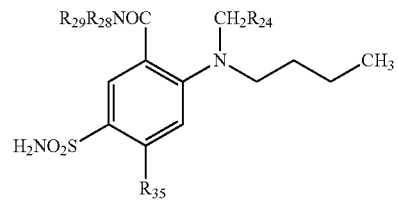

2-N,4-disubstituted
bumetanide-furosemide hybrid
disubstituted amides
$R_{28}$ and $R_{29}$ = lower alkyl, lower alkenyl,
alkaryl, aryl, heterocyclic, heteroaryl and
taken together in 4-8 member cyclic versions
(subst/unsubst. with N, O, S)

Alternatively, ester formation can occur in one step via EDC-HOBt "peptide-type" coupling with $R_{26}$OH.

1) $SOCl_2$
2) $R_{26}OH$

1) $SOCl_2$
2) $R_{27}NH_2$

1) $SOCl_2$
2) $R_{28}R_{29}NH$

Alternatively, amide formation can occur in one step via EDC-HOBt "peptide-type" coupling.

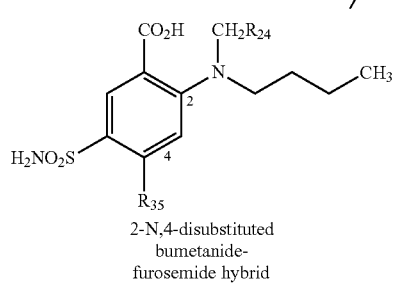

2-N,4-disubstituted
bumetanide-
furosemide hybrid 1) base + 2 equiv. $R_{31}X$; or
2 equiv. diazoalkane
2) acid- or base-cat.
ester hydroylsis 1) base + 2 equiv. $R_{31}X$; or
3 equiv. diazoalkane
2) base + $R_{31}X$
3) acid- or base-cat.
ester hydroylsis 1) acid chloride reduction → $R_{30}$ = CHO, or
2) acid chloride + ammonia → $R_{30}$ = $CONH_2$ or
3) $R_{30}$ = $CONH_2$ amide + $POCl_3$ → $R_{30}$ = CN

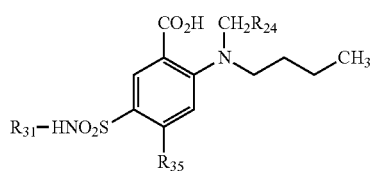

2-N,4-disubstituted
bumetanide-furosemide hybrid
N-substituted sulfonamides
$R_{31}$ = lower alkyl, lower alkenyl,
alkaryl, aryl, heterocyclic, heteroaryl

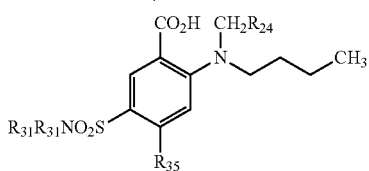

2-N,4-disubstituted
bumetanide-furosemide hybrid
N,N-distributed sulfonamides
$R_{31}$ and $R_{31}$ = lower alkyl, lower alkenyl,
alkaryl, aryl, heterocyclic, heteroaryl and
taken together in 4-8 member cyclic versions
(subst/unsubst. with N, O, S)

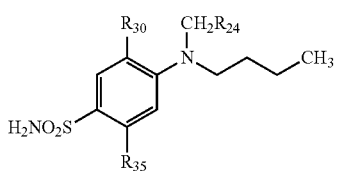

2-N,4-disubstituted
bumetanide-furosemide hybrid
aldehyde, amide, nitrile

-continued

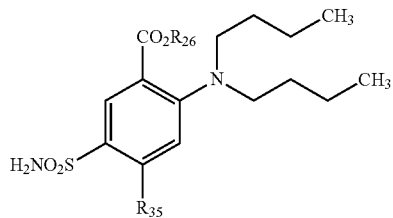
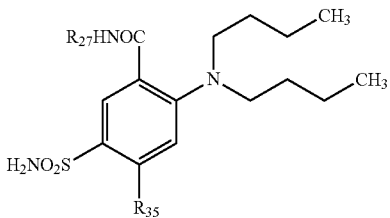
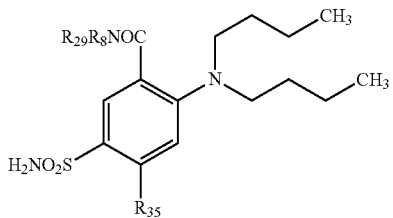

2-N,4-disubstituted bumetanide-furosemide hybrid esters
$R_{26}$ = lower alkyl, lower alkenyl, alkaryl, aryl, heterocyclic, heteroaryl 2-N,4-disubstituted bumetanide-furosemide hybrid monosubstituted amides
$R_{27}$ = lower alkyl, lower alkenyl, alkaryl, aryl, heterocyclic, heteroaryl 2-N,4-disubstituted bumetanide-furosemide hybrid disubstituted amides
$R_{28}$ and $R_{29}$ = lower alkyl, lower alkenyl, alkaryl, aryl, heterocyclic, heteroaryl and taken together in 4-8 member cyclic versions (subst/unsubst. with N, O, S)

Alternatively, ester formation can occur in one step via EDC-HOBt "peptide-type" coupling with $R_{26}$OH.
1) $SOCl_2$
2) $R_{26}$OH 1) $SOCl_2$
2) $R_{27}NH_2$ 1) $SOCl_2$
2) $R_{28}R_{29}NH$ Alternatively, amide formation can occur in one step via EDC-HOBt "peptide-type" coupling.

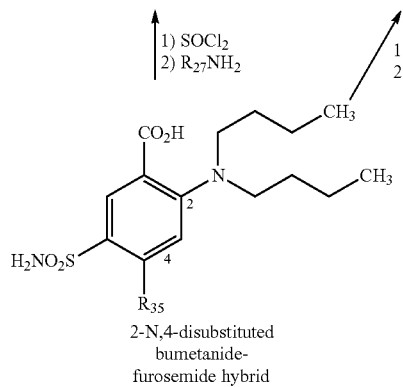

2-N,4-disubstituted bumetanide-furosemide hybrid 1) base + 2 equiv. $R_{31}X$; or 2 equiv. diazoalkane
2) acid- or base-cat. ester hydroylsis 1) base + 2 equiv. $R_{31}X$; or 3 equiv. diazoalkane
2) base + $R_{31}X$
3) acid- or base-cat. ester hydroylsis 1) acid chloride reduction → $R_{30}$ = CHO, or
2) acid chloride + ammonia → $R_{30}$ = $CONH_2$ or
3) $R_{30}$ = $CONH_2$ amide + $POCl_3$ → $R_{30}$ = CN

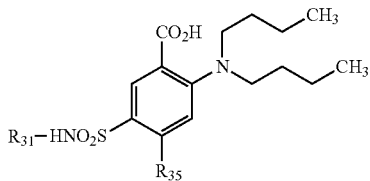
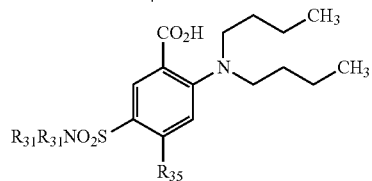
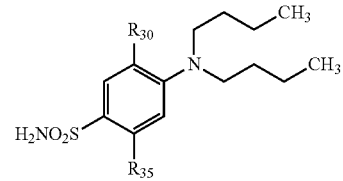

2-N,4-disubstituted bumetanide-furosemide hybrid N-substituted sulfonamides
$R_{31}$ = lower alkyl, lower alkenyl, alkaryl, aryl, heterocyclic, heteroaryl 2-N,4-disubstituted bumetanide-furosemide hybrid N,N-distributed sulfonamides
$R_{31}$ and $R_{31}$ = lower alkyl, lower alkenyl, alkaryl, aryl, heterocyclic, heteroaryl and taken together in 4-8 member cyclic versions (subst/unsubst. with N, O, S)

2-N,4-disubstituted bumetanide-furosemide hybrid aldehyde, amide, nitrile

O. Azosemide Analogs Thereof

Compounds can also be synthesized that are azosemide derivatives and analogs thereof. These so-called "azosemide-bumetanide-furosemide hybrid" compounds, due to the fact that they have the azosemide tetrazole and the bumetanide N-butyl group attached at the same position where furosemide would have its furanyl methyl amino group, can be synthesized according to the syntheses shown below in Schemes 90-94. In the case of an N-substituted sulfonamide having one $R_{31}$ group, $R_{31}$ is lower alkyl, lower alkenyl, alkaryl, aryl, heterocycloalkyl, or heteroaryl. In the case of a disubstituted sulfonamide having two $R_{31}$ groups, each $R_{31}$ group is the same or different and are independently lower alkyl, lower alkenyl, alkaryl, aryl, heterocycloalkyl, heteroaryl or taken together with the nitrogen atom to which they attached form a 4-8 member cycle which can be substituted or unsubstituted and can have one or more heteroatoms (e.g., N, O or S).

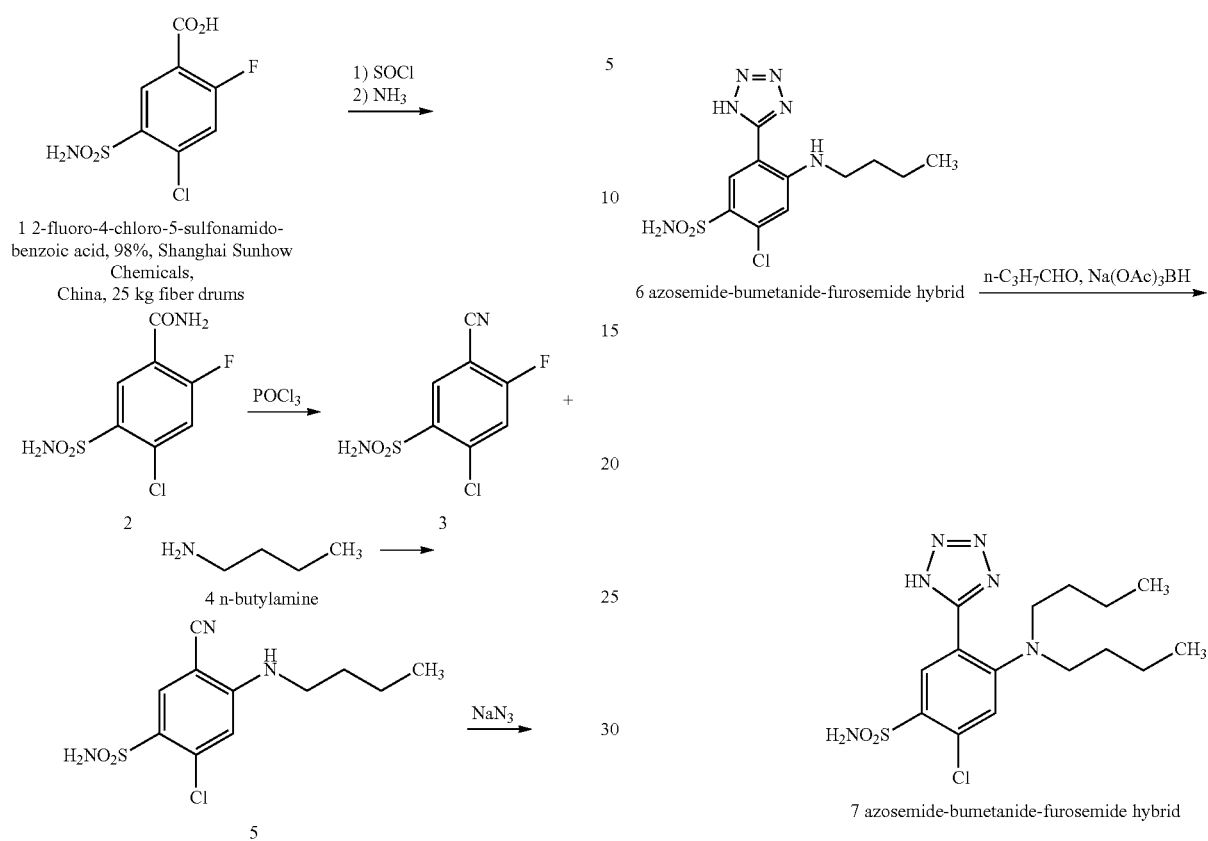
Scheme 90. Synthesis of Azosemide Analogs
Scheme 91. Synthesis of N-substituted Azosemide Analogs -continued

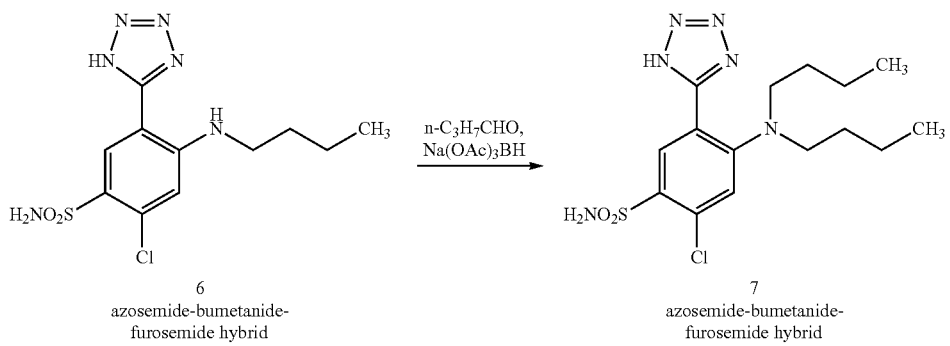

6
azosemide-bumetanide-
furosemide hybrid 7
azosemide-bumetanide-
furosemide hybrid 6 or 7 a) base,
  Ar—NH$_2$,
  Ar—OH or
  Ar—SH or
b) Ar—B(OH)$_2$ or
  Het—B(OH)$_2$),
  Suzuki Reactions or
c) NaBr, NaF,
  pyridine HF

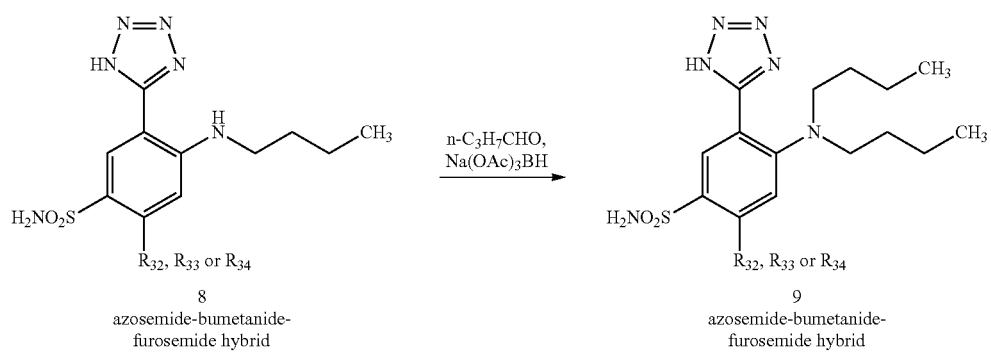

8
azosemide-bumetanide-
furosemide hybrid 9
azosemide-bumetanide-
furosemide hybrid $R_{32}$ = NHAr, OAr, SAr
$R_{33}$ = Ar, Het
$R_{34}$ = halo, bromo, fluoro Schemes 92, 93, and 94. Azosemide Analogs

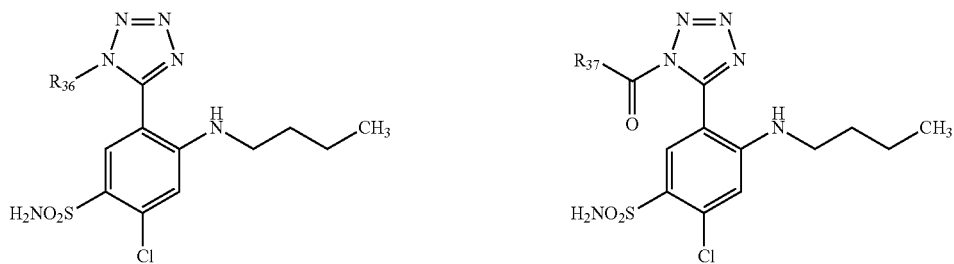

azosemide-bumetanide-furosemide hybrid
$R_{36}$ = lower alkyl, lower alkenyl,
alkaryl, aryl, heterocyclic, heteroaryl azosemide-bumetanide-furosemide hybrid
monosubstituted amides
$R_{37}$ = lower alkyl, lower alkenyl,
alkaryl, aryl, heterocyclic, heteroaryl base, $R_{36}X$ base, $R_{37}COX$ -continued

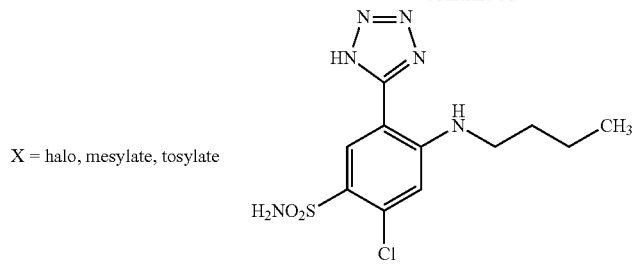

X = halo, mesylate, tosylate azosemide-bumetanide-furosemide hybrid base + 2 equiv. R₃₁X; or
2 equiv. diazoalkane 1) base + 2 equiv. R₃₁X; or 3 equiv. diazoalkane
2) base + R₃₁X

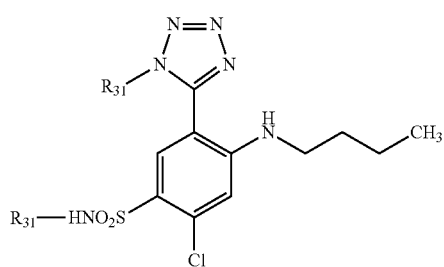

bumetanide-furosemide hybrid
N-substituted sulfonamides
R₃₁ = lower alkyl, lower alkenyl, alkaryl, aryl, heterocyclic, heteroaryl

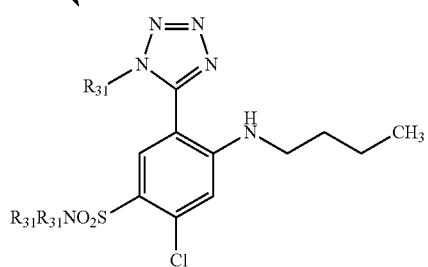

bumetanide-furosemide hybrid
N,N-disubstituted sulfonamides
R₃₁ and R₃₁' = lower alkyl, lower alkenyl, alkaryl, aryl, heterocyclic, heteroaryl and taken together in 4-8 member cyclic versions (subst./unsubst. with N, O, S)

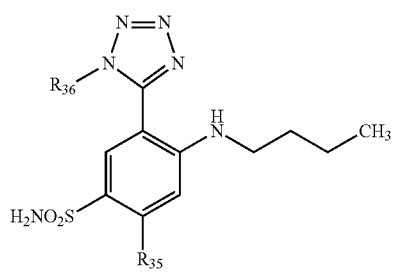

azosemide-bumetanide-furosemide hybrid
R₃₆ = lower alkyl, lower alkenyl, alkaryl, aryl, heterocyclic, heteroaryl

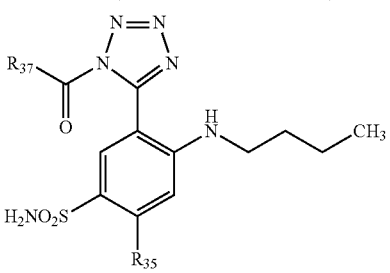

azosemide-bumetanide-furosemide hybrid
monosubstituted amides
R₃₇ = lower alkyl, lower alkenyl, alkaryl, aryl, heterocyclic, heteroaryl base, R₃₆X base, R₃₇COX

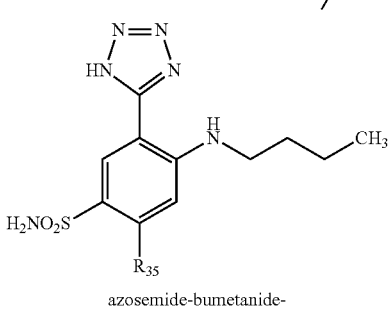

X = halo, mesylate, tosylate
R₃₅ = subst. or unsubst. anilino, thiphenyl, phenyl, pyridyl, furan-yl, thiophen-yl, and halo (especially bromo, fluoro)

azosemide-bumetanide-furosemide hybrid base + 2 equiv. R₃₁X; or
2 equiv. diazoalkane 1) base + 2 equiv. R₃₁X; or 3 equiv. diazoalkane
2) base + R₃₁X -continued

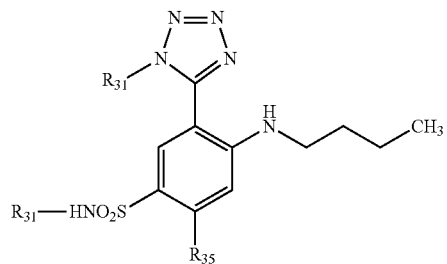

bumetanide-furosemide hybrid
N-substituted sulfonamides
$R_{31}$ = lower alkyl, lower alkenyl,
alkaryl, aryl, heterocyclic, heteroaryl

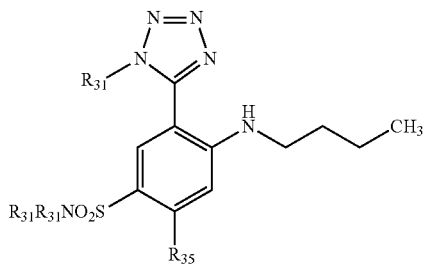

bumetanide-furosemide hybrid
N,N-disubstituted sulfonamides
$R_{31}$ and $R_{31}$ = lower alkyl, lower alkenyl,
alkaryl, aryl, heterocyclic, heteroaryl and
taken together in 4-8 member cyclic versions
(subst./unsubst. with N, O, S)

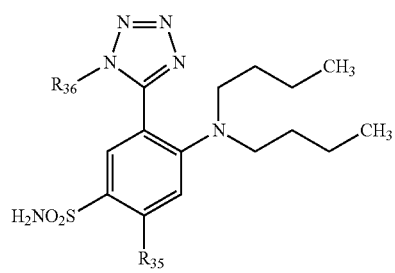

azosemide-bumetanide-furosemide hybrid
$R_{36}$ = lower alkyl, lower alkenyl,
alkaryl, aryl, heterocyclic, heteroaryl

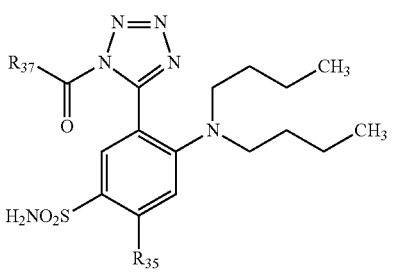

azosemide-bumetanide-furosemide hybrid
monosubstituted amides
$R_{37}$ = lower alkyl, lower alkenyl,
alkaryl, aryl, heterocyclic, heteroaryl ↖ base, $R_{36}$X  ↗ base, $R_{37}$COX

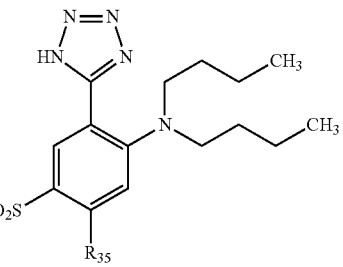

azosemide-bumetanide-
furosemide hybrid

X = halo, mesylate, tosylate
$R_{35}$ = subst. or unsubst. anilino,
thiphenyl, phenyl, pyridyl,
furan-yl, thiophen-yl, and
halo (especially bromo, fluoro)

base + 2 equiv. $R_{31}$X; or
2 equiv. diazoalkane ↙

1) base + 2 equiv.
   $R_{31}$X; or 3 equiv.
   diazoalkane
2) base + $R_{31}$X ↘

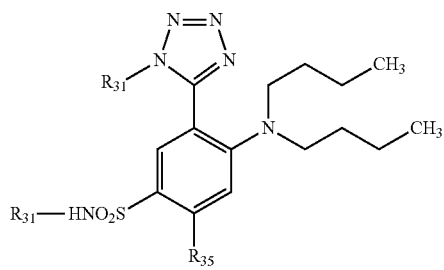

bumetanide-furosemide hybrid
N-substituted sulfonamides
$R_{31}$ = lower alkyl, lower alkenyl,
alkaryl, aryl, heterocyclic, heteroaryl

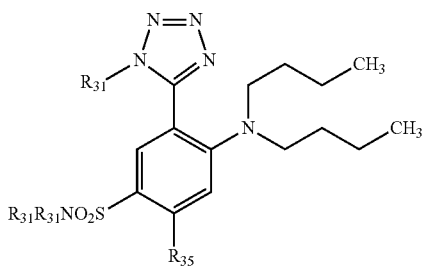

bumetanide-furosemide hybrid
N,N-disubstituted sulfonamides
$R_{31}$ and $R_{31}$ = lower alkyl, lower alkenyl,
alkaryl, aryl, heterocyclic, heteroaryl and
taken together in 4-8 member cyclic versions
(subst./unsubst. with N, O, S)

Starting materials for synthesizing compounds of the present invention can further include compounds described in U.S. Pat. Nos. 3,634,583; 3,806,534; 3,058,882; 4,010,273; 3,665,002; and 3,665,002.

Compounds of the present invention can include isomers, tautomers, zwitterions, enantiomers, diastereomers, racemates, or stereochemical mixtures thereof. Compounds of the present invention can also comprise isosteres.

The term "isosteres" as used herein broadly refers to elements, functional groups, substituents, molecules, or ions having different molecular formulae but exhibiting similar or identical physical properties. For example, tetrazole is an isostere of carboxylic acid because it mimics the properties of carboxylic acid even though they both have different molecular formulae. Typically, two isosteric molecules have similar or identical volumes and shapes. Other physical properties that isosteric compounds usually share include boiling point, density, viscosity, and thermal conductivity. However, certain properties are usually different: dipolar moments, polarity, polarization, size, and shape since the external orbitals may be hybridized differently.

The term "isomers" as used herein refers broadly to compounds having the same number and kind of atoms, and hence the same molecular weight, but differing with respect to the arrangement or configuration of the atoms in space. Additionally, the term "isomers" includes stereoisomers and geometric isomers. The terms "stereoisomer" or "optical isomer" as used herein refer to a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure can exist in some of the compounds of the present invention, which may give rise to stereoisomerism, the invention contemplates stereoisomers and mixtures thereof. The compounds of the present invention and their salts can include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. Tautomers are readily interconvertible constitutional isomers and there is a change in connectivity of a ligand, as in the keto and enol forms of ethyl acetoacetate (including tautomers of any said compounds.) Zwitterions are inner salts or dipolar compounds possessing acidic and basic groups in the same molecule. At neutral pH, the cation and anion of most zwitterions are-equally ionized.

3. Pharmaceutical Compositions

The compounds (e.g., analogs, derivatives, and prodrugs) of the present invention or pharmacologically acceptable salts thereof may be formulated into pharmaceutical compositions of various dosage forms. To prepare the pharmaceutical compositions of the invention, at least one compound or pharmaceutically acceptable salts thereof as the active ingredient is intimately mixed with appropriate carriers and additives according to techniques well known to those skilled in the art of pharmaceutical formulations. *Remington, The Science And Practice of Pharmacy.* 20*th Edition*, (Gennaro, A. R., Chief Editor), Philadelphia College of Pharmacy and Science, 2000, which is incorporated by reference in its entirety.

Pharmaceutically acceptable salts of the compounds described herein include the salt form of the compound permitting its use or formulation as a pharmaceutical and which retains the biological effectiveness of the free acid and base of the specified compound and that is not biologically or otherwise undesirable. Examples of such salts are described in Wermuth and Stahl, (Eds.) (2002) Handbook of Pharmaceutical Salts: Properties, Selection, and Use, Wiley-Verlag Helvetica Acta, Zürich, herein incorporated by references in its-entirety. Examples of such salts-include alkali metal salts andaddition salts of free acids and bases. Examples of pharmaceutically acceptable salts, without limitation, include sulfates, pyrosulfates, bisulfates, sulfites, bisulfites, phosphates, monohydrogenphosphates, dihydrogen phosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, xylenesulfonates, phenylacetates, phenylpropionates, phenylbutyrates, citrates, lactates, γ-hydroxybutyrates, glycollates, tartrates, methanesulfonates, ethane sulfonates, propanesulfonates, toluenesulfonates, naphthalene-1-sulfonates, naphthalene-2-sulfonates, and mandelates. In some embodiments, pharmaceutically acceptable salt includes sodium, potassium, calcium, ammonium, trialkylarylammonium, and tetraalkylammonium salts.

The carriers and additives used for such pharmaceutical compositions can take a variety of forms depending on the anticipated mode of administration. Thus, compositions for oral administration may be solid preparations including but not limited to tablets, sugar-coated tablets, hard capsules, soft capsules, granules, lozenges, and powders, with suitable carriers and additives being starches, sugars, binders, diluents, granulating agents, lubricants, and disintegrating agents. Because of their ease of use and higher patient compliance, tablets and capsules represent advantageous oral dosage forms for many medical conditions.

Similarly, compositions for liquid preparations include solutions, emulsions, dispersions, suspensions, syrups, and elixirs, with suitable carriers and additives including but not limited to water, alcohols, oils, glycols, preservatives, flavoring agents, coloring agents, and suspending agents. Typical preparations for parenteral administration comprise the active ingredient with a carrier such as sterile water or parenterally acceptable oil including but not limited to polyethylene glycol, polyvinyl pyrrolidone, lecithin, arachis oil or sesame oil, with other additives for aiding solubility or preservation may also be included. In the case of a solution, it can be lyophilized to a powder and then reconstituted immediately prior to use. For dispersions and suspensions, appropriate carriers and additives include aqueous gums, celluloses, silicates, or oils.

The pharmaceutical compositions according to embodiments of the present invention include those suitable for oral, rectal, topical, nasal, inhalation (e.g., via an aerosol) buccal (e.g., sub-lingual), vaginal, topical (e.g., both skin and mucosal surfaces, including airway surfaces), transdermal administration and parenteral (e.g., subcutaneous, intramuscular, intradermal, intraarticular, intrapleural, intraperitoneal, intrathecal, intracerebral, intracranially, intraarterial, or intravenous), although the most suitable route in any given case will depend on the nature and severity of the condition being treated and on the nature of the particular active agent which is being used. Pharmaceutical compositions of the present invention are particularly suitable for oral, sublingual, parenteral, implantation, nasal, and inhalational administration.

Compositions for injection will include the active ingredient together with suitable carriers including organic solvents, propylene glycol-alcohol-water, isotonic water, sterile water for injection (USP), emulPhor®-alcohol-water, cremophor-EL® or other suitable carriers known to those skilled in the art. These carriers may be used alone or in combination with other conventional solubilizing agents such as ethanol, a glycol, or other agents known to those skilled in the art.

Where the compounds of the present invention are to be applied in the form of solutions or injections, the compounds may be used by dissolving or suspending in any conventional diluent. The diluents include but are not limited to physiological saline, Ringer's solution, an aqueous glucose solution, an aqueous dextrose solution, an alcohol, a fatty acid ester, glycerol, a glycol, an oil derived from plant or animal sources, and a paraffin. These preparations may be prepared according to any conventional method known to those skilled in the art.

Compositions for nasal administration may be formulated as aerosols, drops, powders, and gels. Aerosol formulations typically comprise a solution or fine suspension of the active ingredient in a physiologically acceptable aqueous or non-aqueous solvent. Such formulations are typically presented in single or multidose quantities in a sterile form in a sealed container. The sealed container can be a cartridge or refill for use with an atomizing device. Alternatively, the sealed container may be a unitary dispensing device such as a single use nasal inhaler, pump atomizer or an aerosol dispenser fitted with a metering valve set to deliver a therapeutically effective amount, which is intended for disposal once the contents have been completely used. When the dosage form comprises an aerosol dispenser, it will contain a propellant such as a compressed gas, air as an example, or an organic propellant including a fluorochlorohydrocarbon or fluorohydrocarbon.

Compositions suitable for buccal or sublingual administration include but are not limited to tablets, lozenges and pastilles, wherein the active ingredient is formulated with a carrier such as sugar and *acacia*, tragacanth or gelatin and glycerin.

Compositions for rectal administration include but are not limited to suppositories containing a conventional suppository base such as cocoa butter.

Compositions suitable for transdermal administration include but are not limited to ointments, gels, and patches.

Other compositions known to those skilled in the art can also be applied for percutaneous or subcutaneous administration, such as plasters.

Further, in preparing such pharmaceutical compositions comprising the active ingredient or ingredients in admixture with components necessary for the formulation of the compositions, other conventional pharmacologically acceptable additives may be incorporated, including but are not limited to excipients, stabilizers, antiseptics, wetting agents, emulsifying agents, lubricants, sweetening agents, coloring agents, flavoring agents, isotonicity agents, buffering agents, and antioxidants. Additives include but are not limited to starch, sucrose, fructose, dextrose, lactose, glucose, mannitol, sorbitol, precipitated calcium carbonate, crystalline cellulose, carboxymethyl cellulose, dextrin, gelatin, *acacia*, EDTA, magnesium stearate, talc, hydroxypropylmethylcellulose, and sodium metabisulfite.

Compounds of the present invention may be used in conjunction with delivery systems that facilitate delivery of the agents to the central-nervous system. For example, various blood brain barrier permeability enhancers may be used, if desired, to transiently and reversibly increase the permeability of the blood brain barrier to a treatment agent. Such BBB permeability enhancers include but are not limited to leukotrienes, bradykinin agonists, histamine, tight junction disruptors (e.g., zonulin, zot), hyperosmotic solutions (e.g., mannitol), cytoskeletal contracting agents, and short chain alkylglycerols (e.g., 1-O-pentylglycerol). Oral, sublingual, parenteral, implantation, nasal and inhalational routes can provide delivery of the active agent to the CNS. In some embodiments, the compounds of the present invention can be administered to the CNS with minimal effects on the peripheral nervous system.

In further embodiments, the present invention provides kits including one or more containers comprising pharmaceutical dosage units comprising an effective amount of one or more compounds of the present invention. Kits may include instructions, directions, labels, warnings, or information pamphlets.

4. Prodrugs

The present invention further provides prodrugs comprising the compounds described herein. The prodrugs can be formed utilizing a hydrolyzable coupling to the compounds described herein. Ettmayer, et al. (2004) "Lessons Learned from Marketed and Investigational Prodrugs." *J. Med. Chem.* 47(10): 2394-2404 Testa and Mayer (2003) *Hydrolysis in Drug and Prodrug Metabolism: Chemistry. Biochemistry and Enzymology* Wiley-Verlag Helvetica Chimica Acta, Zuerich (Chapters 1-12): 1-780.

The term "prodrug" is intended to refer to a compound that is converted under physiological conditions, by solvolysis or metabolically to a specified compound that is pharmaceutically/pharmacologically active. The "prodrug" can be a compound of the present invention that has been chemically derivatized such that it retains some, all or none of the bioactivity of its parent drug compound and is metabolized in a subject to yield the parent drug compound. The prodrug of the present invention may also be a "partial prodrug" in that the compound has been chemically derivatized such that it retains some, all or none of the bioactivity of its parent drug compound and is metabolized in a subject to yield a biologically active derivative of the compound.

The blood-brain barrier (BBB) is a physical barrier and system of cellular transport mechanisms between the blood vessels in the central nervous system CNS) and most areas of the CNS itself. The BBB maintains homeostasis by restricting the entry of potentially harmful chemicals from the blood, and by allowing the entry of essential nutrients. However, the BBB can pose a formidable barrier to delivery of pharmacological agents to the CNS for treatment of disorders or maintaining or enhancing normal and desirable brain functions, such as cognition, learning, and memory. Prodrugs of the present invention are capable of passage across the blood-brain barrier and may undergo hydrolysis by CNS esterases to provide the active compound. Further, the prodrugs provided herein may also exhibit improved bioavailability, improved aqueous solubility, improved passive intestinal absorption, improved transporter-mediated intestinal absorption, protection against accelerated metabolism, tissue-selective delivery, less (or fewer) side effects, lessened or no deleterious drug interaction with other medications, and/or passive enrichment in the target tissue.

Prodrugs of the present invention can include compounds described herein include but are not limited to bumetanide, bumetanide aldehyde, bumetanide methyl ester, bumetanide cyanomethyl ester, bumetanide ethyl ester, bumetanide isoamyl ester, bumetanide octyl ester, bumetanide benzyl ester, bumetanide monobenzylamide, bumetanide monoethylamide, bumetanide monobenzylthioamide, bumetanide monoethylthioamide, bumetanide dibenzylamide, bumetanide diethylamide, bumetanide morpholinoethyl ester, bumetanide 3-(dimethylaminopropyl) ester, bumetanide N,N-diethylglycolamide ester, bumetanide dimethylglycolamide ester, bumetanide pivaxetil ester, furosemide, furosemide ethyl ester, furosemide cyanomethyl ester, furosemide benzyl ester, furosemide morpholinoethyl ester, furosemide 3-(dimethylaminopropyl) ester, furosemide N,N-diethylglycolamide ester, furosemide monoethylamide, furosemide diethylamide, furosemide monobenzylamide, furosemide dibenzylamide, furosemide monobenzylthioamide, furosemide monoethylthioamide, furosemide benzyltrimethylammonium salt, furosemide cetyltrimethylammonium salt, furosemide N,N-dimethylglycolamide ester, piretanide monoethylamide, piretanide monobenzylamide, furosemide pivaxetil ester, furosemide propaxetil ester, piretanide, piretanide methyl ester, piretanide cyanomethyl ester, piretanide benzyl ester, piretanide morpholinoethyl ester, piretanide 3-(dimethylaminopropyl) ester, piretanide N,N-diethylglycolamide ester, piretanide diethylamide, piretanide dibenzylamide, piretanide benzyltrimethylammonium salt, piretanide cetyltrimethylammonium salt, piretanide N,N-dimethylglycolamide ester, piretanide pivaxetil ester, piretanide propaxetil ester, tetrazolyl-substituted azosemides, pyridinium-substituted torsemide salts (also termed pyridine-substituted torsemide quaternary ammonium salts), as well as similar acid, acid salt, ester and amido derivatives of S-thiobumetanide, O-thiobumetanide, dithiobumetanide, S-thiofurosemide, O-thiourosemide, dithiourosemide, S-thiopiretanide, O-thiopiretanide and dithiopiretanide. See schemes presented herein.

Moreover, as shown in the previously presented schemes, prodrugs can be formed by attachment of biocompatible polymers ethylene, such as those previously described including polyethylene glycol (PEG), to compounds of the present invention using linkages degradable under physiological conditions. See also Schacht, et al. (1997) Poly (ethylene glycol) Chemistry and Biological Applications, American Chemical Society, San Francisco, Calif. 297-315. Attachment of PEG to proteins can be employed to reduce immunogenicity and/or extend the half-life of the compounds provided herein. Any conventional PEGylation method can be employed, provided that the PEGylated agent retains at least some pharmaceutical activity.

5. Methods of Use

Diseases and Conditions

The compounds of formula I-XXVI described herein may be used for the regulation, including prevention, management and treatment, of a range of conditions including, but not limited to disorders that involve an $Na^+K^+Cl^-$ cotransporters and/or a $GABA_A$ receptor.

Treatment of NKCC Related Diseases

The compounds described herein modulate, regulate, inhibit, stimulate, activate, and/or bind to electroneutral cation-chloride cotransporter co-transporters including but not limited to $Na^+Cl^-$ cotransporters (e.g., thiazide-sensitive $Na^+Cl^-$ cotransporters); apical bumetanide-sensitive $Na^+K^+Cl^-$ cotransporters (e.g., NKCC2); basolateral bumetanide-sensitive $Na^+K^+Cl^-$ cotransporters (e.g., NKCC1); and $K^+Cl^-$ cotransporters (e.g., KCC1, KCC2, KCC3, KCC4). In a preferred embodiment, the electroneutral cation-chloride cotransporter is a bumetanide-sensitive $Na^+K^+Cl^-$ cotransporter (e.g., NKCC1, NKCC2).

$GABA_A$ Receptors in Disease $GABA_A$ receptors have a pentameric structure generally comprising two α subunits and two β subunits with a fifth regulatory subunit. Specific $GABA_A$ subunits are expressed throughout the brain in distinct spatial and developmental patterns and display different responses to known pharmacological modulators. $GABA_A$ $\alpha_1$ variant receptors are believed to be the major postsynaptic receptors mediating action of GABA at most inhibitory synapses, and as such are responsible for not only the efficacious properties of drugs acting upon $GABA_A$ $\alpha_1$ variant receptors but also the sedative effects of these drugs. $GABA_A$ $\alpha_2$ and $\alpha_3$ variant receptors are expressed in the hippocampus, thalamus, and other CNS locations, and are believed to mediate the anti-anxiety effects of the benzodiazepines. $\alpha_4$ containing $GABA_A$ receptors located in the hippocampus are thought to play a role in epilepsy. $\alpha_5$ containing $GABA_A$ receptors are expressed in the hippocampus and are thought to play a role in learning and memory. $\alpha_4$ and $\alpha_6$ containing $GABA_A$ receptors are insensitive to benzodiazepines. Specific $GABA_A$ subunits such as $\alpha_1$ and $\alpha_4$ show increased expression in patients with epilepsy. $\alpha_4$ variants of the $GABA_A$ receptor are important in acting in a negative feedback loop on presynaptic GABA release, where stimulation of the $\alpha_4$ variants $GABA_A$ receptor acts to suppress GABA release.

The minor "regulatory" subunits ε and θ are expressed in particular CNS locations such as the cortex, the substantia nigra, amygdala and hypothalamus whereas another minor subunit, π, is expressed outside the CNS in the uterus and breast tissue (overexpression of π has been observed in breast cancer). Another "regulatory" subunit, γ is a component of benzodiazepine-sensitive $GABA_A$ receptors. The $GABA_A$ subunits $\gamma_2$ and δ are believed to be involved in the pathologies of certain monogenetic forms of epilepsy. Also, the $GABA_A$ $\alpha_2$ and δ subunits have been implicated in alcohol consumption and addiction. WO 2009/100040.

$GABA_A$ receptors are localized at synaptic and extrasynaptic levels. Whereas synaptic $GABA_A$ receptors are involved in phasic inhibition, extrasynaptic $GABA_A$ receptors are responsible for tonic inhibition. Tonic inhibition is due to persistent inhibitory conductance that contributes to "signal integration" in the brain because it sets the threshold for action potential generation and shunts excitatory synaptic inputs. Thus, tonic inhibition plays a crucial role in regulating neuronal excitability because it sets the threshold for action potential generation and integrates excitatory signals. This conductance is maintained by "ambient" GABA—the amount of neurotransmitter present in the extracellular space. Ambient GABA originates from spillover of the neurotransmitter released at neighboring synapses, from astrocytes, or from non-vesicular release. Further, $GABA_A$ receptors are clustered at the synapse and extrasynaptic areas (e.g., presynaptic cell); $GABA_A$ receptor clustering acts as an additional regulating factor for tonic inhibition because clustered extrasynaptic $GABA_A$ receptors can mediate larger tonic currents. Petrini, et al. (2004) "Clustering of Extrasynaptic $GABA_A$ Receptors Modulates Tonic Inhibition in Cultured Hippocampal Neurons." The Journal of Biological Chemistry 279(44): 45833-45843.

Figure 38:
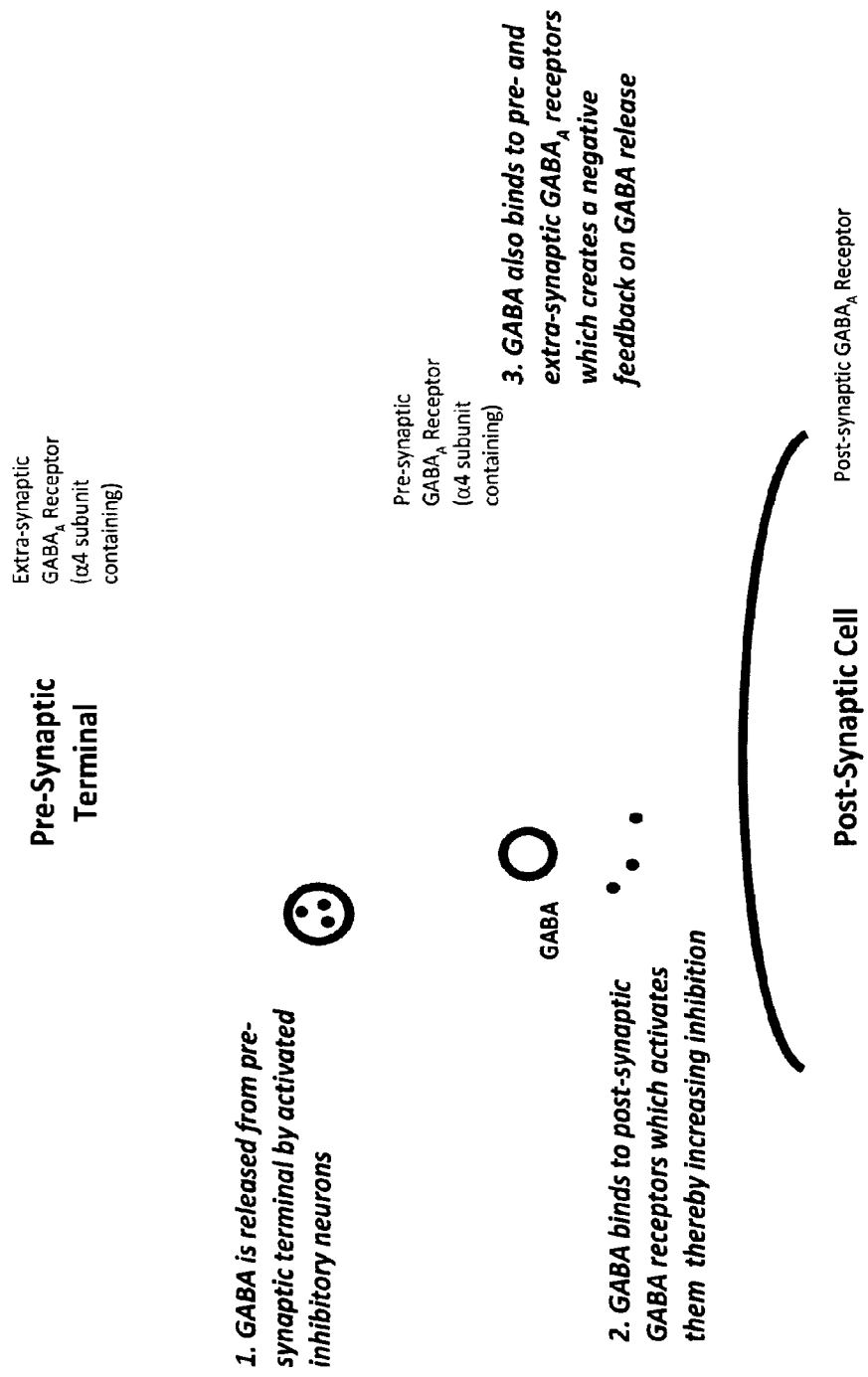
FIG. 38 is a schematic illustration of a possible mechanism for the action of compounds described herein that selectively antagonize parasynaptic $\alpha_4$ $GABA_A$ receptor isoforms in GABAergic interneurons. In this suggested mechanism, (1) GABA is released from the pre-synaptic terminal by activated inhibitory neurons, (2) GABA binds to post-synaptic $GABA_A$ receptors that activates them thereby increasing inhibition (e.g., hyperpolarization of the post-synaptic neuron), (3) GABA also binds to parasynaptic (e.g., presynaptic and extrasynaptic) $GABA_A$ receptors, (4) in one possible mechanism of action, compounds described herein (e.g., NTP-2014) selectively binds to parasynaptic $\alpha_4$ variant $GABA_A$ receptors (inhibiting the negative feedback loop), thus increasing GABA release. This leads to the restoration of the balance of excitation and inhibition by increasing the inhibitory stimulus applied to post-synaptic neurons.

$\alpha_4$ $GABA_A$ receptor variants are primarily located pre-synaptically or extrasynaptically (e.g. on the pre-synaptic cell). See FIG. 38. Activation of the $\alpha_4$ $GABA_A$ receptor variants leads to hyperpolarization of the pre-synaptic cell, decreasing GABA release and thus decreasing inhibition (e.g., agonists specific for $\alpha_4$ $GABA_A$ receptor variants lead to a decrease in GABA release and subsequent decrease in the inhibitory signaling). In contrast, inhibition (antagonism) of $\alpha_4$ $GABA_A$ receptor variants decreases hyperpolarization of the presynaptic cell, thus allowing for GABA release to continue—prolonging and strengthening the inhibitory signal to the postsynaptic cell (e.g., antagonists specific for $\alpha_4$ $GABA_A$ receptor variants lead to an increase GABA release and subsequent increase in the inhibitory signaling). In effect antagonists specific for $\alpha_4$ $GABA_A$ receptor variants achieve physiologic effects similar to those observed in current GABA agonists.

The activation of presynaptic $GABA_A$ receptors depolarizes the presynaptic nerve terminals. The presynaptic actions of neurons can either depress or enhance neurotransmitter release, processes called presynaptic inhibition and presynaptic facilitation, respectively. Some of the best analyzed instances of presynaptic inhibition and facilitation are in the neurons of invertebrate animals and in mechanoreceptor afferent neurons (dorsal root ganglion cells) of vertebrates studied in dissociated cell tissue culture. These studies, and those in the intact spinal cord of mammals, indicate that there are at least two mechanisms for presynaptic inhibition. One is due to a synaptically mediated depression of the $Ca^{2+}$ channel, leading to a decrease in the influx of $Ca^{2+}$ into the terminal. The other is due to an increased conductance to $Cl^-$ that leads to a decrease (or short-circuiting) in the height of the action potential in the presynaptic terminal. As a result, less depolarization is produced, fewer $Ca^{2+}$ channels are activated by the action potential, and therefore, less $Ca^{2+}$ flows into the terminals. Activation of $GABA_A$ presynaptic receptors is of this latter type. Antagonism of the receptor would then lead to presynaptic facilitation. Conversely, presynaptic facilitation is due enhanced influx of $Ca^{2+}$. The neurotransmitter acts to depress a $K^+$ channel, thereby broadening the action potential and allowing the $Ca^{2+}$ influx to persist for a longer period of time.

Proper neural activity depends on maintaining an appropriate balance between excitation and inhibition. Any tipping of the balance too far toward inhibition leads to sedation, and conversely, tipping it too far toward excitation may trigger a seizure. For example, extrasynaptic $\delta$ subunit-containing $GABA_A$ receptors contribute to temporal lobe epilepsy by decreasing inhibitory input onto dentate granule cells and increasing the inhibition of inhibitory interneurons. Peng, et al. (2004) "Altered expression of the $\delta$ subunit of the $GABA_A$ receptor in a mouse model of temporal lobe epilepsy." J. Neurosci. 24: 8629-8639. This increase in the inhibition of the inhibitory interneurons tips the balance too far towards excitation by lessening the inhibitory signaling, leading to seizures.

Presynaptic actions also tend to occur at points of sensory inflow. For example, presynaptic inhibition is found in the retina, spinal cord, and dorsal column nuclei. Presynaptic actions are important because they allow selective control of the actions of individual branches of a neuron. Axoaxonic synapses can inhibit or facilitate transmitter release by altering $Ca^{2+}$ influx. Presynaptic inhibition may occur as a result of the activity of the postsynaptic cell, either a presynaptic inhibitory neuron, or a presynaptic facilitating neuron. In presynaptic inhibition, the result of the activity of the presynaptic inhibitor neuron is to cause a depression of the $Ca^{2+}$ current accompanying the action potential of the presynaptic neuron. Because the decreased $Ca^{2+}$ influx leads to a reduction in the amount of neurotransmitter released, the synaptic potential in the postsynaptic cell is depressed. In presynaptic facilitation, the activity of the presynaptic facilitating neuron causes a depression of the $K^+$ current in the presynaptic neuron leading to an increase in the during of the action potential and therefore of the $Ca^{2+}$ current. Consequently neurotransmitter release is increased and as a result, so is the amplitude of the synaptic potential in the postsynaptic cell. Kandel and Schwartz *Principles of Neural Science* $2^{nd}$ Edition (1985) pages 128-131.

The $\alpha_4$ $GABA_A$ variant is expressed at high levels in the hippocampus, striatum and thalamus, where it contributes to parasynaptic $GABA_A$ receptor mediated tonic inhibition. Further, $\alpha 4$ expression is markedly altered by electroshock, alcohol exposure/withdrawal, steroid withdrawal, social isolation, and epilepsy. $\alpha_4\beta\delta$ subtypes are modulated by nonbezodiazepine GABAergic drugs like steroid, anesthetics, and ethanol. Chandra, et al. (Oct. 10, 2006) *Proc. Natl. Acad. Sci.* 103(41): 15230-15235.

Several clinical conditions are thought to arise, in part, from the imbalance between neurotransmission of GABA including, but not limited to Huntington's Disease, Parkinson's disease, spasticity, epilepsy, schizophrenia, bipolar disease, and tardive dyskinesia. For instance, GABA receptors have been implicated in sleep regulation and rhythmicity as well as the anxiolytic, amnestic, sedative, and anesthetic effects of alcohol. Jia, et al. (2008) The Journal of Pharmacology and Experimental Therapeutics 326(2): 475-482. Decreased GABA activity appears to contribute to the pathogenesis of these diseases. In addition, analgesia and satiety are thought to be regulated by GABA activity. Several diseases and conditions are due, at least in part, to an imbalance between excitation and inhibition in the central nervous system including but not limited to Alzheimer's Disease, addictive disorders, anxiety disorders, autism, bipolar disorder, depression, epilepsy, Huntington's Disease, insomnia, migraine, migraine with aura, neuropathic pain, nociceptive pain, pain, Parkinson's disease, personality disorders, psychosis, schizophrenia, seizure disorders, tinnitus, and withdrawal syndromes. Therefore, antagonists specific for $\alpha_4$ $GABA_A$ receptor variants, which lead to an increase GABA release and subsequent increase in the inhibitory signaling, may be used to treat these disease and conditions because they act to restore a balance between excitation and inhibition in the central nervous system by increasing inhibition. For example, antagonists specific for $\alpha_4$ $GABA_A$ receptor variants (e.g., bumetanide derivatives described herein) bind to extrasynaptic antagonists $\alpha_4$ $GABA_A$ receptor variants preventing their activation by ambient GABA. This prevents the hyperpolarization of the presynaptic cell allowing for prolonged GABA release into the synaptic cleft that leads to a longer, stronger inhibitory signal. This, in turn, provides a means by which the proper balance between excitation and inhibition in the central nervous system may be restored by increasing inhibition to counteract an excess of excitation or a lack of inhibition.

The compounds described herein selectively antagonize $GABA_A$ receptors. In a preferred embodiment, the $GABA_A$ receptor is a $GABA_A$ receptor isoform comprising at least one $\alpha_4$ subunit. In one embodiment, the invention comprises compositions comprising compounds described herein with $GABA_A$ receptor antagonist activity. In a further embodiment, the invention is drawn to pharmaceutical compositions comprising at least one compound with $GABA_A$ receptor antagonist activity and a pharmaceutically acceptable excipient. In one embodiment, compounds described herein have $GABA_A$ receptor antagonist activity. In another embodiment, compounds described herein do not have an effect on $GABA_B$ receptors.

In particular, compounds of Formula I, II, III, IV, V, VI, VII, VIII, IX, X, XI, XII XIII, XIV, XV, XVI, XVII, XVIII, XIX, XX, XXI, XXII, XXIII, XXIV, XXV, and/or XXVI described herein may be used for the regulation, including prevention, prophylaxis, diagnosis, prognostication, management, and treatment, of a range of conditions that involve the $GABA_A$ receptor including but not limited to the disorders described herein.

In another embodiment, the compounds described herein show selective effect on $GABA_A$ receptors in the CNS and less side-effects usually associated with agents that act on $GABA_A$ receptors. For example, the compounds described herein exhibit less sedation, decreased respiration, decreased cognition, or decreased motor function.

For example, the compounds described herein are effective in humans and animals to decrease seizures, decrease pain responses, and decrease migraine. One derivative, NTP-2014, preferentially binds to $GABA_A$ receptor subtypes and has an antagonistic effect on $GABA_A$ receptors that is different from classic benzodiazepine and barbiturate mechanisms. Unlike many bumetanide analogs, NTP-2014 does not act on the $Na^+K^+2Cl^-$ cotransporter (NKCC1 or NKCC2). Other bumetanide analogs that are similarly ineffective with NKCC1 or NKCC2 are contemplated. Unlike bumetanide, the bumetanide analogs described herein (e.g., NTP-2014) do not elicit diuresis in animal models. NTP-2014 did not increase urine output, sodium excretion, or potassium excretion. Further, NTP-2014 has been shown to be active in several CNS efficacy models in animals. For example, NTP-2014, NTP-2024, and NTP-2026 show strong efficacy in three robust and highly predictive models of epilepsy, three pain models (two neuropathic and one nociceptive), and in a cortical spreading depression model of migraine the results of which are summarized in Tables 1-4.

TABLE 1

| NTP Compound Number | In Vivo Efficacy - Acute Nociceptive Pain | | | In Vivo Efficacy - Neuropathic Pain |
| --- | --- | --- | --- | --- |
| | Acute Nociceptive Study (Mice) | Formalin Paw Test (Mice) - Early Phase | Formalin Paw Test (Mice) - Late Phase | Formalin Paw Test (Mice) - Late Phase |
| NTP-2014 | Significant activity in tail-flick test at all doses starting at 32 mg/kg; dose and time-response established - % anti-nociception equal to high dose morphine without behavioral observations | ND | ND | Significant decrease in pain at 50 ($p < 0.05$), 250 ($p < 0.001$), 500 ($p < 0.001$) μmol/kg; 21, 105, 210 mg/kg; much better than gabapentin (584 μmol/kg; 100 mg/kg) at highest two doses |
| NTP-2026 | Significant activity in tail-flick test at all doses starting at 56 mg/kg; dose and time-response established | ND | ND | Significant decrease in pain at 250 ($p < 0.01$), 500 ($p < 0.001$) μmol/kg; 116, 231 mg/kg; better than gabapentin (584 μmol/kg; 100 mg/kg) at highest dose |
| NTP-2024 | Significant activity in tail-flick test at all doses starting at 56 mg/kg; dose and time-response pending | Significant decrease in pain at 346 μmol/kg; 150 mg/kg; ~40%; decrease ($p < 0.05$) | Significant decrease in pain at 346 μmol/kg; 150 mg/kg; >80% decrease ($p < 0.01$) | Significant decrease in pain at 250 ($p < 0.01$), 500 ($p < 0.05$) μmol/kg; 108, 217 mg/kg; slightly less antinociception compared to gabapentin (584 μmol/kg; 100 mg/kg) at highest two doses (lowest dose not significant; 21.7 mg/kg) |
| Bumetanide | ND | Literature data demonstrates bumetanide is active in late phase, but has little activity in early phase formalin paw test. Effects not mediated through opiod receptors. | | Significant decrease in pain at 50 ($p < 0.05$), 250 ($p < 0.01$), 500 ($p < 0.001$) μmol/kg; 18.2, 91.1, 182 mg/kg; better than gabapentin (584 μmol/kg; 100 mg/kg) at highest dose |

TABLE 2

| NTP Compound Number | In vivo Efficacy - Neuropathic Pain | | |
| --- | --- | --- | --- |
| | Exploratory Bennett Neuropathic Pain (Rat) - plus inhibitor | Dose-Response Chung Neuropathic Pain Study (Mice) | Taxol-Induced Peripheral Neuropathy (Rat) |
| NTP-2014 | Significant effects against tactile allodynia ($p = 0.009$); thermal hyperalgesia results comprised by effects of inhibitor in the assay | Dose-dependent, very significant reversal of tactile hypersensitivity. Some minor sedation was noted in the high dose group (180 mg/kg). No other overt toxicity was noted. | Maximal response in pain relief as measured by mechanical allodynia-equal to if not better activity at 75 mg/kg compared to GBP at 100 mg/kg |
| NTP-2026 | Very low doses tested, no significant activity demonstrated | Dose-dependent, significant reversal of tactile hypersensitivity. Some minor sedation was noted in the high dose group (100 mg/kg). No other overt toxicity was noted. | Several animals demonstrated complete responses in pain relief as measured by mechanical allodynia- at 75 mg/kg, some animals did not respond; "all or nothing effect" - variability in dosing/formulation being investigated |
| NTP-2024 | Dose-related activity against tactile allodynia | ND | High activity in mechanical allodynia but preliminary results confounded by inhibitor's activity on mechanical allodynia |
| Bumetanide | ND | ND | ND |

TABLE 3

| NTP Compound Number | Kainic Acid Model (Rat) (15 mg/kg) | MES (Rat) | 6 Hz (Mice) |
|---|---|---|---|
| | In vivo Efficacy Epilepsy - Rodent | | |
| NTP-2014 | ND | Complete suppression at 4 hr in 2/3 rats at 100 mg/kg. Toxic effects seen at 300 mg/kg. No significant adverse events at 100 mg/kg | Complete suppression in all animals to 1 h, and majority of animals through 4 h with 100 mg/kg. No toxicity. |
| NTP-2026 | ND | No activity at 30, 100, 330 mg/kg | Significant activity at 2 timepoints (2 hr, 4 hr) with 100 mg/kg. No toxicity. |
| NTP-2024 | 89% reduction in seizure activity (S); 96% reduction in seizure severity (S) | ND | No activity at doses up to 200 mg/kg - no metabolic inhibitor coadministered |
| Bumetanide | 44% reduction in seizures (NS); 71% reduction in seizure score (S) = at 7.3 mg/kg i.p. = 89% reduction in seizures (S); 96% reduction in seizure score (S) = at 100 mg/kg i.p. | No activity at doses up to 200 mg/kg - no metabolic inhibitor coadministered | ND |

| NTP Compound Number | In vivo Efficacy Epilepsy - Rodent Dose-Response Mesial Temporal Lobe Epilepsy Model (Mice) | In vivo Efficacy - Cortical Spreading Depression (Rat) IP Administration |
|---|---|---|
| NTP-2014 | Dose-response relationship demonstrated in significant decrease in both cumulative duration of and total number of hippocampal discharges. At 25 and 50 mg/kg, near complete suppression of discharges through 80 minutes post-dose (the last observed time-point in the study) | Statistically significant decrease in CSD events at 10, 50 and 75 mg/kg (−38%, −37% and −47% respectively, all at $p < 0.05$.) |
| NTP-2026 | Dose-response relationship demonstrated in significant decrease in both cumulative duration of and total number of hippocampal discharges. At 50 mg/kg, near complete suppression of discharges through 80 minutes post-dose (last observed time-point in the study) | Statistically significant decrease in CSD events (~30-40%) at 10-75 mg/kg in rats ($p < 0.05$) (N = 8) |
| NTP-2024 | Dose-response relationship demonstrated in significant decrease in both cumulative duration of and total number of hippocampal discharges. | 32% decrease in CSD events at 300 mg/kg in rats co-administered general metabolic inhibitor (NS) |
| Bumetanide | ND | Statistically significant decrease in CSD events (~30%) at 10 and 30 mg/kg in rats ($p \sim 0.05$)(N = 8) |

TABLE 4

| NTP Compound Number | Diuresis - Rat | 14 day GLP - Rat (Vehicle control, 100, 225, 500 mg/kg/day | 14 day GLP - Dog (Empty capsules, 1, 4.5, 20 mg/kg/day) |
|---|---|---|---|
| NTP-2014 | No diuresis as measured by increased urine output and Na+/K+ excretion through 8 hours post-dose | NOAEL = 500 mg/kg. | NOAEL = 4.5 mg/kg |
| NTP-2026 | No diuresis as measured by increased urine output and Na+/K+ excretion through 8 hours post-dose | ND | ND |
| NTP-2024 | Rats pretreated with inhibitor demonstrated high concentrations of NTP-2024 in blood and in brain tissue; no increased urine output or sodium or potassium excretion noted through 6 hours post-IP dose | ND | ND |
| Bumetanide | Literature studies showed bumetanide has no diuretic effects in rat due to rapid and extensive metabolism. Pre-treatment of rats with inhibitor increased bumetanide exposures and half-life; diuresis evident | ND | ND |

Overall, NTP-2014 was well-tolerated toxicologically and demonstrated no CNS side effects after oral administration. Based on the information provided herein, the inventors surprisingly discovered that NTP-2014 acts to specifically increase neuronal inhibition via a novel mechanism of action (not NKCC dependent). The inventors surprisingly discovered that NTP-2014 acts at interneuron terminals, that regulate neuronal firing, and therefore, NTP-2014 inhibits abnormal firing. More specifically, NTP-2014 increases-presynaptic inhibition without depressing all GABA receptors. This highly selective mechanism of action is novel and contrasts with the broad, non-specific activity of benzodiazepines and barbiturates. Benzodiazepines and barbiturates are known to be effective but are poorly tolerated because these compounds activate most $GABA_A$ subtype receptors (e.g., "fire-hose effect"). In contrast, NTP-2014 enhances inhibition via action at specific $GABA_A$ receptor subtypes, preferentially $a_4$ variants of $GABA_A$. Due to the selectivity of NTP-2014, it avoids the typical CNS side effects (e.g., sedation) usually associated with known GABAergic compounds.

NTP-2014 shows high selectivity at the terminals of GABA interneurons. In vitro electrophysiology studies with NTP-2014 have demonstrated selective activity at pre- and/or extrasynaptic (parasynaptic) terminals indicating increased GABA release (inhibition). Without being bound to a particular theory of action, the inventors believe that NTP-2014 is a $GABA_A$ receptor antagonist that increases the number of inhibitory events as measured by Inhibitory Postsynaptic Current (IPSCs). For example, the compounds described herein (e.g., NTP-2014) increase the frequency of spontaneous IPSCs (a combination of both action potential and miniature events releasing GABA) and increase the frequency of miniature IPSCs (miniature events are due to tonic release of synaptic vesicles containing GABA into the pre-synaptic space).

In view of the results discussed herein, the inventors surprisingly discovered that NTP-2014 increases $GABA_A$ inhibitory drive, since the increased frequency indicates a pre-synaptic mechanism. The data demonstrate that the interval between miniature and spontaneous inhibitory post-synaptic currents (mIPSCs and sIPSCs, respectively) events are substantially decreased in the presence of NTP-2014. The resulting effects indicate a highly significant increase in the frequency of inhibitory events. While not ruling out other effects of NTP-2014, these data suggest a pre-synaptic mechanism increasing the release of GABA from the neurons, because NTP-2014 antagonizes $GABA_A$ receptors on the pre-synaptic cells preventing hyperpolarization of the pre-terminal cell. This allows for additional GABA to be released into the synaptic cleft, leading to longer, and stronger GABA-mediated inhibition.

$GABA_A$ receptors may be located parasynaptically (e.g., pre- and extra-synaptically) and account for control of frequency of IPSCs. Without being committed to a specific mechanism, the inventors believe that selected compounds described herein (e.g., NTP-2014) act at parasynaptic sites by inhibiting the negative feedback by GABA on the terminal of the synaptic bouton. Parasynaptic $GABA_A$ receptors act to decrease GABA release when sufficient GABA is present in the synaptic cleft to bind to and activate these parasynaptic $GABA_A$ receptors (e.g., negative feedback loop). By inhibiting this negative feedback loop, the compounds described herein (e.g., NTP-2014) increase the GABA levels in the synaptic cleft and decrease neuronal firing. This increase of GABA restores the appropriate excitatory/inhibitory balance for normal neuronal activity.

NTP-2014 selectively antagonizes specific $GABA_A$ receptor isoforms (e.g., $\alpha_4$ variants). $\alpha_4$ $GABA_A$ receptor variants are found at parasynaptic sites and account for less than 1% of the $GABA_A$ receptors in the mammalian brain. The activation of $\alpha_4$ $GABA_A$ receptor isoform can inhibit the release of GABA from a GABAergic neuron (e.g., activation of a $\alpha_4$ $GABA_A$ receptor leads to the hyperpolarization of the synaptic terminal which slows the release of GABA from synaptic vesicles and allows GABA clearance mechanisms to lower the amount of GABA in the synaptic cleft leading to a decrease of GABA in the synaptic cleft). Further, the inventors discovered surprisingly that inhibition of parasynaptic $\alpha_4$ $GABA_A$ receptor isoforms leads to an increase in GABA release, which leads to increased inhibitory stimulation on the post-synaptic neuron. This specific parasynaptic action supports a possible mechanism for the lack of CNS depressant effects (e.g., sedation) demonstrated by compounds described herein (e.g., NTP-2014), even at very high systemic exposure (e.g., after dosages >100 mg/kg/day). This mechanism of action is diametrically opposed to the activation of $GABA_A$ receptors by benzodiazepines which work at low GABA concentrations.

The focus of pharmacological intervention in many disorders of the central and peripheral nervous system has been on reducing neuronal hyperexcitability. Most agents currently used to treat such disorders target synaptic activity in excitatory pathways by, for example, modulating the release or activity of excitatory neurotransmitters, potentiating inhibitory pathways, blocking ion channels involved in impulse generation, and/or acting as membrane stabilizers. Conventional agents and therapeutic approaches for the treatment of central and peripheral nervous system disorders thus reduce neuronal excitability and inhibit synaptic firing. One serious drawback of these therapies is that they are nonselective and exert their actions on both normal and abnormal neuronal populations. This leads to negative and unintended side effects, which may affect normal CNS functions, such as cognition, learning and memory, and produce adverse physiological and psychological effects in the treated patient. Common side effects include over-sedation, dizziness, loss of memory and liver damage.

For example, classic anticonvulsant drugs and anti-nociceptive drugs decrease excitation or increase inhibition via non-selective GABAergic drugs (e.g., benzodiazepines and barbiturates) indiscriminately act on multiple $GABA_A$ receptor isoforms. While this yields good efficacy, the non-selective GABAergic drugs cause undesirable CNS side effects. In contrast, NTP-2014 selective action on specific a $GABA_A$ receptor isoform (e.g., $\alpha_4$ $GABA_A$ variants) generates strong efficacy in hyperexcitable states (e.g., epilepsy, migraine, pain) without generating typical CNS side effects such as sedation and decreased cognition.

Dosages

The amount of active compound in a therapeutic composition according to this invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

It is especially advantageous to formulate parenteral compositions in dosage unit form for ease of administration- and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dose for a patient can be about 0.01, 0.02, 0.03, 0.04, 0.05, 0.06, 0.07, 0.08, 0.09, or 0.10 µg, as well as about 0.1, 0.2, 0.3, 0.4, 0.5, 0.6, 0.7, 0.8, 0.9, or 1.0 µg, as well as about 1, 2, 3, 4, 5, 6, 7, 8, 9, or 10 µg, as well as about 10, 11, 12, 13, 14, 15, 16, 17, 18, 19, or 20 µg, as well as about 10, 20, 25, 30, 35, 40, 45, 50, 55, 60, 65, 70, 75, 80, 85, 90, 95 or 100 µg, as well as about 100, 200, 300, 400, 500, 600, 700, 800, 900, or 1,000 µg and all increments therein. Preferably, the dose for a patient can be about 0.05-5 µg and all increments therein. Alternatively, the dose for a patient can be about 1-10 µg and all increments therein. The dose for a patient can also be about 10-40 µg and all increments therein, about 6-24 µg and all increments therein, about 20-80 µg and all increments therein, about 40-80 µg and all increments therein, about 100-250 µg and all increments therein, or about 100-500 µg and all increments therein. More preferably, the dosage can be about 0.5, 1, 2, 5, 6, 10, 12, 18, 20, 24, 30, 40, 50, 80, or 90 µg. Preferably, the dosage can be 0.5, 2, 6, 8, 10, 12, 18, 20, 30, 40, or 80 µg.

Alternatively, for each of the recited embodiments, the dose for a patient may be about 0.01, 0.02, 0.03, 0.04, 0.05, 0.06, 0.07, 0.08, 0.09, or 0.10 mg, as well as about 0.1, 0.2, 0.3, 0.4, 0.5, 0.6, 0.7, 0.8, 0.9, or 1.0 mg, as well as about 1, 2, 3, 4, 5, 6, 7, 8, 9, or 10 g, as well as about 10, 11, 12, 13, 14, 15, 16, 17, 18, 19, or 20 mg, as well as about 10, 20, 25, 30, 35, 40, 45, 50, 55, 60, 65, 70, 75, 80, 85, 90, 95 or 100 mg, as well as about 100, 200, 300, 400, 500, 600, 700, 800, 900, or 1,000 mg and all increments therein. Preferably, the dose for a patient may be about 0.05-5 mg and all increments therein. Alternatively, the dose for a patient may be about 1-10 mg and all increments therein. The dose for a patient may also be about 10-40 mg and all increments therein, about 6-24 mg and all increments therein, about 20-80 mg and all increments therein, about 40-80 mg and all increments therein, about 100-250 mg and all increments therein, or about 100-500 mg and all increments therein. More preferably, the dosage may be about 0.5, 1, 2, 5, 6, 10, 12, 18, 20, 24, 30, 40, 50, 80, or 90 mg. Preferably, the dosage may be 0.5, 2, 6, 8, 10, 12, 18 20, 30, 40, or 80 mg.

Alternatively, for each of the recited embodiments, the dose for a patient may be about 0.01, 0.02, 0.03, 0.04, 0.05, 0.06, 0.07, 0.08, 0.09, or 0.10 g, as well as about 0.1, 0.2, 0.3, 0.4, 0.5, 0.6, 0.7, 0.8, 0.9, or 1.0 g, as well as about 1, 2, 3, 4, 5, 6, 7, 8, 9, or 10 g, as well as about 10, 11, 12, 13, 14, 15, 16, 17, 18, 19, or 20 g, as well as about 10, 20, 25, 30, 35, 40, 45, 50, 55, 60, 65, 70, 75, 80, 85, 90, 95 or 100 g, as well as about 100, 200, 300, 400, 500, 600, 700, 800, 900, or 1,000 g and all increments therein. Preferably, the dose for a patient may be about 0.05-5 g and all increments therein. Alternatively, the dose for a patient may be about 1-10 g and all increments therein. The dose for a patient may also be about 10-40 g and all increments therein, about 6-24 g and all increments therein, about 20-80 g and all increments therein, about 40-80 g and all increments therein, about 100-250 g and all increments therein, or about 100-500 g and all increments therein. More preferably, the dosage may be about 0.5, 1, 2, 5, 6, 10, 12, 18, 20, 24, 30, 40, 50, 80, or 90 g. Preferably, the dosage may be 0.5, 2, 6, 8, 10, 12, 18 20, 30, 40, or 80 g.

For each of the recited embodiments, the dose for a patient can be about 0.01, 0.02, 0.03, 0.04, 0.05, 0.06, 0.07, 0.08, 0.09, or 0.10 µg/kg, as well as about 0.1, 0.2, 0.3, 0.4, 0.5, 0.6, 0.7, 0.8, 0.9, or 1.0 µg/kg, as well as about 1, 2, 3, 4, 5, 6, 7, 8, 9, or 10 µg/kg, as well as about 10, 11, 12, 13, 14, 15, 16, 17, 18, 19, or 20 µg/kg, as well as about 10, 20, 25, 30, 35, 40, 45, 50, 55, 60, 65, 70, 75, 80, 85, 90, 95 or 100 µg/kg, as well as about 100, 200, 300, 400, 500, 600, 700, 800, 900, or 1,000 µg/kg and all increments therein. Preferably, the dose for a patient can be about 0.05-5 µg/kg and all increments therein. Alternatively, the dose for a patient can be about 1-10 µg/kg and all increments therein. The dose for a patient can also be about 10-40 µg/kg and all increments therein, about 6-24 µg/kg and all increments therein, about 20-80 µg/kg and all increments therein, about 40-80 µg/kg and all increments therein, about 100-250 µg/kg and all increments therein, or about 100-500 µg/kg and all increments therein. More preferably, the dosage can be about 0.5, 1, 2, 5, 6, 10, 12, 18, 20, 24, 30, 40, 50, 80, or 90 µg/kg.

Preferably, the dosage can be 0.5, 2, 6, 8, 10, 12, 18, 20, 30, 40, or 80 µg/kg. Alternatively, for each of the recited embodiments, the dose for a patient may be about 0.01, 0.02, 0.03, 0.04, 0.05, 0.06, 0.07, 0.08, 0.09, or 0.10 mg/kg, as well as about 0.1, 0.2, 0.3, 0.4, 0.5, 0.6, 0.7, 0.8, 0.9, or 1.0 mg/kg, as well as about 1, 2, 3, 4, 5, 6, 7, 8, 9, or 10 mg/kg, as well as about 10, 11, 12, 13, 14, 15, 16, 17, 18, 19, or 20 mg/kg, as well as about 10, 20, 25, 30, 35, 40, 45, 50, 55, 60, 65, 70, 75, 80, 85, 90, 95 or 100 mg/kg, as well as about 100, 200, 300, 400, 500, 600, 700, 800, 900, or 1,000 mg/kg and all increments therein. Preferably, the dose for a patient may be about 0.05-5 mg/kg and all increments therein. Alternatively, the dose for a patient may be about 1-10 mg/kg and all increments therein. The dose for a patient may also be about 10-40 mg/kg and all increments therein, about 6-24 mg/kg and all increments therein, about 20-80 mg/kg and all increments therein, about 40-80 mg/kg and all increments therein, about 100-250 mg/kg and all increments therein, or about 100-500 mg/kg and all increments therein. More preferably, the dosage may be about 0.5, 1, 2, 5, 6, 10, 12, 18, 20, 24, 30, 40, 50, 80, 90, or 100 mg/kg. Preferably, the dosage may be 0.5, 2, 6, 8, 10, 12, 18, 20, 30, 40, 41, 42, 43, 44, 45, 46, 47, 48, 49, 50, 80, 85, 90, or 100 mg/kg.

Alternatively, for each of the recited embodiments, the dose for a patient can be about 0.01, 0.02, 0.03, 0.04, 0.05; 0.06, 0.07, 0.08, 0.09, or 0.10 g/kg, as well as about 0.1, 0.2, 0.3, 0.4, 0.5, 0.6, 0.7, 0.8, 0.9, or 1.0 g/kg, as well as about 1, 2, 3, 4, 5, 6, 7, 8, 9, or 10 g/kg, as well as about 10, 11, 12, 13, 14, 15, 16, 17, 18, 19, or 20 g/kg, as well as about 10, 20, 25, 30, 35, 40, 45, 50, 55, 60, 65, 70, 75, 80, 85, 90, 95 or 100 g/kg, as well as about 100, 200, 300, 400, 500, 600, 700, 800, 900, or 1,000 g/kg and all increments therein. Preferably, the dose for a patient can be about 0.05-5 g/kg and all increments therein. Alternatively, the dose for a patient can be about 1-10 g/kg and all increments therein.

The dose for a patient can also be about 10-40 g/kg and all increments therein, about 6-24 g/kg and all increments therein, about 20-80 g/kg and all increments therein, about 40-80 g/kg and all increments therein, about 100-250 g/kg and all increments therein, or about 100-500 g/kg and all increments therein. More preferably, the dosage can be about 0.5, 1, 2, 5, 6, 10, 12, 18, 20, 24, 30, 40, 50, 30, or 90 g/kg. Preferably, the dosage can be 0.5, 2, 6, 8 10, 12, 18 20, 30, 40, or 80 g/kg.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

For each of the recited embodiments, the patient can receive "pretreatment" with the compounds described herein wherein the compounds described herein are administered every day, every 2 days, every 3 days, every 4 days, every 5 days, every 6 days, and/or every 7 days (once a week). In one embodiment, the dosage can be administered daily for up to and including 30 days, preferably between 7-10 days. In another embodiment, the dosage can be administered twice a day for 10 days. If the patient requires treatment for a chronic disease or condition requiring prolonged treatment, the dosage of alkaline may be administered for as long as symptoms persist.

In one embodiment, the compounds described herein are administered in an initial dose of 20-80 mg on the first day of treatment and then at least two dosages of about 40 mg on the second day. In another embodiment the compounds described herein are administered in an initial dose of 0.5-2 mg on the first day of treatment and then at least two dosages of about 2 mg on the second day. In another embodiment, the compounds described herein are administered in an initial dose of 10-20 mg on the first day of treatment and then at least two dosages of about 20 mg on the second day. In yet another embodiment, the compounds described herein are administered in an initial dose of 5-10 mg on the first day of treatment and then at least two dosages of about 10 mg on the second day.

For administration via injection, in one embodiment the treatment begins as a course of 4 injections at 0, 12, 24, and 36 hours. The injections then may continue once, twice, or thrice a day for as long as signs and/or symptoms persists. Alternatively, the injections may be maintained to prevent the recurrence of disease. Also, the injections may be administered as a prophylaxis for patients at risk, especially asymptomatic patients.

The dosage may be administered as a single dose, a double dose, a triple dose, a quadruple dose, and/or a quintuple dose. The dosages may be administered singularly, simultaneously, and sequentially.

For each of the recited embodiments, the dosage of the compounds described herein may be a therapeutically effective amount of the compounds described herein, an amount effective for prophylaxis, and for acute treatment, or an amount effective for prevention. The dosage of the compounds described herein may be an amount of the compounds described herein effective to reduce signs or symptoms of a disease, an amount effective to prevent signs and/or symptoms of a disease, to reduce the severity of signs and/or symptoms of a disease, to eliminate signs and/or symptoms of a disease, to slow the development of signs or symptoms of a disease, to prevent the development of signs and/or symptoms of a disease, or effect prophylaxis of signs or symptoms of a disease.

The dosage form may be any form of release known to persons of ordinary skill in the art. The compositions of the present invention may be formulated to provide immediate release of the active ingredient or sustained or controlled release of the active ingredient. In a sustained release or controlled release preparation, release of the active ingredient may occur at a rate such that blood levels are maintained within a therapeutic range but below toxic levels over an extended period of time (e.g., 4 to 24 hours). The preferred dosage forms include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics, and combinations thereof is known in the art.

It will be appreciated that the pharmacological activity of the compositions may be monitored using standard pharmacological models that are known in the art. Furthermore, it will be appreciated that the inventive compositions may be incorporated or encapsulated in a suitable polymer matrix or membrane for site-specific delivery, or may be functionalized with specific targeting agents capable of effecting site specific delivery. For instance, the dosage form may be made such that it preferably releases in the central nervous system or peripheral nervous system. These techniques, as well as other drug delivery techniques are well known in the art. Determination of optimal dosages for a particular situation is within the capabilities of those skilled in the art. See e.g., Gennaro (2000) *Remington, The Science And Practice of Pharmacy.* 20*th Edition*, Philadelphia College of Pharmacy and Science.

In further embodiments, bumetanide analogs according to the present invention may be administered 1.5 to 6 mg daily, for example, 1 tablet or capsule three times a day. In some embodiments, furosemide analogs according to the present invention may be administered 60 to 240 mg/day, for example, 1 tablet or capsule three times a day. In other embodiments, piretanide analogs according to the present invention may be administered 10 to 20 mg daily, for, example, 1 tablet or capsule once a day. In some embodiments, azosemide analogs according to the present invention may be administered 60 mg per day. In other embodiments, torsemide analogs according to the present invention may be administered 10 to 20 mg daily, for example, 1 tablet or capsule once a day. It should be noted that lower doses may be administered, particularly for IV administration. Moreover, administration of a lower dose than administered for the parent compound may prevent undesirable peripheral effects such as diuresis.

In additional further embodiments, bumetanide analogs are administered at about 0.5, 1.0, or 2.0 mg; furosemide analogs are administered at about 20-80 mg or two 40 mg doses daily; piretanide analogs are administered 0, 200, 500, or 1,250 mg/kg, preferably at about 10-30 mg/kg or 200-500 mg/kg; torsemide analogs are administered at 5, 10, 20, 40, or 200 mg. More preferably, the analogs are administered orally and daily at about 1, 10, or 20 mg.

Routes of Administration

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

Pharmaceutical Compositions

A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other means of administration.

A "pharmaceutical excipient" or a "pharmaceutically acceptable excipient" is a carrier, usually a liquid, in which an active therapeutic agent is formulated. The excipient generally does not provide any pharmacological activity to the formulation, though it may provide chemical and/or biological stability, and release characteristics. Exemplary formulations can be found, for example, in Remington. The Science And Practice of Pharmacy. 20th Edition. (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

The preferred forms of administration in the present invention are oral forms known in the art of pharmaceutics. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include-one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

Nutritional Compositions

The compositions of the compounds described herein may be used in (or consumed in) nutritional supplements; dietary supplements; medical foods; nutriceuticals; food-stuffs such as pharmaceutical-benefit foods (e.g., "phoods"); beverages including fortified (e.g., orange juice with calcium); traditional (e.g., regular oatmeal, whole-grain breads), and "designer" products (e.g., protein bars, smart spreads, smart bars, energy bars). The compounds described herein may be formulated in health bars, confections, animal feeds, cereals, dietary supplements, yogurts, cereal coatings, foods, nutritive foods, functional foods, and combinations thereof.

Second Agents

Second agents for treatment in combination with compositions of the present invention include, but are not limited to, phenytoin, carbamazepine, barbiturates, phenobarbital, mephobarbital, trimethadione; mephenytoin; paramethadione, phenthenylate, phenacemide, metharbital, benzchlorpropamide, phensuximide, primidone, methsuximide, ethotoin, aminoglutethinide, diazepam, clonazepam, clorazepate, fosphenytoin, ethosuximide, valproate, felbamate, gabapentin, lacosamide, lamotrigine, retigabine, rufinamide, topiramate, vigrabatrin, pregabalin, tiagabine, zonisamide, clobazam., thiopental, midazolam, propofol, levetiracetam, oxcarbazepine, CCPene, GYK152466, serotonin receptor agonists, ergotamine, dihydroergotamine, sumatriptan, propranolol, metoprolol, atenolol, timolol, nadolol, nifeddipine, nimodipine, verapamil, aspirin, ketoprofen, tofenamic acid, mefenamic acid, naproxen, methysergide, paracetamol, clonidine, lisuride, iprazochrome, butalbital, benzodiazepines, divalproex sodium and other similar classes of compounds. See U.S. Pat. No. 6,495,601 and U.S. Patent Application Publication No. 2002/0082252.

For example, in addition to the composition described herein patients may also be treated with antidepressants (e.g., tricyclic antidepressants [e.g., amitriptyline (Elavil®), desipramine (Norpramin®), imipramine (Tofranil®), nortriptyline (Aventyl®, Pamelor®)]; Serotonin and norepinephrine reuptake inhibitors (SNRIs) [e.g., venlafaxine (Effexor®), duloxetine (Cymbalta®)]; norepinephrine and dopamine reuptake inhibitors (NDRIs) [e.g., bupropion (Wellbutrin®)]; combined reuptake inhibitors and receptor blockers [e.g., trazodone (Desyrel®), nefazodone (Serzone®), maprotiline, mirtazpine (Remeron®)]; monamine oxidase inhibitors (MAOIs) [e.g., isocarboxazid (Marplan®), phenelzine (Nardil®), tranlcypromine (Parnate®)] and selective serotonin reuptake inhibitors (SSRIs) [e.g., citalopram (Celexa®), escitalopram (Lexapro®), fluoxetine (Prozac®), paroxetine (Paxil®, Pexeva®), sertraline (Zoloft®)] fluvoxamine (Luvox®), and amitriptyline); anticonvulsants to stabilize abnormal electrical activity in the nervous system caused by injured nerves (e.g., gabapentin (NEURONTIN®), pregabalin (LYRICA®), carbamazepine (Tegretol®), lamotrigine (Lamictal®), topiramate (Topamax®), felbamate (Felbatol®), tiagabine (Gabitril®), diazepam rectal (Diastat®), phenobarbital, phenytoin (Dilantin®) primidone (Mysoline®), valproate (Depakote®3), vigabatrin, oxcarbazepine (Trileptal®), zonisamide (Zonegran®), and levetiracetam (Keppra®)); steroids (e.g., corticosteroid); analgesics (e.g., acetaminophen (Tylenol®), codeine (Tylenol #2, 3, 4®), propoyl APA (Darvocet®), propoeylphene (Darvon®), fentanyl patch (Duragesic®), hydromorphone (Palladone®), morphine (MS Contin®), oxycodone (Percocet®, OxyContin®, Percodan®), pentazocine (Talwin NX®), tramadol APAP (Ultracet®), tramadol (Ultram), hydrocodone APAP (Vicodin®)); lithium, and non-steroidal anti-inflammatory drugs (NSAID) (e.g., Tylenol®, Motrin®, salicylates (e.g., acetylsalicylic acid (Aspirin), amoxiprin, benorylate/benorilate, choline magnesium salicylate, Diflunisal®, ethenzamide, faislamine, methyl salicylate, magnesium salicylate, salicyl salicylate, and salicylamide), arylalkanoic acids (e.g., Diclofenac®, Aceclofenac®, Acemethacin®, Alclofenac®, Bromfenao®, Etodolac®, Indomethacin®, Nabumetone®, Oxametacin®, Proglumetacin®, Sulindac®, and Tolmetin®) 2-Arylpropionic acids (profens) (e.g., Ibuprofen®, Alminoprofen®, Carprofen®, Dexibuprofen®, Dexketoprofen®, Fenbufen®, Fenoprofen®, Flunoxaprofen®, Flurbiprofen®, Ibuproxam®, Indoprofen®, Ketorolac®, Loxoprofen®, Naproxen®, Oxaprozin®, Pirprofen®, Suprofen®, Tiaprofenic acid); N-Arylanthranilic acids (fenamic acids) (e.g., mefenamic acid, flufenamic acid, meclofenamic acid, tolfenamic acid, pyrazolidine derivatives, Phenylbutazone®, Ampyrone®, Azapropazone®, Clofezone®, Kebuzone®, Metamizole®, Mofebutazone®, Oxyphenbutazone®. Phenazone®, and Sulfinpyrazone®); and oxicams (e.g., Piroxicam®, Droxicam®, Lornoxicam®, Meloxicam®, and Tenoxicam®).

Such second agents can be administered in the same formulation (e.g., the same pill) or in a separate formulation as the compounds of the present invention. It is preferred that the second agents described above be co-administered with the compounds of the present invention. The second agents described herein can be administered with the compounds of the present invention simultaneously, sequentially, prior to, or after administering of the compounds of the present invention. Where the administration of the second agents described herein is simultaneous, the second agent and the compounds of the present invention are administered together or within a very short time interval (e.g., 5 minutes). Where the administration of the second agent is administered as pre-treatment, the second agent is administered prior to administration of the compounds of the present invention for any length of time contemplated herein.

Psychotherapy

The compounds, pharmaceutical compositions, and treatment regimes described herein may be used in combination with psychotherapy. In one embodiment, the treatment of addictive disorder, anxiety disorders, bipolar disorders, and/or depression further comprises psychotherapy.

Several types of psychotherapy—or "talk therapy"—can help people with depression. In some embodiments, the regimens are short-term (e.g., 10 to 20 weeks) and other regimens are longer-term (e.g., 1-10 years), depending on the needs of the individual. Two main types of psychotherapies-cognitive-behavioral therapy (CBT) and interpersonal therapy (IPT)-have been shown to be effective in treating neuropsychiatric disorders (e.g., addictive disorders, anxiety disorders, bipolar disorders, and depression).

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

Further embodiments of the present invention will now be described with reference to the following examples. The examples contained herein are offered by way of illustration and not by any way of limitation.

EXAMPLE 1

Methyl 3-Aminosulfonyl-5-butylamino-4-phenoxybenzoate (Bumetanide Methyl Ester)

To a slurry of bumetanide (1.2 g, 3.29 mmol) in methanol (12 mL) under nitrogen, was added a mixture of thionyl chloride (70 µL) in methanol (6 mL) over 5 minutes. After stirring for 5 minutes the reaction mixture became soluble. The reaction stirred for an additional 30 minutes, at which time the reaction was complete by thin layer chromatography (TLC). The methanol was removed under reduced pressure and the residue was brought up in ethyl acetate and washed with saturated sodium bicarbonate, water, and brine. The ethyl acetate was dried over anhydrous magnesium sulfate and concentrated to a yield 1.1 g (89%) of methyl 3-aminosulfonyl-5-butylamino-4-phenoxybenzoate as a white solid. Using similar methodology bumetanide ethyl ester, bumetanide isoamyl ester, bumetanide octyl ester and bumetanide benzyl ester, can be prepared.

EXAMPLE 2

3-Aminosulfonyl-5-butylamino-4-phenoxythiobenzoic Acid (Thiobumetanide, Bumetanide —(C=O)—SH Thioacid)

Bumetanide can be reacted thionyl chloride to make the corresponding acid chloride which can then be reacted with sodium hydrogen sulfide to give 3-aminosulfonyl-5-butylamino-4-phenoxythiobenzoic acid (thiobumetanide, S-bumetanide thioacid) by the methodology of Noble, P. and Tarbell, D. S., Org. Synth., Coll. Vol. IV, John Wiley & Sons, Inc., New York, 1963, 924-927.

EXAMPLE 3

3-Aminosulfonyl-5-butylamino-4-phenoxythiobenzoic Acid Thiobumetanide, Bumetanide —(C=O)—SH Thioacid)

3-Aminosulfonyl-5-butylamino-4-phenoxythiobenzoic Acid, Sodium Salt Thiobumetanide Sodium Salt, Bumetanide —(C=O)—SNa Thioacid Sodium Salt)

Bumetanide methyl ester can be reacted with hydrogen sulfide or sodium hydrogen sulfide to give, following acidification of the sodium salt, 3-aminosulfonyl-5-butylamino-4-phenoxythiobenzoic acid (thiobumetanide, bumetanide thioacid).

EXAMPLE 4

Thiomethyl 3-Aminosulfonyl-5-butylamino-4-phenoxybenzoate (Bumetanide S-Methyl Thioester)

In like manner to EXAMPLE 1, bumetanide can be reacted with a catalytic amount of thionyl chloride in methanethiol (methyl mercaptan) to give thiomethyl 3-aminosulfonyl-5-butylamino-4-phenoxybenzoate. Using similar methodology with bumetanide and the corresponding thiols, bumetanide S-ethyl thioester, bumetanide S-isoamyl thioester, bumetanide S-octyl thioester and bumetanide S-benzyl thioester, can be prepared. Using similar methodology with dithiobumetanide and the corresponding alcohols, bumetanide O-ethyl thioester, bumetanide O-isoamyl thioester, bumetanide O-octyl thioester and bumetanide O-benzyl thioester, can be prepared.

EXAMPLE 5

3-Aminosulfonyl-5-butylamino-4-phenoxy-dithiobenzoic Acid (Dithiobumetanide, Bumetanide —(C=S)—SH Dithioacid)

3-Aminosulfonyl-5-butylamino-4-phenoxydithiobenzoc Acid, Sodium Salt Dithiobumetanide Sodium Salt, Bumetanide —(C=S)—SNa Dithioacid Sodium Salt)

Thiobumetanide can be reacted thionyl chloride to make the corresponding thioacid chloride which can then be reacted with sodium hydrogen sulfide to give, following acidification of the sodium salt, 3-aminosulfonyl-5-butylamino-4-phenoxy-dithiobenzoic acid (dithiobumetanide, bumetanide dithioacid) by the methodology of Noble, P. and Tarbell, D. S., Org. Synth., Coll. Vol. IV, John Wiley & Sons, Inc., New York, 1963, 924-927.

EXAMPLE 6

Methyl 3-Aminosulfonyl-5-butylamino-4-phenoxydithiobenzoate (Bumetanide Methyl Dithioester)

In like manner to EXAMPLE 1, dithiobumetanide can be reacted with a catalytic amount of thionyl chloride in methanethiol (methyl mercaptan) to give methyl 3-aminosulfonyl-5-butylamino-4-phenoxydithiobenzoate. Using similar methodology bumetanide ethyl dithioester, bumetanide isoamyl dithioester, bumetanide octyl dithioester and bumetanide benzyl dithioester, can be prepared.

EXAMPLE 7

Cyanomethyl 3-Aminosulfonyl-5-butylamino-4-phenoxybenzoate (Bumetanide Cyanomethyl Ester)

Bumetanide (1.0 g, 2.7 mmol) was dissolved in dimethylformamide (DMF) and chloroacetonitrile (195 µL, 2.7 mmol) was added followed by triethylamine (465 µL). The reaction was heated to 100° C. for 12 hours, TLC and liquid chromatography-coupled mass spectrometry (LC/MS) indicated the reaction was complete. The reaction was cooled to room temperature brought up in dichloromethane and washed with water, saturated ammonium chloride and reduced to a slurry. To the slurry was added water (25 mL) and crude product precipitated as an off-white solid. Pure cyanomethyl 3-aminosulfonyl-5-butylamino-4-phenoxybenzoate (850 mg) was obtained via recrystallization in acetonitrile. Using similar methodology bumetanide ethyl ester, bumetanide isoamyl ester, bumetanide octyl ester, and bumetanide benzyl ester, can be prepared.

EXAMPLE 8

Benzyl 3-Aminosulfonyl-5-butylamino-4-phenoxybenzoate (Bumetanide Benzyl Ester)

Bumetanide (1.15 g, 3.15 mmol) was dissolved in dimethylformamide (DMF, 10 mL) and benzyl chloride (400 µL, 2.8 mmol) was added followed by triethylamine (480 µL). The reaction was heated to 80° C. for 12 hours, TLC and LC/MS indicated the reaction was complete. The reaction was cooled to room temperature brought up in dichloromethane and washed with water, saturated ammonium chloride and concentrated to a thick slurry. To the slurry was added water (25 mL), the resultant solids were filtered and dried in a vacuum oven at 50° C. for 12 hours to yield 1.0 g (80%) of solid benzyl 3-aminosulfonyl-5-butylamino-4-phenoxybenzoate.

EXAMPLE 9

2-(4-Morpholino)ethyl 3-Aminosulfonyl-5-butylamino-4-phenoxybenzoate (Bumetanide 4-Morpholinoethyl Ester)

Bumetanide (1.2 g, 3.29 mmol) was dissolved in dimethylformamide (DMF, 12 mL) and 4-(2-chloroethyl)morpholine hydrochloride (675 mg, 3.62 mmol) was added followed by triethylamine (1 mL) and sodium iodide (500 mg 3.33 mmol). The reaction was heated to 95° C. for 8 hours, TLC and LC/MS indicated the reaction was complete. The reaction was cooled to room temperature brought up in dichloromethane and washed with water, saturated ammonium chloride and concentrated to dryness. After purification via a Biotage flash chromatography on silica gel, the purified elute, on evaporation under vacuum, yielded 2-(4-morpholino)ethyl 3-aminosulfonyl-5-butylamino-4-phenoxybenzoate as a white solid (600 mg, 62%).

EXAMPLE 10

3-(N,N-Dimethylaminopropyl 3-Aminosulfonyl-5-butylamino-4-phenoxybenzoate [Bumetanide 3-(N,N-Dimethylaminopropyl)Ester]

In similar manner to Example 54, bumetanide can be reacted with 3-(dimethylamino)propyl chloride hydrochloride, triethylamine and sodium iodide in dimethylformamide (DMF) to yield 3-(N,N-dimethylaminopropyl 3-aminosulfonyl-5-butylamino-4-phenoxybenzoate.

EXAMPLE 11

3-(N,N-Dimethylaminopropyl 3-Aminesulfonyl-5-butylamino-4-phenoxy-dithiobenzoate [Bumetanide 3-(N,N-Dimethylaminopropyl)Dithioester]

In similar manner to EXAMPLE 10, dithiobumetanide can be reacted with 3-(dimethylamino)propyl chloride hydrochloride, triethylamine and sodium iodide in dimethylformamide (DMF) to yield 3-(N,N-dimethylaminopropyl 3-aminosulfonyl-5-butylamino-4-phenoxy-dithiobenzoate.

EXAMPLE 12

N,N-Diethylaminocarbonylmethyl 3-Aminosulfonyl-5-butylamino-4-phenoxybenzoate (Bumetanide N,N-Diethylglycolamido Ester)

Bumetanide (1.2 g, 3.29 mmol) was dissolved in dimethylformamide (12 mL) and 2-chloro-N,N-diethylacetamide (500 mg, 3.35 mmol) was added followed by triethylamine (0.68 mL) and sodium iodide (500 mg 3.33 mmol). The reaction was heated to 95° C. for 8 hours, TLC and LC/MS indicated the reaction was complete. The reaction was cooled to room temperature brought up in dichloromethane and washed with water, saturated ammonium chloride and reduced to a thick slurry. To the slurry was added water (25 mL), the resultant solids precipitated from the solution. The product was filtered and dried in a vacuum oven at 50° C. for 12 hours to yield 1.0 g of solid N,N-diethylaminocarbonylmethyl 3-aminosulfonyl-5-butylamino-4-phenoxybenzoate.

EXAMPLE 13

N,N-Diethyl 3-Aminosulfonyl-5-butylamino-4-phenoxybenzamide (Bumetanide Diethylamide)

Bumetanide (1.16 g, 3.2 mmol) was dissolved in dichloromethane (10 mL) and 1-ethyl-3-(3-dimethylaminopropyl) carbodiimide (EDC, 690 mg, 3.6 mmol) was added and after 5 minutes N-hydroxybenzotriazole (HOBt, 498 mg, 3.6 mmol) was added and the solution was allowed to stir for an additional 5 minutes. Diethylamine (332 µL, 3.2 mmol) was added and the reaction was stirred for 2 hours. The reaction was washed with washed with saturated sodium bicarbonate, water, brine and dried with anhydrous magnesium sulfate. The dichloromethane was removed under reduced pressure to yield 860 mg (65%) of pure N,N-diethyl 3-aminosulfonyl-5-butylamino-4-phenoxybenzamide.

EXAMPLE 14

N,N-Diethyl 3-Aminosulfonyl-5-butylamino-4-phenoxythiobenzamide (Bumetanide Diethylthioamide)

In similar manner to Example 5, dithiobumetanide can be reacted with thionyl chloride to give the thioacid chloride, which can be reacted with diethylamine in the manner of EXAMPLE 13 to afford N,N-diethyl 3-aminosulfonyl-5-butylamino-4-phenoxythiobenzamide.

EXAMPLE 15

N,N-Dibenzyl 3-Aminosulfonyl-5-butylamino-4-phenoxybenzamide (Bumetanide Dibenzylamide)

Bumetanide (960 mg, 2.6 mmol) was dissolved in dimethylformamide (DMF, 10 mL) and 1-ethyl-3-(3-dimethylaminopropyl)carbodiimide (EDC, 560 mg, 3.6 mmol) was added and after 10 minutes 1-hydroxybenzotriazole (HOBt, 392 mg, 2.9 mmol) was added and the solution was allowed to stir for an additional 10 minutes. Dibenzylamine (1 mL, 5.2 mmol) was added and the reaction was stirred for 2 hours, at which time the reaction was complete by LC/MS. The reaction was poured into saturated ammonium chloride (20 mL) and extracted with ethyl acetate (2×100 mL). The ethyl acetate was washed with saturated sodium bicarbonate, water, brine and dried over anhydrous magnesium sulfate. The ethyl acetate was removed under reduced pressure to yield 1.0 g (75%) of N,N-dibenzyl 3-aminosulfonyl-5-butylamino-4-phenoxybenzamide as a white solid.

EXAMPLE 16

Benzyltrimethylammonium 3-Aminosulfonyl-5-butylamino-4-phenoxybenzoate (Bumetanide Benzylltrimethylammonium Salt)

To a solution of benzyltrimethylammonium hydroxide (451 mg, 2.7 mmol) in water (10 mL) was added bumetanide (1 g, 2.7 mmol) over a period of 5 minutes. The reaction mixture became clear after 10 minutes of stirring. The water was removed under reduced pressure to yield a colorless oil. Pure product was obtained from recrystallization of the oil with water and heptane to yield 690 mg of benzyltrimethylammonium 3-aminosulfonyl-5-butylamino-4-phenoxybenzoate as light pink crystals.

EXAMPLE 17

Cetyltrimethylammonium 3-Aminosulfonyl-5-butylamino-4-phenoxybenzoate (Bumetanide Cetyltrimethylammonium Salt)

In similar manner to EXAMPLE 16, bumetanide can be reacted with cetyltrimethylammonium hydroxide in water to yield cetyltrimethylammonium 3=aminosulfonyl-5-butylamino-4-phenoxybenzoate.

EXAMPLE 18

N,N-Dimethylaminocarbonylmethyl 3-Aminosulfonyl-5-butylamino-4-phenoxybenzoate (Bumetanide N,N-Dimethylglycolamido Ester)

Bumetanide (1.2 g, 3.29 mmol) was dissolved in dimethylformamide (DMF, 10 mL) and 2-chloro-N,N-dimethylacetamide (410 μL, 3.9 mmol) was added followed by triethylamine (0.70 mL) and sodium iodide (545 mg, 3.6 mmol). The reaction was heated to 50° C. for 10 hours, TLC and LC/MS indicated the reaction was complete. The solvent was removed under reduced pressure and the residue was dissolved in ethyl acetate and washed with saturated sodium bicarbonate, water, and brine and dried over anhydrous magnesium sulfate. The ethyl acetate was removed under reduced pressure and the product was purified via flash chromatography on silica gel to yield 685 mg (60%) of pure N,N-dimethylaminocarbonylmethyl 3-aminosulfonyl-5-butylamino-4-phenoxybenzoate.

EXAMPLE 19 t-Butylcarbonyloxymethyl 3-Aminosulfonyl-5-butylamino-4-phenoxybenzoate (Bumetanide Pivaxetil Ester)

Bumetanide (1.2 g, 3.29 mmol) was dissolved in dimethylformamide (DMF, 10 mL) and chloromethyl pivalate (575 μL, 3.9 mmol) was added followed by triethylamine (0.70 mL) and sodium iodide (545 mg, 3.6 mmol). The reaction was heated to 50° C. for 10 hours, TLC and LC/MS indicated the reaction was complete. The solvent was removed under reduced pressure and the residue was dissolved in ethyl acetate and washed with saturated sodium bicarbonate, water, and brine and dried over anhydrous magnesium sulfate. The ethyl acetate was removed under reduced pressure and the product was purified via flash chromatography on silica gel to yield 653 mg (60%) of pure t-butylcarbonyloxymethyl 3-aminosulfonyl-5-butylamino-4-phenoxybenzoate.

t-Butylcarbonyloxymethyl 3-Aminosulfonyl-5-butylamino-4-phenoxy-dithiobenzoate (Bumetanide Pivaxetil Dithioester)

In a similar manner to EXAMPLE 19, dithiobumetanide can be reacted with chloromethyl pivalate, triethylamine, and sodium iodide in dimethylformamide (DMF) to field t-butylcarbonyloxymethyl 3-aminosulfonyl-5-butylamino-4-phenoxy-dithiobenzoate.

EXAMPLE 20

Ethylcarbonyloxymethyl 3-Aminosulfonyl-5-butylamino-4-phenoxybenzoate (Bumetanide Propaxetil Ester)

In similar manner to EXAMPLE 19, bumetanide can be reacted with chloromethyl propionate, triethylamine, and sodium iodide in dimethylformamide (DMF) to yield ethylcarbonyloxymethyl 3-aminosulfonyl-5-butylamino-4-phenoxybenzoate.

EXAMPLE 21

Ethylcarbonyloxymethyl 3-Aminosulfonyl-5-butylamino-4-phenoxy-dithiobenzoate (Bumetanide Propaxetil Dithioester)

In similar manner to Example 20, dithiobumetanide can be reacted with chloromethyl propionate, triethylamine, and sodium iodide in dimethylformamide (DMF) to yield ethylcarbonyloxymethyl 3-aminosulfonyl-5-butylamino-4-phenoxy-dithiobenzoate.

EXAMPLE 22

Methyl 3-Aminosulfonyl-4-phenoxy-5-(1-pyrrolidinyl)benzoate (Piretanide Methyl Ester)

In similar manner to EXAMPLE 1, piretanide can be reacted with thionyl chloride and methanol to yield methyl 3-aminosulfonyl-4-phenoxy-5-(1-pyrrolidinyl)benzoate. Using similar methodology piretanide ethyl ester, piretanide isoamyl ester, piretanide octyl ester and piretanide benzyl ester can be prepared.

EXAMPLE 23

3-Aminosulfonyl-4-phenoxy-5-(1-pyrrolidinyl)-thiobenzoic Acid (Thiopiretanide, Piretanide —(C=O)—SH Thioacid)

3-Aminosulfonyl-4-phenoxy-5-(1-pyrrolidinyl)-thiobenzoic Acid, Sodium Salt (Thiopiretanide Sodium Salt, Piretanide —(C=O)—SNa Thioacid Sodium Salt)

Piretanide can be reacted thionyl chloride to make the corresponding acid chloride which can then be reacted with sodium hydrogen sulfide to give, following acidification of the sodium salt, 3-aminosulfonyl-4-phenoxy-5-(I-pyrrolidinyl)-thiobenzoic acid (thiopiretanide, S-piretanide thioacid) by the methodology of Noble, P. and Tarbell, D. S., Org. Synth., Coll. Vol. IV, John Wiley & Sons, Inc., New York, 1963, 924-927.

EXAMPLE 24

3-Aminosulfonyl-4-phenoxy-5-(1-pyrrolidinyl)-thiobenzoic Acid (Thiopiretanide, Piretanide —(C=O)—SH Thioacid)

Piretanide methyl ester can be reacted with hydrogen sulfide or sodium hydrogen sulfide to give, following acidification of the sodium salt, 3-aminosulfonyl-4-phenoxy-5-(I-pyrrolidinyl)-thiobenzoic acid (thiopiretanide, S-piretanide thioacid).

EXAMPLE 25

Thiomethyl 3-aminosulfonyl-4-phenoxy-5-(1-pyrrolidinyl)benzoate (Piretanide S-Methyl Thioester)

In like manner to EXAMPLE 1, piretanide can be reacted with a catalytic amount of thionyl chloride in methanethiol (methyl mercaptan) to give thiomethyl 3-aminosulfonyl-4-phenoxy-5-(1-pyrrolidinyl)benzoate. Using similar methodology with piretanide and the corresponding thiols, piretanide S-ethyl thioester, piretanide S-isoamyl thioester, piretanide S-octyl thioester and piretanide S-benzyl thioester, can be prepared. Using similar methodology with dithiopiretanide and the corresponding alcohols, piretanide O-ethyl thioester, piretanide O-isoamyl thioester, piretanide O-octyl thioester and piretanide O-benzyl thioester, can be prepared.

EXAMPLE 26

3-Aminosulfonyl-4-phenoxy-5-(1-pyrrolidinyl)-dithiobenzoic Acid (Dithiopiretanide, Piretanide —(C=S)—SH Dithioacid)

3-Aminosulfonyl-4-phenoxy-5-(1-pyrrolidinyl)-dithiobenzoic Acid, Sodium Salt (Dithiopiretanide Sodium Salt, Piretanide —(C=S)—SNa Dithioacid Sodium Salt)

Thiopiretanide can be reacted thionyl chloride to make the corresponding thioacid chloride which can then be reacted with sodium hydrogen sulfide to give, following acidification of the sodium salt, 3-aminosulfonyl-4-phenoxy-5-(1-pyrrolidinyl)-dithiobenzoic acid (dithiopiretanide, piretanide dithioacid) by the methodology of Noble, P. and Tarbell, D. S., Org. Synth., Coll. Vol. IV, John Wiley & Sons, Inc., New York, 1963, 924-927.

EXAMPLE 27

Methyl 3-aminosulfonyl-4-phenoxy-5-(1-pyrrolidinyl)-dithiobenzoate (Piretanide Methyl Dithioester)

In like manner to EXAMPLE 1, dithiopiretanide can be reacted with a catalytic amount of thionyl chloride in methanethiol (methyl mercaptan) to give methyl 3-aminosulfonyl-4-phenoxy-5-(1-pyrrolidinyl)-dithiobenzoate. Using similar methodology piretanide ethyl dithioester, piretanide isoamyl dithioester, piretanide octyl dithioester and piretanide benzyl dithioester can be prepared.

EXAMPLE 28

Cyanomethyl 3-Aminosulfonyl-4-phenoxy-5-(1-pyrrolidinyl)benzoate (Piretanide Cyanomethyl Ester)

In similar manner to Example 7, piretanide can be reacted with chloroacetonitrile and triethylamine in DMF to yield cyanomethyl 3-aminosulfonyl-4-phenoxy-5-(1-pyrrolidinyl)benzoate.

EXAMPLE 29

Benzyl 3-Aminosulfonyl-4-phenoxy-5-(1-pyrrolidinyl)benzoate (Piretanide Benzyl Ester)

In similar manner to Example 8, piretanide can be reacted with benzyl chloride and triethylamine in DMF to yield benzyl 3-aminosulfonyl-4-phenoxy-5-(1-pyrrolidinyl)benzoate.

EXAMPLE 30

2-(4-Morpholino)ethyl 3-Aminosulfonyl-4-phenoxy-5-(1-pyrrolidinyl)benzoate (Piretanide 4-Morpholinoethyl Ester)

In similar manner to Example 9, piretanide can be reacted with 4-(2-chloroethyl)morpholine hydrochloride, triethylamine, and sodium iodide in DMF to yield 2-(4-morpholino)ethyl 3-aminosulfonyl-4-phenoxy-5-(1-pyrrolidinyl)benzoate.

EXAMPLE 31

3-(N,N-Dimethylaminopropyl 3-Aminosulfonyl-4-phenoxy-5-(1-pyrrolidinyl) benzoate [Piretanide 3-(N,N-Dimethylaminopropyl) Ester]

In similar manner to Examples 10 and 53, piretanide can be reacted with 3-(dimethylamino)propyl chloride hydrochloride, triethylamine and sodium iodide in dimethylformamide (DMF) to yield 3-(N,N-dimethylaminopropyl 3-aminosulfonyl-4-phenoxy-5-(1-pyrrolidinyl)benzoate.

EXAMPLE 32

3-(N,N-Dimethylaminopropyl 3-Aminosulfonyl-4-phenoxy-5-(1-pyrrolidinyl)dithiobenzoate [Piretanide 3-(N,N-Dimethylaminopropyl)Dithioester]

In similar manner to Example 31, dithiopiretanide can be reacted with 3-(dimethylamino)propyl chloride hydrochloride, triethylamine and sodium iodide in dimethylformamide (DMF) to yield 3-(N,N-dimethylaminopropyl 3-aminosulfonyl-4-phenoxy-5-(1-pyrrolidinyl)dithiobenzoate.

EXAMPLE 33

N,N-Diethylaminocarbonylmethyl 3-Aminosulfonyl-4-phenoxy-5-(1-pyrrolidinyl)benzoate (Piretanide N,N-Diethylglycolamide Ester)

In similar manner to EXAMPLE 12, piretanide can be reacted with 2-chloro-N,N-diethylacetamide, triethylamine and sodium iodide in dimethylformamide (DMF) to yield N,N-diethylaminocarbonylmethyl 3-aminosulfonyl-4-phenoxy-5-(1-pyrrolidinyl)benzoate.

EXAMPLE 34

N,N-Diethyl 3-Aminosulfonyl-4-phenoxy-5-(1-pyrrolidinyl)benzoate (Piretanide Diethylamide)

In similar manner to EXAMPLE 13, piretanide can be reacted with EDC, HOBt and diethylamine in DMF to yield N,N-diethyl 3-aminosulfonyl-4-phenoxy-5-(1-pyrrolidinyl) benzamide.

EXAMPLE 35

N,N-Diethyl 3-Aminosulfonyl-4-phenoxy-5-(1-pyrrolidinyl)benzoate (Piretanide Diethylthioamide)

In similar manner to Example 34, dithiopiretanide can be reacted with EDC, HOBt and diethylamine in DMF to yield N,N-diethyl 3-aminosulfonyl-4-phenoxy-5-(1-pyrrolidinyl)thiobenzamide.

EXAMPLE 36

N,N-Dibenzyl 3-Aminosulfonyl-4-phenoxy-5-(1-pyrrolidinyl)benzoate (Piretanide Dibenzylamide)

In similar manner to EXAMPLE 15, piretanide can be reacted with EDC, HOBt and dibenzylamine in DMF to yield N,N-dibenzyl 3-aminosulfonyl-4-phenoxy-5-(1-pyrrolidinyl)benzamide.

EXAMPLE 37

Benzyltrimethylammonium 3-Aminosulfonyl-4-phenoxy-5-(1-pyrrolidinyl)benzoate (Piretanide Benzyltrimethylammonium Salt)

In similar manner to EXAMPLE 16, piretanide can be reacted with benzyltrimethylammonium hydroxide to yield benzyltrimethylammonium 3-aminosulfonyl-4-phenoxy-5-(1-pyrrolidinyl)benzoate.

EXAMPLE 38

Cetyltrimethylammonium 3-Aminosulfonyl-4-phenoxy-5-(1-pyrrolidinyl)benzoate (Piretanide Cetyltrimethylammonium Salt)

In similar manner to EXAMPLE 17, piretanide can be reacted with cetyltrimethylammonium hydroxide in water to yield cetyltrimethylammonium 3-aminosulfonyl-4-phenoxy-5-(1-pyrrolidinyl)benzoate.

EXAMPLE 39

N,N-Dimethylaminocarbonylmethyl 3-Aminosulfonyl-4-phenoxy-5-(1-pyrrolidinyl)benzoate (Piretanide N,N-Dimethylglycolamido Ester)

In similar manner to EXAMPLE 18, piretanide can be reacted with 2-chloro-N,N dimethylacetamide, triethylamine and sodium iodide in DMF to yield N,N-dimethylaminocarbonylmethyl 3-aminosulfonyl-4-phenoxy-5-(1-pyrrolidinyl)benzoate.

EXAMPLE 40 t-Butylcarbonyloxymethyl 3-Aminosulfonyl-4-phenoxy-5-(1-pyrrolidinyl)benzoate (Piretanide Pivaxetil Ester)

In similar manner to EXAMPLE 19, piretanide can be reacted with chloromethyl pivalate, triethylamine and sodium iodide in DMF to yield t-butylcarbonyloxymethyl 3-aminosulfonyl-4-phenoxy-5-(1-pyrrolidinyl)benzoate.

EXAMPLE 41 t-Butylcarbonyloxymethyl 3-Aminesulfonyl-4-phenoxy-5-(1-pyrrolidinyl)dithiobenzoate (Piretanide Pivaxetil Dithioester)

In similar manner to Example 40, dithiopiretanide can be reacted with chloromethyl pivalate, triethylamine and sodium iodide in DMF to yield t-butylcarbonyloxymethyl 3-aminosulfonyl-4-phenoxy-5-(1-pyrrolidinyl)dithiobenzoate.

EXAMPLE 42

Ethylcarbonyloxymethyl 3-Aminosulfonyl-4-phenoxy-5-(1-pyrrolidinyl)benzoate (Piretanide Propaxetil Ester)

In similar manner to Example 20, piretanide can be reacted with chloromethyl propionate, triethylamine and sodium iodide in DMF to yield ethylcarbonyloxymethyl 3-aminosulfonyl-4-phenoxy-5-(1-pyrrolidinyl)benzoate.

EXAMPLE 43

Ethyl 5-Aminosulfonyl-4-chloro-2-[(2-furanylmethyl)amino]benzoate (Furosemide Ethyl Ester)

The method of Bundgaard, et al. (1988) *Int. J. Pharmaceutics* 42: 217-224, can be employed to prepare ethyl 5-aminosulfonyl-4-chloro-2-[(2-furanylmethyl)amino]benzoate, m.p. 163-165°. Using similar methodology furosemide methyl ester, furosemide isoamyl ester, furosemide octyl ester and furosemide benzyl ester can be prepared.

EXAMPLE 44

Methyl 5-Aminosulfonyl-4-chloro-2-[(2-furanylmethyl)amino]benzoate (Furosemide Methyl Ester)

The method of Bundgaard, H., Norgaard, T. and Nielsen, N. M., Int. J. Pharmaceutics, 1988, 42, 217-224, can be employed to prepare methyl 5-aminosulfonyl-4-chloro-2-[(2-furanylmethyl)amino]benzoate.

EXAMPLE 45

5-Aminosulfonyl-4-chloro-2-[(2-furanylmethyl)amino]thiobenzoic Acid (Thiolurosemide, Furosemide —(C=O)—SH Thioacid)

5-Aminosulfonyl-4-chloro-2-[(2-furanylmethyl)amino]thiobenzoic Acid, Sodium Salt (Thiofurosemide Sodium Salt, Furosemide —(C=O)—SNa Thioacid Sodium Salt)

Furosemide can be reacted thionyl chloride to make the corresponding acid chloride which can then be reacted with sodium hydrogen sulfide to give, following acidification of the sodium salt, 5-aminosulfonyl-4-chloro-2-[(2-furanylmethyl)amino]thiobenzoic acid (thiofurosemide, S-furosemide thioacid) by the methodology of Noble, P. and Tarbell, D. S., Org. Synth., Coll. Vol. IV, John Wiley & Sons, Inc., New York, 1963, 924-927.

EXAMPLE 46

5-Aminosulfonyl-4-chloro-2-[(2-furanylmethyl)amino]thiobenzoic Acid (Thiofurosemide, Furosemide —(C=O)—SH Thioacid)

Furosemide methyl ester can be reacted with hydrogen sulfide or sodium hydrogen sulfide to give, following acidification, 3-aminosulfonyl-5-butylamino-4-phenoxythiobenzoic acid (thiofurosemide, S-furosemide thioacid).

EXAMPLE 47

Thiomethyl 5-Aminosulfonyl-4-chloro-2-[(2-furanylmethyl)amino]benzoate (Furosemide S-Methyl Thioester)

In like manner to EXAMPLE 1, bumetanide can be reacted with a catalytic amount of thionyl chloride in methanethiol (methyl mercaptan) to give thiomethyl 5-aminosulfonyl-4-chloro-2-[(2-furanylmethyl)amino]benzoate. Using similar methodology with furosemide and the corresponding thiols, furosemide S-ethyl thioester, furosemide S-isoamyl thioester, furosemide S-octyl thioester and furosemide S-benzyl thioester, can be prepared. Using similar methodology with dithiofurosemide and the corresponding alcohols, furosemide O-ethyl thioester, furosemide O-isoamyl thioester, furosemide O-octyl thioester and furosemide O-benzyl thioester, can be prepared.

EXAMPLE 48

5-Aminosulfonyl-4-chloro-2-[(2-furanylmethyl)amino]-dithiobenzoic Acid (Dithiofurosemide, Furosemide —(C=S)—SH Dithioacid)

5-Aminosulfonyl-4-chloro-2-[(2-furanylmethyl)amino]-dithiobenzoic Acid, Sodium Salt (Dithiofurosemide Sodium Salt, Furosemide —(C=S)—SNa Dithioacid Sodium Salt)

Thiofurosemide can be reacted thionyl chloride to make the corresponding thioacid chloride which can then be reacted with sodium hydrogen sulfide to give, following acidification of the sodium salt, 5-aminosulfonyl-4-chloro-2-[(2-furanylmethyl)amino]-dithiobenzoic acid (dithiofurosemide, furosemide dithioacid) by the methodology of Noble, P. and Tarbell, D. S., Org. Synth., Coll. Vol. IV, John Wiley & Sons, Inc., New York, 1963, 924-927.

EXAMPLE 49

Methyl 5-Aminosulfonyl-4-chloro-2-[(2-furanylmethyl)amino]dithiobenzoate (Furosemide Methyl Dithioester)

In like manner to EXAMPLE 1, dithiofurosemide can be reacted with a catalytic amount of thionyl chloride in methanethiol (methyl mercaptan) to give methyl 5-aminosulfonyl-4-chloro-2-[(2-furanylmethyl)amino]dithiobenzoate. Using similar methodology furosemide ethyl dithioester, furosemide isoamyl dithioester, furosemide octyl dithioester and furosemide benzyl dithioester can be prepared.

EXAMPLE 50

Cyanomethyl 5-Aminosulfonyl-4-chloro-2-[(2-furanylmethyl)amino]benzoate (Furosemide Cyanomethyl Ester)

In similar manner to Example 7, furosemide can be reacted with chloroacetonitrile and triethylamine in DMF to yield cyanomethyl 5-aminosulfonyl-4-chloro-2-[(2-furanylmethyl)amino]benzoate.

EXAMPLE 51

Benzyl 5-Aminosulfonyl-4-chloro-2-[(2-furanylmethyl)amino]benzoate (Furosemide Benzyl Ester)

In similar manner to Example 8, furosemide can be reacted with benzyl chloride and triethylamine in DMF to yield benzyl 5-aminosulfonyl-4-chloro-2-[(2-furanylmethyl)amino]benzoate.

EXAMPLE 52

2-(4-Morpholino)ethyl 5-Aminosulfonyl-4-chloro-2-[(2-furanylmethyl)amino]benzoate (Furosemide 4-Morpholinoethyl Ester)

The method of Mork, N., Bundgaard, H., Shalmi, M. and Christensen, S., Int. J. Pharmaceutics, 1990, 60, 163-169, can be employed to prepare 2-(4-morpholino)ethyl 5-aminosulfonyl-4-chloro-2-[(2-furanylmethyl)amino]benzoate, m.p. 134-135°.

EXAMPLE 53

3-(N,N-Dimethylaminopropyl 5-Aminosulfonyl-4-chloro-2-[(2-furanylmethyl)amino]benzoate [Furosemide 3-(N,N-Dimethylaminopropyl) Ester]

The method of Mork, N., Bundgaard, H., Shalmi, M. and Christensen, S., Int. J. Pharmaceutics, 1990, 60, 163-169, can be employed to prepare 3-(N,N-dimethylaminopropyl 5-aminosulfonyl-4-chloro-2-[(2-furanylmethyl)amino]benzoate, m.p. 212-213°.

EXAMPLE 54

3-(N,N-Dimethylaminopropyl 5-Aminosulfonyl-4-chloro-2-[(2-furanylmethyl)amino]dithiobenzoate [Furosemide 3-(N,N-Dimethylaminopropyl)Dithioester]

In similar manner to Example 53, dithiofurosemide can be reacted with 3-(dimethylamino)propyl chloride hydrochloride, triethylamine and sodium iodide in dimethylformamide (DMF) to yield 3-(N,N-dimethylaminopropyl 5-aminosulfonyl-4-chloro-2-[(2-furanylmethyl)amino]dithiobenzoate.

EXAMPLE 55

N,N-Diethylaminocarbonylmethyl 5-Aminosulfonyl-4-chloro-2-[(2-furanylmethyl)amino]benzoate (Furosemide N,N-Diethylglycolamido Ester)

The method of Mork, N., Bundgaard, H., Shalmi, M. and Christensen, S., Int. J. Pharmaceutics, 1990, 60, 163-169, can be employed to prepare N,N-diethylaminocarbonylmethyl 5-aminosulfonyl-4-chloro-2-[(2-furanylmethyl)amino]benzoate, m.p. 135-136°.

EXAMPLE 56

N,N-Diethyl 5-Aminosulfonyl-4-chloro-2-[(2-furanylmethyl)amino]benzamide (Furosemide Diethylamide)

In similar manner to EXAMPLE 13, furosemide can be reacted with EDC, HOBt and diethylamine in DMF to yield N,N-diethyl 5-aminosulfonyl-4-chloro-2-[(2-furanylmethyl) amino]benzamide.

EXAMPLE 57

N,N-Diethyl 5-Aminosulfonyl-4-chloro-2-[(2-furanylmethyl)amino]benzamide (Furosemide Diethylthioamide)

In similar manner to Example 56, dithiofurosemide can be reacted with EDC, HOBt and diethylamine in DMF to yield N,N-diethyl 5-aminosulfonyl-4-chloro-2-[(2-furanylmethyl) amino]thiobenzamide.

EXAMPLE 58

N,N-Dibenzyl 5-Aminosulfonyl-4-chloro-2-[(2-furanylmethyl)amino]benzamide (Furosemide Dibenzylamide)

In similar manner to EXAMPLE 15, furosemide can be reacted with EDC, HOBt and dibenzylamine in DMF to yield N,N-dibenzyl 5-aminosulfonyl-4-chloro-2-[(2-furanylmethyl)amino]benzamide.

EXAMPLE 59

Benzyltrimethylammonium 5-Aminosulfonyl-4-chloro-2-[(2-furanylmethyl)amino]benzoate (Furosemide Benzyltrimethylammonium Salt)

In similar manner to EXAMPLE 16, furosemide can be reacted with benzyltrimethylammonium hydroxide to yield benzyltrimethylammonium 5-aminosulfonyl-4-chloro-2-[(2-furanylmethyl)amino]benzoate.

EXAMPLE 60

Cetyltrimethylammonium 5-Aminosulfonyl-4-chloro-2-[(2-furanylmethyl)amino]benzoate (Furosemide Cetyltrimethylammonium Salt)

In similar manner to EXAMPLE 17, furosemide can be reacted with cetyltrimethylammonium hydroxide in water to yield cetyltrimethylammonium 5-aminosulfonyl-4-chloro-2-[(2-furanylmethyl)amino]benzoate.

EXAMPLE 61

N,N-Dimethylaminocarbonylmethyl 5-Aminosulfonyl-4-chloro-2-[(2-furanylmethyl)amino]benzoate (Furosemide N,N-Dimethylglycolamido Ester)

The method of Bundgaard, H., Norgaard, T. and Nielsen, N. M., Int. J. Pharmaceutics, 1988, 42, 217-224, can be employed to prepare N,N-dimethylaminocarbonylmethyl 5-aminosulfonyl-4-chloro-2-[(2-furanylmethyl)amino]benzoate, m.p. 193-194°.

EXAMPLE 62 t-Butylcarbonyloxymethyl 5-Aminosulfonyl-4-chloro-2-[(2-furanylmethyl)amino]benzoate (Furosemide Pivaxetil Ester)

The method of Mork, N., Bundgaard, H., Shalmi, M. and Christensen, S., Int. J. Pharmaceutics, 1990, 60, 163-169, can be employed to prepare t-butylcarbonyloxymethyl 5-amino sulfonyl-4-chloro-2-[(2-furanylmethyl)amino]benzoate.

EXAMPLE 63 t-Butylcarbonyloxymethyl 5-Aminosulfonyl-4-chloro-2-[(2-furanylmethyl)amino]dithiobenzoate (Furosemide Pivaxetil Dithioester)

In similar manner to Example 62, dithiofurosemide can be reacted with chloromethyl pivalate, triethylamine and sodium iodide in dimethylformamide (DMF) to yield t-butylcarbonyloxymethyl 5-aminosulfonyl-4-chloro-2-[(2-furanylmethyl)amino]dithiobenzoate.

EXAMPLE 64

Ethylcarbonyloxymethyl 5-Aminosulfonyl-4-chlor-2-[(2-furanylmethyl)amino]benzoate (Furosemide Propaxetil Ester)

The method of Mork, N., Bundgaard, H., Shalmi, M. and Christensen, S., Int. J. Pharmaceutics, 1990, 60, 163-169, can be employed to prepare ethylcarbonyloxymethyl 5-aminosulfonyl-4-chloro-2-[(2-furanylmethyl)amino]benzoate, m.p. 141-142°.

EXAMPLE 65

Ethylcarbonyloxymethyl 5-Aminosulfonyl-4-chloro-2-[(2-furanylmethyl)amino]Dithiobenzoate (Furosemide Propaxetil Dithioester)

In a similar manner to Example 64, the method of Mork, N., Bundgaard, H., Shalmi, M. and Christensen, S., Int J. Pharmaceutics, 1990, 60, 163-169, can be employed to convert dithiofurosemide to ethylcarbonyloxymethyl. 5-aminosulfonyl-4-chloro-2-[(2-furanylmethyl)amino]dithiobenzoate.

EXAMPLE 66

5-[1-(t-Butylcarbonyloxymethyl)-1H-tetrazol-5-yl]-2-chloro-4-[(2-thienylmethyl)amino]benzenesulfonamide (Tetrazolyl-Substituted Azosemide)

In similar manner to EXAMPLE 19, azosemide can be reacted with chloromethyl pivalate, triethylamine and sodium iodide in DMF to yield 5-[1-(t-Butylcarbonyloxymethyl)-1H-tetrazol-5-yl]-2-chloro-4-[(2-thienylmethyl)amino]benzenesulfonamide.

EXAMPLE 67

2-Chloro-5-[1-(ethylcarbonyloxymethyl)-1H-tetrazol-5-yl]-4-[(2-thienylmethyl)amino]benzenesulfonamide (Tetrazolyl-Substituted Azosemide)

In similar manner to EXAMPLE 19, azosemide can be reacted with chloromethyl propionate, triethylamine and sodium iodide in DMF to yield 2-chloro-5-[1-(ethylcarbonyloxymethyl)-1H-tetrazol-5-yl]-4-[(2-thienylmethyl)amino]benzenesulfonamide.

EXAMPLE 68

2-Chloro-5-[1-(hydroxymethyl)-1H-tetrazol-5-yl]-4-[(2-thienylmethyl)amino]benzenesulfonamide (Tetrazolyl-Substituted Azosemide)

Azosemide can be reacted with formaldehyde in methylene chloride, methylene chloride-DMF mixtures or DMF to yield 2-chloro-5-[1-(hydroxymethyl)-1H-tetrazol-5-yl]-4-[(2-thienylmethyl)amino]benzenesulfonamide.

EXAMPLE 69

2-Chloro-5-[1-(methoxymethyl)-1H-tetrazol-5-yl]-4-[(2-thienylmethyl)amino]benzenesulfonamide (Tetrazolyl-Substituted Azosemide)

Azosemide can be reacted with formaldehyde, methanol and a strong acid in methylene chloride, methylene chloride-DMF mixtures or DMF to yield 2-chloro-5-[1-(methoxymethyl)-1H-tetrazol-5-yl]-4-[(2-thienylmethyl)amino]benzenesulfonamide.

EXAMPLE 70

2-Chloro-5-[1-(methylthiomethyl)-1H-tetrazol-5-yl]-4-[(2-thienylmethyl)amino]benzenesulfonamide (Tetrazolyl-Substituted Azosemide)

Azosemide can be reacted with formaldehyde, methanethiol and a strong acid in methylene chloride, methylene chloride-DMF mixtures or DMF to yield 2-chloro-5-[1-(methylthiomethyl)-1H-tetrazol-5-yl]-4-[(2-thienylmethyl)amino]benzenesulfonamide.

EXAMPLE 71

5-[1-(Benzyloxymethyl)-1H-tetrazol-5-yl]-2-chloro-4-[(2-thienylmethyl)amino]benzenesulfonamide (Tetrazolyl-Substituted Azosemide)

Azosemide can be reacted with benzyl chloromethyl ether, triethylamine and sodium iodide in DMF to yield 5-[1-(benzyloxymethyl)-1H-tetrazol-5-yl]-2-chloro-4-[(2-thienylmethyl)amino]benzenesulfonamide.

EXAMPLE 72

Benzyltrimethylammonium Salt of 2-Chloro-5-(1H-tetrazol-5-yl)-4-[(2-thienylmethyl)amino]benzenesulfonamide (Azosemide Benzyltrimethylammonium Salt)

In similar manner to EXAMPLE 16, azosemide can be reacted with benzyltrimethylammonium hydroxide in water to yield the benzyltrimethylammonium salt of 2-chloro-5-(1H-tetrazol-5-yl)-4-[(2-thienylmethyl)amino]benzenesulfonamide.

EXAMPLE 73

Cetyltrimethylammonium Salt of 2-Chloro-5-(1H-tetrazol-5-yl)-4-[(2-thienylmethyl)amino]benzenesulfonamide (Azosemide Cetyltrimethylammonium Salt)

In similar manner to EXAMPLE 16, azosemide can be reacted with cetyltrimethylammonium hydroxide in water to yield the cetyltrimethylammonium salt of 2-chloro-5-(1H-tetrazol-5-yl)-4-[(2-thienylmethyl)amino]benzenesulfonamide.

EXAMPLE 74

3-Isopropylcarbamylsulfonamido-4-(3'-methylphenyl)aminopyridinium t-Butylcarbonyloxymethochloride (Pyridinium-Substituted Torsemide Salt)

3-Isopropylcarbamylsulfonamido-4-(3'-methylphenyl)aminopyridinium t-Butylcarbonyloxymethyl Zwitterion (Pyridinium-Substituted Torsemide Zwitterion)

In similar manner to EXAMPLE 19, torsemide can be reacted with chloromethyl pivalate, triethylamine and sodium iodide in DMF to yield 3-isopropylcarbamylsulfonamido-4-(3'-methylphenyl)aminopyridinium t-butylcarbonyloxymethochloride and some 3-isopropylcarbamylsulfonamido-4-(3'-methylphenyl)aminopyridinium t-butylcarbonyloxymethoiodide. Treatment with mild bases such as aqueous sodium bicarbonate and aqueous triethylamine can then afford the corresponding pure zwitterion.

EXAMPLE 75

3-Isopropylcarbamylsulfonamido-4-(3'-methylphenyl)aminopyridinium Ethylcarbonyloxymethochloride (Pyridinium-Substituted Torsemide Salt)

3-Isopropylcarbamylsulfonamido-4-(3'-methylphenyl)aminopyridinium Ethylcarbonyloxymethyl Zwitterion (Pyridinium-Substituted Torsemide Zwitterion)

In similar manner to EXAMPLE 19, torsemide can be reacted with chloromethyl propionate, triethylamine and sodium iodide in DMF to yield 3-isopropylcarbamylsulfonamido-4-(3'-methylphenyl)aminopyridinium ethylcarbonyloxymethochloride and some 3-isopropylcarbamylsulfonamido-4-(3'-methylphenyl)aminopyridinium ethylcarbonyloxymethoiodide. Treatment with mild bases such as aqueous sodium bicarbonate and aqueous triethylamine can then afford the corresponding pure zwitterion.

EXAMPLE 76

3-Isopropylcarbamylsulfonamido-4-(3'-methylphenyl)aminopyridinium benzyloxymethochloride (Pyridinium-Substituted Torsemide Salt)

3-Isopropylcarbamylsulfonamido-4-(3'-methylphenyl)aminopyridinium benzyloxymethyl Zwitterion (Pyridinium-Substituted Torsemide Zwitterion)

In a similar manner to Example 8, torsemide can be reacted with benzyl chloromethyl ether and triethylamine in DMF to yield 3-isopropylcarbamylsulfonamido-4-(3'-methylphenyl)aminopyridinium benzyloxymethochloride. Treatment with mild bases such as aqueous sodium bicarbonate and aqueous triethylamine can then afford the corresponding pure zwitterion.

EXAMPLE 77

3-Isopropylcarbamylsulfonamido-4-(3'-methylphenyl)aminopyridinium methoxymethochloride (Pyridinium-Substituted Torsemide Salt)

3-Isopropylcarbamylsulfonamido-4-(3'-methylphenyl)aminopyridinium methoxymethyl Zwitterion (Pyridinium-Substituted Torsemide Zwitterion)

In a similar manner to Example 8, torsemide can be reacted with methyl chloromethyl ether and triethylamine and in DMF to yield 3-isopropylcarbamylsulfonamido-4-(3'-methylphenyl)aminopyridinium methoxymethochloride. Treatment with mild bases such as aqueous sodium bicarbonate and aqueous triethylamine can then afford the corresponding pure zwitterion.

EXAMPLE 78

3-Isopropylcarbamylsulfonamido-4-(3'-methylphenyl)aminopyridinium phenylmethochloride (Pyridinium-Substituted Torsemide Salt)

3-Isopropylcarbamylsulfonamido-4-(3'-methylphenyl)aminopyridinium phenylmethyl Zwitterion (Pyridinium-Substituted Torsemide Zwitterion)

In a similar manner to Example 8, torsemide can be reacted with benzyl chloride and triethylamine in DMF to yield 3-isopropylcarbamylsulfonamido-4-(3'-methylphenyl) aminopyridinium phenylmethochloride. Treatment with mild bases such as aqueous sodium bicarbonate and aqueous triethylamine can then afford the corresponding pure zwitterion.

EXAMPLE 79

3-Isopropylcarbamylsulfonamido-4-(3'-methylphenyl)aminopyridinium Benzylthiomethochloride (Pyridinium-Substituted Torsemide Salt)

3-Isopropylcarbamylsulfonamido-4-(3'-methylphenyl)aminopyridinium Benzylthiomethyl Zwitterion (Pyridinium-Substituted Torsemide Zwitterion)

In a similar manner to Example 8, torsemide can be reacted with benzyl chloromethyl thioether and triethylamine in DMF to yield 3-isopropylcarbamylsulfonamido-4-(3'-methylphenyl)aminopyridinium benzylthiamethochloride. Treatment with mild bases such as aqueous sodium bicarbonate and aqueous triethylamine can then afford the corresponding pure zwitterion.

EXAMPLE 80

3-Isopropylcarbamylsulfonamido-4-(3'-methylphenyl)aminopyridinium Methylthiomethochloride (Pyridinium-Substituted Torsemide Salt)

3-Isopropylcarbamylsulfonamido-4-(3'-methylphenyl)aminopyridinium Methylthiomethyl Zwitterion (Pyridinium-Substituted Torsemide Zwitterion)

In a similar manner to Example 8, torsemide can be reacted with methyl chloromethyl thioether and triethylamine and in DMF to yield 3-isopropylcarbamylsulfonamido-4-(3'-methylphenyl)aminopyridinium methylthiamethochloride. Treatment with mild bases such as aqueous sodium bicarbonate and aqueous triethylamine can then afford the corresponding pure zwitterion.

EXAMPLE 81

Methoxy(polyethyleneoxy)$_{n-1}$-ethyl 3-Aminosulfonyl-5-butylamino-4-phenoxybenzoate (Bumetanide mPEG350 Esters)

In a manner similar to Example 8, bumetanide can be reacted with MeO-PEG350-Cl (Biolink Life Sciences, Inc., Cary, N.C., BLS-106-350) and triethylamine in DMF to yield methoxy(polyethyleneoxy)$_{n-1}$-ethyl 3-aminosulfonyl-5-butylamino-4-phenoxybenzoate where n is in the 7-8 range.

EXAMPLE 82

Methoxy(polyethyleneoxy)$_{n-1}$-ethyl 3-Aminosulfonyl-5-butylamino-4-phenoxybenzoate (S-Bumetanide mPEG30S Thioesters)

In a manner similar to Example 8, thiobumetanide can be reacted with MeO-PEG350-Cl (Biolink Life Sciences, Inc., Cary, N.C., BLS-106-350) and triethylamine in DMF to yield methoxy(polyethyleneoxy)$_{n-1}$-ethyl 3-aminosulfonyl-5-butylamino-4-phenoxy-thiobenzoate where n is in the 7-8 range.

EXAMPLE 83

Methoxy(polyethyleneoxy)$_{n-1}$-ethyl 3-Aminosulfonyl-5-butylamino-4-phenoxybenzoate (Bumetanide mPEG1000 Esters)

In a manner similar to Example 8, bumetanide can be reacted with MeO-PEG 1000-OTs (Biolink Life Sciences, Inc., Cary, N.C., BLS-107-1000) and triethylamine in DMF to yield methoxy(polyethyleneoxy)$_{n-1}$-ethyl 3-aminosulfonyl-5-butylamino-4-phenoxybenzoate where n is in the 19-24 range. In similar manner S-bumetanide mPEG1000 thioesters can be formed with S-thiobumetanide, MeO-PEG1000-OTs (Biolink Life Sciences, Inc., Cary, N.C., BLS-107-1000) and triethylamine in DMF.

EXAMPLE 84

Methoxy(polyethyleneoxy)$_{n-1}$-ethyl 3-Aminosulfonyl-5-butylamino-4-phenoxybenzoate (Bumetanide mPEG1000 Dithioesters)

In a manner similar to Example 8, dithiobumetanide can be reacted with MeO-PEG 1000-OTs (Biolink Life Sciences, Inc., Cary, N.C., BLS-107-1000) and triethylamine in DMF to yield methoxy(polyethyleneoxy)$_{n-1}$-ethyl 3-aminosulfonyl-5-butylamino-4-phenoxy-dithiobenzoate where n is in the 19-24 range.

EXAMPLE 85

Methoxy(polyethyleneoxy)$_{n-1}$-ethyl 3-Aminosulfonyl-4-phenoxy-5-(1-pyrrolidinyl)benzoate (Piretanide mPEG350 Esters)

In similar manner to Example 8, piretanide can be reacted with MeO-PEG350-Cl (Biolink Life Sciences, Inc., Cary, N.C., BLS-106-350) and triethylamine in DMF to yield methoxy(polyethyleneoxy)$_{n-1}$-ethyl 3-aminosulfonyl-4-phenoxy-5-(1-pyrrolidinyl)benzoate where n is in the 7-8 range. In similar manner bumetanide mPEG350 dithioesters can be formed with dithiobumetanide. MeO-PEG350-Cl (Biolink Life Sciences, Inc., Cary, N.C., BLS-106-350) and triethylamine in DMF.

EXAMPLE 86

Methoxy(polyethyleneoxy)$_{n-1}$-ethyl 3-Aminosulfonyl-4-phenoxy-5-(1-pyrrolidinyl)benzoate (S-Piretanide mPEG350 Thioesters)

In similar manner to Example 8, thiopiretanide can be reacted with MeO-PEG350-Cl (Biolink Life Sciences, Inc., Cary, N.C., BLS-106-350) and triethylamine in DMF to yield methoxy(polyethyleneoxy)$_{n-1}$-ethyl 3-aminosulfonyl-4-phenoxy-5-(l-pyrrolidinyl)thiobenzoate where n is in the 7-8 range.

EXAMPLE 87

Methoxy(polyethyleneoxy)$_{n-1}$-ethyl 3-Aminosulfonyl-4-phenoxy-5-(1-pyrrolidinyl)benzoate (Piretanide mPEG1000 Esters)

In similar manner to Example 8, piretanide can be reacted with MeO-PEG 1000-OTs (Biolink Life Sciences, Inc., Cary, N.C., BLS-107-1000) and triethylamine in DMF to yield methoxy(polyethyleneoxy)$_{n-1}$-ethyl 3-aminosulfonyl-4-phenoxy-5-(l-pyrrolidinyl)benzoate where n is in the 19-24 range. In similar manner S-piretanide mPEG1000 thioesters can be formed with S-thiopiretanide, MeO-PEG1000-OTs (Biolink Life Sciences, Inc., Cary, N.C., BLS-107-1000) and triethylamine in DMF.

EXAMPLE 88

Methoxy(polyethyleneoxy)$_{n-1}$-ethyl 3-Aminosulfonyl-4-phenoxy-5-(1-pyrrolidinyl)benzoate (Piretanide mPEG1000 Dithioesters)

In similar manner to Example 8, dithiopiretanide can be reacted with MeO-PEG1000-OTs (Biolink Life Sciences, Inc., Cary, N.C., BLS-107-1000) and triethylamine in DMF to yield methoxy(polyethyleneoxy)$_{n-1}$-ethyl 3-aminosulfonyl-4-phenoxy-5-(1-pyrrolidinyl)dithiobenzoate where n is in the 19-24 range. In similar manner piretanide mPEG1000 dithioesters can be formed with dithiopiretanide, MeO-PEG1000-OTs (Biolink Life Sciences, Inc., Cary, N.C., BLS-107-1000) and triethylamine in DMF.

EXAMPLE 89

Methoxy(polyethyleneoxy)$_{n-1}$-ethyl 5-Aminesulfonyl-4-chloro-2-[(2-furanylmethyl)amino]benzoate (Fursenmide mPEG350 Esters)

In similar manner to Example 8, furosemide can be reacted with MeO-PEG350-Cl (Biolink Life Sciences, Inc., Cary, N.C., BLS-106-350) and triethylamine in DMF to yield methoxy(polyethyleneoxy)$_{n-1}$-ethyl 5-aminosulfonyl-4-chloro-2-[(2-furanylmethyl)amino]benzoate where n is in the 7-8 range.

EXAMPLE 90

Methoxy(polyethyleneoxy)$_{n-1}$-ethyl 5-Aminosulfonyl-4-chloro-2-[(2-furanylmethyl)amino]benzoate (S-Furosemide mPEG350 Thioesters)

In similar manner to Example 8, thiofurosemide can be reacted with MeO-PEG350-Cl (Biolink Life Sciences, Inc., Cary, N.C., BLS-106-350) and triethylamine in DMF40 yield methoxy(polyethyleneoxy)$_{n-1}$-ethyl 5-aminosulfonyl-4-chloro-2-[(2-furanylmethyl)amino]thiobenzoate where n is in the 7-8 range.

EXAMPLE 91

Methoxy(polyethyleneoxy)$_{n-1}$-ethyl 5-Aminosulfonyl-4-chloro-2-[(2-furanylmethyl)amino]benzoate (Furosemide mPEG1000 Esters)

In similar manner to Example 8, furosemide can be reacted with MeO-PEG1000-OTs (Biolink Life Sciences, Inc., Cary, N.C., BLS-107-1000) and triethylamine in DMF to yield methoxy(polyethyleneoxy)$_{n-1}$-ethyl 5-aminosulfonyl-4-chloro-2-[(2-furanylmethyl)amino]benzoate where n is in the 19-24 range.

EXAMPLE 92

Methoxy(polyethyleneoxy)$_{n-1}$-ethyl 5-Aminosulfonyl-4-chloro-2-[(2-furanylmethyl)amino]benzoate (Furosemide mPEG1000 Dithioesters)

In similar manner to Example 8, dithiofurosemide can be reacted with MeO-PEG1000-OTs (Biolink Life Sciences, Inc., Cary, N.C., BLS-107-1000) and triethylamine in DMF to yield methoxy(polyethyleneoxy)$_{n-1}$-ethyl 5-aminosulfonyl-4-chloro-2-[(2-furanylmethyl)amino]dithiobenzoate where n is in the 19-24 range. In similar manner furosemide mPEG350 dithioesters can be formed with dithiofurosemide, MeO-PEG350-Cl (Biolink Life Sciences, Inc., Cary. N.C., BLS-106-350) and triethylamine in DMF.

EXAMPLE 93

5-[1-[Methoxy(polyethyleneoxy)$_{n-1}$-ethyl]-1H-tetrazol-5-yl]-2-chloro-4-[(2-thienylmethyl)amino]benzenesulfonamides (N-mPEG350-Tetrazolyl-Substituted Azosemides)

In similar manner to Example 8, azosemide can be reacted with MeO-PEG350-Cl (Biolink Life Sciences, Inc., Cary, N.C., BLS-106-350) and triethylamine in DMF to yield 5-[1-[methoxy(polyethyleneoxy)$_{n-1}$-ethyl]-1H-tetrazol-5-yl]-2-chloro-4-[(2-thienylmethyl)amino]benzenesulfonamides where n is in the 7-8 range.

EXAMPLE 94

5-[1-Methoxy(polyethyleneoxy)$_{n-1}$-ethyl]-1H-tetrazol-5-yl]-2-chloro-4-[(2-thienylmethyl)amino]benzenesulfonamides (N-mPEG1000-Tetrazolyl-Substituted Azosemides)

In similar manner to Example 8, azosemide can be reacted with MeO-PEG1000-OTs (Biolink Life Sciences, Inc., Cary, N.C., BLS-107-1000) and triethylamine in DMF to yield 5-[1-[methoxy(polyethyleneoxy)$_{n-1}$-ethyl]-1H-tetrazol-5-yl]-2-chloro-4-[(2-thienylmethyl)amino]benzenesulfonamides where n is in the 19-24 range.

EXAMPLE 95

3-Isopropylcarbamylsulfonamido-4-(3'-methylphenyl)aminopyridinium Methoxy(polyethyleneoxy)$_{n-1}$-ethochlorides (N-mPEG350-Pyridinium Torsemide Salts)

3-Isopropylcarbamylsulfonamido-4-(3'-methylphenyl)aminopyridinium Methoxy(polyethyleneoxy)$_{n-1}$-ethyl Zwitterions (N-mPEG350-Pyridinium Torsemide Zwitterions)

In similar manner to Example 8, torsemide can be reacted with MeO-PEG350-Cl (Biolink Life Sciences, Inc., Cary, N.C., BLS-106-350) and triethylamine in DMF to yield 3-isopropylcarbamylsulfonamido-4-(3'-methylphenyl) aminopyridinium methoxy(polyethyleneoxy)$_{n-1}$-ethochlorides where n is in the 7-8 range. Treatment with mild bases such as aqueous sodium bicarbonate and aqueous triethylamine can then afford the corresponding pure zwitterion.

EXAMPLE 96

3-Isopropylcarbamylsulfonamido-4-(3'-methylphenyl)aminopyridinium Methoxy(polyethyleneoxy)$_{n-1}$-ethochlorides (N-mPEG1000-Pyridinium Torsemide Salts)

3-Ispropylcarbamylsulfonamido-4-(3'-methylphenyl) aminopyridinium Methoxy(polyethyleneoxy)$_{n-1}$-ethyl Zwitterions (N-mPEG1000-Pyridinium Torsemide Zwitterions)

In similar manner to Example 8, torsemide can be reacted with MeO-PEG1000-OTs (Biolink Life Sciences, Inc., Cary, N.C., BLS-107-1000) and triethylamine in DMF to yield 3-isopropylcarbamylsulfonamido-4-(3'-methylphenyl) aminopyridinium methoxy(polyethyleneoxy)$_{n-1}$-ethochlorides where n is in the 19-24 range. Treatment with mild bases such as aqueous sodium bicarbonate and aqueous triethylamine can then afford the corresponding pure zwitterion.

EXAMPLE 97

3-Aminosulfonyl-5-butylamino-4-phenoxybenzaldehyde (Bumetanide Aldehyde)

By the method of Muraki and Mukiayama (Chem. Letters, 1974, 1447 and Chem. Letters, 1975, 215), bumetanide can be reacted with bis(4-methylpiperazinyl)aluminum hydride to yield 3-aminosulfonyl-5-butylamino-4-phenoxybenzaldehyde.

EXAMPLE 98

3-Aminosulfonyl-4-phenoxy-5-(1-pyrrolidinyl)benzaldehyde (Piretanide Aldehyde)

By the method of Muraki and Mukiayama (Chem. Letters, 1974, 1447 and Chem. Letters, 1975, 215), piretanide can be reacted with bis(4-methylpiperazinyl)aluminum hydride to yield 3-aminosulfonyl-4-phenoxy-5-(1-pyrrolidinyl)benzaldehyde.

EXAMPLE 99

5-Aminosulfonyl-4-chloro-2-[(2-furanylmethyl) amino]benzaldehyde (Furosemide Aldehyde)

By the method of Muraki and Mukiayama (Chem. Letters, 1974, 1447 and Chem. Letters, 1975, 215), furosemide can be reacted with bis(4-methylpiperazinyl)aluminum hydride to yield 5-aminosulfonyl-4-chloro-2-[(2-furanylmethyl) amino]benzaldehyde.

EXAMPLE 100

Octyl-5-Aminosulfonyl-4-chloro-2-[(2-furanylmethyl)amino]benzoate (Furosemide Octyl Ester; NTP-1014)

A mixture of furosemide (10.0 g, 0.032 mol), chlorooctane (4.96 g, 0.033 mol), sodium iodide (0.452 g, 0.003 mol), triethylamine (6.11 g, 0.060 mol) in N,N-dimethylformamide (60 mL) was heated at 70° C. for 18 hours. After 18 hours, liquid chromatography/mass spectrometry (LC/MS) indicated an absence of starting material. The reaction mixture was allowed to cool to room temperature. The reaction mixture was then poured into water (300 mL) and extracted with ethyl acetate (3×150 mL). The organic layer was washed with saturated sodium bicarbonate solution, sodium sulfite solution, and brine. The organic layer was dried over anhydrous sodium sulfate and concentrated to give a tan solid.

EXAMPLE 101

Decyl 5-Aminosulfonyl-4-chloro-2-[(furanylmethyl) amino]benzoate (Furosemide Decyl Ester; NTP-1015)

A mixture of furosemide (10.0 g, 30.2 mmol), decyl chloride (5.88 g, 33 mmol), sodium iodide (0.45 g, 3 mmol), and triethylamine (6.11 g, 0.60 mmol) in N,N-dimethylformamide (60 mL) was heated at 70° C. for fifteen hours. Liquid chromatography/mass spectrometry (LC/MS) indicated an absence of starting material (desired product was detected as [M-1] peak in negative mode). The reaction mixture was poured into water (300 mL) and extracted with ethyl acetate (3×150 mL). The organic layer was washed with saturated sodium bicarbonate (100 mL), water (2×100 mL), sodium sulfite solution, and brine. The ethyl acetate solution was dried over anhydrous sodium sulfate and concentrated to give a tan solid. The product was slurried in tert-butylmethylether (MTBE)/heptanes (1:1) (5 mL/g) to yield 8.3 g (61%) of decyl 5-aminosulfonyl-4-chloro-2-[(furanylmethyl)amino]benzoate.

EXAMPLE 102

Prenyl 5-Aminosulfonyl-4-chloro-2-[(furanylmethyl)amino]benzoate (Furosemide Prenyl Ester; NTP-1016)

Furosemide (10.0 g, 30.2 mmol) and 1,1'-carbonyldiimidazole (CDI) (5.3 g, 33.2 mmol) in tetrahydrofuran (THF) (200 mL) was stirred and heated at 40° C. to form a yellow homogeneous solution for 2.5 hours. In a separate flask, 3-methyl-2-buten-1-ol (prenyl alcohol, 3.38 g, 39.3 mmol) was stirred with potassium tert-butylbutoxide as a 1 M solution in THF (36.2 mmol). Upon addition of the alkoxide solution to the original reaction, the mixture turned orange and formed a precipitate that dissolved instantly. After 20 minutes, LC/MS indicated that the reaction was complete, so the reaction solution was diluted with ethyl acetate (300 mL), washed in water (200 mL), extracted with ethyl acetate (300 mL), washed in saturated sodium bicarbonate (200 mL), the combined organic phases were dried over anhydrous magnesium sulfate, and filtered. The organic solution was concentrated to a yellow solid and dried under vacuum at 50° C. The crude product was purified by eluting through a plug of silica gel, first with dichloromethane/ethyl acetate 98/2, then dichloromethane/methanol 95/5, yielding 6.8 g (56%) of prenyl 5-aminosulfonyl-4-chloro-2-[(furanylmethyl)amino]benzoate.

EXAMPLE 103

4-Methoxybenzyl 5-aminosulfonyl-4-chloro-2-[(furanylmethyl)amino]benzoate (Furosemide Paramethoxy Benzyl Ester; NTP-1018)

Furosemide (7.5 g. 22.7 mmol), p-methoxybenzyl chloride (4.62 g, 29.5 mmol), and triethylamine (2.3 g, 22.7 mmol) were stirred in N,N-dimethylformamide (60 mL) at 60° C. for 3.5 hours. The temperature was heated to 75° C. and stirred overnight. LC/MS determined that the reaction was 91% complete, so the reaction was cooled, quenched with ammonium chloride (30 mL), extracted with ethyl acetate (2×120 mL), producing a white precipitate. The organic layer was washed with water (8×60 mL) and 1N sodium hydroxide (60 mL), dried over anhydrous magnesium sulfate, filtered, and concentrated. The product was slurried in isopropanol (10 mL/g) and filtered to yield 7.8 g (76%) of 4-methoxybenzyl 5-aminosulfonyl-4-chloro-2-[(furanylmethyl)amino]benzoate.

EXAMPLE 104

2-Phenylethyl 5-aminosulfonyl-4-chloro-2-[(furanylmethyl)amino]benzoate (Furosemide Phenethyl Ester; NTP-1020)

Furosemide (10.0 g, 30.2 mmol) and CDI (5.3 g, 33.2 mmol) in THF (200 mL) was stirred and heated at 40° C. to form a yellow homogeneous solution for 3 hours. In a separate flask, 2-phenylethanol (phenethyl alcohol, 4.8 g, 39.3 mmol) was stirred with potassium tert-butylbutoxide as a 1 M solution in THF (36.2 mmol). Upon addition of the alkoxide solution to the original reaction, the mixture turned orange. After 30 minutes, LC/MS indicated that the reaction was complete, so the reaction solution was diluted with ethyl acetate (300 mL), washed in water (200 mL), extracted with ethyl acetate (300 mL), washed in saturated sodium bicarbonate (150 mL), and the combined organic phases were dried over anhydrous magnesium sulfate, and filtered. The organic solution was concentrated to a yellow solid and dried under vacuum at 50° C. Product was purified by eluting through a plug of silica gel with dichloromethane/ethyl acetate 98/2, yielding 8.81 g (67%) of 2-phenylethyl 5-aminosulfonyl-4-chloro-2-[(furanylmethyl)amino]benzoate.

EXAMPLE 105

(R)-α-Methylbenzyl 5-aminosulfonyl-4-chloro-2-[(furanylmethyl)amino]benzoate (Furosemide (R)-α-Methylbenzyl Ester; NTP-1022)

Furosemide (10 g, 30.2 mmol) was reacted with CDI (5.3 g, 33.2 mmol) in THF (200 mL) at 40° C. for 3 hours. (R)-(+)-2-phenylethanol (66 mmol) was combined with potassium tert-butylbutoxide as a 1 M solution in THF (66 mmol) before being added to original reaction at room temperature and allowed to react for 20 minutes, followed by 1 hour at 40° C. Reaction was diluted with ethyl acetate (200 mL) and water (100 mL). To the aqueous layer was added sodium chloride (50 g), followed by extraction with ethyl acetate. The combined organic layers were washed with saturated sodium carbonate (40 mL), brine (2×40 mL). Purification by a silica gel plug (eluted with 0% to 5% ethyl acetate in dichloromethane), followed by recrystallization in heptanes gave 8.74 g (67%) of (R)-α-methylbenzyl 5-aminosulfonyl-4-chloro-2-[(furanylmethyl)amino]benzoate.

EXAMPLE 106

(S)-α-Methylbenzyl 5-aminosulfonyl-4-chloro-2-[(furanylmethyl)amino]benzoate (Furosemide (S)-α-Methylbenzyl Ester; NTP-1023)

The reaction was conducted identically to EXAMPLE 104 (NTP-1022), except using (S)-(−)-2-phenylethanol. The reaction yielded 8.48 g (65%) of (S)-α-methylbenzyl 5-aminosulfonyl-4-chloro-2-[(furanylmethyl)amino]benzoate.

EXAMPLE 107

N-Ethyl 5-aminosulfonyl-4-chloro-2-[(furanylmethyl)amino]benzamide (Furosemide Monoethyl Amide, Furosemide Ethyl Amide; NTP-1026)

Furosemide (8.5 g, 25.7 mmol), ethylamine (2.0 M solution in methanol, 30.8 mmol), N-hydroxybenzotriazole (HOBt) (1.74 g, 12.85 mmol) and 1-ethyl-3-(3-dimethylaminopropyl) carbodiimide hydrochloride (EDC) (5.67 g, 29.6 mmol) were combined in DMF (68 mL) and stirred at room temperature overnight. The reaction was diluted with ethyl acetate (140 mL), washed with water (60 mL), the aqueous layer extracted with ethyl acetate (3×140 mL). The combined organic layers were washed with water (5×100 mL), dried over anhydrous magnesium sulfate, filtered, and concentrated to a white solid. The product was slurried in isopropyl alcohol (10 mL/g) for 20 minutes, filtered, washed with isopropyl alcohol (30 mL), and dried under vacuum at 40° C. for 3 days to yield 8.3 g (90%) of N-ethyl 5-aminosulfonyl-4-chlor-2-[(furanylmethyl)amino]benzamide.

EXAMPLE 108

N-Benzyl 5-aminosulfonyl-4-chloro-2-[(furanylmethyl)amino]benzamide (Furosemide Monobenzyl Amide, Furosemide Benzyl Amide; NTP-1027)

Furosemide (11.0 g, 33.3 mmol) was stirred in THF for 30 minutes, followed by addition of carbonyldiimidazole (CDI, 6.48 g, 39.96 mmol) and stirred for an additional 30 minutes. Benzylamine (3.92 g, 36.6 mmol) was added; the exothermic reaction was completed in 30 minutes. The reaction mixture was concentrated, and the residue was dissolved in ethyl acetate (200 mL), washed with 1M hydrochloric acid (100 mL), aqueous layer back extracted with ethyl acetate (200 mL), organic layer was washed with saturated sodium bicarbonate, then 1 N sodium hydroxide (50 mL), and the organic phases were dried over anhydrous sodium sulfate, filtered, and concentrated to a sticky yellow solid. This solid was slurried in ethanol (5 mL/g), filtered, and dried under vacuum at 40° C. for 3 days to yield 8.81 g (63%) of N-benzyl 5-aminosulfonyl-4-chloro-2-[(furanylmethyl)amino]benzamide.

EXAMPLE 109

N-Piperidinyl 5-aminosulfonyl-4-chloro-2-[(furanylmethyl)amino]benzamide (Furosemide N-Piperidinyl Amide; NTP-1029)

The reaction was conducted similarly to EXAMPLE 108 (NTP-1027), using furosemide (13 g, 39.9 mmol), CDI (7.65 g, 47.2 mmol), and piperidine (3.68 g, 43.2 mmol) in THF (57 mL). The reaction was concentrated, and the residue was dissolved in ethyl acetate (200 mL), washed with 10% copper sulfate solution (100 mL). The aqueous layer was extracted with ethyl acetate (150 mL), and the organic layers were washed with 1N NaOH (100 mL), dried over anhydrous magnesium sulfate, and concentrated to a yellow solid. A black solid precipitated out of the sodium hydroxide layer, which was recrystallized from boiling ethanol and filtered hot.

EXAMPLE 110

N-Morpholinyl 5-aminosulfonyl-4-chloro-2-[(furanylmethyl)amino]benzamide (Furosemide N-Morpholinyl Amide; NTP-1030)

Furosemide (7 g, 21.2 mmol), morpholine (3.69 g, 42.4 mmol), and N-hydroxybenzotriazole (HOBt, 1.43 g, 10.6 mmol) were combined in DMF (56 mL), followed by EDC (8.13 g, 42.4 mmol), with stirring and heated to 55° C. for 30 minutes. The reaction was cooled, diluted with ethyl acetate (120 mL), and washed with water (50 mL). The aqueous layer was extracted with additional ethyl acetate (4×120 mL). The combined organic layers were dried over anhydrous magnesium sulfate, filtered, concentrated, and dried under vacuum at 40° C. to yield 6.8 g (80%) of N-morpholinyl 5-aminosulfonyl-4-chloro-2-[(furanylmethyl)amino]benzamide.

EXAMPLE 111

3-(N,N-Dimethylaminopropyl) 5-Aminosulfonyl-4-chloro-2-[(furanylmethyl)amino]benzamide (Furosemide 3-(N,N-Dimethylaminopropyl)amide; NTP-1031)

The reaction was conducted similarly to EXAMPLE 107 (NTP-1027), with furosemide (10 g, 30.2 mmol), CDI (5.3 g, 33.3 mmol), and 3-(dimethylamino)-1-propylamine (3.4 g, 33.3 mmol) in THF (200 mL). The reaction mixture was diluted with water (200 mL), extracted with ethyl acetate (2×400 mL), washed with saturated sodium bicarbonate (400 mL), and the organic phases were dried over anhydrous magnesium sulfate, filtered, and concentrated to a white solid, which was dried in a vacuum at 50° C. to yield 11.5 g (92%) of 3-(N,N-Dimethylaminopropyl) 5-aminosulfonyl-4-chloro-2-[(furanylmethyl)amino]benzamide.

EXAMPLE 112

3-(N,N-Dimethylaminopropyl)-N-methyl 5-aminosulfonyl-4-chloro-2-[(furanylmethyl)amino]benzamide (Furosemide 3-(N,N-Dimethylaminopropyl)-N-methylamide; NTP-1032)

The reaction was conducted similarly to EXAMPLE 110 (NTP-1031), with furosemide (10 g, 30.2 mmol), CDI (5.3 g, 33.3 mmol), and N,N,N'-trimethyl-1,3-propanediamine (3.6 g, 33.3 mmol) in THF (200 mL). The reaction mixture was diluted with water (200 mL), extracted with ethyl acetate (2×400 mL), washed with saturated sodium bicarbonate (400 mL), and the organic phases were dried over anhydrous magnesium sulfate, filtered, and concentrated to a white solid, which was dried in a vacuum at 50° C. to yield 11.5 g (90%) of 3-(N,N-dimethylamino)propyl-N-methyl 5-aminosulfonyl-4-chloro-2-[(furanylmethyl)amino]benzamide.

EXAMPLE 113

2-(1-Piperidinyl)ethyl 5-aminosulfonyl-4-chloro-2-[(furanylmethyl)amino]benzamide (Furosemide Piperidinylethyl Amide; NTP-1033)

The reaction was conducted similarly to EXAMPLE 107 (NTP-1027), with furosemide (10 g. 30.2 mmol), CDI (5.88 g, 36.2 mmol), and 2-(1-piperidinyl)ethanamine (4.26 g, 33.2 mmol) in THF (44 mL). The reaction mixture was concentrated, dissolved in ethyl acetate (200 mL), and the organic phase was washed in 1M hydrochloric acid (100 mL), then with 1N sodium hydroxide (100 mL). The organic phase was then dried over anhydrous magnesium sulfate, filtered, and concentrated. A precipitate formed in acidic layer that was removed by filtration. The filtrate was neutralized to pH=8 with 1N sodium hydroxide, and extracted with isopropyl acetate (2×200 mL). The organic phase was separated and concentrated, then dried under vacuum at 40° C. to yield 5.3 g (40%) yield of 2-(1-piperidinyl)ethyl 5-aminosulfonyl-4-chloro-2-[(furanylmethyl)amino]benzamide.

EXAMPLE 114

Methyl 3-Aminosulfonyl-5-N,N-dibutylamino-4-phenoxybenzoate (Bumetanide Dibutylamino Methyl Ester)

Bumetanide methyl ester (7.56 g, 20 mmol), sodium triacetoxyborohydride (5.93 g, 28 mmol), and acetic acid (119 mmol) were combined in 1,2-dichloroethane (DCE) (90 mL) and cooled to 0° C. A solution of butyraldehyde (1.8 mL, 20 mmol) in DCE (10 mL) was dispensed over 12 hours via a syringe pump (1 mL/hour) and allowed to warm to room temperature overnight. HPLC showed 51:38 starting material/desired product, so additional sodium triacetoxyborohydride (5.93 g, 28 mmol) was added, the reaction was cooled, and additional butyraldehyde (1.8 mL, 20 mmol) in DCE (10 mL) was added via syringe pump overnight. HPLC showed 24:62:6 starting material/desired product/bisalkylation. The third addition of sodium triacetoxyborohydride and butyraldehyde showed 15:62:9 starting material/desired product/bisalkylation. The reaction was quenched with saturated sodium bicarbonate, extracted with dichloromethane, and concentrated. The crude product was dissolved in dichloromethane (5 mL), diluted with heptanes (200 mL), and the dichloromethane was selectively evaporated, producing a precipitate. The target compound was ultimately purified by silica gel chromatography (5-50% ethyl acetate in hexanes) to yield 2.89 g (33%) of methyl 3-Aminosulfonyl-5-N,N-dibutylamino-4-phenoxybenzoate.

EXAMPLE 115

3-Aminosulfonyl-5-N,N-dibutylamino-4-phenoxybenzoic acid (N-Butyl Bumetanide; NTP-2014)

To a dry, 5 liter flask was added bumetanide (998 g, 2.744 moles, 1 eq) and THF (1.9 L). The resultant clear solution was stirred for 15 minutes and CDI (466 g, 2.88 moles, 1.05 Eq) was added in portions over 1 hour. Mixture gradually thickened and was allowed to stir at room temperature for two hours. To this thick white mixture was added MeOH (600 mL) and the mixture stirred for two hours at room temperature and then cooled to 0° C. for 10 minutes. KOtbu (339 g, 3.01 moles, 1.1 Eq) was added in portions to maintain a reaction temperature of 0-10° C. The resultant mixture was allowed to stir for 6 hours until HPLC showed complete conversion.

The solvent was removed via rotary evaporation and diluted with ethyl acetate (2 L) and water (2 L) and agitated. The aqueous layer was split and extracted with ethyl acetate (2×500 ML) and the combined organics washed with brine, dried (MgSO$_4$), filtered and concentrated to produce ester 2 (1200 g, 85% purity). This white solid was diluted with water (4 L) and warmed to 80° C. for 1.5 hours (still heterogeneous), cooled to 55° C. and then filtered. The filtered solids were washed with water (1 L), dried on the filter for 12 hours, and then transferred to a vacuum oven (35° C.) and dried for 18 hours to produce ester 2 (788 g, 76% yield, 92% purity by HPLC).

To a dry, 50 L flask was added bumetanide methylester 2 (3.12 Kg, 8.27 moles, 1.0 Eq), acetic acid (2.5 L, 43.7 moles, 5.3 Eq), butyraldehyde (850 mL, 9.5 moles, 1.15 Eq) and dichloroethane (16.5 L). The heterogeneous tan mixture was stirred 5 minutes and then cooled to 0° C. over two hours. Sodium triacetoxyborohydride (4 Kg, 19 moles, 2.3 Eq) was added in portions over two hours. The slightly clearer mixture was allowed to age overnight at 0° C. HPLC indicated no starting material remaining. Water (10 L) was added slowly at 0° C. and then stirred for two hours. Stirring was stopped and the layers separated. Organic layer was washed with water (3 L) and the combined aqueous layers were extracted with CH$_2$Cl$_2$ (2×2 L) and the combined organics were washed with brine, dried (MgSO$_4$), filtered and concentrated to produce crude ester 3. This sticky yellow-white solid and heptane (9 L) were added to a 50 L reactor and stirred vigorously for 6 hours. The resulting white suspension was filtered and the solids washed with heptane (1 L).

This crude white solid was placed in a 12 L reactor and ethyl acetate (2 L) and heptane (1.75 L) were added and the mixture brought to reflux for 30 minutes. Stir paddle was removed and the mixture allowed to cool overnight. The resulting white solids were dried in a vacuum oven (60° C.) overnight to produce ester 3 (1790 g, 50%, 98% pure by HPLC).

Figure 10:
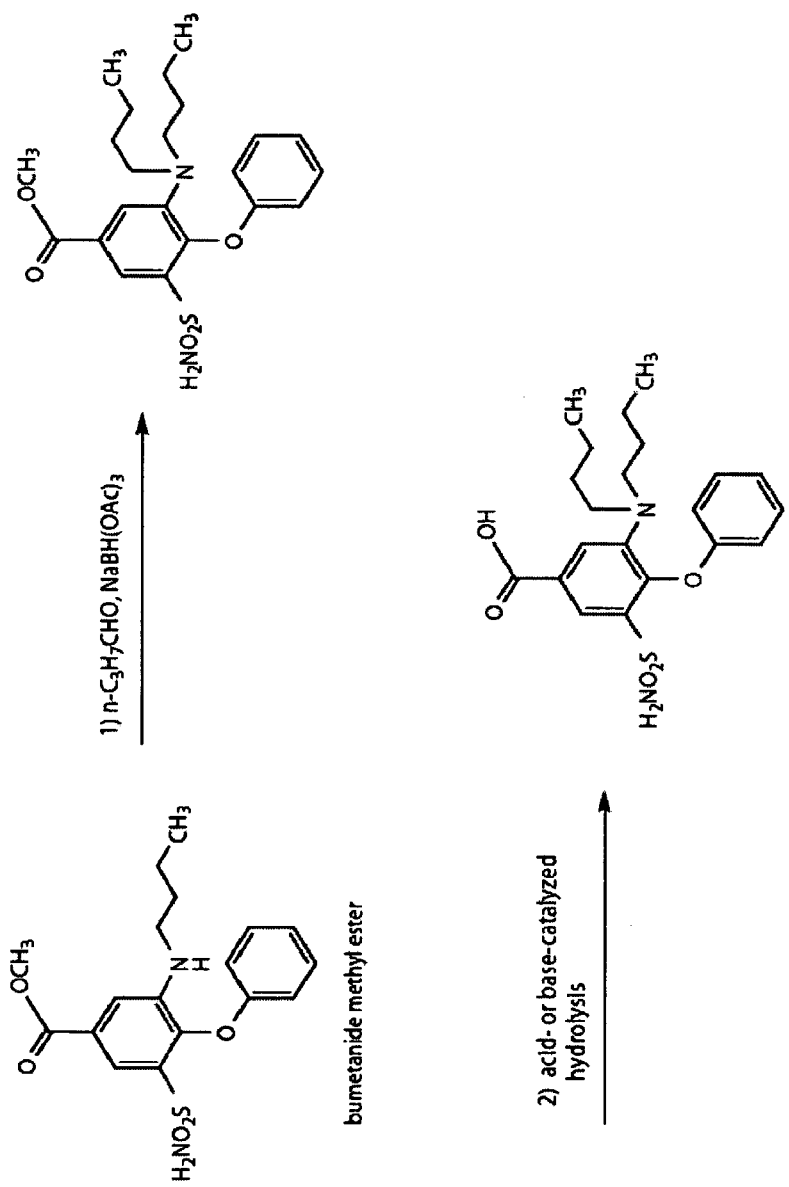
FIG. 10 illustrates an exemplary reaction scheme showing the butylation reaction of the monobutyl methyl ester starting material using butyraldehyde in the presence of sodium triacetoxy borohydide. This reaction was carried out in dichloroethane in the presence of acetic acid. The resulting dibutyl methyl ester can be subsequently hydrolyzed under, e.g., acidic conditions to give the dibutylated benzoic acid product shown after step 3) of the reaction scheme. Bumetanide methyl ester can be/is treated with n-butyraldehyde in the presence of a catalytic amount of acetic acid in dichloromethane at 0° C. to form the Schiff base in situ. To this mixture was then added sodium triacetoxyborohydride to reduce the Schiff base under reductive alkylating conditions to add a second n-butyl group at the 3N-position of the bumetanide ester. This di-n-butylated ester can be/is then submitted to ester hydrolysis conditions to produce 3N-(n-butyl)bumetanide—a.k.a. 3-(n-butyl) bumetanide and more formally named: 3-(di-n-butylamino)-4-phenoxy-5-sulfamoylbenzoic acid.

To a 5 L flask was NaOH (285 g, 6.6 moles, 2.5 Eq) and water (1.75 L). Mixture was cooled to 0° C. and EtOH (2.5 L) was added and the mixture aged for five minutes. To this clear mixture was added bumetanide dibutylamino methyl ester 3 (1.1 Kg, 2.61 moles, 1.0 Eq) in portions over 15 minutes. The heterogeneous mixture was allowed to warm to room temperature over 16 hours. The now homogeneous mixture was sampled by HPLC and determined to be complete. This mixture was filtered and half concentrated via rotovap. The solution was placed back in the reactor and hydrochloric acid (5 M, aq) was added dropwise, resulting in eventual precipitation of the product. Addition of acid was continued until pH reached 2.5 (900 mL of 5 M HCl). The thick white slurry was stirred for one hour and the solids filtered, washed with water (1 L) and heptane (3 L). HPLC analysis showed 0.1% bumetanide and 1.4% sulfonamide alkylation product. The white solids were then placed in a vacuum oven (60° C.) and dried overnight to produce NTP2014 (476 g, 47% yield, 98% purity). See FIG. 10.

EXAMPLE 116

N,N-Dimethyl 3-Aminosulfonyl-5-N-butylamino-4-phenoxybenzamide (Bumetanide Dimethylamide; NTP-2015)

Bumetanide (12.4 g, 34.3 mmol), HOBt (4.63 g, 34.3 mmol), and EDC (13.15 g, 68.6 mmol) were combined in THF (80 mL), followed by the addition of dimethylamine as a 2.0 M solution in THF (80 mL), and the mixture was allowed to stir for 2 hours. T reaction mixture was diluted with water (250 mL) and dichloromethane (150 mL), and organic phase was washed with water and 1 N sodium hydroxide, dried over anhydrous sodium sulfate, filtered, and concentrated. The product was purified by silica gel chromatography (20% ethyl acetate in dichloromethane) to yield 9.64 g (72%) of N,N-dimethyl 3-aminosulfonyl-5-N,N-dibutylamino-4-phenoxybenzamide.

EXAMPLE 117

N-Benzyl 3-Aminosulfonyl-5-N-butylamino-4-phenoxybenzamide (Bumetanide Monobenzylamide, Bumetanide Benzylamide; NTP-2018)

Bumetanide (10.92 g, 30 mmol), HOBt (4.05 g, 30 mmol), benzylamine (16.06 g, 150 mmol), and EDC (11.49 g, 60 mmol) were combined in THF (150 mL) and heated at reflux for 45 minutes. The reaction mixture was cooled, diluted with dichloromethane (200 mL), and the organic phase was washed with 1 N sodium hydroxide (50 mL), then water (100 mL). The organic layer was dried over anhydrous magnesium sulfate, filtered, evaporated, and the residue was filtered through a silica plug with dichloromethane, and evaporated to yield 7.2 g (53%) of N-benzyl 3-aminosulfonyl-5-N-butylamino-4-phenoxybenzamide.

EXAMPLE 118

N-Benzyl-N-methyl 3-Aminesulfonyl-5-N-butylamino-4-phenoxybenzamide (Bumetanide Benzylmethylamide; NTP-2019)

Bumetanide (11.93 g, 32.8 mmol), HOBt (2.21 g, 16.4 mmol), N-benzylmethylamine (19.87 g, 164 mmol), and EDC (12.06 g, 62.9 mmol) combined in THF (160 mL) at room temperature overnight. The reaction solvent was evaporated, and dichloromethane (125 mL) and water (125 mL) were added to the residue. The organic phase was washed with 1N sodium hydroxide (10 mL), and the layers were separated. The aqueous phase was washed with water (100 mL). The organic phase was mixed with water (50 mL), and 1N hydrochloric acid was added until the pH of the mixture was about pH 8. The organic phase was then separated, washed with water (100 mL), and the organic phase was dried over anhydrous sodium sulfate, evaporated, and purified by silica gel chromatography (eluting with dichloromethane, 5% ethyl acetate, and 10% ethyl acetate) to yield 11.56 g (75%) of N-benzyl-N-methyl 3-aminosulfonyl-5-N-butylamino-4-phenoxybenzamide.

EXAMPLE 119

(R)-α-Methylbenzyl 3-Aminosulfonyl-5-N-butylamino-4-phenoxybenzamide ((R)-Bumetanide α-Methylbenzylamine; NTP-220)

This compound was made using bumetanide and (1R)-1-phenylethanamine.

EXAMPLE 120

(S)-α-Methylbenzyl 3-Aminosulfonyl-5-N-butylamino-4-phenoxybenzamide ((S)-Bumetanide α-Methylbenzylamine; NTP-2021)

This compound was made using bumetanide and (1S)-1-phenylethanamine.

EXAMPLE 121

N-Methyl 3-Aminosulfonyl-5-N-butylamino-4-phenoxybenzamide (Bumetanide Monomethylamide, Bumetanide Methylamide; NTP-2016)

The reaction was conducted similarly to EXAMPLE 109 (NTP-1030), with bumetanide (11.66 g, 32.0 mmol), HOBt (4.54 g, 33.6 mmol), EDC (12.22 g, 63.7 mmol), and methylamine (2.0 M solution in THF, 160 mmol) in THF (120 mL). The solvent was evaporated and dichloromethane (175 mL) and water (100 mL) were added to the residue. The organic phase was then separated and washed with 1N sodium hydroxide. The organic layer was then washed with water, dried over anhydrous sodium sulfate, filtered, and concentrated under vacuum. The product was recrystallized from dichloromethane/heptane, yielding 7.41 g (61%) of N-methyl 3-aminosulfonyl-5-N-butylamino-4-phenoxybenzamide.

EXAMPLE 122

N-Ethyl 3-Aminosulfonyl-5-N-butylamino-4-phenoxybenzamide (Bumetanide Monoethylamide, Bumetanide Ethylamide; NTP-2017)

The reaction was conducted similarly to EXAMPLE 119 (NTP-2016), with bumetanide (11.77 g, 32.4 mmol), HOBt (4.37 g, 32.4 mmol), ethylamine (2M solution in THF, 140 mmol), and EDC (12.42 g, 64.5 mmol) in THF (150 mL). The reaction was heated to 50° C. initially and allowed to cool and react overnight. The solvent was evaporated, and the residue was partitioned between dichloromethane (250 mL) and water. A precipitate formed and was removed by filtration. The organic phase was washed with water, dried over anhydrous sodium sulfate, filtered, and evaporated. The product was recrystallized from ethyl acetate, yielding 9.25 g (73%) of N-ethyl 3-aminosulfonyl-5-N-butylamino-4-phenoxybenzamide.

EXAMPLE 123

N-(3-(Dimethylamino)propyl)-N-methyl 3-Aminosulfonyl-5-N-butylamino-4-phenoxybenzamide (Bumetanide N-(3-(Dimethylamino)propyl)-N-methyl Amide; NTP-2026)

Reaction was conducted similarly to EXAMPLE 119 (NTP-2016), with bumetanide (9.71 g, 26.6 mmol), HOBt (3.6 g, 26.6 mmol), N,N,N'-trimethyl-1,3-propanediamine (9.29 g, 80 mmol), and EDC (10.2 g, 53 mmol) in THF (150 mL). After 45 minutes, the reaction solvent was evaporated and the residue was partitioned between dichloromethane (150 mL) and water (100 mL). Organic layer washed with 1N sodium hydroxide followed by water. The organic phase was separated and dried over anhydrous magnesium sulfate, filtered, and evaporated. The crude product was purified on a Biotage silica gel column using dichloromethane/methanol/ammonium hydroxide (90:9:1), recovering 6.41 g (52.1%) of the desired N-(3-(dimethylamino)propyl)-N-methyl 3-aminosulfonyl-5-N-butylamino-4-phenoxybenzamide.

EXAMPLE 124

N-Piperidinyl 3-Aminosulfonyl-5-N-butylamino-4-phenoxybenzamide (Bumetanide N-Piperidinyl Amide; NTP-2023)

The reaction was conducted similarly to EXAMPLE 119 (NTP-2016), with bumetanide (11.64 g, 32 mmol); HOBt (2.16 g, 16 mmol), piperidine (12.75 g, 1.50 mmol), and EDC (9.2 g, 48 mmol) in THF (120 mL). The reaction was heated at reflux overnight. The reaction solvent was evaporated, and the residue was partitioned between dichloromethane (150 mL) and water (150 mL). The organic phase was washed with 1N sodium hydroxide (75 mL), followed by water (75 mL), 0.1M hydrochloric acid (75 mL), saturated sodium bicarbonate (75 mL), and water (75 mL). The organic phase was dried over anhydrous sodium sulfate, filtered, and concentrated. The crude product was purified by silica gel chromatography (10% ethyl acetate in dichloromethane) to yield 8.17 g (59%) of N-piperidin-1-yl 3-aminosulfonyl-5-N-butylamino-4-phenoxybenzamide.

EXAMPLE 125

N-Morpholinyl 3-Aminosulfonyl-5-N-butylamino-4-phenoxybenzamide (Bumetanide N-Morpholinyl Amide; NTP-2024)

The reaction was conducted similarly to EXAMPLE 119 (NTP-2016), with bumetanide (11.48 g, 31.5 mmol), HOBt (2.13 g, 15.8 mmol), morpholine (13.72 g, 158 mmol), and EDC (9.66 g, 50.4 mmol) in THF (160 mL). After 5 hours, the reaction was 85% completed, so additional EDC (2 g, 10.4 mmol) was added, and the reaction was heated to 50° C. The reaction mixture was cooled, and the solvent was evaporated. The residue was partitioned between dichloromethane (150 mL), water (100 mL), and 1N sodium hydroxide (20 mL). The organic phase was then washed with water (100 mL), dried over anhydrous sodium sulfate, filtered, evaporated, and the residue was further purified by silica gel chromatography (25% ethyl acetate in dichloromethane) to yield 12.63 g (92%) of N-morpholinyl 3-aminosulfonyl-5-N-butylamino-4-phenoxybenzamide.

EXAMPLE 126

2-Butylamino-N-(3-dimethylamino-propyl)-4-phenoxy-5-sulfamoyl-benzamide (Bumetanide (3-(N,N-dimethylaminopropyl)amide; NTP-2025

The reaction was conducted similarly to EXAMPLE 119 (NTP-2016), with bumetanide (9.57 g, 26 mmol), HOBt (3.54 g, 26 mmol), 3-dimethylaminopropylamine (8.0 g, 79 mmol), and EDC (10.1 g, 53 mmol) in THF (150 mL). The reaction was heated to reflux for 45 minutes, cooled, and the solvent was evaporated. The residue was partitioned between dichloromethane (150 mL) and water. The organic phase was washed with water (2×100 mL), then dried over anhydrous magnesium sulfate, filtered, and evaporated. The crude product was purified using silica gel chromatography (dichloromethane/methanol/ammonium hydroxide 90:9:1) to yield 6.15 g (53%) of 3-(N,N-dimethylamino)propyl) 3-aminosulfonyl-5-N-butylamino-4-phenoxybenzamide.

EXAMPLE 127

N-Pyrrolidinyl Aminosulfonyl-5-N-butylamino-4-phenoxybenzamide (Bumetanide N-Pyrrolidinyl Amide; NTP-2022)

The reaction was conducted similarly to EXAMPLE 118 (NTP-2016), with bumetanide (11.69 g, 32 mmol), HOBt (4.33 g, 32 mmol), EDC (12.3 g, 64 mmol); pyrrolidine (6.84 g, 96 mmol), and EDC (12.3 g, 64 mmol) in THF (150 mL). The reaction was complete after 45 minutes at reflux. The solvent was evaporated and the residue was partitioned between dichloromethane (200 mL) and water. The organic phase was washed with water (2×100 mL), dried with anhydrous magnesium sulfate, filtered, and evaporated. The crude product was filtered through a plug of silica using ethyl acetate, yielding 7.25 g (54%) of N-pyrrolidinyl aminosulfonyl-5-N-butylamino-4-phenoxybenzamide.

EXAMPLE 128

(R)-α-Methylbenzyl 3-Aminosulfonyl-5-N-butylamino-4-phenoxybenzoate ((R)-Bumetanide α-Methylbenzyl Ester; NTP-2035)

This compound was made similarly to EXAMPLE 127 only using (R)-1-phenylethanol.

EXAMPLE 129

(S)-α-Methylbenzyl 3-Aminosulfonyl-5-N-butylamino-4-phenoxybenzoate ((S)-Bumetanide α-Methylbenzyl Ester; NTP-2036)

Bumetanide (12 g, 32.9 mmol) and carbonyl diimidazole (6.08 g, 37.5 mmol) were combined in THF (100 mL) at room temperature. The reaction was allowed to stir at room temperature for about 1.5 hours, at which point a white precipitate formed. Diethyl ether (360 mL) was added and the reaction was stirred for an additional 1.5 hours. The reaction mixture was filtered through a funnel under vacuum to yield 3-aminosulfonyl-5-N-butylamino-4-phenoxybenzoyl imidazole. The precipitate was washed with diethyl ether and dried in the funnel for 20 minutes. The precipitate was dissolved in acetonitrile (106 mL) and (S)-1-phenylethanol (13.05 g, 106.8 mmol) was added. The reaction was allowed to stir at room temperature for ten minutes. Copper carbonate trihydrate ($Cu(CO_3)_2 \cdot 3H_2O$; 1.2 g) was added. Nitric acid (0.01N, 2.7 mL) was added at which point a light blue heterogeneous mixture formed. The reaction mixture was heated for about eight hours at 45° C. The reaction mixture was concentrated in vacuo. The resulting concentrate was dissolved in ethyl acetate (1.1 L) and washed with ammonium hydroxide (700 mL). The organic layer was dried over anhydrous magnesium sulfate, evaporated, and purified by silica gel chromatography.

EXAMPLE 130 p-Methoxybenzyl 3-Aminosulfonyl-5-N-butylamino-4-phenoxybenzoate (Bumetanide 2-methoxybenzyl Ester; NTP-2032)

Bumetanide (12 g, 32.9 mmol) and carbonyl diimidazole (6.08 g, 37.5 mmol) were combined in THF (100 mL) at room temperature. The reaction was allowed to stir at room temperature for about 1:5 hours, at which point a white precipitate formed, which subsequently dissolved. Diethyl ether (360 mL) was added. Two additional portions of diethyl ether (2×200 mL) were subsequently added to the reaction mixture and a precipitate formed. The reaction was stirred for an additional 1.5 hours. The reaction mixture was filtered through a funnel under vacuum, yielding 3-aminosulfonyl-5-N-butylamino-4-phenoxybenzoyl imidazole. The precipitate was washed with diethyl ether and dried. The precipitate was dissolved in acetonitrile (107 mL) and 2-methoxybenzyl alcohol (14.87 g, 107.6 mmol) was added. The reaction was allowed to stir at room temperature for five minutes. Copper carbonate trihydrate ($Cu(CO_3)_2 \cdot 3H_2O$; 1.3 g) was added. Nitric acid (0.01N, 2.7 mL) was added. The reaction mixture was heated for about eight hours at 45° C. The reaction mixture was concentrated in vacuo. The resulting concentrate was dissolved in a 1:9 mixture of methanol and dichloromethane to form a suspension. The suspension was filtered through a plug of silica gel that was eluted with a 9:1 mixture of dichloromethane and ethyl acetate.

EXAMPLE 131

2-Phenylethyl 3-Aminosulfonyl-5-N-butylamino-4-phenoxybenzoate (Bumetanide Phenethyl Ester; NTP-2033)

Carbonyldiimidazole (CDI, 6.08 g, 37.5 mmol) was added to bumetanide (12 g, 32.5 mmol) in THF (99 mL), forming a white precipitate that dissolved after 45 minutes. Methyl t-butyl ether (MTBE, 760 mL) was added, which formed a precipitate. Heptane (400 mL) was added and the heterogeneous mixture was allowed to stir for 30 minutes. The solid product, aminosulfonyl-5-N-butylamino-4-phenoxybenzoyl imidazole, was filtered, washed with heptane, and dried on a filter funnel. This acyl imidazole (12.31 g, 29.7 mmol) was combined with 2-phenylethanol (14.5 g, 118.8 mmol) in acetonitrile (118 mL), followed by copper (II) nitrate trihydrate (1.44 g, 5.94 mmol) and nitric acid (0.01 N solution, 2.96 mL), to form a dark blue mixture. The reaction was heated to 45° C., followed by precipitate formation after 2.5 hours. After 4 additional hours, the reaction was evaporated to a purple solid that was dissolved/suspended in ethyl acetate (1300 mL), washed with ammonium hydroxide (2M solution, 700 mL). The organic phase was dried over anhydrous magnesium sulfate, filtered, and concentrated. The crude product was slurried in warm heptane and filtered to obtain 7.4 g (48%) of 2-phenylethyl 3-aminosulfonyl-5-N-butylamino-4-phenoxybenzoate.

EXAMPLE 132

4-phenylbutyl 3-Aminosulfonyl-5-N-butylamino-4-phenoxybenzoate (Bumetanide Phenylbutyl Ester; NTP-2034)

This compound was made similarly to EXAMPLE 129 only using 4-phenylbutan-1-ol.

EXAMPLE 133 n-Octyl Aminosulfonyl-5-N-butylamino-4-phenoxybenzoate (Bumetanide n-Octyl Ester; NTP-2027)

Bumetanide (10 g, 27.4 mmol), sodium iodide (0.41 g, 2.74 mmol), triethylamine (5.54 g, 54.8 mmol), and 1-chlorooctane (4.4 g, 30.2 mmol) were combined in DMF (80 mL) and heated to 70° C. overnight. More 1-chlorooctane (4.07 g, 27.4 mmol) was added, and the reaction was again stirred overnight. Water (400 mL) was added, causing formation of a precipitate. Extraction with ethyl acetate/MTBE (1:1, 2×400 mL), followed by organic layer washing with 1N sodium hydroxide (150 mL) led to further precipitation in the organic layer. After filtration to remove the unwanted solids, the organic layer was dried over anhydrous magnesium sulfate and concentrated. The crude product was slurried in MTBE and filtered to provide 7.1 g (54%) of n-octyl aminosulfonyl-5-N-butylamino-4-phenoxybenzoate.

EXAMPLE 134 n-Decyl Aminosulfonyl-5-N-butylamino-4-phenoxybenzoate (Bumetanide n-Decyl Ester; NTP-2028)

The reaction was conducted similarly to EXAMPLE 119 (NTP-2016), with bumetanide (10 g, 27.4 mmol), sodium iodide (0.41 g, 2.74 mmol), triethylamine (5.54 g, 54.8 mmol), and 1-chlorodecane (6.51 g, 41.1 mmol) were combined in DMF (80 mL) and heated to 70° C. overnight. Additional 1-chlorodecane (13.65 g, 27.4 mmol) was added, and the reaction was again stirred overnight before being cooled and diluted with ethyl acetate (200 mL), MTBE (200 mL), and water (400 mL). The aqueous layer was washed with ethyl acetate/MTBE (1:1, 450 mL), and the combined organic phase was washed with 1N sodium hydroxide (150 mL), dried over anhydrous magnesium sulfate, filtered, and concentrated. The crude product was slurried in ethanol (5 mL/g) and filtered to yield 6.6 g (48%) of n-decyl aminosulfonyl-5-N-butylamino-4-phenoxybenzoate.

EXAMPLE 135

3-Methylbut-2-enyl Aminosulfonyl-5-N-butylamino-4-phenoxybenzoate (Bumetanide Prenyl Ester; NTP-2029)

The reaction was conducted similarly to EXAMPLE 129 NTP-2033) by first preparing the intermediate aminosulfonyl-5-N-butylamino-4-phenoxybenzoyl imidazole (11.64 g of unpurified product, 28.1 mmol), which was mixed with 3-methyl but-2-en-1-ol (prenyl alcohol, 9.68 g, 112.3 mmol), copper (11) nitrate trihydrate (1.35 g, 5.6 mmol), and nitric acid (0.01N, 2.8 mL). in acetonitrile (112 mL) and heated to 45° C. for 5 hours. The reaction mixture was concentrated, and the residue was dissolved in dichloromethane/methanol (9:1), introduced to a plug of silica gel, and eluted with dichloromethane/ethyl acetate (9:1). The product fractions were evaporated to dryness and the solid was further purified by slurring in warm heptane (45° C.) for 20 minutes, filtering, and drying to yield 8.3 g (68%) of 3-methylbut-2-enyl aminosulfonyl-5-N-butylamino-4-phenoxybenzoate.

EXAMPLE 136

4-Methoxybenzyl Aminosulfonyl-5-N-butylamino-4-phenoxybenzoate (Bumetanide para-Methoxybenzyl Ester; NTP-2031)

Bumetanide (8 g, 21.95 mmol), 4-methoxybenzyl chloride (4.47 g, 28.54 mmol), and triethylamine (2.22 g, 21.95 mmol) were combined in DMF (64 mL) and stirred overnight at 70° C. After cooling to room temperature, the reaction was diluted with saturated ammonium chloride (32 mL), extracted with ethyl acetate (2×120 mL), and the organic phase was washed with water (8×60 mL) and 1N sodium hydroxide (60 mL). The organic phase was then dried over anhydrous magnesium sulfate, filtered, and concentrated. Slurrying the solid product in isopropyl alcohol (10 mL/g) for 15 minutes, followed by filtration, yielded 6.5 g (61%) of 4-methoxybenzyl aminosulfonyl-5-N-butylamino-4-phenoxybenzoate.

EXAMPLE 137

Assessment of Therapeutic Potential of Bumetanide Analogs in Alleviating Anxiety (Fear Potentiated Startle Paradigm)

Purpose

To evaluate the effects of bumetanide analogs in two tests of anxiety in rats, bumetanide analogs (bumetanide 3-(dimethylaminopropyl) ester, bumetanide benzyltrimethylammonium salt, bumetanide dibenzylamide, bumetanide cyanomethyl ester, bumetanide N,N-diethylglycolamido ester, bumetanide N,N-dimethylglycolamido ester, bumetanide morpholinoethyl ester, bumetanide pivaxetil ester, bumetanide methyl ester, bumetanide diethylamide and benzyl ester) were assessed in the fear potentiated startle paradigm (FPS) test of anxiety. These studies may be repeated using furosemide analogs, piretanide analogs, azosemide analogs and torsemide analogs.

FPS Design

FPS is a commonly used assessment of therapeutic value of anxiolytic compounds in the rat. Rats received a 30 min period of habituation to the FPS apparatus. 24-hr later baseline startle amplitudes were collected. The rats will be divided into two matched groups based on baseline startle amplitudes. Following baseline startle amplitude collection 20 light/shock pairings were delivered on 2 sessions over 2 consecutive days (i.e., 10 light/shock pairings per day). On the final day, one group of rats received an injection (i.v.) of a bumetanide analog and the other group received vehicle only. Immediately following injections, startle amplitudes were assessed during startle alone trials and startle plus fear (light followed by startle) trials. Fear potentiated startle (light+startle amplitudes minus startle alone amplitudes) was compared between the treatment groups.

Method

Fear Potentiated Startle

Animals were trained and tested in four identical stabilimeter devices (Med-Associates). Briefly, each rat was placed in a small Plexiglas cylinder. The floor of each stabilimeter consists of four 6-mm-diameter stainless steel bars spaced 18 mm apart through which shock can be delivered. Cylinder movements result in displacement of an accelerometer where the resultant voltage is proportional to the velocity of the cage displacement. Startle amplitude is defined as the maximum accelerometer voltage that occurs during the first 0.25 sec after the startle stimulus is delivered. The analog output of the accelerometer is amplified, digitized on a scale of 0-4096 units and stored on a microcomputer. Each stabilimeter is enclosed in a ventilated, light-, and sound-attenuating box. All sound level measurements were made with a Precision Sound Level Meter. The noise of a ventilating fan attached to a sidewall of each wooden box produces an overall background noise level of 64 dB. The startle stimulus is a 50 ms burst of white noise (5 ms rise-decay time) generated by a white noise generator. The visual conditioned stimulus used was illumination of a light bulb adjacent to the white noise source. The unconditioned stimulus was a 0.6 mA foot shock with duration of 0.5 sec, generated by four constant-current shockers located outside the chamber. The presentation and sequencing of all stimuli were under the control of the microcomputer.

FPS procedures consisted of 5 days of testing; during days 1 and 2 baseline startle responses were collected, days 3 and 4 light/shock pairings were delivered, day 5-testing for fear potentiated startle was conducted.

Matching. On the first two days all rats were placed in the Plexiglas cylinders and 3 min later presented with 30 startle stimuli at a 30 sec interstimulus interval. An intensity of 105 dB was used. The mean startle amplitude across the 30 startle stimuli on the second day was used to assign rats into treatment groups with similar means.

Training. On the following 2 days, rats were placed in the Plexiglas cylinders. Each day following 3 min after entry 10 CS-shock pairings were delivered. The shock was delivered during the last 0.5 sec of the 3.7 sec CSs at an average intertrial interval of 4 min (range, 3-5 min).

Testing. Rats were placed in the same startle boxes where they were trained and after 3 min were presented with 18 startle-eliciting stimuli (all at 105 dB). These initial startle stimuli were used to again habituate the rats to the acoustic startle stimuli. Thirty seconds after the last of these stimuli, each animal received 60 startle stimuli with half of the stimuli presented alone (startle alone trials) and the other half presented 3.2 sec after the onset of the 3.7 sec CS (CS-startle trials). All startle stimuli were presented at a mean 30 sec interstimulus interval, randomly varying between 20 and 40 sec.

Measures. The treatment groups were compared on the difference in startle amplitude between CS-startle and startle-alone trials (fear potentiation).

In general, this study showed the ability of bumetanide analogs of the present invention to traverse the blood-brain barrier. The bumetanide analogs show the potential for regulation of disorder involving the NKCC co-transporters where bumetanide analogs were shown to affect the startle amplitude where the greater the reduction in fear-potentiated startle, the more compound believed delivered to the CNS. Moreover, several bumetanide analogs were shown to be more potent than or at least as potent as bumetanide. See Table 5 below and FIG. 1.

TABLE 5

| Number of animals | |
| --- | --- |
| Compound | N |
| DMSO | 34 |
| Synexis Bumetanide 35 mg/kg | 11 |
| 3-(Dimethylaminopropyl) Ester | 17 |
| Benzyltrimethylammonium Salt | 12 |
| Dibenzylamide | 15 |
| Cyanomethyl Ester | 17 |
| N,N-Diethylglycolamido Ester | 17 |
| N,N-Dimethylglycolamido Ester | 17 |
| N-Morpholinoethyl Ester | 17 |
| Pivaxetil Ester | 17 |
| Methyl Ester | 17 |
| Diethylamide | 12 |
| Benzyl Ester | 12 |
| Total | 227 |

Therefore the compounds described herein may be used in methods of treating anxiety.

EXAMPLE 138

Assessment of Therapeutic Potential of Bumetanide, Furosemide, Piretanide, Azosemide, and Torsemide Analogs in Alleviating the Symptoms of Intense Anxiety or Post Traumatic Stress Disorder (Contextual Fear Conditioning Model)

Purpose

To evaluate the potential of bumetanide, furosemide, piretanide, azosemide and torsemide analogs to alleviate intense anxiety in contextual fear conditioning in rats.

Design

Contextual fear conditioning involves pairing an aversive event, in this case moderate foot shock, with a distinctive environment. The strength of the fear memory is assessed using freezing, a species-typical defensive reaction in rats, marked by complete immobility, except for breathing. If rats are placed into a distinctive environment and are immediately shocked they do not learn to fear the context. However, if they are allowed to explore the distinctive environment sometime before the immediate shock, they show intense anxiety and fear when placed back into the same environment. By procedurally dividing contextual fear conditioning into two phases, one can separately study effects of treatments on memory for the context (specifically a hippocampus based process) from learning the association between context and shock or experiencing the aversiveness of the shock (which depend upon emotional response circuitry including amygdala). Post-Traumatic Distress Syndrome (PTSD) in humans has been shown to be related to emotional response circuitry in the amygdala, for this reason contextual memory conditioning is a widely accepted model for PTSD.

The experiment will use 24 rats. Each rat will receive a single 5-min episode of exploration of a small, novel environment. 72-hr later they will be placed into the same environment and immediately they will receive a single, moderate foot-shock. 24-hr later, 12 of the rats will receive an injection (i.v.) of a bumetanide analog. The remaining 12 rats will receive an injection of the vehicle. Each rat will again be placed into the same environment for 8-min during which time freezing will be measured, as an index of Pavlovian conditioned fear.

Methods

In this experiment, 4 identical chambers (20×20×15 cm) are used. All aspects of the timing and control of events are under microcomputer control (MedPC, MedAssociates Inc, Vermont, USA). Measurement of freezing is accomplished through an overhead video camera connected to the microcomputer and is automatically scored using a specialty piece of software, FreezeFrame. In Phase 1, rats are placed individually into the chambers for 5 minutes. Phase 2 begins 72 hr later, when again rats are placed individually into the same chambers but they receive an immediate foot shock (1 mA for 2 s). Thirty seconds later they are removed from the chambers. Phase 3, 24 hr later, the rats are returned to the chambers for 8 min during which time scoring freezing, the index of conditioning fear. Total freezing time will be analyzed in a one-way ANOVA with drug dose as the within-groups factor.

Therefore the compounds described herein may be used in a method for treating anxiety or post-traumatic stress disorder.

EXAMPLE 139

Formulations for CNS-Targeted Drugs

Oral Preparations

For oral administration, the pharmaceutical components are used in the range of about 10-60 mg of drug substance together with various inactive ingredients such as microcrystalline cellulose and other excipients, contained in a gelatin capsule. Alternatively, the drug substance is provided in tablet form including about 10-60 mg, of drug substance with microcrystalline cellulose, hydroxypropyl cellulose, magnesium stearate and other excipients.

Additionally, for oral administration, the pharmaceutical components are used in the range of about 10-100 mg/kg of drug substance together with various inactive ingredients such as microcrystalline cellulose and other excipients, contained in a gelatin capsule. Alternatively, the drug substance is provided in tablet form including about 10-100 mg/kg, of drug substance with microcrystalline cellulose, hydroxypropyl cellulose, magnesium stearate and other excipients.

Intravenous Preparations

For intravenous administration, each milliliter of sterile solution can include about 1-25 mg of drug substance formulated with about 20-40% propylene glycol, about 0-10% ethyl alcohol, optionally water, buffers, for example, about 5% sodium benzoate and benzoic acid as buffers, and preservatives, for example, about 1.5% benzyl alcohol as a preservative.

Also, for intravenous administration, each milliliter of sterile solution can include about 1-25 mg/kg of drug substance formulated with about 20-40% propylene glycol, about 0-10% ethyl alcohol, optionally water, buffers, for example, about 5% sodium benzoate and benzoic acid as buffers, and preservatives, for example, about 1.5% benzyl alcohol as a preservative.

EXAMPLE 140

In Vitro Pharmacology: $Na^+K^+Cl^-$ Cotransporter Assay

The effects of selected bumetanide analogs (prodrugs) were assessed for their effect on the $Na^+K^+Cl^-$ Cotransporter in vitro. See Gamba (2005) "Molecular Physiology and Pathophysiology of Electroneutral Cation-Chloride Cotransporters." Physiol. Rev. 85: 423-493.

$Na^+K^+Cl^-$ co-transporter activity was measured in vitro in A7r5 cells by measuring their uptake of $^{86}Rb$ (0.2 µCi) in 10 minutes at 37° C. as detected by scintillation counting. See Chassande, et al. (1988) "The $Na^+/K^+/Cl^-$ Cotransport in C6 glioma cells. Properties and role in volume regulation." Eur. J. Biochem. 171: 425433. Bumetanide was used a positive control compound to establish a specific activity. Selected bumetanide analogs (e.g., NTP-2016, NTP-2018, NTP-2018, NTP-2020, NTP-2021, NTP-2022, NTP-2023, NTP-2024, NTP-2025, NTP-2028, NTP-2029, NTP-2031, NTP-2034, NTP-2035, and NTP-2036) were tested for their inhibition of $Na^+/K^+/Cl^-$ co-transporter activity was measured in vitro in A7r5 cells by measuring their uptake of $^{86}Rb$ (0.2 µCi) in 10 minutes at 37° C. as detected by scintillation counting at $1.0 \times 10^{-5}$ M.

The results are expressed as a percent of control specific activity [(measured specific activity/control specific activity)×100] and as a percent inhibition of control specific activity [100−((measured specific activity/control specific activity)×100)] obtained in the presence of the selected bumetanide analogs (e.g., NTP-2004, NTP-2005, NTP-2006, NTP-2007, NTP-2008, NTP-2011, NTP-2012, NTP-2013, NTP-2014, NTP-2016, NTP-2018, NTP-2020, NTP-2021, NTP-2022, NTP-2023, NTP-2024, NTP-2025, NTP-2028, NTP-2029, NTP-2031, NTP-2034, NTP-2035, and NTP-2036). These results are expressed as % inhibition at 10 μM.

TABLE 6

| Compound | % of Control Value | % Inhibition of Control Values |
| --- | --- | --- |
| Bumetanide | 24.0 | 76 |
| NTP-2004 | 81.0 | 19 |
| NTP-2005 | 48.7 | 51 |
| NTP-2006 | 49.6 | 50 |
| NTP-2007 | 70.4 | 30 |
| NTP-2008 | 82.8 | 17 |
| NTP-2011 | 87.4 | 13 |
| NTP-2012 | 65.5 | 35 |
| NTP-2013 | 69.2 | 31 |
| NTP-2014 | 103.6 | −4 |
| NTP-2016 | 107.2 | −7 |
| NTP-2018 | 87.3 | 13 |
| NTP-2020 | 93.5 | 7 |
| NTP-2021 | 72.6 | 27 |
| NTP-2022 | 92.7 | 7 |
| NTP-2023 | 77.3 | 23 |
| NTP-2024 | 80.2 | 20 |
| NTP-2025 | 127.2 | −27 |
| NTP-2028 | 84.4 | 16 |
| NTP-2029 | 88.4 | 12 |

TABLE 6-continued

| Compound | % of Control Value | % Inhibition of Control Values |
| --- | --- | --- |
| NTP-2031 | 92.6 | 7 |
| NTP-2034 | 78.9 | 21 |
| NTP-2035 | 74.5 | 26 |
| NTP-2036 | 80.1 | 20 |

Bumetanide analogs showing "% Inhibition of Control Values" between 20 and 50% are indicative of weak to moderate inhibition. Bumetanide analogs showing "% Inhibition of Control Values" lower than 20% are indicative of no significance difference between the bumetanide analog and vehicle control values.

EXAMPLE 141

Blood and Brain Levels and Renal Function Assessment of Selected Bumetanide Prodrugs Following Intraperitoneal (i.p.) Administration Selected bumetanide prodrugs (e.g., NTP-2006 and NTP-2024 were administered to rats via i.p injection in a dosage of 100 mg/kg formulated in DMSO. Due to rapid metabolism of bumetanide in the rat species (Schwartz 1981), rats were pretreated with a general metabolic inhibitor, piperonyl butoxide ("PBx") (Halladay, 1978). Pre-treatment with this inhibitor allows for determination of blood levels of prodrugs and/or bumetanide along with determining brain penetration of prodrugs and/or bumetanide. In addition, pre-treatment allows for assessment of diuretic effects related to bumetanide systemic exposures. The concentration-time courses of prodrug and bumetanide were obtained in blood and brain of animals after administration bumetanide prodrugs. The results are shown in the tables 7-10 below:

TABLE 7

Summary of Concentrations of NTP-2024 and Bumetanide Found in Rat Blood Following 100 mg/kg IP Administration
Quenched Whole Blood Sample Collection
Treatment - NTP-2024 (IP)

| Animal Number | Group Number | Sex | Dose Time, Oct. 20, 2008 | Nominal Sample Time | Relative Sample Time | Actual Sample Time | Test Article Concentration (ng/mL) NTP-2024 | NTP-2000 |
| --- | --- | --- | --- | --- | --- | --- | --- | --- |
| 507 | 2 | Male | 10:17 A.M. | Predose | −2 h 32 m | 7:45 A.M. | BLQ | BLQ |
| | | | | 5 m | 5 m | 10:22 A.M. | 1685.74 | 4.15476 |
| | | | | 15 m | 17 m | 10:34 A.M. | 3939.86 | 14.2845 |
| | | | | 30 m | 30 m | 10:47 A.M. | 1520.05 | 13.3456 |
| | | | | 1 h | 1 h | 11:17 A.M. | 1082.93 | 12.2513 |
| | | | | 2 h | 2 h | 12:17 P.M. | 2110.97 | 15.0994 |
| | | | | 4 h | 4 h | 2:17 P.M. | 486.509 | 9.77600 |
| | | | | 6 h | 6 h | 4:17 P.M. | 319.646 | 5.81943 |
| 508 | 2 | Male | 10:19 A.M. | Predose | −2 h 32 m | 7:47 A.M. | BLQ | BLQ |
| | | | | 5 m | 6 m | 10:25 A.M. | 3924.75 | 3.80424 |
| | | | | 15 m | 20 m | 10:39 A.M. | 4358.32 | 7.96973 |
| | | | | 30 m | 30 m | 10:49 A.M. | 4607.28 | 10.0076 |
| | | | | 1 h | 1 h | 11:19 A.M. | 2417.92 | 9.15779 |
| | | | | 2 h | 2 h | 12:19 P.M. | 1755.37 | 8.15983 |
| | | | | 4 h | 4 h | 2:19 P.M. | 228.395 | 3.33021 |
| | | | | 6 h | 6 h | 4:19 P.M. | 279.725 | 2.73906 |
| 509 | 2 | Male | 10:21 A.M. | Predose | −2 h 32 m | 7:49 A.M. | BLQ | BLQ |
| | | | | 5 m | 7 m | 10:28 A.M. | 7638.10 | 3.49339 |
| | | | | 15 m | 20 m | 10:41 A.M. | 6418.34 | 5.80211 |
| | | | | 30 m | 30 m | 10:51 A.M. | 7101.38 | 8.43291 |
| | | | | 1 h | 1 h | 11:21 A.M. | 4321.42 | 8.06547 |
| | | | | 2 h | 2 h | 12:21 P.M. | 4099.07 | 8.94944 |

TABLE 7-continued

Summary of Concentrations of NTP-2024 and Bumetanide Found in
Rat Blood Following 100 mg/kg IP Administration
Quenched Whole Blood Sample Collection
Treatment - NTP-2024 (IP)

| Animal Number | Group Number | Sex | Dose Time, Oct. 20, 2008 | Nominal Sample Time | Relative Sample Time | Actual Sample Time | Test Article Concentration (ng/mL) NTP-2024 | NTP-2000 |
|---|---|---|---|---|---|---|---|---|
| | | | | 4 h | 4 h | 2:21 P.M. | 2358.43 | 9.96111 |
| | | | | 6 h | 6 h | 4:21 P.M. | 1583.21 | 13.0935 | m—minute  
h—hour  
Bold—Late sample  
BLQ—Below Limit of Quantitation (<1.00000 ng/mL)

TABLE 8

Summary of Concentrations of NTP-2024 and Bumetanide Found in
Rat Brain following 100 mg/kg IP Administration
Brain Collection
NTP-2024 (IP)

| Interval | Animal Number | Group Number | Sex | Brain Weight (g) | Volume of ACN added (mL) | Test Article Concentration (ng/mL) NTP-2024 | NTP-2000 |
|---|---|---|---|---|---|---|---|
| 15 m | 510 | 2 | Male | 1.893 | 5.7 | 283.783 | BLQ |
|  | 511 | 2 | Male | 1.831 | 5.5 | 277.985 | BLQ |
|  | 512 | 2 | Male | 1.804 | 5.4 | 226.803 | BLQ |
| 30 m | 513 | 2 | Male | 1.784 | 5.4 | 223.370 | 4.93967 |
|  | 514 | 2 | Male | 1.787 | 5.4 | 340.460 | 1.21679 |
|  | 515 | 2 | Male | 1.776 | 5.3 | 348.182 | 1.00897 |
| 1 h | 516 | 2 | Male | 1.812 | 5.4 | 284.032 | 1.83890 |
|  | 517 | 2 | Male | 1.826 | 5.5 | 568.338 | BLQ |
|  | 518 | 2 | Male | 1.881 | 5.6 | 237.302 | BLQ |
| 2 h | 519 | 2 | Male | 1.883 | 5.6 | 124.854 | BLQ |
|  | 520 | 2 | Male | 1.774 | 5.3 | 112.217 | BLQ |
|  | 521 | 2 | Male | 1.779 | 5.3 | 154.415 | BLQ |
| 4 h | 522 | 2 | Male | 1.841 | 5.5 | 26.6338 | BLQ |
|  | 523 | 2 | Male | 1.882 | 5.6 | 23.4893 | BLQ |
|  | 524 | 2 | Male | 1.933 | 5.8 | 37.1694 | BLQ |
| 6 h | 525 | 2 | Male | 2.037 | 6.1 | 25.4146 | BLQ |
|  | 526 | 2 | Male | 1.849 | 5.5 | 18.4619 | BLQ |
|  | 527 | 2 | Male | 1.903 | 5.7 | 25.7880 | BLQ | m—minute  
h—hour  
BLQ—Below Limit of Quantitation (<1.00000 ng/mL)

TABLE 9

Summary of Concentrations of NTP-2006 and Bumetanide Found in
Rat Blood Following 100 mg/kg IP Administration
Quenched Whole Blood Sample Collection
Treatment - NTP-2006 (IP)

| Animal Number | Group Number | Sex | Dose Time, Oct. 20, 2008 | Nominal Sample Time | Relative Sample Time | Actual Sample Time | Test Article Concentration (ng/mL) NTP-2006 | NTP-2000 |
|---|---|---|---|---|---|---|---|---|
| 534 | 3 | Male | 10:23 A.M. | Predose | -2 h 32 m | 7:51 A.M. | BLQ | BLQ |
|  |  |  |  | 5 m | 8 m | 10:31 A.M. | 17.9938 | 4369.27 |
|  |  |  |  | 15 m | 18 m | 10:41 A.M. | 3.32281 | 10045.6 |
|  |  |  |  | 30 m | 30 m | 10:53 A.M. | BLQ | 8793.14 |
|  |  |  |  | 1 h | 1 h | 11:23 A.M. | BLQ | 9739.37 |
|  |  |  |  | 2 h | 2 h | 12:23 P.M. | BLQ | 1646.51 |
|  |  |  |  | 4 h | 4 h | 2:23 P.M. | BLQ | 172.991 |
|  |  |  |  | 6 h | 6 h | 4:23 P.M. | BLQ | 174.412 |

TABLE 9-continued

Summary of Concentrations of NTP-2006 and Bumetanide Found in
Rat Blood Following 100 mg/kg IP Administration
Quenched Whole Blood Sample Collection
Treatment - NTP-2006 (IP)

| Animal Number | Group Number | Sex | Dose Time, Oct. 20, 2008 | Nominal Sample Time | Relative Sample Time | Actual Sample Time | Test Article Concentration (ng/mL) NTP-2006 | NTP-2000 |
|---|---|---|---|---|---|---|---|---|
| 535 | 3 | Male | 10:25 A.M. | Predose | −2 h 33 m | 7:52 A.M. | BLQ | BLQ |
|  |  |  |  | 5 m | 8 m | 10:33 A.M. | 6.39037 | 4584.54 |
|  |  |  |  | 15 m | 17 m | 10:42 A.M. | 2.00795 | 13016.0 |
|  |  |  |  | 30 m | 30 m | 10:55 A.M. | BLQ | 15141.9 |
|  |  |  |  | 1 h | 1 h | 11:25 A.M. | BLQ | 5656.70 |
|  |  |  |  | 2 h | 2 h | 12:25 P.M. | BLQ | 2248.85 |
|  |  |  |  | 4 h | 4 h | 2:25 P.M. | BLQ | 433.217 |
|  |  |  |  | 6 h | 6 h | 4:25 P.M. | BLQ | 436.340 |
| 536 | 3 | Male | 10:27 A.M. | Predose | NA | NA | BLQ | BLQ |
|  |  |  |  | 5 m | 8 m | 10:35 A.M. | 4.48065 | 8740.40 |
|  |  |  |  | 15 m | 15 m | 10:42 A.M. | 1.72770 | 13681.8 |
|  |  |  |  | 30 m | 30 m | 10:57 A.M. | 3.35269 | 14625.7 |
|  |  |  |  | 1 h | 1 h | 11:27 A.M. | BLQ | 8958.67 |
|  |  |  |  | 2 h | 2 h 1 m | 12:28 P.M. | BLQ | 2354.06 |
|  |  |  |  | 4 h | 4 h | 2:27 P.M. | BLQ | 402.370 |
|  |  |  |  | 6 h | 6 h | 4:27 P.M. | BLQ | 251.010 | m—minute
h—hour
Bold—Late sample
NA—Not Applicable/Not Available
BLQ—Below Limit of Quantitation (<1.00000 ng/ml)

TABLE 10

Summary of Concentrations of NTP-2006 and Bumetanide Found in
Rat Brain Following 100 mg/kg IP Adminstration
Brain Collection
NTP-2006 (IP)

| Interval | Animal Number | Group Number | Sex | Brain Weight (g) | Volume of ACN added (mL) | Test Article Concentration (ng/mL) NTP-2006 | NTP-2000 |
|---|---|---|---|---|---|---|---|
| 15 m | 537 | 3 | Male | 1.491 | 4.8 | 2.95261 | 276.490 |
|  | 538 | 3 | Male | 1.685 | 5.1 | 5.25899 | 297.849 |
|  | 539 | 3 | Male | 1.863 | 5.6 | 2.93671 | 285.789 |
| 30 m | 540 | 3 | Male | 1.782 | 5.3 | 11.0196 | 311.867 |
|  | 541 | 3 | Male | 1.711 | 5.1 | 10.9032 | 393.035 |
|  | 542 | 3 | Male | 1.856 | 5.6 | 29.5315 | 260.280 |
| 1 h | 543 | 3 | Male | 1.995 | 6.0 | 19.7091 | 201.547 |
|  | 544 | 3 | Male | 1.705 | 5.1 | 3.26366 | 163.944 |
|  | 545 | 3 | Male | 1.952 | 5.9 | 1.95104 | 176.997 |
| 2 h | 546 | 3 | Male | 1.838 | 5.5 | 14.8344 | 29.7859 |
|  | 547 | 3 | Male | 1.896 | 5.7 | 20.7020 | 44.0245 |
|  | 548 | 3 | Male | 1.761 | 5.3 | 8.38090 | 25.6467 |
| 4 h | 549 | 3 | Male | 1.918 | 5.8 | 2.68868 | 104.005 |
|  | 550 | 3 | Male | 1.830 | 5.5 | 2.31034 | 15.2353 |
|  | 551 | 3 | Male | 2.035 | 6.1 | 42.7118 | 23.2138 |
| 6 h | 552 | 3 | Male | 1.828 | 5.5 | 1.88149 | 9.10718 |
|  | 553 | 3 | Male | 1.887 | 5.7 | 1.52310 | 10.1157 |
|  | 554 | 3 | Male | 1.922 | 5.8 | 1.57228 | 15.2846 | m—minute
h—hour

Therefore when selected bumetanide prodrugs (e.g., NTP-2006 and NTP-2024) are administered i.p. to rats, prodrug and bumetanide are present and stable in the rat's blood for greater than 6 hours following administration. Further NTP-2024 does not readily degrade to bumetanide in the blood. NTP-2006 degrades into bumetanide following i.p. administration. Renal function assessments including cumulative urine volume, sodium excretion, and potassium excretion were measured in animals administered NTP-2024, NTP-2006, and vehicle controls over 6 hours post-dose.

Figure 27:
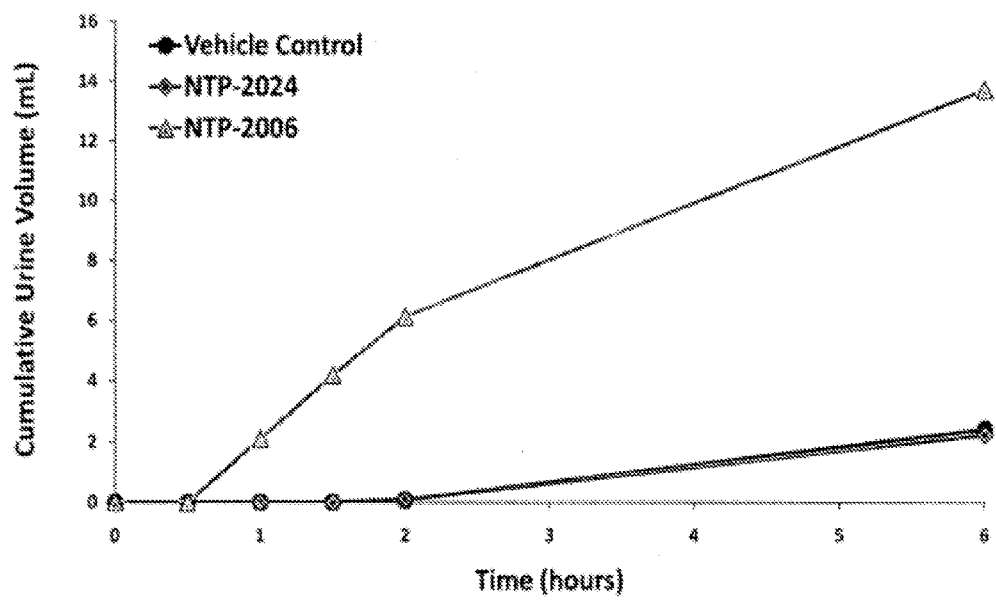
FIG. 27 illustrates cumulative urine volume. The animals were fasted overnight prior to dosing and had no access to drinking water prior to any pretreatment. Food and water were withheld through the terminal sample collection or for the first 6 hours of blood sample collection, where applicable. Prior to test article administration all animals were pretreated with a single IP dose of piperonyl butoxide ("PBx"). At approximately 5 to 6 minutes prior to dosing all animals received a single oral (PO) gavage dose of 0.9% Sodium Chloride for Injection, USP, at a dose volume of 15 mL/kg. The vehicle, DMSO, and the test articles, NTP-2024 and NTP-2006, were administered via a single IP dose at a dose volume of 1 ml/kg.
Figure 28:
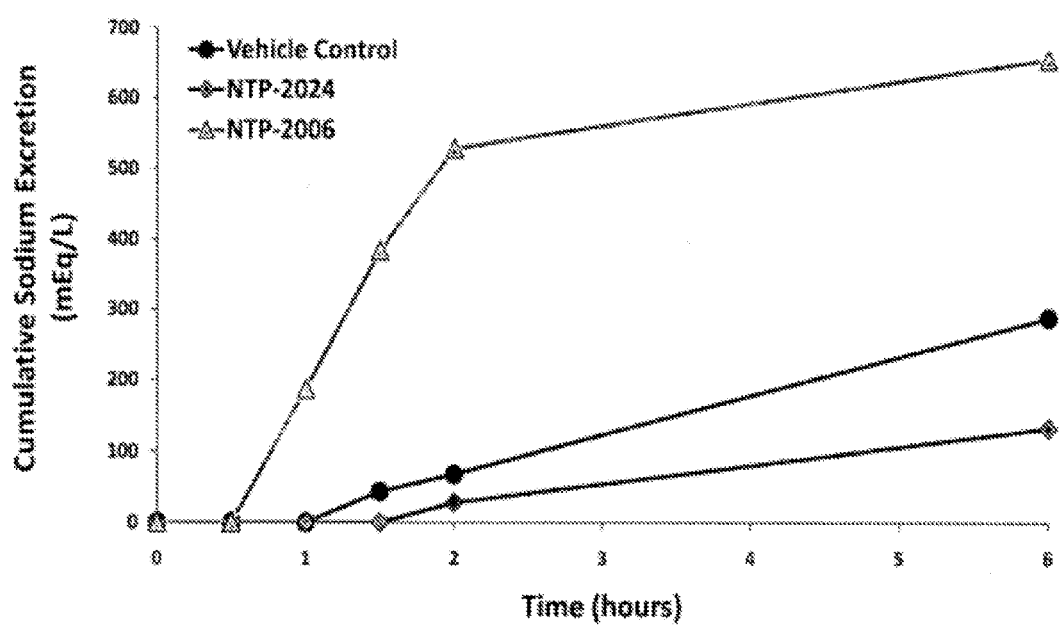
FIG. 28 illustrates cumulative sodium excretion. The animals were fasted overnight prior to dosing and had no access to drinking water prior to any pretreatment. Food and water were withheld through the terminal sample collection or for the first 6 hours of blood sample collection, where applicable. Prior to test article administration all animals were pretreated with a single IP dose of piperonyl butoxide ("PBx"). At approximately 5 to 6 minutes prior to dosing all animals received a single oral (PO) gavage dose of 0.9% Sodium Chloride for Injection, USP, at a dose volume of 15 mL/kg. The vehicle, DMSO, and the test articles, NTP-2024 and NTP-2006, were administered via a single IP dose at a dose volume of 1 mL/kg.
Figure 29:
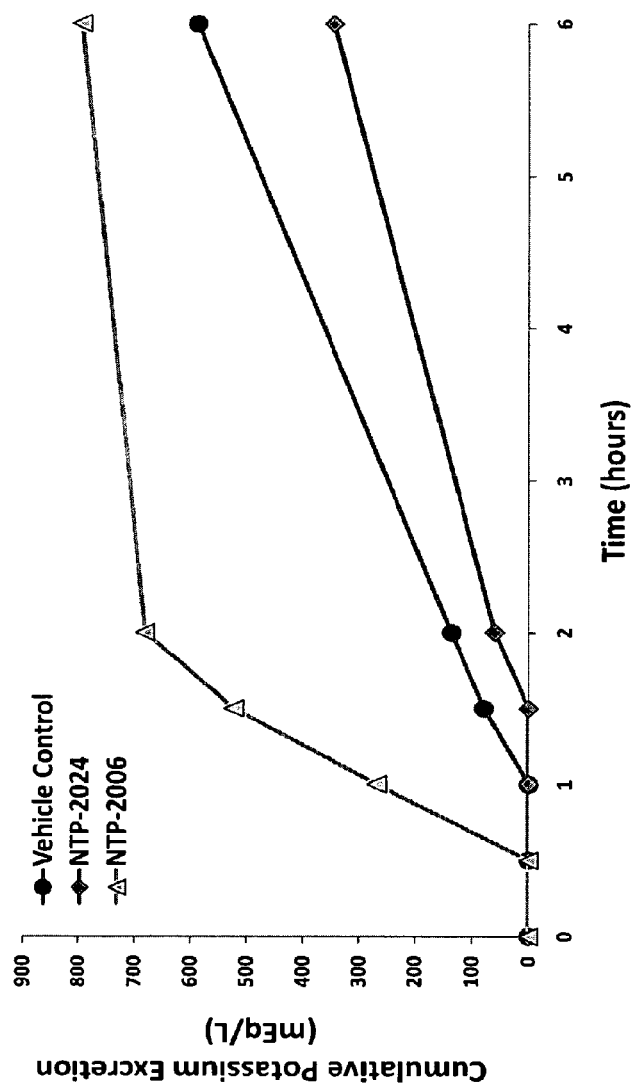
FIG. 29 illustrates cumulative potassium excretion. The animals were fasted overnight prior to dosing and had no access to drinking water prior to any pretreatment. Food and water were withheld through the terminal sample collection or for the first 6 hours of blood sample collection, where applicable. Prior to test article administration all animals were pretreated with a single IP dose of piperonyl butoxide ("PBx"). At approximately 5 to 6 minutes prior to dosing all animals received a single oral (PO) gavage dose of 0.9% Sodium Chloride for Injection, USP, at a dose volume of 15 mL/kg. The vehicle, DMSO, and the test articles, NTP-2024 and NTP-2006, were administered via a single IP dose at a dose volume of 1 mL/kg.

The animals were fasted overnight prior to dosing and had no access to drinking water prior to any pretreatment. Food and water were withheld through the terminal sample collection or for the first 6 hours of blood sample collection, where applicable. Prior to test article administration all animals were pretreated with a single IP dose of PBx. At approximately 5 to 6 minutes prior to dosing all animals received a single oral (PO) gavage dose of 0.9% Sodium Chloride for Injection, USP, at a dose volume of 15 mL/kg. The vehicle, DMSO, and the test articles, NTP-2024 and NTP-2006, were administered via a single IP dose at a dose volume of 1 mL/kg. Cumulative urine volume, sodium excretion, and potassium excretion graphs are illustrated in FIGS. 27, 28, and 29.

Therefore the compounds described herein may be used in methods to treat and/or prevent (prophylactic) for diseases and conditions described herein can be administered and detected in the blood and plasma of the patient. Further, the bumetanide analogs described herein degrade into bumetanide following administration.

EXAMPLE 142

Brain and Plasma Levels of Selected Furosemide Prodrugs Following Oral Administration Furosemide and selected furosemide prodrugs can be orally administered to a rat in a dosage of 30 mg/kg formulated in 0.5%-CMC and/or PEG-200. After 30 or 60 minutes, the amount of the prodrug and bumetanide present in the rat plasma and brain will be assayed.

EXAMPLE 143

Bumetanide, Furosemide, Piretanide, Azosemide, and Torsemide Analogs (Prodrugs) Reduce Seizures in the Rat Model of Kainic Acid Induced Epileptic Seizures Epilepsy is a chronic neurological condition characterized by recurrent seizures that are caused by abnormal cerebral nerve cell activity. Epilepsy is classified as idiopathic or symptomatic. A nerve cell transmits signals to and from the brain in two ways by (1) altering the concentrations of salts (sodium, potassium, calcium) within the cell and (2) releasing chemicals called neurotransmitters (e.g. gamma aminobutyric acid, GABA). The change in salt concentration conducts the impulse from one end of the nerve cell to the other. At the end, a neurotransmitter is released, which carries the impulse to the next nerve cell. Neurotransmitters either slow down or stop cell-to-cell communication (called inhibitory neurotransmitters) or stimulate this process (called excitatory neurotransmitters). Normally, nerve transmission in the brain occurs in an orderly way, allowing a smooth flow of electrical activity. Improper concentration of salts within the cell and overactivity of either type of neurotransmitter can disrupt orderly nerve cell transmission and trigger seizure activity. Certain areas of the brain are more likely than others to be involved in seizure activity. The motor cortex, which is responsible for body movement, and the temporal lobes, including the hippocampus, which is involved in memory, are particularly sensitive to biochemical changes (e.g., decreased oxygen level, metabolic imbalances, infection) that provoke abnormal brain cell activity.

Bumetanide is a loop diuretic of the sulfamyl category to treat heart failure. It is often used in patients in whom high doses of furosemide are ineffective. The main difference between the two substances is in bioavailability. Furosemide is incompletely absorbed in the intestine (40%), and there is substantial inter- and intraindividual differences in bioavailability (range 10-90%). Bumetanide demonstrates near complete absorption (≥80%) after oral administration, and the absorption is not altered when it is taken with food. It is said to be a more predictable diuretic, meaning that the predictable absorption is reflected in a more predictable effect. Bumetanide is 40 times more potent than furosemide (for patients with normal renal function).

A recent study demonstrated that bumetanide may help treat seizures in newborns, which are difficult to control with existing anticonvulsants. Conventional anticonvulsants— phenobarbital and benzodiazepines—are ineffective in newborns because their brains are biochemically different from adult brains. Conventional anticonvulsants work by mimicking the action of GABA, a natural inhibitory chemical in the brain, by activating GABA receptors on the surface of brain cells. In adult nerve cells, GABA activation opens up channels that allow chloride to move into the cell. The cell thereby acquires a negative charge and becomes less excitable, inhibiting seizure activity. But in newborns, chloride is already high, and therefore activating GABA receptors causes chloride to move out of nerve cells, creating a paradoxical excitatory reaction that may actually exacerbate seizures.

Two molecules regulate cellular chloride levels: KCC2; which transports chloride out of cells, and NKCC1, which brings chloride in to the cells. Previous studies in rats had shown that adult nerve cells mostly have KCC2, making their chloride concentrations lower inside than outside. Thus, when GABA receptors are activated, chloride tends to come in, with an inhibitory effect. In newborn rats, the situation is reversed: their nerve cells mostly have NKCC1, so chloride is actively transported inside, making initial chloride concentrations very high. As a result, GABA activation causes chloride to exit the cell, with an excitatory effect. See e.g., Cohen (1981) "Pharmacology of bumetanide." J. Clin. Pharmacol. 21:537-542; Dzhala, et al. (2005) "NKCC1 transporter facilitates seizures in the developing brain." Nat Med. 11: 1205-1213; Martinez, et al. (1998) "Soy isoflavonoids exhibit in vitro biological activities of loop diuretics." Am. J. Clin. Nutr. 68:1354S-1357S, the disclosures of each of which are hereby incorporated by reference in their entireties.

Bumetanide inhibits NKCC2 activity in the kidney, and suggests that the drug might have a similar effect in the brain, lowering chloride levels and making nerve cells responsive to GABA activation. Studies in baby rats found that bumetanide indeed inhibited seizure activity, while phenobarbital, as in humans, worked poorly.

Accordingly, bumetanide ("Bumet") and selected bumetanide prodrugs (e.g., NTP-2007, NTP-2008, NTP-2011, NTP-2012, NTP-2015, NTP-2022, NTP-2024) were tested for efficacy in the kainic acid ("KA") induced epileptic rat seizure model. In particular, bumetanide and selected bumetanide prodrugs (e.g., NTP-2007, NTP-2008, NTP-2011, NTP-2012, NTP-2015, NTP-2022, NTP-2024) were tested for their ability to inhibit seizure activity in the kainic acid induced seizure rat model.

In order to determine the efficacy of the compounds in the rat seizure model, Sprague-Dawley rats ("SD rats") were injected with 15 mg/kg kainic acid and vehicle or compounds (mannitol or bumetanide) intraperitoneal ("i.p.") and were examined for the induction of seizures and the severity of seizures. Rats were injected intraperitoneally with a bolus of kainic acid (15 mg/kg)±bumetanide analogs or bumetanide and examined for changes or protection from seizure activity. Intraperitoneal (i.p.) administration of kainic acid (15 mg/kg) demonstrated seizure activity. Administration of bumetanide (100 mg/kg) or bumetanide analogs (20 μmoles/kg) demonstrated various effects of the compounds on reduction in behavior (e.g., seizure activity)

following kainic acid injections. These data suggest that the some of the bumetanide analogs and bumetanide demonstrate anticonvulsaht activity following i.p. injection in the rat kainic acid induced seizures in the rat epileptic model.

METHODS AND MATERIALS

Animals

Sprague-Dawley rats (Charles River Labs, NC), weighing 260-300 grams each were given free access to food and water before the experiment. These were naïrats (i.e., not previously drug treated or used in other experiments.) Animals were excluded from the study if the animals died prior to completion of study (at any point).

Experimental Groups

Animals were subjected to kainic acid induced seizures and were divided into a control group (saline, n=10), vehicle group (DMSO, n=10) or treated groups (NTP-2007, NTP-2008, NTP-2011, NTP-2012, NTP-2015, NTP-2022, NTP-2024, bumetanide, and mannitol, n=10) treated with an intraperitoneal injection of kainic acid (15 mg/kg). Formulation of kainic acid was performed by NTS as a stock solution by reconstituting kainic acid with (100%) saline that was stored at 4° C. Vehicle control received saline solution. The bolus IP injections with kainic acid were initiated at time 0 and NTP compounds or bumetanide were started at the same time. The research investigators were blinded to the treatment groups.

The selected bumetanide analogs were formulated by adding 5 ml DMSO to a vial containing a pre-weighed amount of compound. Solutions were prepared fresh daily just prior to use; dosing of all 10 rats with any given compound occurred on a single day after preparing the dosing solution. All the selected bumetanide analogs plus the DMSO control were dosed at 1 ml/kg. Unused remaining dosing solutions were stored frozen.

KA-Induced Status Epilepticus

Animals were maintained in a temperature- and light-controlled environment in accord with the principles and procedures of the National Institutes of Health Guidelines for Care and Use of Laboratory Animals. Seizures were induced in adult, male Sprague-Dawley rats (260-300 g) by injection of KA (15 mg/kg, i.p.). In addition, animals were injected with test compounds following kainic acid to determine the effects on protection from epilepsy. Animals were monitored behaviorally for seizures for 2 hours after injection.

Behavior

Seizure activity was initially characterized as either yes (1) or no (0) within a 2 hour period following injection of KA. A seizure severity grade was assigned based on the maximal response achieved on a scale from 0 to IV as follows: 0, no response; I, single limb clonus and scratching; II, multiple limb clonus and staggering gait; I, limb clonus, tonic extension of limbs and falling; IV, continuous grade III seizures for longer than 30 min (status epilepticus).

Statistical Analysis

The results were expressed as the mean±standard deviation (SD). The significance of difference in the epileptic data was analyzed using a one-way analysis of variance (ANOVA) followed by Fisher's post hoc test. Repeated-measures ANOVA were computed on the monitoring data and the significance of the difference among groups were evaluated by Fisher's post hoc test.

Treatment Groups

All groups were subjected to kainic acid. Animals (100 animals) were subjected to i.p. dosing of DMSO vehicle or bumetanide analogs at the indicated dose volume.

TABLE 11

Kainic Acid Rat Model of Epilepsy:

| Group | Compound | Dose volume | Route |
|---|---|---|---|
| 1 (n = 10 rats) | DMSO | 1 ml/kg | IP |
| 2 (n = 10 rats) | NTP-2011 (20 μmoles/kg) | 1 ml/kg | IP |
| 3 (n = 10 rats) | NTP-2022 (20 μmoles/kg) | 1 ml/kg | IP |
| 4 (n = 10 rats) | Bumetanide (20 μmoles/kg) | 1 ml/kg | IP |
| 5 (n = 10 rats) | NTP-2015 (20 μmoles/kg) | 1 ml/kg | IP |
| 6 (n = 10 rats) | Mannitol (20 μmoles/kg) | 1 ml/kg | IP |
| 7 (n = 10 rats) | NTP-2007 (20 μmoles/kg) | 1 ml/kg | IP |
| 8 (n = 10 rats) | NTP-2024 (20 μmoles/kg) | 1 ml/kg | IP |
| 9 (n = 10 rats) | NTP-2012 (20 μmoles/kg) | 1 ml/kg | IP |
| 10 (n = 10 rats) | NTP-2008 (20 μmoles/kg) | 1 ml/kg | IP |

Endpoints

Effects of the selected bumetanide analogs on protection from kainic acid induced injury.

All test groups have been provided to NTS; kainic acid and bumetanide were purchased as solid materials. Kainic acid was purchased from Sigma (#K0250) and bumetanide was purchased from Sigma (#B3023). All animals in the test groups were dosed as indicated above.

RESULTS

Kainic Acid Induced Seizures in Rats.

Animals were injected with KA and the selected bumetanide analogs and examined for 2 hours for the induction of seizures. The induction of seizures in rats with kainic acid was determined as either yes seizures (1) or no seizures (0). Table 12 illustrates the number of seizures per group.

TABLE 12

Percent decrease in seizure activity.

| Group | Treatment | Seizures Mean ± SD | Percent reduction in Seizures | P-value[1] |
|---|---|---|---|---|
| 1 | KA/DMSO | 0.9000 ± 0.3162 | NA | NA |
| 2 | KA/NTP-2011 | 0.2000 ± 0.4216 | −77.8% | 0.0005* |
| 3 | KA/NTP-2022 | 0.6000 ± 0.5164 | −33.3% | 0.1346 |
| 4 | KA/Bumet | 0.5000 ± 0.5270 | −44.4% | 0.0544 |
| 5 | KA/NTP-2015 | 0.5000 ± 0.5270 | −44.4% | 0.0544 |
| 6 | KA/Mannitol | 0.4000 ± 0.5164 | −55.5% | 0.0177* |
| 7 | KA/NTP-2007 | 0.6000 ± 0.5164 | −33.3% | 0.1346 |
| 8 | KA/NTP-2024 | 0.1000 ± 0.3162 | −88.9% | <0.0001* |
| 9 | KA/NTP-2012 | 0.2000 ± 0.4216 | −77.8% | 0.0005* |
| 10 | KA/NTP-2008 | 0.1000 ± 0.3162 | −88.9% | <0.0001* |
| 11 | KA/Bumet | 0.1000 ± 0.3162 | −88.9% | <0.0001* |

[1]Percent decreases are compared to the respective DMSO control animals.
Significantly different from DMSO control group.

Seizures

Seizures were significantly increased in the kainic acid injected animals. When treated with the selected bumetanide analogs or bumetanide, the severity of the seizure activity was significantly reduced (Table 12). The percent decrease in seizure severity is presented in Table 12. As shown in the table, bumetanide showed an 88.9% reduction in seizure activity.

Mortality:

There were no deaths in this study.

Intensity of Kainic Acid Seizures in Rats.

Animals were injected as described above and evaluated for the intensity or severity of the seizures following the selected bumetanide analogs (e.g., NTP-2007, NTP-2008, NTP-2011, NTP-2012, NTP-2015, NTP-2022, NTP-2024) or bumetanide treatment. The relative severity of seizures in these studies was assessed.

Seizure severity is plotted in Table 13. As seen in the data, bumetanide at two different doses showed a 70.8% and 95.8% reduction in seizure severity (doses were 20 umoles/kg and 274 umoles/kg, respectively). The selected bumetanide analogs showed variability in the reduction in severity.

TABLE 13

Percent decrease in seizure severity.

| Group | Treatment | Seizures Severity Mean ± SD | Percent reduction in Seizures Severity | P-value[1] |
|---|---|---|---|---|
| 1 | KA/DMSO | 2.400 ± 0.9661 | NA | NA |
| 2 | KA/NTP-2011 | 0.3000 ± 0.6749 | −87.5% | 0.0005* |
| 3 | KA/NTP-2022 | 1.100 ± 1.101 | −54.2% | 0.0117* |
| 4 | KA/Bumet | 0.7000 ± 0.8233 | −70.8% | 0.0005* |
| 5 | KA/NTP-2015 | 1.100 ± 1.197 | −54.2% | 0.0155* |
| 6 | KA/Mannitol | 0.5000 ± 0.7071 | −79.2% | <0.0001* |
| 7 | KA/NTP-2007 | 1.500 ± 1.354 | −37.5% | 1.042 |
| 8 | KA/NTP-2024 | 0.1000 ± 0.3162 | −95.8% | <0.0001* |
| 9 | KA/NTP-2012 | 0.2000 ± 0.4216 | −91.7% | <0.0001* |
| 10 | KA/NTP-2008 | 0.1000 ± 0.3162 | −95.8% | <0.0001* |
| 11 | KA/Bumet | 0.1000 ± 0.3162 | −95.8% | <0.0001* |

[1]Percent decreases are compared to the respective DMSO control animals.
Significantly different from DMSO control group.

The loop diuretics represent an important class of orally effective drugs that continue to play a major role in controlling and reducing edema formation in a variety of diseases. These compounds work through inhibition of $Na^+$—$K^+$-$2Cl^-$ cotransport in the lumen of the ascending nephronic loop and inhibiting membrane ion transport. They also increase renal blood flow and peripheral venous capacitance. Recent studies have shown that bumetanide may help treat seizures in newborns, which are difficult to control with existing anticonvulsants. Conventional anticonvulsants phenobarbital and benzodiazepines are ineffective in newborns because their brains are biochemically different from adult brains. Conventional anticonvulsants work by mimicking the action of gamma-aminobutyric acid (GABA), a natural inhibitory chemical in the brain, by activating GABA receptors on the surface of brain cells. In adult nerve cells, GABA activation opens up channels that allow chloride to move into the cell. The cell thereby acquires a negative charge and becomes less excitable, inhibiting seizure activity. But in newborns, chloride is already high and therefore activating GABA receptors causes chloride to move out of nerve cells, creating a paradoxical excitatory reaction that may actually exacerbate seizures.

Figure 11:
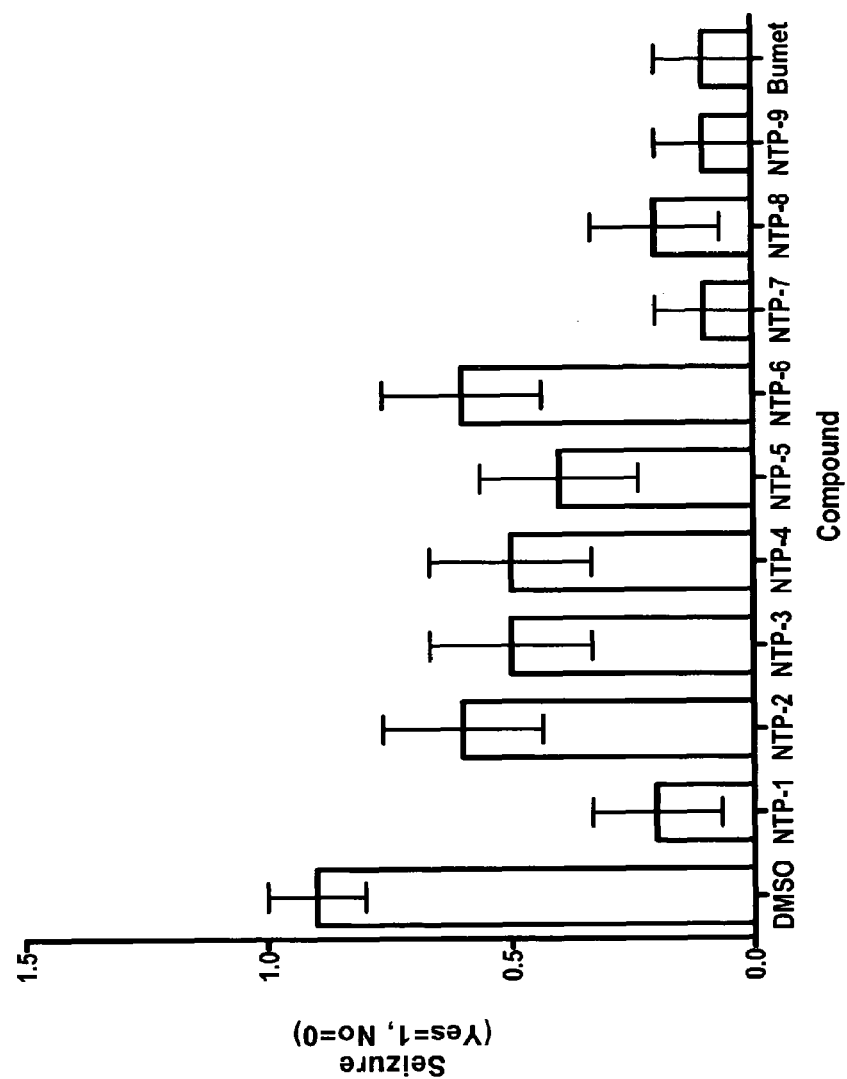
FIG. 11 depicts the effects of NTP compounds and bumetanide on seizure induction in the rat following kainic acid injections. Rats were subjected to kainic acid (KA, 15 mg/kg) injections i.p. and treated with DMSO (vehicle), NTP compounds (20 µmoles/kg), and bumetanide (100 mg/kg) and examined for seizure induction. Seizure induction was graded as described in EXAMPLE 143. NTP-1 (NTP-2011); NTP-2 (NTP-2022); NTP-3 (bumet); NTP-4 (NTP-2015); NTP-5 (mannitol); NTP-6 (NTP-2007); NTP-7 (NTP-2024); NTP-8 (NTP-2012); NTP-9 (NTP-2008); and Bumet (bumetanide).
Figure 12:
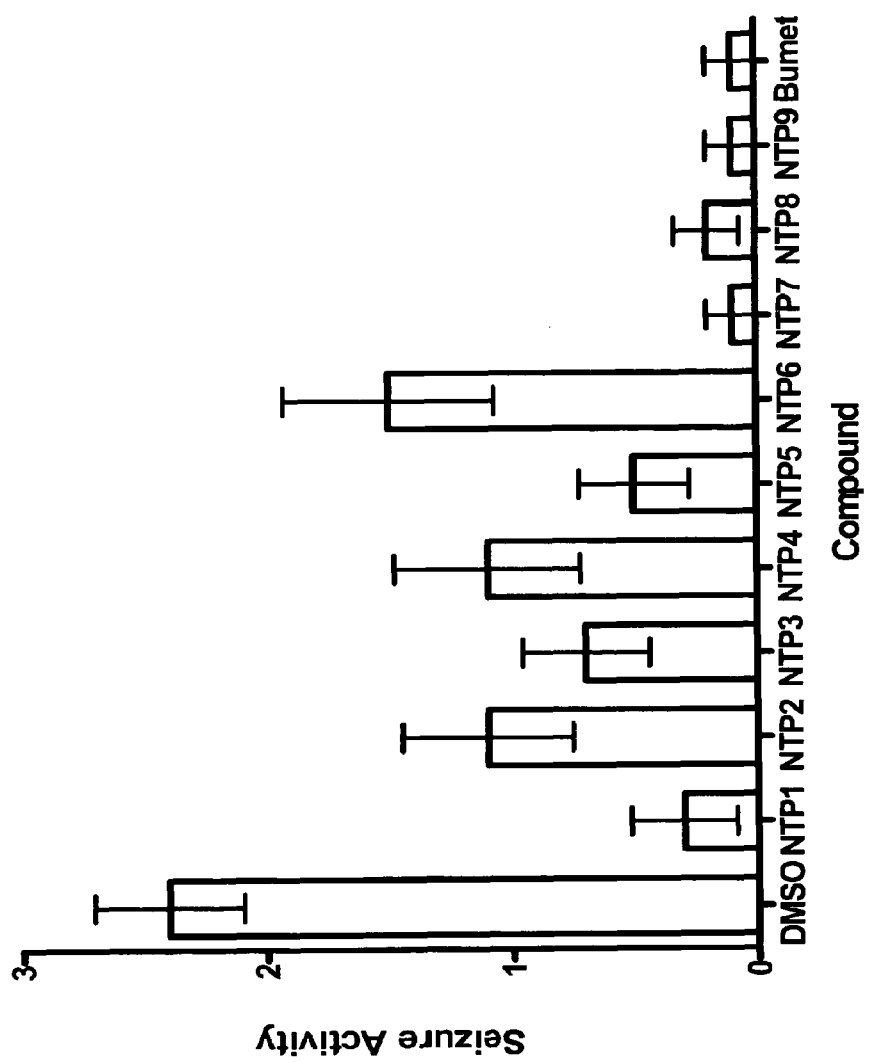
FIG. 12 depicts the effects of NTP compounds and bumetanide on seizure severity (activity) in the rat following kainic acid injections. Rats were subjected to kainic acid (KA, 15 mg/kg) i.p. injections and treated with DMSO (vehicle), NTP compounds (20 µmoles/kg) and bumetanide (100 mg/kg) and examined for seizure severity. Seizure severity was graded as described in EXAMPLE 143. NTP-1 (NTP-2011); NTP-2 (NTP-2022); NTP-3 (bumet); NTP-4 (NTP-2015); NTP-5 (mannitol); NTP-6 (NTP-2007); NTP-7 (NTP-2024); NTP-8 (NTP-2012); NTP-9 (NTP-2008); and Burnet (bumetanide).

In this study, the selected bumetanide analogs (e.g., NTP-2007, NTP-2008, NTP-2011, NTP-2012, NTP-2015, NTP-2022, NTP-2024) and bumetanide were examined in the kainic acid induced seizure model of rats to test the efficacy in protection against seizures. See FIGS. 11 and 12.

When administered intravenously, the bumetanide analogs were found to be protective against kainic acid induced seizures in rats. Therefore the compounds described herein may be used in methods to treat and/or prevent (prophylactic) for seizures, seizure disorders, epilepsy, epileptic seizures, and other neurodegenerative disorders (e.g., those neurodegenerative disorders which involve seizures). In particular, the compounds described herein are used in a method for treating seizures, seizure disorders, epilepsy, epileptic seizures, and other neurodegenerative disorders, wherein said neurodegenerative disorders involve seizures, comprising administering an effective amount of an analog (including prodrugs) of bumetanide, furosemide, piretanide, azosemide, and torsemide described herein.

EXAMPLE 144

Primate Epilepsy Model

Furosemide and Bumetanide Suppress Epileptiform Activity

Furosemide suppresses epileptiform activity in the acute primate seizure models and epileptic activity in humans suffering from intractable epilepsy. Bumetanide also suppresses epileptiform activity in acute primate seizure models, significantly more than furosemide. Amide prodrugs of bumetanide (e.g., NTP-2024) are efficacious in suppressing epileptiform activity in primate seizure models.

Quantification of Epileptiform Activity

Figure 13:
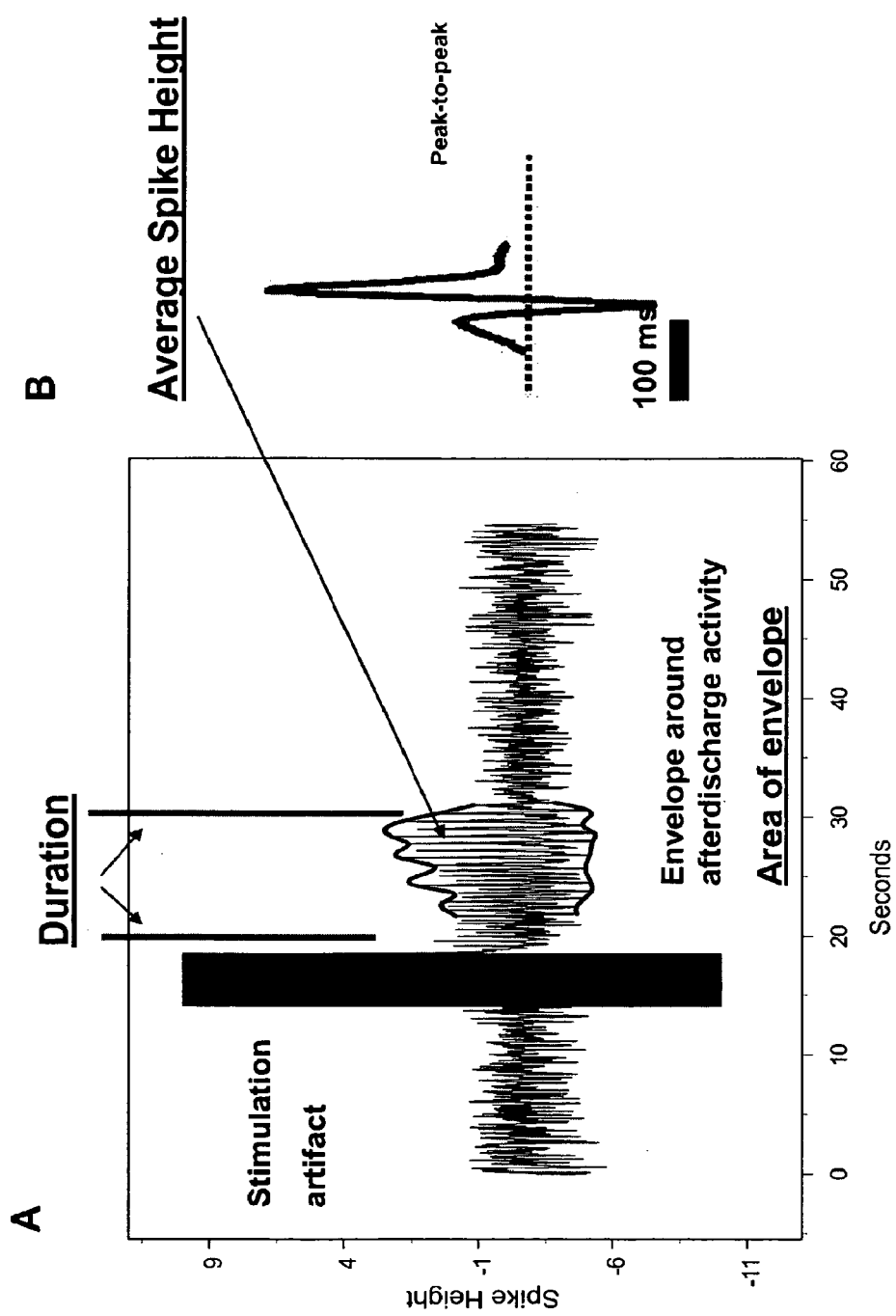
FIG. 13 depicts the quantification of epileptiform activity. See Haglund and Hochman (Feb. 23, 2005) *J. Neurphysiol.* 94: 907-918.

FIG. 13 depicts epileptiform spikes and bursts generated using software for the automatic quantification epileptiform activity. FIG. 13A depicts after-discharge activity that was elicited by 4 seconds of electrical stimulation to primate sensory cortex. The software developed by Haglund and Hochman (2007) finds the envelope around a burst of spikes and calculates the duration of the burst, the number of spikes within the burst, and the average spike amplitude of all spikes comprising the burst.

FIG. 13B depicts a typical spike generated by an acute bicuculline focus in primate motor cortex. The bicuculline model generates epileptiform activity that is similar to spontaneous interictal spiking in human subjects. Analysis of the data by the software identifies the time of occurrence of each spike and its peak-to-peak amplitude. This software can automatically process entire data sets consisting of hours of recorded data from multiple traces and generate an output of the data. Statistical analysis of data sets from multiple experiments can then be used to analyze the effects of various treatments (e.g., compounds that suppress epliptiform activity). See Haglund and Hochman (2007) "Imaging of Intrinsic Optical Signals in Primate Cortex during Epileptiform Activity." Epilepsia 48(Suppl. 4): 65-74; See also Haglund and Hochman (Feb. 23, 2005) J. Neurophysiol. 94: 907-918.

Furosemide Blocks Spontaneous Interictal Spiking in Human Subjects

Figure 14:
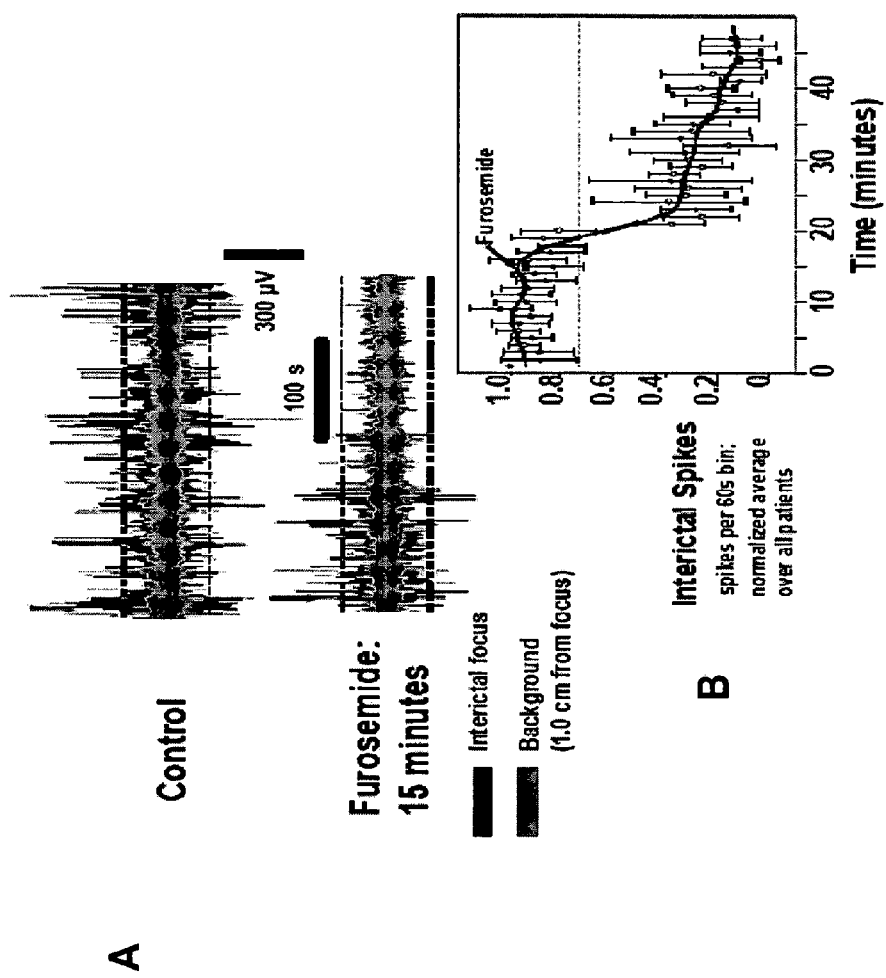
FIG. 14A-B shows that furosemide blocks spontaneous interictal spiking in human subjects. See Haglund and Hochman (Feb. 23, 2005) *J. Neurophysiol.* 94: 907-918.

The data in FIG. 14 were analyzed using the methods described herein. FIG. 14A show data from an individual patient to illustrate the changes in spontaneous interictal spiking following furosemide administration (FIG. 14B). The electrophysiological activity shown was recorded from EEG electrodes placed on the cortical surface (parahippocampal gyrus) before (FIG. 14A) and following administration of a 20 mg intravenous bolus injection of furosemide (FIG. 14B). The darker trace was recorded from an electrode at the interictal focus, and the superimposed lighter trace shows background activity from an electrode 1 cm away. The mean activity of the interictal focus for a 20 minute interval prior to furosemide administration was determined; events that differed from the mean activity by more than 3 standard deviations, indicated by the dashed horizontal lines, were counted as spikes. Furosemide dramatically suppressed the frequency of spontaneous activity within 20 minutes after administration. The arrows on the leftmost side of the traces mark spikes that were plotted at a faster time course (FIG. 14A-B). A graph of the number of spikes occurring per minute averaged over 5 patients treated with furosemide is shown in FIG. 14B, where a smooth cubic-spline curve, fitted through the data, provided a nonparametric estimation based upon the average values. Prior to calculation of the population average values and confidence intervals, the data for each patient was first normalized by dividing by the average pre-furosemide spike-frequency. The black arrow indicates where furosemide was administered; error bars show 0.90 confidence intervals. The average reduction in spiking frequency over these five patients, when comparing the pre-furosemide data to the post-furosemide data, was approximately 60%. It was found that prior to furosemide administration, the average inter-spike interval (i.e., the time between occurrences of consecutive spontaneous interictal spikes that were at least 3 standard deviations from the mean voltage) of the data pooled over all five patients was 9.6 s with the 99% confidence interval (CI) of [7.9 s, 11.3 s] and a standard error of the mean (SEM) of 0.65. Following furosemide treatment, the mean interspike interval was increased to 21.9 s (99% CI=[11.8 s, 31.9s]; SEM=3.9). A t-test of the means of interspike intervals occurring before and after furosemide treatment rejected the null hypothesis that the treatment had no effect (p<0.0001). Spontaneous spiking was more dramatically suppressed in all patients, and completely blocked in three patients, during the last 5 minutes of the recording session. See Haglund and Hochman (2005) "Furosemide and Mannitol Suppression of Epileptic Activity in the Human Brain." J Neurophysiol 94: 907-918. Therefore, bumetanide, bumetanide prodrugs (analogs), furosemide, and furosemide (analogs) reduce the epileptiform activity that leads to a full epileptic episode.

Figure 15:
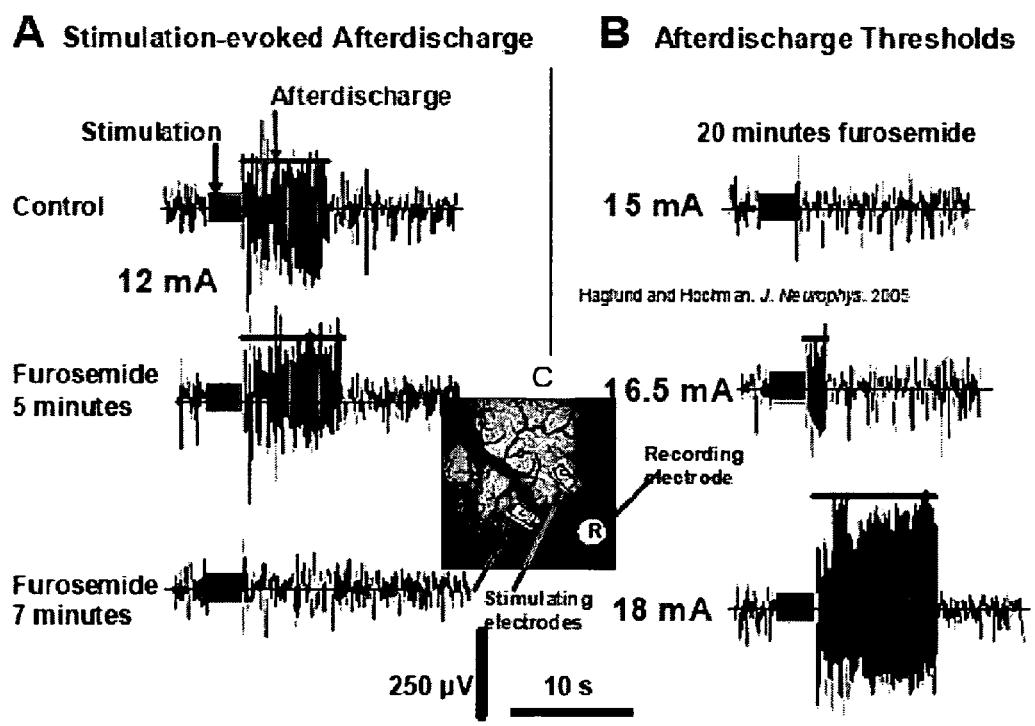
FIGS. 15A-B is a description of the quantification of epileptiform activity.

Furosemide Increases the after-Discharge Threshold in the Cortex of Human Subjects A bipolar stimulating electrode was placed on the cortical surface as shown in FIG. 15C. The distance between the two stimulating electrodes was 5 mm. A recording electrode was placed within 1 cm of the stimulating electrode. A 4-second stimulus (60 Hz; biphasic; 1 ms/phase) was delivered at various currents; the stimulation duration is represented by blue boxes embedded in the beginning of the traces. Prior to furosemide treatment, the minimum current necessary to elicit at least 5 seconds of after-discharge activity in three consecutive trials was determined; this was defined to be the 'after-discharge threshold current' (FIG. 15A). The horizontal bars above each trace mark the episode of after-discharge activity. Following furosemide administration, stimulation trials were performed every 2-5 minutes for the next 40 minutes. In this patient, the after-discharge activity was abruptly blocked soon after furosemide treatment (FIG. 15A, bottom traces). In order to determine whether the blockade of after-discharge activity was mediated by an increase in after-discharge threshold, the stimulation current was incrementally increased (FIG. 15B). It was determined that after-discharge episodes lasting at least as long as those observed during the pre-furosemide trials could be elicited with increased stimulation current. This result suggested that furosemide increased the after-discharge threshold of the cortex. These studies were performed on 8 patients (6 MTE, 2 NE). The furosemide treatment resulted in either a complete blockade (4 patients; 3 MTE; 1 NE) or in a reduction by more than 50% (4 patients; 3 MTE; 1 NE) of the duration and amplitude of the after-discharge activity (FIG. 15A). The average reduction in the duration of stimulation-evoked after-discharge activity over these 8 patients was 85%≤14.6% (SD). In comparing the mean duration of the after-discharge activity before and after furosemide treatment, a Wilcoxon rank-sum test showed significant (p<0.01). Hochman, et al. (Oct. 6, 1995) "Dissociation of Synchronization and Excitability in Furosemide Blockade of Epileptiform Activity." Science 270: 99-102. Therefore, following a seizure (e.g., epileptic episode), Therefore, bumetanide, bumetanide prodrugs (analogs), furosemide, and furosemide (analogs) increase the threshold to lead to a second (e.g., subsequent) epileptic episode. (FIG. 15)

Therefore the compounds described herein may be used in methods to treat and/or prevent (prophylactic) for seizures, seizure disorders, epilepsy, epileptic seizures, and other neurodegenerative disorders (e.g., those neurodegenerative disorders which involve seizures). In particular, the compounds described herein are used in a method for treating seizures, seizure disorders, epilepsy, epileptic seizures, and other neurodegenerative disorders, wherein said neurodegenerative disorders involve seizures, comprising administering an effective amount of an analog (including prodrugs) of bumetanide, furosemide, piretanide, azosemide, and torsemide described herein.

EXAMPLE 145

Selected Bumetanide, Furosemide, Piretanide, Azosemide, and Torsemide Analogs Inhibit Hippocampal Discharges in Mouse Model of Mesial Temporal Lobe Epilepsy (MTLE)

Mesial Temporal Lobe Epilepsy

Mesial temporal lobe epilepsy is the most common form of human epilepsy, and its pathophysiological substrate is usually hippocampal sclerosis, the most common epileptogenic lesion encountered in patients with epilepsy. The disabling seizures associated with mesial temporal lobe epilepsy are typically resistant to antiepileptic drugs but can be abolished in most patients by surgical treatment. Anteromesial temporal resection; therefore, is the most common surgical procedure performed to treat epilepsy, and stereotactically implanted intracerebral electrodes are required in some patients to localize the epileptogenic region. Engel (2001) "Mesial Temporal Lobe Epilepsy: What Have We Learned?". The Neuroscientist 7(4): 340-352.

Intrahippocampal injection of kainic acid in adult mice reproduces most of the morphological characteristics of hippocampal sclerosis (neuronal loss, gliosis, reorganization of neurotransmitter receptors, mossy fiber sprouting, granule cell dispersion) observed in patients with temporal lobe epilepsy. Whereas some neuronal loss is observed immediately after the initial status epilepticus induced by kainate treatment, most reorganization processes develop progressively over a period of several weeks and animals develop spontaneous seizures indicative of epilepsy.

Intrahippocampal electroencephalographic recordings showed three distinct phases of paroxystic activity following unilateral injection of kainic acid (1 nmol in 50 nl) into the dorsal hippocampus of adult mice: (i) a non-convulsive status epilepticus, (ii) a latent phase lasting approximately 2 weeks, during which no organized activity was recorded, and (iii) a phase of chronic seizure activity with recurrent hippocampal paroxysmal discharges characterized by high amplitude sharp wave onset. These recurrent seizures were first seen about 2 weeks post injection. They were limited to the injected area and were not observed in the cerebral cortex, contralateral hippocampus or ipsilateral amygdala. Secondary propagation to the contralateral hippocampus and to the cerebral cortex was rare. In addition hippocampal paroxysmal discharges were not responsive to acute carbamazepine, phenytoin, or valproate treatment, but could be suppressed by diazepam. Riban, et al. (2002) "Evolution of hippocampal epileptic activity during the development of hippocampal sclerosis in a mouse model of temporal lobe epilepsy." Neuroscience 270: 99-102, the disclosure of which is hereby incorporated by reference in its entirety.

Mouse Model of Mesial Temporal Lobe Epilepsy

Antiepileptic protocol: Up to eight adult mice (C57/B16) are injected with kainate (1 nmol in 50 nl) and are implanted with a bipolar electrode in the dorsal hippocampus using stereotaxic techniques under general anesthesia. Between 3 and 7 weeks following KA injection, they are injected with bumetanide or furosemide drugs or vehicle controls in a random order (one week between two injections). Drug conditions are counter-balanced, the animals being used as their own controls. Digital EEG recordings are performed in freely moving animals for 20 min pre-injection and 80 min post-injection. The effects of the injected compound are compared versus vehicle injections and reference period (pre-dose). Upon completion of the experiment, standard histological analysis are performed to verify electrode location, cell losses in CA1, CA3 and hilus, as well as dentate gyrus dispersion. Only animals with all characteristics of MTLE are used in data analysis. Bumetanide, furosemide, piretanide, azosemide, and torsemide esters and amide analogs decreased the cumulative duration and number of hippocampal discharges in this model of mesial temporal lobe epilepsy (e.g., NTP-2014, NTP-2026, NTP-2024, NTP-2006, NTP-1007, and NTP-1003). The results below are normalized to the pre-dose condition for each of the treatment group including DMSO and saline vehicle controls. Doses of test article compounds were 50 mg/kg for NTP-2014 and NTP-2026 and 150 mg/kg for NTP-2024, NTP-2006, NTP-1007, and NTP-1003. See FIGS. 30 and 31. Therefore the bumetanide, furosemide, piretanide, azosemide, and torsemide esters and amide analogs described herein may be used in therapeutic methods to treat seizures.

EXAMPLE 146

Selected Bumetanide, Furosemide, Piretanide, Azosemide, and Torsemide Analogs for Analgesic/Anti-Inflammatory Activity in the Formalin Paw Test (Late Phase) in the Mouse Formalin Paw Test (Late Phase) in the Mouse The method described herein detects analgesic/anti-inflammatory activity, generally used to test compounds for pain relief, in particular diabetic neuropathy or nociceptive neuropathy. See Wheeler-Aceto, et al. (1991) Psychopharmacology 104: 35-44.

Methods

Mice were given an intraplantar injection of 5% formalin (25 µl) into the posterior left paw. This treatment induces paw licking in control animals. Mice were briefly observed at 1 minute intervals between 15 and 50 minutes after the injection of formalin and the number of occasions that the mice were observed licking the injected paw was recorded. There were 10 mice per group and the test was performed "blind."

Figure 16:
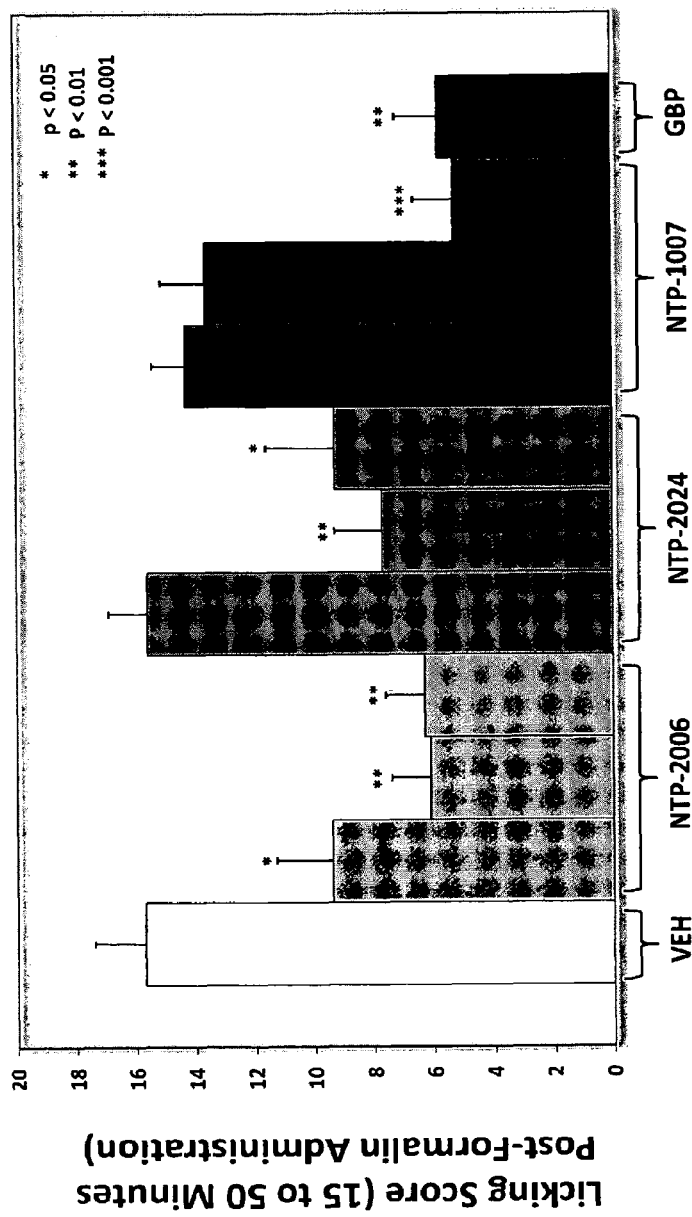
FIG. 16 shows the results of a formalin paw test where analogs of bumetanide, furosemide, piretanide, azosemide, and torsemide NTP-2006, NTP-2024, and NTP-1007 all show anti-inflammatory and analgesic effects in a model of neuropathic pain. VEH=Vehicle; NTP-2006, NTP-2024, and NTP-1007 were administered in three doses: 50 µmole/kg (23 mg/kg for NTP-2006; 21 mg/kg for NTP-2024; and 19 mg/kg for NTP-1007); 250 mole/kg (119 mg/kg for NTP-2006; 108 mg/kg for NTP-2024; and 217 mg/kg for NTP-1007); and 500 µmoles/kg (239 mg/kg for NTP-2006; 217 mg/kg for NTP-2024; and 193 mg/kg for NTP-1007). GBP=gabapentin which was administered at 584 µmole/kg (100 mg/kg). (* $p<0.05$) ( $p<0.01$) (* $p<0.001$)

Bumetanide analogs (e.g., NTP-2006, NTP-2024) and furosemide analog (e.g., NTP-1007) were evaluated at 3 doses each, administered i.p. 30 minutes before the test (i.e., 15 minutes before formalin), and compared with a common vehicle control group. Morphine (8 mg/kg i.p.) or gabapentin (100 mg/kg i.p.) or venlafaxine (32 mg/kg i.p.), administered under the same experimental conditions, were used as reference substance. The experiment included 11 groups. Data was analyzed by comparing treated groups with vehicle control using unpaired Mann-Whitney U tests. See FIG. 16.

Species Used

Male Rj: NMRI mice, weighing 20-30 g (max. range per experiment=5 g) at the beginning of the experiments, obtained from Elevage Janvier, 53940 Le Genest-Saint-Isle, France.

Animal Housing

Mice were housed in groups of 10 in macrolon cages (25×19×13 cm) on wood litter (Litalabo—SPPS, 95100 Argenteuil, France) with free access to food (Code 113—SAFE, 89290 Augy, France) and water until tested (or as indicated otherwise). The animal house was maintained under artificial lighting (12 hours) between 7:00 and 19:00 in a controlled ambient temperature of 21 t 3° C., and relative humidity between 30-80%.

Sacrifice

Mice were sacrificed at the end of the experiments by exposure to a mixture of $O_2/CO_2$ (20%/80%) followed by $CO_2$, except as indicated otherwise in Experimental Procedure.

TABLE 14

| Compound | Molar Dose (µmol/kg) | mg/kg Dose |
|---|---|---|
| NTP-2006 | 50 | 23.9 |
|  | 250 | 119 |
|  | 500 | 239 |
| NTP-2024 | 50 | 21.7 |
|  | 250 | 108 |
|  | 500 | 217 |
| NTP-1007 | 50 | 19.3 |
|  | 250 | 96.5 |
|  | 500 | 193 |

TABLE 15

| Treatment | | | Licking Score (15 to 50 minutes post-formalin injection) | |
|---|---|---|---|---|
|  | mg/kg | µmol/kg | % Change from Control | % Pain Decrease |
| NTP-2006 | 23.9 | 50 | −40 | 40.0 |
|  | 119 | 250 | −61 | 61 |
|  | 239 | 500 | −60 | 60 |
| NTP-2024 | 21.7 | 50 | −1 | 1 |
|  | 108 | 250 | −51 | 51 |
|  | 217 | 500 | −41 | 41 |
| NTP-1007 | 19.3 | 50 | −9 | 9 |
|  | 96.5 | 250 | −13 | 13 |
|  | 193 | 500 | −66 | 66 |
| Gabapentin | 100 | 584 | −63 | 63 |
| Vehicle Control | — | — | — | 1 |

The data recorded for each animal is the amount of time(s) spent licking the affected hind paw in a two minute period. These two minute periods occur at five minute intervals and continue for 45 minutes. Plotting the time spent licking versus time reveals the characteristic biphasic response. From this plot, the area under the curve (AUC) for each animal during both the acute and inflammatory stages was calculated. The AUC for each phase is shown for both control and drug-treated animals. The AUC for each drug-treated animal is compared to the average result from the control group, yielding an average percent of control (reported with the SEM and p value). Significant reductions in this number indicate a reduction in licking and a reduction of perceived pain.

Therefore the compounds described herein may be used in methods to treat and/or prevent (prophylactic) for pain (e.g., neuropathic pain, and in further embodiments the neuropathic pain is associated with a nerve or tract injury or is somatic and/or visceral pain. In yet another embodiment, the pain is chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, postherpetic neuralgia, AIDS-related pain, complex regional pain syndromes type I and II, trigeminal neuralgia, chronic back pain, pain associated with spinal cord injury and/or recurrent acute pain). In particular, the compounds described herein are used in a method for treating pain (e.g., neuropathic pain, and in further embodiments the neuropathic pain is associated with a nerve or tract injury or is somatic and/or visceral pain. In yet another embodiment, the pain is chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, postherpetic neuralgia, AIDS-related pain, complex regional pain syndromes type I and II, trigeminal neuralgia, chronic back pain, pain associated with spinal cord injury and/or recurrent acute pain), comprising administering an effective amount of analog (including prodrugs) of bumetanide, furosemide, piretanide, azosemide, and torsemide described herein.

EXAMPLE 147

Selected Bumetanide Analogs for Analgesic/Anti-Inflammatory Activity in a Formalin Paw Test in Mice Formalin Test The formalin test was performed according to the method of Tjølsen, et al. (October 1992) "The formalin test: an evaluation of the method." Pain 51(1): 5-17. An injection of 0.5% formalin is made into the plantar region of the right hind paw of a mouse. This elicits a distinct behavioral profile in response to the formalin injection characterized by the mouse licking the affected paw. The behavior is characteristically biphasic in nature. For example, immediately following the injection the mouse intensely licks the paw for approximately 5-10 minutes ("min.") This initial behavior was considered phase 1 (acute) and is thought to be mediated primarily by chemical activation of local C-fibers. The acute phase is followed by a brief latent (usually <5 min) period where there is little or no behavioral activity. A more prolonged (about 20 to 30 min) period of licking then ensues which constitutes phase 2 of the response (late phase). See e.g., Tjølsen, et al. (Feb. 7, 1991) "Antinociceptive effect of paracetamol in rats is partly dependent on spinal serotonergic systems. Eur J Pharmacol. 193(2): 193-201 and Tjølsen, et al. (June 1991) Lesions of bulbo-spinal serotonergic or noradrenergic pathways reduce nociception as measured by the formalin test. Acta Physiol Scand. 142(2): 229-36, the disclosures of each of which are hereby incorporated by reference in its entirety.

Prior to the administration of one of the selected bumetanide analogs (e.g., NTP-2008, NTP-2011, NTP-2012, NTP-2024) or vehicle, each mouse underwent a 15-min conditioning period in one of several 6" tall Plexiglas cages (4" diameter) that are placed in front of a mirror. It is in these tubes that mice are later observed for the licking activity for the duration of the experiment. Following the conditioning, the test substance was administered i.p. in a dose equivalent to the MES ED50 and the mouse returned to its home tube. At the TPE of the drug, the formalin is injected subdermally into the plantar surface of the right hind foot. It is given in a volume of 20 μl with a 27 gauge stainless steel needle attached to a Hamilton syringe. The bevel of the needle was placed facing down toward the skin surface. Following the injection of the formalin each animal was observed for the first 2 min of 5-min epochs until 45 min have elapsed since the administration of the one of the selected bumetanide analogs (e.g., NTP-2008, NTP-2011, NTP-2012, NTP-2024). The cumulative length of licking for each 2-min time period was measured. An animal receiving the requisite volume of vehicle was alternated with each mouse given one of the selected bumetanide analogs (e.g., NTP-2008, NTP-2011, NTP-2012, and NTP-2024). Animals are euthanized following the conclusion of the experiment.

Area under the curve (AUC) and subsequent percent of control for drug-treated animal groups is determined using the GraphPad Prism Version 3.03. Total AUC was calculated for both the test and control groups for both the acute and inflammatory phases. The AUC for individual animals for each phase was also calculated and converted to percentage of total AUC of control. The average and S.E.M. for both the drug treated and control percentages were calculated and tested for significant difference.

TABLE 16

| Bumetanide Analog | Dose (mg/kg) | Test | Control | Treated | % of Control | S.E.M. | p Value |
|---|---|---|---|---|---|---|---|
| NTP-2008 | 150 | Acute | 116.1 | 73.94 | 63.69 | 9.09 | >0.05 |
| | 150 | Late Phase | 623.3 | 66.42 | 10.66 | 4.22 | <0.01 |
| NTP-2011 | 150 | Acute | 147.2 | 78.55 | 53.37 | 10.51 | <0.05 |
| | 150 | Late Phase | 752.2 | 5.43 | 0.72 | 0.72 | <0.01 |
| NTP-2012 | 150 | Acute | 154.8 | 75.07 | 48.5 | 4.05 | <0.01 |
| | 150 | Late Phase | 514.5 | 5.08 | 0.49 | 0.26 | <0.01 |
| NTP-2024 | 150 | Acute | 136.7 | 80.03 | 58.55 | 9.65 | <0.05 |
| | 150 | Late Phase | 609.4 | 76.39 | 12.54 | 4.38 | <0.01 |

Therefore bumetande and bumetanide analogs may be used in methods to treat and/or prevent (prophylactic) for pain (e.g., neuropathic pain, and in further embodiments the neuropathic pain is associated with a nerve or tract injury or is somatic and/or visceral pain. In yet another embodiment, the pain is chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, postherpetic neuralgia, AIDS-related pain, complex regional pain syndromes type I and II, trigeminal neuralgia, chronic back pain, pain associated with spinal cord injury and/or recurrent acute pain). In particular, the compounds described herein are used in a method for treating pain (e.g., neuropathic pain, and in further embodiments the neuropathic pain is associated with a nerve or tract injury or is somatic and/or visceral pain. In yet another embodiment, the pain is chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, postherpetic neuralgia, AIDS-related pain, complex regional pain syndromes type I and II, trigeminal neuralgia, chronic back pain, pain associated with spinal cord injury and/or recurrent acute pain), comprising administering an effective amount of a bumetanide, a bumetanide analog (prodrug), furosemide, and/or a furosemide analog (prodrug) as well as piretanide and a piretanide analog (prodrug).

EXAMPLE 148

The Effects of Furosemide on Epileptiform Discharges in Hippocampal Slices

During these studies, spontaneous epileptiform activity was elicited by a variety of treatments. Sprague-Dawley rats (males and females; 25-35 days old) were decapitated, the top of the skull was rapidly removed, and the brain chilled with ice-cold oxygenated slicing medium. The slicing medium was a sucrose-based artificial cerebrospinal fluid (sACSF) consisting of 220 mM sucrose, 3 mM KCl, 1.25 mM $NaH_2PO_4$, 2 mM $MgSO_4$, 26 mM $NaHCO_3$, 2 mM $CaCl_2$, and 10 mM dextrose (295-305 mOsm). A hemisphere of brain containing hippocampus was blocked and glued (cyanoacrylic adhesive) to the stage of a Vibroslicer (Frederick Haer, Brunsick, Me.). Horizontal or transverse slices 400 μm thick were cut in 4° C., oxygenated (95% $O_2$; 5% $CO_2$) slicing medium. The slices were immediately transferred to a holding chamber where they remained submerged in oxygenated bathing medium (ACSF) consisting of 124 mM NaCl, 3 mM KCl, 1.25 mM $NaH_2PO_4$, 2 mM $MgSO_4$, 26 mM $NaHCO_3$, 2 mM $CaCl_2$, and 10 mM dextrose (295-305 mOsm). The slices were held at room temperature for at least 45 minutes before being transferred to a submersion-style recording chamber (all other experiments). In the recording chamber, the slices were perfused with oxygenated recording medium at 34-35° C. All animal procedures were conducted in accordance with NIH and University of Washington animal care guidelines.

In most slice experiments, simultaneous extracellular field electrode recordings were obtained from CA1 and CA3 areas. A bipolar tungsten stimulating electrode was placed on the Schaffer collaterals to evoke synaptically-driven field responses in CA1. Stimuli consisted of 100-300 μsec duration pulses at an intensity of four times the population-spike threshold. After discharges were evoked by a 2 second train of such stimuli delivered at 60 Hz. Spontaneous interictal-like bursts were observed in slices treated by the following modifications or additions to the bathing medium: 10 mM potassium (6 slices; 4 animals; average—81 bursts/min.); 200-300 μM 4-aminopyridine (4 slices; 2 animals; average—33 burst/min.); 50-100 μM bicuculline (4 slices; 3 animals; average—14 bursts/min); [INSERT AMOUNT OF Mg used in Example 1 of U.S. Pat. No. 7,214,711] $Mg^+$ (1 hour of perfusion—3 slices; 2 animals; average—20 bursts/min. or 3 hours of perfusion—2 slices; 2 animals); zero calcium/6 mM KCl and 2 mM EDTA (4 slices; 3 animals). In all treatments, furosemide was added to the recording medium once a consistent level of bursting was established.

Figure 17A:
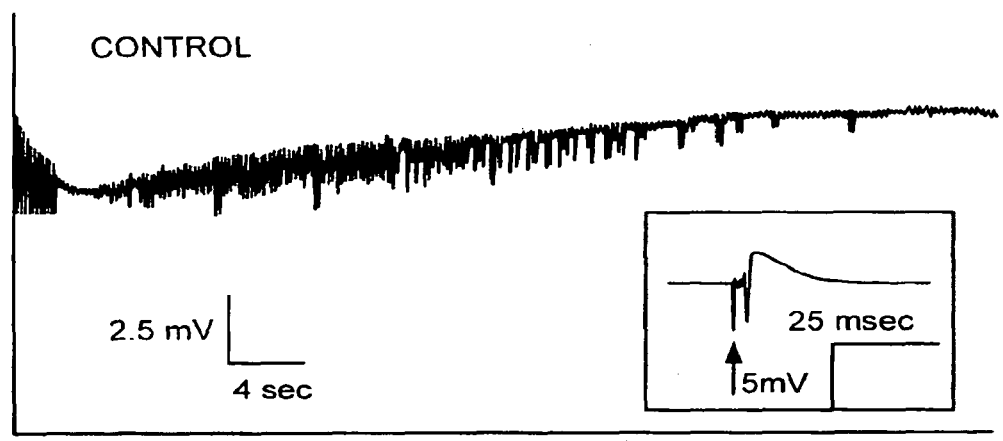
FIG. 17 A-G show the effect of furosemide on stimulation evoked after discharge activity in rat hippocampal slices.

In the first of these procedures, episodes of after discharges were evoked by electrical stimulation of the Schaffer collaterals (Stasheff et al., Brain Res. 344:296, 1985) and the extracellular field response was monitored in the CA1 pyramidal cell region (13 slices; 8 animals). The concentration of Mg in the bathing medium was reduced to 0.9 mM and after discharges were evoked by stimulation at 60 Hz for 2 seconds at an intensity 4 times the population spike threshold (population spike threshold intensity varied between 20-150 μA at 100-300 μsec pulse duration). The tissue was allowed to recover for 10 minutes between stimulation trials. In each experiment, the initial response of CA1 to synaptic input was first tested by recording the field potential evoked by a single stimulus pulse. In the control condition, Schaffer collateral stimulation evoked a single population spike (FIG. 17A, inset). Tetanic stimulation evoked approximately 30 seconds after discharge (FIG. 17A, left) associated with a large change in intrinsic signal (FIG. 17A, right).

For imaging of intrinsic optical signals, the tissue was placed in a perfusion chamber located on the stage of an upright microscope and illuminated with a beam of white light (tungsten filament light and lens system; Dedo Inc.) directed through the microscope condenser. The light was controlled and regulated (power supply—Lamda Inc.) to minimize fluctuations and filtered (695 nm longpass) so that the slice was transilluminated with long wavelengths (red). Field of view and magnification were determined by the choice of microscope objectives (4× for monitoring the entire slice). Image-frames were acquired with: a charge-coupled device (CCD) camera (Dage MTI Inc.) at 30 HZ and were digitized at 8 bits with a spatial resolution of 512×480 pixels using an Imaging Technology Inc. Series 151 imaging system; gains and offsets of the camera-control box and the A/D board were adjusted to optimize the sensitivity of the system. Imaging hardware was controlled by a 486-PC compatible computer. To increase signal/noise, an averaged-image was composed from 16 individual image-frames, integrated over 0.5 sec and averaged together. An experimental series typically involved the continuous acquisition of a series of averaged-images over a several minute time period; at least 10 of these averaged-images were acquired as control-images prior o stimulation. Pseudocolored images were calculated by subtracting the first control-image from subsequently acquired images and assigning a color lookup table to the pixel values. For these images, usually a linear low-pass filter was used to remove high frequency noise and a linear-histogram stretch was used to map the pixel values over the dynamic range of the system. All operations on these images were linear so that quantitative information was preserved. Noise was defined as the maximum standard deviation of fluctuations of AR/R of the sequence of control images within a given acquisition series, where AR/R represented the magnitude of the change in light-transmission through the tissue. Delta R/R was calculated by taking all the difference-images and dividing by the first control image: (subsequent image-first-control-image)/first-control-image. The noise was always <0.01 for each of the chosen image sequences. The absolute change in light transmission through the tissue was estimated during some experiments by acquiring images after placing neutral density filters between the camera and the light source. On average, the camera electronics and imaging system electronics amplified the signal 10-fold prior to digitization so that the peak absolute changes in light transmission through the tissue were usually between 1% and 2%.

Figure 17B:
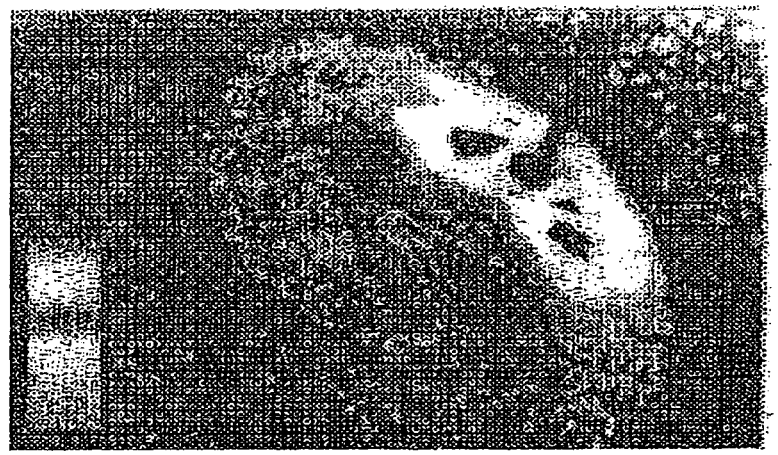
Figure 17C:
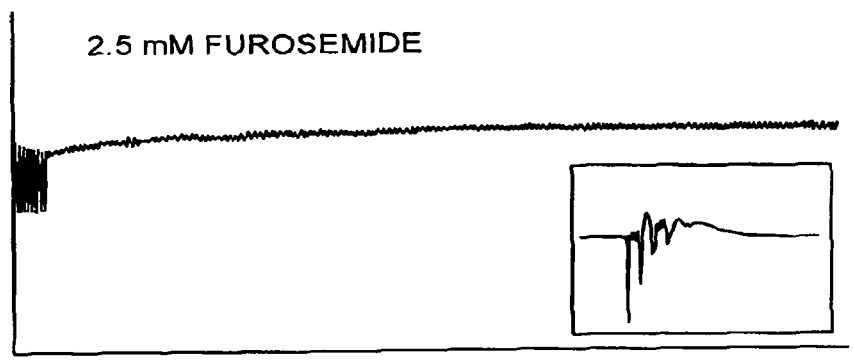
Figure 17D:
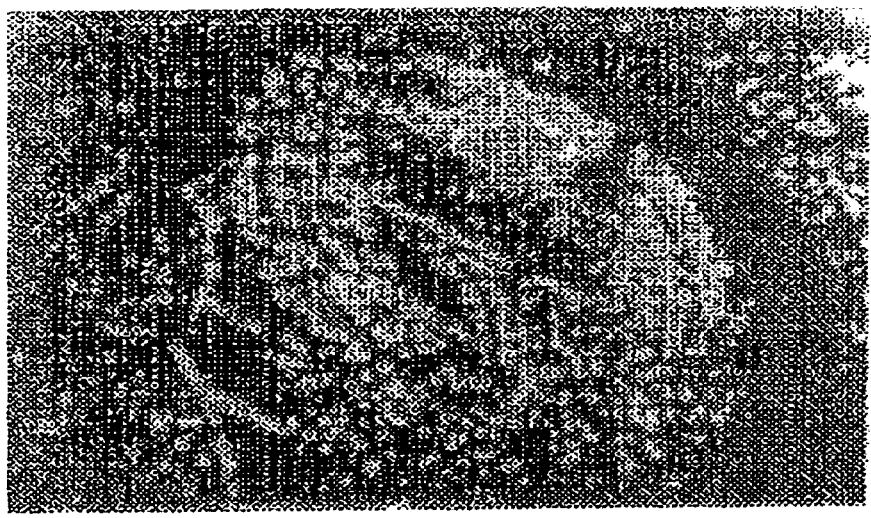
Figure 17E:
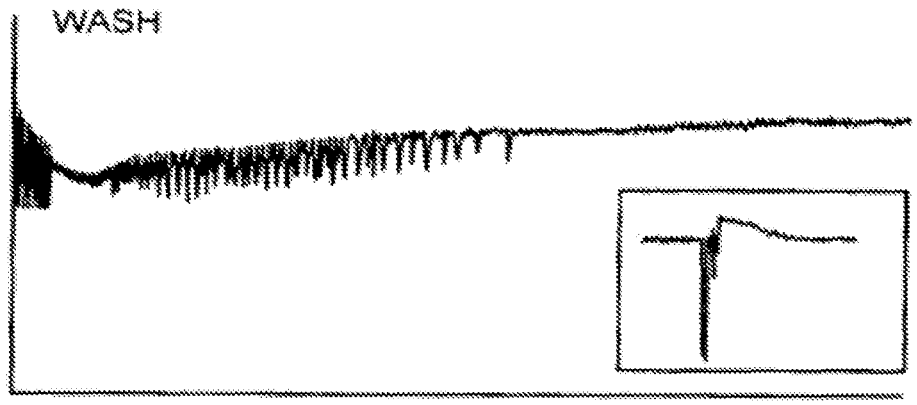
Figure 17F:
Figure 17G:
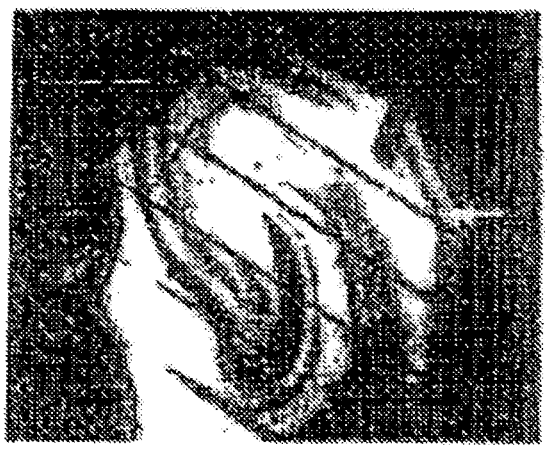

The gray-scale photo shown in FIG. 17D is a video image of a typical hippocampal slice in the recording chamber. The fine gold-wire mesh that was used to hold the tissue in place can be seen as dark lines running diagonally across the slice. A stimulating electrode can be seen in the upper right on the *stratum radiatum* of CA1. The recording electrode (too thin to be seen in the photo) was inserted at the point indicated by the white arrow. FIG. 17A illustrates that two seconds of stimulation at 60 Hz elicited after discharge activity and shows a typical after discharge episode recorded by the extracellular electrode. The inset of FIG. 17A shows the CA1 field response to a single 200 sec test pulse (artifact at arrow) delivered to the Schaffer collaterals. FIG. 17B shows a map of the peak change in optical transmission through the tissue evoked by Schaffer collateral stimulation. The region of maximum optical change corresponds to the apical and basal dendritic regions of CA1 on either side of the stimulating electrode. FIG. 17C illustrates sample traces showing responses to stimulation after 20 minutes of perfusion with medium containing 2.5 mM furosemide. Both the electrical after discharge activity (shown in FIG. 17C) and the stimulation-evoked optical changes (shown in FIG. 17D) were blocked. However, there was a hyper-excitable field response (multiple population spikes) to the test pulse (inset). FIGS. 17E and 17F illustrate that restoration of initial response patterns was seen after 45 minutes of perfusion with normal bathing medium.

The opposing effects of furosemide-blockade of the stimulation-evoked after discharges and a concomitant increase of the synaptic response to a test-pulse illustrate the two key results: (1) furosemide blocked epileptiform activity, and (2) synchronization (as reflected by spontaneous epileptiform activity) and excitability (as reflected by the response to a single synaptic input) were dissociated. Experiments in which the dose-dependency of furosemide was examined determined that a minimum concentration of 1.25 mM was required to block both the after discharges and optical changes.

Other compounds, including the analogs and prodrugs, of bumetanide, furosemide, piretanide, azosemide, and torsemide described herein can be expected to have similar effects. The compounds (including analogs and prodrugs) described herein may be used in methods to treat and/or prevent (prophylactic) for seizures, seizure disorders, epilepsy, epileptic seizures, and other neurodegenerative disorders (e.g., those neurodegenerative disorders which involve seizures). In particular, the compounds described herein are used in a method for treating seizures, seizure disorders, epilepsy, epileptic seizures, and other neurodegenerative disorders, wherein said neurodegenerative disorders involve seizures, comprising administering an effective amount of an analog (including prodrugs) of bumetanide, furosemide, piretanide, azosemide, and torsemide described herein.

EXAMPLE 149

Figure 18:
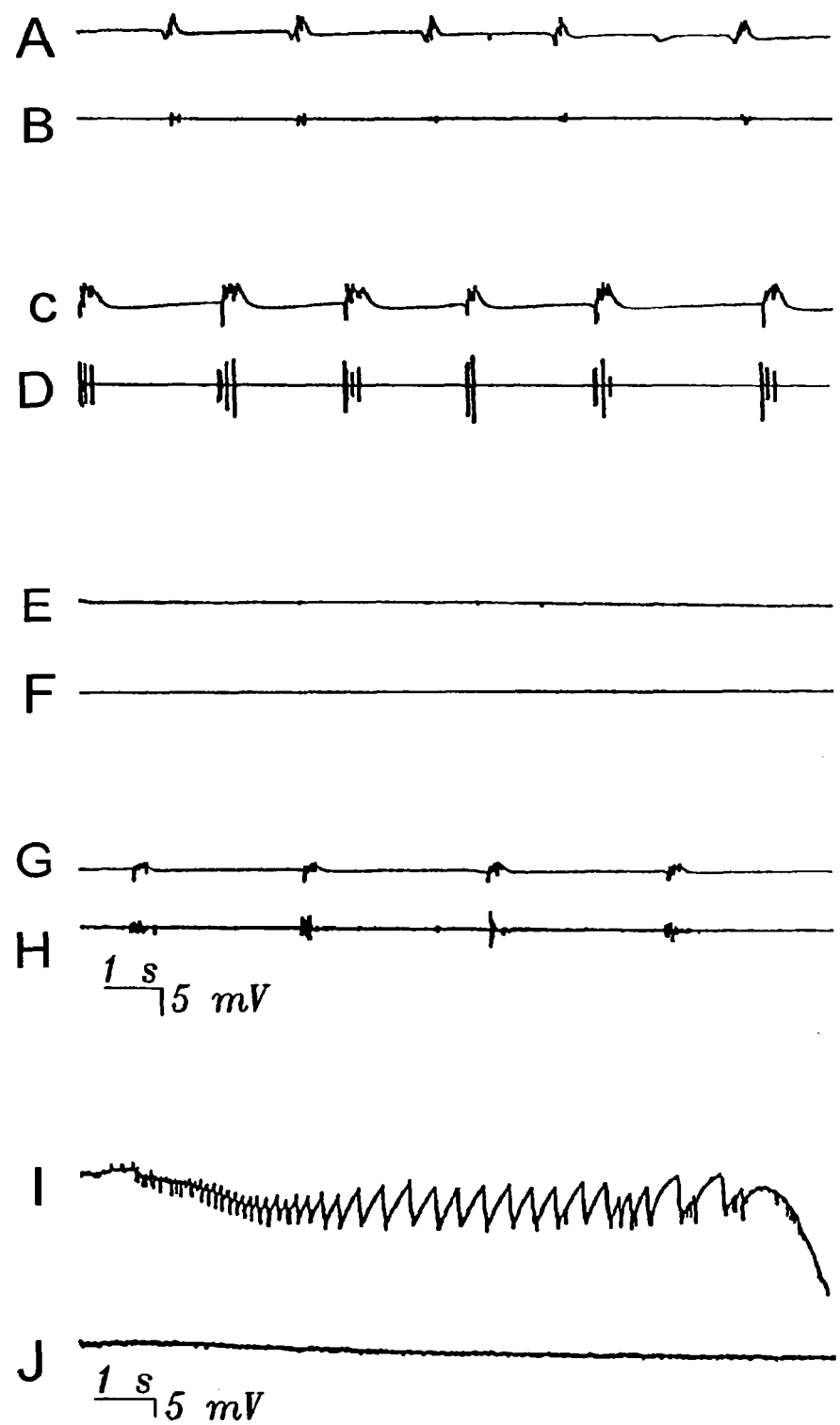
FIG. 18A-R show furosemide blockade of spontaneous epileptiform burst discharges across a spectrum of in vitro models.
Figure 18:
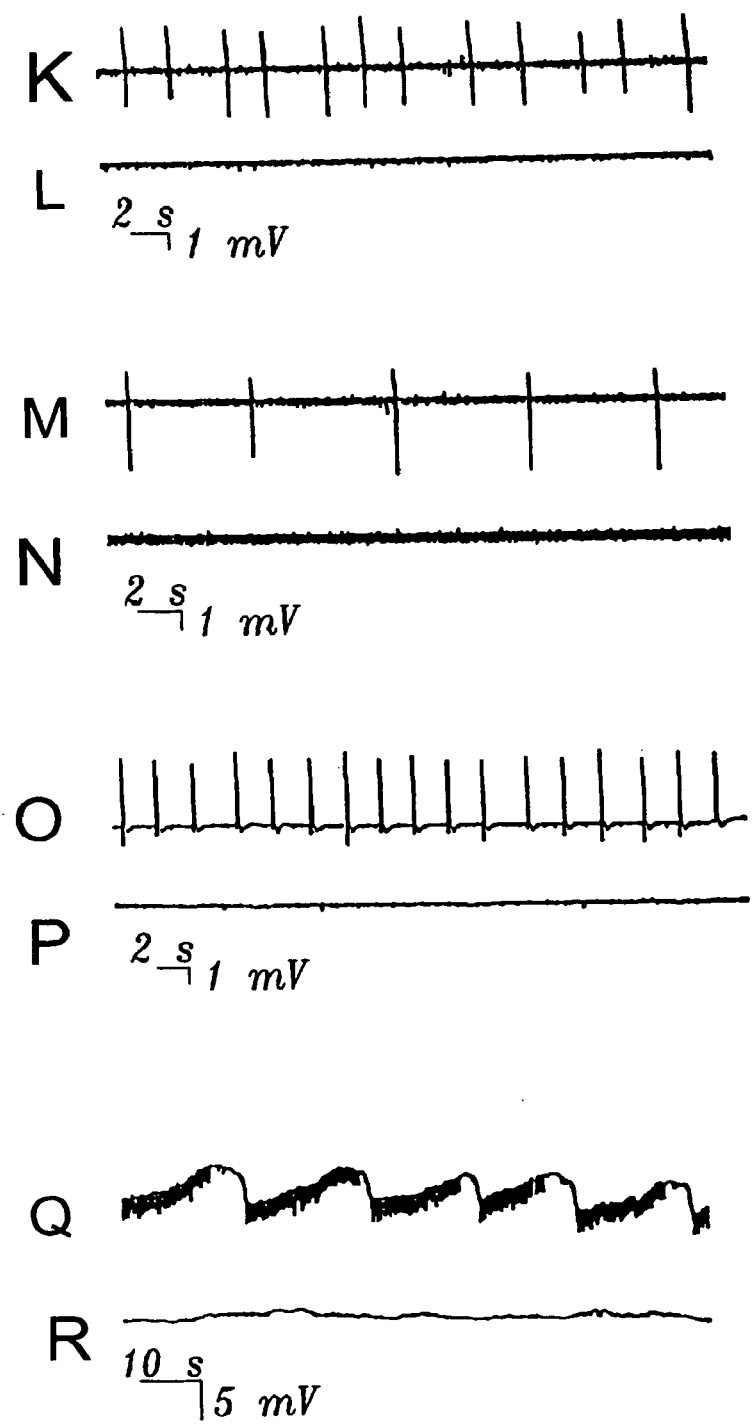

The Effects of Furosemide on Epileptiform Discharges in Hippocampal Slices Perfused with High-$K^+$ (10 mM) Bathing Medium Rat hippocampal slices, prepared as described above, were perfused with a high-$K^+$ solution until extended periods of spontaneous interictal-like bursting were recorded simultaneously in CA3 (top traces) and CA1 (lower traces) pyramidal cell regions (FIGS. 18A and 18B). After 15 minutes of perfusion with furosemide-containing medium (2.5 mM furosemide), the burst discharges increased in magnitude (FIGS. 18C and 18D). However, after 45 minutes of furosemide perfusion, the bursts were blocked in a reversible manner (FIGS. 18E, 18F, 18G and 18H). During this entire sequence of furosemide perfusion, the synaptic response to a single test pulse delivered to the Schaffer collaterals was either unchanged or enhanced (data not shown). It is possible that the initial increase in discharge amplitude reflected a furosemide-induced decrease in inhibition. Misgeld, et al. (1986) Science 232:1413; Thompson, et al. (1988) J. Neurophysiol. 60:105; Thompson and Gahwiler (1989) J. Neuropysiol. 61:512; and Pearce (1993) Neuron 10:189. Furosemide blocks a component of the inhibitory currents in hippocampal slices with a latency (<15 min) similar to the time to onset of the increased excitability observed here. See also Pearce (1993) Neuron 10: 189. The longer latency required for the furosemide-block of the spontaneous bursting might correspond to additional time required for a sufficient block of the furosemide-sensitive cellular volume regulation mechanisms under high-$K^+$ conditions.

After testing the effects of furosemide on slices perfused with high-$K^+$, similar studies were performed with a variety of other commonly studied in vitro models of epileptiform discharge. Galvan, et al. (1982) Brain Res. 241:75; Schwartzkroin and Prince (1980) Brain Res. 183:61; Anderson, et al. (1986) Brain Res. 398:215; and Zhang, et al. (1995) Epilepsy Res. 20:105, each of which is hereby incorporated by reference in its entirety. After prolonged exposure (2-3 hours) to magnesium-free medium (0-$Mg^+$), slices have been shown to develop epileptiform discharges that are resistant to common clinically used anticonvulsant drugs. Zhang, et al. (1995) Epilepsy Res. 20:105, incorporated by reference in its entirety. Recordings from entorhinal cortex (FIG. 18I) and subiculum (not shown) showed that after 3 hours of perfusion with 0-$Mg^+$+ medium, slices developed bursting patterns that appeared similar to these previously described "anticonvulsant resistant" bursts. One hour after the addition of furosemide to the bathing medium, these bursts were blocked (FIG. 18J). Furosemide also blocked spontaneous burst discharges observed with the following additions/modifications to the bathing medium: (1) addition of 200-300 µM 4-aminopyridine (4-AP; a potassium channel blocker) (FIGS. 18K and 18L); (2) addition of the GABA antagonist, bicuculline, at 50-100 µM (FIGS. 18M and 18N); (3) removal of magnesium (0-$Mg^+$)—1 hours perfusion (FIGS. 18O and 18P); and (4) removal of calcium plus extracellular chelation (0-$Ca^2$) (FIGS. 18Q and 18R). With each of these manipulations, spontaneous interictal-like patterns were simultaneously recorded from CA1 and CA3 subfields (FIGS. 18K, 18L, 18M, and 18N show only the CA3 trace and FIGS. 18O, 18P, 18Q, and 18R show only the CA1 trace). In the 0-$Ca^{2+}$ experiments, 5 mM furosemide blocked the bursting with a latency of 15-20 minutes. For all other protocols, bursting was blocked by 2.5 mM furosemide with a latency of 20-60 minutes. Furosemide reversibly blocked the spontaneous bursting activity in both CA1 and CA3 in all experiments (FIGS. 18L, 18N, 18P and 18R).

Other compounds, including the analogs and prodrugs, of bumetanide, furosemide, piretanide, azosemide, and torsemide described herein can be expected to have similar effects. The compounds (including analogs and prodrugs) described herein may be used in methods to treat and/or prevent (prophylactic) for seizures, seizure disorders, epilepsy, epileptic seizures, and other neurodegenerative disorders (e.g., those neurodegenerative disorders which involve seizures). In particular, the compounds described herein are used in a method for treating seizures, seizure disorders, epilepsy, epileptic seizures, and other neurodegenerative disorders, wherein said neurodegenerative disorders involve seizures, comprising administering an effective amount of an analog (including prodrugs) of bumetanide, furosemide, piretanide, azosemide, and torsemide described herein.

EXAMPLE 150

The Effects of Furosemide on Epileptiform Activity Induced by i.v. Injection of Kainic Acid in Anesthetized Rats This example illustrates an in vivo model in which epileptiform activity was induced by i.v. injection of kainic acid (KA) into anesthetized rats. Lothman, et al. (1981) Neurology 31:806, incorporated by reference in its entirety. The results are illustrated in FIGS. 3A-3H. Sprague-Dawley rats (4 animals; weights 250-270 g) were anesthetized with urethane (1.25 g/kg i.p.) and anesthesia maintained by additional urethane injections (0.25 g/kg i.p.) as needed. Body temperature was monitored using a rectal temperature probe and maintained at 35-37° C. with a heating pad; heart rate (EKG) was continuously monitored. The jugular vein was cannulated on one side for intravenous drug administration. Rats were placed in a Kopf stereotaxic device (with the top of the skull level), and a bipolar stainless-steel microelectrode insulated to 0.5 mm of the tip was inserted to a depth of 0.5-1.2 mm from the cortical surface to record electroencephalographic (EEG) activity in the fronto-parietal cortex. In some experiments, a 2M NaCl-containing pipette was lowered to a depth of 2.5-3.0 mm to record hippocampal EEG. Data were stored on VHS videotape and analyzed off-line.

Following the surgical preparation and electrode placement, animals were allowed to recover for 30 minutes before the experiments were initiated with an injection of kainic acid (10-12 mg/kg i.v.). Intense seizure activity, an increased heart rate, and rapid movements of the vibrissae were induced with a latency of about 30 minutes. Once stable electrical seizure was evident, furosemide was delivered in 20 mg/kg boluses every 30 minutes to a total of 3 injections. Experiments were terminated with the intravenous administration of urethane. Animal care was in accordance with NIH guidelines and approved by the University of Washington Animal Care Committee.

Figure 19:
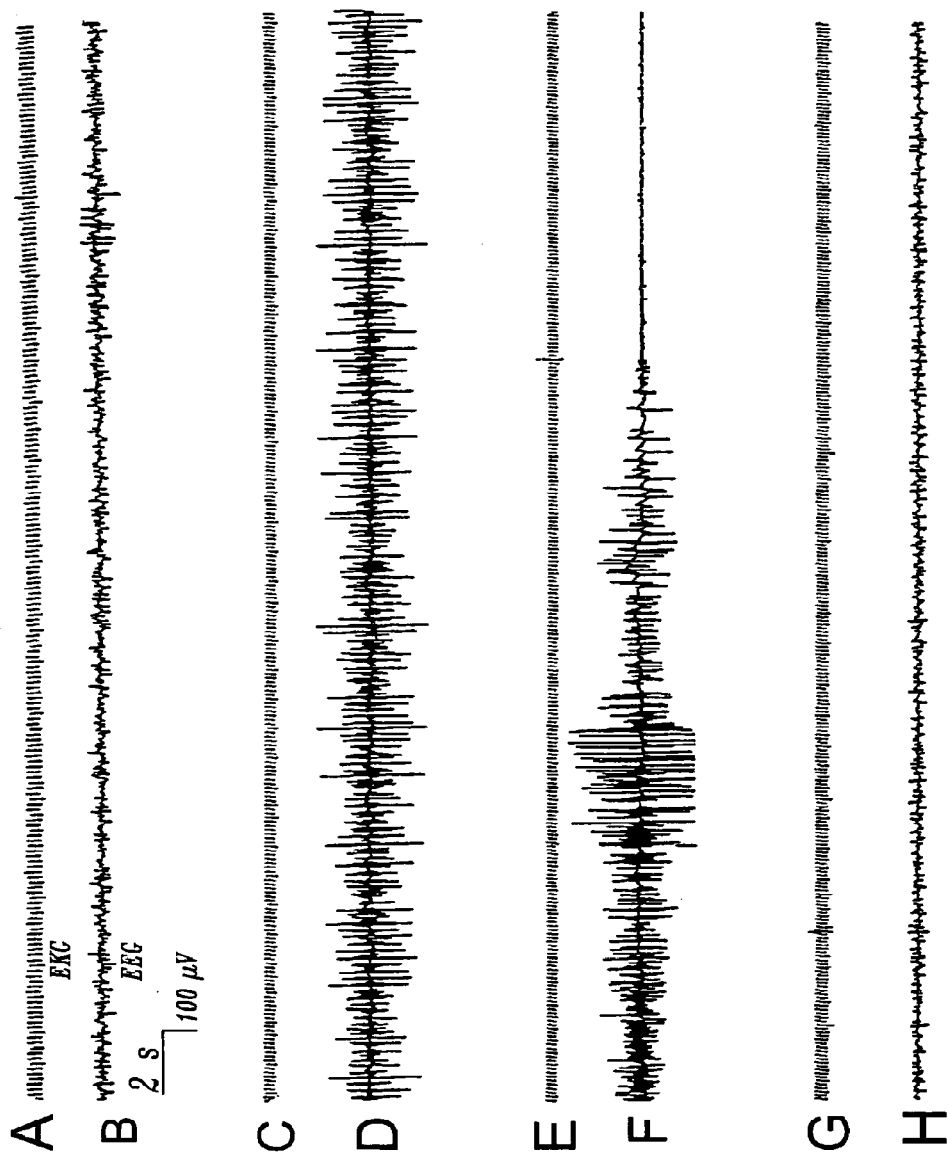
FIG. 19A-H show furosemide blockade of kainic acid-evoked electrical "status epilepticus" in urethane-anesthetized rats, with EKG recordings shown in the upper traces and cortical EEG recordings shown in the bottom traces.

FIGS. 19A-19H show furosemide blockade of kainic acid-evoked electrical "status epilepticus" in urethane-anesthetized rats. EKG recordings are shown as the top traces and EEG recordings are shown as the bottom traces. In this model, intense electrical discharge (electrical "status epilepticus") was recorded from the cortex (or from depth hippocampal electrodes) 30-60 minutes after KA injection (10-12 mg/kg) (FIGS. 19C and 19D). Control experiments (and previous reports, Lothman et al., Neurology, 31:806, 1981) showed that this status-like activity was maintained for well over 3 hours. Subsequent intravenous injections of furosemide (cumulative dose: 40-60 mg/kg) blocked seizure activity with a latency of 30-45 minutes, often producing a relatively flat EEG (FIGS. 19E, 19F, 19G and 19H). Even 90 minutes after the furosemide injection, cortical activity remained near normal baseline levels (i.e., that observed prior to the KA and furosemide injections). Studies on the pharmacokinetics of furosemide in the rat indicate that the dosages used in this example were well below toxic levels. Hammarlund and Paalzow (1982) Biopharmaceutics Drug Disposition, 3:345.

Other compounds, including the analogs and prodrugs, of bumetanide, furosemide, piretanide, azosemide, and torsemide described herein can be expected to have similar effects. The compounds (including analogs and prodrugs) described herein may be used in methods to treat and/or prevent (prophylactic) for seizures, seizure disorders, epilepsy, epileptic seizures, and other neurodegenerative disorders (e.g., those neurodegenerative disorders which involve seizures). In particular, the compounds described herein are used in a method for treating seizures, seizure disorders, epilepsy, epileptic seizures, and other neurodegenerative disorders, wherein said neurodegenerative disorders involve seizures, comprising administering an effective amount of an analog (including prodrugs) of bumetanide, furosemide, piretanide, azosemide, and torsemide described herein.

EXAMPLE 151

Timing of Cessation of Spontaneous Epileptiform Bursting in Areas in CA1 and CA3 Experimental Methods Hippocampal slices were prepared from Sprague-Dawley adult rats as described previously. Transverse hippocampal slices 100 μm thick were cut with a vibrating cutter. Slices typically contained the entire hippocampus and subiculum. After cutting, slices were stored in an oxygenated holding chamber at room temperature for at least one hour before recording. All recordings were acquired in an interface type chamber with oxygenated (95% $O_2$, 5% $CO_2$) artificial cerebral spinal fluid (ACSF) at 34°-35° C. Normal ACSF contained (in mmol/l): 124 NaCl, 3 KCl, 1.25 $NaH_2PO_4$, 1.2 $MgSO_4$, 26 $NaHCO_3$, 2 $CaCl_2$, and 10 dextrose.

Sharp-electrodes for intracellular recordings from CA1 and CA3 pyramidal cells were filled with 4 M potassium acetate. Field recordings from the CA1 and CA3 cell body layers were acquired with low-resistance glass electrodes filled with 2 M NaCl. For stimulation of the Schaffer collateral or hilar pathways, a small monopolar tungsten electrode was placed on the surface of the slice. Spontaneous and stimulation-evoked activities from field and intracellular recordings were digitized (Neurocorder, Neurodata Instruments, New York, N.Y.) and stored on videotape. AxoScope software (Axon Instruments) on a personal computer was used for off-line analysis of data.

In some experiments, normal or low-chloride medium was used containing bicuculline. (20 μM), 4-amino pyridine (4-AP) (100 EM), or high-$K^+$ (7.5 or 12 mM). In all experiments, low-chloride solutions (7, and 21 mM $[Cl^-]_o$) were prepared by equimolar replacement of NaCl with $Na^+$-gluconate (Sigma). All solutions were prepared so that they had a pH of approximately 7.4 and an osmolarity of 290-300 mOsm at 35° C. and at equilibrium from carboxygenation with 95% $O_2$/5% $CO_2$.

After placement in the interface chamber, slices were superfused at approximately 1 ml/min. At this flow-rate, it took 8-10 minutes for changes in the perfusion media to be completed. All of the times reported here have taken this delay into account and have an error of approximately +/−2 minutes.

The relative contributions of the factors that modulate synchronized activity vary between areas CA1 and CA3. These factors include differences in the local circuitry and region-specific differences in cell packing and volume fraction of the extracellular spaces. If the anti-epileptic effects of anion or chloride-cotransport antagonism are due to a desynchronization in the timing of neuronal discharge, chloride-cotransport blockade might be expected to differentially affect areas CA1 and CA3. To test this, a series of experiments was performed to characterize differences in the timing of the blockade of spontaneous epileptiform activity in areas CA1 and CA3.

Field activity was recorded simultaneously in areas CA1 and CA3 (approximately midway between the most proximal and distal extent the CA3 region), and spontaneous bursting was induced by treatment with high-$[K^+]_o$ (12 μM; n=12), bicuculline (20 mM; n=12), or 4-AP (100 μM; n=5). Single electrical stimuli were delivered to the Schaffer collaterals, midway between areas CA1 and CA3, every 30 seconds so that the field responses in areas CA1 and CA3 could be monitored throughout the duration of each experiment. In all experiments, at least 20 minutes of continuous spontaneous epileptiform bursting was observed prior to switching to low $[Cl^-]_o$ (21 mM) or furosemide-containing (2.5 mM) medium.

In all cases, after 30-40 minutes exposure to furosemide or low-chloride medium, spontaneous bursting ceased in area CA1 before the bursting ceased in area CA3. The temporal sequence of events typically observed included an initial increase in burst frequency and amplitude of the spontaneous field events, then a reduction in the amplitude of the burst discharges that was more rapid in CA1 than in CA3. After CA1 became silent, CA3 continued to discharge for 5-10 minutes, until it too no longer exhibited spontaneous epileptiform events.

This temporal pattern of burst cessation was observed with all epileptiform-inducing treatments tested, regardless of whether the agent used for blockade of spontaneous bursting was furosemide or low-$[Cl^-]_o$ medium. Throughout all stages of these experiments, stimulation of the Schaffer collaterals evoked hyperexcited field responses in both the CA1 and CA3 cell body layers. Immediately after spontaneous bursting was blocked in both areas CA1 and CA3, hyperexcited population spikes could still be evoked.

The observation that CA3 continued to discharge spontaneously after CA1 became silent was unexpected since population discharges in CA3 are generally thought to evoke discharges in CA1 through excitatory synaptic transmission. As previously described, single-pulse stimuli delivered to the Schaffer collaterals still evoked multiple population spikes in CA1 even after the blockade of spontaneous bursting; thus, hyperexcited excitatory synaptic transmissions in CA3-to-CA1 synapse was intact. Given this maintained efficacy of synaptic transmission, and the continued spontaneous field discharges in CA3, the loss of spontaneous bursting in CA1 was due to a decrease in synchronization of incoming excitatory drive. Further, since spontaneous epileptiform discharge in CA3 also eventually ceased, perhaps this desynchronization process occurred at different times in the two hippocampal subfields.

The Effect of Chloride-Cotransporter Antagonists on the Synchronization of CA1 and CA3 Field Population Discharges The results presented herein suggest a temporal relationship between the exposure time to low-$[Cl^-]_o$ or furosemide-containing medium and the characteristics of the spontaneous burst activity. Further, this relationship was different between areas CA1 and CA3. In order to better characterize the temporal relationships, comparing the occurrences of CA1 action potentials and the population spike events in the field responses of CA1 and CA3 subfields during spontaneous and stimulation-evoked burst discharge.

Intracellular recordings were obtained from CA1 pyramidal cells, with the intracellular electrode placed close (<100 μM) to the CA1 field electrode. The slice was stimulated every 20 seconds with single stimuli delivered to the Schaffer collaterals. After continuous spontaneous bursting was established for at least 20 minutes, the bathing medium was switched to bicuculline-containing low-$[Cl^-]_o$ (21 mM) medium. After approximately 20 minutes, the burst frequency and amplitude was at its greatest. Simultaneous field and intracellular recordings during this time showed that the CA1 field and intracellular recordings were closely synchronized with the CA3 field discharges. During each spontaneous discharge, the CA3 field response preceded the CA1 discharge by several milliseconds. During stimulation-evoked events, action potential discharges of the CA1 pyramidal cell were closely synchronized to both CA3 and CA1 field discharges.

With continued exposure to low-$[Cl^-]_o$ medium, the latency between the spontaneous discharges of areas CA1 and CA3 increased, with a maximum latency of 30-40 milliseconds occurring after 30-40 minutes exposure to the bicuculline-containing low-chloride medium. During this time, the amplitude of both the CA1 and CA3 spontaneous field discharges decreased. Stimulation-evoked discharges during this time closely mimicked the spontaneously occurring discharges in morphology and relative latency. However, the initial stimulus-evoked depolarization of the neuron (presumably, the monosynaptic EPSP) began without any significant increase in latency. The time interval during which these data were acquired corresponds to the time immediately prior to the cessation of spontaneous bursting in CA1.

After 40-50 minutes perfusion with low-$[Cl^-]_o$ medium, the spontaneous bursts were nearly abolished in CA1 but were unaffected in CA3. Schaffer collateral stimulation during this time showed that monosynaptically-triggered responses of CA1 pyramidal cells occurred without any significant increase in latency, but that stimulation-evoked field responses were almost abolished. The time interval during which these data were acquired corresponds to the moments immediately prior to the cessation of spontaneous bursting in CA3.

After prolonged exposure to low-$[Cl^-]_o$ medium, large increases (>30 milliseconds) developed in the latency between Schaffer collateral stimulation and the consequent CA3 field discharge. Eventually, no field responses could be evoked by Schaffer collateral stimulation in either areas CA1 and CA3. However, action potential discharge from CA1 pyramidal cells in response to Schaffer collateral stimulation could be evoked with little change in response latency. Indeed, for the entire duration of the experiments (greater than two hours), action potential discharges form CA1 pyramidal cells could be evoked at short latency by Schaffer collateral stimulation. Further, although stimulation-evoked hyperexcited discharges of CA3 were eventually blocked after prolonged exposure to low-$[Cl^-]_o$ medium, the antidromic response in CA3 appeared to be preserved.

The Effect of Chloride-Cotransporter Antagonists on Burst Discharges in CA Pyramidal Cells.

The foregoing data suggest the disappearance of the field responses may be due to a desynchronization of the occurrence of action potentials among neurons. That is, although synaptically-driven excitation of CA1 pyramidal cells was not preserved, action potential synchrony among the CA1 neuronal population was not sufficient to summate into a measurable DC field response. In order to test this, paired intracellular recordings of CA1 pyramidal cells were acquired simultaneously with CA1 field responses. In these experiments, both the intracellular electrodes and the field recording electrodes were placed within 200 μm of one another.

During the period of maximum spontaneous activity induced by bicuculline containing low-$[Cl^-]_o$ medium, recordings showed that action potentials between pairs of CA1 neurons and the CA1 field discharges were tightly synchronized both during spontaneous and stimulation-evoked discharges. After continued exposure to low-$[Cl^-]_o$ medium, when the amplitude of the CA1 field discharge began to broaden and diminish, both spontaneous and stimulation-evoked discharges showed a desynchronization in the timing of the occurrences of action potentials between pairs of CA1 neurons, and between the action potentials and the field responses. This desynchronization was coincident with the suppression of CA1 field amplitude. By the time that spontaneous bursting in CA1 ceased, a significant increase in latency had developed between Schaffer collateral stimulation and CA1 field discharge. At this time, paired intracellular recordings showed a dramatic desynchronization in the timing of action potential discharge between pairs of neurons and between the occurrence of action potentials and the field discharges evoked by Schaffer collateral stimulation.

It is possible that the observed desynchronization of CA1 action potential discharge is due to the randomization of mechanisms necessary for synaptically-driven action potential generation, such as a disruption in the timing of synaptic release or random conduction failures at neuronal processes. If this were the case, then one would expect that the occurrence of action potentials between a given pair of neurons would vary randomly with respect to one another, from stimulation to stimulation. This was tested by comparing the patterns of action potential discharge of pairs of neurons between multiple consecutive stimuli of the Schaffer collaterals. During each stimulation event, the action potentials occurred at nearly identical times with respect to one another, and showed an almost identical burst morphology from stimulation to stimulation. Whether the occurrence of action potentials between a given pair of neurons during spontaneous field discharges was fixed in time was examined. The patterns of action potential discharges from a given pair of CA1 neurons was compared between consecutive spontaneous field bursts during the time when the occurrence of action potentials was clearly desynchronized. Just as in the case of stimulation-evoked action potential discharge described above, the action potentials generated during a spontaneous population discharge occurred at nearly identical times with respect to one another, and showed a nearly identical burst morphology from one spontaneous discharge to the next.

Effects of Low-Chloride Treatment on Spontaneous Synaptic Activity

It is possible that the anti-epileptic effects associated with chloride-cotransport antagonism are mediated by some action on transmitter release. Blockade of chloride-cotransport could alter the amount or timing of transmitter released from terminals, thus affecting neuronal synchronization. To test whether low-$[Cl^-]_o$ exposure affected mechanisms associated with transmitter release, intracellular CA1 responses were recorded simultaneously with CA1 and CA3 field responses during a treatment that dramatically increases spontaneous synaptic release of transmitter from presynaptic terminals.

Increased spontaneous release of transmitter was induced by treatment with 4-AP (100 μM). After 40 minutes exposure to 4-AP-containing medium, spontaneous synchronized burst discharges were recorded in area CA1 and CA3. Switching to 4-AP-containing low-$[Cl^-]_o$ medium led initially, as was shown previously, to enhanced spontaneous bursting. High-grain intracellular recordings showed that high-amplitude spontaneous synaptic activity was elicited by 4-AP treatment. Further exposure to low-chloride medium blocked spontaneous burst discharge in CA1, although CA3 continued to discharge spontaneously. At this time, CA1 intracellular recordings showed that spontaneous synaptic noise was further increased, and remained so for prolonged exposure times to 4-AP-containing low-chloride medium. These data suggest that mechanisms responsible for synaptic release from terminals are not adversely affected by low-chloride exposure in a manner that could explain the blockade of 4-AP-induced spontaneous bursting in CA1. These results also eliminate the possibility that the effects of low-$[Cl^-]_o$, exposure are due to alterations in CA1 dendritic properties that would compromise their efficiency in conducting PSPs to the soma.

In all of the following experiments, $[Cl^-]_o$ was reduced by equimolar replacement of NaCl with Na$^+$-gluconate. Gluconate was used rather than other anion replacements for several reasons. First, patch-clamp studies have demonstrated that gluconate appears to be virtually impermeant to chloride channels, whereas other anions (including sulfate, isethionate, and acetate) are permeable to varying degrees. Second, transport of extracellular potassium through glial NKCC1 cotransport is blocked when extracellular chloride is replaced by gluconate but is not completely blocked when replaced by isethionate. Since this furosemide-sensitive cotransporter plays a significant role in cell swelling and volume changes of the extracellular space (ECS), the use of the appropriate anion replacement ensured that the effects of the present treatment would be comparable to previous furosemide experiments. Hochman, et al. (1995) Science 270: 99-102 and U.S. Pat. No. 5,902,732, both of which are herein incorporated by reference in their entirety. Third, formate, acetate, and proprionate generate weak acids when employed as Cl$^-$ substitutes and lead to a prompt fall in intracellular pH; gluconate remains extracellular and has not been reported to induce intracellular pH shifts. Fourth, for purposes of comparison the same anion replacement that had been used in previous studies examining the effects of low-$[Cl^-]_o$ on activity-evoked changes of the ECS were used.

There is some suggestion that certain anion-replacements might chelate calcium. Although subsequent work has failed to demonstrate any significant ability of anion-substitutes to chelate calcium, there is still some concern in the literature regarding this issue. Calcium chelation did not appear to be an issue in the following experiments, since resting membrane potentials remained normal and synaptic responses (indeed, hyperexcitable synaptic responses) could be elicited even after several hours of exposure to medium in which $[Cl^-]_o$ had been reduced by gluconate substitution. Further, it was confirmed that calcium concentration in the low-$[Cl^-]_o$-medium was identical to that in the control-medium by measurements made with $Ca^{2+}$-selective microelectrodes.

Sprague-Dawley adult rats were prepared as previously described. Briefly, transverse hippocampal slices, 400 µm thick, were cut using a vibrating cutter. Slices typically contained the entire hippocampus and subiculum. After cutting, slices were stored in an oxygenated holding chamber for at least one hour prior to recording. All recordings were acquired in an interface type chamber with oxygenated (95% $O_2$/5% $CO_2$) artificial cerebral spinal fluid (ACSF) at 34°-35° C. Normal ACSF contained (in mmol/l): 124 NaCl, 3 KCl, 1.25 $NaH_2PO_4$, 1.2 $MgSO_4$, 26 $NaHCO_3$, 2 $CaCl_2$, and 10 dextrose. In some experiments, normal or low-chloride medium was used containing bicuculline (20 µm), 4-AP (100 µM), or high-$K^+$ (12 mM). Low-chloride solutions (7, 16, and 21 mM $[Cl^-]_o$) were prepared by equimolar replacement of NaCl with $Na^+$-gluconate (Sigma Chemical Co., St. Louis, Mo.). All solutions were prepared so that they had a pH of approximately 7.4 and an osmolarity of 290-300 mOsm at 35° C. and at equilibrium from carboxygenation with 95% $O_2$/5% $CO_2$.

Sharp-electrodes filled with 4 M potassium acetate were used for intracellular recordings from CA1 pyramidal cells. Field recordings from the CA1 or CA3 cell body layers were acquired with low-resistance glass electrodes filled with NaCl (2 M). For stimulation of the Schaffer collateral pathway, a small monopolar electrode was placed on the surface of the slice midway between areas CA1 and CA3. Spontaneous and stimulation-evoked activities from field and intracellular recordings were digitized (Neurocorder, Neurodata Instruments, New York, N.Y.), and stored on video tape. AxoScope software (Axon Instruments Inc.) on a PC-computer was used for off-line analyses of data.

Ion-selective microelectrodes were fabricated according to standard methods well known in the art. Double-barreled pipettes were pulled and broken to a tip diameter of approximately 3.0 µm. The reference barrel was filled with ACSF and the other barrel was sylanized and the tip back-filled with a resin selective for K (Corning 477317). The remainder of the sylanized barrel was filled with KCl (140 mM). Each barrel was led, via Ag/AgCl wires, to a high impedance dual-differential amplifier (WPI FD223). Each ion-selective microelectrode was calibrated by the use of solutions of known ionic composition and was considered suitable if it was characterized by a near-Nemstian slope response and if it remained stable throughout the duration of the experiment.

After placement in the interface chamber, slices were superfused at approximately 1 ml/minute. At this flow-rate, it took approximately 8-10 minutes for changes in perfusion media to be completed. All of the times reported here have taken this time-delay into account and have an error of approximately +/−2 minutes.

Effects of Low-$[Cl^-]_o$ on CA1 Field Recordings

Other studies have shown that prolonged exposure of cortical and hippocampal slices to low-$[Cl^-]_o$ does not affect basic intrinsic and synaptic properties such as input resistance, resting membrane potential, depolarization-induced action-potential generation, or excitatory synaptic transmission. A previous study has also partly characterized the epileptogenic properties of low-$[Cl^-]_o$ exposure to the CA1 area of hippocampus. The following studies were performed to observe the times of onset and possible cessation of low-$[Cl^-]_o$-induced hyperexcitability and hypersynchronization. Slices (n=6) were initially perfused with normal medium until stable intracellular and field recordings were established in a CA1 pyramidal cell and the CA1 cell body layer, respectively. In two experiments, the same cell was held throughout the entire length of the experiment (greater than 2 hours). In the remaining experiments (n=4), the initial intracellular recording was lost during the sequence of medium changes and additional recordings were acquired from different cells. Patterns of neuronal activity in these experiments were identical to those seen when a single cell was observed.

The field and intracellular electrodes were always placed in close proximity to one another (<200 µm). In each case, after approximately 15-20 minutes exposure to the low-$[Cl^-]_o$-medium (7 mM), spontaneous bursting developed, first at the cellular level, and then in the field. This spontaneous field activity, representing synchronized burst discharge in a large population of neurons, lasted from 5-10 minutes, after which time the field recording became silent. When the field first became silent, the cell continued to discharge spontaneously. This result suggests that population activity has been "desynchronized" while the ability of individual cells to discharge has not been impaired. After approximately 30 minutes exposure to low-$[Cl^-]_o$-medium, intracellular recording showed that cells continued to discharge spontaneously even though the field remained silent. The response of the cell to intracellular current injection at two time points demonstrated that the cell's ability to generate action potentials had not been impaired by low-$[Cl^-]_o$ exposure. Further, electrical stimulation in CA1 stratum radiatum elicited burst discharges, indicating that a hyperexcitable state was maintained in the tissue.

Effects of Low-$[Cl^-]_o$ on High-$[K^+]_o$-Induced Epileptiform Activity in CA1

The previous set of experiments showed that tissue exposure to low-$[Cl^-]_o$ medium induced a brief period of spontaneous field potential bursting which ceased within 10 minutes. If a reduction of $[Cl^-]_o$ is indeed eventually capable of blocking spontaneous epileptiform (i.e. synchronized) bursting, then these results suggest that anti-epileptic effects would likely be observable only after this initial period of bursting activity has ceased. The temporal effects of low-$[Cl^-]_o$-treatment on high-$[K^+]_o$-induced bursting activity were examined. Slices (n=12) were exposed to medium in which $[K^+]_o$ had been increased to 12 mM, and field potentials were recorded with a field electrode in the CA1 cell body layer. Spontaneous field potential bursting was observed for at least 20 minutes, and then the slices were exposed to medium in which $[K^+]_o$ was maintained at 12 mM, but $[Cl^-]_o$ was reduced to 21 mM. Within 15-20 minutes after the tissue was exposed to the low-$[Cl^-]_o$/high-$[K^+]_o$-medium, the burst amplitude increased and each field event had a longer duration. After a brief period of this facilitated field activity (lasting 5-10 minutes), the bursting stopped. To test whether this blockade was reversible, after at least 10 minutes of field potential silence, switching back to high-$[K^+]_o$-medium with normal $[Cl^-]$. The bursting returned within 20-40 minutes. Throughout each experiment, the CA1 field response to Schaffer collateral stimulation was monitored. The largest field responses were recorded just before the cessation of spontaneous bursting, during the period when the spontaneous bursts had the largest amplitude. Even after the blockade of spontaneous bursting, however, multiple population spikes were elicited by Schaffer collateral stimulation, indicating that synaptic transmission was intact, and that the tissue remained hyperexcitable.

In four slices, intracellular recordings from CA1 pyramidal cells were acquired along with the CA1 field recording. During the period of high-$[K^+]_o$-induced spontaneous bursting, hyperpolarizing current was injected into the cell so that postsynaptic potentials (PSPs) could be better observed. After low-$[Cl^-]_o$-blockade of spontaneous bursting, spontaneously occurring action potentials and PSPs were still observed. These observations further support the view that synaptic activity, per se, was not blocked by the low-$[Cl^-]_o$ treatment.

Low-$[Cl^-]_o$-Blockade of Epileptiform Activity Induced by 4-AP, High-$[K^+]_o$ and Bicuculline in CA1 and CA3

Whether low-$[Cl^-]_o$ treatment could block epileptiform activity in areas CA1 and CA3, which was elicited by different pharmacological treatments, was shown for furosemide treatment was tested. For this set of experiments, the effects of low-$[Cl^-]_o$ treatment on spontaneous bursting which had been induced by high-$[K^+]_o$ (12 mM) (n=5), 4-AP (100 μM) (n=4), and bicuculline (20 and 100 μM) (n=5) were tested. In each set of experiments, field responses were recorded simultaneously from areas CA1 and CA3, and in each case, the spontaneous epileptiform activity in both areas CA1 and CA3, was reversibly blocked within 30 minutes after $[Cl^-]_o$ in the perfusion medium had been reduced to 21 mM. These data suggest that, like furosemide, low-$[Cl^-]_o$ reversibly blocks spontaneous bursting in several of the most commonly studied in vitro models of epileptiform activity.

Comparison Between Low-$[Cl^-]_o$ and Furosemide on Blockade of High-$[K^+]_o$-Induced Epileptiform Activity The data from the previous sets of experiments are consistent with the hypothesis that the anti-epileptic effects of both low-$[Cl^-]_o$ and furosemide are mediated by their actions on the same physiological mechanisms. To further test this hypothesis, the temporal sequence of effects of low-$[Cl^-]_o$ (n=12) and furosemide (2.5 and 5 mM) (n=4) on high-$[K^+]_o$-induced bursting, as recorded with a field electrode in CA1 were compared. Both low-$[Cl^-]_o$ and furosemide treatment induced a similar temporal sequence of effects: an initial brief period of increased amplitude of field activity, and then blockade (reversible) of spontaneous field activity. In both cases, electrical stimulation of the Schaffer collaterals elicited hyperexcited responses even after the spontaneous bursting had been blocked. Consequences of Prolonged Exposure to Low-$[Cl^-]_o$ Medium with Varied $[K^+]_o$ In the preceding experiments, the filed activity was monitored in some slices for >1 hour after the spontaneous bursting had been blocked by low-$[Cl^-]_o$ exposure. After such prolonged low-$[Cl^-]_o$ exposure, spontaneous, long-lasting, depolarizing shifts developed. The morphology and frequency of these late-occurring field events appeared to be related to the extracellular potassium and chloride concentrations. A set of experiments where performed where the $[Cl^-]_o$ and $[K^+]_o$ were systematically varied and the effects of these ion changes were observed on the late-occurring spontaneous field events.

In the first set of experiments, slices were exposed to medium containing low-$[Cl^-]_o$ (7 mM) and normal-$[K^+]_o$ (3 mM) (n=6). After 50-70 minutes exposure to this medium, spontaneous events were recorded in area CA1; these events appeared as 5-10 mV negative shifts in the DC field, with the first episode lasting for 30-60 seconds. Each subsequent episode was longer than the previous one. This observation suggested that ion-homeostatic mechanisms were diminished over time as a result of the ion concentrations in the bathing medium. In some experiments (n=2) in which these negative DC field shifts had been induced, intracellular recordings from CA1 pyramidal cells were acquired simultaneously with the CA1 field recordings.

For these experiments, the intracellular and field recordings were acquired close to one another (<200 μm). Prior to each negative field shift (10-20 seconds), the neuron began to depolarize. Cellular depolarization was indicated by a decrease in resting membrane potential, an increase in spontaneous firing frequency, and a reduction of action potential amplitude. Coincident with the onset of the negative field shifts, the cells became sufficiently depolarized so that they were unable to fire spontaneous or current-elicited (not shown) action potentials: Since neuronal depolarization began 10-20 seconds prior to the field shift, it may be that a gradual increase in extracellular potassium resulted in the depolarization of a neuronal population, thus initiating these field events. Such an increase in $[K^+]_o$ might be due to alterations of the chloride-dependent glial cotransport mechanisms that normally move potassium from extracellular to intracellular spaces. To test whether increases in $[K^+]_o$ preceded these negative field shifts (and paralleled cellular depolarization), experiments (n=2) were performed in which a $K^+$-selective microelectrode was used to record changes in $[K^+]_o$.

In each experiment, the $K^+$-selective microelectrode and a field electrode were placed in the CA1 pyramidal layer close to one another (<200 m), and a stimulation pulse was delivered to the Schaffer collaterals every 20 seconds so that the magnitude of the population spike could be monitored. Multiple spontaneously occurring negative field shifts were evoked by perfusion with low-$[Cl^-_o]$(7 mM) medium. Each event was associated with a significant increase in $[K^+]_o$, with the $[K^+]_o$ increase starting several seconds prior to the onset of negative field shift. A slow 1.5-2.0 mM increase in $[K^+]_o$ occurred over a time interval of approximately 1-2 minute seconds prior to the onset of each event. The stimulation-evoked field responses slowly increased in amplitude over time, along with the increasing $[K^+]_o$, until just before the negative field shift.

In a second set of experiments (n=4), $[K^+]_o$ was increased to 12 mM and $[Cl^-]_o$ was increased to 16 mM. After 50-90 minutes exposure to this medium, slow oscillations were recorded in area CA1. These oscillations were characterized by 5-10 mV negative DC shifts in the field potential and had a periodicity of approximately 1 cycle/40 seconds. Initially, these oscillations occurred intermittently and had an irregular morphology. Over time, these oscillations became continuous and developed a regular waveform. Upon exposure to furosemide (2.5 mM), the amplitude of the oscillations was gradually decreased and the frequency increased until the oscillations were completely blocked. Such low-$[Cl^-]_o$-induced oscillations in tissue slices have not been previously reported. However, the temporal characteristics of the oscillatory events bear a striking resemblance to the low-$[Cl^-]_o$-induced $[K^+]_o$ oscillations that were previously described in a purely axonal preparation.

In a third set of experiments (n=5) $[Cl^-]_o$ was further increased to 21 mM and $[K^+]_o$ was reduced back to 3 mM. In these experiments, single, infrequently occurring negative shifts of the field potential developed within 40-70 minutes (data not shown). These events (5-10 mV) lasting 40-60 seconds, occurred at random intervals, and maintained a relatively constant duration throughout the experiment.

These events could sometimes be elicited by a single electrical stimulus delivered to the Schaffer collaterals.

Finally, in a final set of experiments (n=5), $[Cl^-]_o$ was kept at 21 mM and $[K^+]_o$ was raised to 12 mM. In these experiments, late-occurring spontaneous field events were not observed during the course of the experiments (2-3 hours).

Changes in $[K^+]_o$ During Low-Chloride Exposure

Sprague-Dawley adult rats were prepared as previously described. Transverse hippocampal slices, 400 μm thick, were cut with a vibrating cutter and stored in an oxygenated holding chamber for 1 hour before recording. A submersion-type chamber was used for $K^+$-selective microelectrode recordings. Slices were perfused with oxygenated (95% $O_2$/5% $CO_2$) artificial cerebrospinal fluid (ACSF) at 34-35° C. Normal ACSF contained 10 mM dextrose, 124 mM NaCl, 3 mM KCl, 1.25 mM $NaH_2PO_4$, 1.2 mM $MgSO_4$, 26 mM $NaHCO_3$ and 2 mM $CaCl_2$. In some experiments, normal or low-chloride medium was used containing 4-aminopyridine (4-AP) at 100 μM. Low-chloride solutions (21 mM $[Cl^-]_o$) were prepared by equimolar replacement of NaCl with Na+-gluconate (Sigma Chemical Co.).

Field recordings from the CA1 or CA3 cell body layers were acquired with low-resistance glass electrodes filled with NaCl (2M). For stimulation of the Schaffer collateral pathway, a monopolar stainless-steel electrode was placed on the surface of the slide midway between areas CA1 and CA3. All recordings were digitized (Neurorocorder, Neurodata Instruments, New York, N.Y.) and stored on videotape.

$K^+$ selective microelectrodes were fabricated according to standard methods. Briefly, the reference barrel of a double-barreled pipette was filled with ACSF, and the other barrel was sylanized and the tip back-filled with KCl with $K^+$-selective resin (Corning 477317). Ion-selective microelectrodes were calibrated and considered suitable if they had a Nemstian slope response and remained stable throughout the duration of the experiment.

Exposure of hippocampal slices to low-$[Cl^-]^o$ medium has been shown to include a temporally-dependent sequence of changes on the activity of CA1 pyramidal cells, with three characteristics phases, as described above. In brief, exposure to low-$[Cl^-]_o$ medium results in a brief period of increased hyperexcitability and spontaneous epileptiform discharge. With further exposure to low-$[Cl^-]_o$ medium, spontaneous epileptiform activity is blocked, but cellular hyperexcitability remains, and action potential firing times become less synchronized with one another. Lastly, with prolonged exposure, the action potential firing times become sufficiently desynchronized so that stimulation-evoked field responses completely disappear, yet individual cells continue to show monosynaptically-evoked responses to Schaffer collateral stimulation. The following results demonstrate that the antiepileptic effects of furosemide on chloride-cotransport antagonism are independent of direct actions on excitatory synaptic transmission, and are a consequence of a desynchronization of population activity with any associated decrease in excitability.

In six hippocampal slices, $K^+$-selective and field microelectrodes were placed in the CA1 cell body layer, and a stimulating electrode was placed on the Schaffer collateral pathway, and single-pulse stimuli (300 μs) were delivered every 20 seconds. After stable baseline $[K^+]_o$ was observed for at least 20 minutes, the perfusion was switched to low-$[Cl^-]_o$ medium. Within 1-2 minutes of exposure to low-$[Cl^-]_o$ medium, the field responses became hyperexcitable as the $[K^+]_o$ began to rise. After approximately 4-5 minutes of exposure to low-$[Cl^-]_o$ medium, the magnitude of the field response diminished until it was completely abolished. The corresponding recording of $[K^+]_o$ showed that potassium began to rise immediately after exposure to low-$[Cl^-]_o$ medium, and that the peak of this $[K^+]_o$ rise corresponded in time to the maximally hyperexcitable CA1 field response: Coincident with the reduction of the magnitude of the field response, the $[K^+]_o$ began to diminish until after 8-10 minutes exposure to low-$[Cl^-]_o$ medium, it became constant for the remainder of the experiment at 1.8-2.5 mM above control levels. Four slices were switched back to control medium and allowed to fully recover. The experiment was then repeated with the $K^+$-selective microelectrode placed in the *stratum radiatum*. A similar sequence of changes in $[K^+]_o$ was observed in the dendritic layer, with the values of $[K^+]_o$ being 0.2-0.3 mM less than those observed in the cell body layers.

In four hippocampal slices, the responses of stimulation-evoked changes in $[K^+]_o$ between control conditions and after the CA1 field response was completely abolished by low-$[Cl^-]_o$ exposure were compared. In each slice, the $[K^+]_o$-selective measurements were acquired first in the cell body layer, and then after allowance for complete recovery in control medium, the experiment was repeated with the $K^+$-selective electrode moved to the *stratum radiatum*. Each stimulation trial consisted of a 10 Hz volley delivered to the Schaffer collateral for 5 seconds. The peak rises in $[K^+]_o$ were similar between control conditions an after prolonged exposure to low-$[Cl^-]_o$ medium, and between the cell body and dendritic layers. However, the recovery times observed after prolonged exposure to low-$[Cl^-]_o$ were significantly longer than those observed during control conditions.

These results demonstrate that the administration of furosemide resulted in increased $[K^+]_o$ in the extracellular spaces. Exposure of the brain tissue to low-$[Cl^-]_o$ medium immediately induced a rise in $[K^+]_o$ by 1-2 mM, which remained throughout the duration of exposure, and was coincident with the initial increase in excitability and the eventual abolishment of the CA1 field response. This loss of CA1 field response during low-$[Cl^-]_o$ exposure is most likely due to the desynchronization of neuronal firing times. Significantly, the stimulation-evoked increases in $[K^+]_o$, in both the cell body and dendritic layers were nearly identical before and after the complete low-$[Cl^-]_o$ blockade of the CA1 field response. This data suggests that comparable stimulation-evoked synaptic drive and action potential generation occurred under control conditions and after low $[Cl^-]_o$ blockade of the field.

Together these data demonstrate that the antiepileptic and desynchronizing effects of the chloride-cotransport antagonist, furosemide, are independent of direct actions on excitatory synaptic transmission and are a consequence of a desynchronization of population activity without decrease in excitability.

Other compounds, including the analogs and prodrugs, of bumetanide, furosemide, piretanide, azosemide, and torsemide described herein can be expected to have similar effects. The compounds (including analogs and prodrugs) described herein may be used in methods to treat and/or prevent (prophylactic) for seizures, seizure disorders, epilepsy, epileptic seizures, and other neurodegenerative disorders (e.g., those neurodegenerative disorders which involve seizures). In particular, the compounds described herein are used in a method for treating seizures, seizure disorders, epilepsy, epileptic seizures, and other neurodegenerative disorders, wherein said neurodegenerative disorders involve seizures, comprising administering an effective amount of an analog (including prodrugs) of bumetanide, furosemide, piretanide, azosemide, and torsemide described herein.

Changes in Extracellular pH During Low-Chloride Exposure

Antagonists of the anion/chloride-dependent cotransporter, such as furosemide and low-$[Cl^-]_o$, may affect extracellular pH transients that might contribute to the maintenance of synchronized population activity. Rat hippocampal brain slices were prepared as described in Example 80, except the $NaHCO_3$ was substituted by equimolar amount of HEPES (26 nM) and an interface-type chamber was used.

In four hippocampal brain slices continuous spontaneous bursting was elicited by exposure to medium containing 100 µM 4-AP. Field recordings were acquired simultaneously from the cell body layers in areas CA1 and CA3. A stimulus delivered every 30 seconds to the Schaffer collaterals throughout the duration of the experiments. After at least 20 minutes of continuous bursting was observed, the slices were exposed to nominally bicarbonate free, 4-AP-containing HEPES medium. There were no significant changes observed in the spontaneous or stimulation-evoked field responses resulting from prolonged exposure (0.2 hours) to HEPES medium. After the slices had been exposed for at least 2 hours to the HEPES medium, the perfusion was switched to 4-AP-containing HEPES medium in which the $[Cl^-]_o$ had been reduced to 21 mM. Exposure to the low-$[Cl^-]_o$ HEPES medium induced the identical sequences of events, and at the same time course, as had previously been observed with low-$[Cl^-]_o$ $NaHCO_3$-containing medium. After complete blockade of spontaneous bursting, the perfusion medium was switched back to HEPES medium with normal $[Cl^-]_o$. Within 20-40 minutes, spontaneous bursting resumed. At the time the spontaneous bursting had resumed, the slices had been perfused with nominally bicarbonate-free HEPES medium for greater than 3 hours.

This data suggests that the actions of chloride-cotransport antagonism on synchronization and excitability are independent of affects on the dynamics of extracellular pH. Other compounds, including the analogs and prodrugs, of bumetanide, furosemide, piretanide, azosemide, and torsemide described herein can be expected to have similar effects. The compounds (including analogs and prodrugs) described herein may be used in methods to treat and/or prevent (prophylactic) for seizures, seizure disorders, epilepsy, epileptic seizures, and other neurodegenerative disorders (e.g., those neurodegenerative disorders which involve seizures). In particular, the compounds described herein are used in a method for treating seizures, seizure disorders, epilepsy, epileptic seizures, and other neurodegenerative disorders, wherein said neurodegenerative disorders involve seizures, comprising administering an effective amount of an analog (including prodrugs) of bumetanide, furosemide, piretanide, azosemide, and torsemide described herein.

EXAMPLE 152

Therapeutic Efficacy of Furosemide in the Alleviation of Pain Symptoms in an Animal Model of Neuropathic Pain The ability of the compounds described herein (e.g., bumetanide, furosemide, piretanide, azosemide, and torsemide, as well as analogs, and prodrugs thereof) to alleviate pain can be examined in rodents using the Chung model of neuropathic pain. Walker, et al. (1999) Mol. Med. Today 5:319-321. Sixteen adult male Long-Evans rats may be used in this study. All rats can receive spinal ligation of the L5 nerve as detailed below. Eight of the sixteen rats can receive an injection (intravenous) of furosemide and the remaining eight can receive intravenous injection of vehicle only. Pain threshold can be assessed immediately using the mechanical paw withdrawal test. Differences in pain thresholds between the two groups can be compared. Evidence of the ability of the compounds described herein (e.g., bumetanide, furosemide, piretanide, azosemide, and torsemide, as well as analogs, and prodrugs thereof) alleviates pain can be seen as a higher pain threshold than the group that received vehicle.

Chung Model of Neuropathy

Spinal nerve ligation is performed under isoflourane anesthesia with animals placed in the prone position to access the left L4-L6 spinal nerves. Under magnification, approximately one-third of the transverse process is removed. The L5 spinal nerve is identified and carefully dissected free from the adjacent LA spinal nerve and then tightly ligated using a 6-0 silk suture. The wound is treated with an antiseptic solution, the muscle layer is sutured, and the incision is closed with wound clips. Behavioral testing of mechanical paw withdrawal threshold takes place within a 3-7 day period following the incision. Briefly, animals are placed within a Plexiglas chamber (20×10.5×40.5 cm) and allowed to habituate for 15 min. The chamber is positioned on top of a mesh screen so that mechanical stimuli can be administered to the plantar surface of both hindpaws. Mechanical threshold measurements for each hindpaw are obtained using an up/down method with eight von Frey monofilaments (5, 7, 13, 26, 43, 64, 106, and 202 mN). Each trial begins with a von Frey force of 13 mN delivered to the right hindpaw for approximately 1 sec, and then the left hindpaw. If there is no withdrawal response, the next higher force is delivered. If there is a response, the next lower force is delivered. This procedure is performed until no response is made at the highest force (202 mN) or until four stimuli are administered following the initial response. The 50% paw withdrawal threshold for each paw is calculated using the following formula: $[Xth]log=[vFr]log+ky$ where $[vFr]$ is the force of the last von Frey used, $k=0.2268$, which is the average interval (in log units) between the von Frey monofilaments, and y, is a value that depends upon the pattern of withdrawal responses. If an animal does not respond to the highest von Frey hair (202 mN), then $y=1.00$ and the 50% mechanical paw withdrawal response for that paw is calculated to be 340.5 mN. Mechanical paw withdrawal threshold testing is performed three times and the 50% withdrawal values are averaged over the three trials to determine the mean mechanical paw withdrawal threshold for the right and left paw for each animal.

EXAMPLE 153

Therapeutic Efficacy of Furosemide and Bumetanide in Alleviating the Symptoms of Intense Anxiety or Post Traumatic Stress Disorder The therapeutic usefulness of furosemide and bumetanide in the treatment of post traumatic stress disorder can be examined by determining the ability of these compounds to alleviate intense anxiety in contextual fear conditioning in rats.

Contextual fear conditioning involves pairing an aversive event, in this case moderate foot shock, with a distinctive environment. The strength of the fear memory is assessed using freezing, a species-typical defensive reaction in rats, marked by complete immobility, except for breathing. If rats are placed into a distinctive environment and are immediately shocked they do not learn to fear the context. However, if they are allowed to explore the distinctive environment sometime before the immediate shock, they show intense anxiety and fear when placed back into the same environment. By procedurally dividing contextual fear conditioning into two phases, the effects of treatments on memory for the context (specifically a hippocampus based process) from learning the association between context and shock or experiencing the aversiveness of the shock (which depend upon emotional response circuitry including amygdala) were separately studied. Post traumatic stress syndrome (PTSD) in humans has been shown to be related to emotional response circuitry in the amygdala, and for this reason contextual memory conditioning is a widely accepted model for PTSD.

The experiment employed 24 rats. Each rat received a single 5 min episode of exploration of a small, novel environment. Seventy-two hours later they were placed into the same environment and immediately received two moderate foot-shocks (1 milliamp) separated by 53 sec. Twenty-four hours later, 8 of the rats received an injection (I.V.) of furosemide (100 mg/kg) in vehicle (DMSO), and 8 of the rats were injected I.V. with bumetanide (50 mg/kg) in vehicle (DMSO). The remaining 8 rats received an injection of DMSO alone. Each rat was again placed into the same environment for 8 min during which time freezing was measured, as an index of Pavlovian conditioned fear.

Four identical chambers (20×20×15 cm) were used. All aspects of the timing and control of events were under microcomputer control (MedPC, MedAssociates Inc., Vermont, USA). Measurement of freezing was accomplished through an overhead video camera connected to the microcomputer and was automatically scored using a specialty piece of software, FreezeFrame (OER Inc., Reston, Va.) Total freezing time was analyzed in a one-way analysis of variance (ANOVA) test, with drug dose as the within-groups factor.

Figure 20:
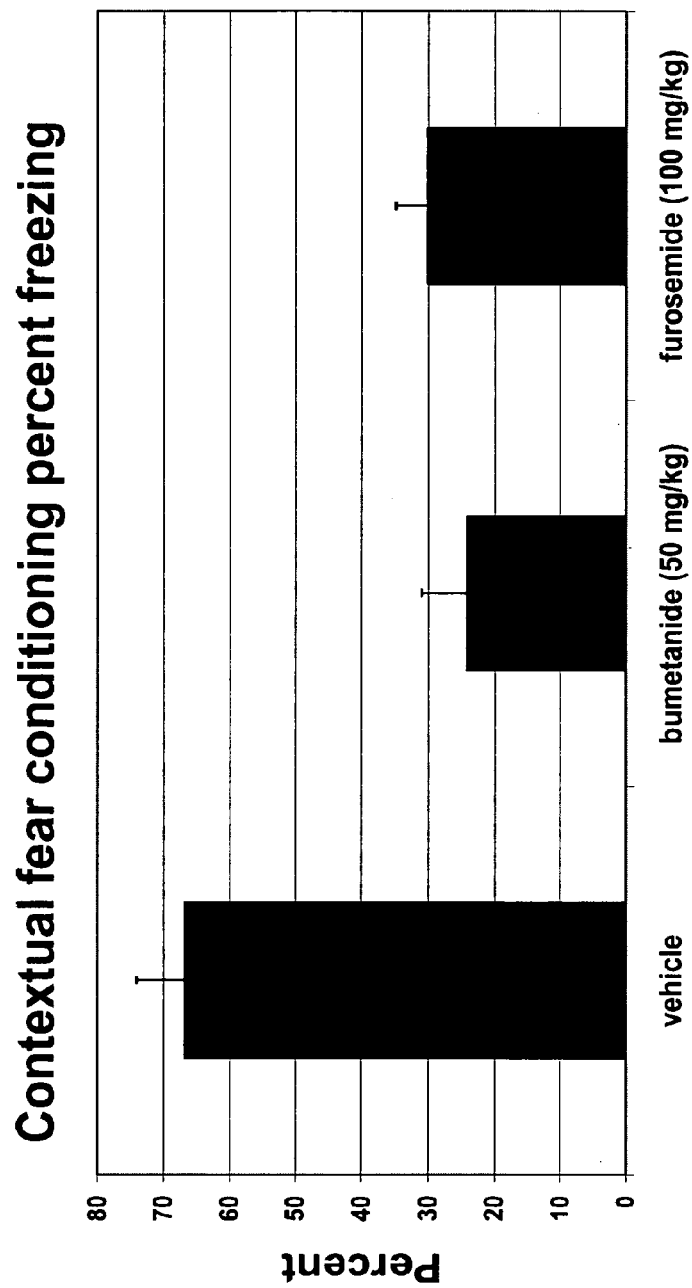
FIG. 20 shows that significantly less freezing was observed in animals treated with either bumetanide or furosemide than in animals receiving vehicle alone in a test of contextual fear conditioning in rats.

As shown in FIG. 20 significantly less freezing was observed in animals treated with either bumetanide or furosemide than in animals receiving vehicle alone, indicating that bumetanide, furosemide, piretanide, azosemide, and torsemide may be effectively employed in the treatment of post traumatic stress disorder and other anxiety disorders (e.g., anxiety, acute anxiety, panic disorder, social anxiety disorder, obsessive compulsive disorder (OCD), post-traumatic stress disorder (PTSD), generalized anxiety disorder, and specific phobia).

EXAMPLE 154

Therapeutic Efficacy of Furosemide and Bumetanide in Alleviating Anxiety

The therapeutic efficacy of furosemide and bumetanide in alleviating anxiety was examined by evaluating the effects of these compounds in fear potentiated startle (FPS) test in rats. This test is commonly used to distinguish anxiolytic drug effects from non-specific effects, such as sedation/muscle relaxation Twenty-four rats received a 30 min period of habituation to the FPS apparatus. Twenty-four hours later, baseline startle amplitudes were collected. The rats were then divided into three matched groups based on baseline startle amplitudes. One of the rats exhibited a significantly higher baseline startle than the others and was excluded from the experiments. Groups 1 and 2 therefore consisted of 8 rats each, with Group 3 consisting of 7 rats. Following baseline startle amplitude collection, 20 light/shock pairings were delivered on two sessions over two consecutive days (i.e., 10 light/shock pairings per day). On the final day (day 5), Groups 2 and 3 received an injection (i.v.) of either furosemide (100 mg/kg) or bumetanide (70 mg/kg) in vehicle (DMSO) and Group 1 received vehicle alone. Immediately following injections, startle amplitudes were assessed during startle alone trials and startle plus fear (light followed by startle) trials. Fear potentiated startle (light+startle amplitudes minus startle alone amplitudes) was compared between the treatment groups.

Pavlovian Conditioned Fear

Animals were trained and tested in four identical stabilimeter devices (Med-Associates). Briefly, each rat was placed in a small Plexiglas cylinder. The floor of each stabilimeter consisted of four 6-mm-diameter stainless steel bars spaced 18 mm apart through which shock can be delivered. Cylinder movements result in displacement of an accelerometer where the resultant voltage is proportional to the velocity of the cage displacement. Startle amplitude is defined as the maximum accelerometer voltage that occurs during the first 0.25 sec after the startle stimulus is delivered. The analog output of the accelerometer was amplified, digitized on a scale of 0-4096 units, and stored on a microcomputer. Each stabilimeter was enclosed in a ventilated, light-, and sound-attenuating box. All sound level measurements were made with a Precision Sound Level Meter. The noise of a ventilating fan attached to a sidewall of each wooden box produced an overall background noise level of 64 dB. The startle stimulus was a 50 ms burst of white noise (5 ms rise-decay time) generated by a white noise generator. The visual conditioned stimulus employed was illumination of a light bulb adjacent to the white noise source. The unconditioned stimulus was a 0.6 mA foot shock with duration of 0.5 sec, generated by four constant-current shockers located outside the chamber. The presentation and sequencing of all stimuli were under the control of the microcomputer.

FPS procedures consisted of 5 days of testing; during days 1 and 2 baseline startle responses were collected, days 3 and 4 light/shock pairings were delivered, day 5 testing for fear potentiated startle was conducted.

Matching: On the first two days all rats were placed in the Plexiglas cylinders and 3 min later presented with 30 startle stimuli at a 30 sec interstimulus interval. An intensity of 105 dB was used. The mean startle amplitude across the 30 startle stimuli on the second day was used to assign rats into treatment groups with similar means.

Training: On the following 2 days, rats were placed in the Plexiglas cylinders. Each day following 3 min after entry, 10 CS-shock pairings were delivered. The shock was delivered during the last 0.5 sec of the 3.7 sec CSs at an average intertrial interval of 4 min (range, 3-5 min).

Testing: Rats were placed in the same startle boxes where they were trained and after-3 min were presented with 18 startle-eliciting stimuli (all at 105 dB). These initial startle stimuli were used to again habituate the rats to the acoustic startle stimuli. Thirty seconds after the last of these stimuli, each animal received 60 startle stimuli with half of the stimuli presented alone (startle alone trials) and the other half presented 3.2 sec after the onset of the 3.7 sec CS (CS-startle trials). All startle stimuli are presented at a mean 30 sec interstimulus interval, randomly varying between 20 and 40 sec.

Measures: The treatment groups were compared on the difference in startle amplitude between CS-startle and startle-alone trials (fear potentiation).

Figure 21:
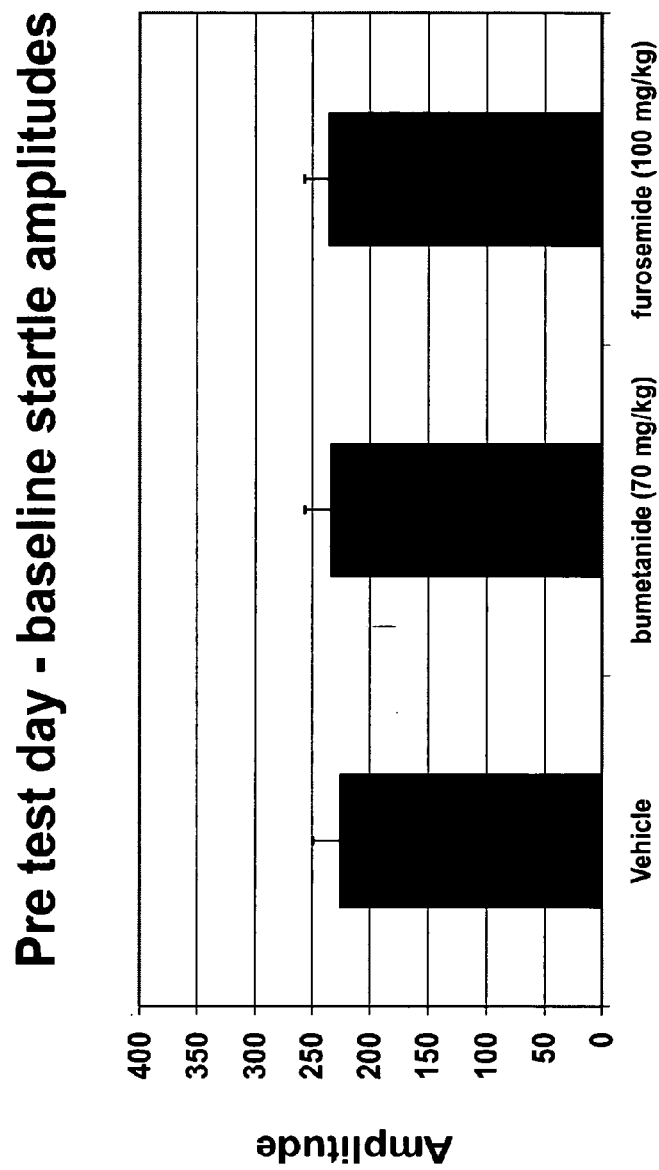
FIG. 21 shows baseline startle amplitudes in a fear potentiated startle test in rats, which can be tested with either bumetanide or furosemide.
Figure 22:
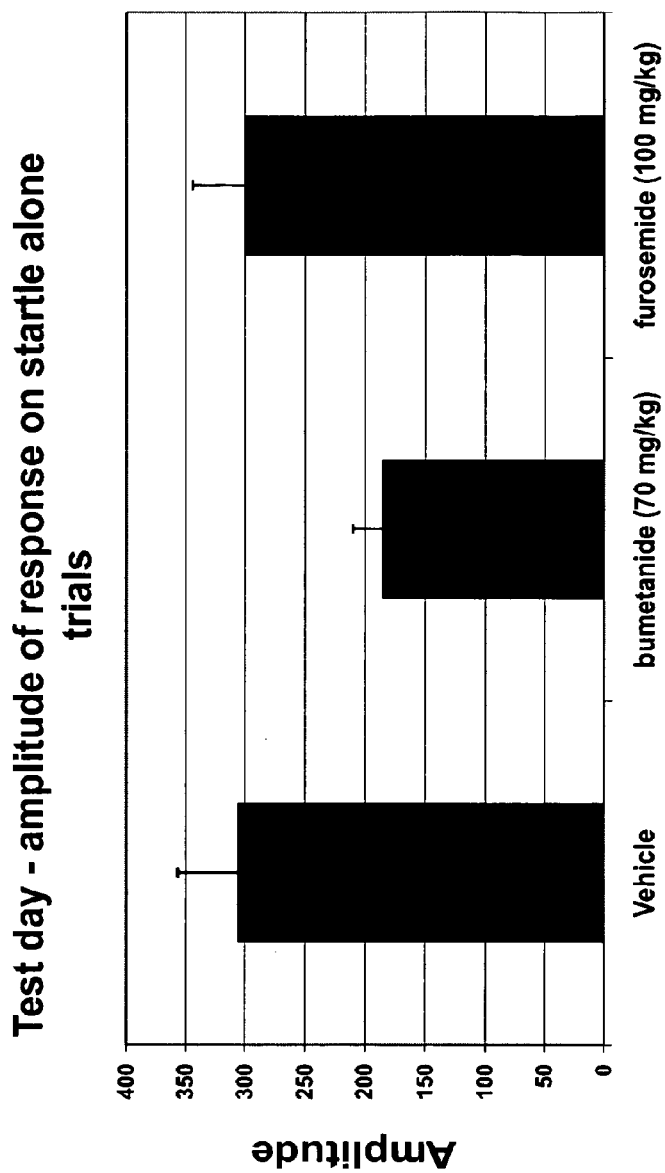
FIG. 22 shows the amplitude of response in rats on startle alone trials determined immediately following administration of either DMSO alone, bumetanide, or furosemide.
Figure 23:
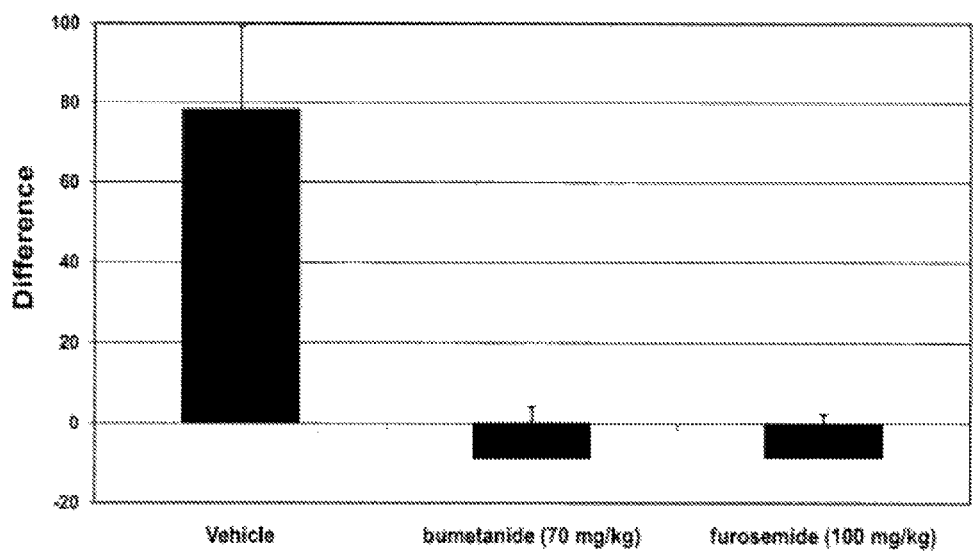
FIG. 23 shows the difference score (startle alone-fear potentiated startle) on the test day in rats treated with either DMSO, bumetanide, or furosemide

FIG. 21 shows the baseline startle amplitudes for each group of rats determined prior to the test day. FIG. 22 shows the amplitude of response on startle alone trials determined on the test day immediately following injection of either DMSO alone, bumetanide or furosemide, with FIG. 23 showing the difference score (startle alone—fear potentiated startle) on the test day. As shown in the figures, a statistically significantly lower difference score was observed in rats treated with either furosemide or bumetanide than in rats treated with vehicle alone, indicating that both furosemide and bumetanide are effective in reducing anxiety.

Figure 24:
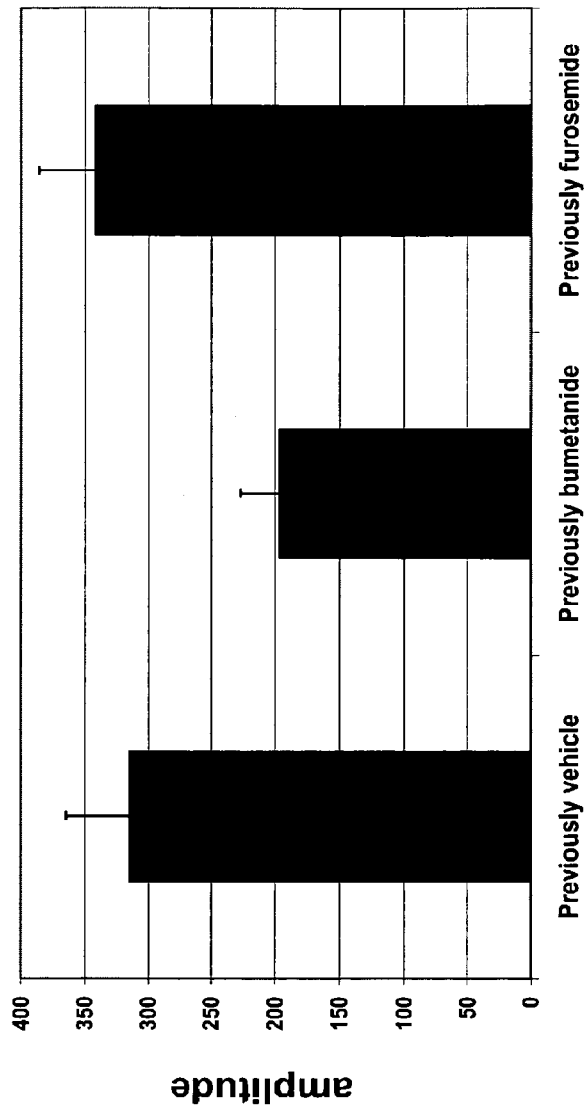
FIG. 24 shows the startle alone amplitude in rats one week after administration of either DMSO, bumetanide, or furosemide.
Figure 25:
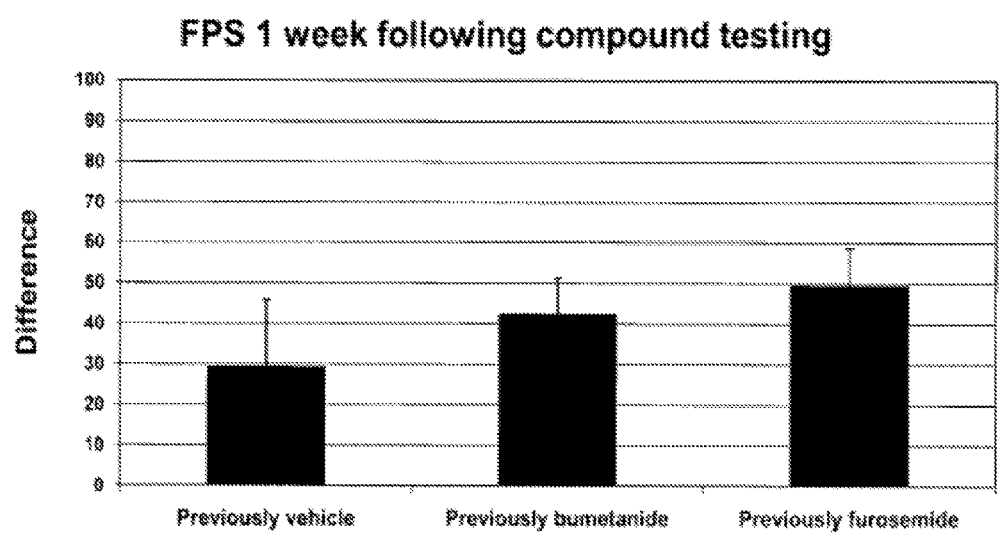
FIG. 25 shows the difference score in rats one week after administration of either DMSO, bumetanide or furosemide.

FIGS. 24 and 25 show the startle alone amplitude and the difference score, respectively, one week after treatment with either furosemide or bumetanide. Animals treated with either furosemide or bumetanide were found to have a higher difference score than animals treated with vehicle alone. Other compounds, including the analogs and prodrugs, of bumetanide, furosemide, piretanide, azosemide, and torsemide described herein can be expected to have similar effects. The compounds (including analogs and prodrugs) described herein may be used in methods to treat and/or prevent (prophylactic) for anxiety disorders (e.g., anxiety, acute anxiety, panic disorder, social anxiety disorder, obsessive compulsive disorder (OCD), post-traumatic stress disorder (PTSD), generalized anxiety disorder, and specific phobia). In particular, the compounds described herein are used in a method for treating anxiety disorders (e.g., anxiety, acute anxiety, panic disorder, social anxiety disorder, obsessive compulsive disorder (OCD), post-traumatic stress disorder (PTSD), generalized anxiety disorder, and specific phobia) comprising administering an effective amount of an analog (including prodrugs) of bumetanide, furosemide, piretanide, azosemide, and torsemide described herein.

EXAMPLE 155

Select Compounds Described Herein May not Act on the $Na^+K^+2Cl^-$ Cotransporter (NKCC1)

A select bumetanide derivative, NTP-2014 was tested for its ability to inhibit NKCC1 compared to a bumetanide control. The protocol may be done in accordance with Panet and Alan The Journal of Cell Biology, Volume 114, Number 2, July 1991 337-342. Human adult skin fibroblasts were seeded at 3 concentrations: 3000/5000/10 000 on 96 well culture plates with DMEM supplemented with 10% FCS and 4 mM glutamine (37° C., $CO_2$). Medium was replaced with DMEM supplemented with 0.2% FCS, 4 mM glutamine and 20 mM HEPES (37° C., $CO_2$). The NKCC assay may be performed according the standard operating procedure as described in Chassande, et al. (1988) "The $Na+/K+/Cl^-$ cotransport in C6 glioma cells." Eur. J. Biochem. 171: 425-433.

Figure 32:
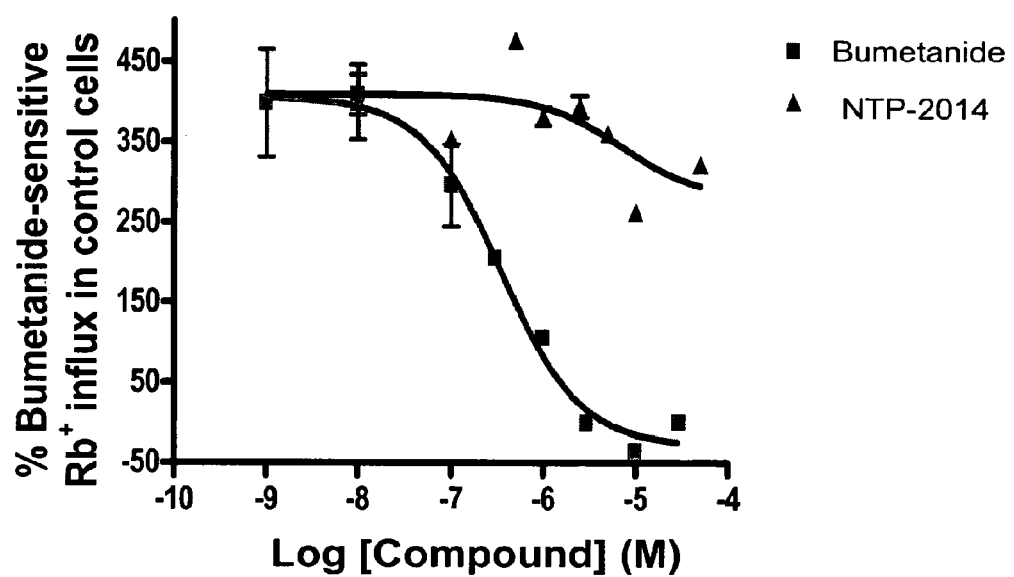
FIG. 32 illustrates that a select bumetanide derivative, NTP-2014, was tested for the ability to inhibit NKCC. In two different in vitro cell reporter systems tested (A7r5 immortalized cells and primary cell cultures), NTP-2014 showed no inhibition of NKCC1 chloride transport. Even in the presence of a co-transporter activating mitogen (e.g., FGF), NTP-2014 did not inhibit NKCC1 or NKCC2 (data not shown).

In the data as shown, 100% represents the $Rb^+$ influx in control cells without the use of Bumetanide and 0% represents the $Rb^+$ influx in control cells with Bumetanide at 30 µM. In two different in vitro cell reporter systems tested (A7r5 immortalized cells and primary cell cultures), NTP-2014 showed no inhibition of NKCC1 chloride transport. Even in the presence of a co-transporter activating mitogen (e.g., FGF), NTP-2014 did not inhibit NKCC1. See FIG. 32. Therefore, the compounds described herein described herein do not act on NKCC1 and are expected to have no diuretic effect. This allows for the administration of the compounds described herein described herein without unwanted diuretic side effects.

EXAMPLE 156

Compounds Described Herein have No Diuretic Effect (e.g., NTP-2014)

Figure 33:
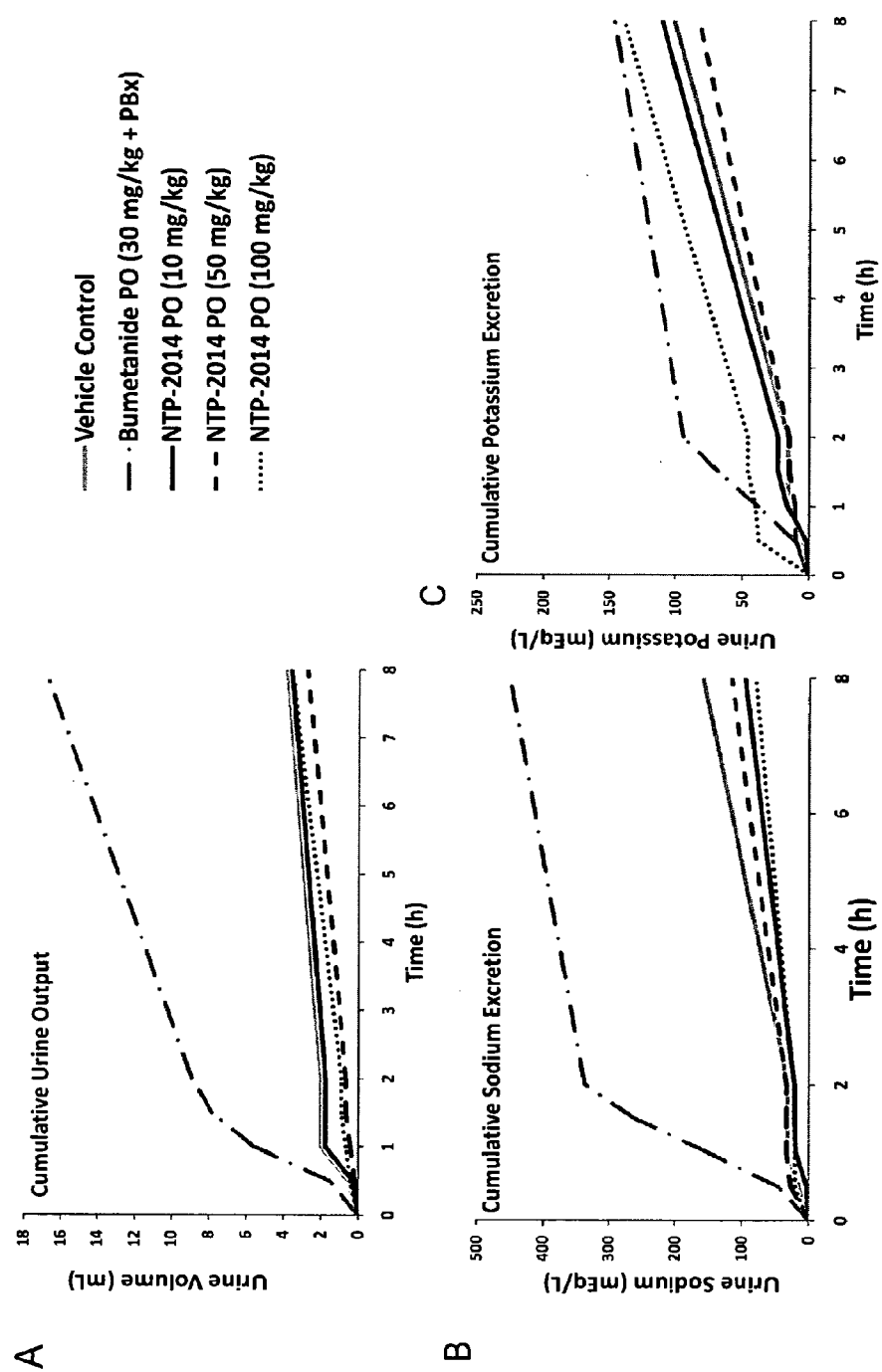
FIG. 33A-C illustrate that select bumetanide derivative, NTP-2014, was tested for its effect on urine output (33A), sodium excretion (33B), and potassium excretion (33C). NTP-2014 does not increase urine output, sodium excretion, and potassium excretion.

Animals were fasted overnight prior to dosing and had no access to drinking water prior to any pretreatment. Food and water were withheld through the terminal sample collection or for the first 6 hours of blood sample collection, where applicable. Prior to test article administration all animals were pretreated with a single IP dose of PBX. At approximately 5 to 6 minutes prior to dosing all animals received a single oral (PO) gavage dose of 0.9% Sodium Chloride for Injection, USP, at a dose volume of 15 mL/g. The vehicle, DMSO, and the test compounds (e.g., NTP-2014) were administered via a single IP dose at a dose volume of 1 mL/kg. The animals were administered a vehicle control, bumetanide PO (30 mg/kg+PBx), or NTP-2014 at 10 mg/kg, 50 mg/kg, or 100 mg/kg. Cumulative urine volume results are shown in FIG. 33A. Cumulative sodium excretion results are shown in FIG. 33B. Cumulative potassium excretion results are shown in FIG. 33C.

The bumetanide curve shows substantial excretion of urine (FIG. 33A), sodium (FIG. 33B), and potassium (FIG. 33C). On the other hand, NTP-2014 does not differ appreciably from the vehicle control. Therefore, the compounds described herein (e.g., NTP-2014) show no diuretic effect and may be administered at high doses (e.g., 100 mg/kg) without unwanted diuretic side effects. Further, treatment with the compounds (including prodrugs thereof) described herein, including the derivatives of bumetanide described herein, are expected to have similar effects.

EXAMPLE 157

Compounds May have Weak or No Diuretic Effect

Animals were fasted overnight prior to dosing and had no access to drinking water prior to any pretreatment. Food and water were withheld through the terminal sample collection or for the first 6 hours of blood sample collection, where applicable. Prior to test article administration all animals were pretreated with a single IP dose of PBx. At approximately 5 to 6 minutes prior to dosing all animals received a single oral (PO) gavage dose of 0.9% Sodium Chloride for Injection, USP, at a dose volume of 0.15 mL/kg. The vehicle, DMSO, and the test articles, NTP-2024 and NTP-2006, were administered via a single IP dose at a dose volume of 1 mL/kg. FIG. 27 illustrates cumulative urine volume.

The animals were fasted overnight prior to dosing and had no access to drinking water prior to any pretreatment. Food and water were withheld through the terminal sample collection or for the first 6 hours of blood sample collection, where applicable. Prior to test article administration all animals were pretreated with a single IP dose of PBX. At approximately 5 to 6 minutes prior to dosing all animals received a single oral (PO) gavage dose of 0.9% Sodium Chloride for Injection, USP, at a dose volume of 15 mL/kg. The vehicle, DMSO, and the test articles, NTP-2024 and NTP-2006, were administered via a single IP dose at a dose volume of 1 mL/kg. FIG. 28 illustrates cumulative sodium excretion.

The animals were fasted overnight prior to dosing and had no access to drinking water prior to any pretreatment. Food and water were withheld through the terminal sample collection or for the first 6 hours of blood sample collection, where applicable. Prior to test article administration all animals were pretreated with a single IP dose of PBX. At approximately 5 to 6 minutes prior to dosing all animals received a single oral (PO) gavage dose of 0.9% Sodium Chloride for Injection, USP, at a dose volume of 15 mL/kg. The vehicle, DMSO, and the test articles, NTP-2024 and NTP-2006, were administered via a single IP dose at a dose volume of 1 mL/kg. FIG. 29 illustrates cumulative potassium excretion.

Figure 30:
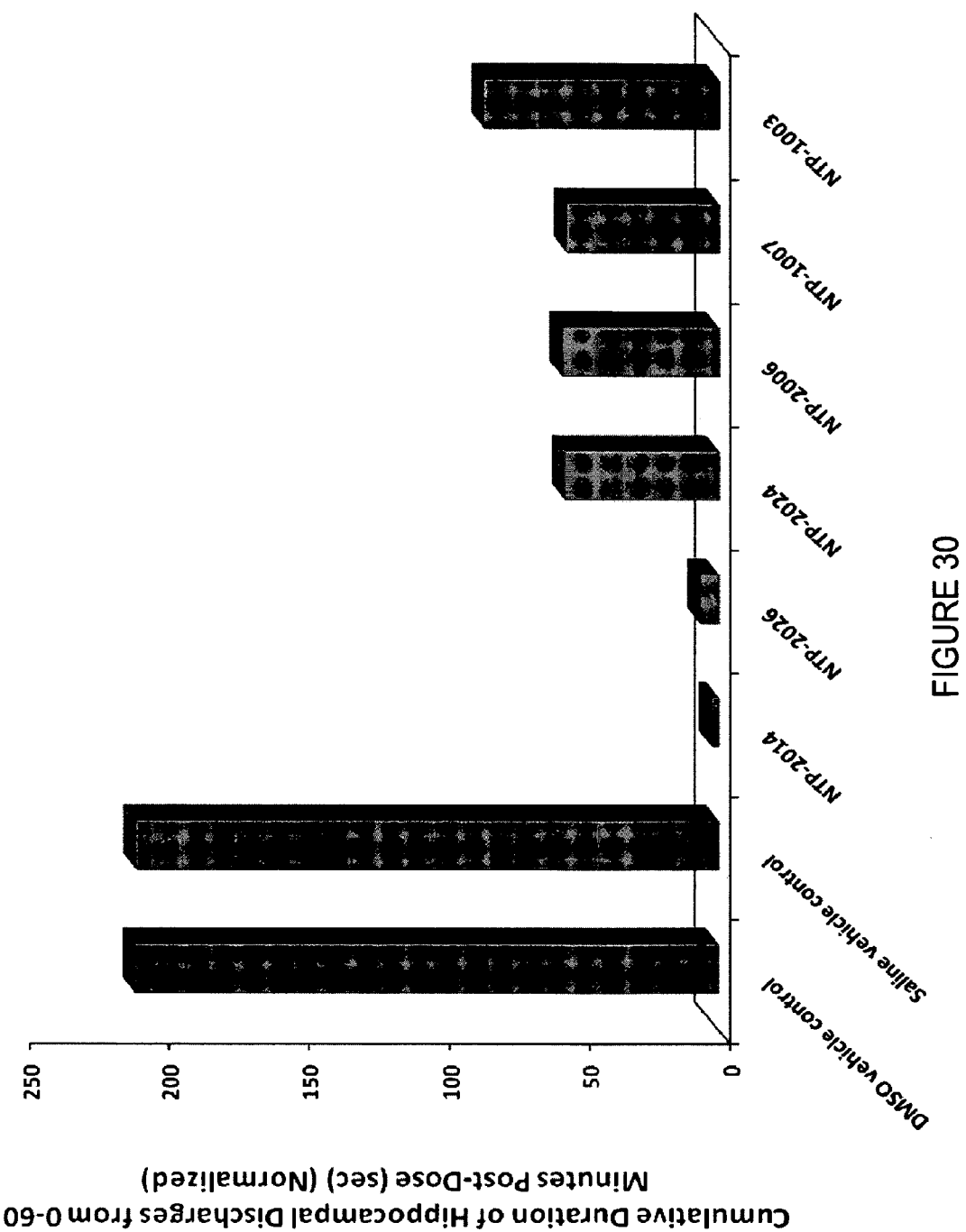
FIG. 30 illustrates decreased cumulative duration of hippocampal discharges in a model of mesial temporal lobe epilepsy following administration of bumetanide, furosemide, piretanide, azosemide, and torsemide esters and amide analogs (e.g., NTP-2014, NTP-2026, NTP-2024, NTP-2006, NTP-1007, and NTP-1003). The results below are normalized to the pre-dose condition for each of the treatment group including DMSO and saline vehicle controls. Doses of test article compounds were 50 mg/kg for NTP-2014 and NTP-2026 and 150 mg/kg for NTP-2024, NTP-2006, NTP-1007, and NTP-1003.

FIG. 30 illustrates decreased cumulative duration of hippocampal discharges in a model of mesial temporal lobe epilepsy following administration of bumetanide, furosemide, piretanide, azosemide, and torsemide esters and amide analogs (e.g., NTP-2014, NTP-2026, NTP-2024, NTP-2006, NTP-1007, and NTP-1003). The results below are normalized to the pre-dose condition for each of the treatment group including DMSO and saline vehicle controls. Doses of test article compounds were 50 mg/kg for NTP-2014 and NTP-2026 and 150 mg/kg for NTP-2024, NTP-2006, NTP-1007, and NTP-1003.

Figure 31:
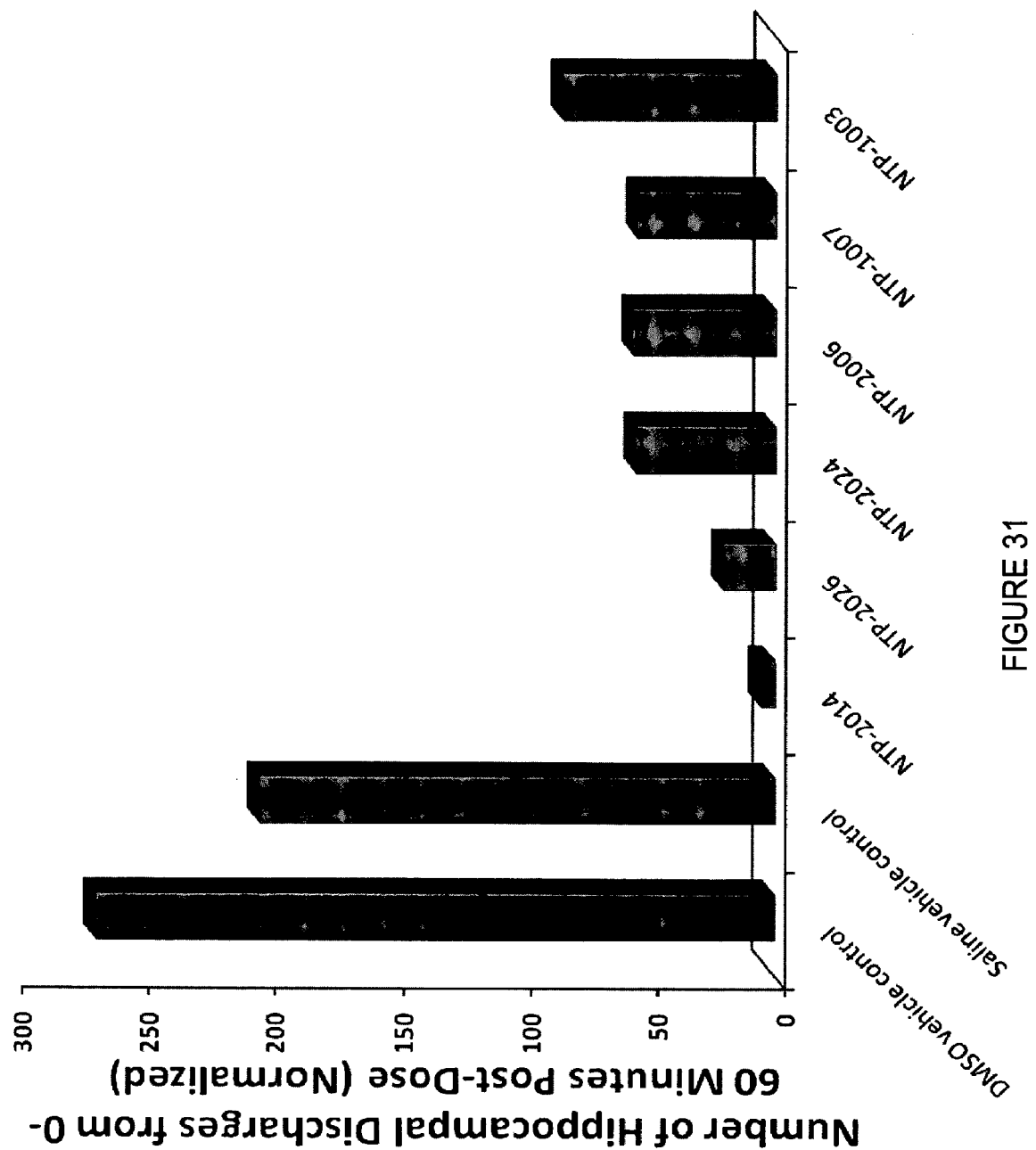
FIG. 31 illustrates decreased cumulative number of hippocampal discharges in a model of mesial temporal lobe epilepsy following administration of bumetanide, furosemide, piretanide, azosemide, and torsemide esters and amide analogs (e.g., NTP-2014, NTP-2026, NTP-2024, NTP-2006, NTP-1007, and NTP-1003). The results below are normalized to the pre-dose condition for each of the treatment group including DMSO and saline vehicle controls. Doses of test article compounds were 50 mg/kg for NTP-2014 and NTP-2026 and 150 mg/kg for NTP-2024, NTP-2006, NTP-1007, and NTP-1003.

FIG. 31 illustrates decreased number of hippocampal discharges in a model of mesial temporal lobe epilepsy following administration of bumetanide, furosemide, piretanide, azosemide, and torsemide esters and amide analogs (e.g., NTP-2014, NTP-2026, NTP-2024, NTP-2006, NTP-1007, and NTP-1003). The results below are normalized to the pre-dose condition for each of the treatment group including DMSO and saline vehicle controls. Doses of test article compounds were 50 mg/kg for NTP-2014 and NTP-2026 and 150 mg/kg for NTP-2024, NTP-2006, NTP-1007, and NTP-1003.

In addition, several of the analogs were observed to have significantly lower diuretic effects than those generally associated with either furosemide or bumetanide.

Therefore treatment with the compounds described herein, including the analogs and prodrugs, of bumetanide, furosemide, piretanide, azosemide, and torsemide described herein can be expected to have similar effects. The compounds (including analogs and prodrugs) described herein may be used in methods to treat and/or prevent (prophylactic) for epilepsy (e.g., seizures, epileptic seizures, seizure disorder, and other neurological disorders involving seizures (e.g., cerebral palsy, Ohtahara Syndrome)). In particular, the compounds described herein are used in a method for treating epilepsy (e.g., seizures, epileptic seizures, seizure disorder, and other neurological disorders involving seizures (e.g., cerebral palsy, Ohtahara Syndrome)) comprising administering an effective amount of an analog (including prodrugs) of bumetanide, furosemide; piretanide, azosemide, and torsemide described herein.

EXAMPLE 158

In Vitro Hippocampal Recordings of Miniature and Spontaneous Inhibitory Post-Synaptic Currents (mIPSCs and sIPSCs)

Figure 34:
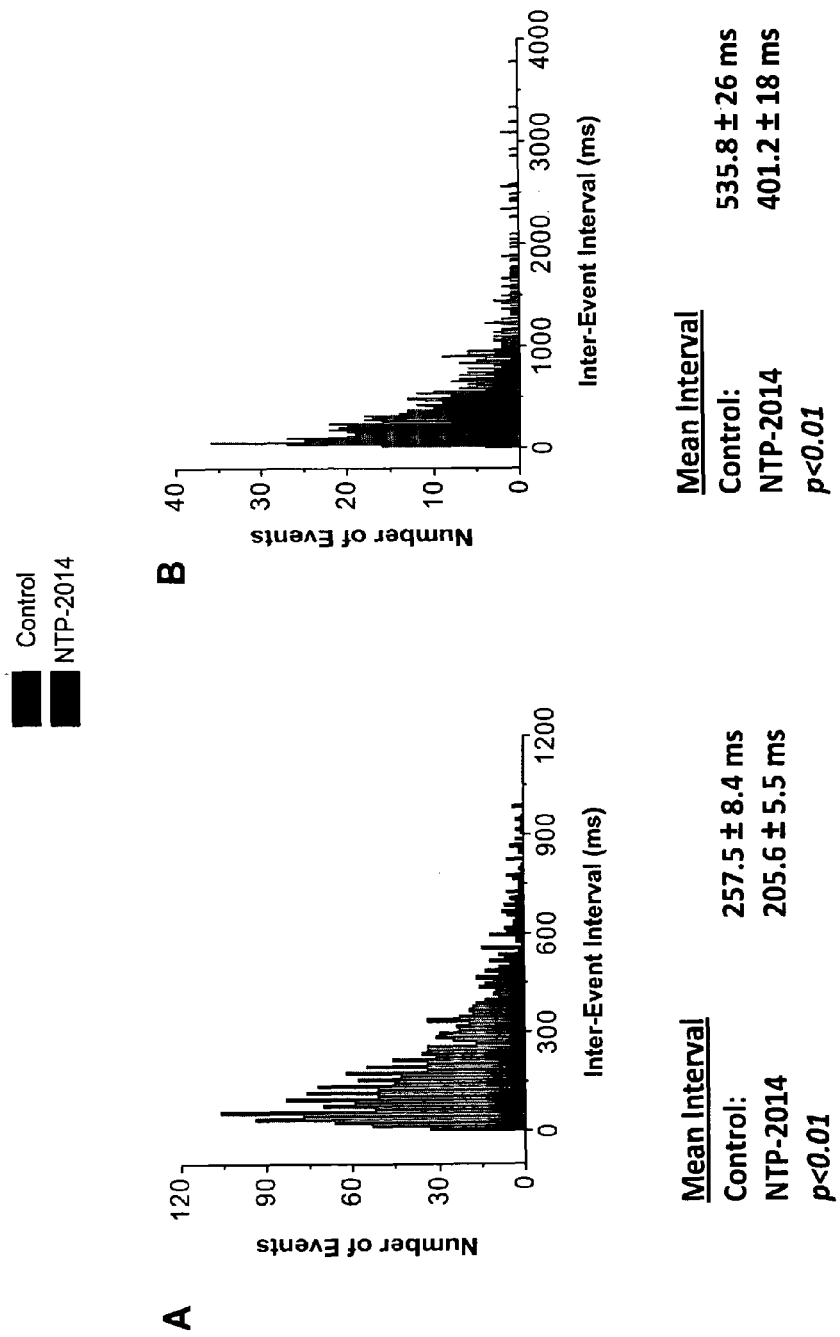
FIG. 34A-B illustrates that select bumetanide derivative, NTP-2014, showed a marked increase in spontaneous IPSCs in a hippocampal slice model where NTP-2014 showed a significant decrease in the time between inhibitory events (e.g., increased frequency of events). NTP-2014 decreased the mean interval between inhibitory events from 257 ms to 205 ms (FIG. 34A) and 535 to 401 ms (FIG. 34B) in two experiments.

Ion flux in neuronal cells was measured using standard techniques. Kandel and Schwartz *Principles of Neural Science* $2^{nd}$ Edition (1985), see, e.g., pages 128-131. Recording was performed in vitro in hippocampal slices (CA1 pyramidal cell layer). For recording $GABA_A$-IPSCs, glutamatergic and $GABA_B$ transmission was blocked by adding DNOX (50 µM), AP-5 (50 µM), and SCH50911 (20 mM) into the medium. The intracellular solution comprised CsCl and OX314. The test bumetanide derivative (e.g., NTP-2014) was applied to the bath media. The results are shown in FIG. 34A-B.

NTP-2014 showed increased $GABA_A$ inhibitory drive, including a marked increase in spontaneous IPSCs in a hippocampal slice model where NTP-2014 consistently showed a significant decrease in the time between inhibitory events (e.g., increased frequency of events). NTP-2014 decreased the mean interval between inhibitory events from 257 ms to 205 ms (FIG. 34A) and 535 to 401 ms (FIG. 34B).

Figure 35:
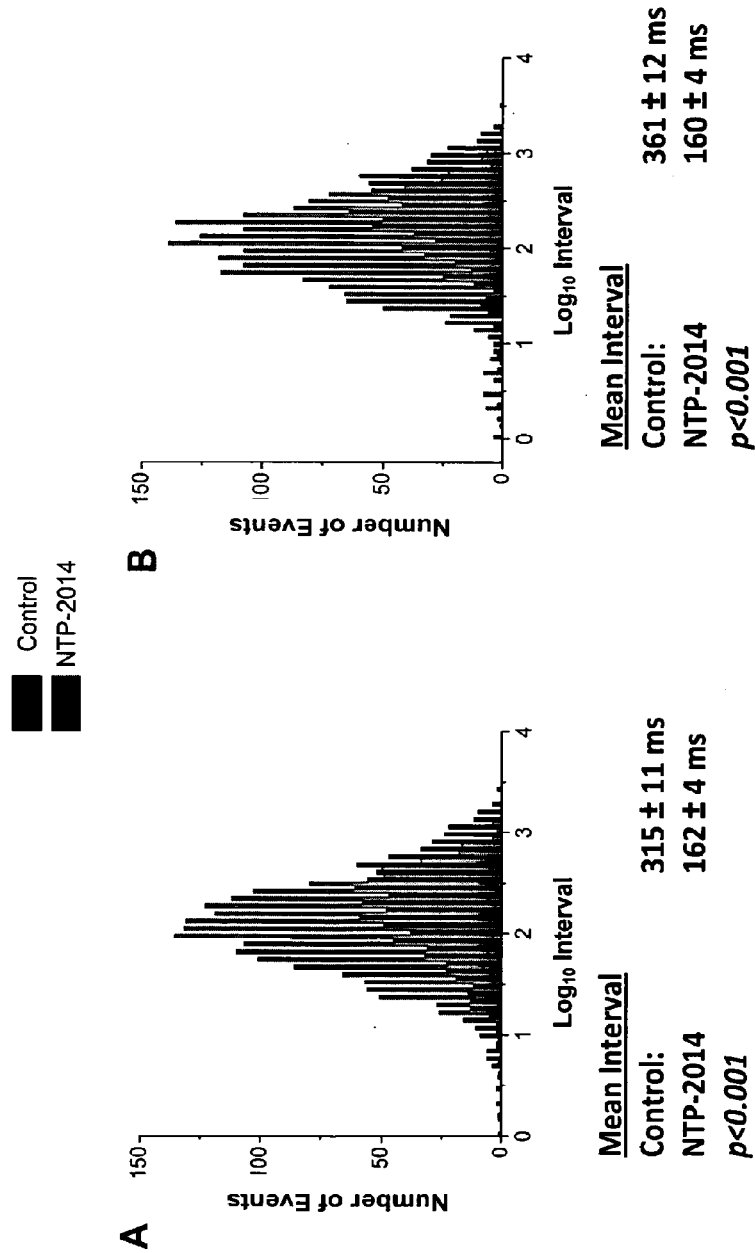
FIG. 35A-B illustrates that select bumetanide derivative, NTP-2014, showed a marked increase in miniature IPSCs in a hippocampal slice model where NTP-2014 showed a significant decrease in the time between inhibitory events (e.g., increased frequency of events). NTP-2014 decreased the mean interval between inhibitory events from 315 ms to 162 ms (FIG. 35A) and 361 to 160 ms (FIG. 35B) in two experiments.

NTP-2014 also showed increased $GABA_A$ inhibitory drive, including a marked increase in miniature IPSCs in a hippocampal slice model where NTP-2014 consistently showed a significant decrease in the time between inhibitory events (e.g., increased frequency of events). NTP-2014 decreased the mean interval between inhibitory events from 315 ms to 162 ms and from 361 to 160 ms. The results are shown in FIG. 35A-B.

The data presented herein demonstrate that the interval between miniature and spontaneous inhibitory post-synaptic currents (mIPSCs and sIPSCs, respectively) events are substantially decreased in the presence of NTP-2014. The resulting effects indicate a highly significant increase in the frequency of inhibitory events. These data suggest a pre-synaptic mechanism increasing the release of GABA from the neurons by the action of compounds described herein.

Therefore, the compounds described herein (e.g., NTP-2014) act parasynaptically and may be administered at high doses (e.g., 100 mg/kg) without the unwanted side effects usually associated with GABAergic compounds (e.g., sedation from benzodiazepines). Further, treatment with the compounds described herein, including the compounds described herein, are expected to have similar effects.

EXAMPLE 159

In Vitro Molecular Tests of Select Bumetanide Derivatives on $GABA_A$ Receptor Isoforms Experimental Design for Selectivity Screen The addition of GABA to GABAergic cells activates the recombinant expressed $GABA_A$ receptors, creating an ion movement through the ion channel in the $GABA_A$ receptor. The electrical current generated by the movement of chloride ions into the cells can be quantified.

HEK-293T cells were transiently transfected with rat or human $GABA_A$ receptor subunits. Whole-cell patch clamp recording was performed at −50 mV unless otherwise indicated. Test compounds was diluted from a freshly made stock in DMSO, GABA was prepared from a frozen stock. For each experiment GABA or GABA+a test compound was applied for 5 seconds, and the electrical current generated by the movement of chloride ions into the cells was measured and recorded as a trace of current versus time.

Classic GABAergic Drugs

Figure 36:
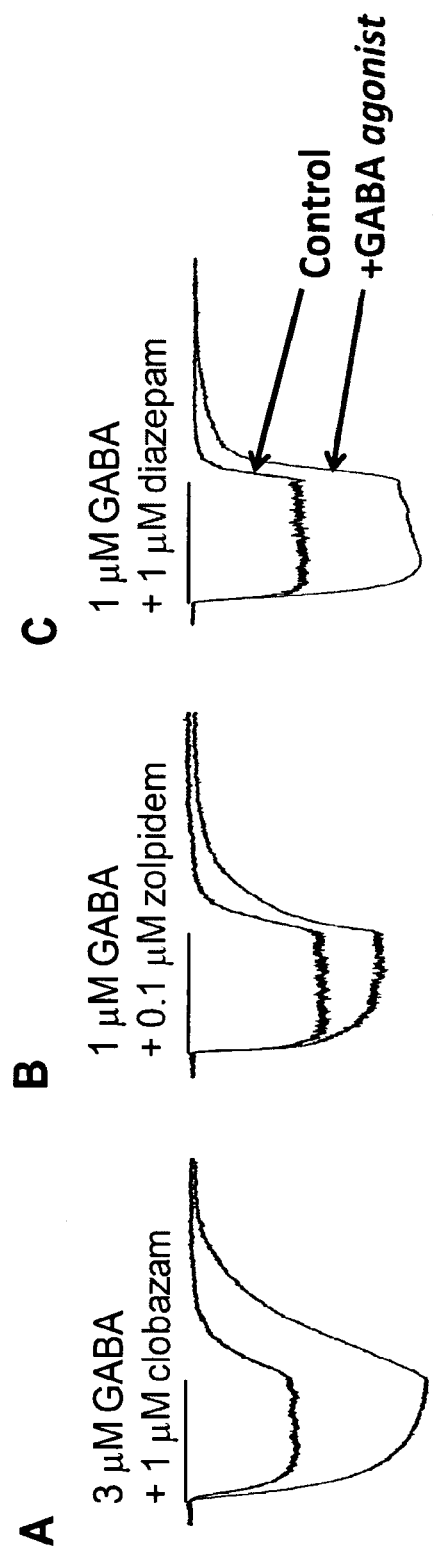
FIG. 36A-C illustrates that classic GABAergic drugs (e.g., benzodiazepines) are agonists that increase both the amplitude and time course of inhibitory currents in a1 subunit containing $GABA_A$ receptors. As shown in (A) FIRISUM (clobazam) an anticonvulsant, (B) AMBIEN (zolpidem) a sleep aid, and (C) VALIUM (diazepam) an anxiolytic drug, all increase both the amplitude and time course of inhibitory currents in $\alpha_1$ subunit containing $GABA_A$ receptors.

Classic GABAergic drugs (e.g., benzodiazepines) are non-selective agonists that increase both the amplitude and time course of inhibitory currents in $GABA_A$ receptor. As shown in FIG. 36, at (A) FRISIUM (clobazam) an anticonvulsant, (B) AMBIEN (zolpidem) a sleep aid, and (C) VALIUM (diazepam) an anxiolytic drug, all increase both the amplitude and time course of inhibitory currents in $GABA_A$ receptor. $GABA_A$ receptor agonists activate $GABA_A$ receptors at low GABA concentrations, and while effective, also induce CNS side effects including sedation, decreased respiration, decreased cognition, and impaired motor function.

Bumetanide Derivatives

Figure 37:
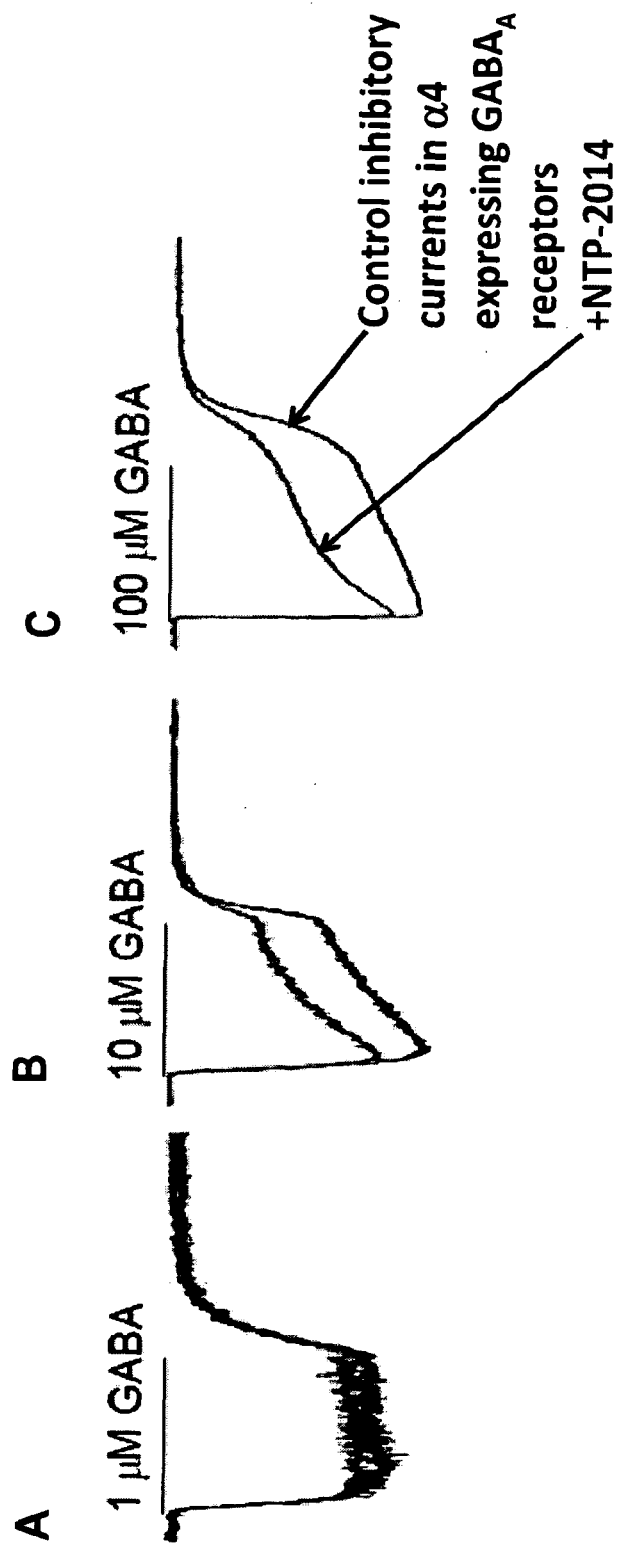
FIG. 37A-C illustrates that select bumetanide derivative, NTP-2014, showed an inhibition of currents in $\alpha_4$ $GABA_A$ receptor isoform at: (A) 1 μM GABA, (B) 10 μM GABA, and (C) 100 μM GABA. Higher GABA concentrations (e.g., 100 μM GABA) leads to a greater inhibition suggesting that NTP-2014 acts a noncompetitive inhibitor of these $GABA_A$ receptors.
Figure 39:
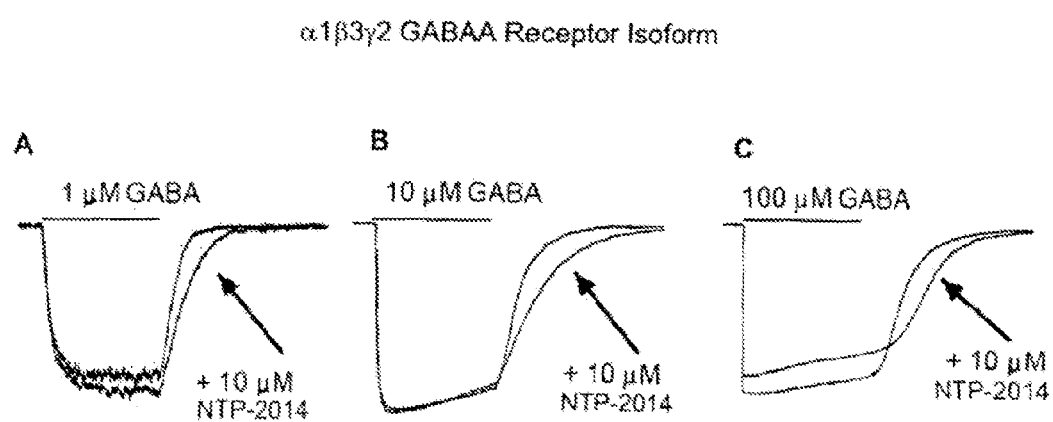
FIG. 39A-C illustrates the effect of NTP-2014 on the current in the $\alpha_1\beta_3\gamma_2$ $GABA_A$ receptor isoform. The amplitude of the current was not increased as agonist agents like benzodiazepines do, in fact it was decreased at concentrations of GABA that are found in high firing rates.
Figure 40:
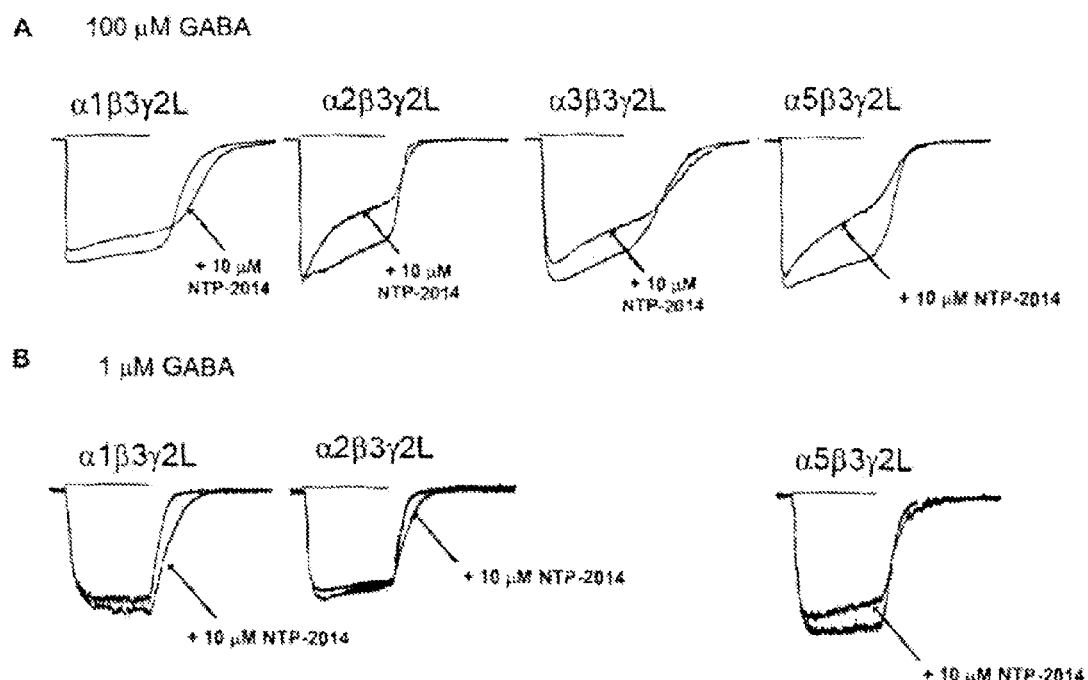
FIG. 40A-B illustrates the effect of NTP-2014 on the current in $\alpha_1/\alpha_2/\alpha_3/\alpha_5$ $GABA_A$ receptor isoforms. In $GABA_A$ receptor isoforms containing $\alpha_2$, $\alpha_3$, $\alpha_5$ subunit subtypes, 10 μM NTP-2014 inhibited these isoforms at high GABA concentrations.
Figure 41:
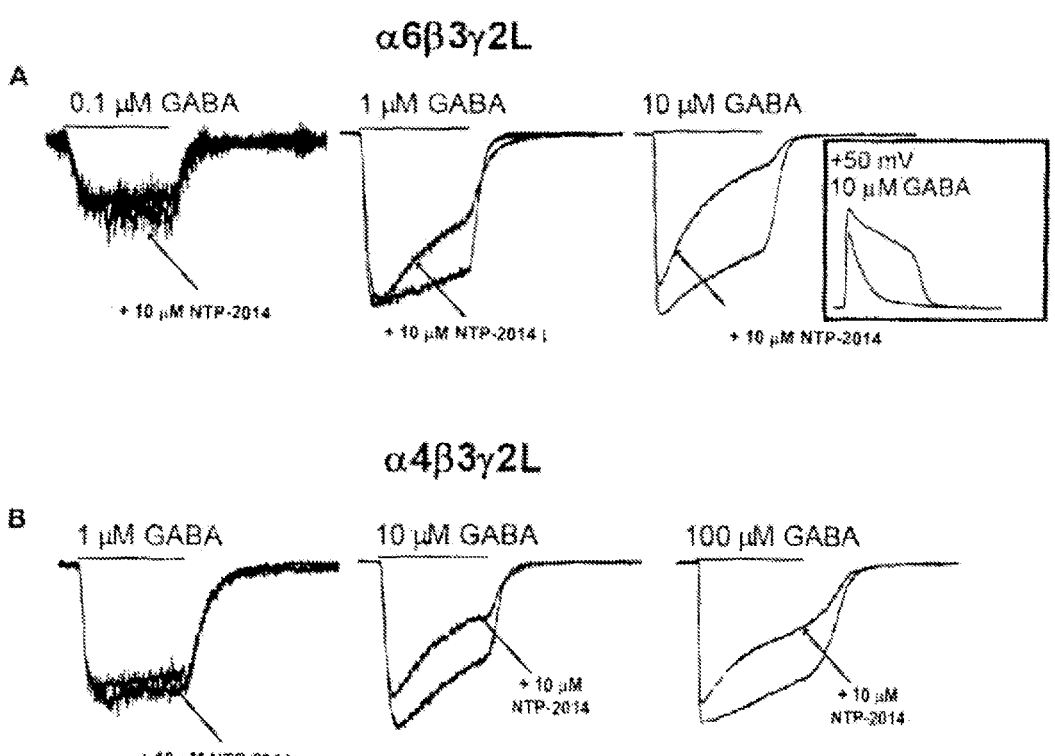
FIG. 41A-C illustrates the inhibiting effect of NTP-2014 on the current in $\alpha_4$ or $\alpha_6$ containing $GABA_A$ receptor isoforms: (A) $\alpha_6\beta_3\gamma_2$ at 0.1 μM GABA, 1 μM GABA, and 10 μM GABA and (B) $\alpha_4\beta_3\gamma_2$ at 0.1 μM GABA, 1 μM GABA, and 10 μM GABA.
Figure 41C:
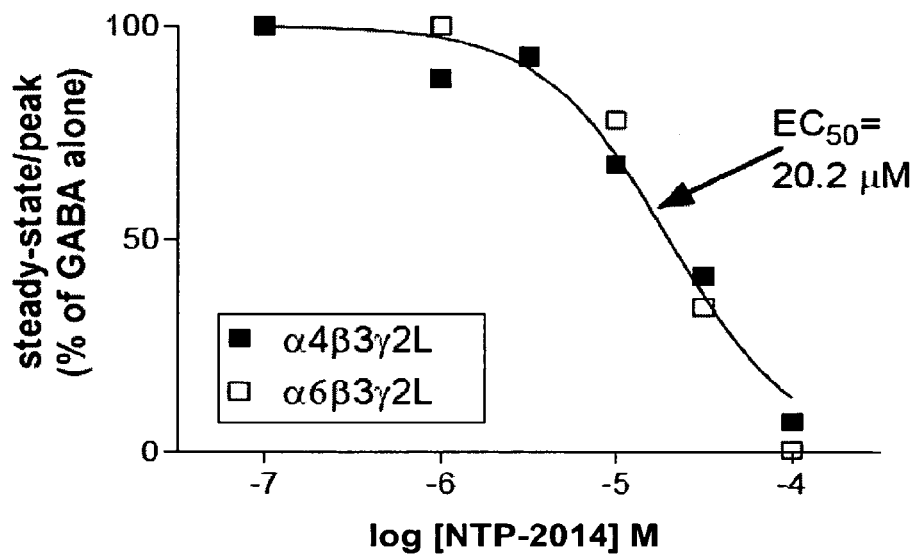

Compounds described herein (e.g., NTP-2014) were tested at high and low GABA concentrations against multiple GABA$_A$ receptor isoforms (e.g., $\alpha_1\beta_3\gamma_2$, $\alpha_2\beta_3\gamma_2$, $\alpha_3\beta_3\gamma_2$, $\alpha_3\beta_3\gamma_2$, $\alpha_4\beta_3\gamma_2$, $\alpha_5\beta_3\gamma_2$, $\alpha_6\beta_3\gamma_2$). NTP-2014 selectively antagonizes the $\alpha_4$ GABA$_A$ receptor isoform by inhibiting currents in the α4 GABA$_A$ receptor isoform. Higher GABA concentrations lead to greater inhibition suggesting that NTP-2014 acts a noncompetitive inhibitor. The results are shown in FIG. 37. NTP-2014 inhibits the currents in the parasynaptic $\alpha_4$ GABA$_A$ receptor isoform in GABAergic interneurons. $\alpha_1\beta_3\gamma_2$ GABA$_A$ receptor isoform The $\alpha_1$-containing receptors showed no significant activation in response to 10 μM NTP-2014. The $\alpha_1$ subunit is the predominant a subunit in the adult brain. In general, the amplitude of the current was not affected, with a mixture of increased decay time and decreased amplitude seen at the highest concentration (10 μM) but no alteration at lower concentrations. This is in contrast to the significantly increased positive modulation seen with action of benzodiazepines and other classic GABA-ergic agents (reference FIG. 37A-C). The results are shown in FIG. 39. $\alpha_2/\alpha_3/\alpha_5$ GABA$_A$ receptor isoforms GABA$_A$ receptor isoforms containing $\alpha_2$, $\alpha_3$, $\alpha_5$ subunit subtypes, 10 μM NTP-2014 slowed the decay rate at (A) 1 μM and (B) 100 μM GABA. There was a varying amount of inhibition of the steady-state current apparent especially prominent for the $\alpha_2$- and $\alpha_5$-containing receptors at higher GABA concentrations. A mixture of small positive effect and negative effect of NTP-2014 was observed at the $\alpha_2$-containing receptors at a lower GABA concentration. The results are shown in FIG. 41. $\alpha_4/\alpha_6$ GABA$_A$ receptor isofonms Receptors containing the $\alpha_4$ and $\alpha_6$ subunits were inhibited by NTP-2014 at higher GABA concentrations, but unaffected at lower GABA concentrations. The results are shown in FIG. 41. This is consistent with noncompetitive inhibition by open channel block and is distinctly different from the inhibitory action of furosemide. The sensitivity of these receptors to inhibition appears to be very similar, with an IC$_{50}$ between 10-30 μM. FIG. 41C illustrates that the EC$_{50}$=20.2 μM for NTP-2014 in $\alpha_4$ or in $\alpha_6$ GABA$_A$ receptor isoforms. The inhibition also appears to be somewhat voltage-dependent, with greater inhibition at positive membrane potentials.

Figure 42:
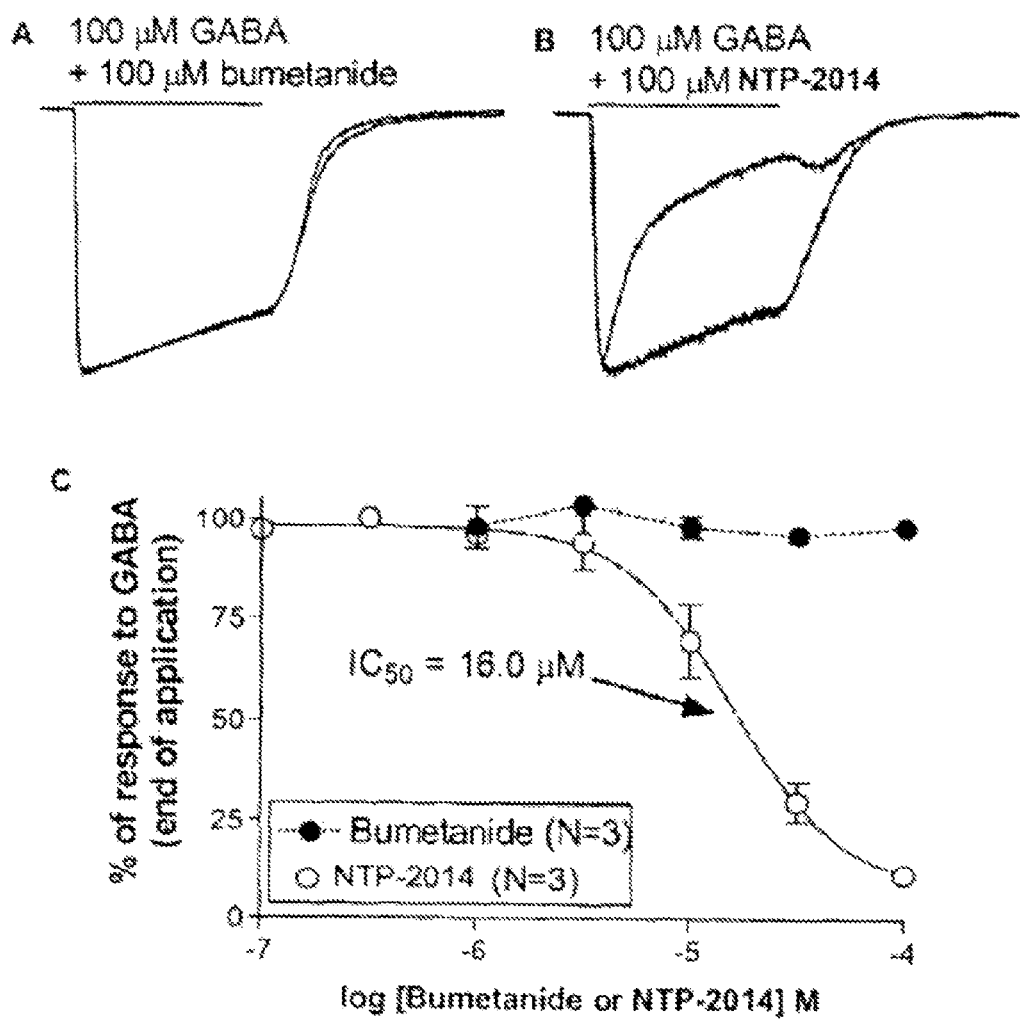
FIG. 42A-C illustrates a comparison of bumetanide (A) and NTP-2014 (B) on the inhibition of $\alpha_4\beta_3\gamma_2$ $GABA_A$ receptor isoforms at 100 μM GABA. In contrast to NTP-2014, bumetanide had no-effect on the $GABA_A$ receptor isoform up to a concentration of 100 μM. This effect is shown graphically in FIG. 42C, where NTP-2014 shows an $IC_{50}$=16 μM.

Further, when compared to NTP-2014, bumetanide had no effect on the GABA$_A$ receptor isoform up to a concentration of 100 μM. NTP-2014 shows an IC$_{50}$=16 μM. These results are shown in FIG. 42.

NTP-2014 appears to have a different mechanism of action upon the GABA$_A$ receptors. The primary effect is an inhibition of chloride current reducing total GABA "drive." It is seen best at $\alpha_4$, then $\alpha_6$, $\alpha_5$, $\alpha_2$ and then $\alpha_3$ and is consistent with noncompetitive antagonism, i.e. open channel block.

The activity of NTP-2014 occurs through at least two paths-inhibition of receptors containing specific subunits, e.g., $\alpha_4$, and through a lack of positive modulation of $\alpha_1$. Increased action via an increase of GABA release at synapses would lead to positive modulation of these receptors and thus would be expected to lead to a decrease in anxiety and seizure frequency. They may also reduce pain, especially neuropathic pain. Inhibition is the only effect observed at $\alpha_4$, $\alpha_5$, and $\alpha_6$-containing receptors. Both these effects may require a γ subunit, as δ-containing receptors were unaffected by 10 μM NTP-2014.

EXAMPLE 160

Formalin Paw Model of Neuropathic Pain

Formalin Paw Test (Late Phase) in the Mouse

The method described herein detects analgesic/anti-inflammatory activity, generally used to test compounds for pain relief, in particular diabetic neuropathy or nociceptive neuropathy. See Wheeler-Aceto, et al. (1991) Psychopharmacology 104: 35-44.

Methods

Mice were given an intraplantar injection of 5% formalin (25 μl) into the posterior left paw. This treatment induces paw licking in control animals. Mice were briefly observed at 1 minute intervals between 15 and 50 minutes after the injection of formalin and the number of occasions that the mice were observed licking the injected paw was recorded. There were 10 mice per group and the test was performed "blind."

Bumetanide derivatives (e.g., NTP-2014, NTP-2026, NTP-2024) were evaluated at 3 doses each, administered i.p. 30 minutes before the test (i.e., 15 minutes before formalin), and compared with a common vehicle control group. Gabapentin (100 mg/kg i.p.) administered under the same experimental conditions, was used as reference substance. The experiment included several groups. Data was analyzed by comparing treated groups with vehicle control using unpaired Mann-Whitney U tests.

Species Used

Male Rj: NMRI mice, weighing 20-30 g (max. range per experiment=5 g) at the beginning of the experiments, obtained from Elevage Janvier, 53940 Le Genest-Saint-Isle, France.

Animal Housing

Mice were housed in groups of 10 in macrolon cages (25×19×13 cm) on wood litter (Litalabo—SPPS, 95100 Argenteuil, France) with free access to food (Code 113—SAFE, 89290 Augy, France) and water until tested (or as indicated otherwise). The animal house was maintained under artificial lighting (12 hours) between 7:00 and 19:00 in a controlled ambient temperature of 21±3° C., and relative humidity between 30-80%.

Sacrifice

Mice were sacrificed at the end of the experiments by exposure to a mixture of $O_2/CO_2$ (20%/80%) followed by $CO_2$.

Figure 43:
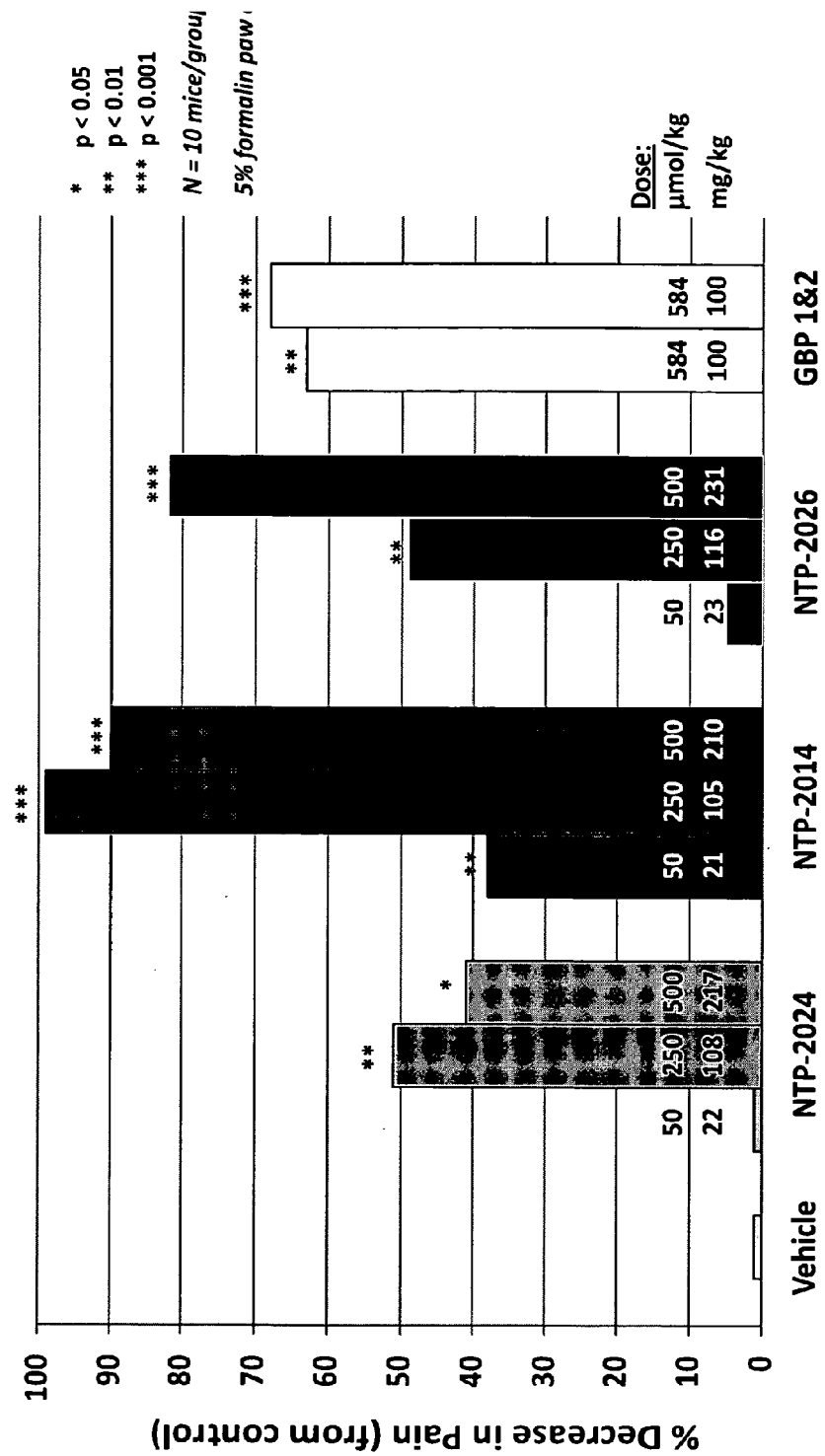
FIG. 43 illustrates that in a mouse model of severe neuropathic pain (e.g. late phase formalin paw model), multiple NTP compounds were more effective or comparable to gabapentin at relieving pain.

NTP-2014 (21, 105 and 210 mg/kg) was administered i.p. 30 minutes before the test (i.e. 15 minutes before formalin). NTP-2014 clearly decreased the licking score from 15 to 50 minutes after injection of formalin, as compared with vehicle controls (−38%, p<0.05; −99%, p<0.001 and −90%, p<0.001, respectively). NTP-2026 (116 and 231 mg/kg) was administered i.p. 30 minutes before the test (i.e. 15 minutes before formalin), dose-dependently decreased the licking score from 15 to 50 minutes after injection of formalin, as compared with vehicle controls (−49%, p<0.01 and −82%, p<0.001, respectively). NTP-2026 was dispersed in 0.2% HPMC in physiological saline with a drop of Tween® 80 (2% of the total volume) to homogenate the preparation. It had no effects at 23.1 mg/kg. Gabapentin (100 mg/kg i.p.), administered under the same experimental conditions, markedly decreased the licking score from 15 to 50 minutes after injection of formalin, as compared with vehicle controls (−68%, p<0.001). These results suggest the presence of clear analgesic/anti-inflammatory activity for NTP-2014 (from 21 to 210 mg/kg i.p.) and NTP-2026 (at 116 and 231 mg/kg i.p.)

during the late phase in the Formalin Paw Test in the mouse. The results are shown in FIG. 43.

Therefore, the compounds described herein (e.g., NTP-2014) act parasynaptically and may be administered to treat neuropathic pain without the unwanted side effects usually associated with GABAergic compounds (e.g., sedation from benzodiazepines). Further, treatment with the compounds described herein, including the compounds described herein, are expected to have similar effects.

EXAMPLE 161

Tail Flick Test

Subjects: Male CD-1 (25-35 g, Charles River) were used for all studies. Mice were housed in groups of five in Plexiglas chambers with food and water available ad libitum. All animals were maintained on a 12 hr light/dark cycle (lights on at 7:00 AM) in a temperature- and humidity-controlled animal colony. The health status of the animals used in this study were examined on arrival. Only animals in good health were acclimatized to laboratory conditions and used in the study. The acclimation period to the vivarium was a minimum of 7 days. All animal experiments were performed under an approved protocol in accordance with institutional guidelines and in accordance with the Guide for the Care and Use of Laboratory Animals as adopted and promulgated by the National Institutes of Health.

Behavioral Testing: Efficacy of the test compounds were assessed using the 52° C. warm water tail-flick test. The latency to the first sign of a rapid tail-flick was taken as the behavioral endpoint (Jannsen, et al. 1963). Each mouse was first tested for baseline latency by immersing its tail in the water and recording the time to response. Mice not responding within 5 seconds were excluded from further testing. Test compounds were then injected and the mice were rested for thermal latencies at 10, 20, 30, 45, 60, 90, 120 and 180 minutes post-injection (if a drug effect dropped below 20% for the group average then the testing was halted for that group). Antinociception was calculated by the following formula: % Antinociception=100×(test latency−control latency)/(10-control latency). A maximum score was assigned (100%) to animals not responding within 10 seconds to avoid tissue damage.

Preparation of Test Materials: NTP-2014 (m.w. 420.52 for free base; lot number: 004JXS047) was dissolved in 0.2% hydroxypropylmethylcellulose (HPMC) in physiological saline to yield final concentrations of between 3.2 and 10 mg/ml (pH ~7.4). NTP-2024 (m.w. 433.52 for free base; lot number: 024DGM048) was dissolved in 0.2% HPMC in physiological saline to yield final concentrations of between 5.6 and 18 mg/ml (pH ~7.4). NTP-2026 (m.w. 462.61 for free base; lot number: 002JRA064) was first dissolved in 100% ETOH (10× solution) and then this stock solution was diluted to final concentrations of 5.6-10 mg/ml using 0.2% HPMC in physiological saline (pH ~7.4). Final ETOH concentration was approximately 10%. Tween 80 (1-2 drops) was added to all solutions to aid in solubilization of compounds. A similar vehicle was used as a control. Morphine sulphate was dissolved in physiological saline.

Experimental Groups: Vehicle control (0.2% HPMC with 2 drops of Tween 80) Morphine control NTP-2014 (32, 56 and 100 mg/kg), NTP-2024 (56, 100 and 180 mg/kg), NTP-2026 (56, 100 and 180 mg/kg). All groups contained n=8-10 mice.

Summary of Results: Antinociceptive A50 Values (and 95% CL): Morphine A50: 9.84 (8.79 to 11.01) mg/kg; NTP-2014 A50: 53.71 (44.41 to 64.95) mg/kg; NTP-2024 A50: Not determined, ~48% at 180 mg/kg*; NTP-2026 A50: Not determined, ~25% at 56 mg/kg** *Mild solubility issues as the highest dose tested (180 mg/kg or 18 mg/ml) Significant solubility issues at the highest dose tested (100 mg/kg or 10 mg/ml). The results are shown in FIG. 44**A-D.

Therefore, the compounds described herein (e.g., NTP-2014) act parasynaptically and may be administered to treat pain without the unwanted side effects usually associated with GABAergic compounds (e.g., sedation from benzodiazepines). Further, treatment with the compounds described herein, including the compounds described herein, are expected to have similar effects.

EXAMPLE 162

Taxol Induced Neuropathy Model

Peripheral neuropathies are chronic conditions that arise when nerves are damaged by trauma, disease, metabolic insufficiency, or by certain drugs and toxins. The sensory disturbances associated with chemotherapeutic agents, such as paclitaxel (Taxol), range from mild tingling to spontaneous burning, typically in the periphery such as the hands and feet. Symptoms become more intense with continued therapy and can lead to weakness, ataxia, numbness and pain, limiting the dose and/or treatment with the chemotherapeutic agent.

In this study, an animal model of Taxol-induced sensory neuropathy was employed to evaluate the effects of the sponsor's test compounds, for response to tactile sensitivity using von Frey test of mechanical allodynia. Thermal hyperalgesia was also tested but found to be an unsuitable endpoint in this model as the results were inconclusive; rats did not consistently develop hyperalgesia after the Taxol treatment. Therefore, Taxol-induced mechanical allodynia was employed as the measured behavioral endpoint.

Gabapentin, 100 mg/kg, IP was able to mitigate the mechanical allodynia seen as a result of the Taxol-induced neuropathic pain. Similarly, rats treated with NTP-2014 (75 mg/kg, IP) showed a significant improvement in allodynia when compared to the vehicle control group.

Rats dosed with NTP-2026 showed a slight improvement on day 32 in comparison to the pre-dose values on day 31, although not near significance. Three of the nine animals in this group showed complete reversal of allodynia.

Due to the rapid and near complete metabolism of NTP-2024 in rats, pre-treatment with a metabolic inhibitor (piperonylbutoxide, PBx) was utilized to increase systemic exposures to the compound. While it did not increase the ability of NTP-2024 to ameliorate pain, its activity against mechanical allodynia compromised the interpretation of the results with NTP-2024. In addition, acute effects of PBx administration may have caused an increase in pain and distress to the animals based on post dose clinical observations.

Preparation of Solution/Suspension

The test substance was homogenized and dispersed using a mortar and a pestle in 0.2% hydroxypropylmethylcellulose (HPMC) in physiological saline, which served as the vehicle. Test articles were administered intraperitoneally in dose volumes of 10 mL/kg body weight. Preparations were made freshly for each day of administration.

Preparation of Metabolic Inhibitor, Piperonyl Butoxide

Prior to test article NTP-2024 and vehicle control group administration, rats were pretreated at 30 minutes and again at 10 minutes prior to test article administration with a general metabolic inhibitor, piperonyl butoxide (150 mg/kg i.p.) in DMSO, at a volume of 1 mL/kg.

An amendment during the conduct of the study, removed the administration of piperonyl butoxide (150 mg/kg i.p.) as a pre-treatment for NTP-2024 (group 3) for the second portion of the study. The animals were pre-treated with Saline for the second portion of the study The reference article, Gabapentin, was formulated in saline to a concentration of 100 mg/mL and delivered subcutaneously at a dose volume of 1 mL/kg body weight (for a dosing concentration of 100 mg/kg).

Experimental Procedures

Animals

A total of one hundred fourteen (114) male Sprague Dawley rats were ordered from Harlan Sprague Dawley Inc., Indianapolis, Ind., USA. The animals were specific pathogen free and approximately 7 weeks old upon arrival at MDSPS—Efficacy Pharmacology. The animals were received in two batches, the first batch contained sixty-three animals and the second batch contained fifty-one animals.

Upon receipt the animals were unpacked and placed in cages. A visual health inspection was performed on each animal to include evaluation of the coat, extremities and orifices. Each animal was also examined for any abnormal signs in posture or movement. One animal arrived with its eye closed and potentially blind, the animal was euthanized the day of arrival. There was no indication of infection or trauma that would have affected the other animals, and the remaining animals were accepted for use on study.

Environment

The animals were housed two (2) per cage at MDSPS in clear polycarbonate plastic cages and received enrichment in the form of Enrich-o-cobs bedding. The temperature was set to be maintained at 18-26° C. (64-79° P) with a relative humidity of 30-70%. Temperature and humidity were monitored daily and minimums and maximums recorded. On several occasions, the humidity was intermittently out of range (lower than 30%). As the animals remained healthy during the course of the study, this is thought to have no impact to the study.

Food and Water

Animals had ad libitum access to oval pellet Certified Picolab Rodent Diet 20 (PMI Feeds Inc., Richmond, Ind., USA) as well as deionized water from MDSPS Efficacy Pharmacology in house production. The rodent diet was analyzed by the manufacturer for levels of specific heavy metals, aflatoxin, organophosphates, and specific nutrients. The water was analyzed for heavy metals and dissolved minerals. Certificates of analysis for food and water are retained in the MDSPS—Efficacy Pharmacology archives. It was not anticipated that the level of known contaminants in the feed and water interfered with the purpose or conduct of this study.

Cage and Animal Identification

Animals were individually identified with a unique ear tag assigned at receipt. In addition, cage cards affixed to their cages identified study number, animal number, treatment designation, species/strain, and gender.

Allocation to Treatment Groups

For inclusion into the study (first portion), the animals had a baseline thermal paw test, which was measured prior to Taxol injections. Animals with a thermal paw score greater than 15 seconds were excluded from study. Two (2) animals having thermal paw scores above 15 seconds were excluded from the study. Sixty one (61) animals met the inclusion criteria and received Taxol.

On day 28, all animals that received Taxol were tested for thermal hyperalgesia. Animals needed to have at least a 20% drop from baseline for inclusion into the treatment segment of the study. Insufficient animals met this criteria and the study was amended to allow mechanical allodynia (von Frey) to replace thermal hyperalgesia as the primary endpoint.

Additional animals were ordered and received to meet the group size. All animals underwent a baseline pre-dose von Frey test, which was measured prior to Taxol injection. For inclusion into the study, the animals needed to have a baseline von Frey score above 12. Eight (8) animals had a von Frey score below 12 and were excluded from the study. Forty three (43) animals met the inclusion criteria and received Taxol.

On Day 31, all animals administered Taxol were tested for mechanical allodynia using von Frey. Animals receiving a score of 13 or below were allocated to treatment groups. The mechanical allodynia scores for each group were reviewed to ensure the mean values and standard deviations were homogeneous. Rats were allocated to treatment groups, 9 rats per group Body weights were taken during the acclimation period, prior to the first day of drug administration and weekly during the study.

Clinical Observations

Animals were observed for signs of abnormal reaction to the Taxol. Clinical observations were recorded for each animal daily beginning the first day of Taxol injection, and for one week following the last Taxol injection. Daily observations of the animals occurred through out the study but were not recorded unless an abnormal finding occurred.

Taxol Administration

All animals were administered Taxol, 2 mg/kg, IP at a dose volume of 1 mL/kg, on Days 1, 3, 5 and 7.

Test Article Administration

On Day 32, all animals received a single intraperitoneal injection of test article or vehicle according to Tables 1 and 2. For group 1 (vehicle), rats were pre-treated with Piperonyl butoxide (150 mg/kg IP, dose volume of 1 mL/kg) at 30 minutes and again at 10 minutes prior to vehicle administration. Four animals in group 3 (NTP-2024) were also pre-treated with Piperonyl butoxide (150 mg/kg IP, dose volume of 1 mL/kg) at 30 minutes and again at 10 minutes prior to vehicle administration. Animals in Groups 2, 3, 4, & 5 were pre-treated with Saline (dose volume of 1 mL/kg, IP) at 30 minutes and again at 10 minutes prior to test article administration. With the exception of animals in group 2, the animals received an IP injection of vehicle or test article 30 min prior to mechanical allodynia testing. Animals were dosed at a volume of 10 mL/kg.

Animals in group 2, received an IP injection of Gabapentin 90 minutes prior to mechanical allodynia testing. Animals were dosed at a volume of 1 mL/kg.

Behavioral Testing—Acclimation

Twice prior to baseline testing, the animals underwent acclimation to the mechanical allodynia apparatus. This habituated the rats to the testing devices so they were calm at the time of testing.

Mechanical Allodynia (von Frey)

All animals underwent von Frey testing for mechanical allodynia. On testing days, the animals were returned to the chambers and allowed approximately 15 minutes to explore their surroundings prior to testing. A series of filaments were applied to the left hind paw. A 2.0 g filament was first applied to the plantar surface, if the animal responded to the filament (by lifting its paw) then the next smaller filament was applied. Conversely, if the animal did not respond, then the next larger filament was applied. This is repeated in an "Up down" method for four responses after the first initial change in response.

Necropsy Following the final behavioral test on Day 32, the animals were euthanized by carbon dioxide asphyxiation. There was no necropsy or tissue collection performed.

Changes to Study Design

The original study design used thermal hyperalgesia as the main parameter for testing the ability of the test compounds to ameliorate the pain associated with the Taxol injection. The treatment inclusion was set at a 20% drop from baseline values as determined on Day 28. The values observed from all animals were insufficient to fulfill the requirements of the study. The study design was amended to use mechanical allodynia as the testing parameter. The positive control was changed from Morphine to Gabapentin, which was more appropriate for this testing parameter. This changed the testing days from Day 28 to Day 31 for allodynia confirmation and Day 29 to Day 32 for testing the article efficacy. Additional animals were received to complete the group size designation. These animals were tested for mechanical allodynia only. The study was then further amended to remove the piperonyl butoxide as a pre-treatment for Group 3 (NTP-2024). It was felt the metabolic inhibitor may have confounded the results. Because this study was conducted in two portions, four (4) animals from Group 3 received the metabolic inhibitor and five (5) received Saline as a pre-treatment. The results for this group are treated as separate groups (Group 3 and Group 3a) for data analysis.

General Health and Observations

All animals who received Taxol remained healthy through out the course of the study. The animals gained weight and no clinical findings were noted. The metabolic inhibitor may have caused irritation to the rats following dosing as demonstrated by vocalization, discomfort, and/or some agitation toward cage mates.

Mechanical Allodynia

The group mean results were analyzed versus the vehicle control group using a two way ANOVA, followed by a Bonferroni post-hoc test. Individual groups were tested pre and post dose using a paired t-test. Gabapentin was able to significantly reverse the anodynia post treatment ($p<0.0001$). The allodynia scores returned to baseline values. There was significant treatment effect ($p<0.0001$) seen in Group 5, NTP-2014, with values comparable to the positive control, Gabapentin.

Figure 45:
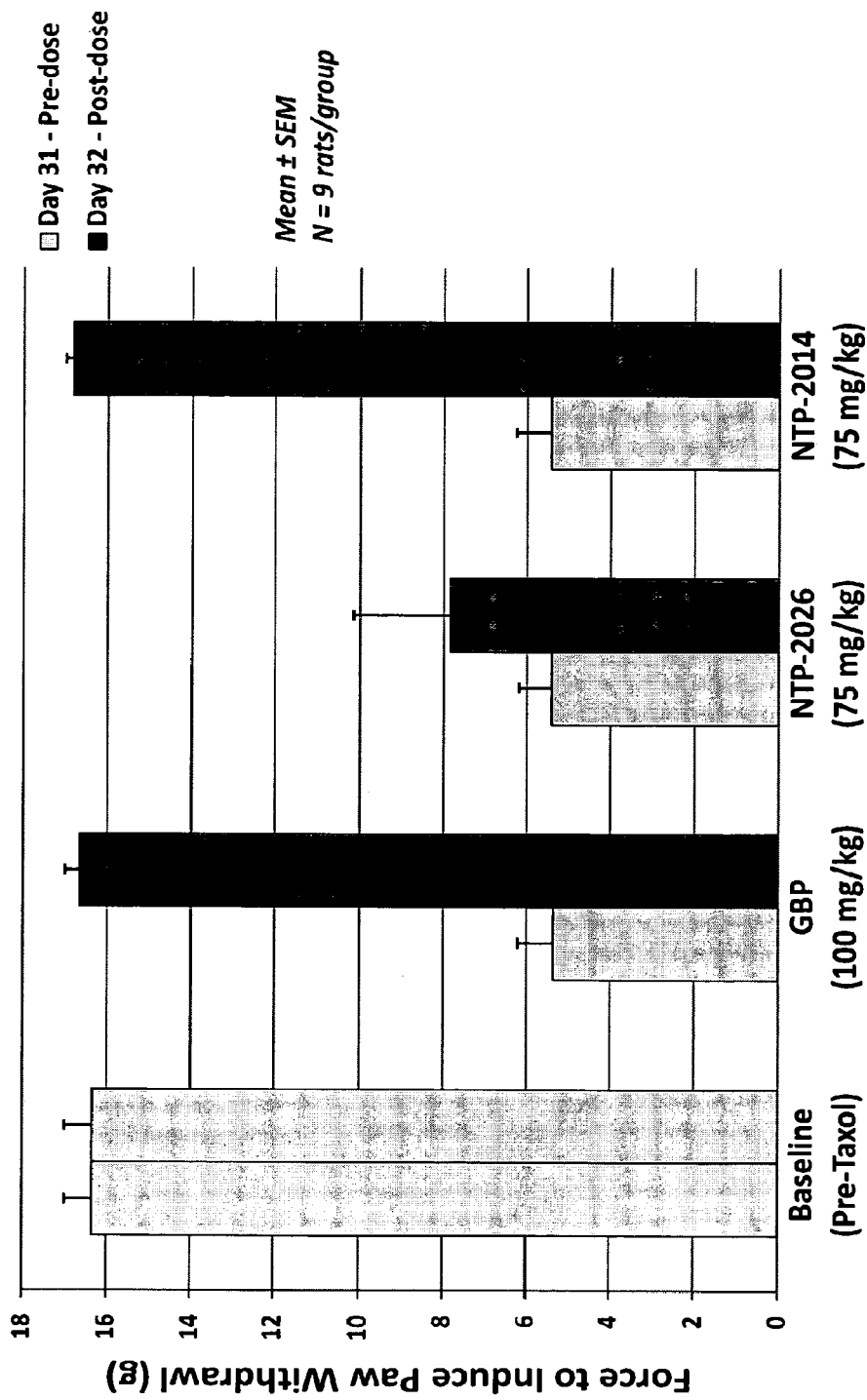
FIG. 45 illustrates that NTP-2014 showed effective analgesic effects in a model of chemotherapy-induced (paclitaxol) neuropathic pain.

The mean allodynia score for Group 3 (NTP-2024) pretreated with the metabolic inhibitor, was 14.92 g while the removal of the metabolic inhibitor pre-treatment was 8.04 g. The reversal of allodynia by the animals pre-treated with the metabolic inhibitor may have been a behavioral response associated with stress induced analgesia instead of a treatment effect. A similar response was shown in the vehicle control group that was also pre-treated with the metabolic inhibitor. The results are shown in FIG. 45.

Therefore, the compounds described herein (e.g., NTP-2014) act parasynaptically and may be administered to treat neuropathic pain without the unwanted side effects usually associated with GABAergic compounds (e.g., sedation from benzodiazepines). Further, treatment with the compounds described herein, including the derivatives (including prodrugs thereof) of bumetanide described herein, are expected to have similar effects.

EXAMPLE 163

Rodent Neuropathic Pain Model

Subjects

Male CD-1 mice (25-35 g, Charles River) were used for all studies. Mice were housed in groups of five in Plexiglas chambers with food and water available ad libitum. All animals were maintained on a 12 hr light/dark cycle (lights on at 7:00 AM) in a temperature- and humidity-controlled animal colony. The health status of the animals used in this study was examined on arrival. Only animals in good health were acclimatized to laboratory conditions and used in the study. The acclimation period to the vivarium was a minimum of 7 days. All animal experiments were performed under an approved protocol in accordance with institutional guidelines and in accordance with the Guide for the Care and Use of Laboratory Animals as adopted and promulgated by the National Institutes of Health.

Drugs and Injections

NTP has provided adequate amounts of NTP-2014 and NTP-2026 along with detailed instructions for preparing injection solutions. Gabapentin (Gallipot, St. Paul, Minn.) was dissolved in physiological saline. Injections were made using a 1-mL syringe with a 30-gauge needle at a volume of 10 ml/kg body weight. Animal body weights were measured prior to surgery and then on the morning of Day 7 (post-SNL testing). For i.p. drug administration, each mouse was firmly grasped by the nape of the neck and the tail was tucked between the last two fingers and palm of the technician's hand. The back of the mouse iwasarched slightly backwards exposing the abdominal region. The needle was inserted through the skin and abdominal musculature into the peritoneal cavity just off of the midline. Mice are immediately returned to the testing cage until behavioral testing.

Experimental Groups

NTP2026 (56, 100 and 180 mg/kg, i.p.); NTP 2014 (32, 56 and 100 mg/kg, i.p.); Gabapentin (100 mg/kg, i.p.); Vehicle Control (10% TPGS in benzoate buffer, i.p.).

SNL Surgeries

SNL surgeries were performed based on the procedures described for rats (Kim and Chung, 1992) and modified for mice (Wang et al., 2001). Anesthesia was maintained with 0.5% halothane in $O_2$ and body temperature was maintained using a heated water blanket. After surgical preparation of the mice, a 1-cm paraspinal incision was made at the level L4-S2. The L5 and L6 spinal nerves were exposed and tightly ligated using a 4-0 silk suture. The ligation was made distal to the dorsal root ganglion but before the fibers joined the sciatic nerve. The incisions were then closed, and animals are allowed to recover. Animals that exhibited motor deficiency (e.g., paw dragging or dropping) or who failed to exhibit subsequent tactile hypersensitivity were excluded from the future testing (typically less than 10% of the animals are excluded). Mechanical thresholds were determined by measuring the paw withdrawal threshold to probing with a series of calibrated von Frey filaments as described below.

Behavioral Tests

Non-noxious sensory thresholds of the mice were determined by paw withdrawal latency to probing with a series of calibrated (0.02-2.34 gm on a logarithmic scale) von Frey filaments ("up and down" method) according to Chaplan et al. (1994) and analyzed using a Dixon (1980) nonparametric test. Results are expressed as the mean withdrawal thresholds. Baseline latencies/thresholds were determined prior to surgery, on the morning of Day 7, and then between 20-60 minutes post dosing with the test drugs. The post-drug time corresponds to the time of maximal activity for these compounds in the tail-flick assay.

Behavioral Observations

Figure 46C:
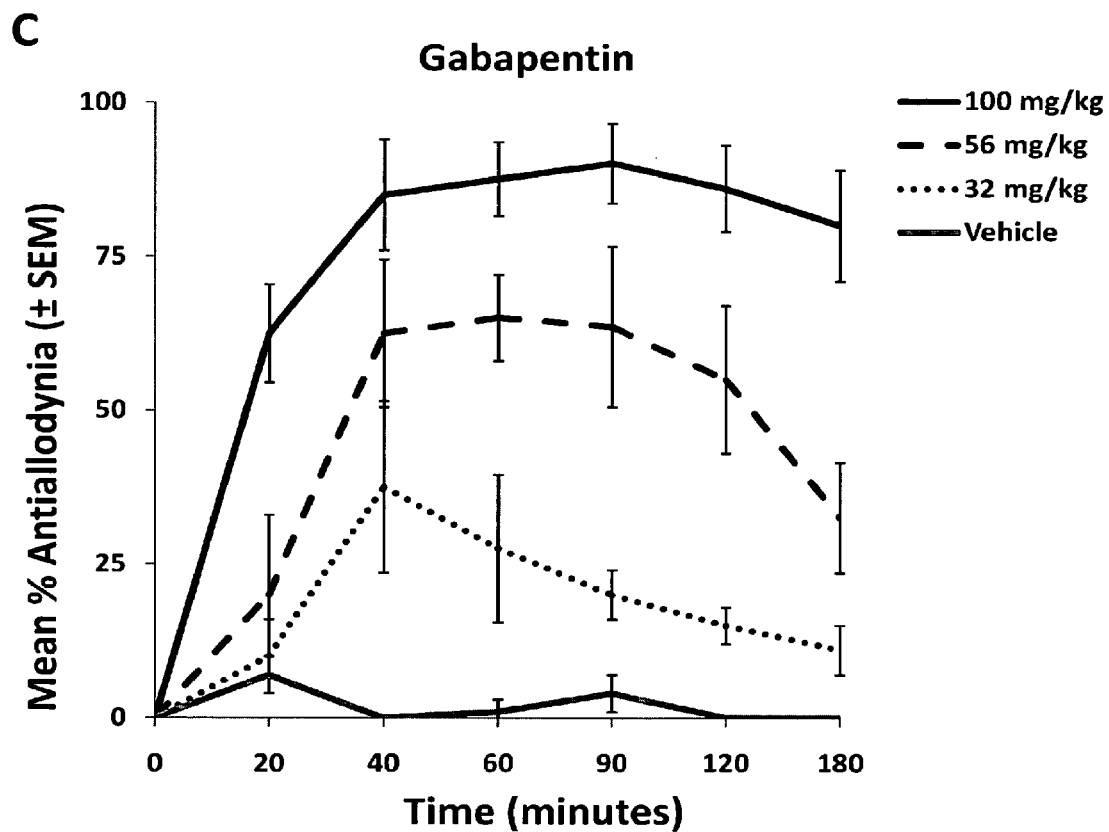

NTP-2014 and NTP-2026 both produced dose-dependent reversal of tactile hypersensitivity in the mouse SNL model of neuropathic pain. Some minor sedation was noted in the high dose groups. No other overt toxicity was noted with these compounds. Gabapentin also produced dose-dependent activity in this model with minor sedation and incoordination noted at the high dose (100 mg/kg, i.p.). The results are shown in FIG. 46A-C.

Therefore, the compounds described herein (e.g., NTP-2014) act parasynaptically and may be administered to treat neuropathic pain without the unwanted side effects usually associated with GABAergic compounds (e.g., sedation from benzodiazepines). Further, treatment with the compounds described herein, including the compounds described herein, are expected to have similar effects.

EXAMPLE 164

Therapeutic Efficacy of Bumetanide Analogs in Alleviating Anxiety

The therapeutic efficacy of several bumetanide analogs in alleviating anxiety was examined using the fear potentiated startle (FPS) test in rats as described above.

Figure 26:
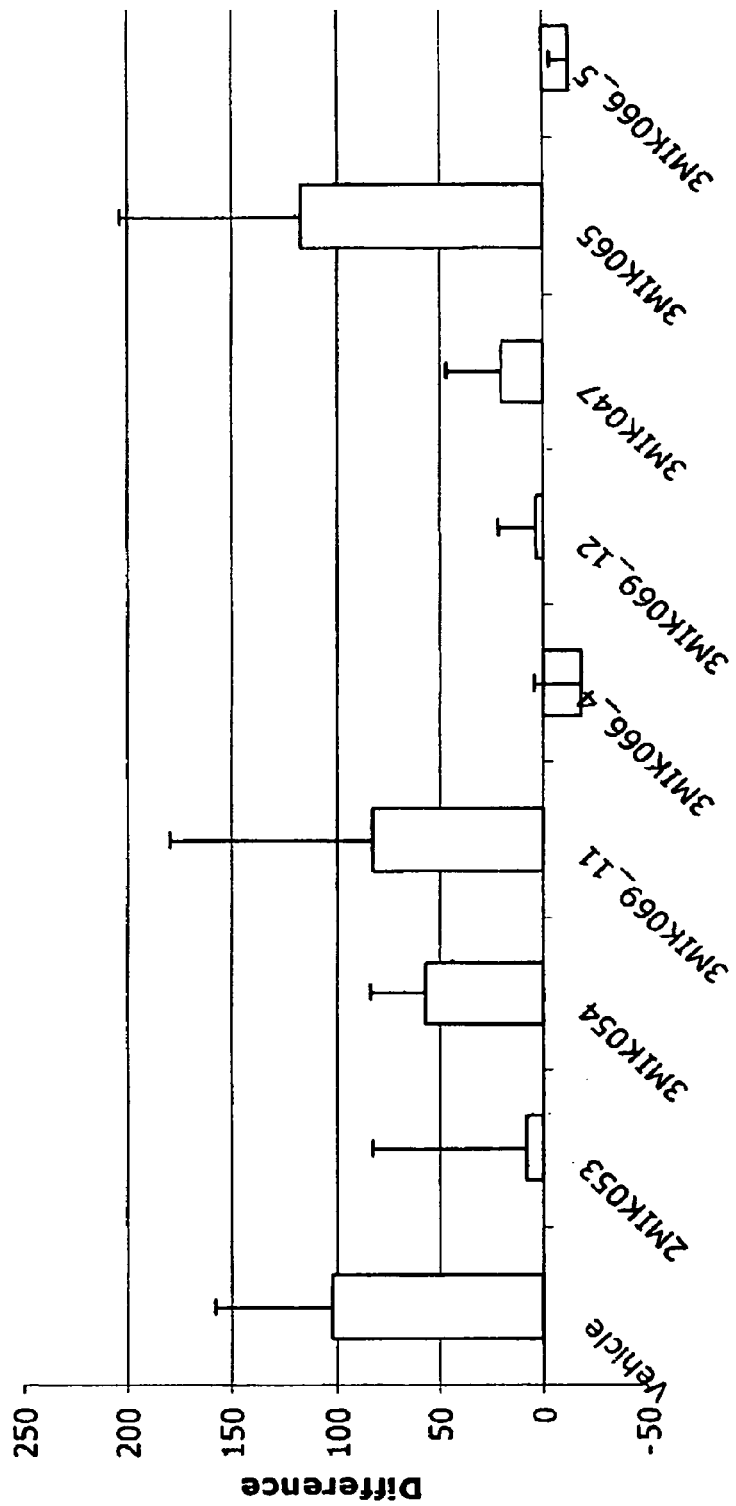
FIG. 26 shows the difference score (startle alone-fear potentiated startle) on the test day in rats treated with one of the following bumetanide analogs: bumetanide N,N-diethylglycolamide ester (referred to as 2MIK053); bumetanide methyl ester (referred to as 3MIK054); bumetanide N,N-dimethylglycolamide ester (referred to as 3MIK069-11); bumetanide morpholinodethyl ester (referred to as 3MIK066-4); bumetanide pivaxetil ester (referred to as 3MIK069-12); bumetanide cyanomethyl ester (referred to as 3MIK047); bumetanide dibenzylamide (referred to as 3MIK065); and bumetanide 3-(dimethylaminopropyl) ester (referred to as 3MIK066-5). The vehicle was DMSO.

FIG. 26 shows the difference score (startle alone—fear potentiated startle) on the test day in rats treated with one of the following bumetanide analogs: bumetanide N,N-diethylglycolamide ester (referred to as 2MIK053); bumetanide methyl ester (referred to as 3MIK054); bumetanide N,N-dimethylglycolamide ester (referred to as 3MIK069-11); bumetanide morpholinodethyl ester (referred to as 3MIK066-4); bumetanide pivaxetil ester (referred to as 3MIK069-12); bumetanide cyanomethyl ester (referred to as 3MIK047); bumetanide dibenzylamide (referred to as 3MIK065); or bumetanide 3-(dimethylaminopropyl) ester (referred to as 3MIK066-5). The vehicle was DMSO. As cant be seen from FIG. 26, the difference score obtained after administration of most of the bumetanide analogs was significantly lower than that observed following administration of vehicle alone, demonstrating that these analogs may be effectively employed to reduce anxiety. In addition, several of the bumetanide analogs were observed to have significantly lower diuretic effects than those generally associated with either furosemide or bumetanide.

EXAMPLE 165

Treatment of an Addictive Disorder

A human patient diagnosed with an addictive disorder can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with a cocaine addiction may be treated by administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the lessening of the symptoms of the addiction or the development of side effects.

A human patient diagnosed with a heroin addiction may be treated by administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the lessening of the symptoms of the addiction or the development of side effects.

A human patient diagnosed with an alcohol addiction (e.g., alcoholism) may be treated by administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the lessening of the symptoms of the addiction or the development of side effects.

EXAMPLE 166

Treatment of an Anxiety Disorder

A human patient diagnosed with an anxiety disorder can be treated by administering a pharmaceutical composition comprising any one or combination of analogs (including prodrugs) of bumetanide, furosemide, piretanide, azosemide, and torsemide described herein. The human patient is rally administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with an anxiety disorder may be treated by administering a pharmaceutical composition comprising any one or combination of the compounds described herein. The human patient is orally administered a pharmaceutical composition comprising 40 mg/kg of any one or combination of the compounds described herein daily. The human patient is monitored and treated according to the lessening of the symptoms and/or the development of side effects.

EXAMPLE 167

Treatment of Ascites

A human patient diagnosed with ascites can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with peritoneal cavity fluid can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with peritoneal fluid excess can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with hydroperitoneum can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with abdominal dropsy can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with cancer, related to ascites can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with tumors related to ascites can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

EXAMPLE 168

Treatment of Glaucoma

A human patient diagnosed with glaucoma can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with increased intraocular pressure can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with angle-closure glaucoma can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with neovascular glaucoma can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with open-angle glaucoma can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The

EXAMPLE 169

Treatment of Ischemia

A human patient diagnosed with ischemia can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with cardiac ischemia (myocardial ischemia) can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with intestinal ischemia can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with mesenteric artery ischemia (acute mesenteric ischemia) can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with hepatic ischemia can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with cerebral ischemia (brain ischemia) can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

EXAMPLE 170

Treatment of Migraine

A human patient diagnosed with migraine can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with headache can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with migraine variant can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with migraine headache can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with cervical migraine syndrome can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with acute confusional migraine can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with migraine with aura can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with migraine without aura can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with migraine may be acutely treated by administering a pharmaceutical composition comprising any one or combination of the compounds described herein. The human patient is orally administered a pharmaceutical composition comprising 10 mg/kg of any one or combination of the compounds described herein once or daily. The human patient is monitored and treated according to the lessening of the symptoms and/or the development of side effects.

A human patient diagnosed with a risk of migraine may receive a prophylactic treatment comprising administering a pharmaceutical composition comprising any one or combination of the compounds described herein. The human patient is orally administered a pharmaceutical composition comprising 20 mg/kg of any one or combination of the compounds described herein once or daily. The human patient is monitored and treated according to the delay of onset of migraines or the development of side effects.

A human patient diagnosed with headache may be treated by administering a pharmaceutical composition comprising any one or combination of the compounds described herein. The human patient is orally administered a pharmaceutical composition comprising 10 mg/kg of any one or combination of the compounds described herein once or daily. The human patient is monitored and treated according to the lessening of the symptoms and/or the development of side effects.

A human patient diagnosed with a medical history headache may receive a prophylactic treatment comprising administering a pharmaceutical composition comprising any one or combination of the compounds described herein. The human patient is orally administered a pharmaceutical composition comprising 20 mg/kg of any one or combination of the compounds described herein once or daily. The human patient is monitored and treated according to the delay of reoccurrence of headaches or the development of side effects.

A human patient diagnosed with migraine variant may be treated by administering a pharmaceutical composition comprising any one or combination of the compounds described herein. The human-patient is orally administered a pharmaceutical composition comprising 10 mg/kg of any one or combination of the compounds described herein daily. The human patient is monitored and treated according to the lessening of the symptoms and/or the development of side effects.

A human patient diagnosed with medical history migraine variant may receive a prophylactic treatment comprising administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the delay or prevention of the reoccurrence of migraine variant or the development of side effects.

A human patient diagnosed with migraine headache may be treated by administering a pharmaceutical composition comprising any one or combination of the compounds described herein. The human patient is orally administered a pharmaceutical composition comprising 10 mg/kg of any one or combination of the compounds described herein daily. The human patient is monitored and treated according to the lessening of the symptoms and/or the development of side effects.

A human patient diagnosed with medical history of migraine headaches may receive prophylactic treatment comprising administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the delay of onset of symptoms, prevention of reoccurrence of migraine headaches, or the development of side effects.

A human patient diagnosed with cervical migraine syndrome may be treated by administering a pharmaceutical composition comprising any one or combination of the compounds described herein. The human patient is orally administered a pharmaceutical composition comprising 10 mg/kg of any one or combination of the compounds described herein daily. The human patient is monitored and treated according to the lessening of the symptoms and/or the development of side effects.

A human patient diagnosed with a risk of cervical migraine syndrome may be treated by prophylactic administration of a pharmaceutical composition comprising any one or combination of the compounds described herein. The human patient is orally administered a pharmaceutical composition comprising 20 mg/kg of any one or combination of the compounds described herein daily. The human patient is monitored and treated according to the lessening of the reoccurrence of cervical migraines or the development of side effects.

A human patient diagnosed with acute confusional migraine may be treated by administering a pharmaceutical composition comprising any one or combination of the compounds described herein. The human patient is orally administered a pharmaceutical composition comprising 10 mg/kg of any one or combination of the compounds described herein daily. The human patient is monitored and treated according to the lessening of the symptoms and/or the development of side effects.

A human patient diagnosed with a risk of acute confusional migraine may be treated by prophylactic administration of a pharmaceutical composition comprising any one or combination of the compounds described herein. The human patient is orally administered a pharmaceutical composition comprising 10 mg/kg of any one or combination of the compounds described herein daily. The human patient is monitored and treated according to the delay in onset, lessening of occurrence of acute confusional migraines, or the development of side effects.

A human patient diagnosed with migraine with aura may be acutely treated by administering a pharmaceutical composition comprising any one or combination of the compounds described herein. The human patient is orally administered a pharmaceutical composition comprising 10 mg/kg of any one or combination of the compounds described herein daily. The human patient is monitored and treated according to the lessening of the symptoms and/or the development of side effects.

A human patient diagnosed with a medical history migraine with aura may be treated by a prophylactic administration of a pharmaceutical composition comprising any one or combination of the compounds described herein. The human patient is orally administered a pharmaceutical composition comprising 10 mg/kg of any one or combination of the compounds described herein daily. The human patient is monitored and treated according to the delay or prevention of onset of migraine with aura or the development of side effects.

A human patient diagnosed with migraine without aura may be acutely treated by administering a pharmaceutical composition comprising any one or combination of the compounds described herein. The human patient is orally administered a pharmaceutical composition comprising 10 mg/kg of any one or combination of the compounds described herein daily. The human patient is monitored and treated according to the lessening of the symptoms and/or the development of side effects.

A human patient at risk for migraine may be treated by a prophylactic administration of a pharmaceutical composition comprising any one or combination of the compounds described herein. The human patient is orally administered a pharmaceutical composition comprising 10 mg/kg of any one or combination of the compounds described herein daily to prevent migraine. The human patient is monitored and treated according to the lessening of the symptoms, the development of side effects, and prevention of the onset of migraines.

EXAMPLE 171

Treatment of Neuropathic Pain

A human patient diagnosed with neuropathic pain can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with diabetic neuropathy can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with neuropathic pain may be treated by administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the lessening of the symptoms and/or the development of side effects.

A human patient diagnosed with diabetic neuropathy may be treated by administering a pharmaceutical composition comprising any one or combination of the compounds described herein. The human patient is orally administered a pharmaceutical composition comprising 20 mg/kg of any one or combination of the compounds described herein daily: The human patient is monitored and treated according to the lessening of the symptoms and/or the development of side effects.

A human patient diagnosed with diabetes may be treated by prophylactic administration of a pharmaceutical composition comprising any one or combination of the compounds described herein. The human patient is orally administered a pharmaceutical composition comprising 20 mg/kg of any one or combination of the compounds described herein daily. The human patient is monitored and treated according to the delay in onset of diabetic neuropathy, prevention of the development of diabetic neuropathy, or the lessening of symptoms associated with diabetic neuropathy.

A human patient diagnosed with postherpetic neuralgia may be treated by administering a pharmaceutical composition comprising any one or combination of the compounds described herein. The human patient is orally administered a pharmaceutical composition comprising 20 mg/kg of any one or combination of the compounds described herein once or daily. The human patient is monitored and treated according to the lessening of the symptoms and/or the development of side effects.

EXAMPLE 172

Treatment of Nociceptive Neuralgia

A human patient diagnosed with nociceptive neuralgia can be treated by administering a pharmaceutical composition comprising any one or combination of analogs (including prodrugs) of bumetanide, furosemide, piretanide, azosemide, and torsemide described herein. The human patient is administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

EXAMPLE 173

Treatment of Postherpetic Neuralgia

A human patient diagnosed with postherpetic neuralgia can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with shingles can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with a herpes zoster infection can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

EXAMPLE 174

Treatment of Seizures

A human patient diagnosed with seizures can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein every day for 7-10 days. The human patient is monitored and treated according to the lessening of the symptoms and/or the development of side effects.

A human patient diagnosed with epilepsy can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with epileptic seizures can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with a seizure disorder can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with cerebral palsy (a neurological condition involving seizures) can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg of any one or combination of analogs (including prodrugs) of bumetanide, furosemide, piretanide, azosemide, and torsemide described herein daily. The human patient is monitored and treated according to the lessening of the symptoms and/or the development of side effects.

A human patient diagnosed with seizures may be treated by administering a pharmaceutical composition comprising any one or combination of the compounds described herein. The human patient is orally administered a pharmaceutical composition comprising from 20 mg/kg of any one or combination of the compounds described herein. The human patient is monitored and treated according to the lessening of the symptoms and/or the development of side effects, as well as potentially through monitoring of pseudo steady-state concentrations of serum levels of the agent.

A human patient diagnosed with epilepsy may be treated by administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the lessening of the symptoms and/or the development of side effects.

A human patient diagnosed with epileptic seizures may be treated by administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the lessening of the symptoms and/or the development of side effects.

A human patient diagnosed with a seizure disorder may be treated by administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the lessening of the symptoms and/or the development of side effects.

A human patient diagnosed with cerebral palsy (a neurological condition involving seizures) may be treated by administering a pharmaceutical composition comprising any one or combination of the compounds described herein. The human patient is orally administered a pharmaceutical composition comprising 20 mg/kg of any one or combination of the compounds described herein daily. The human patient is monitored and treated according to the lessening of the symptoms and/or the development of side effects.

EXAMPLE 175

Treatment of a Patient with at Least One Tumor

A human patient diagnosed with at least one tumor can be treated by administering a pharmaceutical composition comprising any one or combination of analogs (including prodrugs) of bumetanide, furosemide, piretanide, azosemide, and torsemide described herein. The human patient is orally administered a pharmaceutical composition comprising 10 mg/kg or combination of analogs (including prodrugs) of bumetanide, furosemide, piretanide, azosemide, and torsemide described herein daily. The human patient is monitored and treated according to the lessening of the symptoms and/or the development of side effects.

EXAMPLE 176

Treatment of a Withdrawal Syndrome

A human patient diagnosed with a cocaine addiction who has ceased cocaine use and is at risk for suffering from cocaine withdrawal syndrome may be treated by administering a pharmaceutical composition comprising any one or combination of the compounds described herein. The human patient is orally administered a pharmaceutical composition comprising 40 mg/kg of any one or combination of the compounds described herein daily. The human patient is monitored and treated according to the lessening of the symptoms of the withdrawal syndrome or the development of side effects.

A human patient diagnosed with a heroin addiction who has ceased heroin use and is at risk for suffering from heroin withdrawal syndrome may be treated by administering a pharmaceutical composition comprising any one or combination of the compounds described herein. The human patient is orally administered a pharmaceutical composition comprising 40 mg/kg of any one or combination of the compounds described herein daily. The human patient is monitored and treated according to the lessening of the symptoms of the withdrawal syndrome or the development of side effects.

A human patient diagnosed with an opiate addiction, for example, to OXYCONTIN who has ceased OXYCONTIN use and is at risk for suffering from OXYCONTIN withdrawal syndrome may be treated by administering a pharmaceutical composition comprising any one or combination of the compounds described herein. The human patient is orally administered a pharmaceutical composition comprising 40 mg/kg of any one or combination of the compounds described herein daily. The human patient is monitored and treated according to the lessening of the symptoms of the withdrawal syndrome or the development of side effects.

A human patient diagnosed with alcoholism who has ceased drinking alcohol and is at risk for suffering from an alcohol withdrawal syndrome may be treated by administering a pharmaceutical composition comprising any one or combination of the compounds described herein. The human patient is orally administered a pharmaceutical composition comprising 40 mg/kg of any one or combination of the compounds described herein daily. The human patient is monitored and treated according to the lessening of the symptoms of the withdrawal syndrome or the development of side effects.

TABLE 17

Compound Designations/Chemical Name/Chemical Structure

| Compound Number | Compound Name | Compound structure |
|---|---|---|
| NTP-1007 | Furosemide diethylamide | (structure) |

TABLE 17-continued

Compound Designations/Chemical Name/Chemical Structure

| Compound Number | Compound Name | Compound structure |
|---|---|---|
| NTP-2006 | Bumetanide N,N-diethylglycolamide ester | 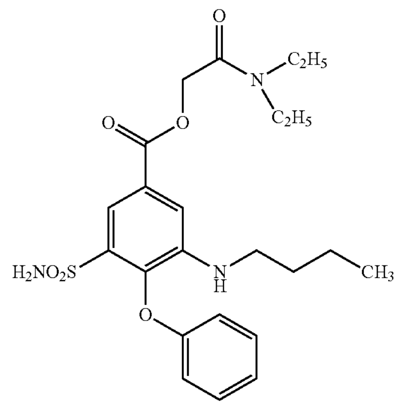 [SMILES: CCCCNc1cc(C(=O)OCC(=O)N(CC)CC)cc(S(N)(=O)=O)c1Oc1ccccc1] |
| NTP-2007 | Bumetanide diethylamide | 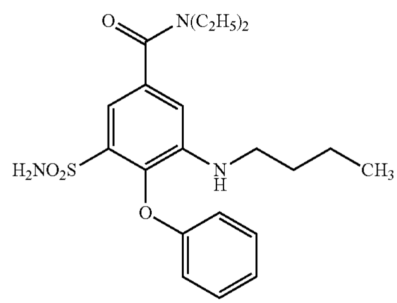 |
| NTP-2008 | Bumetanide dibenzylamide | 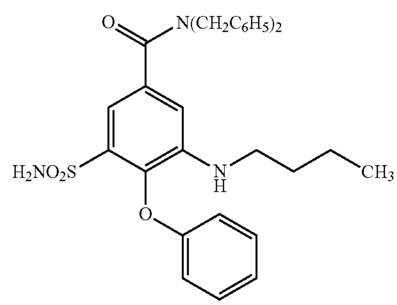 |
| NTP-2011 | Bumetanide N,N-dimethylglycolamide ester | 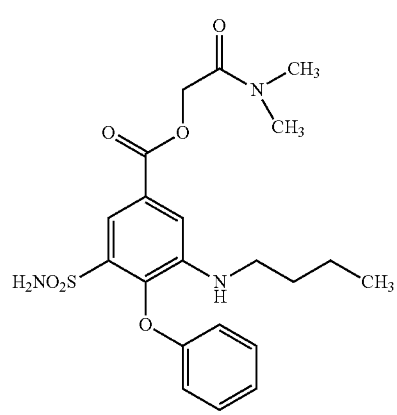 [SMILES: CCCCNc1cc(C(=O)OCC(=O)N(C)C)cc(S(N)(=O)=O)c1Oc1ccccc1] |

TABLE 17-continued

Compound Designations/Chemical Name/Chemical Structure

| Compound Number | Compound Name | Compound structure |
|---|---|---|
| NTP-2012 | Bumetanide pivaxetil ester | 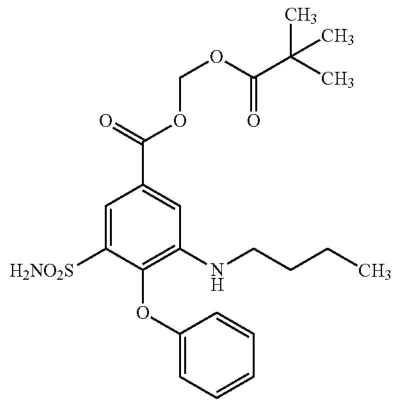 [SMILES: CCCCNc1cc(C(=O)OCOC(=O)C(C)(C)C)cc(S(N)(=O)=O)c1Oc1ccccc1] |
| NTP-2014 | 3-aminosulfonyl-5-N,N-dibutylamino-4-phenoxybenzoic acid | 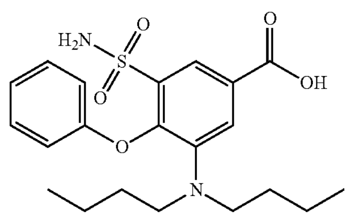 [SMILES: CCCCN(CCCC)c1cc(C(=O)O)cc(S(N)(=O)=O)c1Oc1ccccc1] |
| NTP-2015 | Bumetanide dimethylamide | 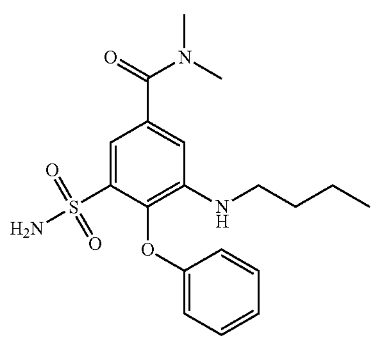 [SMILES: CCCCNc1cc(C(=O)N(C)C)cc(S(N)(=O)=O)c1Oc1ccccc1] |
| NTP-2022 | Bumetanide N-pyrrolidinyl amide | 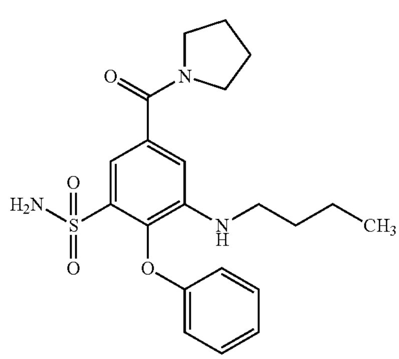 [SMILES: CCCCNc1cc(C(=O)N2CCCC2)cc(S(N)(=O)=O)c1Oc1ccccc1] |

TABLE 17-continued

Compound Designations/Chemical Name/Chemical Structure

| Compound Number | Compound Name | Compound structure |
|---|---|---|
| NTP-2023 | Bumetanide N-piperidinyl amide | 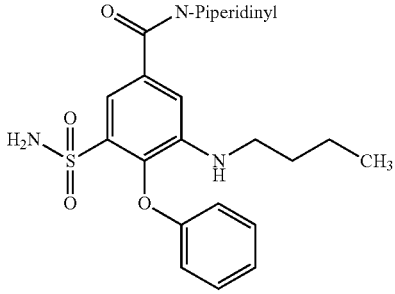 |
| NTP-2024 | Bumetanide N-morpholino amide | 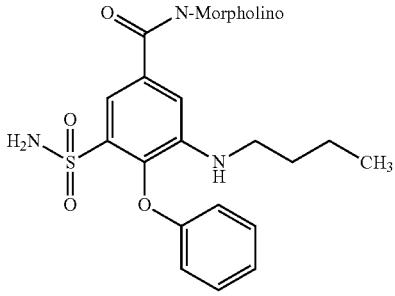 |
| NTP-2025 | 3-(N,N-Dimethylamino)propyl 3-aminosulfonyl-5-N,N-dibutylamino-4-phenoxybenzamide | 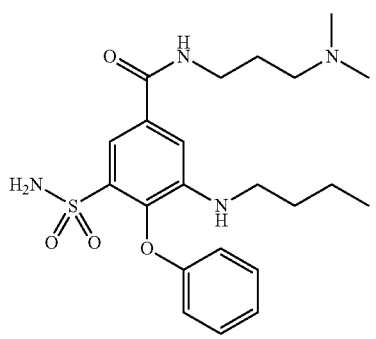 [SMILES: CCCCNc1cc(C(=O)NCCCN(C)C)cc(S(N)(=O)=O)c1Oc1ccccc1] |
| NTP-2026 | Bumetanide 3-(N,N-dimethylaminopropyl)-N-methyl amide | 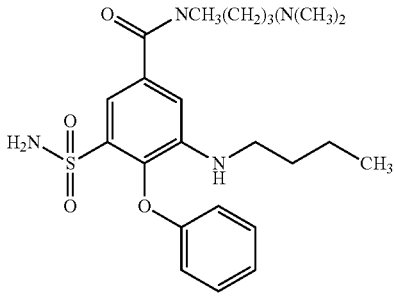 |
| NTP-2002 | Bumetanide 2-cyanomethyl ester | 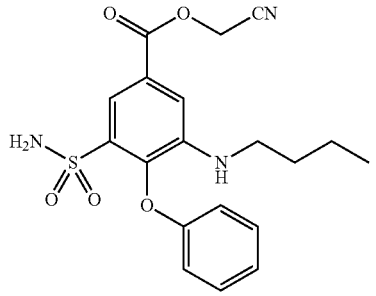 [SMILES: CCCCNc1cc(C(=O)OCC#N)cc(S(N)(=O)=O)c1Oc1ccccc1] |

TABLE 17-continued

Compound Designations/Chemical Name/Chemical Structure

| Compound Number | Compound Name | Compound structure |
|---|---|---|
| NTP-2030 | Bumetanide S-fluoromethyl thioester | 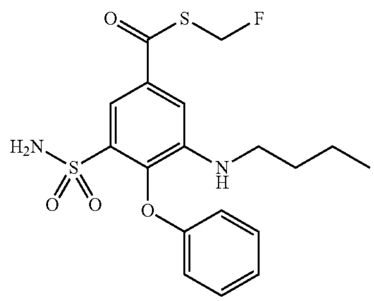 [SMILES: CCCCNc1cc(C(=O)SCF)cc(S(N)(=O)=O)c1Oc1ccccc1] |
| | Bumetanide 2-(1-piperidinyl)ethyl ester | |
| | Furosemide 2-cyanoethyl ester | |
| NTP-1017 | Furosemide S-fluoromethyl thioester | 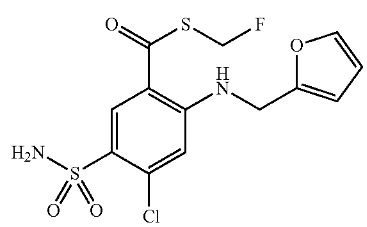 [SMILES: NS(=O)(=O)c1cc(C(=O)SCF)c(NCc2ccco2)cc1Cl] |
| NTP-1019 | Furosemide ortho-methoxy benzyl ester | 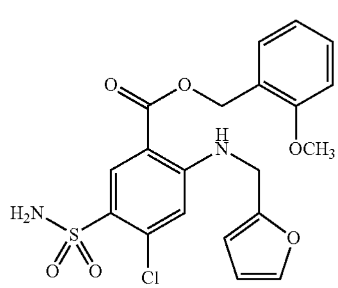 [SMILES: COc1ccccc1COC(=O)c1cc(S(N)(=O)=O)c(Cl)cc1NCc1ccco1] |

TABLE 17-continued

Compound Designations/Chemical Name/Chemical Structure

| Compound Number | Compound Name | Compound structure |
|---|---|---|
| NTP-1021 | Furosemide 4-phenylbutyl ester | 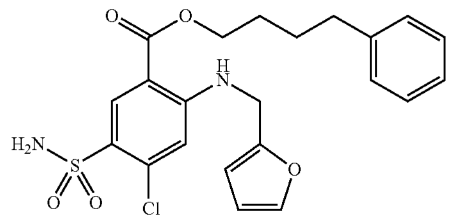 [SMILES: NS(=O)(=O)c1cc(C(=O)OCCCCc2ccccc2)c(NCc2ccco2)cc1Cl] |
| NTP-1028 | Furosemide pyrrolidinyl amide | 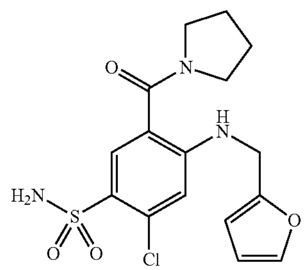 [SMILES: NS(=O)(=O)c1cc(C(=O)N2CCCC2)c(NCc2ccco2)cc1Cl] |
| NTP-1032 | Furosemide 3-(N,N-dimethylaminopropyl)-N-methyl amide | 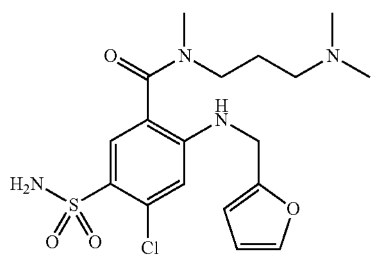 [SMILES: CN(C)CCCN(C)C(=O)c1cc(S(N)(=O)=O)c(Cl)cc1NCc1ccco1] |

Although the invention has been described in some detail by way of illustration and example for purposes of clarity of understanding, it will be obvious that certain changes and modifications may be practiced within the scope of the appended claims. Modifications of the above-described modes for carrying out the invention that are obvious to persons of skill in medicine, pharmacology, microbiology, and/or related fields are intended to be within the scope of the following claims.

All publications (e.g., Non-Patent Literature), patent application publications, and patent applications mentioned in this specification are indicative of the level of skill of those skilled in the art to which this invention pertains. All such publications (e.g., Non-Patent Literature), patent application publications, and patent applications are herein incorporated by reference to the same extent as if each individual publication, patent, patent application publication, or patent application was specifically and individually indicated to be incorporated by reference.

The invention claimed is:
1. A compound bumetanide N-morpholinylthioamide:

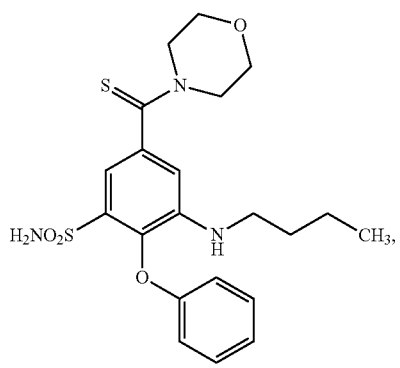 [SMILES: CCCCNc1cc(C(=S)N2CCOCC2)cc(S(N)(=O)=O)c1Oc1ccccc1]

or a pharmaceutically acceptable salt thereof.

* * * * *